(12) United States Patent
Aissaoui et al.

(10) Patent No.: US 8,575,158 B2
(45) Date of Patent: Nov. 5, 2013

(54) 1-PHENYL-SUBSTITUTED HETEROCYCLYL DERIVATIVES AND THEIR USE AS PROSTAGLANDIN D$_2$ RECEPTOR MODULATORS

(75) Inventors: Hamed Aissaoui, Allschwil (CH); Christoph Boss, Allschwil (CH); Heinz Fretz, Allschwil (CH); Julien Pothier, Allschwil (CH); Sylvia Richard-Bildstein, Allschwil (CH); Philippe Risch, Allschwil (CH); Romain Siegrist, Allschwil (CH)

(73) Assignee: Actelion Pharmaceuticals Ltd., Allschwil (CH)

(*) Notice: Subject to any disclaimer, the term of this patent is extended or adjusted under 35 U.S.C. 154(b) by 0 days.

(21) Appl. No.: 13/808,857

(22) PCT Filed: Jul. 4, 2011

(86) PCT No.: PCT/IB2011/052944
§ 371 (c)(1),
(2), (4) Date: Jan. 7, 2013

(87) PCT Pub. No.: WO2012/004722
PCT Pub. Date: Jan. 12, 2012

(65) Prior Publication Data
US 2013/0109685 A1    May 2, 2013

(30) Foreign Application Priority Data
Jul. 5, 2010    (WO) ................. 2010/053071

(51) Int. Cl.
*C07D 265/36* (2006.01)
*C07D 221/04* (2006.01)

(52) U.S. Cl.
USPC ....................... 514/230.5; 546/112

(58) Field of Classification Search
None
See application file for complete search history.

(56) References Cited

U.S. PATENT DOCUMENTS

| | | | |
|---|---|---|---|
| 5,736,564 A * | 4/1998 | Elliott et al. | 514/414 |
| 5,929,106 A * | 7/1999 | Elliott et al. | 514/414 |
| 7,534,897 B2 | 5/2009 | Tanimoto et al. | |
| 7,842,692 B2 | 11/2010 | Kugimiya et al. | |
| 7,956,082 B2 | 6/2011 | Kugimiya et al. | |
| 8,143,285 B2 | 3/2012 | Kugimiya et al. | |
| 2009/0197959 A1 | 8/2009 | Hutchinson et al. | |

FOREIGN PATENT DOCUMENTS

| | | |
|---|---|---|
| EP | 1413306 | 4/2004 |
| EP | 1435356 | 7/2004 |
| EP | 1471057 | 1/2006 |
| GB | 2388540 | 11/2003 |
| WO | WO 02/094830 | 11/2002 |
| WO | WO 03/097042 | 11/2003 |
| WO | WO 03/097598 | 11/2003 |
| WO | WO 2004/032848 | 4/2004 |
| WO | WO 2004/035543 | 4/2004 |
| WO | WO 2004/058164 | 7/2004 |
| WO | WO 2004/089884 | 10/2004 |
| WO | WO 2004/089885 | 10/2004 |
| WO | WO 2004/096777 | 11/2004 |
| WO | WO 2005/018529 | 3/2005 |
| WO | WO 2005/073234 | 8/2005 |
| WO | WO 2005/087743 | 9/2005 |
| WO | WO 2005/100321 | 10/2005 |
| WO | WO 2005/102338 | 11/2005 |
| WO | WO 2005/105727 | 11/2005 |
| WO | WO 2005/115382 | 12/2005 |
| WO | WO 2006/005909 | 1/2006 |
| WO | WO 2006/021759 | 3/2006 |
| WO | WO 2006/037982 | 4/2006 |
| WO | WO 2006/044732 | 4/2006 |
| WO | WO 2006/056752 | 6/2006 |
| WO | WO 2006/091674 | 8/2006 |
| WO | WO 2006/125593 | 11/2006 |
| WO | WO 2006/125596 | 11/2006 |

(Continued)

OTHER PUBLICATIONS

Solid Phase Synthesis of Tetrahydroisoquinolines & Tetrahydroimidazopyridines, 1996, Tetrahedron Letters, 37, pp. 4865-4868.*
Kukkola et al., Isoindolines: A New Series of Potent and Selective Endothelin-A Receptor Antagonists, Bioorganic & Medicinal Chemistry Letters, 2001, 11, 1737-1740.*
Kukkola et al., A Novel Regio- and Stereoselective Synthesis of Isoindolines, Tetrahedron Letters, 1996, 37, 5065-6068.*
Stebbins et al., Therapeutic efficacy of AM156, a novel prostanoid DP2 receptor antagonist, in murine models of allergic rhinitis and house dust mite-induced pulmonary inflammation, European Journal of Pharmacology, 2010, 638, 142-149.*

(Continued)

*Primary Examiner* — Dennis Heyer
*Assistant Examiner* — Daniel M Podgorski
(74) *Attorney, Agent, or Firm* — Hunton & Williams LLP

(57) ABSTRACT

The present invention relates to 1-phenyl-substituted heterocyclyl derivatives of the formula (I),

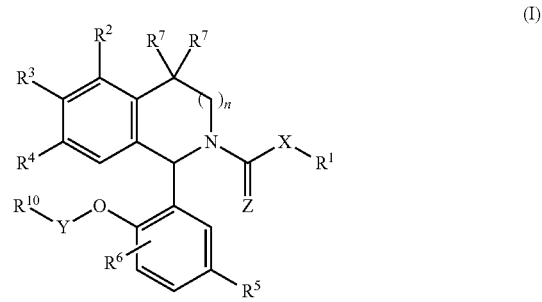

wherein X, Y, Z, n, $R^1$, $R^2$, $R^3$, $R^4$, $R^5$, $R^6$, $R^7$ and $R^{10}$ are as described in the description and their use as prostaglandin receptor modulators, most particularly as prostaglandin D$_2$ receptor modulators, in the treatment of various prostaglandin-mediated diseases and disorders, to pharmaceutical compositions containing these compounds and to processes for their preparation.

16 Claims, No Drawings

(56) References Cited

FOREIGN PATENT DOCUMENTS

| | | | |
|---|---|---|---|
| WO | WO 2007/010964 | 1/2007 | |
| WO | WO 2007/010965 | 1/2007 | |
| WO | WO 2007/029629 | 3/2007 | |
| WO | WO 2007/036743 | 4/2007 | |
| WO | WO 2007/037187 | 4/2007 | |
| WO | WO 2007/039736 | 4/2007 | |
| WO | WO 2007/039741 | 4/2007 | |
| WO | WO 2007/052023 | 5/2007 | |
| WO | WO 2007/062678 | 6/2007 | |
| WO | WO 2007/062773 | 6/2007 | |
| WO | WO 2007/121280 | 10/2007 | |
| WO | WO 2007/143745 | 12/2007 | |
| WO | WO 2007/144625 | 12/2007 | |
| WO | WO 2007/146838 | 12/2007 | |
| WO | WO 2008/072784 | 6/2008 | |
| WO | WO 2008/119917 | 10/2008 | |
| WO | WO 2008/122784 | 10/2008 | |
| WO | WO 2008122784 A1 * | 10/2008 | ......... C07D 215/233 |
| WO | WO 2009/004379 | 1/2009 | |
| WO | WO 2009/060209 | 5/2009 | |
| WO | WO 2009/061730 | 5/2009 | |
| WO | WO 2009/089192 | 7/2009 | |
| WO | WO 2009/099902 | 8/2009 | |
| WO | WO 2009/102893 | 8/2009 | |
| WO | WO 2009/108720 | 9/2009 | |
| WO | WO 2009/145989 | 12/2009 | |
| WO | WO 2010/003120 | 1/2010 | |
| WO | WO 2010/003127 | 1/2010 | |
| WO | WO 2010/018109 | 2/2010 | |
| WO | WO 2010/018112 | 2/2010 | |
| WO | WO 2010/018113 | 2/2010 | |
| WO | WO 2010/042652 | 4/2010 | |
| WO | WO 2010/055004 | 5/2010 | |
| WO | WO 2010/089391 | 8/2010 | |
| WO | WO 2010/092043 | 8/2010 | |
| WO | WO 2010/102154 | 9/2010 | |
| WO | WO 2011/002814 | 1/2011 | |
| WO | WO 2011/014587 | 2/2011 | |
| WO | WO 2011/014588 | 2/2011 | |
| WO | WO 2011/017201 | 2/2011 | |
| WO | WO 2011/055270 | 5/2011 | |
| WO | WO 2012/087861 | 6/2012 | |

OTHER PUBLICATIONS

Arimura A. et al., "Prevention of Allergic Inflammation by a Novel Prostaglandin Receptor Antagonist, S-5751," J Pharmacol Exp Ther Aug. 1, 2001, 298, pp. 411-419.

Charette, Andre B. et al., "Enantioselective Cyclopropanation of Allylic Alcohols with Dioxaborolane Ligands: Scope and Synthetic Applications" J. Am. Chem. Soc. (1998), 120, p. 11943-11952.

Cho Sung Jin et al., "Selective 5-Hydroxytrytamine 2C Receptor Agonists Derived from the Lead Compound Tranylcypromise—Identification of Drugs with Antideperessant-Like-Action," J. Med. Chem. (2009), 52(7), pp. 1885-1902.

Crosignani Stefano et al., "Discovery of Potent, Selective, and Orally Bioavailable Alkynlphenoxyacetic Acid CRTH2 (DP2) Receptor Antagonists for the Treatment of Allergic Inflammatory Diseases," J. Med. Chem. (2011), 54, pp. 7299-7317.

Fortini A et al., "Heparin Does Not Interfere with Prostacyclin and prostaglandin $D_2$ Binding to Platelets" (1985) Thromb Res 40 (3), pp. 319-328.

Ghaffar Talit et al., "A New Homogeneous Platinum Containing Catalyst for the Hydrolysis of Nitriles", Tet. Lett., (1995), 36(47), pp. 8657-8660.

Gould, Philip, "Salt selection for basic drugs," International Journal of Pharmaceutics, (1986) 33, pp. 201-217.

Greene, T. W. et al., "Protective Groups in Organic Synthesis," Protecting Groups in Organic Synthesis, $3^{rd}$ Edition, (1999) pp. 749-779.

Ishizuka, T. et al., "Ramatroban (BAY u3405): A Novel Dual Antagonist of $TXA_2$ Receptor and CRTH2, A Newly Identified Prostagladin $D_2$ Receptor" Cardiovascular Drug Rev. 2004, 22(2), pp. 71-90.

Jain, Abhisek et al., "QSAR study of 2,4-disubstituted phenoxyacetic acid derivatives as a $CRTh_2$ receptor antagonists," Chemical Papers, (2009), 63(4), pp. 464-470.

Liu Jiwan et al., "Benzodiazepinione Derivatives as CRTH2 Antagonists," ACS Medicinal Chemistry Letters (2011), 2, pp. 515-518.

Luker, Tim et al., "Switching Between Agonists and Antagonists at CRTh2 in a Series of Highly Potent and Selective Biaryl Phenoxyacetic Acids," Bioorganic & Medicinal Chemistry Letters. (2011), 21, pp. 3616-3621.

Moghaddam F. M., "KF/Al2O3 Mediated Aza-Michael Addition of Indoles to Electron-Deficient Olefins", Letters in Organic Chemistry (2006) 3, pp. 157-160.

Remington: The Science and Practice of Pharmacy, $21^{st}$ Edition, Lippincott, Williams and Wilkins Publishing, The University of the Sciences in Philadelphia, 2005.

Reiss, Regine et al., "Evaluation of Protecting Groups for 3-Hydroxyisoxazoles—Short Access to 3-Alkoxyisoxazole-5-carbaldhydes and 3-Hydroxyisoxazoles-5- carbaldhyde, the Putative Toxic Metabolite of Muscimol," Eur. J. Org. Chem (1998), pp. 473-479.

Sandham, David A. et al., "2-Cycloalkyl Phenoxyacetic Acid CRTH2 Receptor Antagonists" Bioorg. & Med. Chem Let. (2007), 17, pp. 4347-4350.

Sandham, David A. et al., "7-Azaindole-3-acetic Acid Derivatives: Potent and Selective CRTH2 Receptor Antagonist" Bioorg. & Med. Chem Let. (2009), 19, pp. 4794-4798.

Sawyer, N. et al., "Molecular Pharmacology of the Human Prostaglandin $D_2$ Receptor, CRTH2" Br. J. Pharmacology, (2002) 137, pp. 1163-1172.

Scott, Jill M. et al., "Discovery and Optimization of a Biphenylacetic Acid Series of Prostaglandin $D_2$ Receptor DP2 Antagonists with Efficacy in a Murine Model of Allergic Rhinitis," Bioorg. & Med. Chem Let. (2011), 11, pp. 6608-6612.

Shimizu, T. et al., "Specific Binding of Prostaglandin $D_2$ to Rat Brain Synaptic Membrane", J. Biol. Chem., (1982), 257, pp. 13570-13575.

Stebbins, Karin J. et al., "Therapeutic Efficacy of AM156, a Novel Prostanoid $DP_2$ Receptor Antagonist, in Murine Models of Allergic Rhinitis and House Dust Mite-Induced Pulmonary Inflammation", Eur. Journal of Pharmacology, (2010), 638, pp. 142-149.

Stebbins, Karin J. et al., "DP2 (CRth2) Antagonism Reduces Ocular Inflammation Induced by Allergen Challenge and respiratory Syncytial Virus", International Achives of Allergy and Immunology, (2012), 157(3), pp. 259-268.

Stock, Nicholas et al., "Sodium [2'-[(Cyclopropanecarbonyl-ethyl-amino)-methyl]-4'-(6-ethoxy-pyridin-3-yl)-6-methoxy-biphenyl-3-yl]-acetate (AM432): A potent, selective prostaglandin $D_2$ Receptor Antagonist", Bioorg. & Med. Chem Let. (2011), 21, pp. 1036-1040.

Sugimoto, H. et al., "An Orally Bioavailable Small Molecule Antagonist of CRTH2, Ramatroban (BAY u3405), Inhibits Prostagladin $D_2$-Induced Eosinophie Migration in Vitro" J Pharmacol Exp Ther Apr. 1, 2003, pp. 305347-305352.

Ulven T. et al., "Minor Structural Modifications Convert the Dual TP/CRTH2 Antagonist Ramatroban into a Highly Selective and Potent CRTH2 Antagonist", J. Med. Chem., (2005), 48 (4), pp. 897-900.

Ulven, T. et al., "Novel Selective Orally Active CRTH2 Antagonists for Allergic Inflammation Developed from in silico Derived Hits" J. Med. Chem (2006), 49, pp. 6638-6641.

International Search Report of PCT/IB2011/052944, mailed Dec. 12, 2011.

* cited by examiner

1-PHENYL-SUBSTITUTED HETEROCYCLYL DERIVATIVES AND THEIR USE AS PROSTAGLANDIN D₂ RECEPTOR MODULATORS

CROSS-REFERENCE TO RELATED APPLICATIONS

This application is the national phase application of PCT/IB2011/052944, filed Jul. 4, 2011, which claims the benefit of PCT/IB2010/053071, filed Jul. 5, 2010, the contents of each are hereby incorporated by reference in their entirety.

FIELD OF THE INVENTION

The present invention relates to 1-phenyl-substituted heterocyclyl derivatives of formula (I) and their use as prostaglandin receptor modulators, most particularly as prostaglandin $D_2$ receptor ("DP receptor") modulators, in the treatment of various prostaglandin-mediated diseases and disorders, to pharmaceutical compositions containing these compounds and to processes for their preparation. In particular, such derivatives may be used alone or in pharmaceutical compositions for the treatment of both, chronic and acute allergic/immune diseases/disorders such as asthma, allergic asthma, eosinophilic asthma, severe asthma, rhinitis, allergic rhinitis, angioedema, insect venom allergy, drug allergies, allergic sinusitis, allergic nephritis, allergic conjunctivitis, atopic dermatitis, bronchial asthma, food allergy, systemic mast cell disorders, anaphylactic shock, urticaria, eczema, ulcerative colitis, chronic obstructive pulmonary disease (COPD), inflammatory bowel disease and rheumatoid arthritis; eosinophil-related diseases comprising small vessel vasculitides like Churg-Strauss syndrome, Wegener's granulomatosis, microscopic polyangiitis (and organ-specific subsets of the latter), hypereosinophilic syndromes like eosinophilic pneumonia, eosinophilic esophagitis, reflux esophagitis, eosinohilic endocarditis (Loeffler's endocarditis), eosinophilia-myalgia syndrome, eosinophilic fasciitis, eosinohilic pustular folliculitis (Ofuji's disease), eosinophilic ulcers, angiolymphoid hyperplasia with eosinophilia (ALHE), eosinophilic cellulitis (Wells syndrome), chronic eosinophilic leukemia and DRESS syndrome (Drug Rash with Eosinophilia and Systemic Symptoms); and basophil-related diseases, comprising basophilic leukemia and basophilic leukocytosis.

BACKGROUND OF THE INVENTION

As a response to allergen exposure in allergic conditions, mast cells are activated and release mediators like histamine, thromboxane A2 (TxA2), cysteinyl leukotrienes (CysLTs) and prostaglandin $D_2$ ($PGD_2$). These mediators interact with their respective receptors and cause physiological effects such as increased vascular permeability, edema, pruritus, nasal and pulmonary congestion, bronchoconstriction, and mucus secretion. An increased vascular permeability for example, allows excessive infiltration of eosinophilic and basophilic leukocytes into the tissue and thus amplifies the allergic response.

Current treatments of allergic diseases comprise agents that can block or otherwise interrupt such interactions, e.g. anti-histamines (histamine H1 receptor antagonists), leukotriene receptor antagonists, beta-adrenergic receptor agonists, and corticosteroids. Generally, treatments with anti-histamines and leukotriene antagonists are limited in efficacy, and long-term usage of corticosteroids is often associated with unwanted side effects.

$PGD_2$ is an agonist known to act on two G-protein-coupled receptors, the $PGD_2$ receptor DP1 and the recently identified CRTH2 (chemoattractant receptor-homologous molecule expressed on Th2 cells) receptor (also referred to as "DP2 receptor").

Elevated $PGD_2$ levels are considered to cause inflammation as observed in allergic diseases such as allergic rhinitis, allergic asthma, allergic conjunctivitis, atopic dermatitis and the like. Therefore, blocking the interaction of $PGD_2$ with its receptors is considered a useful therapeutic strategy for the treatment of such diseases.

GB 2388540 discloses the use of ramatroban ((3R)-3-(4-fluorobenzene-sulfonamido)-1,2,3,4-tetrahydrocarbazole-9-propionic acid), a TxA2 receptor (also referred to as "TP receptor") antagonist with additional antagonistic activity on CRTH2, for the prophylaxis and treatment of allergic diseases, such as asthma, allergic rhinitis or allergic conjunctivitis. In T. Ishizuka et al., *Cardiovascular Drug Rev.* 2004, 22(2), 71-90 effects of ramatroban on late-phase inflammation are described. Furthermore, oral bioavailability of ramatroban and its ability to inhibit prostaglandin $D_2$-induced eosinophil migration in vitro has been reported (*Journal of Pharmacology and Experimental Therapeutics,* 305(1), p. 347-352 (2003)).

WO 03/097598 and WO 03/097042 disclose Ramatroban analogues with CRTH2 antagonistic activity. Ulven et al, *J. Med. Chem.* 2005, 48(4), 897-900 disclose further ramatroban analogues.

CRTH2 antagonists containing a phenoxy-acetic acid moiety have been for instance described in WO 05/105727, WO 06/056752, WO 07/037,187 and WO 07/052,023.

DESCRIPTION OF THE INVENTION

1) The present invention relates to 1-phenyl-substituted heterocyclyl derivatives of the formula (I),

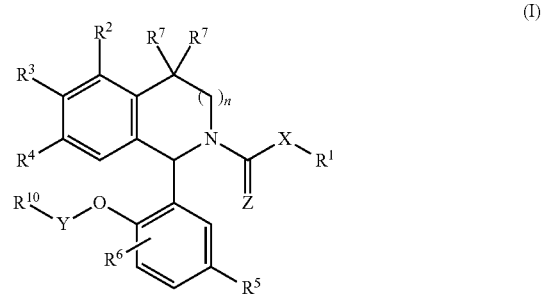

wherein
X represents —NH—, —O— or a bond;
Y represents $(C_1-C_4)$alkandiyl;
Z represents O or S;
n represents 0 or 1;
$R^1$ represents
  $(C_4-C_6)$alkyl;
  $(C_1-C_4)$alkyl which is mono-substituted with $(C_3-C_6)$cycloalkyl, $(C_1-C_4)$alkoxy, optionally substituted aryl, optionally substituted heteroaryl, optionally substituted heterocyclyl, optionally substituted aryloxy, optionally substituted heteroaryloxy, optionally substituted aryl-$(C_1-C_2)$alkoxy, optionally substituted heteroaryl-$(C_1-C_2)$alkoxy, optionally substituted heteroarylsulfanyl or —$NR^8R^9$;

($C_2$-$C_4$)alkenyl which is mono-substituted with optionally substituted aryl;

($C_2$-$C_4$)alkynyl which is mono-substituted with optionally substituted aryl;

($C_3$-$C_6$)cycloalkyl which is mono- or di-substituted with ($C_1$-$C_4$)alkyl, mono-substituted with ($C_1$-$C_4$)alkoxy, mono-substituted with optionally substituted aryl or mono-substituted with optionally substituted heteroaryl;

optionally substituted aryl; or a 10-membered partially unsaturated ring system;

$R^2$ represents hydrogen, ($C_1$-$C_4$)alkyl, ($C_1$-$C_4$)alkoxy, ($C_1$-$C_4$)fluoroalkyl, halogen, ($C_1$-$C_4$)alkylsulfonyl, phenylsulfonyl or ($C_1$-$C_4$)alkylsulfonylamino;

$R^3$ represents hydrogen, ($C_1$-$C_4$)alkoxy or halogen;

$R^4$ represents hydrogen, ($C_1$-$C_4$)alkoxy, halogen, ($C_1$-$C_4$)alkylsulfonyl, optionally substituted aryl or optionally substituted heteroaryl;

$R^5$ represents hydrogen, ($C_1$-$C_4$)alkyl, ($C_1$-$C_4$)alkoxy, ($C_1$-$C_4$)fluoroalkyl, halogen, cyano, —$CONH_2$, optionally substituted aryl, optionally substituted heteroaryl, ($C_1$-$C_4$) alkylsulfonyl, phenylsulfonyl or dimethylamino-sulfonyl; and $R^6$ represents hydrogen or halogen; or $R^5$ and $R^6$ together form a methylendioxy-group;

$R^7$ represents hydrogen or methyl;

$R^8$ represents hydrogen or methyl;

$R^9$ represents optionally substituted aryl, optionally substituted arylsulfonyl or optionally substituted heteroarylsulfonyl; and $R^{10}$ represents —C(O)OH, —C(O)NH—CN, —C(O)NH—OH, —C(O)NH—S(O)$_2$CF$_3$ or optionally substituted heteroaryl;

with the proviso that $R^1$ is different from optionally substituted aryl if X represents —NH— or a bond;

and to the salts (in particular pharmaceutically acceptable salts) of such compounds.

The compounds of formula (I) according to embodiment 1) may contain one or more stereogenic or asymmetric centers, such as one or more asymmetric carbon atoms. Substituents at a double bond may be present in the (Z)- or (E)-configuration unless indicated otherwise. The compounds of formula (I) may thus be present as mixtures of stereoisomers or preferably as pure stereoisomers. Mixtures of stereoisomers may be separated in a manner known to a person skilled in the art.

The following paragraphs provide definitions of the various chemical moieties for the compounds according to the invention and are intended to apply uniformly throughout the specification and claims unless an otherwise expressly set out definition provides a broader or narrower definition.

In this patent application, variably attached bonds may be used for substituents or groups. In such case it is meant that the substituent or group is attached to any carbon atom of the ring system to which the variable attached bond is drawn into, provided that said carbon atom is not already specifically substituted. For example, formula (I) encompasses the following three formulas:

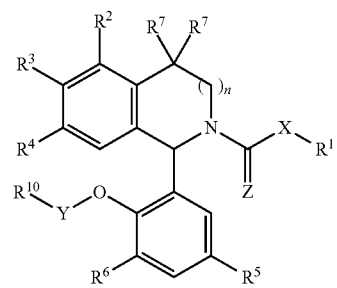

(I-1)

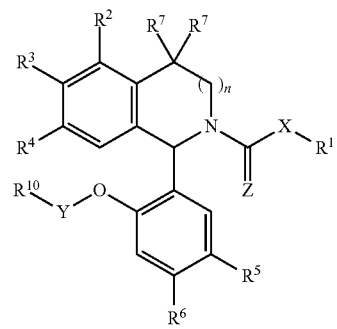

(I-2)

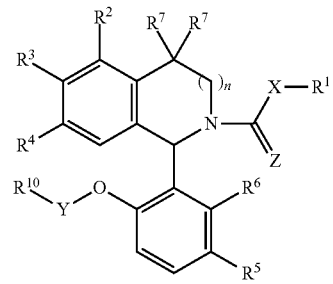

(I-3)

For avoidance of any doubt, compounds of formula I wherein n represents 0 are represented by formula $I_{ISO}$; and compounds of formula I wherein n represents 1 are represented by formula $I_{TET}$:

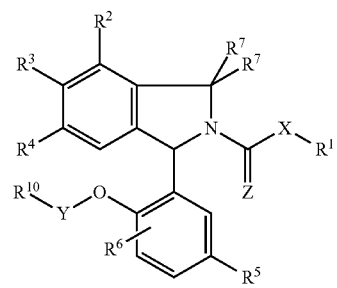

$I_{ISO}$

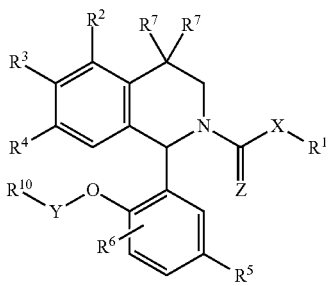

The term "alkyl", used alone or in combination, refers to a straight or branched chain alkyl group containing one to six carbon atoms. The term "$(C_x\text{-}C_y)$alkyl" (x and y each being an integer), refers to an alkyl group as defined before containing x to y carbon atoms. For example a $(C_1\text{-}C_4)$alkyl group contains from one to four carbon atoms. Representative examples of $(C_1\text{-}C_4)$alkyl groups include methyl, ethyl, n-propyl, iso-propyl, n-butyl, iso-butyl, sec-butyl and tert-butyl.

Representative examples of $(C_4\text{-}C_6)$alkyl groups include n-butyl, iso-butyl, sec-butyl, tert-butyl, pent-1-yl, pent-2-yl, pent-3-yl, 2-methyl-but-1-yl, 3-methyl-but-1-yl, 2-methyl-but-2-yl, 3-methyl-but-2-yl, 2,2-dimethyl-prop-1-yl and the isomeric hexyls. The alkyl group may be unsubstituted or substituted as explicitly defined.

In case "$R^1$" represents "$(C_4\text{-}C_6)$alkyl" the term means $(C_4\text{-}C_6)$alkyl groups as defined above. Examples of said groups are n-butyl, iso-butyl, sec-butyl, tert-butyl, pent-1-yl, pent-2-yl, pent-3-yl, 2-methyl-but-1-yl, 3-methyl-but-1-yl, 2-methyl-but-2-yl, 3-methyl-but-2-yl, 2,2-dimethyl-prop-1-yl and the isomeric hexyls. Preferred are n-butyl, iso-butyl, tert-butyl, pent-1-yl, 2-methyl-but-1-yl, 3-methyl-but-1-yl and 2,2-dimethyl-prop-1-yl, more preferred are n-butyl, iso-butyl, tert-butyl and 2,2-dimethyl-prop-1-yl and most preferred are n-butyl, iso-butyl and 2,2-dimethyl-prop-1-yl.

In case "$R^1$" represents monosubstituted $(C_1\text{-}C_4)$alkyl the term "$(C_1\text{-}C_4)$alkyl" means $(C_1\text{-}C_4)$alkyl groups as defined above. Examples of said groups are methyl, ethyl, n-propyl, iso-propyl, n-butyl, iso-butyl, sec-butyl and tert-butyl. Preferred are methyl, ethyl and n-propyl; most preferred are methyl and ethyl. The $(C_1\text{-}C_4)$alkyl groups are mono-substituted with $(C_3\text{-}C_6)$cycloalkyl, $(C_1\text{-}C_4)$alkoxy, optionally substituted aryl, optionally substituted heteroaryl, optionally substituted heterocyclyl, optionally substituted aryloxy, optionally substituted heteroaryloxy, optionally substituted aryl-$(C_1\text{-}C_2)$alkoxy, optionally substituted heteroaryl-$(C_1\text{-}C_2)$alkoxy, optionally substituted heteroarylsulfanyl or —$NR^8R^9$ (and especially with optionally substituted aryl, optionally substituted heteroaryl, optionally substituted aryloxy, optionally substituted heteroaryloxy or optionally substituted aryl-$(C_1\text{-}C_2)$alkoxy).

In case "$R^1$" represents "$(C_3\text{-}C_6)$cycloalkyl which is mono- or di-substituted with $(C_1\text{-}C_4)$alkyl" the term "$(C_1\text{-}C_4)$alkyl" means $(C_1\text{-}C_4)$alkyl groups as defined above. Examples of said groups are methyl, ethyl, n-propyl, iso-propyl, n-butyl, iso-butyl, sec-butyl and tert-butyl. Preferred are methyl, ethyl and isopropyl and most preferred is methyl.

In case "$R^2$" represents "$(C_1\text{-}C_4)$alkyl" the term means $(C_1\text{-}C_4)$alkyl groups as defined above. Examples of said groups are methyl, ethyl, n-propyl, iso-propyl, n-butyl, iso-butyl, sec-butyl and tert-butyl. Preferred is methyl.

In case "$R^5$" represents "$(C_1\text{-}C_4)$alkyl" the term means $(C_1\text{-}C_4)$alkyl groups as defined above. Examples of said groups are methyl, ethyl, n-propyl, iso-propyl, n-butyl, iso-butyl, sec-butyl and tert-butyl. Preferred are methyl and iso-propyl; most preferred is methyl.

In case "$(C_1\text{-}C_4)$alkyl" is a substituent to an aryl, a heteroaryl, a heterocyclyl, an aryloxy, a heteroaryloxy, an aryl-$(C_1\text{-}C_2)$alkoxy, a heteroaryl-$(C_1\text{-}C_2)$alkoxy, a heteroarylsulfanyl, an arylsulfonyl or a heteroarylsulfonyl group, the term "$(C_1\text{-}C_4)$alkyl" means $(C_1\text{-}C_4)$alkyl groups as defined above. Examples of said groups are methyl, ethyl, n-propyl, iso-propyl, n-butyl, iso-butyl, sec-butyl and tert-butyl. Preferred are methyl and ethyl; most preferred is methyl.

The term "$(C_1\text{-}C_4)$alkandiyl" as used in Y refers to a carbon chain containing from one to four carbon atoms, which is attached to the oxygen-atom and to $R^{10}$ as depicted in formula (I). The respective two residues may be attached to the same or to different carbon atoms of the alkandiyl group. Preferred examples of $(C_1\text{-}C_4)$alkandiyl groups are methandiyl, ethan-1,1-diyl, ethan-1,2-diyl, propan-1,3-diyl and butan-1,4-diyl. More preferred are methandiyl and ethan-1,1-diyl. Most preferred is methandiyl.

The term "alkenyl", used alone or in combination, refers to a straight or branched chain alkenyl group containing two to four carbon atoms. The term "$(C_x\text{-}C_y)$alkenyl" (x and y each being an integer), refers to an alkenyl group as defined before containing x to y carbon atoms. For example a $(C_2\text{-}C_4)$alkenyl group contains from two to four carbon atoms. Representative examples of $(C_2\text{-}C_4)$alkenyl groups include ethenyl, propenyl, 2-methyl-propenyl and butenyl. Preferred is ethenyl. The $(C_2\text{-}C_4)$alkenyl group is mono-substituted with optionally substituted aryl.

The term "alkynyl", used alone or in combination, refers to a straight or branched chain alkynyl group containing two to four carbon atoms. The term "$(C_x\text{-}C_y)$alkynyl" (x and y each being an integer), refers to an alkynyl group as defined before containing x to y carbon atoms. For example a $(C_2\text{-}C_4)$alkynyl group contains from two to four carbon atoms. Representative examples of $(C_2\text{-}C_4)$alkynyl groups include ethynyl, propynyl and butynyl. Preferred is ethynyl. The $(C_2\text{-}C_4)$alkynyl group is mono-substituted with optionally substituted aryl.

The term "alkoxy", used alone or in combination, refers to an alkyl-O— group wherein the alkyl group is as defined before. The term "$(C_x\text{-}C_y)$alkoxy" (x and y each being an integer) refers to an alkoxy group as defined before containing x to y carbon atoms. For example a $(C_1\text{-}C_4)$alkoxy group contains from one to four carbon atoms. Representative examples of alkoxy groups include methoxy, ethoxy, n-propoxy, iso-propoxy, n-butoxy, iso-butoxy, sec-butoxy and tert-butoxy.

In case "$R^1$" represents "$(C_1\text{-}C_4)$alkyl which is mono-substituted with $(C_1\text{-}C_4)$alkoxy" the term "$(C_1\text{-}C_4)$alkoxy" means $(C_1\text{-}C_4)$alkoxy groups as defined above. Examples of said groups are methoxy, ethoxy, n-propoxy, iso-propoxy, n-butoxy, iso-butoxy, sec-butoxy and tert-butoxy. Preferred are methoxy and iso-butoxy. Most preferred is methoxy.

In case "$R^1$" represents "$(C_3\text{-}C_6)$cycloalkyl which is mono-substituted with $(C_1\text{-}C_4)$alkoxy" the term "$(C_1\text{-}C_4)$alkoxy" means $(C_1\text{-}C_4)$alkoxy groups as defined above. Examples of said groups are methoxy, ethoxy, n-propoxy, iso-propoxy, n-butoxy, iso-butoxy, sec-butoxy and tert-butoxy. Preferred are methoxy and ethoxy. Most preferred is ethoxy.

In case "$R^2$" represents "$(C_1\text{-}C_4)$alkoxy" the term means $(C_1\text{-}C_4)$alkoxy groups as defined above.

Examples of said groups are methoxy, ethoxy, n-propoxy, iso-propoxy, n-butoxy, iso-butoxy, sec-butoxy and tert-butoxy. Preferred is methoxy.

In case "$R^3$" represents "$(C_1\text{-}C_4)$alkoxy" the term means $(C_1\text{-}C_4)$alkoxy groups as defined above. Examples of said groups are methoxy, ethoxy, n-propoxy, iso-propoxy, n-butoxy, iso-butoxy, sec-butoxy and tert-butoxy. Preferred is methoxy.

In case "$R^4$" represents "$(C_1-C_4)$alkoxy" the term means $(C_1-C_4)$alkoxy groups as defined above. Examples of said groups are methoxy, ethoxy, n-propoxy, iso-propoxy, n-butoxy, iso-butoxy, sec-butoxy and tert-butoxy. Preferred is methoxy.

In case "$R^5$" represents "$(C_1-C_4)$alkoxy" the term means $(C_1-C_4)$alkoxy groups as defined above. Examples of said groups are methoxy, ethoxy, n-propoxy, iso-propoxy, n-butoxy, iso-butoxy, sec-butoxy and tert-butoxy. Preferred is methoxy.

In case "$(C_1-C_4)$alkoxy" is a substituent to an aryl, a heteroaryl, a heterocyclyl, an aryloxy, a heteroaryloxy, an aryl-$(C_1-C_2)$alkoxy, a heteroaryl-$(C_1-C_2)$alkoxy, a heteroarylsulfanyl, an arylsulfonyl or a heteroarylsulfonyl group, the term "$(C_1-C_4)$alkoxy" means $(C_1-C_4)$alkoxy groups as defined above. Examples of said groups are methoxy, ethoxy, n-propoxy, iso-propoxy, n-butoxy, iso-butoxy, sec-butoxy and tert-butoxy. Preferred is methoxy.

The term "aryl-$(C_1-C_2)$alkoxy" refers to an $(C_1-C_2)$alkoxy group as defined above in which one hydrogen atom has been replaced with an aryl group as defined below. Examples of aryl-$(C_1-C_2)$alkoxy groups are aryl-methoxy, 1-aryl-ethoxy and 2-aryl-ethoxy. Preferred is aryl-methoxy.

The term "heteroaryl-$(C_1-C_2)$alkoxy" refers to an $(C_1-C_2)$ alkoxy group as defined above in which one hydrogen atom has been replaced with a heteroaryl group as defined below. Examples of heteroaryl-$(C_1-C_2)$alkoxy groups are heteroaryl-methoxy, 1-heteroaryl-ethoxy and 2-heteroaryl-ethoxy. Preferred is heteroaryl-methoxy.

The term "$(C_1-C_4)$alkylsulfonyl", used alone or in combination, refers to an alkyl-$S(O)_2$— group wherein the alkyl group is as defined before, which is attached to the rest of the molecule via the sulfur-atom. The term "$(C_x-C_y)$alkylsulfonyl" (x and y each being an integer) refers to an alkylsulfonyl group as defined before containing x to y carbon atoms. For example a $(C_1-C_4)$alkylsulfonyl group contains from one to four carbon atoms. Representative examples of alkylsulfonyl groups include methylsulfonyl, ethylsulfonyl, n-propylsulfonyl, iso-propylsulfonyl, n-butylsulfonyl, iso-butylsulfonyl, sec-butylsulfonyl and tert-butylsulfonyl.

In case "$R^2$" represents "$(C_1-C_4)$alkylsulfonyl" the term means $(C_1-C_4)$alkylsulfonyl groups as defined above. Examples of said groups are methylsulfonyl, ethylsulfonyl, n-propylsulfonyl, iso-propylsulfonyl, n-butylsulfonyl, iso-butylsulfonyl, sec-butylsulfonyl and tert-butylsulfonyl. Preferred are methylsulfonyl and ethylsulfonyl; most preferred is methylsulfonyl.

In case "$R^4$" represents "$(C_1-C_4)$alkylsulfonyl" the term means $(C_1-C_4)$alkylsulfonyl groups as defined above. Examples of said groups are methylsulfonyl, ethylsulfonyl, n-propylsulfonyl, iso-propylsulfonyl, n-butylsulfonyl, iso-butylsulfonyl, sec-butylsulfonyl and tert-butylsulfonyl. Preferred are methylsulfonyl and ethylsulfonyl; most preferred is ethylsulfonyl.

In case "$R^5$" represents "$(C_1-C_4)$alkylsulfonyl" the term means $(C_1-C_4)$alkylsulfonyl groups as defined above. Examples of said groups are methylsulfonyl, ethylsulfonyl, n-propylsulfonyl, iso-propylsulfonyl, n-butylsulfonyl, iso-butylsulfonyl, sec-butylsulfonyl and tert-butylsulfonyl. Preferred are methylsulfonyl and ethylsulfonyl; most preferred is ethylsulfonyl.

In case "$(C_1-C_4)$alkylsulfonyl" is a substituent to an aryl, a heteroaryl, a heterocyclyl, an aryloxy, a heteroaryloxy, an aryl-$(C_1-C_2)$alkoxy, a heteroaryl-$(C_1-C_2)$alkoxy, a heteroarylsulfanyl, an arylsulfonyl or a heteroarylsulfonyl group, the term "$(C_1-C_4)$alkylsulfonyl" means $(C_1-C_4)$alkylsulfonyl groups as defined above. Examples of said groups are methylsulfonyl, ethylsulfonyl, n-propylsulfonyl, iso-propylsulfonyl, n-butylsulfonyl, iso-butylsulfonyl, sec-butylsulfonyl and tert-butylsulfonyl. Preferred is methylsulfonyl.

The term "$(C_1-C_4)$alkylsulfonylamino", used alone or in combination, refers to an alkyl-$S(O)_2N$-group wherein the alkyl group is as defined before, which is attached to the rest of the molecule via the nitrogen-atom. The term "$(C_x-C_y)$alkylsulfonylamino" (x and y each being an integer) refers to an alkylsulfonylamino group as defined before containing x to y carbon atoms. For example a $(C_1-C_4)$alkylsulfonylamino group contains from one to four carbon atoms. Representative examples of alkylsulfonylamino groups include methylsulfonylamino, ethylsulfonylamino, n-propylsulfonylamino, iso-propylsulfonylamino, n-butylsulfonylamino, iso-butylsulfonylamino, sec-butylsulfonylamino and tert-butylsulfonylamino. Preferred is methylsulfonylamino.

The term "cycloalkyl", used alone or in combination, refers to a cycloalkyl group containing three to six carbon atoms. The term "$(C_x-C_y)$cycloalkyl" (x and y each being an integer), refers to a cycloalkyl group as defined before containing x to y carbon atoms. For example a $(C_3-C_6)$cycloalkyl group contains from three to six carbon atoms. A cycloalkyl group containing five or six carbon atoms may optionally be annelated to a benzene ring. Examples of $(C_3-C_6)$cycloalkyl groups are cyclopropyl, cyclobutyl, cyclopentyl, indanyl, cyclohexyl and 1,2,3,4-tetrahydronaphthyl. The cycloalkyl group may be unsubstituted or substituted as explicitly defined.

In case "$R^1$" represents "$(C_1-C_4)$alkyl which is mono-substituted with $(C_3-C_6)$cycloalkyl" the term "$(C_3-C_6)$cycloalkyl" means $(C_3-C_6)$cycloalkyl groups as defined above. Examples of said groups are cyclopropyl, cyclobutyl, cyclopentyl, indanyl, cyclohexyl and 1,2,3,4-tetrahydronaphthyl. Preferred are cyclopropyl, indanyl and 1,2,3,4-tetrahydronaphthyl; most preferred is indanyl (especially indan-2-yl). In another embodiment cyclopentyl and cyclohexyl are preferred.

In case "$R^1$" represents "$(C_3-C_6)$cycloalkyl" the term means $(C_3-C_6)$cycloalkyl groups as defined above. Examples of said groups are cyclopropyl, cyclobutyl, cyclopentyl, indanyl, cyclohexyl and 1,2,3,4-tetrahydronaphthyl. Preferred are cyclopropyl, cyclobutyl, cyclopentyl and cyclohexyl; most preferred is cyclopropyl. The $(C_3-C_6)$cycloalkyl groups are mono- or di-substituted with $(C_1-C_4)$alkyl, mono-substituted with $(C_1-C_4)$alkoxy, mono-substituted with optionally substituted aryl or mono-substituted with optionally substituted heteroaryl (and preferably mono-substituted with optionally substituted aryl).

The term "$(C_x-C_y)$fluoroalkyl" (x and y each being an integer) refers to an alkyl group as defined before containing x to y carbon atoms in which one or more (and possibly all) hydrogen atoms have been replaced with fluoro. For example a $(C_1-C_4)$fluoroalkyl group contains from one to four carbon atoms in which one to nine hydrogen atoms have been replaced with fluoro.

In case "$R^2$" represents "$(C_1-C_4)$fluoroalkyl" the term means a $(C_1-C_4)$fluoroalkyl group as defined above. Examples of said groups are difluoromethyl, trifluoromethyl, 2,2-difluoroethyl and 2,2,2-trifluoroethyl. Preferred is trifluoromethyl.

In case "$R^5$" represents "$(C_1-C_4)$fluoroalkyl" the term means a $(C_1-C_4)$fluoroalkyl group as defined above.

Examples of said groups are difluoromethyl, trifluoromethyl, 2,2-difluoroethyl and 2,2,2-trifluoroethyl. Preferred is trifluoromethyl.

In case "$(C_1-C_4)$fluoroalkyl" is a substituent to an aryl, a heteroaryl, a heterocyclyl, an aryloxy, a heteroaryloxy, an aryl-$(C_1-C_2)$alkoxy, a heteroaryl-$(C_1-C_2)$alkoxy, a heteroarylsulfanyl, an arylsulfonyl or a heteroarylsulfonyl group, the term "$(C_1-C_4)$fluoroalkyl" means $(C_1-C_4)$fluoroalkyl groups as defined above. Examples of said groups are difluoromethyl, trifluoromethyl, 2,2-difluoroethyl and 2,2,2-trifluoroethyl. Preferred is trifluoromethyl.

The term halogen means fluoro, chloro, bromo or iodo.

In case "$R^2$" represents "halogen" the term means preferably fluoro, chloro and bromo and most preferably fluoro.

In case "$R^3$" represents "halogen" the term means preferably fluoro and chloro and most preferably fluoro.

In case "$R^4$" represents "halogen" the term means preferably fluoro, chloro and bromo and most preferably fluoro.

In case "$R^5$" represents "halogen" the term means preferably fluoro, chloro and bromo and most preferably fluoro and chloro.

In case "$R^6$" represents "halogen" the term means preferably fluoro, chloro and bromo and most preferably fluoro.

In case "halogen" is a substituent to an aryl, a heteroaryl, a heterocyclyl, an aryloxy, a heteroaryloxy, an aryl-$(C_1-C_2)$alkoxy, a heteroaryl-$(C_1-C_2)$alkoxy, a heteroarylsulfanyl, an arylsulfonyl or a heteroarylsulfonyl group, the term means fluoro, chloro, bromo or iodo. Preferred examples are fluoro and chloro; most preferred is chloro.

The term "aryl", used alone or in any combination, means a phenyl or a naphthyl group. Preferred is a phenyl group. An "optionally substituted aryl" group means an aryl group as defined before which is unsubstituted or substituted as explicitly defined.

In case $R^1$ represents "optionally substituted aryl" the term means the above-mentioned groups (preferably phenyl), which groups are independently unsubstituted, mono-, di- or tri-substituted (preferably unsubstituted or mono-substituted and most preferably mono-substituted), wherein the substituents are independently selected from the group consisting of halogen, $(C_1-C_4)$alkyl, $(C_1-C_4)$alkoxy and $(C_1-C_4)$fluoroalkyl. Preferably the substituents are independently selected from the group consisting of halogen and $(C_1-C_4)$alkoxy. Examples of such optionally substituted aryl groups are phenyl, 2-chloro-phenyl, 3-chloro-phenyl, 2-methoxy-phenyl and 4-methoxy-phenyl.

In case $R^1$ represents "$(C_1-C_4)$alkyl which is mono-substituted with optionally substituted aryl" the term "optionally substituted aryl" means the above-mentioned groups (preferably phenyl), which groups are independently unsubstituted, mono-, di- or tri-substituted (preferably unsubstituted, mono- or di-substituted and most preferably unsubstituted or mono-substituted), wherein the substituents are independently selected from the group consisting of halogen, $(C_1-C_4)$alkyl, $(C_1-C_4)$alkoxy, $(C_1-C_4)$fluoroalkyl, $(C_1-C_4)$alkylsulfonyl, cyano, phenyl and 5-methyl-tetrazol-1-yl. Preferably the substituents are independently selected from the group consisting of halogen, $(C_1-C_4)$alkyl, $(C_1-C_4)$alkoxy, $(C_1-C_4)$fluoroalkyl, $(C_1-C_4)$alkylsulfonyl, phenyl and 5-methyl-tetrazol-1-yl. More preferably the substituents are independently selected from the group consisting of halogen, $(C_1-C_4)$alkyl, $(C_1-C_4)$alkoxy and $(C_1-C_4)$fluoroalkyl. In addition the term "optionally substituted aryl" may represent 2,3-dihydro-benzo[1,4]dioxinyl. Examples of such optionally substituted aryl groups are phenyl, 2-fluoro-phenyl, 3-fluoro-phenyl, 4-fluoro-phenyl, 2-chloro-phenyl, 3-chloro-phenyl, 4-chloro-phenyl, 2,3-dichloro-phenyl, 2,6-dichloro-phenyl, 2-methyl-phenyl, 3-methyl-phenyl, 4-methyl-phenyl, 2-methoxy-phenyl, 3-methoxy-phenyl, 4-methoxy-phenyl, 2-trifluoromethyl-phenyl, 3-trifluoromethyl-phenyl, 4-methylsulfonyl-phenyl, biphenyl-4-yl, 4-(5-methyl-tetrazol-1-yl)-phenyl and 2,3-dihydro-benzo[1,4]dioxin-6-yl (and especially phenyl, 2-fluoro-phenyl, 3-fluoro-phenyl, 4-fluoro-phenyl, 2-chloro-phenyl, 3-chloro-phenyl, 4-chloro-phenyl, 2,3-dichloro-phenyl, 2-methyl-phenyl, 3-methyl-phenyl, 4-methyl-phenyl, 2-methoxy-phenyl, 3-methoxy-phenyl, 2-trifluoromethyl-phenyl and 3-trifluoromethyl-phenyl). Further examples of such optionally substituted aryl groups are naphthyl, 2,3-difluoro-phenyl, 2,4-difluoro-phenyl, 2,5-difluoro-phenyl, 2,6-difluoro-phenyl, 2,4-dichloro-phenyl, 2,5-dichloro-phenyl, 2-bromo-phenyl, 2-chloro-6-fluoro-phenyl, 2-chloro-5-fluoro-phenyl, 5-chloro-2-fluoro-phenyl, 2,3-dimethyl-phenyl, 2,4-dimethyl-phenyl, 2,6-dimethyl-phenyl, 2,4,6-trimethyl-phenyl, 2,3-dimethoxy-phenyl, 2,4-dimethoxy-phenyl, 2,6-dimethoxy-phenyl, 4-trifluoromethyl-phenyl, 2-cyano-phenyl (and especially 2,3-difluoro-phenyl, 2,4-difluoro-phenyl, 2,4-dichloro-phenyl, 2-chloro-6-fluoro-phenyl, 2,3-dimethyl-phenyl and 2,4-dimethyl-phenyl). In a preferred embodiment, in case X represents —NH—, the term "optionally substituted aryl" preferably means a phenyl group which is unsubstituted or mono-substituted, wherein the substituent is selected from halogen or $(C_1-C_4)$alkoxy (especially from fluoro, chloro or methoxy). In another preferred embodiment, in case X represents —O—, the term "optionally substituted aryl" preferably means a phenyl group which is unsubstituted, mono-, di- or tri-substituted (preferably unsubstituted, mono- or di-substituted), wherein the substituents are independently selected from the group consisting of halogen, $(C_1-C_4)$alkyl, $(C_1-C_4)$alkoxy, $(C_1-C_4)$fluoroalkyl and cyano (and preferably from fluoro, chloro, methyl, methoxy and trifluoromethyl). In still another preferred embodiment, in case X represents a bond, the term "optionally substituted aryl" means a phenyl or naphthyl group (preferably phenyl), which groups are independently unsubstituted, mono-, di- or tri-substituted (preferably unsubstituted, mono- or di-substituted and most preferably unsubstituted or mono-substituted), wherein the substituents are independently selected from the group consisting of halogen, $(C_1-C_4)$alkyl, $(C_1-C_4)$alkoxy, $(C_1-C_4)$fluoroalkyl, $(C_1-C_4)$alkylsulfonyl, phenyl and 5-methyl-tetrazol-1-yl (and preferably from fluoro, chloro, methyl, methoxy and trifluoromethyl).

In case $R^1$ represents "$(C_2-C_4)$alkenyl which is mono-substituted with optionally substituted aryl" the term "optionally substituted aryl" means the above-mentioned groups (preferably phenyl), which groups are independently unsubstituted, mono-, di- or tri-substituted (preferably unsubstituted or mono-substituted and most preferably mono-substituted), wherein the substituents are independently selected from the group consisting of halogen, $(C_1-C_4)$alkyl, $(C_1-C_4)$alkoxy and $(C_1-C_4)$fluoroalkyl. Preferably the substituents are independently selected from the group consisting of halogen and $(C_1-C_4)$alkyl. Examples of such optionally substituted aryl groups are 2-fluoro-phenyl and 2-methyl-phenyl.

In case $R^1$ represents "$(C_2-C_4)$alkynyl which is mono-substituted with optionally substituted aryl" the term "optionally substituted aryl" means the above-mentioned groups (preferably phenyl), which groups are independently unsubstituted, mono-, di- or tri-substituted (preferably unsubstituted or mono-substituted and most preferably unsubstituted), wherein the substituents are independently selected from the group consisting of halogen, $(C_1-C_4)$alkyl, $(C_1-C_4)$alkoxy and $(C_1-C_4)$fluoroalkyl. An example of such an optionally substituted aryl group is phenyl.

In case $R^1$ represents "$(C_3-C_6)$cycloalkyl which is monosubstituted with optionally substituted aryl" the term "optionally substituted aryl" means the above-mentioned groups (preferably phenyl), which groups are independently unsubstituted, mono-, di- or tri-substituted (preferably unsubstituted, mono- or di-substituted and most preferably unsubstituted or mono-substituted), wherein the substituents are independently selected from the group consisting of halogen, $(C_1-C_4)$alkyl, $(C_1-C_4)$alkoxy and $(C_1-C_4)$fluoroalkyl. Examples of such optionally substituted aryl groups are phenyl, 2-fluoro-phenyl, 2-chloro-phenyl, 3-chloro-phenyl, 4-chloro-phenyl, 2,4-dichloro-phenyl, 2-methyl-phenyl, 2-methoxy-phenyl and 2-trifluoromethyl-phenyl. Further examples of such optionally substituted aryl groups are 3-fluoro-phenyl, 4-fluoro-phenyl, 3-methyl-phenyl, 4-methyl-phenyl, 3-methoxy-phenyl, 4-methoxy-phenyl, 3-trifluoromethyl-phenyl and 4-trifluoromethyl-phenyl.

In case $R^4$ represents "optionally substituted aryl" the term means the above-mentioned groups (preferably phenyl), which groups are independently unsubstituted, mono-, di- or tri-substituted (preferably unsubstituted or mono-substituted and most preferably mono-substituted), wherein the substituents are independently selected from the group consisting of halogen, $(C_1-C_4)$alkyl, $(C_1-C_4)$alkoxy and $(C_1-C_4)$fluoroalkyl. Preferably the substituents are independently selected from the group consisting of halogen. An example of such an optionally substituted aryl group is 4-fluoro-phenyl.

In case $R^5$ represents "optionally substituted aryl" the term means the above-mentioned groups (preferably phenyl), which groups are independently unsubstituted, mono-, di- or tri-substituted (preferably unsubstituted or mono-substituted and most preferably mono-substituted), wherein the substituents are independently selected from the group consisting of halogen, $(C_1-C_4)$alkyl, $(C_1-C_4)$alkoxy and $(C_1-C_4)$fluoroalkyl. Preferably the substituents are independently selected from the group consisting of halogen. An example of such an optionally substituted aryl group is 4-fluoro-phenyl.

In case $R^9$ represents "optionally substituted aryl" the term means the above-mentioned groups (preferably phenyl), which groups are independently unsubstituted, mono-, di- or tri-substituted (preferably unsubstituted or mono-substituted and most preferably unsubstituted), wherein the substituents are independently selected from the group consisting of halogen, $(C_1-C_4)$alkyl, $(C_1-C_4)$alkoxy and $(C_1-C_4)$fluoroalkyl. An example of such an optionally substituted aryl group is phenyl.

The term "aryloxy", used alone or in combination, refers to an aryl-O— group wherein the aryl group is as defined before. An "optionally substituted aryloxy" group means an aryloxy group as defined before which is unsubstituted or substituted as explicitly defined.

In case $R^1$ represents "$(C_1-C_4)$alkyl which is mono-substituted with optionally substituted aryloxy" the term "optionally substituted aryloxy" means the above-mentioned groups (preferably phenoxy), which are independently unsubstituted, mono-, di- or tri-substituted (preferably unsubstituted or mono-substituted and most preferably mono-substituted), wherein the substituents are independently selected from the group consisting of halogen, $(C_1-C_4)$alkyl, $(C_1-C_4)$alkoxy, $(C_1-C_4)$fluoroalkyl and phenyl. Preferably the substituents are independently selected from the group consisting of halogen, $(C_1-C_4)$alkyl, $(C_1-C_4)$alkoxy and $(C_1-C_4)$fluoroalkyl and most preferably from halogen and $(C_1-C_4)$alkyl. Examples of such optionally substituted aryloxy groups are phenoxy, 2-fluoro-phenoxy, 3-fluoro-phenoxy, 4-fluoro-phenoxy, 2-chloro-phenoxy, 3-chloro-phenoxy, 4-chloro-phenoxy, 2-methyl-phenoxy, 3-methyl-phenoxy, 4-methyl-phenoxy and biphenyl-2-yl. Further examples of such optionally substituted aryloxy groups are 2,4-dimethyl-phenoxy, 2-methoxy-phenoxy and 4-methoxy-phenoxy.

The term "optionally substituted aryl-$(C_1-C_2)$alkoxy", used alone or in combination, refers to an aryl-$(C_1-C_2)$alkoxy group as defined above wherein the aryl group is unsubstituted or substituted as explicitly defined.

In case $R^1$ represents "$(C_1-C_4)$alkyl which is mono-substituted with optionally substituted aryl-$(C_1-C_2)$alkoxy" the term "optionally substituted aryl-$(C_1-C_2)$alkoxy" means the above-mentioned groups, wherein the term "aryl" means a phenyl or a naphthyl group (preferably a phenyl group). The aryl groups are independently unsubstituted, mono-, di- or tri-substituted (preferably unsubstituted or mono-substituted), wherein the substituents are independently selected from the group consisting of halogen, $(C_1-C_4)$alkyl, $(C_1-C_4)$alkoxy and $(C_1-C_4)$fluoroalkyl. Preferably the substituents are independently selected from the group consisting of halogen, $(C_1-C_4)$alkyl and $(C_1-C_4)$alkoxy. Examples of such aryl groups are phenyl, 2-chloro-phenyl, 3-chloro-phenyl, 4-chloro-phenyl, 2-methyl-phenyl, 3-methyl-phenyl, 4-methyl-phenyl, 2-methoxy-phenyl, 3-methoxy-phenyl and 4-methoxy-phenyl.

The term "arylsulfonyl", used alone or in combination, refers to an aryl-$S(O)_2$— group wherein the aryl group is as defined before, which is attached to the rest of the molecule via the sulfur-atom. An "optionally substituted arylsulfonyl" group means an arylsulfonyl group as defined before which is unsubstituted or substituted as explicitly defined.

In case $R^9$ represents "optionally substituted arylsulfonyl" the term means the above-mentioned groups (preferably phenylsulfonyl), which groups are independently unsubstituted, mono-, di- or tri-substituted (preferably unsubstituted, mono- or di-substituted), wherein the substituents are independently selected from the group consisting of halogen, $(C_1-C_4)$alkyl, $(C_1-C_4)$alkoxy and $(C_1-C_4)$fluoroalkyl. Preferably the substituents are independently selected from the group consisting of halogen (especially fluoro). Examples of such optionally substituted arylsulfonyl groups are phenylsulfonyl, 2-fluoro-phenylsulfonyl, 3-fluoro-phenylsulfonyl and 3,4-difluoro-phenylsulfonyl.

The term "heteroaryl", used alone or in combination, means a 5- to 10-membered monocyclic or bicyclic aromatic ring containing 1, 2, 3 or 4 heteroatoms (preferably 1, 2 or 3 heteroatoms, more preferably 1 or 2 heteroatoms) independently selected from oxygen, nitrogen and sulfur. Examples of such heteroaryl groups are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl, pyrazinyl, indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzo[2,1,3]oxadiazolyl, benzo[2,1,3]thiadiazolyl, benzo[1,2,3]thiadiazolyl, quinolinyl, isoquinolinyl, cinnolinyl, quinazolinyl, quinoxalinyl and phthalazinyl. Further examples are tetrazolyl, pyrrolo[2,3-b]pyridinyl, pyrrolo[2,3-c]pyridinyl, pyrrolo[3,2-b]pyridinyl, pyrrolo[3,2-c]pyridinyl, 5H-pyrrolo[2,3-b]pyrazinyl and imidazo[4,5-b]pyridinyl. Preferred examples of such heteroaryl groups are isoxazolyl (notably isoxazol-3-yl, isoxazol-4-yl and isoxazol-5-yl), oxadiazolyl (notably [1,2,4]oxadiazol-3-yl and [1,3,4]oxadiazol-2-yl), thiazolyl (notably thiazol-2-yl, thiazol-4-yl and thiazol-5-yl), imidazolyl (notably imidazol-2-yl and imidazol-4-yl), pyrazolyl (notably pyrazol-1-yl and pyrazol-3-yl), triazolyl (notably [1,2,3]triazol-1-yl, [1,2,3]triazol-2-yl and [1,2,3]triazol-4-yl), tetrazolyl (notably tetrazol-5-yl), pyridyl (notably pyridin-2-yl, pyridin-3-yl and pyridin-4-yl), pyrimidyl (notably pyrimidin-4-yl and pyrimidin-5-yl), pyrazinyl (notably pyrazin-2-yl), indolyl (notably indol-1-yl, indol-2-yl and indol-3-yl), benzofuranyl (notably benzofuran-3-yl), benzothiophenyl (notably benzothiophen-3-yl), indazolyl (notably indazol-1-yl indazol-2-yl and indazol-3-yl), benzimidazolyl (notably benzimidazol-1-yl and benzimidazol-2-yl), benzoxazolyl (notably benzoxazol-2-yl)benzisoxazolyl (notably benzisoxazol-3-yl), benzothiazolyl (notably benzothiazol-2-yl), pyrrolo[2,3-b]pyridinyl (notably pyrrolo[2,3-b]pyridin-1-yl), pyrrolo[2,3-c]pyridinyl (notably pyrrolo[2,3-c]pyridin-1-yl), pyrrolo[3,2-b]pyridinyl (notably pyrrolo[3,2-b]pyridin-1-yl), pyrrolo[3,2-c]pyridinyl (notably pyrrolo[3,2-c]pyridin-1-yl), 5H-pyrrolo[2,3-b]pyrazinyl (notably 5H-pyrrolo[2,3-b]pyrazin-5-yl), imidazo[4,5-b]pyridinyl (notably imidazo[4,5-b]pyridin-6-yl) and quinolinyl (notably quinolin-6-yl, quinolin-7-yl and quinolin-8-yl). More preferred examples of such heteroaryl groups are isoxazolyl (notably isoxazol-4-yl), oxadiazolyl (notably [1,2,4]oxadiazol-3-yl), thiazolyl (notably thiazol-4-yl), imidazolyl (notably imidazol-2-yl and imidazol-4-yl), pyrazolyl (notably pyrazol-3-yl), triazolyl (notably [1,2,3]triazol-1-yl, [1,2,3]triazol-2-yl and [1,2,3]triazol-4-yl), pyridyl (notably pyridin-3-yl), pyrimidyl (notably pyrimidin-5-yl), indolyl (notably indol-1-yl, indol-2-yl and indol-3-yl), benzofuranyl (notably benzofuran-3-yl), benzothiophenyl (notably benzothiophen-3-yl), indazolyl (notably indazol-2-yl), benzimidazolyl (notably benzimidazol-1-yl and benzimidazol-2-yl), benzisoxazolyl (notably benzisoxazol-3-yl), benzothiazolyl (notably benzothiazol-2-yl) and quinolinyl (notably quinolin-6-yl and quinolin-7-yl). An "optionally substituted heteroaryl" group means an heteroaryl group as defined before which is unsubstituted or substituted as explicitly defined.

In case $R^1$ represents "$(C_1-C_4)$alkyl which is mono-substituted with optionally substituted heteroaryl" the term "heteroaryl" means the above-mentioned groups. Preferred examples of such heteroaryl groups are isoxazolyl (notably isoxazol-3-yl, isoxazol-4-yl and isoxazol-5-yl), thiazolyl (notably thiazol-2-yl, thiazol-4-yl and thiazol-5-yl), imidazolyl (notably imidazol-2-yl and imidazol-4-yl), pyrazolyl (notably pyrazol-1-yl and pyrazol-3-yl), triazolyl (notably [1,2,3]triazol-4-yl), pyridyl (notably pyridin-2-yl and pyridin-3-yl), pyrimidyl (notably pyrimidin-4-yl and pyrimidin-5-yl), pyrazinyl (notably pyrazin-2-yl), indolyl (notably indol-1-yl, indol-2-yl and indol-3-yl), benzofuranyl (notably benzofuran-3-yl), benzothiophenyl (notably benzothiophen-3-yl), indazolyl (notably indazol-1-yl, indazol-2-yl and indazol-3-yl), benzimidazolyl (notably benzimidazol-1-yl and benzimidazol-2-yl), benzoxazolyl (notably benzoxazol-2-yl), benzisoxazolyl (notably benzisoxazol-3-yl), benzothiazolyl (notably benzothiazol-2-yl), pyrrolo[2,3-b]pyridinyl (notably pyrrolo[2,3-b]pyridin-1-yl), pyrrolo[2,3-c]pyridinyl (notably pyrrolo[2,3-c]pyridin-1-yl), pyrrolo[3,2-b]pyridinyl (notably pyrrolo[3,2-b]pyridin-1-yl), pyrrolo[3,2-c]pyridinyl (notably pyrrolo[3,2-c]pyridin-1-yl), 5H-pyrrolo[2,3-b]pyrazinyl (notably 5H-pyrrolo[2,3-b]pyrazin-5-yl) and quinolinyl (notably quinolin-6-yl and quinolin-7-yl). More preferred examples of such heteroaryl groups are thiazolyl (notably thiazol-4-yl), imidazolyl (notably imidazol-2-yl and imidazol-4-yl), triazolyl (notably [1,2,3]triazol-4-yl), indolyl (notably indol-1-yl, indol-2-yl and indol-3-yl), benzofuranyl (notably benzofuran-3-yl), benzothiophenyl (notably benzothiophen-3-yl), indazolyl (notably indazol-2-yl), benzimidazolyl (notably benzimidazol-1-yl and benzimidazol-2-yl), benzisoxazolyl (notably benzisoxazol-3-yl), benzothiazolyl (notably benzothiazol-2-yl) and quinolinyl (notably quinolin-6-yl and quinolin-7-yl). Most preferred are imidazolyl (notably imidazol-4-yl), indolyl (notably indol-3-yl), benzofuranyl (notably benzofuran-3-yl), benzisoxazolyl (notably benzisoxazol-3-yl) and quinolinyl (notably quinolin-6-yl). Preferred examples, in case X represents —O—, are isoxazolyl (notably isoxazol-3-yl, isoxazol-4-yl and isoxazol-5-yl), thiazolyl (notably thiazol-2-yl, thiazol-4-yl and thiazol-5-yl), imidazolyl (notably imidazol-4-yl), pyrazolyl (notably pyrazol-1-yl and pyrazol-3-yl), pyridyl (notably pyridin-3-yl), pyrimidyl (notably pyrimidin-4-yl and pyrimidin-5-yl), pyrazinyl (notably pyrazin-2-yl), indazolyl (notably indazol-1-yl and indazol-3-yl), benzimidazolyl (notably benzimidazol-1-yl), benzoxazolyl (notably benzoxazol-2-yl) and benzisoxazolyl (notably benzisoxazol-3-yl). Preferred examples, in case X represents a bond, are thiazolyl (notably thiazol-4-yl), imidazolyl (notably imidazol-2-yl and imidazol-4-yl), triazolyl (notably [1,2,3]triazol-4-yl), pyridyl (notably pyridin-2-yl and pyridin-3-yl), indolyl (notably indol-1-yl, indol-2-yl and indol-3-yl), benzofuranyl (notably benzofuran-3-yl), benzothiophenyl (notably benzothiophen-3-yl), indazolyl (notably indazol-1-yl and indazol-2-yl), benzimidazolyl (notably benzimidazol-1-yl and benzimidazol-2-yl), benzisoxazolyl (notably benzisoxazol-3-yl), benzothiazolyl (notably benzothiazol-2-yl), pyrrolo[2,3-b]pyridinyl (notably pyrrolo[2,3-b]pyridin-1-yl), pyrrolo[2,3-c]pyridinyl (notably pyrrolo[2,3-c]pyridin-1-yl), pyrrolo[3,2-b]pyridinyl (notably pyrrolo[3,2-b]pyridin-1-yl), pyrrolo[3,2-c]pyridinyl (notably pyrrolo[3,2-c]pyridin-1-yl), 5H-pyrrolo[2,3-b]pyrazinyl (notably 5H-pyrrolo[2,3-b]pyrazin-5-yl) and quinolinyl (notably quinolin-6-yl and quinolin-7-yl); most preferred, in case X represents a bond, are imidazolyl (notably imidazol-4-yl), indolyl (notably indol-1-yl and indol-3-yl), benzofuranyl (notably benzofuran-3-yl), indazolyl (notably indazol-1-yl), benzisoxazolyl (notably benzisoxazol-3-yl) and pyrrolo[2,3-b]pyridinyl (notably pyrrolo[2,3-b]pyridin-1-yl). The heteroaryl groups are independently unsubstituted, mono-, di- or tri-substituted (preferably unsubstituted, mono- or di-substituted and most preferably unsubstituted or mono-substituted), wherein the substituents are independently selected from the group consisting of halogen, $(C_1-C_4)$alkyl, $(C_1-C_4)$alkoxy, trifluoromethyl, cyano and phenyl, wherein the phenyl is unsubstituted or mono- or di-substituted with methyl. Preferably the substituents are independently selected from the group consisting of halogen, $(C_1-C_4)$alkyl, $(C_1-C_4)$alkoxy and phenyl, wherein the phenyl is unsubstituted or mono- or di-substituted with methyl. Most preferably the substituents are independently selected from the group consisting of $(C_1-C_4)$alkyl and $(C_1-C_4)$alkoxy. Examples of such optionally substituted heteroaryl groups are 2-methyl-thiazol-4-yl, 1-phenyl-imidazol-2-yl, 3-(2,3-dimethyl-phenyl)-imidazol-4-yl (preferred), 3-phenyl-[1,2,3]triazol-4-yl, indol-1-yl, 5-methoxy-indol-2-yl, indol-3-yl, 5-fluoro-indol-3-yl, 5-chloro-indol-3-yl, 1-methyl-indol-3-yl (preferred), 2-methyl-indol-3-yl (preferred), 1-ethyl-2-methyl-indol-3-yl, 5-methoxy-indol-3-yl (preferred), 6-methoxy-benzofuran-3-yl, benzothiophen-3-yl, 5-chloro-benzothiophen-3-yl, indazol-2-yl, benzimidazol-1-yl, benzimidazol-2-yl, benzisoxazol-3-yl, 5-methyl-benzisoxazol-3-yl, 5-methoxy-benzisoxazol-3-yl (preferred), benzothiazol-2-yl, quinolin-6-yl and quinolin-7-yl. Further examples are 4-methyl-isoxazol-3-yl, 5-methyl-isoxazol-3-yl, 3,5-dimethyl-isoxazol-4-yl, 3-methyl-isoxazol-5-yl, thiazol-2-yl, 4-methyl-thiazol-2-yl, 5-methyl-thiazol-2-yl, 2-methyl-thiazol-4-yl, 4-methyl-thiazol-5-yl, 4-methyl-pyrazol-1-yl, 3,5-dimethyl-pyrazol-1-yl, 2-methyl-pyrazol-3-yl, 2,5-dimethyl-pyrazol-3-yl, 2-ethyl-5-methyl-pyrazol-3-yl, 1,5-dimethyl-pyrazol-3-yl, 3-methyl-imidazol-4-yl, 2,6-dimethyl-pyridin- 3-yl, pyrimidin-4-yl, pyrimidin-5-yl, pyrazin-2-yl, 3-methyl-indol-1-yl, 6-methyl-indol-1-yl, 6-methoxy-indol-1-yl, 4,6-dimethoxy-indol-1-yl, 6-chloro-indol-1-yl, 2-trifluoromethyl-indol-1-yl, indazol-1-yl, 4-fluoro-indazol-1-yl, 5-fluoro-indazol-1-yl, 6-fluoro-indazol-1-yl, 7-fluoro-indazol-1-yl, 4-fluoro-3-methyl-indazol-1-yl, 6-fluoro-3-methyl-indazol-1-yl, 7-fluoro-3-methyl-indazol-1-yl, 4-chloro-indazol-1-yl, 5-chloro-indazol-1-yl, 6-chloro-indazol-1-yl, 7-chloro-indazol-1-yl, 4-chloro-3-methyl-indazol-1-yl, 6-chloro-3-methyl-indazol-1-yl, 3-methyl-indazol-1-yl, 1-methyl-indazol-3-yl, 3-chloro-indazol-1-yl, benzoxazol-2-yl, 3-chloro-5H-pyrrolo[2,3-b]pyrazin-5-yl, and 6-methoxy-pyrrolo[2,3-b]pyridin-1-yl.

In case $R^1$ represents "$(C_3-C_6)$cycloalkyl which is mono-substituted with optionally substituted heteroaryl" the term "heteroaryl" means the above-mentioned groups. Preferred are 5- or 6-membered monocyclic heteroaryl groups containing 1, 2 or 3 heteroatoms (preferably 1 or 2 heteroatoms) independently selected from oxygen, nitrogen and sulfur. Examples of such 5- or 6-membered monocyclic heteroaryl groups are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl and pyrazinyl. A preferred example of such a heteroaryl group is thiazolyl (notably thiazol-5-yl). The heteroaryl groups are independently unsubstituted, mono-, di- or tri-substituted (preferably unsubstituted, mono- or di-substituted and most preferably di-substituted), wherein the substituents are independently selected from the group consisting of halogen, $(C_1-C_4)$alkyl, $(C_1-C_4)$alkoxy and trifluoromethyl. Most preferably the substituents are selected from $(C_1-C_4)$alkyl. An example of such an optionally substituted heteroaryl group is 2,4-dimethyl-thiazol-5-yl.

In case $R^4$ represents "optionally substituted heteroaryl" the term "heteroaryl" means the above-mentioned groups. Preferred are 5- or 6-membered monocyclic heteroaryl groups containing 1, 2 or 3 heteroatoms (preferably 1 or 2 heteroatoms) independently selected from oxygen, nitrogen and sulfur. Examples of such 5- or 6-membered monocyclic heteroaryl groups are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl and pyrazinyl. A preferred example of such a heteroaryl group is pyrimidyl (notably pyrimidin-5-yl). The heteroaryl groups are independently unsubstituted, mono-, di- or tri-substituted (preferably unsubstituted, mono- or di-substituted and most preferably unsubstituted), wherein the substituents are independently selected from the group consisting of halogen, $(C_1-C_4)$alkyl and $(C_1-C_4)$alkoxy. Most preferably the substituents are selected from $(C_1-C_4)$alkyl. An example of such an optionally substituted heteroaryl group is pyrimidin-5-yl.

In case $R^5$ represents "optionally substituted heteroaryl" the term "heteroaryl" means the above-mentioned groups. Preferred are 5- or 6-membered monocyclic heteroaryl groups containing 1, 2 or 3 heteroatoms (preferably 1 or 2 heteroatoms) independently selected from oxygen, nitrogen and sulfur. Examples of such 5- or 6-membered monocyclic heteroaryl groups are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl and pyrazinyl. Preferred examples of such heteroaryl groups are oxadiazolyl (notably [1,2,4]oxadiazol-3-yl), triazolyl (notably [1,2,3]triazol-1-yl and [1,2,3]triazol-2-yl) and pyrimidyl (notably pyrimidin-5-yl). The heteroaryl groups are independently unsubstituted, mono-, di- or tri-substituted (preferably unsubstituted or mono-substituted and most preferably unsubstituted), wherein the substituents are independently selected from the group consisting of halogen, $(C_1-C_4)$alkyl, $(C_1-C_4)$alkoxy and mercapto (preferred). Examples of such optionally substituted heteroaryl groups are 5-mercapto-[1,2,4]oxadiazol-3-yl (tautomer to 5-thioxo-4,5-dihydro-[1,2,4]oxadiazol-3-yl), [1,2,3]triazol-1-yl (preferred), [1,2,3]triazol-2-yl (preferred) and pyrimidin-5-yl.

In case $R^{10}$ represents "optionally substituted heteroaryl" the term "heteroaryl" means the above-mentioned groups. Preferred are 5- or 6-membered monocyclic heteroaryl groups containing 1, 2, 3 or 4 heteroatoms (preferably 2, 3 or 4 heteroatoms) independently selected from oxygen, nitrogen and sulfur. Examples of such 5- or 6-membered monocyclic heteroaryl groups are furanyl, oxazolyl, isoxazolyl, oxadiazolyl, thienyl, thiazolyl, isothiazolyl, thiadiazolyl, pyrrolyl, imidazolyl, pyrazolyl, triazolyl, tetrazolyl, pyridyl, pyrimidyl, pyridazinyl and pyrazinyl. Preferred examples of such heteroaryl groups are isoxazolyl (notably isoxazol-5-yl), oxadiazolyl (notably [1,2,4]oxadiazol-3-yl and [1,3,4]oxadiazol-2-yl) and tetrazolyl (notably tetrazol-5-yl). The heteroaryl groups are independently unsubstituted, mono-, di- or tri-substituted (preferably unsubstituted or mono-substituted), wherein the substituents are independently selected from the group consisting of halogen, $(C_1-C_4)$alkyl, $(C_1-C_4)$alkoxy and hydroxy (preferred). Examples of such optionally substituted heteroaryl groups are 3-hydroxy-isoxazol-5-yl (tautomer to isoxazol-3(2H)-on-5-yl), 5-hydroxy-[1,2,4]oxadiazol-3-yl (tautomer to 1,2,4-oxadiazol-5(4H)-on-3-yl), 5-hydroxy-[1,3,4]oxadiazol-2-yl (tautomer to 1,3,4-oxadiazol-5(4H)-on-2-yl) and tetrazol-5-yl.

The term "heteroaryloxy", used alone or in combination, refers to an heteroaryl-O— group wherein the heteroaryl group is as defined before. An "optionally substituted heteroaryloxy" group means a heteroaryloxy group as defined before which is unsubstituted or substituted as explicitly defined.

In case $R^1$ represents "$(C_1-C_4)$alkyl which is mono-substituted with optionally substituted heteroaryloxy" the term "optionally substituted heteroaryloxy" means the above-mentioned groups. Preferred are 5- or 6-membered monocyclic heteroaryloxy groups containing in the heteroaryl moiety 1, 2 or 3 heteroatoms (preferably 1 or 2 heteroatoms) independently selected from oxygen, nitrogen and sulfur. Examples of such 5- or 6-membered monocyclic heteroaryloxy groups are furanyloxy, oxazolyloxy, isoxazolyloxy, oxadiazolyloxy, thienyloxy, thiazolyloxy, isothiazolyloxy, thiadiazolyloxy, pyrrolyloxy, imidazolyloxy, pyrazolyloxy, triazolyloxy, pyridyloxy, pyrimidyloxy, pyridazinyloxy and pyrazinyloxy. A preferred example of such heteroaryloxy group is pyridyloxy (notably pyridin-3-yloxy). Further preferred examples are imidazo[4,5-b]pyridinyloxy (notably imidazo[4,5-b]pyridin-6-yloxy) and quinolinyloxy (notably quinolin-8-yloxy). The heteroaryloxy groups are independently unsubstituted, mono-, di- or tri-substituted (preferably unsubstituted, mono- or di-substituted and most preferably di-substituted), wherein the substituents are independently selected from the group consisting of halogen, $(C_1-C_4)$alkyl, $(C_1-C_4)$alkoxy, 2-hydroxy-ethoxy, cyano, —C(O)NH$_2$ and trifluoromethyl (preferably from halogen, $(C_1-C_4)$alkyl and $(C_1-C_4)$alkoxy and most preferably from $(C_1-C_4)$alkyl). An example of such an optionally substituted heteroaryloxy group is 2,6-dimethyl-pyridin-3-yloxy. Further examples are pyridin-3-yloxy, 2-fluoro-pyridin-3-yloxy, 5-fluoro-pyridin-3-yloxy, 2-chloro-pyridin-3-yloxy, 4-chloro-pyridin-3-yloxy, 5-chloro-pyridin-3-yloxy, 6-chloro-pyridin-3-yloxy, 2-methyl-pyridin-3-yloxy, 5-methyl-pyridin-3-yloxy, 6-methyl-pyridin-3-yloxy, 5-methyl-2-methoxy-pyridin-3-yloxy, 5-methoxy-pyridin-3-yloxy, 6-methoxy-pyridin-3-yloxy, 2,6-dimethoxy-pyridin-3-yloxy, 5,6-dimethoxy-pyridin-3-yloxy, 2-(2-hydroxy-ethoxy)-pyridin-3-yloxy, 2-cyano-pyridin-3-yloxy, 2-carbamoyl-pyridin-3-yloxy, 6-trifluoromethyl-pyridin-3-yloxy, 2,6-dichloro-pyridin-4-yloxy, 3-methyl-imidazo[4,5-b]pyridin-6-yloxy and quinolin-8-yloxy.

The term "heteroarylsulfanyl", used alone or in combination, refers to a heteroaryl-S— group wherein the heteroaryl group is as defined before. An "optionally substituted heteroarylsulfanyl" group means a heteroarylsulfanyl group as defined before which is unsubstituted or substituted as explicitly defined.

In case $R^1$ represents "$(C_1-C_4)$alkyl which is mono-substituted with optionally substituted heteroarylsulfanyl" the term "optionally substituted heteroarylsulfanyl" means the above-mentioned groups. Preferred are 5- or 6-membered monocyclic heteroarylsulfanyl groups containing in the heteroaryl moiety 1, 2 or 3 heteroatoms (preferably 1 or 2 heteroatoms) independently selected from oxygen, nitrogen and sulfur. Examples of such 5- or 6-membered monocyclic heteroarylsulfanyl groups are furanylsulfanyl, oxazolylsulfanyl, isoxazolylsulfanyl, oxadiazolylsulfanyl, thienylsulfanyl, thiazolylsulfanyl, isothiazolylsulfanyl, thiadiazolylsulfanyl, pyrrolylsulfanyl, imidazolylsulfanyl, pyrazolylsulfanyl, triazolylsulfanyl, pyridylsulfanyl, pyrimidylsulfanyl, pyridazinylsulfanyl and pyrazinylsulfanyl. A preferred example of such a heteroarylsulfanyl group is triazolylsulfanyl (notably [1,2,3]triazol-4-ylsulfanyl). The heteroarylsulfanyl groups are independently unsubstituted, mono-, di- or tri-substituted (preferably mono-substituted), wherein the substituents are independently selected from the group consisting of halogen, $(C_1-C_4)$alkyl, $(C_1-C_4)$alkoxy and phenyl (and preferably from phenyl). An example of such an optionally substituted heteroarylsulfanyl group is 3-phenyl-3H-[1,2,3]triazol-4-ylsulfanyl.

The term "heteroarylsulfonyl", used alone or in combination, refers to a heteroaryl-S(O)$_2$— group wherein the heteroaryl group is as defined before, which is attached to the rest of the molecule via the sulfur-atom. An "optionally substituted heteroarylsulfonyl" group means a heteroarylsulfonyl group as defined before which is unsubstituted or substituted as explicitly defined.

In case $R^9$ represents "optionally substituted heteroarylsulfonyl" the term means the above-mentioned groups. Preferred are 5- or 6-membered monocyclic heteroarylsulfonyl groups containing in the heteroaryl moiety 1, 2 or 3 heteroatoms (preferably 1 or 2 heteroatoms) independently selected from oxygen, nitrogen and sulfur. Examples of such 5- or 6-membered monocyclic heteroarylsulfonyl groups are furanylsulfonyl, oxazolylsulfonyl, isoxazolylsulfonyl, oxadiazolylsulfonyl, thienylsulfonyl, thiazolylsulfonyl, isothiazolylsulfonyl, thiadiazolylsulfonyl, pyrrolylsulfonyl, imidazolylsulfonyl, pyrazolylsulfonyl, triazolylsulfonyl, pyridylsulfonyl, pyrimidylsulfonyl, pyridazinylsulfonyl and pyrazinylsulfonyl. A preferred example of such a heteroarylsulfonyl group is isoxazolylsulfonyl (notably isoxazole-4-sulfonyl). The heteroarylsulfonyl groups are independently unsubstituted, mono-, di- or tri-substituted (preferably di-substituted), wherein the substituents are independently selected from the group consisting of halogen, $(C_1-C_4)$alkyl and $(C_1-C_4)$alkoxy (and preferably from $(C_1-C_4)$alkyl). An example of such an optionally substituted heteroarylsulfonyl group is 3,5-dimethyl-isoxazole-4-sulfonyl.

The term "optionally substituted heteroaryl-$(C_1-C_2)$alkoxy", used alone or in combination, refers to an heteroaryl-$(C_1-C_2)$alkoxy group as defined above wherein the heteroaryl group is unsubstituted or substituted as explicitly defined.

In case $R^1$ represents "$(C_1-C_4)$alkyl which is mono-substituted with optionally substituted heteroaryl-$(C_1-C_2)$alkoxy" the term "optionally substituted heteroaryl-$(C_1-C_2)$alkoxy" means the above-mentioned groups, wherein the term "heteroaryl" means a heteroaryl group as defined above and preferably a 5- or 6-membered monocyclic heteroaryl group containing 1, 2 or 3 heteroatoms (preferably 1 or 2 heteroatoms) independently selected from oxygen, nitrogen and sulfur. Examples of such 5- or 6-membered monocyclic heteroaryl groups as used in "optionally substituted heteroaryl-$(C_1-C_2)$alkoxy" are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl and pyrazinyl. A preferred example of such a heteroaryl group is pyrazolyl (notably pyrazol-3-yl). The heteroaryl groups as used in "optionally substituted heteroaryl-$(C_1-C_2)$alkoxy" are independently unsubstituted, mono-, di- or tri-substituted (preferably mono-substituted), wherein the substituents are independently selected from the group consisting of halogen, $(C_1-C_4)$alkyl and $(C_1-C_4)$alkoxy (and preferably from $(C_1-C_4)$alkyl). An example of such an optionally substituted heteroaryl group as used in "optionally substituted heteroaryl-$(C_1-C_2)$alkoxy" is 1-methyl-1H-pyrazol-3-yl. A preferred example of an optionally substituted heteroaryl-$(C_1-C_2)$alkoxy group is 1-methyl-1H-pyrazol-3-ylmethoxy.

The term "heterocyclyl", used alone or in combination, refers to a saturated monocyclic moiety of 5 to 7 ring members containing 1 or 2 heteroatoms selected from nitrogen, oxygen and sulfur, it being understood that a heterocyclyl group does not contain 2 sulfur atoms. The sulfur atom of a heterocyclyl group may be in an oxidised form, i.e. as a sulfoxide or sulfonyl. A heterocyclyl group may optionally be annealed to a benzene ring. An "optionally substituted heterocyclyl" group means a heterocyclyl group as defined before which is unsubstituted or substituted as explicitly defined.

In case $R^1$ represents "$(C_1-C_4)$alkyl which is mono-substituted with optionally substituted heterocyclyl" the term "heterocyclyl" means the above-mentioned groups. Examples of such heterocyclyl groups are pyrrolidinyl, imidazolidinyl, oxazolidinyl, thiazolidinyl, piperidinyl, piperazinyl, morpholinyl, thiomorpholinyl, dioxanyl, indolinyl, isoindolinyl, dihydrobenzofuranyl, tetrahydroquinolinyl, tetrahydroisoquinolinyl, tetrahydroquinoxalinyl, chromanyl, dihydrobenzooxazinyl, dihydrobenzothiazinyl and dihydrobenzodioxinyl. Preferred examples are thiazolidinyl (notably thiazolidin-3-yl), indolinyl (notably indolin-1-yl), isoindolinyl (notably isoindolin-2-yl), tetrahydroquinolinyl (notably 1,2,3,4-tetrahydroquinolin-1-yl) and dihydrobenzooxazinyl (notably 2,3-dihydro-benzo[1,4]oxazin-4-yl). A further preferred example is pyrrolidinyl (notably pyrrolidin-1-yl). The heterocyclyl groups are independently unsubstituted, mono-, di- or tri-substituted (preferably unsubstituted, mono- or di-substituted), wherein the substituents are independently selected from the group consisting of halogen, oxo and phenyl. Examples of such optionally substituted heterocyclyl groups are 4-oxo-2-phenyl-thiazolidin-3-yl, indolin-1-yl, isoindolin-2-yl, 1,2,3,4-tetrahydroquinolin-1-yl and 6-chloro-3-oxo-2,3-dihydro-benzo[1,4]oxazin-4-yl. Further examples are 2-oxo-pyrrolidin-1-yl, 4-methyl-2-oxo-thiazolidin-3-yl, 2-oxo-thiazolidin-3-yl and 1-oxo-isoindolin-2-yl.

The term "10-membered partially unsaturated ring system", means a tetrahydronaphthyl (notably 1,2,3,4-tetrahydronaphth-2-yl) or a chromenyl (notably 2H-chromen-3-yl) group.

2) A further embodiment of the invention relates to compounds of formula (I) according to embodiment 1) that are also compounds of formula (I$_P$),

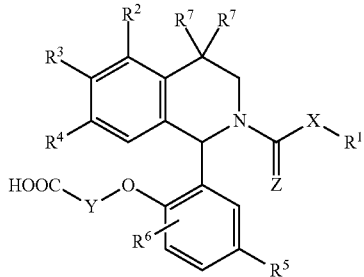

(I$_P$)

wherein
X represents —NH—, —O— or a bond;
Y represents (C$_1$-C$_4$)alkandiyl;
Z represents O or S;
R$^1$ represents
  (C$_4$-C$_6$)alkyl;
  (C$_1$-C$_4$)alkyl which is mono-substituted with (C$_3$-C$_6$)cycloalkyl, (C$_1$-C$_4$)alkoxy, optionally substituted aryl, optionally substituted heteroaryl, optionally substituted heterocyclyl, optionally substituted aryloxy, optionally substituted heteroaryloxy, optionally substituted aryl-(C$_1$-C$_2$)alkoxy, optionally substituted heteroaryl-(C$_1$-C$_2$)alkoxy, optionally substituted heteroarylsulfanyl or —NR$^8$R$^9$;
  (C$_2$-C$_4$)alkenyl which is mono-substituted with optionally substituted aryl;
  (C$_2$-C$_4$)alkynyl which is mono-substituted with optionally substituted aryl;
  (C$_3$-C$_6$)cycloalkyl which is mono-substituted with optionally substituted aryl;
  optionally substituted aryl; or
  a 10-membered partially unsaturated ring system;
R$^2$ represents hydrogen, (C$_1$-C$_4$)alkyl, (C$_1$-C$_4$)alkoxy, (C$_1$-C$_4$)fluoroalkyl, halogen, (C$_1$-C$_4$)alkylsulfonyl, phenylsulfonyl or (C$_1$-C$_4$)alkylsulfonylamino;
R$^3$ represents hydrogen, (C$_1$-C$_4$)alkoxy or halogen;
R$^4$ represents hydrogen, (C$_1$-C$_4$)alkoxy, halogen or (C$_1$-C$_4$)alkylsulfonyl;
R$^5$ represents hydrogen, (C$_1$-C$_4$)alkyl, (C$_1$-C$_4$)alkoxy, (C$_1$-C$_4$)fluoroalkyl, halogen, cyano, —CONH$_2$, optionally substituted aryl, optionally substituted heteroaryl, (C$_1$-C$_4$)alkylsulfonyl, phenylsulfonyl or dimethylamino-sulfonyl;
R$^6$ represents hydrogen or halogen; or
R$^5$ and R$^6$ together form a methylendioxy-group;
R$^7$ represents hydrogen or methyl;
R$^8$ represents hydrogen or methyl; and
R$^9$ represents optionally substituted arylsulfonyl or optionally substituted heteroarylsulfonyl;
with the proviso that
  (1) R$^1$ is different from optionally substituted aryl if X represents —NH— or a bond; and
  (2) at least one of R$^5$ and R$^6$ is different from hydrogen;
and to the salts (in particular pharmaceutically acceptable salts) of such compounds.

3) A further embodiment of the invention relates to compounds according to embodiment 1), wherein
X represents —NH—, —O— or a bond;
Y represents (C$_1$-C$_4$)alkandiyl;
Z represents O;
n represents 0 or 1;
R$^1$ represents
  (C$_1$-C$_4$)alkyl which is mono-substituted with (C$_3$-C$_6$)cycloalkyl, (C$_1$-C$_4$)alkoxy, optionally substituted aryl, optionally substituted heteroaryl, optionally substituted heterocyclyl, optionally substituted aryloxy, optionally substituted heteroaryloxy, optionally substituted aryl-(C$_1$-C$_2$)alkoxy, optionally substituted heteroaryl-(C$_1$-C$_2$)alkoxy or optionally substituted heteroarylsulfanyl;
  (C$_3$-C$_6$)cycloalkyl which is mono- or di-substituted with (C$_1$-C$_4$)alkyl, mono-substituted with (C$_1$-C$_4$)alkoxy, mono-substituted with optionally substituted aryl or mono-substituted with optionally substituted heteroaryl;
R$^2$ represents hydrogen, (C$_1$-C$_4$)alkyl, (C$_1$-C$_4$)alkoxy, (C$_1$-C$_4$)fluoroalkyl, halogen or (C$_1$-C$_4$)alkylsulfonyl;
R$^3$ represents hydrogen, (C$_1$-C$_4$)alkoxy or halogen;
R$^4$ represents hydrogen, (C$_1$-C$_4$)alkoxy or halogen;
R$^5$ represents hydrogen, (C$_1$-C$_4$)alkyl, (C$_1$-C$_4$)alkoxy, (C$_1$-C$_4$)fluoroalkyl, halogen, cyano, optionally substituted aryl, optionally substituted heteroaryl or phenylsulfonyl;
R$^6$ represents hydrogen or halogen; or
R$^7$ represents hydrogen; and
R$^{10}$ represents —C(O)OH, —C(O)NH—CN, —C(O)NH—OH, —C(O)NH—S(O)$_2$CF or optionally substituted heteroaryl;
and to the salts (in particular pharmaceutically acceptable salts) of such compounds.

4) A further embodiment of the invention relates to compounds according to embodiment 1) or 2), wherein
X represents —NH—, —O— or a bond;
Y represents (C$_1$-C$_4$)alkandiyl;
Z represents O;
R$^1$ represents
  (C$_1$-C$_4$)alkyl which is mono-substituted with (C$_3$-C$_6$)cycloalkyl, (C$_1$-C$_4$)alkoxy, optionally substituted aryl, optionally substituted heteroaryl, optionally substituted heterocyclyl, optionally substituted aryloxy, optionally substituted heteroaryloxy, optionally substituted aryl-(C$_1$-C$_2$)alkoxy, optionally substituted heteroaryl-(C$_1$-C$_2$)alkoxy or optionally substituted heteroarylsulfanyl; or
  (C$_3$-C$_6$)cycloalkyl which is mono-substituted with optionally substituted aryl;
R$^2$ represents hydrogen, (C$_1$-C$_4$)alkyl, (C$_1$-C$_4$)alkoxy, (C$_1$-C$_4$)fluoroalkyl, halogen or (C$_1$-C$_4$)alkylsulfonyl;
R$^3$ represents hydrogen, (C$_1$-C$_4$)alkoxy or halogen;
R$^4$ represents hydrogen, (C$_1$-C$_4$)alkoxy or halogen;
R$^5$ represents (C$_1$-C$_4$)alkyl, (C$_1$-C$_4$)alkoxy, (C$_1$-C$_4$)fluoroalkyl, halogen, cyano, optionally substituted aryl, optionally substituted heteroaryl or phenylsulfonyl;
R$^6$ represents hydrogen or halogen; and
R$^7$ represents hydrogen or methyl;
and to the salts (in particular pharmaceutically acceptable salts) of such compounds.

5) A further embodiment of the invention relates to compounds according to any one of embodiments 1) to 4), wherein
X represents —NH—, —O— or a bond;
Y represents (C$_1$-C$_4$)alkandiyl;
Z represents O;
R$^1$ represents
  (C$_1$-C$_4$)alkyl which is mono-substituted with optionally substituted aryl, optionally substituted heteroaryl, optionally substituted aryloxy, optionally substituted heteroaryloxy or optionally substituted aryl-(C$_1$-C$_2$)alkoxy; or cyclopropyl which is mono-substituted with optionally substituted aryl;

$R^2$ represents hydrogen, methyl, methoxy, trifluoromethyl or halogen;

$R^3$ represents hydrogen or fluoro;

$R^4$ represents hydrogen, methoxy or fluoro;

$R^5$ represents trifluoromethyl, halogen, cyano, optionally substituted aryl or optionally substituted heteroaryl;

$R^6$ represents hydrogen or fluoro; and $R^7$ represents hydrogen;

and to the salts (in particular pharmaceutically acceptable salts) of such compounds.

6) A further embodiment of the invention relates to compounds according to any one of embodiments 1) to 5), wherein X represents —O— or a bond;

Y represents methandiyl;

Z represents O;

n represents 0 or 1;

$R^1$ represents
  $(C_1-C_2)$alkyl which is mono-substituted with optionally substituted aryl, optionally substituted heteroaryl or optionally substituted aryl-$(C_1-C_2)$alkoxy (preferably with optionally substituted aryl or optionally substituted heteroaryl); or
  cyclopropyl which is mono-substituted with optionally substituted aryl;

$R^2$ represents hydrogen, trifluoromethyl or fluoro (preferably hydrogen or fluoro);

$R^3$ represents hydrogen or fluoro;

$R^4$ represents hydrogen;

$R^5$ represents halogen or cyano (preferably chloro);

$R^6$ represents hydrogen;

$R^7$ represents hydrogen; and $R^{10}$ represents —C(O)OH;

and to the salts (in particular pharmaceutically acceptable salts) of such compounds.

7) A further embodiment of the invention relates to compounds according to embodiment 1) or 2), wherein X represents —NH—;

Y represents $(C_1-C_4)$alkandiyl (preferably methandiyl);

Z represents O or S;

$R^1$ represents $(C_1-C_4)$alkyl (preferably methyl or ethyl) which is mono-substituted with phenyl, which phenyl is unsubstituted or mono-substituted with halogen or $(C_1-C_4)$alkoxy (and preferably with chloro or methoxy);

$R^2$ represents hydrogen;

$R^3$ represents hydrogen;

$R^4$ represents hydrogen;

$R^5$ represents halogen (preferably fluoro or chloro);

$R^6$ represents hydrogen;

$R^7$ represents hydrogen;

and to the salts (in particular pharmaceutically acceptable salts) of such compounds.

8) A further embodiment of the invention relates to compounds according to embodiment 1) or 2), wherein X represents —O—;

Y represents $(C_1-C_4)$alkandiyl;

Z represents O;

$R^1$ represents
  $(C_4-C_6)$alkyl;
  $(C_1-C_4)$alkyl which is mono-substituted with $(C_1-C_4)$alkoxy or optionally substituted aryl; or
  optionally substituted aryl;

$R^2$ represents hydrogen, $(C_1-C_4)$alkyl, $(C_1-C_4)$alkoxy, $(C_1-C_4)$fluoroalkyl, halogen, $(C_1-C_4)$alkylsulfonyl, phenylsulfonyl or $(C_1-C_4)$alkylsulfonylamino;

$R^3$ represents hydrogen, $(C_1-C_4)$alkoxy or halogen;

$R^4$ represents hydrogen, $(C_1-C_4)$alkoxy, halogen or $(C_1-C_4)$alkylsulfonyl;

$R^5$ represents hydrogen, $(C_1-C_4)$alkyl, $(C_1-C_4)$alkoxy, $(C_1-C_4)$fluoroalkyl, halogen, cyano, —$CONH_2$, optionally substituted aryl, optionally substituted heteroaryl, $(C_1-C_4)$alkylsulfonyl, phenylsulfonyl or dimethylamino-sulfonyl;

$R^6$ represents hydrogen or halogen; or $R^5$ and $R^6$ together form a methylendioxy-group;

$R^7$ represents hydrogen or methyl;

with the proviso that at least one of $R^5$ and $R^6$ is different from hydrogen;

and to the salts (in particular pharmaceutically acceptable salts) of such compounds.

9) A further embodiment of the invention relates to compounds according to any one of embodiments 1), 2) or 8), wherein X represents —O—;

Y represents $(C_1-C_4)$alkandiyl;

Z represents O;

$R^1$ represents $(C_1-C_4)$alkyl which is mono-substituted with optionally substituted aryl;

$R^2$ represents hydrogen, methyl, methoxy, trifluoromethyl or halogen;

$R^3$ represents hydrogen, methoxy or fluoro;

$R^4$ represents hydrogen, methoxy or fluoro;

$R^5$ represents trifluoromethyl, halogen, cyano, optionally substituted aryl or optionally substituted heteroaryl;

$R^6$ represents hydrogen or fluoro;

$R^7$ represents hydrogen;

and to the salts (in particular pharmaceutically acceptable salts) of such compounds.

10) A further embodiment of the invention relates to compounds according to embodiment 1), wherein X represents —O—;

Y represents $(C_1-C_2)$alkandiyl (preferably methandiyl);

Z represents O;

n represents 0 or 1;

$R^1$ represents $(C_1-C_2)$alkyl which is mono-substituted with $(C_3-C_6)$cycloalkyl, $(C_1-C_4)$alkoxy, optionally substituted aryl or optionally substituted heteroaryl (preferably with optionally substituted aryl or optionally substituted heteroaryl);

$R^2$ represents hydrogen, methyl, methoxy, trifluoromethyl or halogen (preferably hydrogen, trifluoromethyl or fluoro);

$R^3$ represents hydrogen or halogen (preferably hydrogen or fluoro);

$R^4$ represents hydrogen, $(C_1-C_4)$alkoxy or halogen (preferably hydrogen or fluoro);

$R^5$ represents halogen, cyano, optionally substituted aryl or optionally substituted heteroaryl (preferably fluoro, chloro or cyano);

$R^6$ represents hydrogen;

$R^7$ represents hydrogen; and $R^{10}$ represents —C(O)OH, —C(O)NH—S(O)$_2$CF or optionally substituted heteroaryl (preferably —C(O)OH);

and to the salts (in particular pharmaceutically acceptable salts) of such compounds.

11) A further embodiment of the invention relates to compounds according to embodiment 1) or 2), wherein X represents a bond;

Y represents $(C_1-C_4)$alkandiyl;

Z represents O;

$R^1$ represents
  $(C_1-C_4)$alkyl which is mono-substituted with $(C_3-C_6)$cycloalkyl, $(C_1-C_4)$alkoxy, optionally substituted aryl, optionally substituted heteroaryl, optionally substituted heterocyclyl, optionally substituted aryloxy, optionally substituted heteroaryloxy, optionally substituted aryl-($C_1$-$C_2$)alkoxy, optionally substituted heteroaryl-($C_1$-$C_2$)alkoxy, optionally substituted heteroarylsulfanyl or —$NR^8R^9$;

($C_2$-$C_4$)alkenyl which is mono-substituted with optionally substituted aryl;

($C_2$-$C_4$)alkynyl which is mono-substituted with optionally substituted aryl; or ($C_3$-$C_6$)cycloalkyl which is mono-substituted with optionally substituted aryl;

$R^2$ represents hydrogen or halogen;
$R^3$ represents hydrogen;
$R^4$ represents hydrogen;
$R^5$ represents halogen or cyano;
$R^6$ represents hydrogen;
$R^7$ represents hydrogen;
$R^8$ represents hydrogen or methyl; and
$R^9$ represents optionally substituted arylsulfonyl or optionally substituted heteroarylsulfonyl;

and to the salts (in particular pharmaceutically acceptable salts) of such compounds.

12) A further embodiment of the invention relates to compounds according to embodiment 1), wherein X represents a bond;
Y represents methandiyl;
Z represents O;
n represents 0 or 1;
$R^1$ represents
  ($C_1$-$C_4$)alkyl (preferably ($C_1$-$C_3$)alkyl) which is mono-substituted with ($C_3$-$C_6$)cycloalkyl, optionally substituted aryl, optionally substituted heteroaryl, optionally substituted heterocyclyl, optionally substituted aryloxy, optionally substituted heteroaryloxy or optionally substituted aryl-($C_1$-$C_2$)alkoxy (preferably with optionally substituted aryl, optionally substituted heteroaryl, optionally substituted aryloxy or optionally substituted aryl-($C_1$-$C_2$)alkoxy);
  cyclopropyl which is di-substituted with methyl, mono-substituted with optionally substituted aryl or mono-substituted with optionally substituted heteroaryl (preferably mono-substituted with optionally substituted aryl);

$R^2$ represents hydrogen or halogen (preferably hydrogen or fluoro);
$R^3$ represents hydrogen or halogen (preferably hydrogen or fluoro);
$R^4$ represents hydrogen;
$R^5$ represents halogen or cyano (preferably fluoro or chloro);
$R^6$ represents hydrogen;
$R^7$ represents hydrogen; and
$R^{10}$ represents —C(O)OH;

and to the salts (in particular pharmaceutically acceptable salts) of such compounds.

13) A further embodiment of the invention relates to compounds according to any one of embodiments 1), 2) 11) or 12), wherein X represents a bond;
Y represents methandiyl;
Z represents O;
$R^1$ represents
  ($C_1$-$C_4$)alkyl which is mono-substituted with optionally substituted aryl, optionally substituted heteroaryl, optionally substituted aryloxy, optionally substituted heteroaryloxy or optionally substituted aryl-($C_1$-$C_2$)alkoxy; or cyclopropyl which is mono-substituted with optionally substituted aryl;

$R^2$ represents hydrogen or fluoro;
$R^3$ represents hydrogen;
$R^4$ represents hydrogen;
$R^5$ represents fluoro, chloro or cyano;
$R^6$ represents hydrogen;
$R^7$ represents hydrogen;

and to the salts (in particular pharmaceutically acceptable salts) of such compounds.

14) A further embodiment of the invention relates to compounds according to embodiment 1), wherein X represents —NH—, —O— or a bond;
Y represents methandiyl;
Z represents O;
n represents 0;
$R^1$ represents
  ($C_1$-$C_4$)alkyl (preferably ($C_1$-$C_2$)alkyl) which is mono-substituted with optionally substituted aryl, optionally substituted heteroaryl, optionally substituted heterocyclyl, optionally substituted aryloxy, optionally substituted heteroaryloxy or optionally substituted aryl-($C_1$-$C_2$)alkoxy;
  cyclopropyl which is mono-substituted with optionally substituted aryl;

$R^2$ represents hydrogen or halogen (preferably hydrogen or fluoro);
$R^3$ represents hydrogen or halogen (preferably hydrogen or fluoro);
$R^4$ represents hydrogen;
$R^5$ represents halogen (preferably fluoro or chloro);
$R^6$ represents hydrogen;
$R^7$ represents hydrogen;
$R^{10}$ represents —C(O)OH;

and to the salts (in particular pharmaceutically acceptable salts) of such compounds.

15) A further embodiment of the invention relates to compounds according to any one of embodiments 1) to 5), 7) or 14), wherein X represents —NH—;
and to the salts (in particular pharmaceutically acceptable salts) of such compounds.

16) A further embodiment of the invention relates to compounds according to any one of embodiments 1) to 6), 8) to 10) or 14), wherein X represents —O—;
and to the salts (in particular pharmaceutically acceptable salts) of such compounds.

17) A further embodiment of the invention relates to compounds according to any one of embodiments 1) to 6) or 11) to 14), wherein X represents a bond;
and to the salts (in particular pharmaceutically acceptable salts) of such compounds.

18) A further embodiment of the invention relates to compounds according to any one of embodiments 1) to 5), 7) to 11) or 15) to 17), wherein Y represents methandiyl, ethan-1,1-diyl or propan-1,3-diyl (and preferably methandiyl or ethan-1,1-diyl);
and to the salts (in particular pharmaceutically acceptable salts) of such compounds.

19) A further embodiment of the invention relates to compounds according to any one of embodiments 1) to 11) or 15) to 17), wherein Y represents methandiyl or (R)-configured ethan-1,1-diyl (and preferably methandiyl); and to the salts (in particular pharmaceutically acceptable salts) of such compounds.

20) A further embodiment of the invention relates to compounds according to any one of embodiments 1) to 19), wherein Z represents O;

and to the salts (in particular pharmaceutically acceptable salts) of such compounds.

21) A further embodiment of the invention relates to compounds according to any one of embodiments 1) or 3) to 20), wherein n represents 0;

and to the salts (in particular pharmaceutically acceptable salts) of such compounds.

22) A further embodiment of the invention relates to compounds according to any one of embodiments 1) to 20), wherein n represents 1;

and to the salts (in particular pharmaceutically acceptable salts) of such compounds.

23) A further embodiment of the invention relates to compounds according to any one of embodiments 1), 2), 8) or 15) to 22), wherein $R^1$ represents $(C_4-C_6)$alkyl;

and to the salts (in particular pharmaceutically acceptable salts) of such compounds.

24) A further embodiment of the invention relates to compounds according to any one of embodiments 1) or 15) to 22), wherein $R^1$ represents
  $(C_1-C_4)$alkyl (preferably $(C_1-C_2)$alkyl) which is mono-substituted with $(C_3-C_6)$cycloalkyl, $(C_1-C_4)$alkoxy, optionally substituted aryl, optionally substituted heteroaryl, optionally substituted heterocyclyl, optionally substituted aryloxy, optionally substituted heteroaryloxy, optionally substituted aryl-$(C_1-C_2)$alkoxy, optionally substituted heteroaryl-$(C_1-C_2)$alkoxy, optionally substituted heteroarylsulfanyl or —$NR^8R^9$; or
  $(C_3-C_6)$cycloalkyl (preferably cyclopropyl) which is mono- or di-substituted with $(C_1-C_4)$alkyl, mono-substituted with $(C_1-C_4)$alkoxy, mono-substituted with optionally substituted aryl or mono-substituted with optionally substituted heteroaryl;

and to the salts (in particular pharmaceutically acceptable salts) of such compounds.

25) A further embodiment of the invention relates to compounds according to any one of embodiments 1), 3) or 15) to 22), wherein $R^1$ represents
  $(C_1-C_4)$alkyl (preferably $(C_1-C_3)$alkyl) which is mono-substituted with $(C_3-C_6)$cycloalkyl, optionally substituted aryl, optionally substituted heteroaryl, optionally substituted heterocyclyl, optionally substituted aryloxy, optionally substituted heteroaryloxy, optionally substituted aryl-$(C_1-C_2)$alkoxy or optionally substituted heteroaryl-$(C_1-C_2)$alkoxy; or
  cyclopropyl which is mono- or di-substituted with $(C_1-C_4)$alkyl, mono-substituted with optionally substituted aryl or mono-substituted with optionally substituted heteroaryl (preferably mono- or di-substituted with $(C_1-C_4)$alkyl or mono-substituted with optionally substituted aryl and most preferably mono-substituted with optionally substituted aryl);

and to the salts (in particular pharmaceutically acceptable salts) of such compounds.

26) A further embodiment of the invention relates to compounds according to any one of embodiments 1) to 4), 11) or 15) to 22), wherein $R^1$ represents
  $(C_1-C_4)$alkyl which is mono-substituted with $(C_3-C_6)$cycloalkyl, $(C_1-C_4)$alkoxy, optionally substituted aryl, optionally substituted heteroaryl, optionally substituted heterocyclyl, optionally substituted aryloxy, optionally substituted heteroaryloxy, optionally substituted aryl-$(C_1-C_2)$alkoxy, optionally substituted heteroaryl-$(C_1-C_2)$alkoxy or optionally substituted heteroarylsulfanyl; or
  $(C_3-C_6)$cycloalkyl which is mono-substituted with optionally substituted aryl;

and to the salts (in particular pharmaceutically acceptable salts) of such compounds.

27) A further embodiment of the invention relates to compounds according to any one of embodiments 1) to 5) or 11) to 22), wherein $R^1$ represents
  $(C_1-C_4)$alkyl which is mono-substituted with optionally substituted aryl, optionally substituted heteroaryl, optionally substituted aryloxy, optionally substituted heteroaryloxy or optionally substituted aryl-$(C_1-C_2)$alkoxy; or
  cyclopropyl which is mono-substituted with optionally substituted aryl;

and to the salts (in particular pharmaceutically acceptable salts) of such compounds.

28) A further embodiment of the invention relates to compounds according to any one of embodiments 1) to 5) or 11) to 22), wherein $R^1$ represents $(C_1-C_4)$alkyl which is mono-substituted with optionally substituted aryl, optionally substituted heteroaryl, optionally substituted aryloxy, optionally substituted heteroaryloxy or optionally substituted aryl-$(C_1-C_2)$alkoxy (and preferably with optionally substituted aryl or optionally substituted heteroaryl);

and to the salts (in particular pharmaceutically acceptable salts) of such compounds.

29) A further embodiment of the invention relates to compounds according to any one of embodiments 1) to 6) or 10) to 28), wherein the substituent for a $(C_1-C_4)$alkyl group, a $(C_1-C_3)$alkyl group or a $(C_1-C_2)$alkyl group, if representing $R^1$, is selected from optionally substituted aryl or optionally substituted heteroaryl;

and to the salts (in particular pharmaceutically acceptable salts) of such compounds.

30) A further embodiment of the invention relates to compounds according to any one of embodiments 1) to 22) or 24) to 29), wherein the mono-substituted $(C_1-C_4)$alkyl group, if representing $R^1$, is selected from methyl; ethyl substituted in 2-position; and n-propyl substituted in 3-position;

and to the salts (in particular pharmaceutically acceptable salts) of such compounds.

31) A further embodiment of the invention relates to compounds according to any one of embodiments 1), 3) or 15) to 22), wherein $R^1$ represents $(C_3-C_6)$cycloalkyl (preferably cyclopropyl) which is mono- or di-substituted with $(C_1-C_4)$alkyl, mono-substituted with $(C_1-C_4)$alkoxy, mono-substituted with optionally substituted aryl or mono-substituted with optionally substituted heteroaryl;

and to the salts (in particular pharmaceutically acceptable salts) of such compounds.

32) A further embodiment of the invention relates to compounds according to any one of embodiments 1), 3), 12) or 15) to 22), wherein $R^1$ represents $(C_3-C_6)$cycloalkyl (preferably cyclopropyl) which is mono-substituted with optionally substituted aryl or mono-substituted with optionally substituted heteroaryl;
and to the salts (in particular pharmaceutically acceptable salts) of such compounds.

33) A further embodiment of the invention relates to compounds according to any one of embodiments 1) to 6) or 11) to 22), wherein
$R^1$ represents $(C_3-C_6)$cycloalkyl (preferably cyclopropyl) which is mono-substituted with optionally substituted aryl;
and to the salts (in particular pharmaceutically acceptable salts) of such compounds.

34) A further embodiment of the invention relates to compounds according to any one of embodiments 1) to 5), 8) to 10) or 15) to 33), wherein
$R^2$ represents hydrogen, $(C_1-C_4)$alkyl, $(C_1-C_4)$alkoxy, $(C_1-C_4)$fluoroalkyl or halogen (and preferably hydrogen, methyl, methoxy, trifluoromethyl, fluoro, chloro or bromo);
and to the salts (in particular pharmaceutically acceptable salts) of such compounds.

35) A further embodiment of the invention relates to compounds according to any one of embodiments 1) to 6), 8) to 10) or 15) to 33), wherein
$R^2$ represents hydrogen, $(C_1-C_4)$fluoroalkyl or halogen (and preferably hydrogen, trifluoromethyl or fluoro);
and to the salts (in particular pharmaceutically acceptable salts) of such compounds.

36) A further embodiment of the invention relates to compounds according to any one of embodiments 1) to 6) or 8) to 33), wherein
$R^2$ represents halogen (and preferably fluoro);
and to the salts (in particular pharmaceutically acceptable salts) of such compounds.

37) A further embodiment of the invention relates to compounds according to any one of embodiments 1) to 33), wherein
$R^2$ represents hydrogen;
and to the salts (in particular pharmaceutically acceptable salts) of such compounds.

38) A further embodiment of the invention relates to compounds according to any one of embodiments 1) to 6), 8) to 10), 12) or 14) to 37), wherein
$R^3$ represents hydrogen or halogen (and preferably hydrogen or fluoro);
and to the salts (in particular pharmaceutically acceptable salts) of such compounds.

39) A further embodiment of the invention relates to compounds according to any one of embodiments 1) to 37), wherein
$R^3$ represents hydrogen;
and to the salts (in particular pharmaceutically acceptable salts) of such compounds.

40) A further embodiment of the invention relates to compounds according to any one of embodiments 1) to 5), 8) to 10) or 15) to 39), wherein
$R^4$ represents hydrogen, $(C_1-C_4)$alkoxy or halogen (and preferably hydrogen, methoxy or fluoro);
and to the salts (in particular pharmaceutically acceptable salts) of such compounds.

41) A further embodiment of the invention relates to compounds according to any one of embodiments 1) to 5), 8) to 10) or 15) to 39), wherein
$R^4$ represents hydrogen or halogen (and preferably hydrogen or fluoro);
and to the salts (in particular pharmaceutically acceptable salts) of such compounds.

42) A further embodiment of the invention relates to compounds according to any one of embodiments 1) to 39), wherein
$R^4$ represents hydrogen;
and to the salts (in particular pharmaceutically acceptable salts) of such compounds.

43) A further embodiment of the invention relates to compounds according to any one of embodiments 1) to 4), 8) or 15) to 42), wherein
$R^5$ represents $(C_1-C_4)$alkyl, $(C_1-C_4)$alkoxy, $(C_1-C_4)$fluoroalkyl, halogen, cyano, optionally substituted aryl, optionally substituted heteroaryl or phenylsulfonyl;
and to the salts (in particular pharmaceutically acceptable salts) of such compounds.

44) A further embodiment of the invention relates to compounds according to any one of embodiments 1) to 5), 8), 9) or 15) to 42), wherein
$R^5$ represents $(C_1-C_4)$fluoroalkyl, halogen, cyano, optionally substituted aryl or optionally substituted heteroaryl (and preferably trifluoromethyl, fluoro, chloro, bromo, cyano, 4-fluorophenyl, [1,2,3]triazol-1-yl or [1,2,3]triazol-2-yl);
and to the salts (in particular pharmaceutically acceptable salts) of such compounds.

45) A further embodiment of the invention relates to compounds according to any one of embodiments 1) to 6), 8) to 13) or 15) to 42), wherein
$R^5$ represents halogen or cyano (and preferably fluoro, chloro or cyano);
and to the salts (in particular pharmaceutically acceptable salts) of such compounds.

46) A further embodiment of the invention relates to compounds according to any one of embodiments 1) to 42), wherein
$R^5$ represents halogen (and preferably fluoro or chloro);
and to the salts (in particular pharmaceutically acceptable salts) of such compounds.

47) A further embodiment of the invention relates to compounds according to any one of embodiments 1) to 5), 8) to 10) or 15) to 42), wherein
$R^5$ represents optionally substituted aryl or optionally substituted heteroaryl (and preferably 4-fluorophenyl, [1,2,3]triazol-1-yl or [1,2,3]triazol-2-yl);
and to the salts (in particular pharmaceutically acceptable salts) of such compounds.

48) A further embodiment of the invention relates to compounds according to any one of embodiments 1) to 47), wherein
at least one of $R^5$ and $R^6$ is different from hydrogen;
and to the salts (in particular pharmaceutically acceptable salts) of such compounds.

49) A further embodiment of the invention relates to compounds according to any one of embodiments 1) to 3), 8) or 15) to 42), wherein
$R^5$ represents hydrogen; and
$R^6$ represents halogen (preferably fluoro);
and to the salts (in particular pharmaceutically acceptable salts) of such compounds.

50) A further embodiment of the invention relates to compounds according to any one of embodiments 1) to 48), wherein
$R^6$ represents hydrogen;
and to the salts (in particular pharmaceutically acceptable salts) of such compounds.

51) A further embodiment of the invention relates to compounds according to any one of embodiments 1) to 50), wherein
R⁷ represents hydrogen;
and to the salts (in particular pharmaceutically acceptable salts) of such compounds.

52) A further embodiment of the invention relates to compounds according to any one of embodiments 1), 3) to 5), 7) to 11), 13) or 15) to 51), wherein
R¹⁰ represents —C(O)OH, —C(O)NH—S(O)₂CF₃ or optionally substituted heteroaryl;
and to the salts (in particular pharmaceutically acceptable salts) of such compounds.

53) A further embodiment of the invention relates to compounds according to any one of embodiments 1), 3) to 5), 7) to 11), 13) or 15) to 51), wherein
R¹⁰ represents —C(O)OH or optionally substituted heteroaryl;
and to the salts (in particular pharmaceutically acceptable salts) of such compounds.

54) A further embodiment of the invention relates to compounds according to any one of embodiments 1) to 51), wherein
R¹⁰ represents —C(O)OH;
and to the salts (in particular pharmaceutically acceptable salts) of such compounds.

55) A further embodiment of the invention relates to compounds according to any one of embodiments 1) to 54), wherein the absolute configuration of the stereogenic center is as depicted in formula ($I_{St1}$)

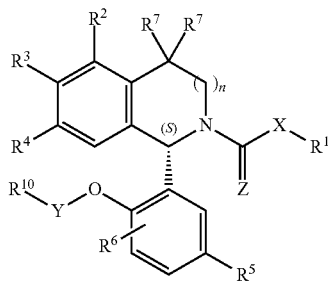

and to the salts (in particular pharmaceutically acceptable salts) of such compounds.

56) A further embodiment of the invention relates to compounds according to any one of embodiments 1) to 54), wherein the absolute configuration of the stereogenic center is as depicted in formula ($I_{St2}$)

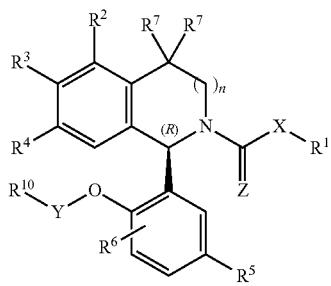

and to the salts (in particular pharmaceutically acceptable salts) of such compounds.

57) Preferred compounds of formula (I) as defined in embodiment 1) are selected from the group consisting of:
1-(2-Carboxymethoxy-5-fluoro-phenyl)-3,4-dihydro-1H-isoquinoline-2-carboxylic acid benzyl ester;
1-[2-((S)-1-Carboxy-ethoxy)-5-fluoro-phenyl]-3,4-dihydro-1H-isoquinoline-2-carboxylic acid benzyl ester;
1-(2-Carboxymethoxy-5-methyl-phenyl)-3,4-dihydro-1H-isoquinoline-2-carboxylic acid benzyl ester;
1-(5-Bromo-2-carboxymethoxy-phenyl)-3,4-dihydro-1H-isoquinoline-2-carboxylic acid benzyl ester;
7-Bromo-1-(2-carboxymethoxy-5-fluoro-phenyl)-3,4-dihydro-1H-isoquinoline-2-carboxylic acid benzyl ester;
1-(2-Carboxymethoxy-4,5-difluoro-phenyl)-3,4-dihydro-1H-isoquinoline-2-carboxylic acid benzyl ester;
5-Bromo-1-(2-carboxymethoxy-5-fluoro-phenyl)-3,4-dihydro-1H-isoquinoline-2-carboxylic acid benzyl ester;
1-[2-((R)-1-Carboxy-ethoxy)-5-fluoro-phenyl]-3,4-dihydro-1H-isoquinoline-2-carboxylic acid benzyl ester;
1-(2-Carboxymethoxy-5-fluoro-phenyl)-6,7-difluoro-3,4-dihydro-1H-isoquinoline-2-carboxylic acid benzyl ester;
1-(5-Bromo-2-carboxymethoxy-phenyl)-6,7-difluoro-3,4-dihydro-1H-isoquinoline-2-carboxylic acid benzyl ester;
1-(2-Carboxymethoxy-5-cyano-phenyl)-6,7-difluoro-3,4-dihydro-1H-isoquinoline-2-carboxylic acid benzyl ester;
1-(2-Carboxymethoxy-5-fluoro-phenyl)-5-trifluoromethyl-3,4-dihydro-1H-isoquinoline-2-carboxylic acid benzyl ester;
1-[2-((R)-1-Carboxy-ethoxy)-5-cyano-phenyl]-3,4-dihydro-1H-isoquinoline-2-carboxylic acid benzyl ester;
1-(2-Carboxymethoxy-5-fluoro-phenyl)-5,6-difluoro-3,4-dihydro-1H-isoquinoline-2-carboxylic acid benzyl ester;
1-(2-Carboxymethoxy-5-chloro-phenyl)-5,6-difluoro-3,4-dihydro-1H-isoquinoline-2-carboxylic acid benzyl ester;
1-(2-Carboxymethoxy-5-cyano-phenyl)-5,6-difluoro-3,4-dihydro-1H-isoquinoline-2-carboxylic acid benzyl ester;
1-(2-Carboxymethoxy-5-dimethylsulfamoyl-phenyl)-3,4-dihydro-1H-isoquinoline-2-carboxylic acid benzyl ester;
1-(2-Carboxymethoxy-5-chloro-phenyl)-5-fluoro-3,4-dihydro-1H-isoquinoline-2-carboxylic acid benzyl ester;
1-(2-Carboxymethoxy-5-cyano-phenyl)-5-fluoro-3,4-dihydro-1H-isoquinoline-2-carboxylic acid benzyl ester;
1-(2-Carboxymethoxy-5-trifluoromethyl-phenyl)-3,4-dihydro-1H-isoquinoline-2-carboxylic acid benzyl ester;
1-(2-Carboxymethoxy-5-chloro-phenyl)-3,4-dihydro-1H-isoquinoline-2-carboxylic acid benzyl ester;
1-(2-Carboxymethoxy-5-isopropyl-phenyl)-3,4-dihydro-1H-isoquinoline-2-carboxylic acid benzyl ester;
1-(6-Carboxymethoxy-benzo[1,3]dioxol-5-yl)-3,4-dihydro-1H-isoquinoline-2-carboxylic acid benzyl ester;
1-(2-Carboxymethoxy-5-methoxy-phenyl)-3,4-dihydro-1H-isoquinoline-2-carboxylic acid benzyl ester;
(S)-1-(2-Carboxymethoxy-5-cyano-phenyl)-3,4-dihydro-1H-isoquinoline-2-carboxylic acid benzyl ester;
(S)-1-(2-Carboxymethoxy-5-chloro-phenyl)-3,4-dihydro-1H-isoquinoline-2-carboxylic acid benzyl ester;
(S)-1-[2-((R)-1-Carboxy-ethoxy)-5-fluoro-phenyl]-3,4-dihydro-1H-isoquinoline-2-carboxylic acid benzyl ester;
(S)-1-[2-((S)-1-Carboxy-ethoxy)-5-fluoro-phenyl]-3,4-dihydro-1H-isoquinoline-2-carboxylic acid benzyl ester;
{4-Fluoro-2-[(S)-2-((trans)-2-phenyl-cyclopropanecarbonyl)-1,2,3,4-tetrahydro-isoquinolin-1-yl]-phenoxy}-acetic acid;
(S)-1-(2-Carboxymethoxy-5-chloro-phenyl)-5-fluoro-3,4-dihydro-1H-isoquinoline-2-carboxylic acid benzyl ester;

(S)-1-(2-Carboxymethoxy-5-cyano-phenyl)-5-fluoro-3,4-dihydro-1H-isoquinoline-2-carboxylic acid benzyl ester;

1-(2-Carboxymethoxy-3,5-difluoro-phenyl)-3,4-dihydro-1H-isoquinoline-2-carboxylic acid benzyl ester;

1-(2-Carboxymethoxy-5-fluoro-phenyl)-5-fluoro-3,4-dihydro-1H-isoquinoline-2-carboxylic acid benzyl ester;

1-(2-Carboxymethoxy-5-fluoro-phenyl)-5-methoxy-3,4-dihydro-1H-isoquinoline-2-carboxylic acid benzyl ester;

1-(2-Carboxymethoxy-5-fluoro-phenyl)-6,7-dimethoxy-3,4-dihydro-1H-isoquinoline-2-carboxylic acid benzyl ester;

1-(2-Carboxymethoxy-5-fluoro-phenyl)-7-methoxy-3,4-dihydro-1H-isoquinoline-2-carboxylic acid benzyl ester;

1-(2-Carboxymethoxy-5-fluoro-phenyl)-5-chloro-3,4-dihydro-1H-isoquinoline-2-carboxylic acid benzyl ester;

1-(2-Carboxymethoxy-5-fluoro-phenyl)-5-methyl-3,4-dihydro-1H-isoquinoline-2-carboxylic acid benzyl ester;

5-Bromo-1-(2-carboxymethoxy-5-fluoro-phenyl)-6-fluoro-3,4-dihydro-1H-isoquinoline-2-carboxylic acid benzyl ester;

1-(2-Carboxymethoxy-5-fluoro-phenyl)-7-fluoro-3,4-dihydro-1H-isoquinoline-2-carboxylic acid benzyl ester;

1-(2-Carboxymethoxy-5-fluoro-phenyl)-5,7-difluoro-3,4-dihydro-1H-isoquinoline-2-carboxylic acid benzyl ester;

1-(2-Carboxymethoxy-5-chloro-phenyl)-5,7-difluoro-3,4-dihydro-1H-isoquinoline-2-carboxylic acid benzyl ester;

1-(2-Carboxymethoxy-5-cyano-phenyl)-5,7-difluoro-3,4-dihydro-1H-isoquinoline-2-carboxylic acid benzyl ester;

{2-[2-(2-Benzo[d]isoxazol-3-yl-acetyl)-1,2,3,4-tetrahydro-isoquinolin-1-yl]-4-fluoro-phenoxy}-acetic acid;

{4-Fluoro-2-[2-(3-methyl-3-phenyl-butyryl)-1,2,3,4-tetrahydro-isoquinolin-1-yl]-phenoxy}-acetic acid;

{4-Fluoro-2-[2-(2-naphthalen-1-yl-acetyl)-1,2,3,4-tetrahydro-isoquinolin-1-yl]-phenoxy}-acetic acid;

{4-Fluoro-2-[2-(2-quinolin-7-yl-acetyl)-1,2,3,4-tetrahydro-isoquinolin-1-yl]-phenoxy}-acetic acid;

{4-Fluoro-2-[2-(2-quinolin-6-yl-acetyl)-1,2,3,4-tetrahydro-isoquinolin-1-yl]-phenoxy}-acetic acid;

{2-[2-(2-2,3-Dihydro-benzo[1,4]dioxin-6-yl-acetyl)-1,2,3,4-tetrahydro-isoquinolin-1-yl]-4-fluoro-phenoxy}-acetic acid;

{4-Fluoro-2-[2-(3-1H-indol-3-yl-propionyl)-1,2,3,4-tetrahydro-isoquinolin-1-yl]-phenoxy}-acetic acid;

(2-{2-[3-(1-Ethyl-2-methyl-1H-indol-3-yl)-propionyl]-1,2,3,4-tetrahydro-isoquinolin-1-yl}-4-fluoro-phenoxy)-acetic acid;

(2-{2-[3-(2,6-Dichloro-phenyl)-propionyl]-1,2,3,4-tetrahydro-isoquinolin-1-yl}-4-fluoro-phenoxy)-acetic acid;

(4-Fluoro-2-{2-[3-(2-fluoro-phenoxy)-propionyl]-1,2,3,4-tetrahydro-isoquinolin-1-yl}-phenoxy)-acetic acid;

[4-Fluoro-2-(2-{2-[4-(5-methyl-tetrazol-1-yl)-phenyl]acetyl}-1,2,3,4-tetrahydro-isoquinolin-1-yl)-phenoxy]-acetic acid;

(2-{2-[3-(6-Chloro-3-oxo-2,3-dihydro-benzo[1,4]oxazin-4-yl)-propionyl]-1,2,3,4-tetrahydro-isoquinolin-1-yl}-4-fluoro-phenoxy)-acetic acid;

(4-Fluoro-2-{2-[2-(2-methyl-thiazol-4-yl)-acetyl]-1,2,3,4-tetrahydro-isoquinolin-1-yl}-phenoxy)-acetic acid;

{2-[2-(2-Benzo[b]thiophen-3-yl-acetyl)-1,2,3,4-tetrahydro-isoquinolin-1-yl]-4-fluoro-phenoxy}-acetic acid;

{2-[2-(3-Benzothiazol-2-yl-propionyl)-1,2,3,4-tetrahydro-isoquinolin-1-yl]-4-fluoro-phenoxy}-acetic acid;

{2-[2-(2-Biphenyl-4-yl-acetyl)-1,2,3,4-tetrahydro-isoquinolin-1-yl]-4-fluoro-phenoxy}-acetic acid;

{4-Fluoro-2-[2-(2-indol-1-yl-acetyl)-1,2,3,4-tetrahydro-isoquinolin-1-yl]-phenoxy}-acetic acid;

{2-[2-(2-1H-Benzoimidazol-2-yl-acetyl)-1,2,3,4-tetrahydro-isoquinolin-1-yl]-4-fluoro-phenoxy}-acetic acid;

{2-[2-(2-1,3-Dihydro-isoindol-2-yl-acetyl)-1,2,3,4-tetrahydro-isoquinolin-1-yl]-4-fluoro-phenoxy}-acetic acid;

(4-Fluoro-2-{2-[3-(5-methoxy-1H-indol-3-yl)-propionyl]-1,2,3,4-tetrahydro-isoquinolin-1-yl}-phenoxy)-acetic acid;

(4-Fluoro-2-{2-[3-(2-methyl-1H-indol-3-yl)-propionyl]-1,2,3,4-tetrahydro-isoquinolin-1-yl}-phenoxy)-acetic acid;

(4-Fluoro-2-{2-[3-(1-methyl-1H-indol-3-yl)-propionyl]-1,2,3,4-tetrahydro-isoquinolin-1-yl}-phenoxy)-acetic acid;

{4-Fluoro-2-[2-(trans-2-phenyl-cyclopropanecarbonyl)-1,2,3,4-tetrahydro-isoquinolin-1-yl]-phenoxy}-acetic acid;

{4-Chloro-2-[2-(2-cyclopropyl-acetyl)-1,2,3,4-tetrahydro-isoquinolin-1-yl]-phenoxy}-acetic acid;

{4-Chloro-2-[2-(2H-chromene-3-carbonyl)-1,2,3,4-tetrahydro-isoquinolin-1-yl]-phenoxy}-acetic acid;

{4-Chloro-2-[2-(3-methoxy-propionyl)-1,2,3,4-tetrahydro-isoquinolin-1-yl]-phenoxy}-acetic acid;

(4-Chloro-2-{2-[2-(2-chloro-phenyl)-acetyl]-1,2,3,4-tetrahydro-isoquinolin-1-yl}-phenoxy)-acetic acid;

{4-Chloro-2-[2-(2-indol-1-yl-acetyl)-1,2,3,4-tetrahydro-isoquinolin-1-yl]-phenoxy}-acetic acid;

(4-Chloro-2-{2-[3-(2-methyl-1H-indol-3-yl)-propionyl]-1,2,3,4-tetrahydro-isoquinolin-1-yl}-phenoxy)-acetic acid;

(4-Chloro-2-{2-[3-(5-methoxy-1H-indol-3-yl)-propionyl]-1,2,3,4-tetrahydro-isoquinolin-1-yl}-phenoxy)-acetic acid;

(4-Chloro-2-{2-[2-(2,6-dimethyl-pyridin-3-yloxy)-acetyl]-1,2,3,4-tetrahydro-isoquinolin-1-yl}-phenoxy)-acetic acid;

(4-Chloro-2-{2-[3-(1-methyl-1H-indol-3-yl)-propionyl]-1,2,3,4-tetrahydro-isoquinolin-1-yl}-phenoxy)-acetic acid;

{4-Chloro-2-[2-(1,2,3,4-tetrahydro-naphthalene-2-carbonyl)-1,2,3,4-tetrahydro-isoquinolin-1-yl]-phenoxy}-acetic acid;

{2-[2-(2-Benzoimidazol-1-yl-acetyl)-1,2,3,4-tetrahydro-isoquinolin-1-yl]-4-chloro-phenoxy}-acetic acid;

{4-Chloro-2-[2-(2-3,4-dihydro-2H-quinolin-1-yl-acetyl)-1,2,3,4-tetrahydro-isoquinolin-1-yl]-phenoxy}-acetic acid;

{4-Chloro-2-[2-(2-indazol-2-yl-acetyl)-1,2,3,4-tetrahydro-isoquinolin-1-yl]-phenoxy}-acetic acid;

(4-Chloro-2-{2-[3-(3-trifluoromethyl-phenyl)-propionyl]-1,2,3,4-tetrahydro-isoquinolin-1-yl}-phenoxy)-acetic acid;

(4-Chloro-2-{2-trans-[2-(2-chloro-phenyl)-cyclopropanecarbonyl]-1,2,3,4-tetrahydro-isoquinolin-1-yl}-phenoxy)-acetic acid;

(4-Chloro-2-{2-[3-(1-phenyl-1H-imidazol-2-yl)-propionyl]-1,2,3,4-tetrahydro-isoquinolin-1-yl}-phenoxy)-acetic acid;

(4-Chloro-2-{2-[3-(4-oxo-2-phenyl-thiazolidin-3-yl)-propionyl]-1,2,3,4-tetrahydro-isoquinolin-1-yl}-phenoxy)-acetic acid;

[4-Chloro-2-(2-{3-[3-(2,3-dimethyl-phenyl)-3H-imidazol-4-yl]-propionyl}-1,2,3,4-tetrahydro-isoquinolin-1-yl)-phenoxy]-acetic acid;

(2-{2-[2-(Biphenyl-2-yloxy)-acetyl]-1,2,3,4-tetrahydro-isoquinolin-1-yl}-4-chloro-phenoxy)-acetic acid;

(4-Chloro-2-{2-[3-(3-fluoro-phenoxy)-propionyl]-1,2,3,4-tetrahydro-isoquinolin-1-yl}-phenoxy)-acetic acid;

{4-Chloro-2-[2-(3-p-tolyloxy-propionyl)-1,2,3,4-tetrahydro-isoquinolin-1-yl]-phenoxy}-acetic acid;

(4-Chloro-2-{2-[3-(4-chloro-phenoxy)-propionyl]-1,2,3,4-tetrahydro-isoquinolin-1-yl}-phenoxy)-acetic acid;

(4-Chloro-2-{2-[3-(2-trifluoromethyl-phenyl)-propionyl]-1,2,3,4-tetrahydro-isoquinolin-1-yl}-phenoxy)-acetic acid;

(4-Chloro-2-{2-[2-(5-fluoro-1H-indol-3-yl)-acetyl]-1,2,3,4-tetrahydro-isoquinolin-1-yl}-phenoxy)-acetic acid;

(4-Chloro-2-{2-[2-(6-methoxy-benzofuran-3-yl)-acetyl]-1,2,3,4-tetrahydro-isoquinolin-1-yl}-phenoxy)-acetic acid;
(4-Chloro-2-{2-[4-(4-chloro-phenyl)-butyryl]-1,2,3,4-tetrahydro-isoquinolin-1-yl}-phenoxy)-acetic acid;
{4-Chloro-2-[2-(3-m-tolyloxy-propionyl)-1,2,3,4-tetrahydro-isoquinolin-1-yl]-phenoxy}-acetic acid;
(4-Chloro-2-{2-[3-(3-chloro-phenoxy)-propionyl]-1,2,3,4-tetrahydro-isoquinolin-1-yl}-phenoxy)-acetic acid;
(4-Chloro-2-{2-[2-(5-chloro-1H-indol-3-yl)-acetyl]-1,2,3,4-tetrahydro-isoquinolin-1-yl}-phenoxy)-acetic acid;
{4-Chloro-2-[2-(4-p-tolyl-butyryl]-1,2,3,4-tetrahydro-isoquinolin-1-yl]-phenoxy}-acetic acid;
(4-Chloro-2-{2-[2-(5-chloro-benzo[b]thiophen-3-yl)-acetyl]-1,2,3,4-tetrahydro-isoquinolin-1-yl}-phenoxy)-acetic acid;
(4-Chloro-2-{2-[2-(5-methoxy-1H-indol-2-yl)-acetyl]-1,2,3,4-tetrahydro-isoquinolin-1-yl}-phenoxy)-acetic acid;
(4-Chloro-2-{2-[2-(5-methyl-benzo[d]isoxazol-3-yl)-acetyl]-1,2,3,4-tetrahydro-isoquinolin-1-yl}-phenoxy)-acetic acid;
(4-Chloro-2-{2-[2-(5-methoxy-benzo[d]isoxazol-3-yl)-acetyl]-1,2,3,4-tetrahydro-isoquinolin-1-yl}-phenoxy)-acetic acid;
(4-Chloro-2-{2-[3-(4-fluoro-phenoxy)-propionyl]-1,2,3,4-tetrahydro-isoquinolin-1-yl}-phenoxy)-acetic acid;
(4-Chloro-2-{2-[4-(4-fluoro-phenyl)-butyryl]-1,2,3,4-tetrahydro-isoquinolin-1-yl}-phenoxy)-acetic acid;
{4-Chloro-2-[2-(3-o-tolyl-propionyl)-1,2,3,4-tetrahydro-isoquinolin-1-yl]-phenoxy}-acetic acid;
{2-[2-(2-Benzyloxy-acetyl)-1,2,3,4-tetrahydro-isoquinolin-1-yl]-4-chloro-phenoxy}-acetic acid;
(4-Chloro-2-{2-[2-(2-chloro-benzyloxy)-acetyl]-1,2,3,4-tetrahydro-isoquinolin-1-yl}-phenoxy)-acetic acid;
{4-Chloro-2-[2-(4-phenyl-butyryl)-1,2,3,4-tetrahydro-isoquinolin-1-yl]-phenoxy}-acetic acid;
(4-Chloro-2-{2-[4-(3-fluoro-phenyl)-butyryl]-1,2,3,4-tetrahydro-isoquinolin-1-yl}-phenoxy)-acetic acid;
(4-Chloro-2-{2-[4-(2,3-dichloro-phenyl)-butyryl]-1,2,3,4-tetrahydro-isoquinolin-1-yl}-phenoxy)-acetic acid;
{4-Chloro-2-[2-(4-m-tolyl-butyryl)-1,2,3,4-tetrahydro-isoquinolin-1-yl]-phenoxy}-acetic acid;
{4-Chloro-2-[2-(4-o-tolyl-butyryl)-1,2,3,4-tetrahydro-isoquinolin-1-yl]-phenoxy}-acetic acid;
(4-Chloro-2-{2-[4-(3-chloro-phenyl)-butyryl]-1,2,3,4-tetrahydro-isoquinolin-1-yl}-phenoxy)-acetic acid;
(4-Chloro-2-{2-[4-(2-chloro-phenyl)-butyryl]-1,2,3,4-tetrahydro-isoquinolin-1-yl}-phenoxy)-acetic acid;
(4-Chloro-2-{2-[4-(3-methoxy-phenyl)-butyryl]-1,2,3,4-tetrahydro-isoquinolin-1-yl}-phenoxy)-acetic acid;
(4-Chloro-2-{2-[4-(2-fluoro-phenyl)-butyryl]-1,2,3,4-tetrahydro-isoquinolin-1-yl}-phenoxy)-acetic acid;
{4-Chloro-2-[2-(trans-2-phenyl-cyclopropanecarbonyl)-1,2,3,4-tetrahydro-isoquinolin-1-yl]-phenoxy}-acetic acid;
{4-Chloro-2-[5-fluoro-2-(trans-2-phenyl-cyclopropanecarbonyl)-1,2,3,4-tetrahydro-isoquinolin-1-yl]-phenoxy}-acetic acid;
{4-Chloro-2-[5-fluoro-2-(3-o-tolyl-propionyl)-1,2,3,4-tetrahydro-isoquinolin-1-yl]-phenoxy}-acetic acid;
{2-[2-(2-Benzyloxy-acetyl)-5-fluoro-1,2,3,4-tetrahydro-isoquinolin-1-yl]-4-chloro-phenoxy}-acetic acid;
(4-Chloro-2-{2-[2-(2-chloro-benzyloxy)-acetyl]-5-fluoro-1,2,3,4-tetrahydro-isoquinolin-1-yl}-phenoxy)-acetic acid;
{4-Chloro-2-[5-fluoro-2-(4-phenyl-butyryl)-1,2,3,4-tetrahydro-isoquinolin-1-yl]-phenoxy}-acetic acid;
{4-Chloro-2-[5-fluoro-2-(3-phenyl-propynoyl)-1,2,3,4-tetrahydro-isoquinolin-1-yl]-phenoxy}-acetic acid;
{4-Fluoro-2-[2-(3-phenyl-propionyl)-1,2,3,4-tetrahydro-isoquinolin-1-yl]-phenoxy}-acetic acid;
[4-Fluoro-2-(2-phenylacetyl-1,2,3,4-tetrahydro-isoquinolin-1-yl)-phenoxy]-acetic acid;
{4-Fluoro-2-[2-(2-phenoxy-acetyl)-1,2,3,4-tetrahydro-isoquinolin-1-yl]-phenoxy}-acetic acid;
{2-[2-(2-Benzyloxy-acetyl)-1,2,3,4-tetrahydro-isoquinolin-1-yl]-4-fluoro-phenoxy}-acetic acid;
{4-Fluoro-2-[2-(4-phenyl-butyryl)-1,2,3,4-tetrahydro-isoquinolin-1-yl]-phenoxy}-acetic acid;
(4-Fluoro-2-{2-[3-(2-methoxy-phenyl)-propionyl]-1,2,3,4-tetrahydro-isoquinolin-1-yl}-phenoxy)-acetic acid;
(4-Fluoro-2-{2-[3-(3-methoxy-phenyl)-propionyl]-1,2,3,4-tetrahydro-isoquinolin-1-yl}-phenoxy)-acetic acid;
(4-Fluoro-2-{2-[3-(4-methoxy-phenyl)-propionyl]-1,2,3,4-tetrahydro-isoquinolin-1-yl}-phenoxy)-acetic acid;
(2-{2-[3-(2-Chloro-phenyl)-propionyl]-1,2,3,4-tetrahydro-isoquinolin-1-yl}-4-fluoro-phenoxy)-acetic acid;
(2-{2-[3-(3-Chloro-phenyl)-propionyl]-1,2,3,4-tetrahydro-isoquinolin-1-yl}-4-fluoro-phenoxy)-acetic acid;
(2-{2-[3-(4-Chloro-phenyl)-propionyl]-1,2,3,4-tetrahydro-isoquinolin-1-yl}-4-fluoro-phenoxy)-acetic acid;
{4-Fluoro-2-[2-(3-o-tolyl-propionyl)-1,2,3,4-tetrahydro-isoquinolin-1-yl]-phenoxy}-acetic acid;
{4-Fluoro-2-[2-(2-naphthalen-2-yl-acetyl) 1,2,3,4-tetrahydro-isoquinolin-1-yl]-phenoxy}-acetic acid;
{4-Fluoro-2-[2-(2-o-tolyloxy-acetyl)-1,2,3,4-tetrahydro-isoquinolin-1-yl]-phenoxy}-acetic acid;
(4-Fluoro-2-{2-[2-(1-methyl-1H-indol-3-yl)-acetyl]-1,2,3,4-tetrahydro-isoquinolin-1-yl}-phenoxy)-acetic acid;
(2-{2-[2-(2-Chloro-phenoxy)-acetyl]-1,2,3,4-tetrahydro-isoquinolin-1-yl}-4-fluoro-phenoxy)-acetic acid;
(4-Fluoro-2-{2-[3-(2-fluoro-phenyl)-propionyl]-1,2,3,4-tetrahydro-isoquinolin-1-yl}-phenoxy)-acetic acid;
{4-Fluoro-2-[2-(2-indan-2-yl-acetyl)-1,2,3,4-tetrahydro-isoquinolin-1-yl]-phenoxy}-acetic acid;
(4-Fluoro-2-{2-[(E)-3-(2-fluoro-phenyl)-acryloyl]-1,2,3,4-tetrahydro-isoquinolin-1-yl}-phenoxy)-acetic acid;
{4-Fluoro-2-[2-((E)-3-o-tolyl-acryloyl)-1,2,3,4-tetrahydro-isoquinolin-1-yl]-phenoxy}-acetic acid;
{4-Fluoro-2-[2-(5-phenyl-pentanoyl)-1,2,3,4-tetrahydro-isoquinolin-1-yl]-phenoxy}-acetic acid;
{4-Fluoro-2-[2-(3-phenoxy-propionyl)-1,2,3,4-tetrahydro-isoquinolin-1-yl]-phenoxy}-acetic acid;
(4-Fluoro-2-{2-[3-(4-methanesulfonyl-phenyl)-propionyl]-1,2,3,4-tetrahydro-isoquinolin-1-yl}-phenoxy)-acetic acid;
{2-[2-(3-2,3-Dihydro-indol-1-yl-propionyl)-1,2,3,4-tetrahydro-isoquinolin-1-yl]-4-fluoro-phenoxy}-acetic acid;
{4-Fluoro-2-[2-(3-o-tolyloxy-propionyl)-1,2,3,4-tetrahydro-isoquinolin-1-yl]-phenoxy}-acetic acid;
(4-Fluoro-2-{2-[2-(2-fluoro-phenoxy)-acetyl]-1,2,3,4-tetrahydro-isoquinolin-1-yl}-phenoxy)-acetic acid;
(4-Fluoro-2-{2-[4-(2-methoxy-phenyl)-butyryl]-1,2,3,4-tetrahydro-isoquinolin-1-yl}-phenoxy)-acetic acid;
(2-{2-[2-(2-Chloro-benzyloxy)-acetyl]-1,2,3,4-tetrahydro-isoquinolin-1-yl}-4-fluoro-phenoxy)-acetic acid;
(4-Chloro-2-{2-[(trans)-2-(3-chloro-phenyl)-cyclopropanecarbonyl]-1,2,3,4-tetrahydro-isoquinolin-1-yl}-phenoxy)-acetic acid;
{4-Chloro-2-[2-((trans)-2-o-tolyl-cyclopropanecarbonyl)-1,2,3,4-tetrahydro-isoquinolin-1-yl]-phenoxy}-acetic acid;
(4-Chloro-2-{2-[(trans)-2-(2-trifluoromethyl-phenyl)-cyclopropanecarbonyl]-1,2,3,4-tetrahydro-isoquinolin-1-yl}-phenoxy)-acetic acid;

(4-Chloro-2-{2-[trans-2-(4-chloro-phenyl)-cyclopropanecarbonyl]-1,2,3,4-tetrahydro-isoquinolin-1-yl}-phenoxy)-acetic acid;
(4-Chloro-2-{2-[trans-2-(2,4-dichloro-phenyl)-cyclopropanecarbonyl]-1,2,3,4-tetrahydro-isoquinolin-1-yl}-phenoxy)-acetic acid;
(4-Chloro-2-{2-[trans-2-(2-methoxy-phenyl)-cyclopropanecarbonyl]-1,2,3,4-tetrahydro-isoquinolin-1-yl}-phenoxy)-acetic acid;
(4-Chloro-2-{2-[trans-2-(2-fluoro-phenyl)-cyclopropanecarbonyl]-1,2,3,4-tetrahydro-isoquinolin-1-yl}-phenoxy)-acetic acid;
(4-Chloro-2-{2-[3-(3-phenyl-3H-[1,2,3]triazol-4-yl)-propionyl]-1,2,3,4-tetrahydro-isoquinolin-1-yl}-phenoxy)-acetic acid;
(4-Chloro-2-{2-[2-(3-phenyl-3H-[1,2,3]triazol-4-ylsulfanyl)-acetyl]-1,2,3,4-tetrahydro-isoquinolin-1-yl}-phenoxy)-acetic acid;
1-(2-Carboxymethoxy-5-fluoro-phenyl)-6-fluoro-3,4-dihydro-1H-isoquinoline-2-carboxylic acid benzyl ester;
1-(2-Carboxymethoxy-5-chloro-phenyl)-3,4-dihydro-1H-isoquinoline-2-carboxylic acid 2-chloro-benzyl ester;
1-(2-Carboxymethoxy-5-fluoro-phenyl)-3,4-dihydro-1H-isoquinoline-2-carboxylic acid 2-chloro-benzyl ester;
1-(2-Carboxymethoxy-5-fluoro-phenyl)-3,4-dihydro-1H-isoquinoline-2-carboxylic acid 2,2-dimethyl-propyl ester;
1-(2-Carboxymethoxy-5-fluoro-phenyl)-3,4-dihydro-1H-isoquinoline-2-carboxylic acid butyl ester;
1-(2-Carboxymethoxy-5-fluoro-phenyl)-3,4-dihydro-1H-isoquinoline-2-carboxylic acid 2-methoxy-phenyl ester;
1-(2-Carboxymethoxy-5-fluoro-phenyl)-3,4-dihydro-1H-isoquinoline-2-carboxylic acid phenyl ester;
1-(2-Carboxymethoxy-5-fluoro-phenyl)-3,4-dihydro-1H-isoquinoline-2-carboxylic acid 2-chloro-phenyl ester;
1-(2-Carboxymethoxy-5-fluoro-phenyl)-3,4-dihydro-1H-isoquinoline-2-carboxylic acid isobutyl ester;
1-(2-Carboxymethoxy-5-fluoro-phenyl)-3,4-dihydro-1H-isoquinoline-2-carboxylic acid 2-methoxy-ethyl ester;
1-(2-Carboxymethoxy-5-fluoro-phenyl)-3,4-dihydro-1H-isoquinoline-2-carboxylic acid 4-methoxy-phenyl ester;
(S)-1-(2-Carboxymethoxy-5-chloro-phenyl)-3,4-dihydro-1H-isoquinoline-2-carboxylic acid 2-chloro-benzyl ester;
1-(2-Carboxymethoxy-5-chloro-phenyl)-5-fluoro-3,4-dihydro-1H-isoquinoline-2-carboxylic acid 2-chloro-benzyl ester;
1-(2-Carboxymethoxy-5-chloro-phenyl)-3,4-dihydro-1H-isoquinoline-2-carboxylic acid 2-(2-chloro-phenyl)-ethyl ester;
1-(2-Carboxymethoxy-5-fluoro-phenyl)-3,4-dihydro-1H-isoquinoline-2-carboxylic acid 2-(2-chloro-phenyl)-ethyl ester;
1-(2-Carboxymethoxy-5-fluoro-phenyl)-3,4-dihydro-1H-isoquinoline-2-carboxylic acid 3-chloro-phenyl ester;
1-(2-Carboxymethoxy-5-chloro-phenyl)-5-fluoro-3,4-dihydro-1H-isoquinoline-2-carboxylic acid 2-(2-chloro-phenyl)-ethyl ester;
1-(2-Carboxymethoxy-5-chloro-phenyl)-4,4-dimethyl-3,4-dihydro-1H-isoquinoline-2-carboxylic acid benzyl ester;
1-(2-Carboxymethoxy-5-fluoro-phenyl)-7-ethanesulfonyl-3,4-dihydro-1H-isoquinoline-2-carboxylic acid benzyl ester;
1-(2-Carboxymethoxy-5-methanesulfonyl-phenyl)-3,4-dihydro-1H-isoquinoline-2-carboxylic acid benzyl ester;
1-(5-Benzenesulfonyl-2-carboxymethoxy-phenyl)-3,4-dihydro-1H-isoquinoline-2-carboxylic acid benzyl ester;
1-(2-Carboxymethoxy-5-ethanesulfonyl-phenyl)-3,4-dihydro-1H-isoquinoline-2-carboxylic acid benzyl ester;
1-(2-Carboxymethoxy-5-fluoro-phenyl)-5-methanesulfonyl-3,4-dihydro-1H-isoquinoline-2-carboxylic acid benzyl ester;
1-(2-Carboxymethoxy-5-fluoro-phenyl)-5-ethanesulfonyl-3,4-dihydro-1H-isoquinoline-2-carboxylic acid benzyl ester;
5-Benzenesulfonyl-1-(2-carboxymethoxy-5-fluoro-phenyl)-3,4-dihydro-1H-isoquinoline-2-carboxylic acid benzyl ester;
1-(2-Carboxymethoxy-5-pyrimidin-5-yl-phenyl)-3,4-dihydro-1H-isoquinoline-2-carboxylic acid benzyl ester;
1-(4-Carboxymethoxy-4'-fluoro-biphenyl-3-yl)-3,4-dihydro-1H-isoquinoline-2-carboxylic acid benzyl ester;
(2-{2-[2-(3-Chloro-benzyloxy)-acetyl]-1,2,3,4-tetrahydro-isoquinolin-1-yl}-4-fluoro-phenoxy)-acetic acid;
(2-{2-[2-(4-Chloro-benzyloxy)-acetyl]-1,2,3,4-tetrahydro-isoquinolin-1-yl}-4-fluoro-phenoxy)-acetic acid;
(4-Fluoro-2-{2-[2-(2-methyl-benzyloxy)-acetyl]-1,2,3,4-tetrahydro-isoquinolin-1-yl}-phenoxy)-acetic acid;
(4-Fluoro-2-{2-[2-(3-methyl-benzyloxy)-acetyl]-1,2,3,4-tetrahydro-isoquinolin-1-yl}-phenoxy)-acetic acid;
(4-Fluoro-2-{2-[2-(4-methyl-benzyloxy)-acetyl]-1,2,3,4-tetrahydro-isoquinolin-1-yl}-phenoxy)-acetic acid;
(4-Fluoro-2-{2-[2-(3-methoxy-benzyloxy)-acetyl]-1,2,3,4-tetrahydro-isoquinolin-1-yl}-phenoxy)-acetic acid;
(4-Fluoro-2-{2-[2-(4-methoxy-benzyloxy)-acetyl]-1,2,3,4-tetrahydro-isoquinolin-1-yl}-phenoxy)-acetic acid;
(4-Fluoro-2-{2-[2-(1-methyl-1H-pyrazol-3-ylmethoxy)-acetyl]-1,2,3,4-tetrahydro-isoquinolin-1-yl}-phenoxy)-acetic acid;
(4-Fluoro-2-{2-[2-(2-methoxy-benzyloxy)-acetyl]-1,2,3,4-tetrahydro-isoquinolin-1-yl}-phenoxy)-acetic acid;
[2-(2-Benzylcarbamoyl-1,2,3,4-tetrahydro-isoquinolin-1-yl)-4-fluoro-phenoxy]-acetic acid;
[4-Fluoro-2-(2-phenethylcarbamoyl-1,2,3,4-tetrahydro-isoquinolin-1-yl)-phenoxy]-acetic acid;
{4-Fluoro-2-[2-(2-methoxy-benzylcarbamoyl)-1,2,3,4-tetrahydro-isoquinolin-1-yl]-phenoxy}-acetic acid;
{4-Chloro-2-[2-(2-methoxy-benzylcarbamoyl)-1,2,3,4-tetrahydro-isoquinolin-1-yl]-phenoxy}-acetic acid;
{2-[2-(2-Chloro-benzylcarbamoyl)-1,2,3,4-tetrahydro-isoquinolin-1-yl]-4-fluoro-phenoxy}-acetic acid;
(2-{2-[2-(2-Chloro-phenyl)-ethylcarbamoyl]-1,2,3,4-tetrahydro-isoquinolin-1-yl}-4-fluoro-phenoxy)-acetic acid;
{2-[2-(2-Benzenesulfonylamino-acetyl)-1,2,3,4-tetrahydro-isoquinolin-1-yl]-4-fluoro-phenoxy}-acetic acid;
(2-{2-[2-(3,5-Dimethyl-isoxazole-4-sulfonylamino)-acetyl]-1,2,3,4-tetrahydro-isoquinolin-1-yl}-4-fluoro-phenoxy)-acetic acid;
(4-Fluoro-2-{2-[2-(3-fluoro-benzenesulfonylamino)-acetyl]-1,2,3,4-tetrahydro-isoquinolin-1-yl}-phenoxy)-acetic acid;
(4-Fluoro-2-{2-[2-(2-fluoro-benzenesulfonylamino)-acetyl]-1,2,3,4-tetrahydro-isoquinolin-1-yl}-phenoxy)-acetic acid;
(2-{2-[2-(3,4-Difluoro-benzenesulfonylamino)-acetyl]-1,2,3,4-tetrahydro-isoquinolin-1-yl}-4-fluoro-phenoxy)-acetic acid;
(2-{2-[2-(N-Benzenesulfonyl-N-methyl-amino)-acetyl]-1,2,3,4-tetrahydro-isoquinolin-1-yl}-4-fluoro-phenoxy)-acetic acid;
[4-Fluoro-2-(2-{2-[N-(3-fluoro-benzenesulfonyl)-N-methyl-amino]-acetyl}-1,2,3,4-tetrahydro-isoquinolin-1-yl)-phenoxy]-acetic acid;
[2-(2-{2-[N-(3,4-Difluoro-benzenesulfonyl)-N-methyl-amino]-acetyl}-1,2,3,4-tetrahydro-isoquinolin-1-yl)-4-fluoro-phenoxy]-acetic acid;

1-(5-Carbamoyl-2-carboxymethoxy-phenyl)-3,4-dihydro-1H-isoquinoline-2-carboxylic acid benzyl ester;
1-[2-Carboxymethoxy-5-(5-thioxo-4,5-dihydro-[1,2,4]oxadiazol-3-yl)-phenyl]-3,4-dihydro-1H-isoquinoline-2-carboxylic acid benzyl ester;
1-(2-Carboxymethoxy-4-fluoro-phenyl)-3,4-dihydro-1H-isoquinoline-2-carboxylic acid benzyl ester;
1-(2-Carboxymethoxy-6-fluoro-phenyl)-3,4-dihydro-1H-isoquinoline-2-carboxylic acid benzyl ester;
1-[2-(3-Carboxy-propoxy)-5-fluoro-phenyl]-3,4-dihydro-1H-isoquinoline-2-carboxylic acid benzyl ester;
{4-Cyano-2-[2-(trans-2-phenyl-cyclopropanecarbonyl)-1,2,3,4-tetrahydro-isoquinolin-1-yl]-phenoxy}-acetic acid;
1-(2-Carboxymethoxy-5-cyano-phenyl)-3,4-dihydro-1H-isoquinoline-2-carboxylic acid benzyl ester;
(R)-1-[2-(1-Carboxy-ethoxy)-5-chloro-phenyl]-3,4-dihydro-1H-isoquinoline-2-carboxylic acid benzyl ester;
(S)-1-(2-Carboxymethoxy-5-fluoro-phenyl)-3,4-dihydro-1H-isoquinoline-2-carboxylic acid benzyl ester;
1-(2-Carboxymethoxy-5-fluoro-phenyl)-5-methanesulfonylamino-3,4-dihydro-1H-isoquinoline-2-carboxylic acid benzyl ester;
1-(2-Carboxymethoxy-5-[1,2,3]triazol-1-yl-phenyl)-3,4-dihydro-1H-isoquinoline-2-carboxylic acid benzyl ester;
1-(2-Carboxymethoxy-5-[1,2,3]triazol-2-yl-phenyl)-3,4-dihydro-1H-isoquinoline-2-carboxylic acid benzyl ester; and
{4-Chloro-2-[2-(2-methoxy-benzylthiocarbamoyl)-1,2,3,4-tetrahydro-isoquinolin-1-yl]-phenoxy}-acetic acid;
or salts (in particular pharmaceutically acceptable salts) of such compounds;
it is to be understood for any of the above listed compounds, that a stereogenic center, which is not specifically assigned, may be in absolute (R)- or absolute (S)-configuration and that a double bond, which is not specifically assigned, may be in (E)- or (Z)-configuration; for example, the stereogenic center at the 1-position of the 1,2,3,4-tetrahydroisoquinoline core-structure may be in absolute (R)-configuration or absolute (S)-configuration (and preferably in absolute (S)-configuration). Notably, compounds containing more than one stereogenic center may be at each stereogenic center, which is not specifically assigned, in absolute (R)- or absolute (S)-configuration; for example a compound listed as {4-Fluoro-2-[2-(trans-2-phenyl-cyclopropanecarbonyl)-1,2,3,4-tetrahydro-isoquinolin-1-yl]-phenoxy}-acetic acid may be 2-{4-fluoro-2-[(S)-2-((1R,2R)-2-phenyl-cyclopropanecarbonyl)-1,2,3,4-tetrahydroisoquinolin-1-yl]-phenoxy}-acetic acid, 2-{4-fluoro-2-[(S)-2-((1S,2S)-2-phenyl-cyclopropanecarbonyl)-1,2,3,4-tetrahydroisoquinolin-1-yl]-phenoxy}-acetic acid, 2-{4-fluoro-2-[(R)-2-((1R,2R)-2-phenyl-cyclopropanecarbonyl)-1,2,3,4-tetrahydroisoquinolin-1-yl]-phenoxy}-acetic acid, 2-{4-fluoro-2-[(R)-2-((1S,2S)-2-phenyl-cyclopropanecarbonyl)-1,2,3,4-tetrahydroisoquinolin-1-yl]-phenoxy}-acetic acid or a mixture thereof (and preferably 2-{4-fluoro-2-[(S)-2-((1R,2R)-2-phenyl-cyclopropanecarbonyl)-1,2,3,4-tetrahydroisoquinolin-1-yl]-phenoxy}-acetic acid or 2-{4-fluoro-2-[(S)-2-((1S,2S)-2-phenyl-cyclopropanecarbonyl)-1,2,3,4-tetrahydroisoquinolin-1-yl]-phenoxy}acetic acid).

58) Further preferred compounds of formula (I) as defined in embodiment 1) are selected from the group consisting of:
1-(2-Carboxymethoxy-5-chloro-phenyl)-6-fluoro-3,4-dihydro-1H-isoquinoline-2-carboxylic acid benzyl ester;
1-(2-Carboxymethoxy-5-chloro-phenyl)-3,4-dihydro-1H-isoquinoline-2-carboxylic acid 2-bromo-benzyl ester;
(S)-1-(2-Carboxymethoxy-5-chloro-phenyl)-5,6-difluoro-3,4-dihydro-1H-isoquinoline-2-carboxylic acid benzyl ester;
1-(2-Carboxymethoxy-5-chloro-phenyl)-1,3-dihydro-isoindole-2-carboxylic acid benzyl ester;
{4-Chloro-2-[(S)-2-((1R,2R)-2-phenyl-cyclopropanecarbonyl)-1,2,3,4-tetrahydro-isoquinolin-1-yl]-phenoxy}-acetic acid;
1-(2-Carboxymethoxy-5-chloro-phenyl)-3,4-dihydro-1H-isoquinoline-2-carboxylic acid 2-methoxy-benzyl ester;
1-(2-Carboxymethoxy-5-chloro-phenyl)-3,4-dihydro-1H-isoquinoline-2-carboxylic acid 2-fluoro-benzyl ester;
1-(2-Carboxymethoxy-5-chloro-phenyl)-3,4-dihydro-1H-isoquinoline-2-carboxylic acid 2-methyl-benzyl ester;
1-(2-Carboxymethoxy-5-chloro-phenyl)-3,4-dihydro-1H-isoquinoline-2-carboxylic acid 2-trifluoromethyl-benzyl ester;
1-(2-Carboxymethoxy-5-chloro-phenyl)-3,4-dihydro-1H-isoquinoline-2-carboxylic acid 3-methoxy-benzyl ester;
1-(2-Carboxymethoxy-5-chloro-phenyl)-3,4-dihydro-1H-isoquinoline-2-carboxylic acid 3-fluoro-benzyl ester;
1-(2-Carboxymethoxy-5-chloro-phenyl)-3,4-dihydro-1H-isoquinoline-2-carboxylic acid 3-methyl-benzyl ester;
1-(2-Carboxymethoxy-5-chloro-phenyl)-3,4-dihydro-1H-isoquinoline-2-carboxylic acid 3-trifluoromethyl-benzyl ester;
1-(2-Carboxymethoxy-5-chloro-phenyl)-3,4-dihydro-1H-isoquinoline-2-carboxylic acid 2,4-dichloro-benzyl ester;
1-(2-Carboxymethoxy-5-chloro-phenyl)-3,4-dihydro-1H-isoquinoline-2-carboxylic acid 2,3-dichloro-benzyl ester;
1-(2-Carboxymethoxy-5-chloro-phenyl)-3,4-dihydro-1H-isoquinoline-2-carboxylic acid 2,6-dichloro-benzyl ester;
1-(2-Carboxymethoxy-5-chloro-phenyl)-3,4-dihydro-1H-isoquinoline-2-carboxylic acid 2,6-dimethoxy-benzyl ester;
1-(2-Carboxymethoxy-5-chloro-phenyl)-3,4-dihydro-1H-isoquinoline-2-carboxylic acid 2,4-dimethyl-benzyl ester;
1-(2-Carboxymethoxy-5-chloro-phenyl)-3,4-dihydro-1H-isoquinoline-2-carboxylic acid 2,3-dimethyl-benzyl ester;
1-(2-Carboxymethoxy-5-chloro-phenyl)-3,4-dihydro-1H-isoquinoline-2-carboxylic acid 2,6-dimethyl-benzyl ester;
1-(2-Carboxymethoxy-5-chloro-phenyl)-3,4-dihydro-1H-isoquinoline-2-carboxylic acid 2,4-difluoro-benzyl ester;
1-(2-Carboxymethoxy-5-chloro-phenyl)-3,4-dihydro-1H-isoquinoline-2-carboxylic acid 2,3-difluoro-benzyl ester;
1-(2-Carboxymethoxy-5-chloro-phenyl)-3,4-dihydro-1H-isoquinoline-2-carboxylic acid 2,6-difluoro-benzyl ester;
1-(2-Carboxymethoxy-5-chloro-phenyl)-3,4-dihydro-1H-isoquinoline-2-carboxylic acid 2,4,6-trimethyl-benzyl ester;
1-(2-Carboxymethoxy-5-chloro-phenyl)-3,4-dihydro-1H-isoquinoline-2-carboxylic acid 2-chloro-6-fluoro-benzyl ester;
1-(2-Carboxymethoxy-5-chloro-phenyl)-3,4-dihydro-1H-isoquinoline-2-carboxylic acid 2,5-dichloro-benzyl ester;
1-(2-Carboxymethoxy-5-chloro-phenyl)-3,4-dihydro-1H-isoquinoline-2-carboxylic acid 2,4-dimethoxy-benzyl ester;
1-(2-Carboxymethoxy-5-chloro-phenyl)-3,4-dihydro-1H-isoquinoline-2-carboxylic acid 2,3-dimethoxy-benzyl ester;
1-(2-Carboxymethoxy-5-chloro-phenyl)-3,4-dihydro-1H-isoquinoline-2-carboxylic acid 2,6-dimethyl-pyridin-3-yl-methyl ester;
1-(2-Carboxymethoxy-5-chloro-phenyl)-3,4-dihydro-1H-isoquinoline-2-carboxylic acid 3-cyano-benzyl ester;
1-(2-Carboxymethoxy-5-chloro-phenyl)-3,4-dihydro-1H-isoquinoline-2-carboxylic acid 2,5-difluoro-benzyl ester;

1-(2-Carboxymethoxy-5-chloro-phenyl)-3,4-dihydro-1H-isoquinoline-2-carboxylic acid 5-chloro-2-fluoro-benzyl ester;
1-(2-Carboxymethoxy-5-chloro-phenyl)-3,4-dihydro-1H-isoquinoline-2-carboxylic acid 2-chloro-5-fluoro-benzyl ester;
1-(2-Carboxymethoxy-5-chloro-phenyl)-3,4-dihydro-1H-isoquinoline-2-carboxylic acid cyclohexylmethyl ester;
1-(2-Carboxymethoxy-5-chloro-phenyl)-3,4-dihydro-1H-isoquinoline-2-carboxylic acid 1-methyl-1H-pyrazol-3-ylmethyl ester;
1-(2-Carboxymethoxy-5-chloro-phenyl)-3,4-dihydro-1H-isoquinoline-2-carboxylic acid cyclopentylmethyl ester;
1-(2-Carboxymethoxy-5-chloro-phenyl)-3,4-dihydro-1H-isoquinoline-2-carboxylic acid isobutyl ester;
1-(2-Carboxymethoxy-5-chloro-phenyl)-3,4-dihydro-1H-isoquinoline-2-carboxylic acid butyl ester;
1-(2-Carboxymethoxy-5-chloro-phenyl)-3,4-dihydro-1H-isoquinoline-2-carboxylic acid 2-methoxy-ethyl ester;
1-(2-Carboxymethoxy-5-chloro-phenyl)-3,4-dihydro-1H-isoquinoline-2-carboxylic acid cyclopropylmethyl ester;
1-(2-Carboxymethoxy-5-chloro-phenyl)-3,4-dihydro-1H-isoquinoline-2-carboxylic acid 3,5-dimethyl-pyrazol-1-ylmethyl ester;
1-(2-Carboxymethoxy-5-chloro-phenyl)-3,4-dihydro-1H-isoquinoline-2-carboxylic acid 5-methyl-isoxazol-3-ylmethyl ester;
1-(2-Carboxymethoxy-5-chloro-phenyl)-3,4-dihydro-1H-isoquinoline-2-carboxylic acid 1,5-dimethyl-1H-pyrazol-3-ylmethyl ester;
1-(2-Carboxymethoxy-5-chloro-phenyl)-3,4-dihydro-1H-isoquinoline-2-carboxylic acid 4-chloro-benzyl ester;
(S)-1-(2-Carboxymethoxy-5-chloro-phenyl)-3,4-dihydro-1H-isoquinoline-2-carboxylic acid thiazol-2-ylmethyl ester;
(S)-1-(2-Carboxymethoxy-5-chloro-phenyl)-3,4-dihydro-1H-isoquinoline-2-carboxylic acid 2-(4-methyl-thiazol-5-yl)-ethyl ester;
(S)-1-(2-Carboxymethoxy-5-chloro-phenyl)-3,4-dihydro-1H-isoquinoline-2-carboxylic acid 5-methyl-thiazol-2-ylmethyl ester;
(S)-1-(2-Carboxymethoxy-5-chloro-phenyl)-3,4-dihydro-1H-isoquinoline-2-carboxylic acid 4-methyl-thiazol-2-ylmethyl ester;
(S)-1-(2-Carboxymethoxy-5-chloro-phenyl)-3,4-dihydro-1H-isoquinoline-2-carboxylic acid 2-methyl-thiazol-5-ylmethyl ester;
(S)-1-(2-Carboxymethoxy-5-chloro-phenyl)-3,4-dihydro-1H-isoquinoline-2-carboxylic acid 2-methyl-thiazol-4-ylmethyl ester;
(S)-1-(2-Carboxymethoxy-5-chloro-phenyl)-3,4-dihydro-1H-isoquinoline-2-carboxylic acid 3-methyl-isoxazol-5-ylmethyl ester;
(S)-1-(2-Carboxymethoxy-5-chloro-phenyl)-3,4-dihydro-1H-isoquinoline-2-carboxylic acid 4-methyl-isoxazol-3-ylmethyl ester;
(S)-1-(2-Carboxymethoxy-5-chloro-phenyl)-3,4-dihydro-1H-isoquinoline-2-carboxylic acid 3,5-dimethyl-isoxazol-4-ylmethyl ester;
(S)-1-(2-Carboxymethoxy-5-chloro-phenyl)-3,4-dihydro-1H-isoquinoline-2-carboxylic acid pyrazin-2-ylmethyl ester;
(S)-1-(2-Carboxymethoxy-5-chloro-phenyl)-3,4-dihydro-1H-isoquinoline-2-carboxylic acid pyrimidin-4-ylmethyl ester;
(S)-1-(2-Carboxymethoxy-5-chloro-phenyl)-3,4-dihydro-1H-isoquinoline-2-carboxylic acid pyrimidin-5-ylmethyl ester;
(S)-1-(2-Carboxymethoxy-5-chloro-phenyl)-3,4-dihydro-1H-isoquinoline-2-carboxylic acid phenethyl ester;
(S)-1-(2-Carboxymethoxy-5-chloro-phenyl)-3,4-dihydro-1H-isoquinoline-2-carboxylic acid 2-(3-fluoro-phenyl)-ethyl ester;
(S)-1-(2-Carboxymethoxy-5-chloro-phenyl)-3,4-dihydro-1H-isoquinoline-2-carboxylic acid 2-methyl-2H-pyrazol-3-ylmethyl ester;
(S)-1-(2-Carboxymethoxy-5-chloro-phenyl)-3,4-dihydro-1H-isoquinoline-2-carboxylic acid 2,5-dimethyl-2H-pyrazol-3-ylmethyl ester;
(S)-1-(2-Carboxymethoxy-5-chloro-phenyl)-3,4-dihydro-1H-isoquinoline-2-carboxylic acid 2-(2-ethyl-5-methyl-2H-pyrazol-3-yl)-ethyl ester;
(S)-1-(2-Carboxymethoxy-5-chloro-phenyl)-3,4-dihydro-1H-isoquinoline-2-carboxylic acid 3-methyl-3H-imidazol-4-ylmethyl ester;
(S)-1-(2-Carboxymethoxy-5-chloro-phenyl)-3,4-dihydro-1H-isoquinoline-2-carboxylic acid 2-(3,5-dimethyl-pyrazol-1-yl)-ethyl ester;
(S)-1-(2-Carboxymethoxy-5-chloro-phenyl)-3,4-dihydro-1H-isoquinoline-2-carboxylic acid 4-methyl-pyrazol-1-ylmethyl ester;
(S)-1-(2-Carboxymethoxy-5-chloro-phenyl)-3,4-dihydro-1H-isoquinoline-2-carboxylic acid benzothiazol-2-ylmethyl ester;
(S)-1-(2-Carboxymethoxy-5-chloro-phenyl)-3,4-dihydro-1H-isoquinoline-2-carboxylic acid benzooxazol-2-ylmethyl ester;
(S)-1-(2-Carboxymethoxy-5-chloro-phenyl)-3,4-dihydro-1H-isoquinoline-2-carboxylic acid 1-methyl-1H-indazol-3-ylmethyl ester;
(S)-1-(2-Carboxymethoxy-5-chloro-phenyl)-3,4-dihydro-1H-isoquinoline-2-carboxylic acid indazol-1-ylmethyl ester;
(S)-1-(2-Carboxymethoxy-5-chloro-phenyl)-3,4-dihydro-1H-isoquinoline-2-carboxylic acid benzo[d]isoxazol-3-ylmethyl ester;
(S)-1-(2-Carboxymethoxy-5-chloro-phenyl)-5,6-difluoro-3,4-dihydro-1H-isoquinoline-2-carboxylic acid thiazol-2-ylmethyl ester;
(S)-1-(2-Carboxymethoxy-5-chloro-phenyl)-5,6-difluoro-3,4-dihydro-1H-isoquinoline-2-carboxylic acid 2-(4-methyl-thiazol-5-yl)-ethyl ester;
(S)-1-(2-Carboxymethoxy-5-chloro-phenyl)-5,6-difluoro-3,4-dihydro-1H-isoquinoline-2-carboxylic acid 5-methyl-thiazol-2-ylmethyl ester;
(S)-1-(2-Carboxymethoxy-5-chloro-phenyl)-5,6-difluoro-3,4-dihydro-1H-isoquinoline-2-carboxylic acid 4-methyl-thiazol-2-ylmethyl ester;
(S)-1-(2-Carboxymethoxy-5-chloro-phenyl)-5,6-difluoro-3,4-dihydro-1H-isoquinoline-2-carboxylic acid 2-methyl-thiazol-5-ylmethyl ester;
(S)-1-(2-Carboxymethoxy-5-chloro-phenyl)-5,6-difluoro-3,4-dihydro-1H-isoquinoline-2-carboxylic acid 2-methyl-thiazol-4-ylmethyl ester;
(S)-1-(2-Carboxymethoxy-5-chloro-phenyl)-5,6-difluoro-3,4-dihydro-1H-isoquinoline-2-carboxylic acid 3-methyl-isoxazol-5-ylmethyl ester;
(S)-1-(2-Carboxymethoxy-5-chloro-phenyl)-5,6-difluoro-3,4-dihydro-1H-isoquinoline-2-carboxylic acid 4-methyl-isoxazol-3-ylmethyl ester;

(S)-1-(2-Carboxymethoxy-5-chloro-phenyl)-5,6-difluoro-3,4-dihydro-1H-isoquinoline-2-carboxylic acid 3,5-dimethyl-isoxazol-4-ylmethyl ester;
(S)-1-(2-Carboxymethoxy-5-chloro-phenyl)-5,6-difluoro-3,4-dihydro-1H-isoquinoline-2-carboxylic acid pyrazin-2-ylmethyl ester;
(S)-1-(2-Carboxymethoxy-5-chloro-phenyl)-5,6-difluoro-3,4-dihydro-1H-isoquinoline-2-carboxylic acid pyrimidin-4-ylmethyl ester;
(S)-1-(2-Carboxymethoxy-5-chloro-phenyl)-5,6-difluoro-3,4-dihydro-1H-isoquinoline-2-carboxylic acid phenethyl ester;
(S)-1-(2-Carboxymethoxy-5-chloro-phenyl)-5,6-difluoro-3,4-dihydro-1H-isoquinoline-2-carboxylic acid 2-(3-fluorophenyl)-ethyl ester;
(S)-1-(2-Carboxymethoxy-5-chloro-phenyl)-5,6-difluoro-3,4-dihydro-1H-isoquinoline-2-carboxylic acid 2-methyl-2H-pyrazol-3-ylmethyl ester;
(S)-1-(2-Carboxymethoxy-5-chloro-phenyl)-5,6-difluoro-3,4-dihydro-1H-isoquinoline-2-carboxylic acid 2,5-dimethyl-2H-pyrazol-3-ylmethyl ester;
(S)-1-(2-Carboxymethoxy-5-chloro-phenyl)-5,6-difluoro-3,4-dihydro-1H-isoquinoline-2-carboxylic acid 2-(2-ethyl-5-methyl-2H-pyrazol-3-yl)-ethyl ester;
(S)-1-(2-Carboxymethoxy-5-chloro-phenyl)-5,6-difluoro-3,4-dihydro-1H-isoquinoline-2-carboxylic acid 3-methyl-3H-imidazol-4-ylmethyl ester;
(S)-1-(2-Carboxymethoxy-5-chloro-phenyl)-5,6-difluoro-3,4-dihydro-1H-isoquinoline-2-carboxylic acid 2-(3,5-dimethyl-pyrazol-1-yl)-ethyl ester;
(S)-1-(2-Carboxymethoxy-5-chloro-phenyl)-5,6-difluoro-3,4-dihydro-1H-isoquinoline-2-carboxylic acid 4-methyl-pyrazol-1-ylmethyl ester;
(S)-1-(2-Carboxymethoxy-5-chloro-phenyl)-5,6-difluoro-3,4-dihydro-1H-isoquinoline-2-carboxylic acid benzothiazol-2-ylmethyl ester;
(S)-1-(2-Carboxymethoxy-5-chloro-phenyl)-5,6-difluoro-3,4-dihydro-1H-isoquinoline-2-carboxylic acid benzooxazol-2-ylmethyl ester;
(S)-1-(2-Carboxymethoxy-5-chloro-phenyl)-5,6-difluoro-3,4-dihydro-1H-isoquinoline-2-carboxylic acid 1-methyl-1H-indazol-3-ylmethyl ester;
(S)-1-(2-Carboxymethoxy-5-chloro-phenyl)-5,6-difluoro-3,4-dihydro-1H-isoquinoline-2-carboxylic acid indazol-1-ylmethyl ester;
(S)-1-(2-Carboxymethoxy-5-chloro-phenyl)-5,6-difluoro-3,4-dihydro-1H-isoquinoline-2-carboxylic acid benzo[d]isoxazol-3-ylmethyl ester;
(S)-1-(2-Carboxymethoxy-5-chloro-phenyl)-6-fluoro-3,4-dihydro-1H-isoquinoline-2-carboxylic acid thiazol-2-ylmethyl ester;
(S)-1-(2-Carboxymethoxy-5-chloro-phenyl)-6-fluoro-3,4-dihydro-1H-isoquinoline-2-carboxylic acid 2-(4-methyl-thiazol-5-yl)-ethyl ester;
(S)-1-(2-Carboxymethoxy-5-chloro-phenyl)-6-fluoro-3,4-dihydro-1H-isoquinoline-2-carboxylic acid 5-methyl-thiazol-2-ylmethyl ester;
(S)-1-(2-Carboxymethoxy-5-chloro-phenyl)-6-fluoro-3,4-dihydro-1H-isoquinoline-2-carboxylic acid 4-methyl-thiazol-2-ylmethyl ester;
(S)-1-(2-Carboxymethoxy-5-chloro-phenyl)-6-fluoro-3,4-dihydro-1H-isoquinoline-2-carboxylic acid 2-methyl-thiazol-5-ylmethyl ester;
(S)-1-(2-Carboxymethoxy-5-chloro-phenyl)-6-fluoro-3,4-dihydro-1H-isoquinoline-2-carboxylic acid 2-methyl-thiazol-4-ylmethyl ester;
(S)-1-(2-Carboxymethoxy-5-chloro-phenyl)-6-fluoro-3,4-dihydro-1H-isoquinoline-2-carboxylic acid 3-methyl-isoxazol-5-ylmethyl ester;
(S)-1-(2-Carboxymethoxy-5-chloro-phenyl)-6-fluoro-3,4-dihydro-1H-isoquinoline-2-carboxylic acid 4-methyl-isoxazol-3-ylmethyl ester;
(S)-1-(2-Carboxymethoxy-5-chloro-phenyl)-6-fluoro-3,4-dihydro-1H-isoquinoline-2-carboxylic acid pyrazin-2-ylmethyl ester;
(S)-1-(2-Carboxymethoxy-5-chloro-phenyl)-6-fluoro-3,4-dihydro-1H-isoquinoline-2-carboxylic acid pyrimidin-4-ylmethyl ester;
(S)-1-(2-Carboxymethoxy-5-chloro-phenyl)-6-fluoro-3,4-dihydro-1H-isoquinoline-2-carboxylic acid pyrimidin-5-ylmethyl ester;
(S)-1-(2-Carboxymethoxy-5-chloro-phenyl)-6-fluoro-3,4-dihydro-1H-isoquinoline-2-carboxylic acid phenethyl ester;
(S)-1-(2-Carboxymethoxy-5-chloro-phenyl)-6-fluoro-3,4-dihydro-1H-isoquinoline-2-carboxylic acid 2-(3-fluorophenyl)-ethyl ester;
(S)-1-(2-Carboxymethoxy-5-chloro-phenyl)-6-fluoro-3,4-dihydro-1H-isoquinoline-2-carboxylic acid 2-methyl-2H-pyrazol-3-ylmethyl ester;
(S)-1-(2-Carboxymethoxy-5-chloro-phenyl)-6-fluoro-3,4-dihydro-1H-isoquinoline-2-carboxylic acid 2,5-dimethyl-2H-pyrazol-3-ylmethyl ester;
(S)-1-(2-Carboxymethoxy-5-chloro-phenyl)-6-fluoro-3,4-dihydro-1H-isoquinoline-2-carboxylic acid 2-(2-ethyl-5-methyl-2H-pyrazol-3-yl)-ethyl ester;
(S)-1-(2-Carboxymethoxy-5-chloro-phenyl)-6-fluoro-3,4-dihydro-1H-isoquinoline-2-carboxylic acid 3-methyl-3H-imidazol-4-ylmethyl ester;
(S)-1-(2-Carboxymethoxy-5-chloro-phenyl)-6-fluoro-3,4-dihydro-1H-isoquinoline-2-carboxylic acid 2-(3,5-dimethyl-pyrazol-1-yl)-ethyl ester;
(S)-1-(2-Carboxymethoxy-5-chloro-phenyl)-6-fluoro-3,4-dihydro-1H-isoquinoline-2-carboxylic acid 4-methyl-pyrazol-1-ylmethyl ester;
(S)-1-(2-Carboxymethoxy-5-chloro-phenyl)-6-fluoro-3,4-dihydro-1H-isoquinoline-2-carboxylic acid benzothiazol-2-ylmethyl ester;
(S)-1-(2-Carboxymethoxy-5-chloro-phenyl)-6-fluoro-3,4-dihydro-1H-isoquinoline-2-carboxylic acid benzooxazol-2-ylmethyl ester;
(S)-1-(2-Carboxymethoxy-5-chloro-phenyl)-6-fluoro-3,4-dihydro-1H-isoquinoline-2-carboxylic acid 1-methyl-1H-indazol-3-ylmethyl ester;
(S)-1-(2-Carboxymethoxy-5-chloro-phenyl)-6-fluoro-3,4-dihydro-1H-isoquinoline-2-carboxylic acid indazol-1-ylmethyl ester;
(S)-1-(2-Carboxymethoxy-5-chloro-phenyl)-6-fluoro-3,4-dihydro-1H-isoquinoline-2-carboxylic acid benzo[d]isoxazol-3-ylmethyl ester;
(S)-1-(2-Carboxymethoxy-5-chloro-phenyl)-5,6-difluoro-3,4-dihydro-1H-isoquinoline-2-carboxylic acid 2-fluoro-benzyl ester;
(S)-1-(2-Carboxymethoxy-5-chloro-phenyl)-5,6-difluoro-3,4-dihydro-1H-isoquinoline-2-carboxylic acid 3-fluoro-benzyl ester;
(S)-1-(2-Carboxymethoxy-5-chloro-phenyl)-5,6-difluoro-3,4-dihydro-1H-isoquinoline-2-carboxylic acid 2,3-difluoro-benzyl ester;
(S)-1-(2-Carboxymethoxy-5-chloro-phenyl)-6-fluoro-3,4-dihydro-1H-isoquinoline-2-carboxylic acid 2-fluoro-benzyl ester;

(S)-1-(2-Carboxymethoxy-5-chloro-phenyl)-6-fluoro-3,4-dihydro-1H-isoquinoline-2-carboxylic acid 3-fluoro-benzyl ester;
(S)-1-(2-Carboxymethoxy-5-chloro-phenyl)-6-fluoro-3,4-dihydro-1H-isoquinoline-2-carboxylic acid 2,3-difluoro-benzyl ester;
(S)-1-(2-Carboxymethoxy-5-chloro-phenyl)-3,4-dihydro-1H-isoquinoline-2-carboxylic acid 3-fluoro-benzyl ester;
(S)-1-(2-Carboxymethoxy-5-chloro-phenyl)-3,4-dihydro-1H-isoquinoline-2-carboxylic acid 2-methoxy-benzyl ester;
(S)-1-(2-Carboxymethoxy-5-chloro-phenyl)-3,4-dihydro-1H-isoquinoline-2-carboxylic acid 2-fluoro-benzyl ester;
(S)-1-(2-Carboxymethoxy-5-chloro-phenyl)-5-fluoro-3,4-dihydro-1H-isoquinoline-2-carboxylic acid 3-fluoro-benzyl ester;
(S)-1-(2-Carboxymethoxy-5-chloro-phenyl)-5-fluoro-3,4-dihydro-1H-isoquinoline-2-carboxylic acid 2-fluoro-benzyl ester;
1-(2-Carboxymethoxy-5-chloro-phenyl)-3,4-dihydro-1H-isoquinoline-2-carboxylic acid 4-methyl-benzyl ester;
1-(2-Carboxymethoxy-5-chloro-phenyl)-3,4-dihydro-1H-isoquinoline-2-carboxylic acid 4-methoxy-benzyl ester;
1-(2-Carboxymethoxy-5-chloro-phenyl)-3,4-dihydro-1H-isoquinoline-2-carboxylic acid 4-fluoro-benzyl ester;
1-(2-Carboxymethoxy-5-chloro-phenyl)-3,4-dihydro-1H-isoquinoline-2-carboxylic acid 4-trifluoromethyl-benzyl ester;
1-(2-Carboxymethoxy-5-chloro-phenyl)-3,4-dihydro-1H-isoquinoline-2-carboxylic acid 3-chloro-benzyl ester;
1-(2-Carboxymethoxy-5-chloro-phenyl)-7-fluoro-3,4-dihydro-1H-isoquinoline-2-carboxylic acid benzyl ester;
1-(2-Carboxymethoxy-phenyl)-3,4-dihydro-1H-isoquinoline-2-carboxylic acid benzyl ester;
1-(2-Carboxymethoxy-5-chloro-phenyl)-6-fluoro-3,4-dihydro-1H-isoquinoline-2-carboxylic acid benzyl ester;
(4-Chloro-2-{2-[3-(5-fluoro-3-methyl-indol-1-yl)-propionyl]-1,2,3,4-tetrahydro-isoquinolin-1-yl}-phenoxy)-acetic acid;
(4-Chloro-2-{2-[3-(6-methoxy-pyrrolo[2,3-b]pyridin-1-yl)-propionyl]-1,2,3,4-tetrahydro-isoquinolin-1-yl}-phenoxy)-acetic acid;
(4-Chloro-2-{2-[3-(4,6-dimethoxy-pyrrolo[2,3-b]pyridin-1-yl)-propionyl]-1,2,3,4-tetrahydro-isoquinolin-1-yl}-phenoxy)-acetic acid;
(4-Chloro-2-{2-[3-(4,6-dimethoxy-indol-1-yl)-propionyl]-1,2,3,4-tetrahydro-isoquinolin-1-yl}-phenoxy)-acetic acid;
{4-Chloro-2-[2-(3-indol-1-yl-propionyl)-1,2,3,4-tetrahydro-isoquinolin-1-yl]-phenoxy}-acetic acid;
(4-Chloro-2-{2-[3-(5-fluoro-indol-1-yl)-propionyl]-1,2,3,4-tetrahydro-isoquinolin-1-yl}-phenoxy)-acetic acid;
(4-Chloro-2-{2-[3-(7-chloro-indol-1-yl)-propionyl]-1,2,3,4-tetrahydro-isoquinolin-1-yl}-phenoxy)-acetic acid;
{4-Chloro-2-[2-(3-pyrrolo[3,2-b]pyridin-1-yl-propionyl)-1,2,3,4-tetrahydro-isoquinolin-1-yl]-phenoxy}-acetic acid;
(4-Chloro-2-{2-[3-(4-methoxy-indol-1-yl)-propionyl]-1,2,3,4-tetrahydro-isoquinolin-1-yl}-phenoxy)-acetic acid;
(4-Chloro-2-{2-[3-(3-chloro-indazol-1-yl)-propionyl]-1,2,3,4-tetrahydro-isoquinolin-1-yl}-phenoxy)-acetic acid;
(4-Chloro-2-{2-[3-(6-methyl-indol-1-yl)-propionyl]-1,2,3,4-tetrahydro-isoquinolin-1-yl}-phenoxy)-acetic acid;
(4-Chloro-2-{2-[3-(6-chloro-indol-1-yl)-propionyl]-1,2,3,4-tetrahydro-isoquinolin-1-yl}-phenoxy)-acetic acid;
(4-Chloro-2-{2-[3-(4-fluoro-indol-1-yl)-propionyl]-1,2,3,4-tetrahydro-isoquinolin-1-yl}-phenoxy)-acetic acid;
(4-Chloro-2-{2-[3-(6-fluoro-indol-1-yl)-propionyl]-1,2,3,4-tetrahydro-isoquinolin-1-yl}-phenoxy)-acetic acid;
(4-Chloro-2-{2-[3-(6-methoxy-indol-1-yl)-propionyl]-1,2,3,4-tetrahydro-isoquinolin-1-yl}-phenoxy)-acetic acid;
(4-Chloro-2-{(S)-6-fluoro-2-[3-(5-fluoro-indazol-1-yl)-propionyl]-1,2,3,4-tetrahydro-isoquinolin-1-yl}-phenoxy)-acetic acid;
(4-Chloro-2-{(S)-6-fluoro-2-[3-(3-methyl-indazol-1-yl)-propionyl]-1,2,3,4-tetrahydro-isoquinolin-1-yl}-phenoxy)-acetic acid;
(4-Chloro-2-{(S)-2-[3-(6-chloro-indazol-1-yl)-propionyl]-6-fluoro-1,2,3,4-tetrahydro-isoquinolin-1-yl}-phenoxy)-acetic acid;
(4-Chloro-2-{2-[3-(3-chloro-pyrrolo[2,3-b]pyrazin-5-yl)-propionyl]-1,2,3,4-tetrahydro-isoquinolin-1-yl}-phenoxy)-acetic acid;
(4-Chloro-2-{2-[2-(2-methoxy-phenoxy)-acetyl]-1,2,3,4-tetrahydro-isoquinolin-1-yl}-phenoxy)-acetic acid;
(4-Chloro-2-{2-[2-(4-fluoro-phenoxy)-acetyl]-1,2,3,4-tetrahydro-isoquinolin-1-yl}-phenoxy)-acetic acid;
(4-Chloro-2-{2-[2-(quinolin-8-yloxy)-acetyl]-1,2,3,4-tetrahydro-isoquinolin-1-yl}-phenoxy)-acetic acid;
(4-Chloro-2-{2-[2-(4-chloro-phenoxy)-acetyl]-1,2,3,4-tetrahydro-isoquinolin-1-yl}-phenoxy)-acetic acid;
(4-Chloro-2-{2-[trans-2-(4-fluoro-phenyl)-cyclopropanecarbonyl]-1,2,3,4-tetrahydro-isoquinolin-1-yl}-phenoxy)-acetic acid;
(4-Chloro-2-{2-[trans-2-(3-chloro-phenyl)-cyclopropanecarbonyl]-1,2,3,4-tetrahydro-isoquinolin-1-yl}-phenoxy)-acetic acid;
{4-Chloro-2-[2-(trans-2-o-tolyl-cyclopropanecarbonyl)-1,2,3,4-tetrahydro-isoquinolin-1-yl]-phenoxy}-acetic acid;
(4-Chloro-2-{2-[trans-2-(2-trifluoromethyl-phenyl)-cyclopropanecarbonyl]-1,2,3,4-tetrahydro-isoquinolin-1-yl}-phenoxy)-acetic acid;
(4-Chloro-2-{2-[trans-2-(3-fluoro-phenyl)-cyclopropanecarbonyl]-1,2,3,4-tetrahydro-isoquinolin-1-yl}-phenoxy)-acetic acid;
(4-Chloro-2-{2-[trans-2-(3-methoxy-phenyl)-cyclopropanecarbonyl]-1,2,3,4-tetrahydro-isoquinolin-1-yl}-phenoxy)-acetic acid;
{4-Chloro-2-[2-(trans-2-m-tolyl-cyclopropanecarbonyl)-1,2,3,4-tetrahydro-isoquinolin-1-yl]-phenoxy}-acetic acid;
{4-Chloro-2-[6-fluoro-2-(trans-2-phenyl-cyclopropanecarbonyl)-1,2,3,4-tetrahydro-isoquinolin-1-yl]-phenoxy}-acetic acid;
(4-Chloro-2-{6-fluoro-2-[trans-2-(2-trifluoromethyl-phenyl)-cyclopropanecarbonyl]-1,2,3,4-tetrahydro-isoquinolin-1-yl}-phenoxy)-acetic acid;
(4-Chloro-2-{2-[trans-2-(2-chloro-phenyl)-cyclopropanecarbonyl]-6-fluoro-1,2,3,4-tetrahydro-isoquinolin-1-yl}-phenoxy)-acetic acid;
{4-Chloro-2-[6-fluoro-2-(trans-2-o-tolyl-cyclopropanecarbonyl)-1,2,3,4-tetrahydro-isoquinolin-1-yl]-phenoxy}-acetic acid;
(4-Chloro-2-{2-[2-(2,6-dimethyl-pyridin-3-yloxy)-acetyl]-6-fluoro-1,2,3,4-tetrahydro-isoquinolin-1-yl}-phenoxy)-acetic acid;
(4-Chloro-2-{6-fluoro-2-[3-(1-methyl-1H-indol-3-yl)-propionyl]-1,2,3,4-tetrahydro-isoquinolin-1-yl}-phenoxy)-acetic acid;
{4-Chloro-2-[6-fluoro-2-(3-o-tolyl-propionyl)-1,2,3,4-tetrahydro-isoquinolin-1-yl]-phenoxy}-acetic acid;
(4-Chloro-2-{6-fluoro-2-[4-(2-fluoro-phenyl)-butyryl]-1,2,3,4-tetrahydro-isoquinolin-1-yl}-phenoxy)-acetic acid;
(4-Chloro-2-{2-[2-(2-chloro-benzyloxy)-acetyl]-6-fluoro-1,2,3,4-tetrahydro-isoquinolin-1-yl}-phenoxy)-acetic acid;

{4-Chloro-2-[2-(3-2,3-dihydro-indol-1-yl-propionyl)-1,2,3,4-tetrahydro-isoquinolin-1-yl]-phenoxy}-acetic acid;
(4-Chloro-2-{2-[3-(3-methyl-indol-1-yl)-propionyl]-1,2,3,4-tetrahydro-isoquinolin-1-yl}-phenoxy)-acetic acid;
{4-Chloro-2-[2-(3-indazol-1-yl-propionyl)-1,2,3,4-tetrahydro-isoquinolin-1-yl]-phenoxy}-acetic acid;
{4-Chloro-2-[2-(3-3,4-dihydro-2H-quinolin-1-yl-propionyl)-1,2,3,4-tetrahydro-isoquinolin-1-yl]-phenoxy}-acetic acid;
(4-Chloro-2-{2-[2-(2,4-dimethyl-phenoxy)-acetyl]-1,2,3,4-tetrahydro-isoquinolin-1-yl}-phenoxy)-acetic acid;
(4-Chloro-2-{2-[3-(5-methoxy-1-methyl-1H-indol-3-yl)-propionyl]-1,2,3,4-tetrahydro-isoquinolin-1-yl}-phenoxy)-acetic acid;
{4-Chloro-2-[2-(3-1H-indol-3-yl-propionyl)-1,2,3,4-tetrahydro-isoquinolin-1-yl]-phenoxy}-acetic acid;
{4-Chloro-2-[2-(2,2-dimethyl-cyclopropanecarbonyl)-1,2,3,4-tetrahydro-isoquinolin-1-yl]-phenoxy}-acetic acid;
{4-Chloro-2-[2-(2-chloro-benzylcarbamoyl)-1,2,3,4-tetrahydro-isoquinolin-1-yl]-phenoxy}-acetic acid;
{4-Chloro-2-[2-(3-fluoro-benzylcarbamoyl)-1,2,3,4-tetrahydro-isoquinolin-1-yl]-phenoxy}-acetic acid;
[2-(2-Benzylcarbamoyl-1,2,3,4-tetrahydro-isoquinolin-1-yl)-4-chloro-phenoxy]-acetic acid;
[4-Chloro-2-(2-phenethylcarbamoyl-1,2,3,4-tetrahydro-isoquinolin-1-yl)-phenoxy]-acetic acid;
{4-Chloro-2-[2-(4-fluoro-benzylcarbamoyl)-1,2,3,4-tetrahydro-isoquinolin-1-yl]-phenoxy}-acetic acid;
{4-Chloro-2-[2-(2-fluoro-benzylcarbamoyl)-1,2,3,4-tetrahydro-isoquinolin-1-yl]-phenoxy}-acetic acid;
1-(2-Carboxymethoxy-5-fluoro-phenyl)-1,3-dihydro-isoindole-2-carboxylic acid benzyl ester;
1-(2-Carboxymethoxy-5-chloro-phenyl)-5-fluoro-1,3-dihydro-isoindole-2-carboxylic acid benzyl ester;
1-(2-Carboxymethoxy-5-chloro-phenyl)-4-fluoro-1,3-dihydro-isoindole-2-carboxylic acid benzyl ester;
{4-Chloro-2-[2-trans-(2-phenyl-cyclopropanecarbonyl)-2,3-dihydro-1H-isoindol-1-yl]-phenoxy}-acetic acid;
(4-Chloro-2-{2-[2-(4-fluoro-phenoxy)-acetyl]-2,3-dihydro-1H-isoindol-1-yl}-phenoxy)-acetic acid;
(4-Chloro-2-{2-[2-(quinolin-8-yloxy)-acetyl]-2,3-dihydro-1H-isoindol-1-yl}-phenoxy)-acetic acid;
(4-Chloro-2-{2-[3-(5-methoxy-1H-indol-3-yl)-propionyl]-2,3-dihydro-1H-isoindol-1-yl}-phenoxy)-acetic acid;
(4-Chloro-2-{2-[2-(2,6-dimethyl-pyridin-3-yloxy)-acetyl]-2,3-dihydro-1H-isoindol-1-yl}-phenoxy)-acetic acid;
(4-Chloro-2-{2-[3-(1-methyl-1H-indol-3-yl)-propionyl]-2,3-dihydro-1H-isoindol-1-yl}-phenoxy)-acetic acid;
{4-Chloro-2-[2-(3-2,3-dihydro-indol-1-yl-propionyl)-2,3-dihydro-1H-isoindol-1-yl]-phenoxy}-acetic acid;
{4-Chloro-2-[2-(3-indazol-1-yl-propionyl)-2,3-dihydro-1H-isoindol-1-yl]-phenoxy}-acetic acid;
(4-Chloro-2-{2-[2-(5-methoxy-benzo[d]isoxazol-3-yl)-acetyl]-2,3-dihydro-1H-isoindol-1-yl}-phenoxy)-acetic acid;
(4-Chloro-2-{2-[3-(3-methyl-indol-1-yl)-propionyl]-2,3-dihydro-1H-isoindol-1-yl}-phenoxy)-acetic acid;
(4-Chloro-2-{2-[2-(2-chloro-benzyloxy)-acetyl]-2,3-dihydro-1H-isoindol-1-yl}-phenoxy)-acetic acid;
(4-Chloro-2-{2-[3-(2-fluoro-phenoxy)-propionyl]-2,3-dihydro-1H-isoindol-1-yl}-phenoxy)-acetic acid;
(4-Chloro-2-{2-trans-[2-(3-fluoro-phenyl)-cyclopropanecarbonyl]-2,3-dihydro-1H-isoindol-1-yl}-phenoxy)-acetic acid;
(4-Chloro-2-{2-trans-[2-(2-fluoro-phenyl)-cyclopropanecarbonyl]-2,3-dihydro-1H-isoindol-1-yl}-phenoxy)-acetic acid;
{4-Chloro-2-[5-fluoro-2-(3-indazol-1-yl-propionyl)-2,3-dihydro-1H-isoindol-1-yl]-phenoxy}-acetic acid;
(4-Chloro-2-{2-[3-(5-fluoro-indazol-1-yl)-propionyl]-2,3-dihydro-1H-isoindol-1-yl}-phenoxy)-acetic acid;
(4-Chloro-2-{2-[3-(4-fluoro-3-methyl-indazol-1-yl)-propionyl]-2,3-dihydro-1H-isoindol-1-yl}-phenoxy)-acetic acid;
(4-Chloro-2-{2-[3-(6-fluoro-3-methyl-indazol-1-yl)-propionyl]-2,3-dihydro-1H-isoindol-1-yl}-phenoxy)-acetic acid;
(4-Chloro-2-{2-[3-(6-chloro-3-methyl-indazol-1-yl)-propionyl]-2,3-dihydro-1H-isoindol-1-yl}-phenoxy)-acetic acid;
(4-Chloro-2-{2-[3-(3-methyl-indazol-1-yl)-propionyl]-2,3-dihydro-1H-isoindol-1-yl}-phenoxy)-acetic acid;
(4-Chloro-2-{2-[3-(6-fluoro-indazol-1-yl)-propionyl]-2,3-dihydro-1H-isoindol-1-yl}-phenoxy)-acetic acid;
(4-Chloro-2-{2-[3-(4-fluoro-indazol-1-yl)-propionyl]-2,3-dihydro-1H-isoindol-1-yl}-phenoxy)-acetic acid;
(4-Chloro-2-{2-[3-(7-fluoro-indazol-1-yl)-propionyl]-2,3-dihydro-1H-isoindol-1-yl}-phenoxy)-acetic acid;
{4-Chloro-2-[2-(2-fluoro-benzylcarbamoyl)-2,3-dihydro-1H-isoindol-1-yl]-phenoxy}-acetic acid;
{4-Chloro-2-[2-(3-fluoro-benzylcarbamoyl)-2,3-dihydro-1H-isoindol-1-yl]-phenoxy}-acetic acid;
{4-Chloro-2-[2-(4-fluoro-benzylcarbamoyl)-2,3-dihydro-1H-isoindol-1-yl]-phenoxy}-acetic acid;
[2-(2-Benzylcarbamoyl-2,3-dihydro-1H-isoindol-1-yl)-4-chloro-phenoxy]-acetic acid;
[4-Chloro-2-(2-phenethylcarbamoyl-2,3-dihydro-1H-isoindol-1-yl)-phenoxy]-acetic acid;
{4-Chloro-2-[2-(2-chloro-benzylcarbamoyl)-2,3-dihydro-1H-isoindol-1-yl]-phenoxy}-acetic acid;
1-(2-Carboxymethoxy-5-chloro-phenyl)-4,5-dichloro-1,3-dihydro-isoindole-2-carboxylic acid benzyl ester;
1-(2-Carboxymethoxy-5-chloro-phenyl)-4,5-difluoro-1,3-dihydro-isoindole-2-carboxylic acid benzyl ester;
{4-Chloro-2-[(S)-2-((1R,2R)-2-o-tolyl-cyclopropanecarbonyl)-1,2,3,4-tetrahydro-isoquinolin-1-yl]-phenoxy}-acetic acid;
(4-Chloro-2-{(S)-2-[(1R,2R)-2-(2-trifluoromethyl-phenyl)-cyclopropanecarbonyl]-1,2,3,4-tetrahydro-isoquinolin-1-yl}-phenoxy)-acetic acid;
(4-Chloro-2-{(S)-2-[(1R,2R)-2-(3-chloro-phenyl)-cyclopropanecarbonyl]-1,2,3,4-tetrahydro-isoquinolin-1-yl}-phenoxy)-acetic acid;
(4-Chloro-2-{(S)-2-[(1R,2R)-2-(3-fluoro-phenyl)-cyclopropanecarbonyl]-1,2,3,4-tetrahydro-isoquinolin-1-yl}-phenoxy)-acetic acid;
(4-Chloro-2-{(S)-2-[(1R,2R)-2-(4-fluoro-phenyl)-cyclopropanecarbonyl]-1,2,3,4-tetrahydro-isoquinolin-1-yl}-phenoxy)-acetic acid;
(S)-1-[5-Chloro-2-(2-oxo-2-trifluoromethanesulfonylamino-ethoxy)-phenyl]-3,4-dihydro-1H-isoquinoline-2-carboxylic acid benzyl ester;
(S)-1-[5-Chloro-2-(5-oxo-4,5-dihydro-[1,3,4]oxadiazol-2-ylmethoxy)-phenyl]-3,4-dihydro-1H-isoquinoline-2-carboxylic acid benzyl ester; and
1-[5-Chloro-2-(3-hydroxy-isoxazol-5-ylmethoxy)-phenyl]-3,4-dihydro-1H-isoquinoline-2-carboxylic acid benzyl ester;

or salts (in particular pharmaceutically acceptable salts) of such compounds;

it is to be understood for any of the above listed compounds, that a stereogenic center, which is not specifically assigned, may be in absolute (R)- or absolute (S)-configuration and that a double bond, which is not specifically assigned, may be in (E)- or (Z)-configuration; for example, the stereogenic center at the 1-position of the 1,2,3,4-tetrahydroisoquinoline or isoindoline core-structure may be in absolute (R)-configuration or absolute (S)-configuration (and preferably in absolute (S)-configuration). Notably, compounds containing more than one stereogenic center may be at each stereogenic center, which is not specifically assigned, in absolute (R)- or absolute (S)-configuration; for example a compound listed as (4-Chloro-2-{2-trans-[2-(2-fluoro-phenyl)-cyclopropanecarbonyl]-2,3-dihydro-1H-isoindol-1-yl}-phenoxy)-acetic acid may be (4-Chloro-2-{(S)-2-[(1S,2S)-2-(2-fluoro-phenyl)-cyclopropanecarbonyl]-2,3-dihydro-1H-isoindol-1-yl}-phenoxy)-acetic acid, (4-Chloro-2-{(S)-2-[(1R,2R)-2-(2-fluoro-phenyl)-cyclopropanecarbonyl]-2,3-dihydro-1H-isoindol-1-yl}-phenoxy)-acetic acid, (4-Chloro-2-{(R)-2-[(1S,2S)-2-(2-fluoro-phenyl)-cyclopropanecarbonyl]-2,3-dihydro-1H-isoindol-1-yl}-phenoxy)-acetic acid, (4-Chloro-2-{(R)-2-[(1R,2R)-2-(2-fluoro-phenyl)-cyclopropanecarbonyl]-2,3-dihydro-1H-isoindol-1-yl}-phenoxy)-acetic acid or a mixture thereof (and preferably (4-Chloro-2-{(S)-2-[(1S,2S)-2-(2-fluoro-phenyl)-cyclopropanecarbonyl]-2,3-dihydro-1H-isoindol-1-yl}-phenoxy)-acetic acid or (4-Chloro-2-{(S)-2-[(1R,2R)-2-(2-fluoro-phenyl)-cyclopropanecarbonyl]-2,3-dihydro-1H-isoindol-1-yl}-phenoxy)-acetic acid).

Unless explicitly stated otherwise, the general terms and names used hereinbefore and hereinafter preferably have within the context of this disclosure the following meanings:

Where the plural form is used for compounds, salts, pharmaceutical compositions, diseases and the like, this is intended to mean also a single compound, salt, pharmaceutical composition, disease or the like.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

The compounds of formula (I) according to any one of embodiments 1) to 58), or pharmaceutically acceptable salts thereof, may be used for the preparation of a medicament, and are suitable for the prevention and/or treatment of diseases selected from the group consisting of chronic and acute allergic/immune diseases/disorders, comprising asthma, allergic asthma, eosinophilic asthma, severe asthma, rhinitis, allergic rhinitis, angioedema, insect venom allergy, drug allergies, allergic sinusitis, allergic nephritis, allergic conjunctivitis, atopic dermatitis, bronchial asthma, food allergy, systemic mast cell disorders, anaphylactic shock, urticaria, eczema, ulcerative colitis, chronic obstructive pulmonary disease (COPD), inflammatory bowel disease and rheumatoid arthritis; eosinophil-related diseases comprising small vessel vasculitides like Churg-Strauss syndrome, Wegener's granulomatosis, microscopic polyangiitis (and organ-specific subsets of the latter), hypereosinophilic syndromes like eosinophilic pneumonia, eosinophilic esophagitis, reflux esophagitis, eosinohilic endocarditis (Loeffler's endocarditis), eosinophilia-myalgia syndrome, eosinophilic fasciitis, eosinohilic pustular folliculitis (Ofuji's disease), eosinophilic ulcers, angiolymphoid hyperplasia with eosinophilia (ALHE), eosinophilic cellulitis (Wells syndrome), chronic eosinophilic leukemia and DRESS syndrome (Drug Rash with Eosinophilia and Systemic Symptoms); and basophil-related diseases, comprising basophilic leukemia and basophilic leukocytosis.

In a preferred embodiment, the compounds of formula (I) according to any one of embodiments 1) to 58), or pharmaceutically acceptable salts thereof, may be used for the preparation of a medicament, and are suitable for the prevention and/or treatment of diseases selected from the group consisting of asthma, allergic asthma, eosinophilic asthma, severe asthma, allergic rhinitis, angioedema, insect venom allergy, drug allergies, allergic sinusitis, allergic nephritis, allergic conjunctivitis, atopic dermatitis, food allergy, systemic mast cell disorders, anaphylactic shock, urticaria and eczema.

In another preferred embodiment, the compounds of formula (I) according to any one of embodiments 1) to 58), or pharmaceutically acceptable salts thereof, may be used for the preparation of a medicament, and are suitable for the prevention and/or treatment of diseases selected from the group consisting of eosinophil-related diseases comprising small vessel vasculitides like Churg-Strauss syndrome, Wegener's granulomatosis, microscopic polyangiitis (and organ-specific subsets of the latter), hypereosinophilic syndromes like eosinophilic pneumonia, eosinophilic esophagitis, reflux esophagitis, eosinohilic endocarditis (Loeffler's endocarditis), eosinophilia-myalgia syndrome, eosinophilic fasciitis, eosinohilic pustular folliculitis (Ofuji's disease), eosinophilic ulcers, angiolymphoid hyperplasia with eosinophilia (ALHE), eosinophilic cellulitis (Wells syndrome), chronic eosinophilic leukemia and DRESS syndrome (Drug Rash with Eosinophilia and Systemic Symptoms).

In yet another preferred embodiment, the compounds of formula (I) according to any one of embodiments 1) to 58), or pharmaceutically acceptable salts thereof, may be used for the preparation of a medicament, and are suitable for the prevention and/or treatment of diseases selected from the group consisting of basophil-related diseases, comprising basophilic leukemia and basophilic leukocytosis.

The invention also relates to the use of a compound of formula (I) according to any one of embodiments 1) to 58) for the preparation of pharmaceutical compositions for the treatment and/or prophylaxis of the above-mentioned diseases.

The present invention also relates to pharmaceutically acceptable salts and to pharmaceutical compositions and formulations of compounds of formula (I) according to any one of embodiments 1) to 58).

A pharmaceutical composition according to the present invention contains at least one compound of formula (I) according to any one of embodiments 1) to 58) (or a pharmaceutically acceptable salt thereof) as the active agent and optionally carriers and/or diluents and/or adjuvants.

The compounds of formula (I) according to any one of embodiments 1) to 58) and their pharmaceutically acceptable salts can be used as medicaments, e.g. in the form of pharmaceutical compositions for enteral (such as especially oral) or parenteral (including topical application or inhalation) administration.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) according to any one of embodiments 1) to 58), or a pharmaceutically acceptable salt thereof.

The present invention also includes isotopically labelled, especially $^2$H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

Any reference to a compound of formula (I), (I$_{ST1}$), (I$_{ST2}$), (I$_P$), (I-1), (I-2), (I-3), (I$_{ISO}$) or (I$_{TET}$), in this text is to be understood as referring also to the salts (and especially the pharmaceutically acceptable salts) of such compounds, as appropriate and expedient. The preferences indicated for the compounds of formula (I) of course apply *mutatis mutandis* to the compounds of formula (I$_{ST1}$), the compounds of formula (I$_{ST2}$), the compounds of formula (I$_P$), the compounds of formula (I-1), the compounds of formula (I-2), the compounds of formula (I-3), the compounds of formula (I$_{ISO}$) and the compounds of formula (I$_{TET}$) as well as to the salts and pharmaceutically acceptable salts of the compounds of formula (I), of formula (I$_{ST1}$), of formula (I$_{ST2}$), of formula (I$_P$), of formula (I-1), of formula (I-2), of formula (I-3), of formula (I$_{ISO}$) or of formula (I$_{TET}$). The same applies to these compounds as medicaments, to pharmaceutical compositions containing these compounds as active principles or to the uses of these compounds for the manufacture of a medicament for the treatment of the diseases according to this invention.

Unless used regarding temperatures, the term "about" (or alternatively "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively "around") placed before a temperature "Y" refers in the current application to an interval extending from the temperature Y minus 10° C. to Y plus 10° C., and preferably to an interval extending from Y minus 5° C. to Y plus 5° C. Besides, the term "room temperature" (r.t.) as used herein refers to a temperature of about 25° C.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range or if a variable is defined as being an integer between 1 and 4, this means that the variable is the integer 1, 2, 3, or 4.

As mentioned earlier, compounds of formula (I) modulate the PGD$_2$ activation of the CRTH2 receptor. The biological effect of such compounds may be tested in a variety of in vitro, ex vivo and in vivo assays. The ability of the compounds of formula (I) to bind to the CRTH2 receptor may be measured by methods similar to those described in the literature (Arimura A. et al., *J. Pharmacol. Exp. Ther.* 2001, 298(2), 411-419; and Sawyer N. et al., *Br. J. Pharmacol*, 2002, 137, 1163-1172, respectively) and by the assays described below in the experimental part.

A further aspect of the invention is a process for the preparation of compounds of Formula (I). Compounds according to Formula (I) of the present invention can be prepared according to the sequence of reactions outlined in the schemes below wherein X, Y, Z, n, R$^1$, R$^2$, R$^3$, R$^4$, R$^5$, R$^6$, R$^7$, R$^8$, R$^9$ and R$^{10}$ are as defined for Formula (I). Other abbreviations used are defined in the experimental section. In some instances the generic groups X, Y, Z, n, R$^1$, R$^2$, R$^3$, R$^4$, R$^5$, R$^6$, R$^7$, R$^8$, R$^9$ and R$^{10}$ might be incompatible with the assembly illustrated in the schemes below and, therefore, will require the use of protecting groups (PG). For example it may be necessary to protect reactive functional groups such as hydroxy, amino, imino, thio or carboxy groups, where these are desired in the final product, to avoid their unwanted participation in the reactions. The use of protecting groups is well known in the art (see for example "Protective Groups in Organic Synthesis", T. W. Greene, P. G. M. Wuts, Wiley-Interscience, 1999). It will be assumed that such protecting groups are as necessary in place. In the following description, for example, "PG", when used as amino-protecting group, preferably refers to a group such as tert-butoxycarbonyl, benzyloxycarbonyl, or allyloxycarbonyl, most preferably benzyloxycarbonyl. Further, "L" refers to a leaving group, such as an activated hydroxy group (for examples as mesylate, tosylate, active ester etc.), an in-situ activated hydroxy group (as used, for instance, in Mitsunobu reactions), or a halogen, in particular chloro or bromo. Further, "R" refers to a (C$_1$-C$_4$)alkyl group, preferably methyl, ethyl or tert-butyl.

In general, all chemical transformations can be performed according to well-known standard methodologies as described in the literature or as described in the procedures below. The compounds obtained may also be converted into pharmaceutically acceptable salts thereof in a manner known per se.

Generally, compounds of Formula (I), wherein R$^{10}$ represents —COOH, are obtained from an ester of Structure 1, wherein R represents (C$_1$-C$_4$)alkyl (preferably methyl, ethyl, or tert-butyl) by hydrolysis of the ester group using routine procedures, for example by stirring an intermediate of Structure 1, wherein R represents methyl or ethyl, with an aqueous solution of LiOH, NaOH or KOH in an organic co-solvent such as an alcohol (like MeOH or EtOH), THF, acetone, MeCN, or DMF; or by stirring an intermediate of Structure 1, wherein R represents tert.-butyl, in an acid like TFA.

Structure 1

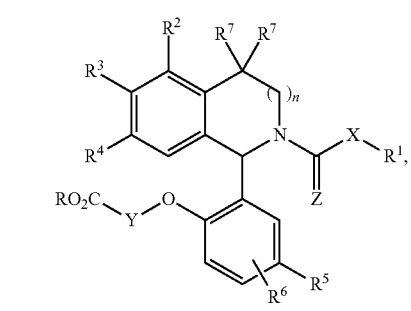

wherein R represents (C$_1$-C$_4$)alkyl

An intermediate of Structure 1 is for instance obtained by reacting an intermediate of Structure 2, or a salt thereof, such as a hydrochloride salt, with a reagent of Formula L-C(O)

X—R¹, wherein X and R¹ are as defined for Formula (I) and L is a leaving group such as an halogen (in particular chloro), in the presence of a base like NEt₃, DIPEA, N-ethyl-morpholine, N-methylpiperidine, or pyridine, in a suitable solvent, such as THF, or DCM. The starting material L-C(O)X—R¹ may be a chloroformate; an acyl anhydride; or an acyl halide like an acid chloride or an acid bromide. The acyl halide may be commercially available, known in the art or obtainable in situ from the corresponding commercially available or well known carboxylic acid in a reaction with a halogenating reagent like oxalyl chloride or phosphorous oxychloride under conditions known to a skilled person.

Structure 2

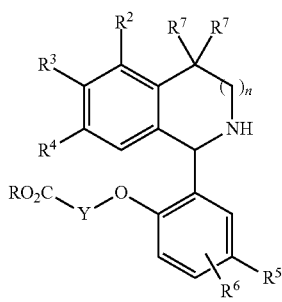

In another aspect, an intermediate of Structure 2 is reacted with a commercially available or well known isocyanate or isothiocyanate in the presence of a base to form an intermediate of Structure 1.

In another aspect, an intermediate of Structure 2 is activated with triphosgene, CDI, or the like and the reactive intermediate is then treated with an alcohol or an amine to give an intermediate of Structure 1, wherein X represents —NH— or —O—.

In a further aspect, an intermediate of Structure 2 is condensed with a commercially available or well known carboxylic acid in the presence of a coupling reagent, such as EDC, TBTU, diisopropylcarbodiimide, HATU, DCC, Ghosez's reagent or the like, in the presence of a base like NEt₃, DIPEA, or pyridine to form an intermediate of Structure 1.

In a further aspect, an intermediate of Structure 2 is reacted with bromoacetyl bromide in the presence of a base like NEt₃ or DIPEA to give the bromide 3, which is then used in an etherification reaction with alcohols R$^A$OH (wherein R$^A$ represents optionally substituted aryl-(C₁-C₂)alkyl or optionally substituted heteroaryl-(C₁-C₂)alkyl) in the presence of a base like sodium hydride to give a compound of Structure 1-A (Scheme 1). Alternatively, an intermediate of Structure 2 is used in an amide coupling with a N-protected amino acid to give an amide 4. Deprotection (for example catalytic hydrogenolysis of a Cbz protecting group), followed by reaction of the resulting amine with a sulfonyl chloride R$^B$SO₂Cl (wherein R$^B$ represents optionally substituted aryl or optionally substituted heteroaryl) yields a derivative of Structure 1-B. The resulting sulfonamide may be alkylated with Me-L (wherein L is a bromide or iodide) in the presence of a base like sodium hydride to give an intermediate of Structure 1-C (Scheme 2).

Scheme 1. Synthesis of intermediates of Structure 1-A

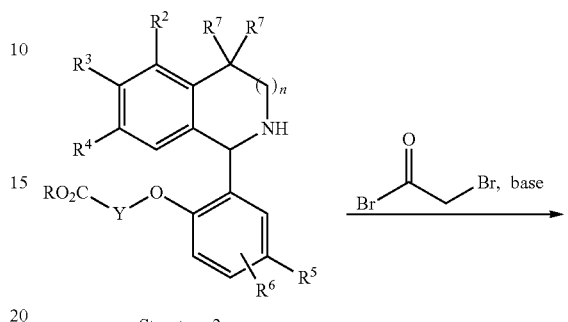

Structure 2

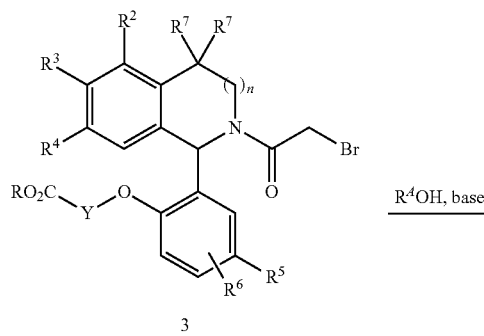

3

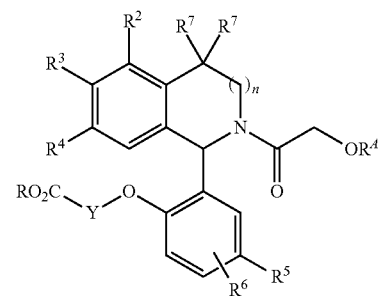

Structure 1-A

Scheme 2. Synthesis of intermediates of Structure 1-B and 1-C.

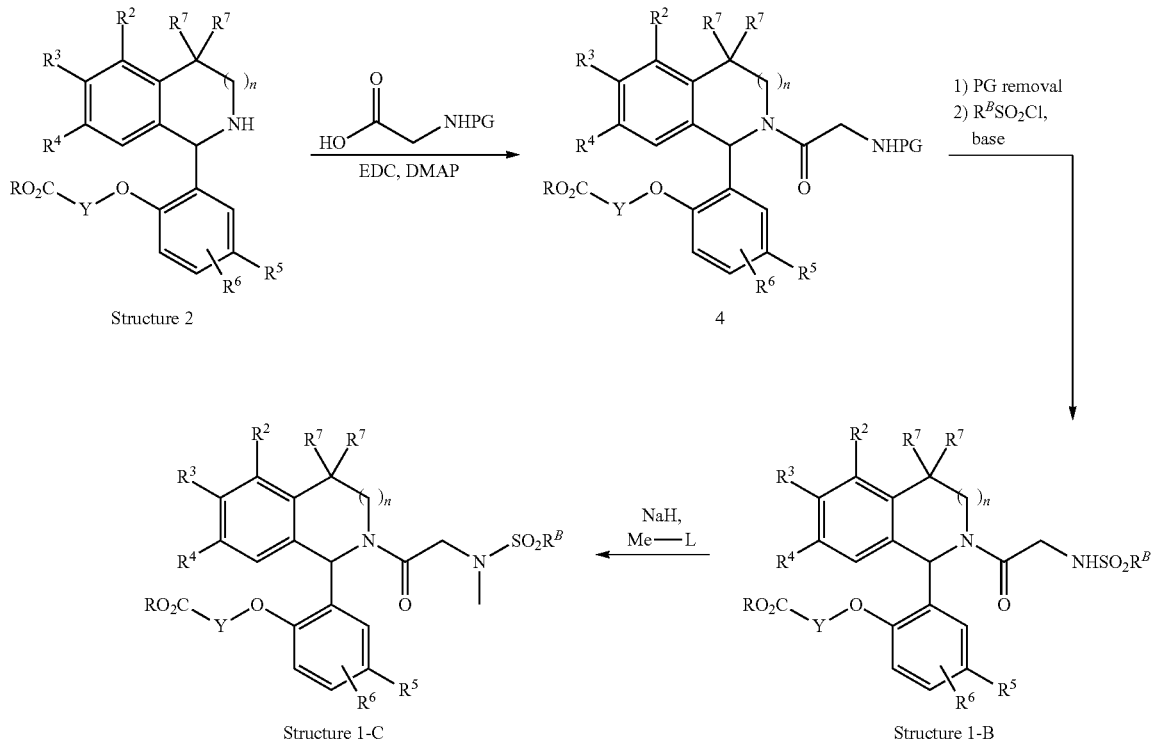

In another aspect an intermediate of Structure 2 is reacted with a carbonate 5 (wherein $R^C$ represents optionally substituted aryl) in the presence of a base like $NEt_3$ or DIPEA to give an intermediate of Structure 1-D (Scheme 3). A carbonate 5 is prepared by reaction of a benzyl alcohol 6 with N,N'-disuccinimidyl carbonate in the presence of a base like DMAP.

Scheme 3. Synthesis of intermediates of Structure 1-D.

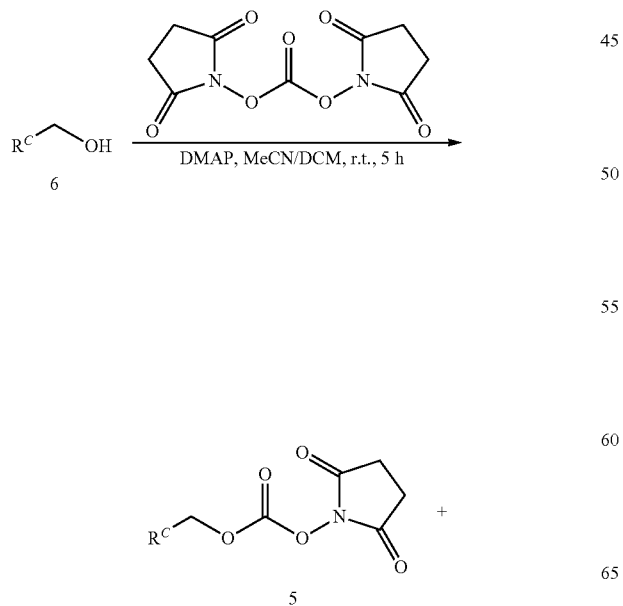

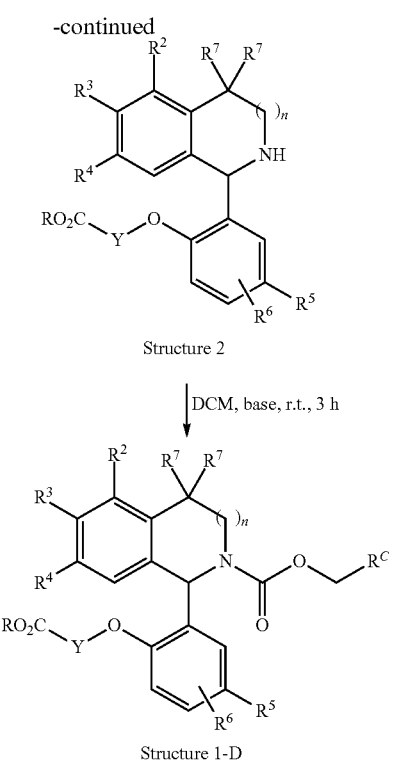

Alternatively an intermediate of Structure 2 is condensed with 4-nitrophenyl chloroformate in the presence of a base like $NEt_3$ or DIPEA to give a carbamate 7 (Scheme 4). The carbamate 7 is then treated with an alcohol $R^EOH$ (wherein R$^E$ represents (C$_1$-C$_4$)alkyl which is mono-substituted with (C$_3$-C$_6$)cycloalkyl, (C$_1$-C$_4$)alkoxy, optionally substituted aryl, optionally substituted heteroaryl, optionally substituted heterocyclyl, optionally substituted aryloxy, optionally substituted heteroaryloxy, optionally substituted aryl-(C$_1$-C$_2$)alkoxy, optionally substituted heteroaryl-(C$_1$-C$_2$)alkoxy, optionally substituted heteroarylsulfanyl or —NR$^8$R$^9$) in the presence of potassium tert-butoxide to give a compound of Formula (I-A). Under these specific conditions, the saponification and the substitution take place during the same reaction.

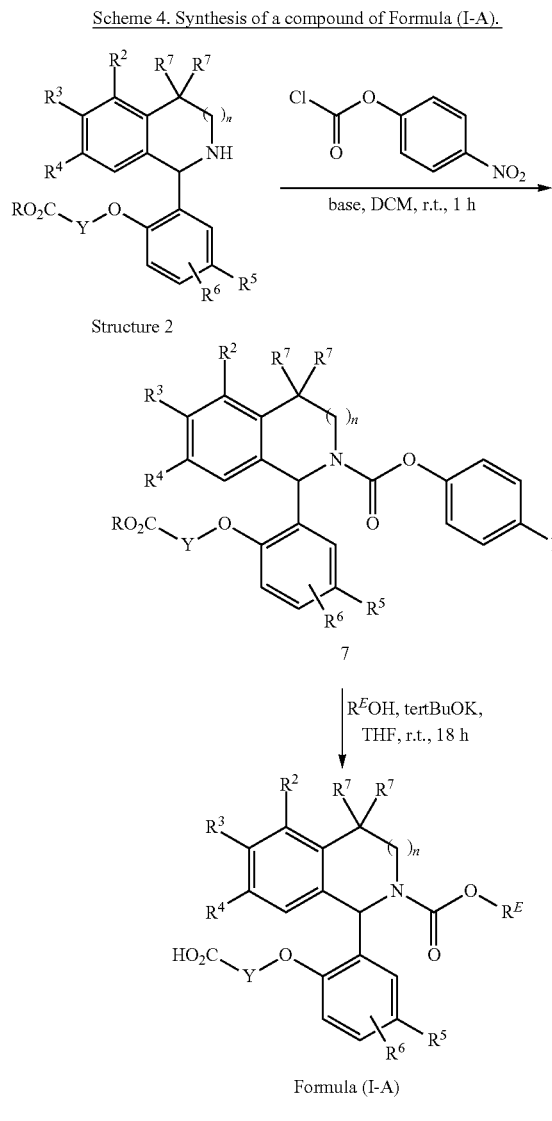

Scheme 4. Synthesis of a compound of Formula (I-A).

In another alternative, an intermediate of Structure 2 is treated with acryloyl chloride in the presence of a base like NEt$_3$ or DIPEA to give the vinyl amide 8 (Scheme 5). The vinyl amide 8 can undergo a Michael addition with R$^G$H (9), wherein R$^G$H represents an optionally substituted heteroaryl group containing an hydrogenated nitrogen atom in the ring system, like an optionally substituted indole, azaindole or indazole derivative. The reaction may be performed in the presence of potassium fluoride on alumina (F. M. Moghaddam et al., Lett. Org. Chem. 2006, 3, 157-160) and takes place at the nitrogen atom of the heteroaryl group to give a compound of Formula (I-B). Under these specific reaction conditions, potassium hydroxide is generated and the Michael addition and the saponification take place during the same reaction.

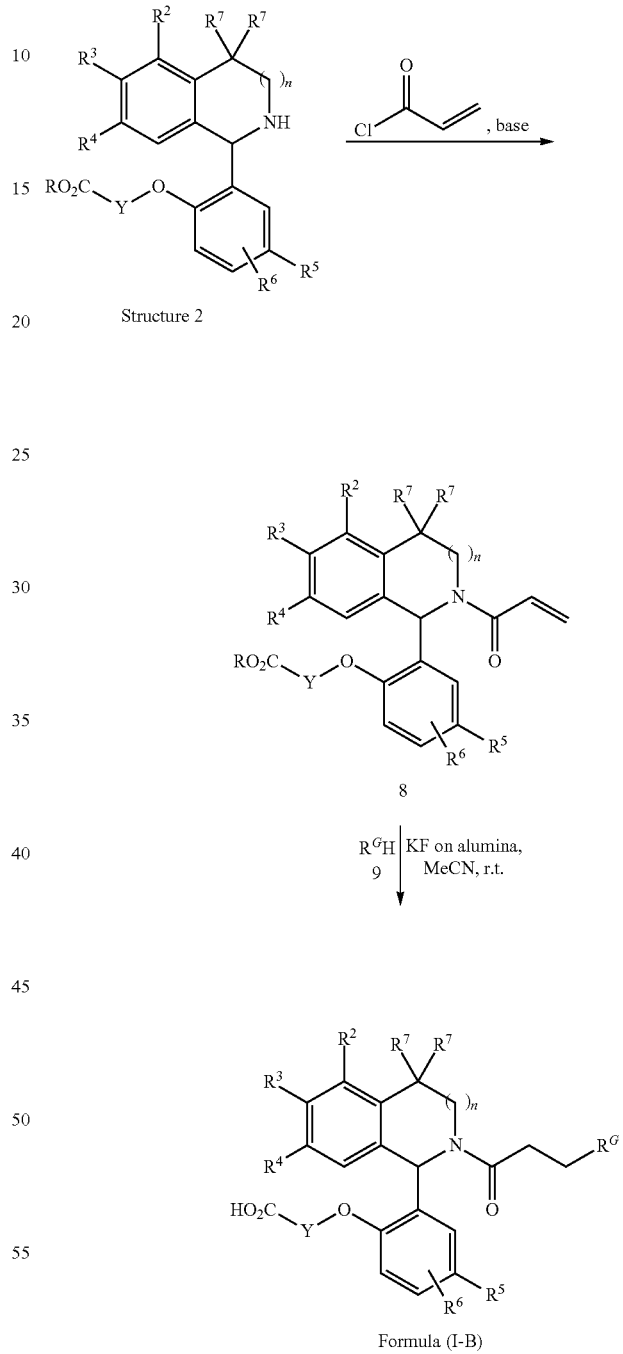

Scheme 5. Synthesis of intermediates of Formula (I-B).

An intermediate of Structure 2 is obtained after removal of a protecting group (PG) from an intermediate of Structure 10, applying reaction conditions known to a skilled person. Preferably, PG is a group such as tert-butoxycarbonyl or benzyloxycarbonyl. A benzyloxycarbonyl protecting group is removed by hydrogenolysis or treatment with an acid; a tert-butoxycarbonyl group is cleaved under acidic conditions.

Structure 10

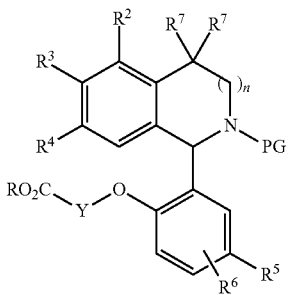

An intermediate of Structure 10, wherein n represents 1 (a tetrahydroisoquinoline) is obtained by one of the synthetic pathways described below. For example, an intermolecular α-aminoalkylation reaction between a 3,4-dihydroisoquinoline 11 and a phenol 12 (Scheme 6) gives the tetrahydroisoquinoline 13. In this reaction, the 3,4-dihydroisoquinoline 11 is first activated at r.t. in MeCN with a protecting group precursor PGL such as di-tert-butyl dicarbonate or a chloroformate (like benzyl chloroformate). The resulting activated species undergoes an electrophilic substitution with an electron rich aromatic compound (such as phenol 12) in MeCN at a temperature of about 60-80° C. A subsequent alkylation of phenol 13 with an electrophile L-Y—CO$_2$R, wherein Y is as defined in Formula (I) and L is a leaving group such as bromide, in the presence of a base like Cs$_2$CO$_3$ or K$_2$CO$_3$ affords an intermediate of Structure 10 (n=1).

Scheme 6. Synthesis of intermediate of Structure 10 (n = 1).

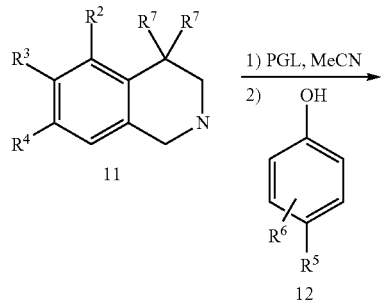

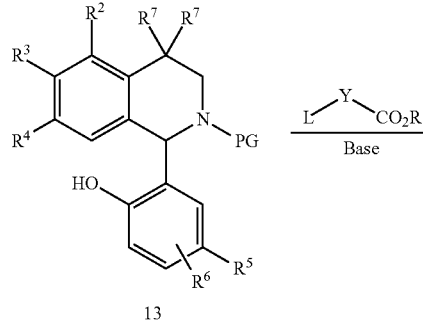

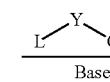

In another aspect, treatment of a dihydroisoquinoline 11 with a protecting group precursor PG$^1$L such as di-tert-butyl dicarbonate or a chloroformate (like benzyl chloroformate), followed by the addition of a Grignard reagent 14 affords the tetrahydroisoquinoline 15 (Scheme 3). The Grignard reagent 14 is prepared by treatment of the bromide 16 with a solution of isopropylmagnesium chloride/lithium chloride complex. Compound 16 is obtained through protection of the phenol 17 with an allyl halide (e.g. allyl bromide) or a benzyl halide (e.g. benzyl bromide) as protecting group precursor PG$^2$L in the presence of a base like K$_2$CO$_3$ in a solvent like acetone. Selective deprotection of the phenol protecting group of structure 15, like an selective removal of an allyl group in the presence of a carbamate protecting group (PG$^1$) with Pd(PPh$_3$)$_4$ and a barbituric acid derivative and a subsequent alkylation with an electrophile L-Y—CO$_2$R, wherein Y is as defined in Formula (I) and L is a leaving group such as bromide, in the presence of a base like Cs$_2$CO$_3$ or K$_2$CO$_3$ yields an intermediate of Structure 10-A.

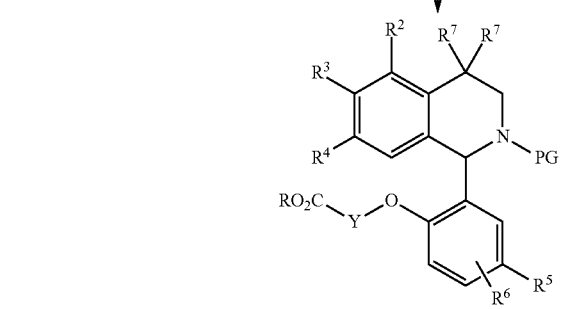

Structure 10 (n = 1)

Scheme 7. Synthesis of intermediate of Structure 10-A.

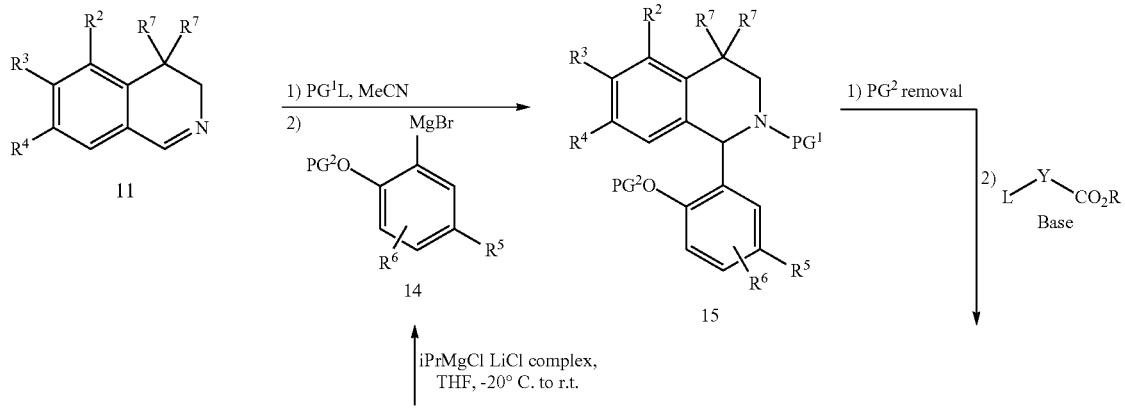

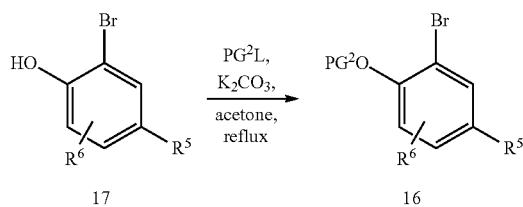

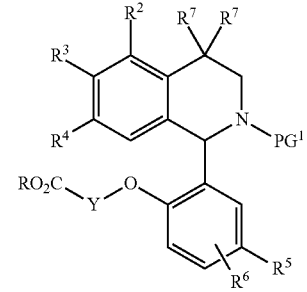

Structure 10-A

In another aspect, Suzuki reaction of bromide 18 with a boronic acid R⁵B(OH)₂ in the presence of a palladium catalyst affords an intermediate of Structure 10-B. A bromide 18 could also be used in a Stifle cross-coupling reaction. A bromide 18 can also be converted into a sulfone of Structure 10-C using a sulfinate derivative R$^I$S(O)ONa (wherein R$^I$ represents ($C_1$-$C_4$)alkyl or phenyl) in the presence of a copper catalyst like CuI and a ligand like prolinate. Finally, a bromide 18 can be converted into a triazole derivative of Structure 10-D using a copper catalyst like CuI in the presence of a bidentate ligand like N,N'-dimethyl-1,2-cyclohexanediamine (Scheme 8).

Alternatively, a bromide 19 can be converted in a sulfone of Structure 10-E using a sulfinate derivative R$^I$S(O)ONa (wherein R$^I$ represents ($C_1$-$C_4$)alkyl or phenyl) in the presence of a copper catalyst like CuI and a ligand like prolinate. A bromide 19 can be converted into a sulphonamide of Structure 10-F using a sulphonamide derivative R$^J$SO₂NH₂ (wherein R$^J$ represents ($C_1$-$C_4$)alkyl) in the presence of a copper catalyst like CuI in the presence of a bidentate ligand like N,N-dimethylglycine (Scheme 9).

Scheme 8. Synthesis of intermediates of Structure 10-B, 10-C and 10-D.

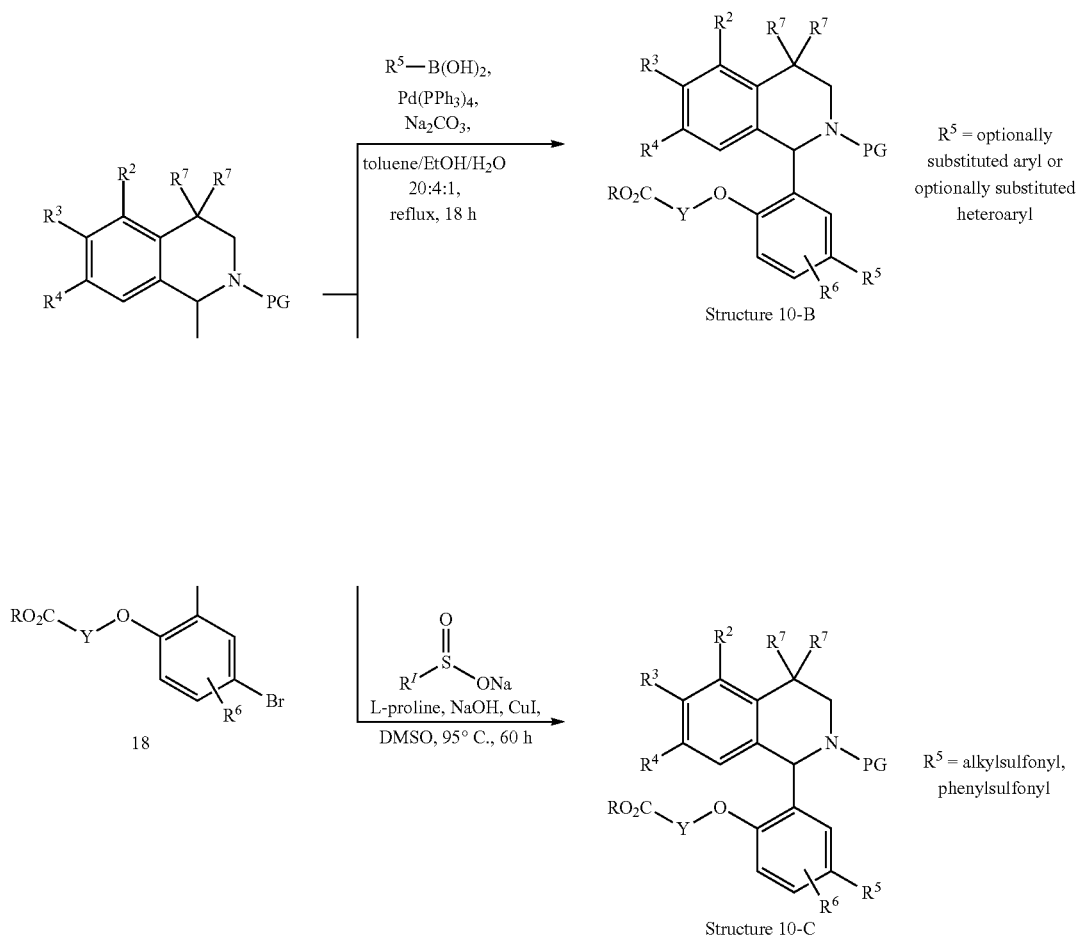

-continued

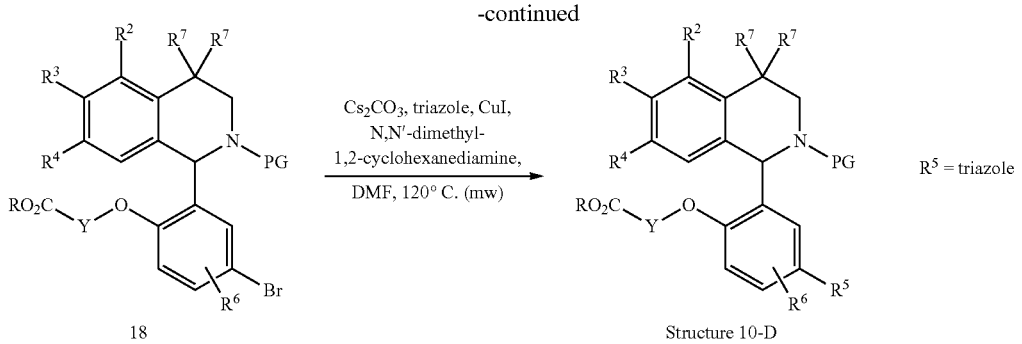

18 → Structure 10-D, R⁵ = triazole

Reagents: Cs₂CO₃, triazole, CuI, N,N′-dimethyl-1,2-cyclohexanediamine, DMF, 120° C. (mw)

Scheme 9. Synthesis of intermediates of Structure 10-E and 10-F.

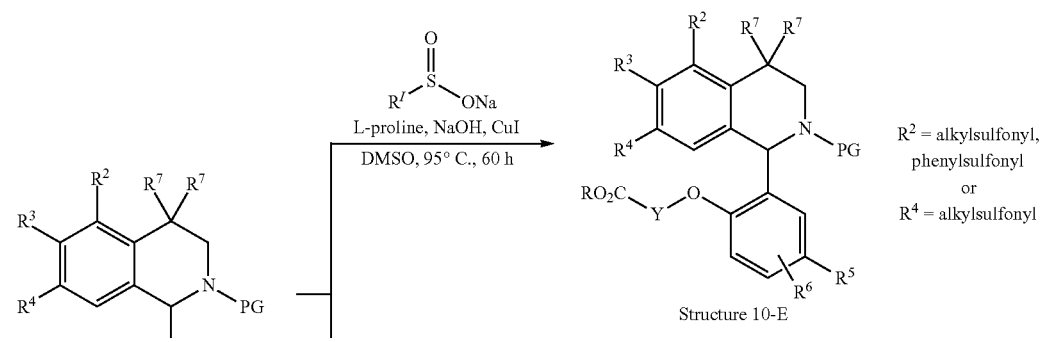

Structure 10-E
R² = alkylsulfonyl, phenylsulfonyl
or
R⁴ = alkylsulfonyl

Reagents: R¹S(O)ONa, L-proline, NaOH, CuI, DMSO, 95° C., 60 h

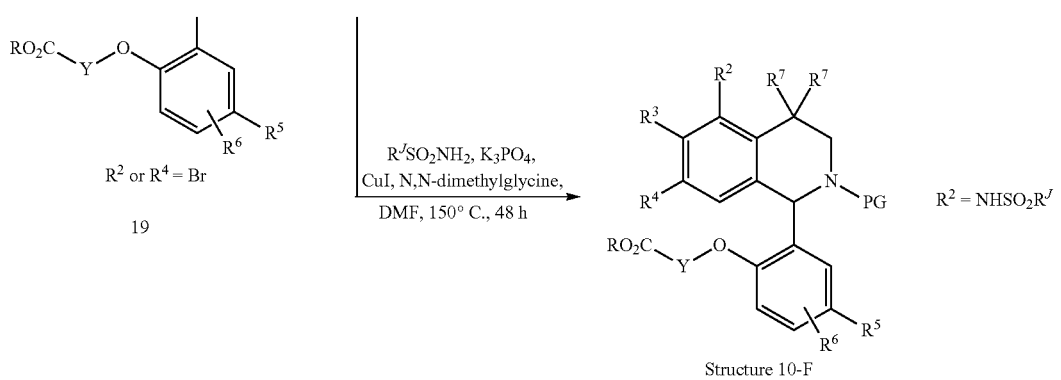

19, R² or R⁴ = Br → Structure 10-F, R² = NHSO₂R^J

Reagents: R^J SO₂NH₂, K₃PO₄, CuI, N,N-dimethylglycine, DMF, 150° C., 48 h

In another aspect, a nitrile 20, obtainable following the sequence depicted in Scheme 6 ($R^5$=CN), is converted to an amide of Structure 10-G by nitrile hydrolysis using water and the platinum catalyst developed by Ghaffar et al. (Tet. Lett. 1995, 36, 8657). Alternatively, nitrile 20 is transformed into an oxadiazole derivative by condensation with hydroxylamine and thiocarbonyldiimidazole (Scheme 10).

Scheme 10. Synthesis of intermediates of Structure 10-G and 10-H.

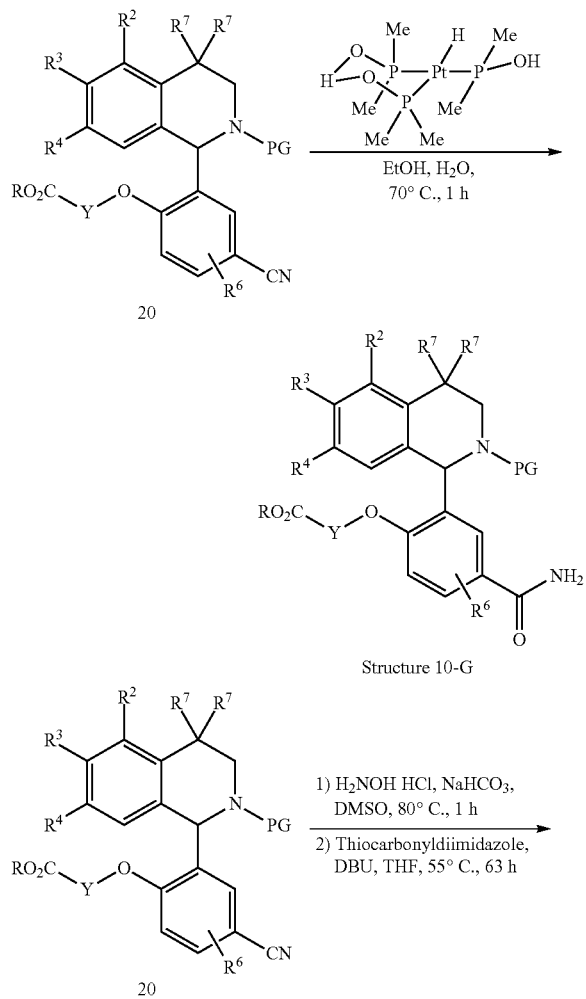

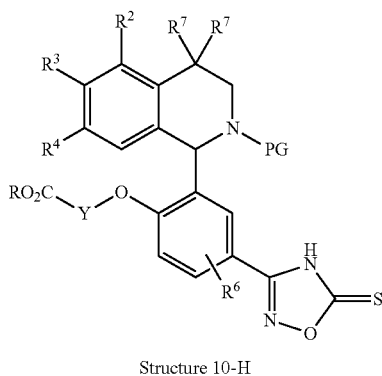

Structure 10-H

The required 3,4-dihydroisoquinolines 11 are prepared from the corresponding phenethylamines 21 (or the corresponding hydrochloride salts) using a modified Bischler-Napieralski reaction (Scheme 11). Thus, reaction of a phenethylamine 21 with ethyl formate affords the corresponding formamide, which is transformed into an oxazolo intermediate upon treatment with oxalyl chloride and iron(III) chloride. Treatment of the oxazolo derivative with methanol in the presence of an acid like sulphuric acid yields the desired 3,4-dihydroisoquinolines 11. If not commercially available, the phenethylamines 21 may be synthesized by reduction of the corresponding α,β-unsaturated nitro derivatives 22, which are prepared from the aldehydes 23 through an Henry reaction. Alternatively, the phenethylamines 21, wherein $R^7$ represents methyl, are obtained from the corresponding benzyl cyanide 24 through double alkylation with methyl iodide in the presence of a base like sodium hydroxide followed by a reduction of the nitrile with lithium aluminum hydride. Finally, dihydroisoquinolines 11 can be obtained by oxidation of the corresponding tetrahydroisoquinolines 25 with N-bromosuccinimide followed by a basic workup (Scheme 11).

Scheme 11. Synthesis of the dihydroisoquinolines 11.

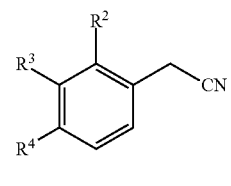

24

1) MeI, base
2) LiAlH$_4$, Et$_2$O

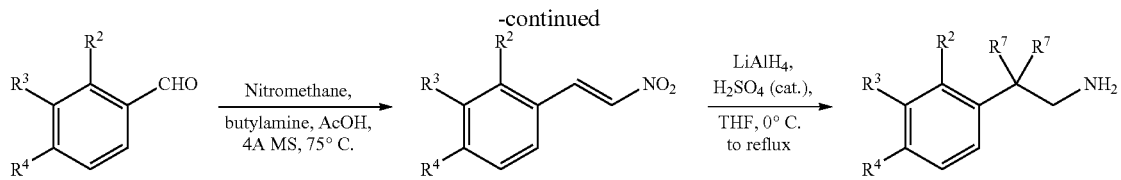

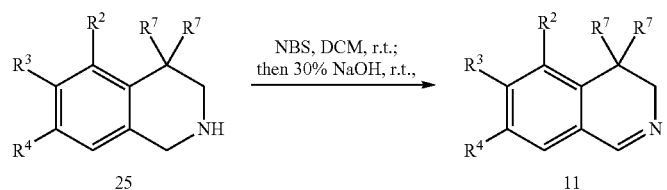

An intermediate of Structure 10, wherein n represents 0 (an isoindoline) may be prepared as described in Scheme 12. The bromide 26 is submitted to a lithium halogen exchange mediated by nBuLi and the resulting lithiated species is treated with the sulfinamide 27 to afford the isoindoline 28. The sulfinamide auxiliary is then cleaved under acidic conditions (for example in the presence of HCl) and the resulting amine is treated with a protecting group precursor PG$^1$L such as di-tert-butyl dicarbonate or a chloroformate (like benzyl chloroformate) to give the isoindoline 29. Selective deprotection of the phenol protecting group of structure 29, like an selective removal of an allyl group in the presence of a carbamate protecting group (PG$^1$) with Pd(PPh$_3$)$_4$ and a barbituric acid derivative gives a phenol 30. Alkylation of compound 30 with an electrophile L-Y—CO$_2$R, wherein Y is as defined in Formula (I) and L is a leaving group such as bromide, in the presence of a base like Cs$_2$CO$_3$ or K$_2$CO$_3$ yields an intermediate of Structure 10-J. Compound 27 is prepared from salicylaldehyde derivative 31 through protection of the phenol moiety with an allyl halide (e.g. PG$^2$L=allyl chloride) or a benzyl halide (e.g. PG$^2$L=benzyl bromide) in the presence of a base like potassium carbonate in a solvent like DMF. The aldehyde 32 is treated with tert-butylsulfinamide in the presence of Ti(OEt)$_4$ in a solvent like THF to give the sulfinamide 27.

Scheme 12. Synthesis of isoindolines of Structure 10-J.

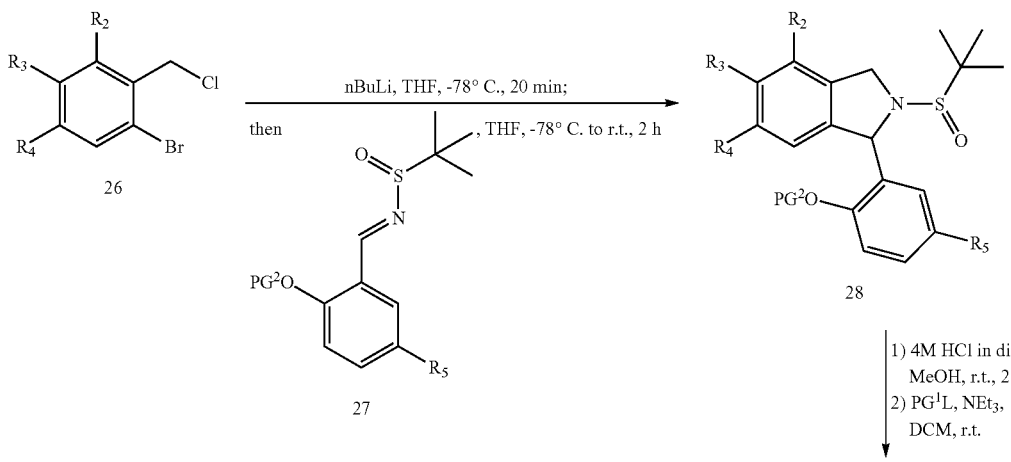

-continued

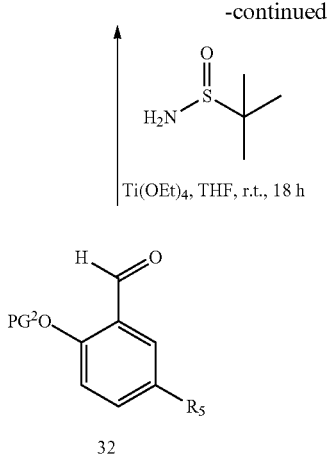

32

↑ PG²L, K₂CO₃,
DMF, 50° C., 18 h

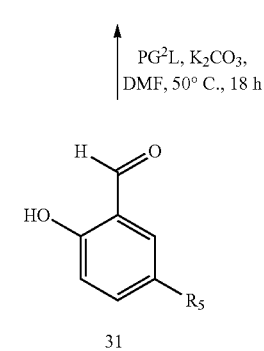

31

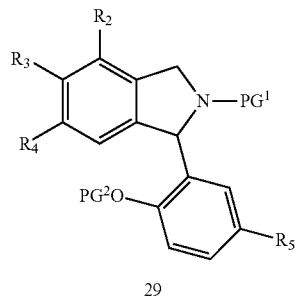

29

| PG² removal
↓

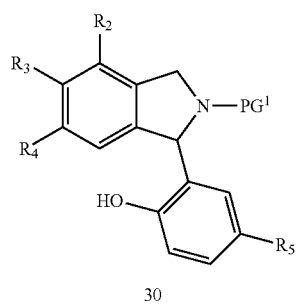

30

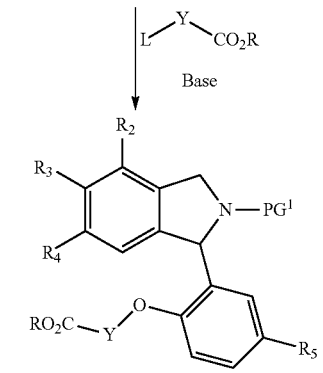

Structure 10-J

The required bromides 26 are prepared from the corresponding benzyl alcohols 33 through a chlorination with thionyl chloride (Scheme 13). If not commercially available, the benzyl alcohols 33 are synthesized by reduction of the corresponding aldehydes 34 by using, for instance, sodium borohydride in a solvent like MeOH. The aldehydes 34 can be prepared from the corresponding bromide 35 through deprotonation with a strong base like LDA and subsequent addition of DMF.

Scheme 13. Synthesis of bromides 26.

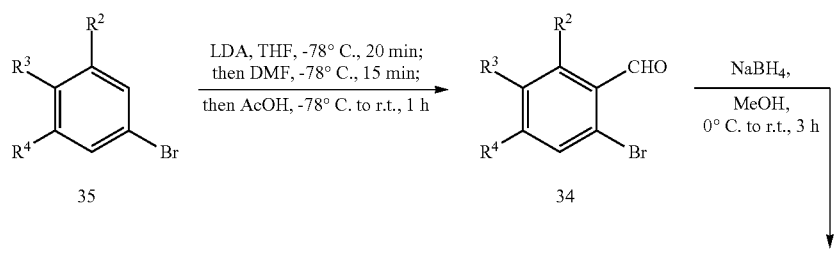

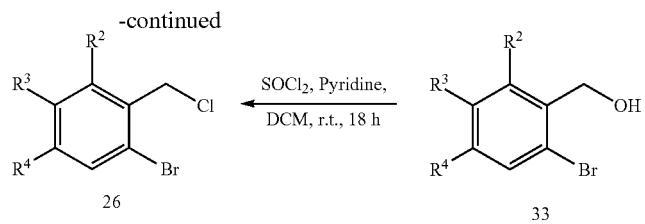

In another aspect, the carboxylic acid moiety in compounds of Formula (I—C) can be replaced by a bioisostere. For example, the carboxylic acid can undergo an amide coupling with hydrazine in the presence of a coupling reagent like TBTU and a base such as DIPEA to give an hydrazide intermediate 36. The hydrazide 36 can then undergo a CDI mediated cyclization in the presence of a base like NEt₃ to form a 5-oxo-4,5-dihydro-[1,3,4]oxadiazol derivative of Formula (I-D) (Scheme 14). Alternatively, an amide coupling between the carboxylic acid moiety and trifluoromethanesulfonamide in the presence of a coupling reagent like HATU and a base such as DIPEA gives a trifluoromethylsulfonamido derivative of Formula (I-E). In another aspect, the carboxylic acid moiety can undergo an amide coupling with cyanamide in the presence of a coupling reagent such as HATU and a base like NEt₃ to give a cyanamido derivative of Formula (I-F) (Scheme 14).

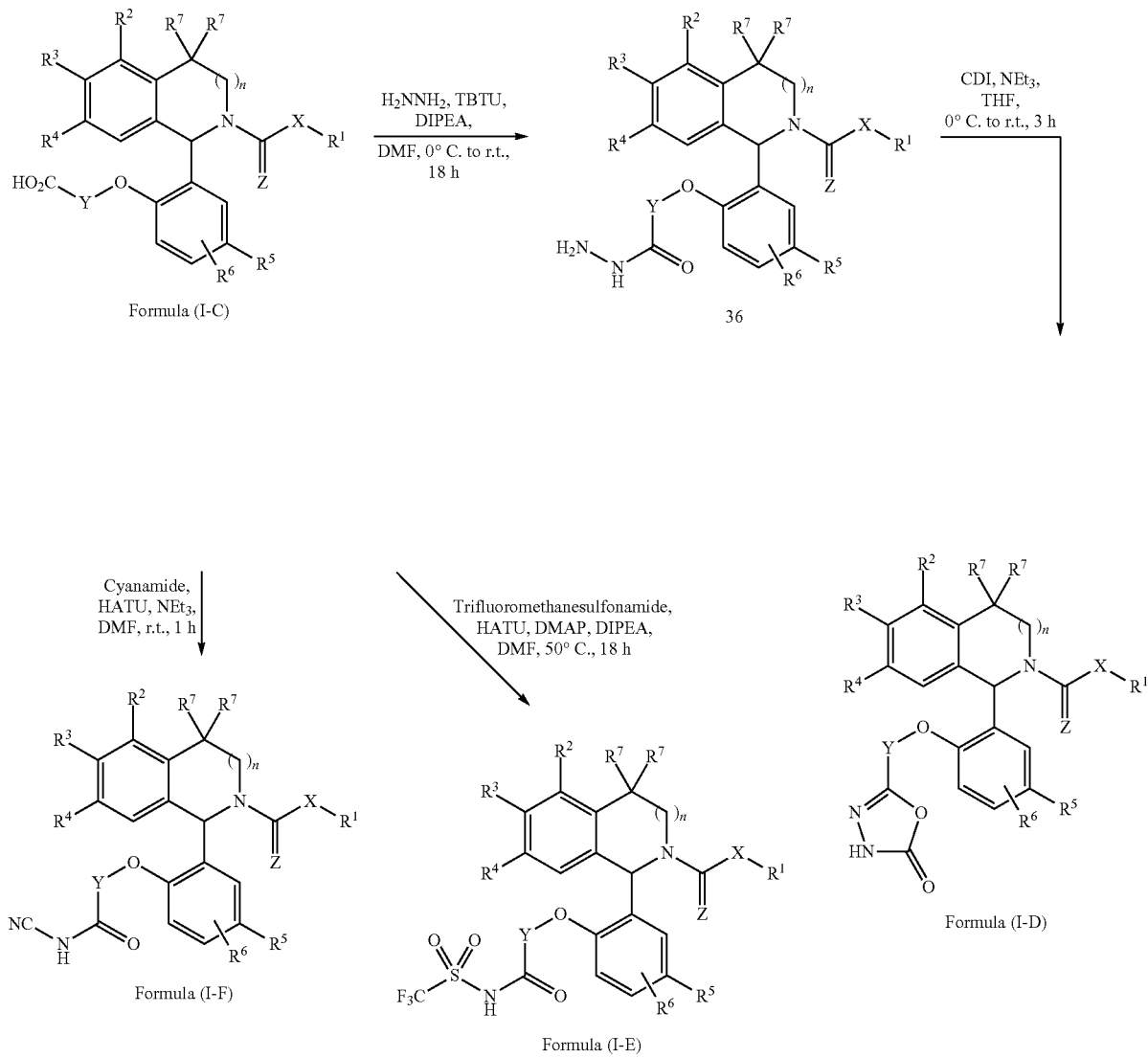

Alternatively, an ester of Structure 1 can be treated with aqueous hydroxylamine in a solvent like isopropanol to form an hydroxamate of Formula (I-G) (Scheme 15).

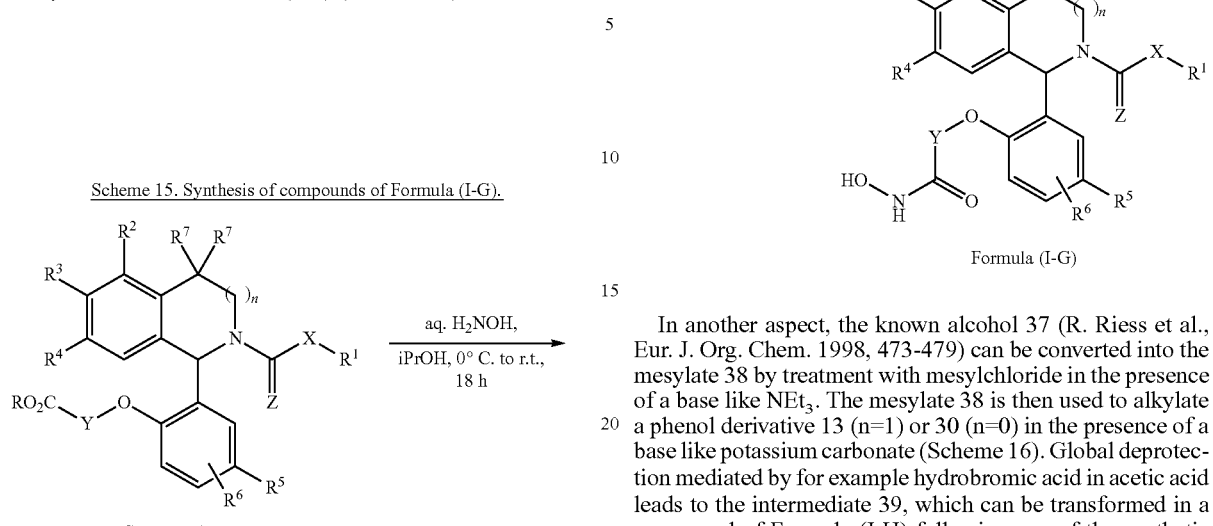

In another aspect, the known alcohol 37 (R. Riess et al., Eur. J. Org. Chem. 1998, 473-479) can be converted into the mesylate 38 by treatment with mesylchloride in the presence of a base like $NEt_3$. The mesylate 38 is then used to alkylate a phenol derivative 13 (n=1) or 30 (n=0) in the presence of a base like potassium carbonate (Scheme 16). Global deprotection mediated by for example hydrobromic acid in acetic acid leads to the intermediate 39, which can be transformed in a compound of Formula (I-H) following one of the synthetic pathways describing the transformation of a compound of Structure 2 into a compound of Formula I (see above).

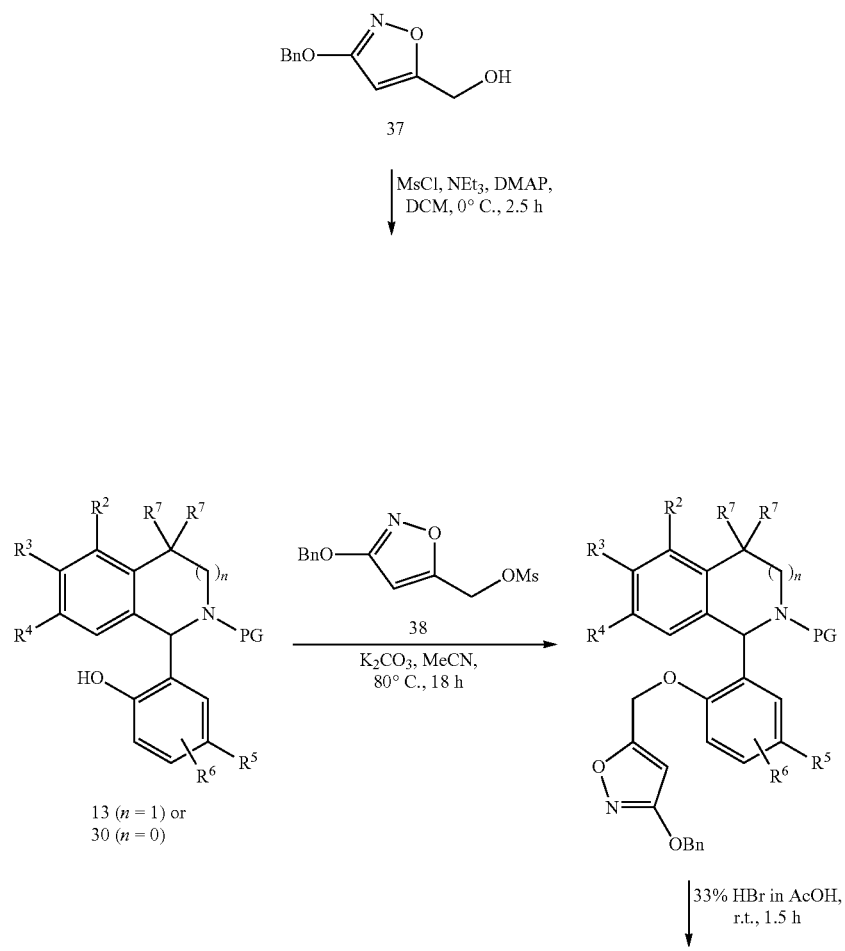

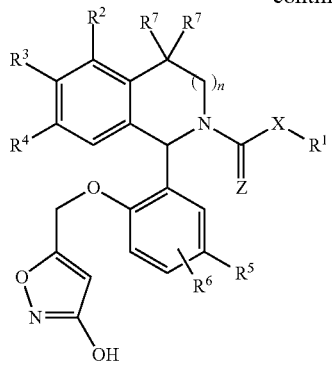

Formula (I-H)

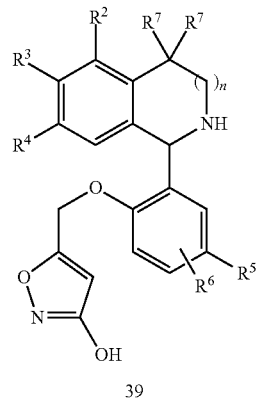

39

Alternatively, a phenol 13 (n=1) or 30 (n=0) can be alkylated with chloroacetonitrile in the presence of a base such as potassium carbonate to give a nitrile derivative 40 (Scheme 17). Protecting group removal under acidic conditions and introduction of the desired residue R¹—X—C(Z)— as described for the transformation of a compound of Structure 2 into a compound of Formula (I) gives an intermediate 41. The nitrile derivative 41 can be converted into a tetrazole of Formula (I-J) by treatment with sodium azide. In a different approach, a compound 41 can react with hydroxylamine in the presence of a base like potassium carbonate. The resulting N-hydroxycarbamimidoyl derivative 42 may undergo a CDI mediated cyclization in the presence of a base such as DBU to give a 5-oxo-4,5-dihydro-[1,2,4]oxadiazol derivative of Formula (I-K).

Scheme 17. Synthesis of compounds of Formula (I-J) and (I-K).

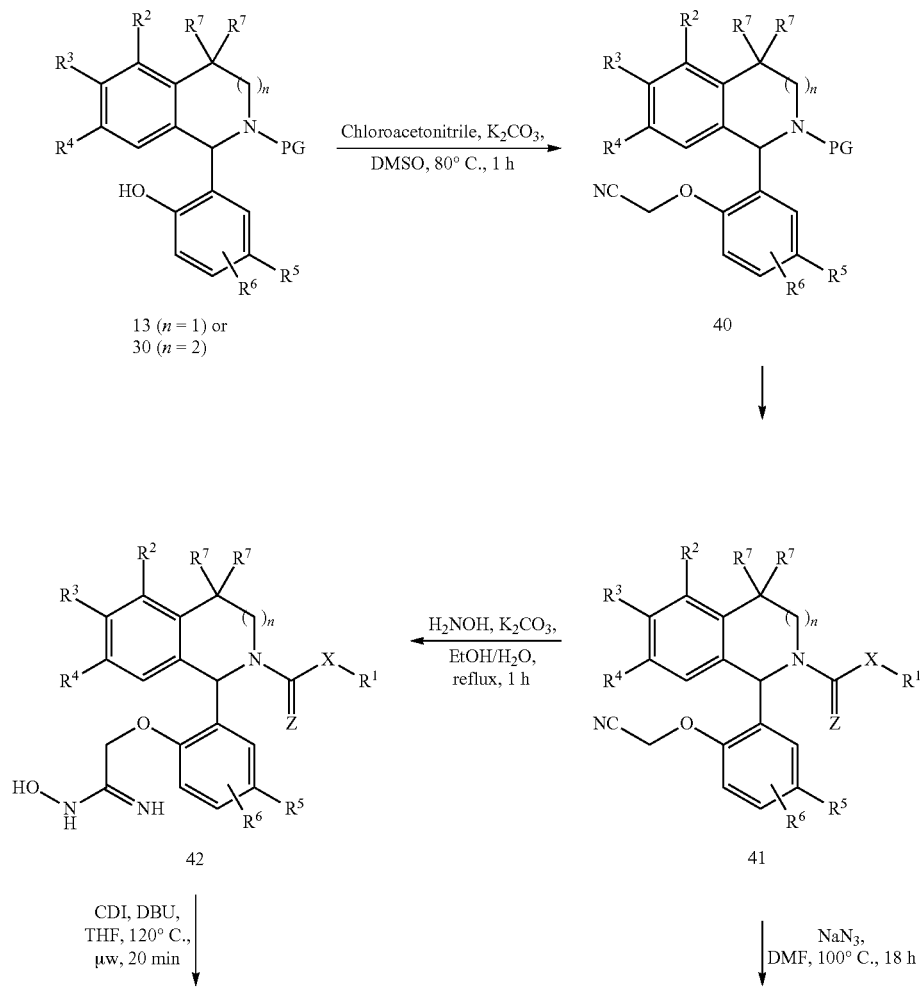

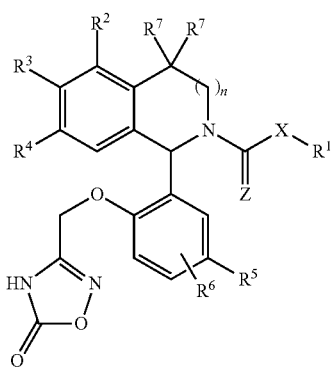

Formula (I-K)

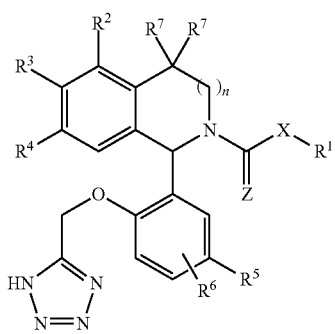

Formula (I-J)

Acid derivatives used in the amide coupling with compounds of Structure 2 are commercially available, known in the art or obtainable according to Schemes 18 and 19. A Negishi cross-coupling reaction between the bromo derivative 43, wherein $R^K$ and $R^L$ independently represent hydrogen, $(C_1-C_4)$alkyl, $(C_1-C_4)$alkoxy, chloro, or fluoro, and a zinc bromide derivative affords the ester 44 which is saponified to the corresponding carboxylic acid 45 (Scheme 18).

Scheme 18. Synthesis of acid derivatives 45.

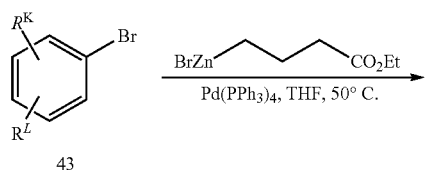

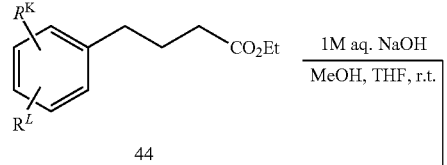

Alternatively, a cinnamic acid 46, wherein $R^M$ and $R^N$ independently represent hydrogen, $(C_1-C_4)$alkyl, $(C_1-C_4)$alkoxy, $(C_1-C_4)$fluoroalkyl, or halogen, is converted to the Weinreb amide 47. Corey-Chaykovsky cyclopropanation gives the cyclopropane 48, which is hydrolyzed to the corresponding carboxylic acid 49 (Scheme 19).

Scheme 19. Synthesis of acid derivatives 49.

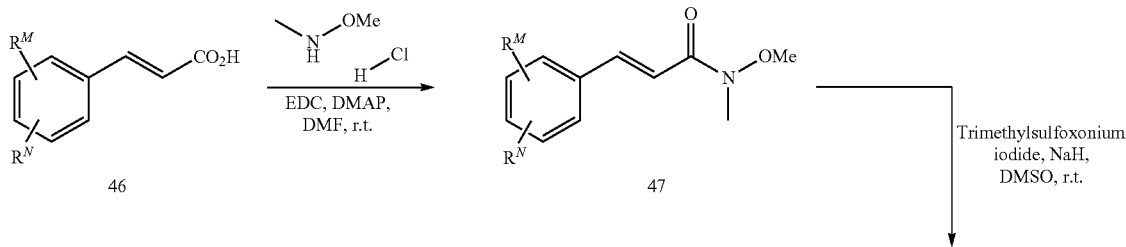

-continued

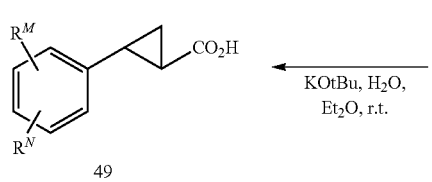 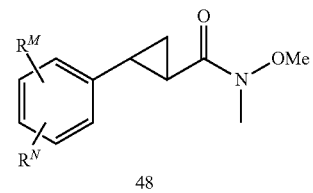

Whenever the compounds of Formula (I) are obtained in the form of mixtures of enantiomers or diastereoisomers, the enantiomers or diastereoisomers can be separated using methods known to one skilled in the art: e.g. by formation and separation of diastereomeric salts or by HPLC over a chiral stationary phase such as a Daicel ChiralPak AD-H (5 µm) column, a Daicel ChiralCel OD-H (5 µm) column, a Daicel ChiralCel OD (10 µm) column, a Daicel ChiralPak IA (5 µm) column, a Daicel ChiralPak IB (5 µm) column, a Daicel ChiralPak IC (5 µm) column, or a (R,R)-Whelk-01 (5 µm). Typical conditions of chiral HPLC are an isocratic mixture of eluent A (EtOH, in presence or absence of a base like $NEt_3$ and/or diethylamine or of an acid like TFA) and eluent B (heptane), at a flow rate of 8 to 34 mL/min.

EXPERIMENTAL SECTION

Abbreviations (as Used Herein):
AcOEt Ethyl acetate
AcOH Acetic acid
aq. aqueous
Bdg Binding
BSA Bovine Serum Albumin
Bu n-butyl
ca. circa (latin)—approximately
Cbz Benzyloxycarbonyl
CC Column chromatography on silica gel
CDI Carbonyldiimidazole
comb. combined
conc. concentrated
DBU 1,8-Diazabicyclo[5.4.0]undec-7-ene
DCC 1,3-Dicyclohexylcarbodiimide
DCM Dichloromethane
DIPEA N,N-Diisopropylethylamine
DMAP N,N-Dimethyl-4-aminopyridine
DME 1,2-Dimethoxyethane
DMF Dimethylformamide
DMSO Dimethylsulfoxide
dpm decays per minute
EDTA Ethylene Diamine Tetraacetic Acid
EDC 1-Ethyl-3-(3-dimethylaminopropyl)carbodiimide
ee enantiomeric excess
eq. Equivalent
EtOH ethanol
ESI-MS Electrospray Ionization Mass Spectroscopy
Ghosez's reagent 1-Chloro-N,N,2-trimethyl-1-propenylamine
h hour(s)
HATU O-(7-Aza-1H-benzotriazole-1-yl)-1,1,3,3-tetramethyluronium hexafluorophosphate
Hept Heptane
HPLC High Performance Liquid Chromatography
HSA human serum albumin
hv high vacuum
iPr isopropyl
L liter(s)
LAH lithium aluminum hydride
LC-MS Liquid Chromatography—Mass Spectroscopy
M molarity [mol $L^{-1}$]
Me Methyl
MeCN Acetonitrile
MeI Methyl iodide
MeOH Methanol
mesyl Methanesulfonyl
Meth. Method
min minute(s)
MS Mass Spectroscopy
MW Molecular Weight
N Normality of solution
NBS N-bromo-succinimide
$NEt_3$ Triethylamine
NMR Nuclear magnetic resonance
org. organic
PBS Phosphate Buffered Saline
PG Protecting Group
$PGD_2$ Prostaglandin $D_2$
PMSF Phenylmethylsulfonyl fluoride
prep. preparative
r.t. room temperature
second(s)
sat. saturated
Si-carbonate Polymer supported carbonate
Si-DEA Polymer supported diethyl amine
soln. solution
subst. Substituted
TBTU O-(Benzotriazol-1-yl)-N,N,N',N'-tetramethyluronium
tert. tertiary
TFA Trifluoroacetic acid
THF Tetrahydrofuran
tosyl Toluenesulfonyl
$t_R$ retention time
Tris Tris-(hydroxymethyl)aminomethane buffer
Chemistry
General Remarks All solvents and reagents are used as obtained from commercial sources unless otherwise indicated.

Temperatures are indicated in degrees Celsius (° C.). Unless otherwise indicated, the reactions take place at room temperature (r.t.).

In mixtures, relations of parts of solvent or eluent or reagent mixtures in liquid form are given as volume relations (v/v), unless indicated otherwise.

Analytical HPLC conditions as used in the Examples below:

LC-MS 1

LC-MS-conditions: Analytical. Pump: Waters Acquity Binary Solvent Manager, MS: Waters SQ Detector, DAD: Acquity UPLC PDA Detector, ELSD: Acquity UPLC ELSD. Column: Acquity UPLC BEH C18 1.7 mm 2.1×50 mm ID from Waters, thermostated in the Acquity UPLC Column Manager. Eluents: A: $H_2O$+0.05% formic acid or TFA; B:

MeCN+0.05% formic acid or TFA. Method: Gradient: 2% B to 98% B over 2.00 min. Flow: 1.2 mL/min. Detection: UV/Vis and/or ELSD, and MS, $t_R$ is given in min LC-MS 1 FA: Eluents: A: H$_2$O+0.05% formic acid; B: MeCN+0.05% formic acid LC-MS 1TFA: Eluents: A: H$_2$O+0.05% TFA; B: MeCN+0.05% TFA LC-MS 2 to LC-MS 5

HPLC/MS analyses are performed on a Ultimate 3000RS Dionex HPLC instrument, equipped with a Dionex Ultimate 3000 RS Photodiode Array Detector, a Dionex Ultimate 3000RS pump and a Dionex MSQ$^+$ mass spectrometer.

The LC retention times are obtained using the following elution conditions:
  LC-MS 2: Analytical HPLC on a Waters X-Bridge C18 column (4.6×30 mm, 2.5 μm, Waters); Linear gradient of water/0.04% TFA (A) and MeCN (B) from 5% to 95% B over 1.5 min; flow rate 4.5 mL/min, detection at 215 nm.
  LC-MS 3: Analytical HPLC on a Zorbax® SB-AQ column (4.6×50 mm, 3.5 μm, Agilent); Linear gradient of water/0.04% TFA (A) and MeCN (B) from 5% to 95% B over 1.5 min; flow rate 4.5 mL/min, detection at 215 nm.
  LC-MS 4: Analytical HPLC on a Waters Atlantis T3 column (4.6×30 mm, 5 urn, Waters); Linear gradient of water/0.04% TFA (A) and MeCN (B) from 5% to 95% B over 1.5 min; flow rate 4.5 mL/min, detection at 215 nm.
  LC-MS 5: Analytical HPLC on a Supelco Ascentis Express C18 column (5×2.1 mm, 2.7 μm, Supelco); Linear gradient of water/0.05% formic acid (A) and MeCN (B) from 5% to 95% B over 2.5 min; flow rate 1.8 mL/min, detection at 214 and 254 nm.

Preparative HPLC/MS purifications are performed on a Gilson HPLC system, equipped with a Gilson 215 autosampler, Gilson 333/334 pumps, Finnigan AQA MS detector system, and a Dionex UV detector, using a Waters Xbridge C18 or an Waters Atlantis column, with a linear gradient of water/formic acid 0.02% (A) and MeCN (B) (acidic conditions) or water/ammonia 0.02% (A) and MeCN (B) (basic conditions).

$^1$H-NMR spectra are recorded either on a Varian Mercury 300VX FT-NMR spectrometer or on a Bruker Advance II 400 spectrometer. All spectra were recorded at r.t., unless otherwise stated. Chemical shifts (δ) are reported in parts per million (ppm) relative to proton resonances resulting from incomplete deuteration of the NMR solvent, e.g. for DMSO δ(H) 2.49 ppm, and the abbreviations s, d, t, q, m and br refer to singlet, doublet, triplet, quartet, multiplet, and broad, respectively. Coupling constant J are given in Hz.

Synthesis of Compounds of Formula (I):

The following examples illustrate the preparation of compounds of the invention but do not at all limit the scope thereof. First the synthesis of Example compounds of Formula (I) is described, followed by the description of the synthesis of intermediates and starting materials. Whenever used in the experimental part, generic Structures 1, 2, 3 etc. refer to the respective Structures described in preceeding general description of the preparation of compounds of Formula (I).

General Method for the Preparation of Compounds of Formula (I):

Saponification

To a solution of an ester of Structure 1 (0.10 mmol, 1 eq.) in THF (0.5 mL), 1M aq. NaOH (0.13 mL) was added. The resulting solution was stirred at r.t. for 14 hours. The org. solvent was removed in vacuo. The residue was diluted with water (2 mL) and acidified with 1M aq. HCl. The mixture was extracted with DCM (3×5 mL). The comb. org. phases were concentrated in vacuo. The crude product was purified by prep. HPLC (column: Waters X-Bridge, 30×75 mm, 10 um, UV/MS, acidic conditions) and evaporated to give the desired acid as a white solid. Listed in Table 1 below are examples of compounds of Formula (I), prepared according to the above-mentioned method with the corresponding compound of Structure 1 as starting material.

TABLE 1

| Example | Compound of Formula (I) | Formula MW | $t_R$ [min] LC-MS Method | MS-data m/z [M + H]$^+$ |
|---|---|---|---|---|
| 1 | (±)-1-(2-Carboxymethoxy-5-fluoro-phenyl)-3,4-dihydro-1H-isoquinoline-2-carboxylic acid benzyl ester | C25H22NO5F 435.25 | 0.87 LC-MS 1FA | 436.2 |
| 2 | 1-[2-((S)-1-Carboxy-ethoxy]-5-fluoro-phenyl]-3,4-dihydro-1H-isoquinoline-2-carboxylic acid benzyl ester | C26H24NO5F 449.48 | 0.90 LC-MS 1FA | 450.2 |
| 3 | (±)-1-(2-Carboxymethoxy-5-methyl-phenyl)-3,4-dihydro-1H-isoquinoline-2-carboxylic acid benzyl ester | C26H25NO5 431.49 | 0.90 LC-MS 1FA | 432.2 |
| 4 | (±)-1-(5-Bromo-2-carboxymethoxy-phenyl)-3,4-dihydro-1H-isoquinoline-2-carboxylic acid benzyl ester | C25H22NO5Br 496.36 | 0.92 LC-MS 1FA | 496.0 |
| 5 | (±)-7-Bromo-1-(2-carboxymethoxy-5-fluoro-phenyl)-3,4-dihydro-1H-isoquinoline-2-carboxylic acid benzyl ester | C25H21NO5BrF 514.35 | 0.91 LC-MS 1FA | 514.0 |
| 6 | (±)-1-(2-Carboxymethoxy-4,5-difluoro-phenyl)-3,4-dihydro-1H-isoquinoline-2-carboxylic acid benzyl ester | C25H21NO5F2 453.44 | 0.88 LC-MS 1FA | 454.1 |
| 7 | (±)-5-Bromo-1-(2-carboxymethoxy-5-fluoro-phenyl)-3,4-dihydro-1H-isoquinoline-2-carboxylic acid benzyl ester | C25H21NO5BrF 514.35 | 0.94 LC-MS 1FA | 514.0 |

TABLE 1-continued

| Example | Compound of Formula (I) | Formula MW | $t_R$ [min] LC-MS Method | MS-data m/z [M + H]+ |
|---|---|---|---|---|
| 8 | 1-[2-((R)-1-Carboxy-ethoxy)-5-fluoro-phenyl]-3,4-dihydro-1H-isoquinoline-2-carboxylic acid benzyl ester | C26H24NO5F 449.48 | 0.90 LC-MS 1FA | 450.2 |
| 9 | (±)-1-(2-Carboxymethoxy-5-fluoro-phenyl)-6,7-difluoro-3,4-dihydro-1H-isoquinoline-2-carboxylic acid benzyl ester | C25H20NO5F3 471.43 | 0.88 LC-MS 1FA | 472.1 |
| 10 | (±)-1-(5-Bromo-2-carboxymethoxy-phenyl)-6,7-difluoro-3,4-dihydro-1H-isoquinoline-2-carboxylic acid benzyl ester | C25H20NO5BrF2 532.34 | 0.93 LC-MS 1FA | 532.0 |
| 11 | (±)-1-(2-Carboxymethoxy-5-cyano-phenyl)-6,7-difluoro-3,4-dihydro-1H-isoquinoline-2-carboxylic acid benzyl ester | C26H20N2O5F2 478.45 | 0.82 LC-MS 1FA | 479.1 |
| 12 | (±)-1-(2-Carboxymethoxy-5-fluoro-phenyl)-5-trifluoromethyl-3,4-dihydro-1H-isoquinoline-2-carboxylic acid benzyl ester | C26H21NO5F4 503.45 | 0.93 LC-MS 1FA | 504.1 |
| 13 | 1-[2-((R)-1-Carboxy-ethoxy)-5-cyano-phenyl]-3,4-dihydro-1H-isoquinoline-2-carboxylic acid benzyl ester | C27H24N2O5 456.50 | 0.85 LC-MS 1FA | 457.1 |
| 14 | (±)-1-(2-Carboxymethoxy-5-fluoro-phenyl)-5,6-difluoro-3,4-dihydro-1H-isoquinoline-2-carboxylic acid benzyl ester | C25H20NO5F3 471.43 | 0.89 LC-MS 1FA | 472.1 |
| 15 | (±)-1-(2-Carboxymethoxy-5-chloro-phenyl)-5,6-difluoro-3,4-dihydro-1H-isoquinoline-2-carboxylic acid benzyl ester | C25H20NO5ClF2 487.89 | 0.93 LC-MS 1FA | 488.1 |
| 16 | (±)-1-(2-Carboxymethoxy-5-cyano-phenyl)-5,6-difluoro-3,4-dihydro-1H-isoquinoline-2-carboxylic acid benzyl ester | C26H20N2O5F2 478.45 | 0.84 LC-MS 1FA | 479.1 |
| 17 | (±)-1-(2-Carboxymethoxy-5-dimethylsulfamoyl-phenyl)-3,4-dihydro-1H-isoquinoline-2-carboxylic acid benzyl ester | C27H28N2O7S 524.59 | 0.80 LC-MS 1FA | 525.1 |
| 18 | (±)-1-(2-Carboxymethoxy-5-chloro-phenyl)-5-fluoro-3,4-dihydro-1H-isoquinoline-2-carboxylic acid benzyl ester | C25H21NO5ClF 469.90 | 0.92 LC-MS 1FA | 470.1 |
| 19 | (±)-1-(2-Carboxymethoxy-5-cyano-phenyl)-5-fluoro-3,4-dihydro-1H-isoquinoline-2-carboxylic acid benzyl ester | C26H21N2O5F 460.46 | 0.83 LC-MS 1FA | 461.1 |
| 20 | (±)-1-(2-Carboxymethoxy-5-trifluoromethyl-phenyl)-3,4-dihydro-1H-isoquinoline-2-carboxylic acid benzyl ester | C26H22NO5F3 485.46 | 0.91 LC-MS 1FA | 486.1 |
| 21 | (±)-1-(2-Carboxymethoxy-5-chloro-phenyl)-3,4-dihydro-1H-isoquinoline-2-carboxylic acid benzyl ester | C25H22NO5Cl 451.91 | 0.91 LC-MS 1FA | 452.1 |
| 22 | (±)-1-(2-Carboxymethoxy-5-isopropyl-phenyl)-3,4-dihydro-1H-isoquinoline-2-carboxylic acid benzyl ester | C28H29NO5 459.54 | 0.96 LC-MS 1FA | 460.2 |
| 23 | (±)-1-(6-Carboxymethoxy-benzo[1,3]dioxol-5-yl)-3,4-dihydro-1H-isoquinoline-2-carboxylic acid benzyl ester | C26H23NO7 461.47 | 0.85 LC-MS 1FA | 462.1 |
| 24 | (±)-1-(2-Carboxymethoxy-5-methoxy-phenyl)-3,4-dihydro-1H-isoquinoline-2-carboxylic acid benzyl ester | C26H25NO6 447.49 | 0.85 LC-MS 1FA | 448.2 |
| 25 | (S)-1-(2-Carboxymethoxy-5-cyano-phenyl)-3,4-dihydro-1H-isoquinoline-2-carboxylic acid benzyl ester | C26H22N2O5 442.47 | 0.81 LC-MS 1FA | 443.2 |
| 26 | (S)-1-(2-Carboxymethoxy-5-chloro-phenyl)-3,4-dihydro-1H- | C25H22NO5Cl 451.91 | 0.91 LC-MS 1FA | 452.1 |

TABLE 1-continued

| Example | Compound of Formula (I) | Formula MW | $t_R$ [min] LC-MS Method | MS-data m/z [M + H]$^+$ |
|---|---|---|---|---|
| | isoquinoline-2-carboxylic acid benzyl ester | | | |
| 27 | (S)-1-[2-((R)-1-Carboxy-ethoxy)-5-fluoro-phenyl]-3,4-dihydro-1H-isoquinoline-2-carboxylic acid benzyl ester | C26H24NO5F 449.48 | 0.90 LC-MS 1FA | 450.1 |
| 28 | (S)-1-[2-((S)-1-Carboxy-ethoxy)-5-fluoro-phenyl]-3,4-dihydro-1H-isoquinoline-2-carboxylic acid benzyl ester | C26H24NO5F 449.48 | 0.89 LC-MS 1FA | 450.2 |
| 29 | {4-Fluoro-2-[(S)-2-((trans)-2-phenyl-cyclopropanecarbonyl)-1,2,3,4-tetrahydro-isoquinolin-1-yl]-phenoxy}-acetic acid (diastereoisomer 1) | C27H24NO4F 445.49 | 0.85 LC-MS 1FA | 446.2 |
| 30 | {4-Fluoro-2-[(S)-2-((trans)-2-phenyl-cyclopropanecarbonyl)-1,2,3,4-tetrahydro-isoquinolin-1-yl]-phenoxy}-acetic acid (diastereoisomer 2) | C27H24NO4F 445.49 | 0.85 LC-MS 1FA | 446.2 |
| 31 | (S)-1-(2-Carboxymethoxy-5-chloro-phenyl)-5-fluoro-3,4-dihydro-1H-isoquinoline-2-carboxylic acid benzyl ester | C25H21NO5ClF 469.90 | 0.92 LC-MS 1FA | 470.1 |
| 32 | (S)-1-(2-Carboxymethoxy-5-cyano-phenyl)-5-fluoro-3,4-dihydro-1H-isoquinoline-2-carboxylic acid benzyl ester | C26H21N2O5F 460.46 | 0.83 LC-MS 1FA | 461.2 |

Phenol Alkylation and Subsequent Saponification

To a solution of a phenol 13 (0.20 mmol, 1.0 eq.) and K$_2$CO$_3$ (83 mg, 0.60 mmol, 3.0 eq.) in DMF (1 mL), ethyl bromoacetate (33 µL, 0.30 mmol, 1.5 eq.) was added. The reaction mixture was stirred at r.t. for 5 hours. 1M aq. NaOH (0.5 mL) was added. The mixture was stirred at r.t. for 89 hours. The solution was carefully neutralized with formic acid (0.5 mL), filtered, and purified by prep. HPLC (column: Waters X-bridge, 30×75 mm, 10 um, UV/MS, acidic conditions) to give the desired acid as a white solid.

Listed in Table 2 below are examples of compounds of Formula (I), prepared according to the above-mentioned method with the corresponding phenol 13 as starting material.

TABLE 2

| Example | Compound of Formula (I) | Formula MW | $t_R$ [min] LC-MS Method | MS-data m/z [M + H]$^+$ |
|---|---|---|---|---|
| 33 | (±)-1-(2-Carboxymethoxy-3,5-difluoro-phenyl)-3,4-dihydro-1H-isoquinoline-2-carboxylic acid benzyl ester | C25H21NO5F2 453.44 | 0.87 LC-MS 1FA | 454.1 |
| 34 | (±)-1-(2-Carboxymethoxy-5-fluoro-phenyl)-5-fluoro-3,4-dihydro-1H-isoquinoline-2-carboxylic acid benzyl ester | C25H21NO5F2 453.44 | 0.88 LC-MS 1FA | 454.1 |
| 35 | (±)-1-(2-Carboxymethoxy-5-fluoro-phenyl)-5-methoxy-3,4-dihydro-1H-isoquinoline-2-carboxylic acid benzyl ester | C26H24NO6F 465.48 | 0.89 LC-MS 1FA | 466.2 |
| 36 | (±)-1-(2-Carboxymethoxy-5-fluoro-phenyl)-6,7-dimethoxy-3,4-dihydro-1H-isoquinoline-2-carboxylic acid benzyl ester | C27H26NO7F 495.50 | 0.82 LC-MS 1FA | 496.2 |
| 37 | (±)-1-(2-Carboxymethoxy-5-fluoro-phenyl)-7-methoxy-3,4-dihydro-1H-isoquinoline-2-carboxylic acid benzyl ester | C26H24NO6F 465.48 | 0.86 LC-MS 1FA | 466.1 |
| 38 | (±)-1-(2-Carboxymethoxy-5-fluoro-phenyl)-5-chloro-3,4-dihydro-1H-isoquinoline-2-carboxylic acid benzyl ester | C25H21NO5ClF 469.90 | 0.93 LC-MS 1FA | 470.1 |
| 39 | (±)-1-(2-Carboxymethoxy-5-fluoro-phenyl)-5-methyl-3,4-dihydro-1H-isoquinoline-2-carboxylic acid benzyl ester | C26H24NO5F 449.48 | 0.91 LC-MS 1FA | 450.1 |

TABLE 2-continued

| Example | Compound of Formula (I) | Formula MW | $t_R$ [min] LC-MS Method | MS-data m/z [M + H]$^+$ |
|---|---|---|---|---|
| 40 | (±)-5-Bromo-1-(2-carboxymethoxy-5-fluoro-phenyl)-6-fluoro-3,4-dihydro-1H-isoquinoline-2-carboxylic acid benzyl ester | C25H20NO5BrF2 532.34 | 0.94 LC-MS 1FA | 532.0 |
| 41 | (±)-1-(2-Carboxymethoxy-5-fluoro-phenyl)-7-fluoro-3,4-dihydro-1H-isoquinoline-2-carboxylic acid benzyl ester | C25H21NO5F2 453.44 | 0.87 LC-MS 1FA | 454.1 |
| 42 | (±)-1-(2-Carboxymethoxy-5-fluoro-phenyl)-5,7-difluoro-3,4-dihydro-1H-isoquinoline-2-carboxylic acid benzyl ester | C25H20NO5F3 471.43 | 0.89 LC-MS 1FA | 472.1 |
| 43 | (±)-1-(2-Carboxymethoxy-5-chloro-phenyl)-5,7-difluoro-3,4-dihydro-1H-isoquinoline-2-carboxylic acid benzyl ester | C25H20NO5ClF2 487.89 | 0.93 LC-MS 1FA | 488.1 |
| 44 | (±)-1-(2-Carboxymethoxy-5-cyano-phenyl)-5,7-difluoro-3,4-dihydro-1H-isoquinoline-2-carboxylic acid benzyl ester | C26H20N2O5F2 478.45 | 0.84 LC-MS 1FA | 479.1 |

Amide Coupling and Subsequent Saponification

Method A: To a solution of 2-(1,2-benzisoxazol-3-yl)acetic acid (20 mg, 0.10 mmol, 1.0 eq.) in DMF (0.5 mL), TBTU (32 mg, 0.10 mmol, 1.0 eq.) and Si-DEA (400 mg, 0.50 mmol, 5.0 eq.) were added. The resulting mixture was stirred at r.t. for 5 min. A solution of (±)-[4-fluoro-2-(1,2,3,4-tetrahydro-isoquinolin-1-yl)-phenoxy]-acetic acid ethyl ester hydrochloride (44 mg, 0.12 mmol, 1.2 eq.) in DCM (1 mL) was added. The mixture was stirred at r.t. for 18 hours. The resulting suspension was filtered, the solids were rinsed with DCM (5 mL), and the filtrate was concentrated in vacuo. The residue was dissolved in THF (1 mL) and 0.2M aq. NaOH (1 mL) was added. The mixture was stirred at r.t. for 30 min. The mixture was neutralized with 0.2M aq. HCl soln. and concentrated in vacuo. The residue was purified by prep. HPLC (column: Waters X-Bridge, 30×75 mm, 10 um, UV/MS, acidic conditions) and evaporated to give the desired acid as a white solid.

Listed in Table 3 below are examples of compounds of Formula (I), prepared according to the above-mentioned method with the corresponding amine of Structure 2 and the corresponding acid as starting materials.

TABLE 3

| Example | Compound of Formula (I) | Formula MW | $t_R$ [min] LC-MS Method | MS-data m/z [M + H]$^+$ |
|---|---|---|---|---|
| 45 | (±)-{2-[2-(2-Benzo[d]isoxazol-3-yl-acetyl)-1,2,3,4-tetrahydro-isoquinolin-1-yl]-4-fluoro-phenoxy}-acetic acid | C26H21N2O5F 460.46 | 0.80 LC-MS 1FA | 461.1 |
| 46 | (±)-{4-Fluoro-2-[2-(3-methyl-3-phenyl-butyryl)-1,2,3,4-tetrahydro-isoquinolin-1-yl]-phenoxy}-acetic acid | C28H28NO4F 461.53 | 0.90 LC-MS 1FA | 462.2 |
| 47 | (±)-{4-Fluoro-2-[2-(2-naphthalen-1-yl-acetyl)-1,2,3,4-tetrahydro-isoquinolin-1-yl]-phenoxy}-acetic acid | C29H24NO4F 469.51 | 0.87 LC-MS 1FA | 470.2 |
| 48 | (±)-{4-Fluoro-2-[2-(2-quinolin-7-yl-acetyl)-1,2,3,4-tetrahydro-isoquinolin-1-yl]-phenoxy}-acetic acid | C28H23N2O4F 470.50 | 0.61 LC-MS 1FA | 471.2 |
| 49 | (±)-{4-Fluoro-2-[2-(2-quinolin-6-yl-acetyl)-1,2,3,4-tetrahydro-isoquinolin-1-yl]-phenoxy}-acetic acid | C28H23N2O4F 470.50 | 0.62 LC-MS 1FA | 471.2 |
| 50 | (±)-{2-[2-(2-2,3-Dihydro-benzo[1,4]dioxin-6-yl-acetyl)-1,2,3,4-tetrahydro-isoquinolin-1-yl]-4-fluoro-phenoxy}-acetic acid | C27H24NO6F 477.49 | 0.78 LC-MS 1FA | 478.1 |
| 51 | (±)-{4-Fluoro-2-[2-(3-1H-indol-3-yl-propionyl)-1,2,3,4-tetrahydro-isoquinolin-1-yl]-phenoxy}-acetic acid | C28H25N2O4F 472.51 | 0.81 LC-MS 1FA | 473.2 |

TABLE 3-continued

| Example | Compound of Formula (I) | Formula MW | $t_R$ [min] LC-MS Method | MS-data m/z [M + H]+ |
|---|---|---|---|---|
| 52 | (±)-(2-{2-[3-(1-Ethyl-2-methyl-1H-indol-3-yl)-propionyl]-1,2,3,4-tetrahydro-isoquinolin-1-yl}-4-fluoro-phenoxy)-acetic acid | C31H31N2O4F 514.60 | 0.92 LC-MS 1FA | 515.2 |
| 53 | (±)-(2-{2-[3-(2,6-Dichloro-phenyl)-propionyl]-1,2,3,4-tetrahydro-isoquinolin-1-yl}-4-fluoro-phenoxy)-acetic acid | C26H22NO4Cl2F 502.37 | 0.91 LC-MS 1FA | 502.1 |
| 54 | (±)-(4-Fluoro-2-{2-[3-(2-fluoro-phenoxy)-propionyl]-1,2,3,4-tetrahydro-isoquinolin-1-yl}-phenoxy)-acetic acid | C26H23NO5F2 467.47 | 0.84 LC-MS 1FA | 468.1 |
| 55 | (±)-[4-Fluoro-2-(2-{2-[4-(5-methyl-tetrazol-1-yl)-phenyl]-acetyl}-1,2,3,4-tetrahydro-isoquinolin-1-yl)-phenoxy]-acetic acid | C27H24N5O4F 501.52 | 0.73 LC-MS 1FA | 502.2 |
| 56 | (±)-(2-{2-[3-(6-Chloro-3-oxo-2,3-dihydro-benzo[1,4]oxazin-4-yl)-propionyl]-1,2,3,4-tetrahydro-isoquinolin-1-yl}-4-fluoro-phenoxy)-acetic acid | C28H24N2O6ClF 538.96 | 0.83 LC-MS 1FA | 539.1 |
| 57 | (±)-(4-Fluoro-{2-[2-(2-methyl-thiazol-4-yl)-acetyl]-1,2,3,4-tetrahydro-isoquinolin-1-yl}-phenoxy)-acetic acid | C23H21N2O4FS 440.49 | 0.73 LC-MS 1FA | 441.1 |
| 58 | (±)-{2-[2-(2-Benzo[b]thiophen-3-yl-acetyl)-1,2,3,4-tetrahydro-isoquinolin-1-yl]-4-fluoro-phenoxy}-acetic acid | C27H22NO4FS 475.54 | 0.87 LC-MS 1FA | 476.1 |
| 59 | (±)-{2-[2-(3-Benzothiazol-2-yl-propionyl)-1,2,3,4-tetrahydro-isoquinolin-1-yl]-4-fluoro-phenoxy}-acetic acid | C27H23N2O4FS 490.55 | 0.83 LC-MS 1FA | 491.1 |
| 60 | (±)-{2-[2-(2-Biphenyl-4-yl-acetyl)-1,2,3,4-tetrahydro-isoquinolin-1-yl]-4-fluoro-phenoxy}-acetic acid | C31H26NO4F 495.55 | 0.92 LC-MS 1FA | 496.2 |
| 61 | (±)-{4-Fluoro-2-[2-(2-indol-1-yl-acetyl)-1,2,3,4-tetrahydro-isoquinolin-1-yl]-phenoxy}-acetic acid | C27H23N2O4F 458.49 | 0.83 LC-MS 1FA | 459.2 |
| 62 | (±)-{2-[2-(2-1H-Benzoimidazol-2-yl-acetyl)-1,2,3,4-tetrahydro-isoquinolin-1-yl]-4-fluoro-phenoxy}-acetic acid | C26H22N3O4F 459.48 | 0.57 LC-MS 1FA | 460.2 |
| 63 | (±)-{2-[2-(2-1,3-Dihydro-isoindol-2-yl-acetyl)-1,2,3,4-tetrahydro-isoquinolin-1-yl]-4-fluoro-phenoxy}-acetic acid | C27H25N2O4F 460.50 | 0.64 LC-MS 1TFA | 461.2 |
| 64 | (±)-(4-Fluoro-2-{2-[3-(5-methoxy-1H-indol-3-yl)-propionyl]-1,2,3,4-tetrahydro-isoquinolin-1-yl}-phenoxy)-acetic acid | C29H27N2O5F 502.54 | 0.79 LC-MS 1FA | 503.2 |
| 65 | (±)-(4-Fluoro-2-{2-[3-(2-methyl-1H-indol-3-yl)-propionyl]-1,2,3,4-tetrahydro-isoquinolin-1-yl}-phenoxy)-acetic acid | C29H27N2O4F 486.54 | 0.83 LC-MS 1FA | 487.2 |
| 66 | (±)-(4-Fluoro-2-{2-[3-(1-methyl-1H-indol-3-yl)-propionyl]-1,2,3,4-tetrahydro-isoquinolin-1-yl}-phenoxy)-acetic acid | C29H27N2O4F 486.54 | 0.87 LC-MS 1FA | 487.2 |
| 67 | (±)-{4-Fluoro-2-[2-(trans-2-phenyl-cyclopropanecarbonyl)-1,2,3,4-tetrahydro-isoquinolin-1-yl]-phenoxy}-acetic acid | C27H24NO4F 445.49 | 0.85 LC-MS 1FA | 446.2 |
| 68 | (±)-{4-Chloro-2-[2-(2-cyclopropyl-acetyl)-1,2,3,4-tetrahydro-isoquinolin-1-yl]-phenoxy}-acetic acid | C22H22NO4Cl 399.87 | 0.81 LC-MS 1FA | 400.1 |
| 69 | (±)-{4-Chloro-2-[2-(2H-chromene-3-carbonyl)-1,2,3,4-tetrahydro-isoquinolin-1-yl]-phenoxy}-acetic acid | C27H22NO5Cl 475.93 | 0.88 LC-MS 1FA | 476.1 |
| 70 | (±)-{4-Chloro-2-[2-(3-methoxy-propionyl)-1,2,3,4-tetrahydro-isoquinolin-1-yl]-phenoxy}-acetic acid | C21H22NO5Cl 403.86 | 0.75 LC-MS 1FA | 404.1 |

TABLE 3-continued

| Example | Compound of Formula (I) | Formula MW | $t_R$ [min] LC-MS Method | MS-data m/z $[M + H]^+$ |
|---|---|---|---|---|
| 71 | (±)-(4-Chloro-2-{2-[2-(2-chloro-phenyl)-acetyl]-1,2,3,4-tetrahydro-isoquinolin-1-yl}-phenoxy)-acetic acid | C25H21NO4Cl2 470.35 | 0.88 LC-MS 1FA | 470.0 |
| 72 | (±)-{4-Chloro-2-[2-(2-indol-1-yl-acetyl)-1,2,3,4-tetrahydro-isoquinolin-1-yl]-phenoxy}-acetic acid | C27H23N2O4 Cl 474.94 | 0.87 LC-MS 1FA | 475.1 |
| 73 | (±)-(4-Chloro-2-{2-[3-(2-methyl-1H-indol-3-yl)-propionyl]-1,2,3,4-tetrahydro-isoquinolin-1-yl}-phenoxy)-acetic acid | C29H27N2O4 Cl 503.00 | 0.86 LC-MS 1FA | 503.1 |
| 74 | (±)-(4-Chloro-2-{2-[3-(5-methoxy-1H-indol-3-yl)-propionyl]-1,2,3,4-tetrahydro-isoquinolin-1-yl}-phenoxy)-acetic acid | C29H27N2O5 Cl 519.00 | 0.83 LC-MS 1FA | 519.2 |
| 75 | (±)-(4-Chloro-2-{2-[2-(2,6-dimethyl-pyridin-3-yloxy)-acetyl]-1,2,3,4-tetrahydro-isoquinolin-1-yl}-phenoxy)-acetic acid | C26H25N2O5 Cl 480.95 | 0.58 LC-MS 1FA | 481.1 |
| 76 | (±)-(4-Chloro-2-{2-[3-(1-methyl-1H-indol-3-yl)-propionyl]-1,2,3,4-tetrahydro-isoquinolin-1-yl}-phenoxy)-acetic acid | C29H27N2O4 Cl 503.00 | 0.91 LC-MS 1FA | 503.2 |
| 77 | {4-Chloro-2-[2-(1,2,3,4-tetrahydro-naphthalene-2-carbonyl)-1,2,3,4-tetrahydro-isoquinolin-1-yl]-phenoxy}-acetic acid | C28H26NO4Cl 475.97 | 0.93 LC-MS 1FA | 476.1 |
| 78 | (±)-{2-[2-(2-Benzoimidazol-1-yl-acetyl)-1,2,3,4-tetrahydro-isoquinolin-1-yl]-4-chloro-phenoxy}-acetic acid | C26H22N3O4Cl 475.93 | 0.63 LC-MS 1FA | 476.1 |
| 79 | (±)-{4-Chloro-2-[2-(2-3,4-dihydro-2H-quinolin-1-yl-acetyl)-1,2,3,4-tetrahydro-isoquinolin-1-yl]-phenoxy}-acetic acid | C28H27N2O4Cl 490.99 | 0.91 LC-MS 1FA | 491.2 |
| 80 | (±)-{4-Chloro-2-[2-(2-indazol-2-yl-acetyl)-1,2,3,4-tetrahydro-isoquinolin-1-yl]-phenoxy}-acetic acid | C26H22N3O4 Cl 475.93 | 0.80 LC-MS 1FA | 476.1 |
| 81 | (±)-(4-Chloro-2-{2-[3-(3-trifluoromethyl-phenyl)-propionyl]-1,2,3,4-tetrahydro-isoquinolin-1-yl}-phenoxy)-acetic acid | C27H23NO4ClF3 517.93 | 0.93 LC-MS 1FA | 518.1 |
| 82 | (4-Chloro-2-{2-[trans-2-(2-chloro-phenyl)-cyclopropanecarbonyl]-1,2,3,4-tetrahydro-isoquinolin-1-yl}-phenoxy)-acetic acid | C27H23NO4Cl2 496.39 | 0.91 LC-MS 1FA | 496.1 |
| 83 | (±)-(4-Chloro-2-{2-[3-(1-phenyl-1H-imidazol-2-yl)-propionyl]-1,2,3,4-tetrahydro-isoquinolin-1-yl}-phenoxy)-acetic acid | C29H26N3O4Cl 516.00 | 0.64 LC-MS 1FA | 516.2 |
| 84 | (4-Chloro-2-{2-[3-(4-oxo-2-phenyl-thiazolidin-3-yl)-propionyl]-1,2,3,4-tetrahydro-isoquinolin-1-yl}-phenoxy)-acetic acid | C29H27N2O5ClS 551.06 | 0.84 LC-MS 1FA | 551.2 |
| 85 | (±)-[4-Chloro-2-(2-{3-[3-(2,3-dimethyl-phenyl)-3H-imidazol-4-yl]-propionyl}-1,2,3,4-tetrahydro-isoquinolin-1-yl)-phenoxy]-acetic acid | C31H30N3O4Cl 544.05 | 0.66 LC-MS 1FA | 544.2 |
| 86 | (±)-(2-{2-[2-(Biphenyl-2-yloxy)-acetyl]-1,2,3,4-tetrahydro-isoquinolin-1-yl}-4-chloro-phenoxy)-acetic acid | C31H26NO5Cl 528.00 | 0.95 LC-MS 1FA | 528.2 |
| 87 | (±)-(4-Chloro-2-{2-[3-(3-fluoro-phenoxy)-propionyl]-1,2,3,4-tetrahydro-isoquinolin-1-yl}-phenoxy)-acetic acid | C26H23NO5ClF 483.92 | 0.88 LC-MS 1FA | 484.1 |
| 88 | (±)-{4-Chloro-2-[2-(3-p-tolyloxy-propionyl)-1,2,3,4-tetrahydro-isoquinolin-1-yl]-phenoxy}-acetic acid | C27H26NO5Cl 479.96 | 0.91 LC-MS 1FA | 480.1 |

TABLE 3-continued

| Example | Compound of Formula (I) | Formula MW | $t_R$ [min] LC-MS Method | MS-data m/z $[M + H]^+$ |
|---|---|---|---|---|
| 89 | (±)-(4-Chloro-2-{2-[3-(4-chloro-phenoxy)-propionyl]-1,2,3,4-tetrahydro-isoquinolin-1-yl}-phenoxy)-acetic acid | C26H23NO5Cl2 500.38 | 0.92 LC-MS 1FA | 500.1 |
| 90 | (±)-(4-Chloro-2-{2-[3-(2-trifluoromethyl-phenyl)-propionyl]-1,2,3,4-tetrahydro-isoquinolin-1-yl}-phenoxy)-acetic acid | C27H23NO4ClF3 517.93 | 0.93 LC-MS 1FA | 518.1 |
| 91 | (±)-(4-Chloro-2-{2-[2-(5-fluoro-1H-indol-3-yl)-acetyl]-1,2,3,4-tetrahydro-isoquinolin-1-yl}-phenoxy)-acetic acid | C27H22N2O4ClF 492.93 | 0.82 LC-MS 1FA | 493.1 |
| 92 | (±)-(4-Chloro-2-{2-[2-(6-methoxy-benzofuran-3-yl)-acetyl]-1,2,3,4-tetrahydro-isoquinolin-1-yl}-phenoxy)-acetic acid | C28H24NO6Cl 505.95 | 0.87 LC-MS 1FA | 506.1 |
| 93 | (±)-(4-Chloro-2-{2-[4-(4-chloro-phenyl)-butyryl]-1,2,3,4-tetrahydro-isoquinolin-1-yl}-phenoxy)-acetic acid | C27H25NO4Cl2 498.41 | 0.95 LC-MS 1FA | 498.1 |
| 94 | (±)-{4-Chloro-2-[2-(3-m-tolyloxy-propionyl)-1,2,3,4-tetrahydro-isoquinolin-1-yl]-phenoxy}-acetic acid | C27H26NO5Cl 479.96 | 0.91 LC-MS 1FA | 480.1 |
| 95 | (±)-(4-Chloro-2-{2-[3-(3-chloro-phenoxy)-propionyl]-1,2,3,4-tetrahydro-isoquinolin-1-yl}-phenoxy)-acetic acid | C26H23NO5Cl2 500.38 | 0.92 LC-MS 1FA | 500.1 |
| 96 | (±)-(4-Chloro-2-{2-[2-(5-chloro-1H-indol-3-yl)-acetyl]-1,2,3,4-tetrahydro-isoquinolin-1-yl}-phenoxy)-acetic acid | C27H22N2O4Cl2 509.39 | 0.86 LC-MS 1FA | 509.1 |
| 97 | (±)-{4-Chloro-2-[2-(4-p-tolyl-butyryl)-1,2,3,4-tetrahydro-isoquinolin-1-yl]-phenoxy}-acetic acid | C28H28NO4Cl 477.99 | 0.95 LC-MS 1FA | 478.2 |
| 98 | (±)-(4-Chloro-2-{2-[2-(5-chloro-benzo[b]thiophen-3-yl)-acetyl]-1,2,3,4-tetrahydro-isoquinolin-1-yl}-phenoxy)-acetic acid | C27H21NO4Cl2S 526.44 | 0.94 LC-MS 1FA | 526.0 |
| 99 | (±)-(4-Chloro-2-{2-[2-(5-methoxy-1H-indol-2-yl)-acetyl]-1,2,3,4-tetrahydro-isoquinolin-1-yl}-phenoxy)-acetic acid | C28H25N2O5Cl 504.97 | 0.83 LC-MS 1FA | 505.1 |
| 100 | (±)-(4-Chloro-2-{2-[2-(5-methyl-benzo[d]isoxazol-3-yl)-acetyl]-1,2,3,4-tetrahydro-isoquinolin-1-yl}-phenoxy)-acetic acid | C27H23N2O5Cl 490.94 | 0.87 LC-MS 1FA | 491.1 |
| 101 | (±)-(4-Chloro-2-{2-[2-(5-methoxy-benzo[d]isoxazol-3-yl)-acetyl]-1,2,3,4-tetrahydro-isoquinolin-1-yl}-phenoxy)-acetic acid | C27H23N2O6Cl 506.94 | 0.84 LC-MS 1FA | 507.1 |
| 102 | (±)-(4-Chloro-2-{2-[3-(4-fluoro-phenoxy)-propionyl]-1,2,3,4-tetrahydro-isoquinolin-1-yl}-phenoxy)-acetic acid | C26H23NO5ClF 483.92 | 0.88 LC-MS 1FA | 484.1 |
| 103 | (±)-(4-Chloro-2-{2-[4-(4-fluoro-phenyl)-butyryl]-1,2,3,4-tetrahydro-isoquinolin-1-yl}-phenoxy)-acetic acid | C27H25NO4ClF 481.95 | 0.91 LC-MS 1FA | 482.1 |

Method B: To a solution of 2-methylhydrocinnamic acid (12 mg, 0.08 mmol, 1.5 eq.) in DMF (1 mL), DIPEA (34 µL, 0.20 mmol, 4.0 eq.), and TBTU (24 mg, 0.08 mmol, 1.5 eq.) were added in sequence. The resulting solution was stirred at r.t. for 30 min. Then (±)-[4-chloro-2-(1,2,3,4-tetrahydro-isoquinolin-1-yl)-phenoxy]-acetic acid ethyl ester (17 mg, 0.05 mmol, 1.0 eq.) was added and the resulting mixture was stirred at r.t. for 18 hours. 1M aq. NaOH (0.50 mL) was added. The mixture was stirred at r.t. for 2 hours. The solution was neutralized with formic acid (0.50 mL), filtered, and then purified by prep. HPLC (column: Atlantis, 30×75 mm, 10 um, UV/MS, acidic conditions) to give the desired acid as a white solid.

Listed in Table 4 below are examples of compounds of Formula (I), prepared according to the above-mentioned method with the corresponding amine of Structure 2 and the corresponding acid as starting materials.

TABLE 4

| Example | Compound of Formula (I) | Formula MW | $t_R$ [min] LC-MS Method | MS-data m/z [M + H]+ |
|---|---|---|---|---|
| 104 | (±)-{4-Chloro-2-[2-(3-o-tolyl-propionyl)-1,2,3,4-tetrahydro-isoquinolin-1-yl]-phenoxy}-acetic acid | C27H26NO4Cl 463.96 | 0.91 LC-MS 1FA | 464.1 |
| 105 | (±)-{2-[2-(2-Benzyloxy-acetyl)-1,2,3,4-tetrahydro-isoquinolin-1-yl]-4-chloro-phenoxy}-acetic acid | C26H24NO5Cl 465.93 | 0.85 LC-MS 1FA | 466.1 |
| 106 | (±)-(4-Chloro-2-{2-[2-(2-chloro-benzyloxy)-acetyl]-1,2,3,4-tetrahydro-isoquinolin-1-yl}-phenoxy)-acetic acid | C26H23NO5Cl2 500.38 | 0.89 LC-MS 1FA | 500.1 |
| 107 | (±)-{4-Chloro-2-[2-(4-phenyl-butyryl)-1,2,3,4-tetrahydro-isoquinolin-1-yl]-phenoxy}-acetic acid | C27H26NO4Cl 463.96 | 0.91 LC-MS 1FA | 464.1 |
| 108 | (±)-(4-Chloro-2-{2-[4-(3-fluoro-phenyl)-butyryl]-1,2,3,4-tetrahydro-isoquinolin-1-yl}-phenoxy)-acetic acid | C27H25NO4ClF 481.95 | 0.92 LC-MS 1FA | 482.1 |
| 109 | (±)-(4-Chloro-2-{2-[4-(2,3-dichloro-phenyl)-butyryl]-1,2,3,4-tetrahydro-isoquinolin-1-yl}-phenoxy)-acetic acid | C27H24NO4Cl3 532.85 | 0.98 LC-MS 1FA | 532.0 |
| 110 | (±)-{4-Chloro-2-[2-(4-m-tolyl-butyryl)-1,2,3,4-tetrahydro-isoquinolin-1-yl]-phenoxy}-acetic acid | C28H28NO4Cl 477.99 | 0.95 LC-MS 1FA | 478.1 |
| 111 | (±)-{4-Chloro-2-[2-(4-o-tolyl-butyryl)-1,2,3,4-tetrahydro-isoquinolin-1-yl]-phenoxy}-acetic acid | C28H28NO4Cl 477.99 | 0.94 LC-MS 1FA | 478.2 |
| 112 | (±)-(4-Chloro-2-{2-[4-(3-chloro-phenyl)-butyryl]-1,2,3,4-tetrahydro-isoquinolin-1-yl}-phenoxy)-acetic acid | C27H25NO4Cl2 498.41 | 0.95 LC-MS 1FA | 498.1 |
| 113 | (±)-(4-Chloro-2-{2-[4-(2-chloro-phenyl)-butyryl]-1,2,3,4-tetrahydro-isoquinolin-1-yl}-phenoxy)-acetic acid | C27H25NO4Cl2 498.41 | 0.95 LC-MS 1FA | 498.1 |
| 114 | (±)-(4-Chloro-2-{2-[4-(3-methoxy-phenyl)-butyryl]-1,2,3,4-tetrahydro-isoquinolin-1-yl}-phenoxy)-acetic acid | C28H28NO5Cl 493.99 | 0.90 LC-MS 1FA | 494.2 |
| 115 | (±)-(4-Chloro-2-{2-[4-(2-fluoro-phenyl)-butyryl]-1,2,3,4-tetrahydro-isoquinolin-1-yl}-phenoxy)-acetic acid | C27H25NO4ClF 481.95 | 0.92 LC-MS 1FA | 482.1 |
| 116 | (±)-{4-Chloro-2-[2-(trans-2-phenyl-cyclopropanecarbonyl)-1,2,3,4-tetrahydro-isoquinolin-1-yl]-phenoxy}-acetic acid | C27H24NO4Cl 461.94 | 0.88 LC-MS 1FA | 462.1 |
| 117 | {4-Chloro-2-[5-fluoro-2-(trans-2-phenyl-cyclopropanecarbonyl)-1,2,3,4-tetrahydro-isoquinolin-1-yl]-phenoxy}-acetic acid | C27H23NO4ClF 479.93 | 0.90 LC-MS 1FA | 480.1 |
| 118 | (±)-{4-Chloro-2-[5-fluoro-2-(3-o-tolyl-propionyl)-1,2,3,4-tetrahydro-isoquinolin-1-yl]-phenoxy}-acetic acid | C27H25NO4ClF 481.95 | 0.92 LC-MS 1FA | 482.1 |
| 119 | (±)-{2-[2-(2-Benzyloxy-acetyl)-5-fluoro-1,2,3,4-tetrahydro-isoquinolin-1-yl]-4-chloro-phenoxy}-acetic acid | C26H23NO5ClF 483.92 | 0.86 LC-MS 1FA | 484.1 |
| 120 | (±)-(4-Chloro-2-{2-[2-(2-chloro-benzyloxy)-acetyl]-5-fluoro-1,2,3,4-tetrahydro-isoquinolin-1-yl}-phenoxy)-acetic acid | C26H22NO5Cl2F 518.37 | 0.90 LC-MS 1FA | 518.0 |
| 121 | (±)-{4-Chloro-2-[5-fluoro-2-(4-phenyl-butyryl)-1,2,3,4-tetrahydro-isoquinolin-1-yl]-phenoxy}-acetic acid | C27H25NO4ClF 481.95 | 0.93 LC-MS 1FA | 482.1 |
| 122 | (±)-{4-Chloro-2-[5-fluoro-2-(3-phenyl-propynoyl)-1,2,3,4-tetrahydro-isoquinolin-1-yl]-phenoxy}-acetic acid | C26H19NO4ClF 463.89 | 0.90 LC-MS 1FA | 464.1 |

Method C: To a solution of 3-phenylpropionic acid (23 mg, 0.16 mmol, 1.1 eq.) in DMF/THF (4:1, 1 mL), HATU (108 mg, 0.28 mmol, 2.0 eq.) and DIPEA (49 µL, 0.28 mmol, 2.0 eq.) were added. The mixture was stirred at r.t. for 30 min. A solution of (±)-[4-fluoro-2-(1,2,3,4-tetrahydro-isoquinolin-1-yl)-phenoxy]-acetic acid ethyl ester hydrochloride (51 mg, 0.14 mmol, 1.0 eq.) and DIPEA (49 µL, 0.28 mmol, 2.0 eq.) in DMF/THF (4:1, 1 mL) was added at 0° C. The mixture was stirred at r.t. for 18 hours. The reaction mixture was diluted with DCM and washed with sat. aq. NaHCO$_3$ soln. and water. The org. phase was concentrated in vacuo. The residue was dissolved in THF (2 mL) and 1M aq. NaOH soln. (2 mL) was added. The mixture was stirred at r.t. for 5 hours. The mixture was acidified with acetic acid (pH<5). Water (2 mL) and DCM (2 mL) were added. The layers were separated and the org. phase was concentrated in vacuo. The residue was purified by prep. HPLC (column: Atlantis, 30×75 mm, 10 um, UV/MS, acidic conditions) to give the desired acid as a white solid.

Listed in Table 5 below are examples of compounds of Formula (I), prepared according to the above-mentioned method with the corresponding amine of Structure 2 and the corresponding acid as starting materials.

TABLE 5

| Example | Compound of Formula (I) | Formula MW | $t_R$ [min] LC-MS Method | MS-data m/z [M + H]$^+$ |
|---|---|---|---|---|
| 123 | (±)-{4-Fluoro-2-[2-(3-phenyl-propionyl)-1,2,3,4-tetrahydro-isoquinolin-1-yl]-phenoxy}-acetic acid | C26H24NO4F 433.48 | 0.84 LC-MS 1FA | 434.2 |
| 124 | (±)-[4-Fluoro-2-(2-phenylacetyl-1,2,3,4-tetrahydro-isoquinolin-1-yl)-phenoxy]-acetic acid | C25H22NO4F 419.45 | 0.81 LC-MS 1FA | 420.2 |
| 125 | (±)-{4-Fluoro-2-[2-(2-phenoxy-acetyl)-1,2,3,4-tetrahydro-isoquinolin-1-yl]-phenoxy}-acetic acid | C25H22NO5F 435.45 | 0.80 LC-MS 1FA | 436.1 |
| 126 | (±)-{2-[2-(2-Benzyloxy-acetyl)-1,2,3,4-tetrahydro-isoquinolin-1-yl]-4-fluoro-phenoxy}-acetic acid | C26H24NO5F 449.48 | 0.81 LC-MS 1FA | 450.1 |
| 127 | (±)-{4-Fluoro-2-[2-(4-phenyl-butyryl)-1,2,3,4-tetrahydro-isoquinolin-1-yl]-phenoxy}-acetic acid | C27H26NO4F 447.50 | 0.88 LC-MS 1FA | 448.2 |
| 128 | (±)-(4-Fluoro-2-{2-[3-(2-methoxy-phenyl)-propionyl]-1,2,3,4-tetrahydro-isoquinolin-1-yl}-phenoxy)-acetic acid | C27H26NO5F 463.50 | 0.86 LC-MS 1FA | 464.1 |
| 129 | (±)-(4-Fluoro-2-{2-[3-(3-methoxy-phenyl)-propionyl]-1,2,3,4-tetrahydro-isoquinolin-1-yl}-phenoxy)-acetic acid | C27H26NO5F 463.50 | 0.84 LC-MS 1FA | 464.2 |
| 130 | (±)-(4-Fluoro-2-{2-[3-(4-methoxy-phenyl)-propionyl]-1,2,3,4-tetrahydro-isoquinolin-1-yl}-phenoxy)-acetic acid | C27H26NO5F 463.50 | 0.83 LC-MS 1FA | 464.2 |
| 131 | (±)-(2-{2-[3-(2-Chloro-phenyl)-propionyl]-1,2,3,4-tetrahydro-isoquinolin-1-yl}-4-fluoro-phenoxy)-acetic acid | C26H23NO4ClF 467.92 | 0.88 LC-MS 1FA | 468.1 |
| 132 | (±)-(2-{2-[3-(3-Chloro-phenyl)-propionyl]-1,2,3,4-tetrahydro-isoquinolin-1-yl}-4-fluoro-phenoxy)-acetic acid | C26H23NO4ClF 467.92 | 0.89 LC-MS 1FA | 468.1 |
| 133 | (±)-(2-{2-[3-(4-Chloro-phenyl)-propionyl]-1,2,3,4-tetrahydro-isoquinolin-1-yl}-4-fluoro-phenoxy)-acetic acid | C26H23NO4ClF 467.92 | 0.89 LC-MS 1FA | 468.1 |
| 134 | (±)-{4-Fluoro-2-[2-(3-o-tolyl-propionyl)-1,2,3,4-tetrahydro-isoquinolin-1-yl]-phenoxy}-acetic acid | C27H26NO4F 447.50 | 0.88 LC-MS 1FA | 448.2 |

Method D: To a suspension of (±)-[4-fluoro-2-(1,2,3,4-tetrahydro-isoquinolin-1-yl)-phenoxy]-acetic acid ethyl ester hydrochloride (37 mg, 0.10 mmol, 1.0 eq.) in DCM (1 mL), Si-carbonate (220 mg) was added. The mixture was stirred at r.t. for 1 hour, filtered, and the filtrate was concentrated in vacuo to give the free amine.

To a solution of 2-naphthylacetic acid (28 mg, 0.15 mmol, 1.5 eq.) in DCM (1 mL), a solution of the Ghosez's reagent in DCM (0.21 mmol, 2.1 eq.) was added. The resulting mixture was stirred at r.t. for 10 min. A solution of the free amine and Si-DEA (0.45 mmol, 4.5 eq.) in DCM (0.5 mL) was added. The mixture was stirred at r.t. for 1 hour, filtered, and concentrated in vacuo. The residue was dissolved in THF (0.5 mL) and 0.2M aq. NaOH soln. was added. The mixture was stirred at r.t. for 20 min, then neutralized with 1M aq. HCl soln., and concentrated in vacuo. The residue was purified by prep. HPLC (column: Waters X-bridge, 30×75 mm, 10 um, UV/MS, acidic conditions) to give the desired acid as a white solid.

Listed in Table 6 below are examples of compounds of Formula (I), prepared according to the above-mentioned method with the corresponding amine of Structure 2 and the corresponding acid as starting materials.

TABLE 6

| Example | Compound of Formula (I) | Formula MW | $t_R$ [min] LC-MS Method | MS-data m/z $[M + H]^+$ |
|---|---|---|---|---|
| 135 | (±)-{4-Fluoro-2-[2-(2-naphthalen-2-yl-acetyl)-1,2,3,4-tetrahydro-isoquinolin-1-yl]-phenoxy}-acetic acid | C29H24NO4F 469.51 | 0.87 LC-MS 1FA | 470.2 |
| 136 | (±)-{4-Fluoro-2-[2-(2-o-tolyloxy-acetyl)-1,2,3,4-tetrahydro-isoquinolin-1-yl]-phenoxy}-acetic acid | C26H24NO5F 449.48 | 0.85 LC-MS 1FA | 450.2 |
| 137 | (±)-(4-Fluoro-2-{2-[2-(1-methyl-1H-indol-3-yl)-acetyl]-1,2,3,4-tetrahydro-isoquinolin-1-yl}-phenoxy)-acetic acid | C28H25N2O4F 472.51 | 0.84 LC-MS 1FA | 473.2 |
| 138 | (±)-(2-{2-[2-(2-Chloro-phenoxy)-acetyl]-1,2,3,4-tetrahydro-isoquinolin-1-yl}-4-fluoro-phenoxy)-acetic acid | C25H21NO5ClF 469.90 | 0.84 LC-MS 1FA | 470.1 |
| 139 | (±)-(4-Fluoro-2-{2-[3-(2-fluoro-phenyl)-propionyl]-1,2,3,4-tetrahydro-isoquinolin-1-yl}-phenoxy)-acetic acid | C26H23NO4F2 451.47 | 0.85 LC-MS 1FA | 452.1 |
| 140 | (±)-{4-Fluoro-2-[2-(2-indan-2-yl-acetyl)-1,2,3,4-tetrahydro-isoquinolin-1-yl]-phenoxy}-acetic acid | C28H26NO4F 459.52 | 0.89 LC-MS 1FA | 460.2 |
| 141 | (±)-(4-Fluoro-2-{2-[(E)-3-(2-fluoro-phenyl)-acryloyl]-1,2,3,4-tetrahydro-isoquinolin-1-yl}-phenoxy)-acetic acid | C26H21NO4F2 449.45 | 0.85 LC-MS 1FA | 450.1 |
| 142 | (±)-{4-Fluoro-2-[2-((E)-3-o-tolyl-acryloyl)-1,2,3,4-tetrahydro-isoquinolin-1-yl]-phenoxy}-acetic acid | C27H24NO4F 445.49 | 0.87 LC-MS 1FA | 446.2 |
| 143 | (±)-{4-Fluoro-2-[2-(5-phenyl-pentanoyl)-1,2,3,4-tetrahydro-isoquinolin-1-yl]-phenoxy}-acetic acid | C28H28NO4F 461.53 | 0.91 LC-MS 1FA | 462.2 |
| 144 | (±)-{4-Fluoro-2-[2-(3-phenoxy-propionyl)-1,2,3,4-tetrahydro-isoquinolin-1-yl]-phenoxy}-acetic acid | C26H24NO5F 449.48 | 0.84 LC-MS 1FA | 450.2 |
| 145 | (±)-(4-Fluoro-2-{2-[3-(4-methanesulfonyl-phenyl)-propionyl]-1,2,3,4-tetrahydro-isoquinolin-1-yl}-phenoxy)-acetic acid | C27H26NO6FS 511.57 | 0.73 LC-MS 1FA | 512.1 |
| 146 | (±)-{2-[2-(3-2,3-Dihydro-indol-1-yl-propionyl)-1,2,3,4-tetrahydro-isoquinolin-1-yl]-4-fluoro-phenoxy}-acetic acid | C28H27N2O4F 474.53 | 0.85 LC-MS 1FA | 475.2 |
| 147 | (±)-{4-Fluoro-2-[2-(3-o-tolyloxy-propionyl)-1,2,3,4-tetrahydro-isoquinolin-1-yl]-phenoxy}-acetic acid | C27H26NO5F 463.50 | 0.88 LC-MS 1FA | 464.2 |
| 148 | (±)-(4-Fluoro-2-{2-[2-(2-fluoro-phenoxy)-acetyl]-1,2,3,4-tetrahydro-isoquinolin-1-yl}-phenoxy)-acetic acid | C25H21NO5F2 453.44 | 0.81 LC-MS 1FA | 454.1 |

TABLE 6-continued

| Example | Compound of Formula (I) | Formula MW | t$_R$ [min] LC-MS Method | MS-data m/z [M + H]$^+$ |
|---|---|---|---|---|
| 149 | (±)-(4-Fluoro-2-{2-[4-(2-methoxy-phenyl)-butyryl]-1,2,3,4-tetrahydro-isoquinolin-1-yl}-phenoxy)-acetic acid | C28H28NO5F 477.53 | 0.88 LC-MS 1FA | 478.2 |

Method E: To a solution of (±)-[4-fluoro-2-(1,2,3,4-tetrahydro-isoquinolin-1-yl)-phenoxy]-acetic acid ethyl ester hydrochloride (42 mg, 0.10 mmol, 1.0 eq.) and [(2-chlorobenzyl)oxy]acetic acid (20 mg, 0.10 mmol, 1.0 eq.) in DMF (1.2 mL), N-(3-dimethylaminopropyl)-N'-ethylcarbodiimide hydrochloride (29 mg, 0.15 mmol, 1.5 eq.) and 4-(dimethylamino)pyridine (31 mg, 0.25 mmol, 2.5 eq.) were added in sequence. The mixture was stirred at r.t. for 86 hours. The mixture was diluted with AcOEt (10 mL). The diluted solution was washed with 1M aq. HCl soln. (2×5 mL), sat. aq. NaHCO$_3$ soln. (2×5 mL), sat. aq. NaCl soln. (1×5 mL), dried over MgSO$_4$, and concentrated in vacuo. The residue was dissolved in THF (0.5 mL). 1M aq. NaOH (0.28 mL) was added. The mixture was stirred at r.t. for 17 hours. The mixture was concentrated in vacuo. The residue was diluted with water (2 mL) and acidified with 1M aq. HCl soln. The mixture was extracted with DCM/THF 2:1 (3×6 mL). The comb. org. phases were concentrated in vacuo.

The residue was purified by prep. HPLC (column: Waters X-bridge, 19×50 mm, 10 um, UV/MS, acidic conditions) to give the acid as a white solid.

Listed in Table 7 below are examples of compounds of Formula (I), prepared according to the above-mentioned method with the corresponding amine of Structure 2 and the corresponding acid as starting materials.

TABLE 7

| Example | Compound of Formula (I) | Formula MW | t$_R$ [min] LC-MS Method | MS-data m/z [M + H]$^+$ |
|---|---|---|---|---|
| 150 | (±)-(2-{2-[2-(2-Chloro-benzyloxy)-acetyl]-1,2,3,4-tetrahydro-isoquinolin-1-yl}-4-fluoro-phenoxy)-acetic acid | C26H23NO5ClF 483.92 | 0.86 LC-MS 1FA | 484.1 |
| 151 | (±)-(4-Chloro-2-{2-[(trans)-2-(3-chloro-phenyl)-cyclopropanecarbonyl]-1,2,3,4-tetrahydro-isoquinolin-1-yl}-phenoxy)-acetic acid (diastereoisomer 1) | C27H23NO4Cl2 496.39 | 0.94 LC-MS 1FA | 496.1 |
| 152 | (±)-(4-Chloro-2-{2-[(trans)-2-(3-chloro-phenyl)-cyclopropanecarbonyl]-1,2,3,4-tetrahydro-isoquinolin-1-yl}-phenoxy)-acetic acid (diastereoisomer 2) | C27H23NO4Cl2 496.39 | 0.92 LC-MS 1FA | 496.1 |
| 153 | (±)-{4-Chloro-2-[2-((trans)-2-o-tolyl-cyclopropanecarbonyl)-1,2,3,4-tetrahydro-isoquinolin-1-yl]-phenoxy}-acetic acid (diastereosiomer 1) | C28H26NO4Cl 475.97 | 0.93 LC-MS 1FA | 476.2 |
| 154 | (±)-{4-Chloro-2-[2-((trans)-2-o-tolyl-cyclopropanecarbonyl)-1,2,3,4-tetrahydro-isoquinolin-1-yl]-phenoxy}-acetic acid (diastereosiomer 2) | C28H26NO4Cl 475.97 | 0.91 LC-MS 1FA | 476.2 |
| 155 | (±)-(4-Chloro-2-{2-[(trans)-2-(2-trifluoromethyl-phenyl)-cyclopropanecarbonyl]-1,2,3,4-tetrahydro-isoquinolin-1-yl}-phenoxy)-acetic acid (diatereoisomer 1) | C28H23NO4ClF3 529.94 | 0.93 LC-MS 1FA | 530.2 |
| 156 | (±)-(4-Chloro-2-{2-[(trans)-2-(2-trifluoromethyl-phenyl)-cyclopropanecarbonyl]-1,2,3,4-tetrahydro-isoquinolin-1-yl}-phenoxy)-acetic acid (diatereoisomer 2) | C28H23NO4ClF3 529.94 | 0.92 LC-MS 1FA | 530.2 |
| 157 | (±)-(4-Chloro-2-{2-[trans-2-(4-chloro-phenyl)-cyclopropanecarbonyl]-1,2,3,4-tetrahydro-isoquinolin-1-yl}-phenoxy)-acetic acid | C27H23NO4Cl2 496.39 | 0.93 LC-MS 1FA | 496.1 |
| 158 | (±)-(4-Chloro-2-{2-[trans-2-(2,4-dichloro-phenyl)-cyclopropanecarbonyl]-1,2,3,4- | C27H22NO4Cl3 530.83 | 0.97 LC-MS 1FA | 530.0 |

TABLE 7-continued

| Example | Compound of Formula (I) | Formula MW | $t_R$ [min] LC-MS Method | MS-data m/z [M + H]$^+$ |
|---|---|---|---|---|
| | tetrahydro-isoquinolin-1-yl}-phenoxy)-acetic acid | | | |
| 159 | (±)-(4-Chloro-2-{2-[trans-2-(2-methoxy-phenyl)-cyclopropanecarbonyl]-1,2,3,4-tetrahydro-isoquinolin-1-yl}-phenoxy)-acetic acid | C28H26NO5Cl 491.97 | 0.89 LC-MS 1FA | 492.1 |
| 160 | (±)-(4-Chloro-2-{2-[trans-2-(2-fluoro-phenyl)-cyclopropanecarbonyl]-1,2,3,4-tetrahydro-isoquinolin-1-yl}-phenoxy)-acetic acid | C27H23NO4ClF 479.93 | 0.88 LC-MS 1FA | 480.1 |
| 161 | (±)-(4-Chloro-2-{2-[3-(3-phenyl-3H-[1,2,3]triazol-4-yl)-propionyl]-1,2,3,4-tetrahydro-isoquinolin-1-yl}-phenoxy)-acetic acid | C28H25N4O4Cl 516.98 | 0.80 LC-MS 1FA | 517.2 |
| 162 | (±)-(4-Chloro-2-{2-[2-(3-phenyl-3H-[1,2,3]triazol-4-ylsulfanyl)-acetyl]-1,2,3,4-tetrahydro-isoquinolin-1-yl}-phenoxy)-acetic acid | C27H23N4O4ClS 535.02 | 0.82 LC-MS 1FA | 535.2 |

Carbamate Formation and Subsequent Saponification

Method A: To a solution of an (±)-[4-fluoro-2-(6-fluoro-1,2,3,4-tetrahydro-isoquinolin-1-yl)-phenoxy]-acetic acid ethyl ester (5 mg, 0.014 mmol, 1.0 eq.) and NEt$_3$ (4 µL, 0.028 mmol, 2.0 eq.) in DCM (1 mL), benzyl chloroformate (2 µL, 0.016 mmol, 1.1 eq.) was added. The resulting solution was stirred at r.t. for 18 hours. The solvent was evaporated and the residue was dissolved in DMF (0.5 mL). 1M aq. NaOH (0.50 mL) was added. The mixture was stirred at r.t. for 2 hours. The solution was neutralized with formic acid (0.50 mL) and then purified by prep. HPLC (column: Atlantis, 18×50 mm, 10 um, UV/MS, acidic conditions) to give the desired acid as a white solid.

Listed in Table 8 below are examples of compounds of Formula (I), prepared according to the above-mentioned method with the corresponding amine of Structure 2 and the corresponding chloroformate as starting materials.

TABLE 8

| Example | Compound of Formula (I) | Formula MW | $t_R$ [min] LC-MS Method | MS-data m/z [M + H]$^+$ |
|---|---|---|---|---|
| 163 | (±)-1-(2-Carboxymethoxy-5-fluoro-phenyl)-6-fluoro-3,4-dihydro-1H-isoquinoline-2-carboxylic acid benzyl ester | C25H21NO5F2 453.44 | 0.87 LC-MS 1FA | 454.1 |
| 164 | (±)-1-(2-Carboxymethoxy-5-chloro-phenyl)-3,4-dihydro-1H-isoquinoline-2-carboxylic acid 2-chloro-benzyl ester | C25H21NO5Cl2 486.35 | 0.94 LC-MS 1FA | 486.0 |
| 165 | (±)-1-(2-Carboxymethoxy-5-fluoro-phenyl)-3,4-dihydro-1H-isoquinoline-2-carboxylic acid 2-chloro-benzyl ester | C25H21NO5ClF 469.90 | 0.91 LC-MS 1FA | 470.1 |
| 166 | (±)-1-(2-Carboxymethoxy-5-fluoro-phenyl)-3,4-dihydro-1H-isoquinoline-2-carboxylic acid 2,2-dimethyl-propyl ester | C23H26NO5F 415.46 | 0.91 LC-MS 1FA | 416.2 |
| 167 | (±)-1-(2-Carboxymethoxy-5-fluoro-phenyl)-3,4-dihydro-1H-isoquinoline-2-carboxylic acid butyl ester | C22H24NO5F 401.43 | 0.88 LC-MS 1FA | 402.2 |
| 168 | (±)-1-(2-Carboxymethoxy-5-fluoro-phenyl)-3,4-dihydro-1H-isoquinoline-2-carboxylic acid 2-methoxy-phenyl ester | C25H22NO6F 451.45 | 0.85 LC-MS 1FA | 452.1 |
| 169 | (±)-1-(2-Carboxymethoxy-5-fluoro-phenyl)-3,4-dihydro-1H-isoquinoline-2-carboxylic acid phenyl ester | C24H20NO5F 421.42 | 0.85 LC-MS 1FA | 422.1 |
| 170 | (±)-1-(2-Carboxymethoxy-5-fluoro-phenyl)-3,4-dihydro-1H-isoquinoline-2-carboxylic acid 2-chloro-phenyl ester | C24H19NO5ClF 455.87 | 0.88 LC-MS 1FA | 456.1 |
| 171 | (±)-1-(2-Carboxymethoxy-5-fluoro-phenyl)-3,4-dihydro-1H- | C22H24NO5F 401.43 | 0.88 LC-MS 1FA | 402.2 |

TABLE 8-continued

| Example | Compound of Formula (I) | Formula MW | $t_R$ [min] LC-MS Method | MS-data m/z [M + H]$^+$ |
|---|---|---|---|---|
| | isoquinoline-2-carboxylic acid isobutyl ester | | | |
| 172 | (±)-1-(2-Carboxymethoxy-5-fluoro-phenyl)-3,4-dihydro-1H-isoquinoline-2-carboxylic acid 2-methoxy-ethyl ester | C21H22NO6F 403.41 | 0.76 LC-MS 2 | 404.0 |
| 173 | (±)-1-(2-Carboxymethoxy-5-fluoro-phenyl)-3,4-dihydro-1H-isoquinoline-2-carboxylic acid 4-methoxy-phenyl ester | C25H22NO6F 451.45 | 0.85 LC-MS 1FA | 452.1 |
| 174 | (S)-1-(2-Carboxymethoxy-5-chloro-phenyl)-3,4-dihydro-1H-isoquinoline-2-carboxylic acid 2-chloro-benzyl ester | C25H21NO5Cl2 486.35 | 0.94 LC-MS 1FA | 486.1 |
| 175 | (±)-1-(2-Carboxymethoxy-5-chloro-phenyl)-5-fluoro-3,4-dihydro-1H-isoquinoline-2-carboxylic acid 2-chloro-benzyl ester | C25H20NO5Cl2F 504.34 | 0.96 LC-MS 1FA | 504.0 |

Method B: To a solution of triphosgene (22 mg, 0.07 mmol, 0.33 eq.) in MeCN (0.15 mL) at −10° C. (acetone/ice bath), a solution of an alcohol (0.25 mmol, 1.10 eq.) and NEt$_3$ (41 μL, 0.31 mmol, 1.4 eq.) in MeCN (0.8 mL) was added over a period of 15 min. The mixture was stirred for an additional 30 min at −10° C. and then a solution of (±)-[4-fluoro-2-(1,2,3,4-tetrahydro-isoquinolin-1-yl)-phenoxy]-acetic acid ethyl ester hydrochloride (77 mg, 0.22 mmol, 1.00 eq.) and NEt$_3$ (87 μL, 0.62 mmol, 2.8 eq.) in MeCN (0.46 mL) was slowly added. The reaction mixture was slowly warmed to r.t. (ice bath during 30 min, then r.t.) and stirred at r.t. for 18 hours. The reaction mixture was diluted with AcOEt, washed with water and sat. aq. NaCl, dried over MgSO$_4$, filtered and evaporated. To a solution of the residue in DMF (0.5 mL), 1M aq. NaOH soln. (0.5 mL) was added. The solution was stirred at r.t. for 18 hours. The reaction mixture was neutralized with formic acid, then purified by prep. HPLC (column: Atlantis, 30×75 mm, 5 um, UV/MS, acidic conditions) to give the desired acid as a white solid.

Listed in Table 9 below are examples of compounds of Formula (I), prepared according to the above-mentioned method with the corresponding amine of Structure 2 and the corresponding alcohol as starting materials.

Example 180

(±)-1-(2-Carboxymethoxy-5-chloro-phenyl)-4,4-dimethyl-3,4-dihydro-1H-isoquinoline-2-carboxylic acid benzyl ester (C27H26NO5Cl, MW=479.96)

Trifluoroacetic acid (0.92 mL, 11.8 mmol, 20.0 eq.) was added to a solution of (±)-1-(5-chloro-2-ethoxycarbonyl-methoxy-phenyl)-4,4-dimethyl-3,4-dihydro-1H-isoquinoline-2-carboxylic acid tert-butyl ester (280 mg, 0.59 mmol, 1.0 eq.) in DCM (1 mL). The resulting mixture was stirred at r.t. during 5 hours. The mixture was concentrated in vacuo. To an-ice cooled suspension of the residue and triethylamine (0.41 mL, 2.95 mmol, 5.0 eq.) in DCM (1 mL), benzyl chloroformate (0.18 mL, 1.18 mmol, 2.0 eq.) was added dropwise. Upon completion of the addition, the cooling bath was removed and the suspension was stirred at r.t. for 18 hours. The reaction was quenched with 1M aq. citric acid soln. (5 mL). The layers were separated. The aq. phase was extracted with DCM (3×2 mL). The comb. org. phases were dried over MgSO$_4$ and concentrated in vacuo. The residue was dissolved in DMF (1 mL), 1M aq. NaOH soln. (1 mL) was added. The resulting solution was stirred at r.t. for 18 hours. The solution

TABLE 9

| Example | Compound of Formula (I) | Formula MW | $t_R$ [min] LC-MS Method | MS-data m/z [M + H]$^+$ |
|---|---|---|---|---|
| 176 | (±)-1-(2-Carboxymethoxy-5-chloro-phenyl)-3,4-dihydro-1H-isoquinoline-2-carboxylic acid 2-(2-chloro-phenyl)-ethyl ester | C26H23NO5Cl2 500.38 | 0.97 LC-MS 1FA | 500.1 |
| 177 | (±)-1-(2-Carboxymethoxy-5-fluoro-phenyl)-3,4-dihydro-1H-isoquinoline-2-carboxylic acid 2-(2-chloro-phenyl)-ethyl ester | C26H23NO5ClF 483.92 | 0.94 LC-MS 1FA | 484.1 |
| 178 | (±)-1-(2-Carboxymethoxy-5-fluoro-phenyl)-3,4-dihydro-1H-isoquinoline-2-carboxylic acid 3-chloro-phenyl ester | C24H19NO5ClF 455.87 | 0.90 LC-MS 1FA | 456.1 |
| 179 | (±)-1-(2-Carboxymethoxy-5-chloro-phenyl)-5-fluoro-3,4-dihydro-1H-isoquinoline-2-carboxylic acid 2-(2-chloro-phenyl)-ethyl ester | C26H22NO5Cl2F 518.37 | 0.98 LC-MS 1FA | 518.0 | was neutralized with formic acid (1 mL), filtered, and then purified by prep. HPLC (column: Atlantis, 30×75 mm, 10 um, UV/MS, acidic conditions) and concentrated in vacuo to give the desired acid.

LC-MS 1 FA: $t_R$=0.98 min; [M+H]$^+$=480.1

Copper Mediated Sulfonylation and Subsequent Saponification

A mixture of (±)-7-bromo-1-(2-ethoxycarbonylmethoxy-5-fluoro-phenyl)-3,4-dihydro-1H-isoquinoline-2-carboxylic acid benzyl ester (54 mg, 0.10 mmol, 1.0 eq.), a sodium sulfinate (0.10 mmol, 1.0 eq.), L-proline (2.3 mg, 0.02 mmol, 0.2 eq.), 1M NaOH (20 μL, 0.02 mmol, 0.2 eq.), and copper (I) iodide (1.9 mg, 0.01 mmol, 0.1 eq.) in DMSO (1 mL) was stirred at 100° C. for 48 hours. The mixture was allowed to cool to r.t. and partitioned between AcOEt (15 mL), and H$_2$O (15 mL). The layers were separated and the aq. phase was extracted with AcOEt (2×15 mL). The comb. org. phases were dried over MgSO$_4$ and concentrated in vacuo. The residue was dissolved in THF (0.5 mL), 1M aq. NaOH (0.28 mL) was added and the mixture was stirred at r.t. for 14 hours. The org. solvent was removed in vacuo. The residue was diluted with water (2 mL) and acidified with 1M aq. HCl soln. The mixture was extracted with DCM (3×5 mL). The comb. org. phases were concentrated in vacuo. The residue was purified by prep. HPLC (column: Waters Atlantis, 19×50 mm, 10 um, UV/MS, acidic conditions) to give the desired acid as a white solid.

Listed in Table 10 below are examples of compounds of Formula (I), prepared according to the above-mentioned method with (±)-7-bromo-1-(2-ethoxycarbonylmethoxy-5-fluoro-phenyl)-3,4-dihydro-1H-isoquinoline-2-carboxylic acid benzyl ester, (±)-5-bromo-1-(2-ethoxycarbonylmethoxy-5-fluoro-phenyl)-3,4-dihydro-1H-isoquinoline-2-carboxylic acid benzyl ester, or (±)-1-(5-bromo-2-ethoxycarbonylmethoxy-phenyl)-3,4-dihydro-1H-isoquinoline-2-carboxylic acid benzyl ester and the corresponding sodium sulfinate as starting materials.

TABLE 10

| Example | Compound of Formula (I) | Formula MW | $t_R$ [min] LC-MS Method | MS-data m/z [M + H]$^+$ |
|---|---|---|---|---|
| 181 | (±)-1-(2-Carboxymethoxy-5-fluoro-phenyl)-7-ethanesulfonyl-3,4-dihydro-1H-isoquinoline-2-carboxylic acid benzyl ester | C27H26NO7FS 527.57 | 0.78 LC-MS 1FA | 528.1 |
| 182 | (±)-1-(2-Carboxymethoxy-5-methanesulfonyl-phenyl)-3,4-dihydro-1H-isoquinoline-2-carboxylic acid benzyl ester | C26H25NO7S 495.55 | 0.74 LC-MS 1FA | 496.1 |
| 183 | (±)-1-(5-Benzenesulfonyl-2-carboxymethoxy-phenyl)-3,4-dihydro-1H-isoquinoline-2-carboxylic acid benzyl ester | C31H27NO7S 557.62 | 0.84 LC-MS 1FA | 558.1 |
| 184 | (±)-1-(2-Carboxymethoxy-5-ethanesulfonyl-phenyl)-3,4-dihydro-1H-isoquinoline-2-carboxylic acid benzyl ester | C27H27NO7S 509.58 | 0.77 LC-MS 1FA | 510.1 |
| 185 | (±)-1-(2-Carboxymethoxy-5-fluoro-phenyl)-5-methanesulfonyl-3,4-dihydro-1H-isoquinoline-2-carboxylic acid benzyl ester | C26H24NO7FS 513.54 | 0.75 LC-MS 1FA | 514.1 |
| 186 | (±)-1-(2-Carboxymethoxy-5-fluoro-phenyl)-5-ethanesulfonyl-3,4-dihydro-1H-isoquinoline-2-carboxylic acid benzyl ester | C27H26NO7FS 527.57 | 0.78 LC-MS 1FA | 528.1 |
| 187 | (±)-5-Benzenesulfonyl-1-(2-carboxymethoxy-5-fluoro-phenyl)-3,4-dihydro-1H-isoquinoline-2-carboxylic acid benzyl ester | C31H26NO7FS 575.61 | 0.85 LC-MS 1FA | 576.1 |

Suzuki Cross-coupling and Subsequent Saponification

To a mixture under $N_2$ of (±)-1-(5-bromo-2-ethoxycarbonylmethoxy-phenyl)-3,4-dihydro-1H-isoquinoline-2-carboxylic acid benzyl ester (52 mg, 0.10 mmol, 1.00 eq.), a boronic acid (0.10 mmol, 1.0 eq.), and sodium carbonate (42 mg, 0.40 mmol, 4.00 eq.) in toluene/EtOH/water 20:4:1 (2.5 mL), tetrakis(triphenylphosphine) palladium (0) (6 mg, 0.005 mmol, 0.05 eq.) was added. The mixture was stirred at 100° C. for 24 hours. The mixture was allowed to cool to r.t. and concentrated in vacuo. The residue was partitioned between AcOEt (10 mL) and water (10 mL). The layers were separated. The org. phase was washed with sat. aq. NaCl soln. (1×5 mL), dried over $MgSO_4$, and filtered through Celite. The filtrate was concentrated in vacuo. The residue was dissolved in THF (0.5 mL). 1M aq. NaOH (0.28 mL) was added and the mixture was stirred at r.t. for 14 hours. The org. solvent was removed in vacuo. The residue was diluted with water (2 mL) and acidified with 1M aq. HCl soln. The mixture was extracted with DCM (3×5 mL). The comb. org. phases were concentrated in vacuo. The residue was purified by prep. HPLC (column: Waters Atlantis, 19×50 mm, 10 um, UV/MS, acidic conditions) to give the desired acid as a white solid.

Listed in Table 11 below are examples of compounds of Formula (I), prepared according to the above-mentioned method with the corresponding boronic acid as starting material.

TABLE 11

| Example | Compound of Formula (I) | Formula MW | $t_R$ [min] LC-MS Method | MS-data m/z $[M + H]^+$ |
|---|---|---|---|---|
| 188 | (±)-1-(2-Carboxymethoxy-5-pyrimidin-5-yl-phenyl)-3,4-dihydro-1H-isoquinoline-2-carboxylic acid benzyl ester | C29H25N3O5 495.53 | 0.76 LC-MS 1FA | 496.2 |
| 189 | (±)-1-(4-Carboxymethoxy-4'-fluoro-biphenyl-3-yl)-3,4-dihydro-1H-isoquinoline-2-carboxylic acid benzyl ester | C31H26NO5F 511.55 | 0.96 LC-MS 1FA | 512.2 |

Alcohol Alkylation and Subsequent Saponification

Method A: To an ice-cooled solution of an alcohol (0.42 mmol, 5.0 eq.) in DMF (0.6 mL), sodium hydride (25 mg, 0.62 mmol, 7.0 eq.) was added. The mixture was stirred at 0° C. for 1 hour. A solution of (±)-{2-[2-(2-bromo-acetyl)-1,2,3,4-tetrahydro-isoquinolin-1-yl]-4-fluoro-phenoxy}-acetic acid ethyl ester (40 mg, 0.09 mmol, 1.0 eq.) in DMF (0.6 mL) was added and the reaction mixture was stirred at r.t. for 18 hours. Water (20 μL) was added and the mixture was further stirred at r.t. during 1 hour. The reaction mixture was concentrated in vacuo. The residue was dissolved in THF (0.7 mL). 1M aq. NaOH soln. (0.3 mL) was added. The solution was stirred at r.t. for 18 hours. The reaction mixture was acidified with 1M aq. HCl soln. (0.5 mL) and concentrated in vacuo. The residue, redissolved in DMF (1.2 mL), was purified by prep. HPLC (column: Atlantis, 19×50 mm, 5 um, UV/MS, acidic conditions) to give the desired acid.

Listed in Table 12 below are examples of compounds of Formula (I), prepared according to the above-mentioned method with the corresponding alcohol as starting material.

TABLE 12

| Example | Compound of Formula (I) | Formula MW | $t_R$ [min] LC-MS Method | MS-data m/z $[M + H]^+$ |
|---|---|---|---|---|
| 190 | (±)-(2-{2-[2-(3-Chloro-benzyloxy)-acetyl]-1,2,3,4-tetrahydro-isoquinolin-1-yl}-4-fluoro-phenoxy)-acetic acid | C26H23NO5ClF 483.92 | 0.86 LC-MS 1FA | 484.1 |
| 191 | (±)-(2-{2-[2-(4-Chloro-benzyloxy)-acetyl]-1,2,3,4-tetrahydro-isoquinolin-1-yl}-4-fluoro-phenoxy)-acetic acid | C26H23NO5ClF 483.92 | 0.86 LC-MS 1FA | 484.1 |
| 192 | (±)-(4-Fluoro-2-{2-[2-(2-methyl-benzyloxy)-acetyl]-1,2,3,4-tetrahydro-isoquinolin-1-yl}-phenoxy)-acetic acid | C27H26NO5F 463.50 | 0.85 LC-MS 1FA | 464.2 |
| 193 | (±)-(4-Fluoro-2-{2-[2-(3-methyl-benzyloxy)-acetyl]-1,2,3,4-tetrahydro-isoquinolin-1-yl}-phenoxy)-acetic acid | C27H26NO5F 463.50 | 0.85 LC-MS 1FA | 464.2 |

TABLE 12-continued

| Example | Compound of Formula (I) | Formula MW | $t_R$ [min] LC-MS Method | MS-data m/z [M + H]⁺ |
|---|---|---|---|---|
| 194 | (±)-(4-Fluoro-2-{2-[2-(4-methyl-benzyloxy)-acetyl]-1,2,3,4-tetrahydro-isoquinolin-1-yl}-phenoxy)-acetic acid | C27H26NO5F 463.50 | 0.85 LC-MS 1FA | 464.1 |
| 195 | (±)-(4-Fluoro-2-{2-[2-(3-methoxy-benzyloxy)-acetyl]-1,2,3,4-tetrahydro-isoquinolin-1-yl}-phenoxy)-acetic acid | C27H26NO6F 479.50 | 0.81 LC-MS 1FA | 480.2 |
| 196 | (±)-(4-Fluoro-2-{2-[2-(4-methoxy-benzyloxy)-acetyl]-1,2,3,4-tetrahydro-isoquinolin-1-yl}-phenoxy)-acetic acid | C27H26NO6F 479.50 | 0.80 LC-MS 1FA | 480.1 |

Method B: To a solution of (±)-{2-[2-(2-bromo-acetyl)-1,2,3,4-tetrahydro-isoquinolin-1-yl]-4-fluoro-phenoxy}-acetic acid ethyl ester (50 mg, 0.11 mmol, 1.0 eq.) and an alcohol (0.13 mmol, 1.2 eq.) in toluene (1 mL), 30% aq. NaOH (1 mL) and tetrabutyl ammonium hydrogen sulfate (7.3 mg, 0.02 mmol, 0.2 eq.) were added. After 18 hours of vigorous stirring at r.t., the reaction mixture was diluted with water (2 mL), acidified with 1M aq. HCl and extracted with DCM (3×). The comb. org. layers were dried over MgSO₄, filtered and concentrated in vacuo. The crude mixture, redissolved in DMF (1.2 mL), was purified by prep. HPLC (column: Atlantis, 19×50 mm, 5 um, UV/MS, acidic conditions) to give the desired acid.

Listed in Table 13 below are examples of compounds of Formula (I), prepared according to the above-mentioned method with the corresponding alcohol as starting material.

Urea Synthesis and Subsequent Saponification

Method A: An isocyanate (0.22 mmol, 1.1 eq.) was added dropwise to an ice-cooled solution of (±)-[4-fluoro-2-(1,2,3,4-tetrahydro-isoquinolin-1-yl)-phenoxy]-acetic acid ethyl ester hydrochloride (73 mg, 0.20 mmol, 1.0 eq.) and NEt₃ (0.09 mL, 0.62 mmol, 3.1 eq.) in DCM (5.5 mL). The resulting reaction mixture was stirred at r.t. for 60 hours. The mixture was diluted with DCM and washed with sat. aq. NaHCO₃ soln. and water. The organic layer was dried over MgSO₄, filtered and concentrated in vacuo. To a solution of the crude product in DMF (0.9 mL), 1M aq. NaOH soln. (0.25 mL) was added. The solution was stirred at r.t. for 18 hours. The solution was acidified with 1M aq. HCl (0.25 mL), filtered, and purified by prep. HPLC (column: Waters X-Bridge, 30×75 mm, 10 um, UV/MS, acidic conditions) to give the desired acid.

Listed in Table 14 below are examples of compounds of Formula (I), prepared according to the above-mentioned method with the corresponding amine of Structure 2 and the corresponding isocyanate as starting materials.

TABLE 13

| Example | Compound of Formula (I) | Formula MW | $t_R$ [min] LC-MS Method | MS-data m/z [M + H]⁺ |
|---|---|---|---|---|
| 197 | (±)-(4-Fluoro-2-{2-[2-(1-methyl-1H-pyrazol-3-ylmethoxy)-acetyl]-1,2,3,4-tetrahydro-isoquinolin-1-yl}-phenoxy)-acetic acid | C24H24N3O5F 453.47 | 0.68 LC-MS 1FA | 454.2 |
| 198 | (±)-(4-Fluoro-2-{2-[2-(2-methoxy-benzyloxy)-acetyl]-1,2,3,4-tetrahydro-isoquinolin-1-yl}-phenoxy)-acetic acid | C27H26NO6F 479.50 | 0.82 LC-MS 1FA | 480.2 |

TABLE 14

| Example | Compound of Formula (I) | Formula MW | $t_R$ [min] LC-MS Method | MS-data m/z [M + H]⁺ |
|---|---|---|---|---|
| 199 | (±)-[2-(2-Benzylcarbamoyl-1,2,3,4-tetrahydro-isoquinolin-1-yl)-4-fluoro-phenoxy]-acetic acid | C25H23N2O4F 434.47 | 0.79 LC-MS 1FA | 435.2 |
| 200 | (±)-[4-Fluoro-2-(2-phenethylcarbamoyl-1,2,3,4-tetrahydro-isoquinolin-1-yl)-phenoxy]-acetic acid | C26H25N2O4F 448.49 | 0.82 LC-MS 1FA | 449.2 |
| 201 | (±)-{4-Fluoro-2-[2-(2-methoxy-benzylcarbamoyl)-1,2,3,4-tetrahydro-isoquinolin-1-yl]-phenoxy}-acetic acid | C26H25N2O5F 464.49 | 0.79 LC-MS 1FA | 465.2 |

TABLE 14-continued

| Example | Compound of Formula (I) | Formula MW | $t_R$ [min] LC-MS Method | MS-data m/z [M + H]$^+$ |
|---|---|---|---|---|
| 202 | (±)-{4-Chloro-2-[2-(2-methoxy-benzylcarbamoyl)-1,2,3,4-tetrahydro-isoquinolin-1-yl]-phenoxy}-acetic acid | C26H25N2O5Cl 480.95 | 0.83 LC-MS 1FA | 481.1 |
| 203 | (±)-{2-[2-(2-Chloro-benzylcarbamoyl)-1,2,3,4-tetrahydro-isoquinolin-1-yl]-4-fluoro-phenoxy}-acetic acid | C25H22N2O4ClF 468.91 | 0.82 LC-MS 1FA | 469.1 |

Method B: Example 204: (±)-(2-{2-[2-(2-Chloro-phenyl)-ethylcarbamoyl]-1,2,3,4-tetrahydro-isoquinolin-1-yl}-4-fluoro-phenoxy)-acetic acid (C26H24N2O4ClF, MW=482.94)

To a solution of triphosgene (20 mg, 0.07 mmol, 0.33 eq.) in MeCN (0.3 mL) at −10° C. (acetone/ice bath), a solution of 2-(2-chlorophenyl)ethylamine (33 µL, 0.22 mmol, 1.10 eq.) and triethylamine (39 µL, 0.28 mmol, 1.30 eq.) in MeCN (2 mL) was added over a period of 15 min. The mixture was stirred for an additional 30 min at 0° C. and then a solution of (±)-[4-fluoro-2-(1,2,3,4-tetrahydro-isoquinolin-1-yl)-phenoxy]-acetic acid ethyl ester hydrochloride (73 mg, 0.20 mmol, 1.00 eq.) and triethylamine (78 µL, 0.56 mmol, 2.80 eq.) in MeCN (1 mL) was slowly added. The reaction mixture was slowly warmed to r.t. (ice bath during 30 min, then r.t.) and stirred at r.t. for 60 hours. The mixture was diluted with AcOEt, washed with water and sat. aq. NaCl soln., dried over MgSO$_4$, filtered, and evaporated. To a solution of the crude product in DMF (0.9 mL), 1M aq. NaOH soln. (0.25 mL) was added. The solution was stirred at r.t. for 18 hours. The solution was acidified with 1M aq. HCl soln. (0.25 mL) then purified by prep. HPLC (column: Waters X-Bridge, 30×75 mm, 10 um, UV/MS, acidic conditions) to afford the title compound.

LC-MS 1 FA: $t_R$=0.84 min; [M+H]$^+$=483.1

Sulfonamide Formation and Subsequent Saponification

A sulfonyl chloride (0.18 mmol, 1.0 eq.) and DIPEA (0.33 mL, 1.92 mmol, 10.6 eq.) were added to a solution of (±)-{2-[2-(2-amino-acetyl)-1,2,3,4-tetrahydro-isoquinolin-1-yl]-4-fluoro-phenoxy}-acetic acid ethyl ester hydrochloride (81 mg, 0.18 mmol, 1.0 eq.) in DCM (3 mL). The mixture was stirred at r.t. for 2 hours. 1M aq. KH$_2$PO$_4$ soln. (3 mL) was added to the mixture. The layers were separated and the aq. phase was extracted with DCM (2×). The comb. org. phases were concentrated in vacuo. The residue was dissolved in THF (0.8 mL) and 1M aq. NaOH soln. (0.4 mL) was added. The solution was stirred at r.t. for 18 hours. The solution was diluted with water (2 mL) and 1M aq. HCl soln. (0.4 mL) followed by DCM. The mixture was shaked then the layers were separated and the aq. phase was extracted with DCM (2×). The comb. org. phases were concentrated in vacuo. The crude mixture, redissolved in DMF (1.2 mL), was purified by prep. HPLC (column: Atlantis, 19×50 mm, 5 um, UV/MS, acidic conditions) to give the desired acid.

Listed in Table 15 below are examples of compounds of Formula (I), prepared according to the above-mentioned method with the corresponding sulfonyl chloride as starting material.

TABLE 15

| Example | Compound of Formula (I) | Formula MW | $t_R$ [min] LC-MS Method | MS-data m/z [M + H]$^+$ |
|---|---|---|---|---|
| 205 | (±)-{2-[2-(2-Benzenesulfonylamino-acetyl)-1,2,3,4-tetrahydro-isoquinolin-1-yl]-4-fluoro-phenoxy}-acetic acid | C25H23N2O6FS 498.53 | 0.75 LC-MS 1FA | 499.1 |
| 206 | (±)-(2-{2-[2-(3,5-Dimethyl-isoxazole-4-sulfonylamino)-acetyl]-1,2,3,4-tetrahydro-isoquinolin-1-yl}-4-fluoro-phenoxy)-acetic acid | C24H24N3O7FS 517.53 | 0.75 LC-MS 1FA | 518.1 |
| 207 | (±)-(4-Fluoro-2-{2-[2-(3-fluoro-benzenesulfonylamino)-acetyl]-1,2,3,4-tetrahydro-isoquinolin-1-yl}-phenoxy)-acetic acid | C25H22N2O6F2S 516.52 | 0.77 LC-MS 1FA | 517.1 |
| 208 | (±)-(4-Fluoro-2-{2-[2-(2-fluoro-benzenesulfonylamino)-acetyl]-1,2,3,4-tetrahydro-isoquinolin-1-yl}-phenoxy)-acetic acid | C25H22N2O6F2S 516.52 | 0.76 LC-MS 1FA | 517.1 |
| 209 | (±)-(2-{2-[2-(3,4-Difluoro-benzenesulfonylamino)-acetyl]-1,2,3,4-tetrahydro-isoquinolin-1-yl}-4-fluoro-phenoxy)-acetic acid | C25H21N2O6F3S 534.51 | 0.79 LC-MS 1FA | 535.1 |

Sulfonamide Formation, Alkylation, and Subsequent Saponification

A sulfonyl chloride (0.18 mmol, 1.0 eq.) and DIPEA (0.33 mL, 1.92 mmol, 10.6 eq.) were added to a solution of (±)-{2-[2-(2-amino-acetyl)-1,2,3,4-tetrahydro-isoquinolin-1-yl]-4-fluoro-phenoxy}-acetic acid ethyl ester hydrochloride (81 mg, 0.18 mmol, 1.0 eq.) in DCM (3 mL). The mixture was stirred at r.t. for 2 hours. 1M aq. KH$_2$PO$_4$ soln. (3 mL) was added to the mixture. The layers were separated and the aq. phase was extracted with DCM (2×). The comb. org. phases were concentrated in vacuo. To an ice-cooled solution of the residue in DMF (1 mL), sodium hydride (9 mg, 0.22 mmol, 1.2 eq.) was added. The reaction mixture was stirred at r.t. for 30 min. Methyl iodide (23 µl, 0.36 mmol, 2.0 eq.) was added and the resulting mixture was stirred at r.t. for 18 hours. The mixture was poured in H$_2$O and extracted with DCM (3×). The comb. org. phases were concentrated in vacuo. The residue was dissolved in DMF (0.8 mL) and 1M aq. NaOH soln. (0.4 mL) was added. The solution was stirred at r.t. for 18 hours. The solution was diluted with water (2 mL) and 1M aq. HCl soln. (0.4 mL) followed by DCM. The mixture was shaked then the layers were separated and the aq. phase was extracted with DCM (2×). The comb. org. phases were concentrated in vacuo. The crude mixture, redissolved in DMF (1.2 mL), was purified by prep. HPLC (column: Atlantis, 19×50 mm, 5 um, UV/MS, acidic conditions) to give the desired acid.

Listed in Table 16 below are examples of compounds of Formula (I), prepared according to the above-mentioned method with the corresponding sulfonyl chloride as starting material.

Example 214

(±)-1-[2-Carboxymethoxy-5-(5-thioxo-4,5-dihydro-[1,2,4]oxadiazol-3-yl)-phenyl]-3,4-dihydro-1H-isoquinoline-2-carboxylic acid benzyl ester (C27H23N3O6S, MW=517.56)

A mixture of hydroxylamine hydrochloride (139 mg, 2.00 mmol, 10.0 eq.) and NaHCO$_3$ (202 mg, 2.40 mmol, 12.0 eq.) in DMSO (1 mL) was stirred at 50° C. for 1 hour. (±)-1-(5-Cyano-2-ethoxycarbonylmethoxy-phenyl)-3,4-dihydro-1H-isoquinoline-2-carboxylic acid benzyl ester (94 mg, 0.20 mmol, 1.0 eq.) was added and the resulting new mixture was stirred at 80° C. for 1 hour. Water was added to the reaction mixture followed by AcOEt. The layers were separated and the org. phase was washed with sat. aq. NaCl, dried over MgSO$_4$, filtered and concentrated in vacuo. The residue was dissolved in THF (1 mL). 1,1'-thiocarbonyldiimidazole (39 mg, 0.21 mmol, 1.05 eq) and DBU (21 µL, 0.14 mmol, 0.7 eq.) were added and the mixture was stirred at r.t. for 3 hours. Water was added and the mixture was extracted with AcOEt. The layers were separated and the org. phase was successively washed with sat. aq. NaHCO$_3$ soln. and sat. aq. NaCl

TABLE 16

| Example | Compound of Formula (I) | Formula MW | $t_R$ [min] LC-MS Method | MS-data m/z [M + H]$^+$ |
|---|---|---|---|---|
| 210 | (±)-(2-{2-[2-(N-Benzenesulfonyl-N-methyl-amino)-acetyl]-1,2,3,4-tetrahydro-isoquinolin-1-yl}-4-fluoro-phenoxy)-acetic acid | C26H25N2O6FS 512.56 | 0.79 LC-MS 1FA | 513.1 |
| 211 | (±)-[4-Fluoro-2-(2-{2-[N-(3-fluoro-benzenesulfonyl)-N-methyl-amino]-acetyl}-1,2,3,4-tetrahydro-isoquinolin-1-yl)-phenoxy]-acetic acid | C26H24N2O6F2S 530.55 | 0.80 LC-MS 1FA | 531.1 |
| 212 | (±)-[2-(2-{2-[N-(3,4-Difluoro-benzenesulfonyl)-N-methyl-amino]-acetyl}-1,2,3,4-tetrahydro-isoquinolin-1-yl)-4-fluoro-phenoxy]-acetic acid | C26H23N2O6F3S 548.54 | 0.82 LC-MS 1FA | 549.1 |

Example 213

(±)-1-(5-Carbamoyl-2-carboxymethoxy-phenyl)-3,4-dihydro-1H-isoquinoline-2-carboxylic acid benzyl ester (C26H24N2O6, MW=460.49)

To a solution of (±)-1-(5-cyano-2-ethoxycarbonylmethoxy-phenyl)-3,4-dihydro-1H-isoquinoline-2-carboxylic acid benzyl ester (141 mg, 0.30 mmol, 1.0 eq.) in EtOH (0.5 mL) and water (0.12 mL), hydrido(dimethylphosphinous acid-kP)[hydrogen bis(dimethylphosphinito-kP)]platinum (II) (26 mg, 0.06 mmol, 0.2 eq.) was added in one portion at r.t. The reaction mixture was stirred at 70° C. for 1 hour, then allow to cool to r.t. The product solution was then filtered through a short column containing a layer of Na$_2$SO$_4$ on top of a layer of SiO$_2$ (each 1 cm deep), eluting with AcOEt (200 mL). The filtrate was concentrated in vacuo. To a solution of the residue in DMF (2 mL), 1M aq. NaOH (0.5 ml) was added. The resulting solution was stirred at r.t. for 6 hours. The mixture was neutralized with formic acid (0.5 mL), filtered, and purified by prep. HPLC (column: Waters X-Bridge, 19×50 mm, 5 um, UV/MS, acidic conditions) to give the desired acid as a white solid.

LC-MS 1 FA: $t_R$=0.67 min; [M+H]$^+$=461.2 soln. then dried over MgSO$_4$, filtered and concentrated in vacuo. To a solution of the residue in THF (0.9 mL), 1M aq. NaOH soln. (0.25 mL) was added. The solution was stirred at r.t. for 18 hours.

The solution was diluted with water (2 mL) and 1M aq. HCl soln. (0.25 mL) followed by DCM. The mixture was shaked then the layers were separated and the aq. phase was extracted with DCM (2×). The comb. org. phases were concentrated in vacuo. The crude mixture, redissolved in DMF (1.2 mL), was purified by prep. HPLC (column: Atlantis, 19×50 mm, 5 um, UV/MS, acidic conditions) to give the desired acid.

LC-MS 1FA: $t_R$=0.79 min; [M+H]$^+$=518.1

Example 215

(±)-1-(2-Carboxymethoxy-4-fluoro-phenyl)-3,4-dihydro-1H-isoquinoline-2-carboxylic acid benzyl ester (C25H22NO5F, MW=435.45)

A mixture under N$_2$ of (±)-1-(2-allyloxy-4-fluoro-phenyl)-3,4-dihydro-1H-isoquinoline-2-carboxylic acid benzyl ester (200 mg, 0.48 mmol, 1.00 eq.), 1,3-dimethylbarbituric acid (150 mg, 0.96 mmol, 2.00 eq.) and tetrakis(triphenylphosphine) palladium (0) (28 mg, 0.02 mmol, 0.05 eq.) in MeOH (5 mL) was stirred at r.t. for 5 hours. The mixture was partitioned between AcOEt (25 mL) and water (25 mL). The layers were separated and the aq. phase was extracted with AcOEt (2×25 mL). The comb. org. phases were washed with sat. aq. NaCl soln. (1×25 mL), dried over MgSO$_4$, and concentrated in vacuo. To a solution of the residue and Cs$_2$CO$_3$ (468 mg, 1.44 mmol, 3.00 eq.) in DMF (3 mL), ethyl bromoacetate (79 µL, 0.72 mmol, 1.50 eq.) was added. The reaction mixture was stirred at 50° C. for 5 hours. The reaction mixture was diluted with water (25 mL) and AcOEt (50 mL). The layers were separated. The aq. phase was extracted with AcOEt (2×25 mL). The comb. org. phases were washed with water (1×25 mL), sat. aq. NaCl soln. (1×25 mL), dried over MgSO$_4$, and concentrated in vacuo. To a solution of the residue in DMF (2 mL), 1M aq. NaOH (2 mL) was added. The resulting solution was stirred at 50° C. for 5 hours. The solution was neutralized with formic acid (1 mL) and then purified by prep. HPLC (column: Atlantis, 30×75 mm, 10 um, UV/MS, acidic conditions) and concentrated in vacuo to give the desired acid.

LC-MS 1 FA: $t_R$=0.87 min; [M+H]$^+$=436.1

Example 216

(±)-1-(2-Carboxymethoxy-6-fluoro-phenyl)-3,4-dihydro-1H-isoquinoline-2-carboxylic acid benzyl ester (C25H22NO5F, MW=435.45)

A mixture under N$_2$ of (±)-1-(2-allyloxy-6-fluoro-phenyl)-3,4-dihydro-1H-isoquinoline-2-carboxylic acid benzyl ester (60 mg, 0.14 mmol, 1.00 eq.), 1,3-dimethylbarbituric acid (45 mg, 0.29 mmol, 2.00 eq.) and tetrakis(triphenylphosphine) palladium (0) (8 mg, 7 µmol, 0.05 eq.) in MeOH (5 mL) was stirred at 50° C. for 5 hours. The mixture was partitioned between AcOEt (25 mL) and water (25 mL). The layers were separated and the aq. phase was extracted with AcOEt (2×25 mL). The comb. org. phases were washed with sat. aq. NaCl soln. (1×25 mL), dried over MgSO$_4$, and concentrated in vacuo. To a solution of the residue and Cs$_2$CO$_3$ (140 mg, 0.43 mmol, 3.00 eq.) in DMF (2 mL), ethyl bromoacetate (24 µL, 0.22 mmol, 1.50 eq.) was added. The reaction mixture was stirred at 50° C. for 5 hours. The reaction mixture was diluted with water (25 mL) and AcOEt (50 mL). The layers were separated. The aq. phase was extracted with AcOEt (2×25 mL). The comb. org. phases were washed with water (1×25 mL), sat. aq. NaCl soln. (1×25 mL), dried over MgSO$_4$, and concentrated in vacuo. To a solution of the residue in DMF (2 mL), 1M aq. NaOH (2 mL) was added. The resulting solution was stirred at 50° C. for 5 hours. The solution was neutralized with formic acid (1 mL) and then purified by prep. HPLC (column: Atlantis, 30×75 mm, 10 um, UV/MS, acidic conditions) and concentrated in vacuo to give the desired acid.

LC-MS 1 FA: $t_R$=0.86 min; [M+H]$^+$=436.2

Example 217

(±)-1-[2-(3-Carboxy-propoxy)-5-fluoro-phenyl]-3,4-dihydro-1H-isoquinoline-2-carboxylic acid benzyl ester (C27H26NO5F, MW=463.50)

Ethyl-4-bromobutyrate (45 µL, 0.30 mmol, 1.50 eq.) was added to a solution of (±)-1-(5-fluoro-2-hydroxy-phenyl)-3,4-dihydro-1H-isoquinoline-2-carboxylic acid benzyl ester (75 mg, 0.20 mmol, 1.00 eq.) and K$_2$CO$_3$ (83 mg, 0.60 mmol) in DMF (0.7 mL). The mixture was stirred at r.t. for 2 hours. Ethyl-4-bromobutyrate (22 µL, 0.15 mmol, 0.75 eq.) was added again and the mixture was stirred at r.t. for 18 hours. The reaction mixture was diluted with AcOEt and water. The layers were separated and the aq. phase was extracted with AcOEt (2×). The combined org. phases were washed with water and sat. aq. NaCl soln., dried over MgSO$_4$, filtered and concentrated in vacuo. To a solution of the crude ester in THF (0.9 mL), 1M aq. NaOH soln. (0.50 mL) was added. The resulting solution was stirred at r.t. during 62 hours. The org. solvent was removed in vacuo. The residue was diluted with water and 1M aq. HCl soln. (0.8 mL) followed by DCM. The mixture was shaked then the layers were separated and the aq. phase was extracted with DCM (2×). The comb. org. phases were dried over MgSO$_4$, filtered and concentrated in vacuo. The crude mixture, redissolved in DMF (1.2 mL), was purified by prep. HPLC (column: Atlantis, 19×50 mm, 5 um, UV/MS, acidic conditions) and evaporated (genevac) to give the desired acid.

LC-MS 1 FA: $t_R$=0.89 min; [M+H]$^+$=464.2

Example 218

(±)-{4-Cyano-2-[2-(trans-2-phenyl-cyclopropanecarbonyl)-1,2,3,4-tetrahydro-isoquinolin-1-yl]-phenoxy}-acetic acid (C28H24N2O4, MW=452.51)

To a solution of (±)-1-(5-cyano-2-ethoxycarbonylmethoxy-phenyl)-3,4-dihydro-1H-isoquinoline-2-carboxylic acid benzyl ester (188 mg, 0.40 mmol, 1.0 eq.) in DCM (1 mL), a solution of 2-bromo-1,3,2-benzodioxaborole (159 mg, 0.80 mmol, 2.0 eq.) in DCM (2 mL) was added dropwise. The mixture was stirred at r.t. for 2 hours. Water (2 mL) was added. The mixture was stirred at r.t. for 20 min, then diluted with DCM (30 mL). The mixture was washed with 10% aq. NaOH soln. (2×15 mL), with sat. aq. NaCl soln. (1×15 mL), and dried over MgSO$_4$. The dried org. layer was treated with 4M HCl in dioxane (4 mL), stirred at r.t. for 1 hour, and concentrated in vacuo. The residue was triturated with heptane and filtered to give the HCl salt as a white solid. To a mixture of the resulting salt and trans-2-phenylcyclopropane-1-carboxylic acid (65 mg, 0.40 mmol, 1.0 eq.) in DMF (2 mL), N-(3-dimethylaminopropyl)-N'-ethylcarbodiimid hydrochlorid (115 mg, 0.60 mmol, 1.5 eq.) and 4-(dimethylamino)pyridine (147 mg, 1.20 mmol, 3.0 eq.) were added in sequence. The mixture was stirred at r.t. for 20 hours. The mixture was diluted with AcOEt (15 mL). The diluted solution was washed with 1M aq. HCl soln. (2×5 mL), sat. aq. NaHCO$_3$ soln. (2×5 mL), sat. aq. NaCl soln. (1×5 mL), dried over MgSO$_4$, and concentrated in vacuo. The residue was dissolved in THF (1 mL). 1M aq. NaOH (0.56 mL) was added. The mixture was stirred at r.t. for 18 hours. The mixture was concentrated in vacuo. The residue was diluted with water (2 mL) and acidified with 1M aq. HCl soln. The mixture was extracted with DCM/THF 2:1 (3×6 mL). The comb. org. phases were concentrated in vacuo. The residue was purified by prep. HPLC (column: Waters X-bridge, 19×50 mm, 10 um, UV/MS, acidic conditions) to give the desired acid as a white foam.

LC-MS 1 FA: $t_R$=0.79 min; [M+H]$^+$=453.2

Example 219

(±)-1-(2-Carboxymethoxy-5-cyano-phenyl)-3,4-dihydro-1H-isoquinoline-2-carboxylic acid benzyl ester (C26H22N2O5, MW=442.47)

To a solution of (±)-1-(5-bromo-2-ethoxycarbonylmethoxy-phenyl)-3,4-dihydro-1H-isoquinoline-2-carboxylic acid benzyl ester (105 mg, 0.20 mmol, 1.0 eq.) in DMF (10 mL) were added zinc cyanide (23 mg, 0.20 mmol, 1.0 eq.) and tetrakis(triphenylphosphine) palladium (0) (23 mg, 0.02 mmol, 0.1 eq.). The resulting suspension was stirred at 110° C. for 18 hours. After cooling, Et$_2$O (100 mL) was added and the solution was washed with sat. aq. NaCl soln. (2×120 mL). The organic layer was dried over MgSO$_4$, filtered, and the solvent was removed under vacuum. To a solution of the crude product in DMF (0.9 mL) 1M aq. NaOH soln. (0.25 mL) was added. The solution was stirred at r.t. for 18 hours. The solution was acidified with 1M aq. HCl soln. (0.25 mL) then purified by prep. HPLC (column: Waters X-Bridge, 30×75 mm, 10 um, UV/MS, acidic conditions) to give the desired acid.

LC-MS 1 FA: $t_R$=0.81 min; [M+H]$^+$=443.1

Example 220

1-[2-((R)-1-Carboxy-ethoxy)-5-chloro-phenyl]-3,4-dihydro-1H-isoquinoline-2-carboxylic acid benzyl ester (C26H24NO5Cl, MW=465.93)

To a solution of (±)-1-(5-chloro-2-hydroxy-phenyl)-3,4-dihydro-1H-isoquinoline-2-carboxylic acid benzyl ester (192 mg, 0.30 mmol, 1.0 eq.) in MeCN (1 mL), (S)-2-(toluene-4-sulfonyloxy)-propionic acid methyl ester (80 mg, 0.30 mmol, 1.0 eq.) and potassium carbonate anhydrous (83 mg, 0.60 mmol, 2.0 eq.) were added and the mixture was heated to 65° C. for 18 hours. (S)-2-(Toluene-4-sulfonyloxy)-propionic acid methyl ester (40 mg, 0.15 mmol, 0.5 eq.) was added again and the mixture was heated at 90° C. for 4 hours. The mixture was allowed to cool to r.t. and extracted with Et$_2$O (2×), dried over MgSO$_4$, filtered, and concentrated in vacuo. To a solution of the crude ester in THF (1.3 mL), 1M aq. NaOH soln. (0.38 mL) was added. The solution was stirred at r.t. for 18 hours. The solution was diluted with water (2 mL) and 1M aq. HCl soln. (0.38 mL) followed by DCM. The mixture was shaked then the layers were separated and the aq. phase was extracted with DCM (2×). The comb. org. phases were concentrated in vacuo. The crude mixture, redissolved in DMF (1.2 mL), was purified by prep. HPLC (column: Atlantis, 19×50 mm, 5 um, UV/MS, acidic conditions) to give the desired acid.

LC-MS 1 FA: $t_R$=0.93 min; [M+H]$^+$=466.1

Example 221

(S)-1-(2-Carboxymethoxy-5-fluoro-phenyl)-3,4-dihydro-1H-isoquinoline-2-carboxylic acid benzyl ester (C25H22NO5F, MW=435.45)

(±)-1-(2-Carboxymethoxy-5-fluoro-phenyl)-3,4-dihydro-1H-isoquinoline-2-carboxylic acid benzyl ester was separated by chiral prep. HPLC (column: ChiralPak AD-H, 20×250 mm, 5 μm, UV, eluent: Hept/EtOH+0.1% TFA 70/30) to yield 30.5 mg of the (R)-enantiomer and 26.1 mg of the (S)-enantiomer. Due the presence of EtOH in the eluent mixture, the acids were partially esterified. To a solution of the (S)-enantiomer in THF (0.6 mL), 1M aq. NaOH soln. (0.18 mL) was added. The solution was stirred at r.t. during 2 hours. The org. solvent was removed in vacuo. The residue was diluted with water and 1M aq. HCl soln. (0.18 mL) followed by DCM. The mixture was shaked then the layers were separated and the aq. phase was extracted with DCM (2×). The comb. org. phases were concentrated in vacuo. The residue, redissolved in DMF (1.2 mL) was purified by prep. HPLC (column: Waters X-Bridge, 19×50 mm, 5 um, UV/MS, acidic conditions) to give the desired acid LC-MS 1 FA: $t_R$=0.87 min; [M+H]$^+$=436.1

Example 222

(±)-1-(2-Carboxymethoxy-5-fluoro-phenyl)-5-methanesulfonylamino-3,4-dihydro-1H-isoquinoline-2-carboxylic acid benzyl ester (C26H25N2O7FS, MW=528.56)

A mixture under Ar of (±)-5-bromo-1-(2-ethoxycarbonylmethoxy-5-fluoro-phenyl)-3,4-dihydro-1H-isoquinoline-2-carboxylic acid benzyl ester (108 mg, 0.20 mmol, 1.00 eq.), methanesulfonamide (23 mg, 0.24 mmol, 1.20 eq.), N,N-dimethylglycine (4.3 mg, 0.04 mmol, 0.2 eq.), potassium phosphate tribasic (106 mg, 0.50 mmol, 2.5 eq.), and copper (I) iodide (7.6 mg, 0.04 mmol, 0.2 eq.) in DMF (2 mL) was stirred at 150° C. for 48 hours. The mixture was allowed to cool to r.t. and partitioned between AcOEt (25 mL) and H$_2$O (25 mL). The layers were separated and the aq. phase was extracted with AcOEt (2×25 mL). The comb. org. phases were dried over MgSO$_4$ and concentrated in vacuo. The residue was dissolved in DMF (1.0 mL). 1M aq. NaOH soln. (1.0 mL) was added. The mixture was stirred at r.t. for 18 hours. The solution was neutralized with 1M aq. HCl soln. (1.0 mL), then purified by prep. HPLC (column: Atlantis, 30×75 mm, 10 uM, acidic conditions, detection: UV/MS) to give the desired acid.

LC-MS 1 FA: $t_R$=0.72 min; [M+H]$^+$=529.1

Example 223

(±)-1-(2-Carboxymethoxy-5-[1, 2, 3]triazol-1-yl-phenyl)-3,4-dihydro-1H-isoquinoline-2-carboxylic acid benzyl ester (C27H24N4O5, MW=484.51) and Example 224

(±)-1-(2-Carboxymethoxy-5-[1, 2, 3]triazol-2-yl-phenyl)-3,4-dihydro-1H-isoquinoline-2-carboxylic acid benzyl ester (C27H24N4O5, MW=484.51)

1H-1,2,3-triazole (23 μL, 0.400 mmol, 2.00 eq.), copper (I) iodide (1.9 mg, 0.010 mmol, 0.05 eq.), cesium carbonate (130. mg, 0.400 mmol, 2.00 eq.) and N,N'-dimethyl-cyclohexane-1,2-diamine (7 μL, 0.040 mmol, 0.20 eq.) were added at r.t. to a solution of (±)-1-(5-bromo-2-ethoxycarbonylmethoxy-phenyl)-3,4-dihydro-1H-isoquinoline-2-carboxylic acid benzyl ester (105 mg, 0.200 mmol, 1.00 eq.) in DMF (0.1 mL) in a microwave tube. The tube was flushed with N$_2$, sealed, and heated to 120° C. for 60 hours. The reaction mixture was diluted with water and washed with AcOEt. The remaining aqueous phase was acidified with 1N aq. HCl and extracted with AcOEt (3×). The combined organic extracts were dried over MgSO$_4$, filtered and concentrated in vacuo. The crude residue, redissolved in DMF (1.2 mL), was purified by prep. HPLC (column: Atlantis, 19×50 mm, 5 um, UV/MS, acidic conditions) to give (±)-1-(2-carboxymethoxy-5-[1,2,3]triazol-1-yl-phenyl)-3,4-dihydro-1H-isoquinoline-2-carboxylic acid benzyl ester (LC-MS 1FA: $t_R$=0.75 min; [M+H]$^+$= 485.2) and (±)-1-(2-carboxymethoxy-5-[1,2,3]triazol-2-ylphenyl)-3,4-dihydro-1H-isoquinoline-2-carboxylic acid benzyl ester (LC-MS 1FA: $t_R$=0.85 min; [M+H]$^+$=485.1).

Example 225

(±)-{4-Chloro-2-[2-(2-methoxy-benzylthiocarbamoyl)-1,2,3,4-tetrahydro-isoquinolin-1-yl]-phenoxy}-acetic acid (C26H25N2O4ClS, MW=497.01)

To a solution of (±)-[4-chloro-2-(1,2,3,4-tetrahydro-isoquinolin-1-yl)-phenoxy]-acetic acid ethyl ester hydrochloride (76 mg, 0.20 mmol, 1.0 eq.) and N-ethyldiisopropylamine (42 µL, 0.24 mmol, 1.2 eq) in DCM (2 mL), 2-methoxybenzyl isothiocyanate (36 mg, 0.20 mmol, 1.0 eq.) was added. The resulting mixture was stirred at r.t. for 19 hours. The mixture was diluted with DCM (20 mL), washed with 10% aq. AcOH (2×5 mL) and with sat. aq. NaCl (1×5 mL). The org. layer was concentrated in vacuo. The residue was dissolved in DMF (1 mL). 1M aq. NaOH soln. (0.5 mL) was added. The mixture was stirred at r.t. for 7 hours. The solution was carefully neutralized with formic acid (0.5 mL), filtered, and purified by prep. HPLC (column: Waters X-bridge, 30×75 mm, 10 um, UV/MS, acidic conditions) to give the desired acid as a white solid.

LC-MS 1 FA: $t_R$=0.89 min; [M+H]$^+$=497.1

Example 226

(±)-1-(2-Carboxymethoxy-5-chloro-phenyl)-6-fluoro-3,4-dihydro-1H-isoquinoline-2-carboxylic acid benzyl ester (C25H21NO5ClF, MW=469.90)

A mixture under N$_2$ of (±)-1-(2-allyloxy-5-chloro-phenyl)-6-fluoro-3,4-dihydro-1H-isoquinoline-2-carboxylic acid benzyl ester (65 mg, 0.14 mmol, 1.00 eq.), 1,3-dimethylbarbituric acid (45 mg, 0.29 mmol, 2.00 eq.) and tetrakis(triphenylphosphine) palladium (0) (8.3 mg, 0.007 mmol, 0.05 eq.) in MeOH (3 mL) was stirred at r.t. for 3 hours. The mixture was partitioned between AcOEt (15 mL) and water (15 mL). The layers were separated and the aq. phase was extracted with AcOEt (2×15 mL). The comb. org. phases were washed with sat. aq. NaCl soln. (1×15 mL), dried over MgSO$_4$, filtered, and concentrated in vacuo. To a solution of the residue and potassium carbonate anhydrous (60 mg, 0.43 mmol, 3.0 eq.) in DMF (2 mL), ethyl bromoacetate (48 µL, 0.43 mmol, 3.0 eq.) was added. The reaction mixture was stirred at r.t. during 2 hours. The reaction mixture was diluted with water (15 mL) and AcOEt (30 mL). The layers were separated. The aq. phase was extracted with AcOEt (2×15 mL). The comb. org. phases were washed with water (1×15 mL), sat. aq. NaCl soln. (1×15 mL), dried over MgSO$_4$, filtered, and concentrated in vacuo. To a solution of the residue in DMF (1.1 mL), 1M aq. NaOH (0.6 mL) was added. The resulting solution was stirred at r.t. for 24 hours. The solution was acidified with formic acid (0.6 mL). The crude product was purified by prep. HPLC (column: Atlantis, 30×75 mm, 10 um, UV/MS, acidic conditions) and evaporated to give the title compound.

LC-MS 3: $t_R$=0.95 min; [M+H]$^+$=470.1

Saponification

To a solution of an ester of Structure 1 (0.10 mmol, 1 eq.) in THF (0.5 mL), 1M aq. NaOH (0.13 mL) was added. The resulting solution was stirred at r.t. for 14 hours. The org. solvent was removed in vacuo. The residue was diluted with water (2 mL) and acidified with 1M aq. HCl. The mixture was extracted with DCM (3×5 mL). The comb. org. phases were concentrated in vacuo. The crude product was purified by prep. HPLC (column: Waters X-Bridge, 30×75 mm, 10 um, UV/MS, acidic conditions) and evaporated to give the desired acid as a white solid.

Listed in Table 17 below are examples of compounds of Formula (I), prepared according to the above-mentioned method with the corresponding compound of Structure 1 as starting material.

TABLE 17

| Example | Compound of Formula (I) | Formula MW | $t_R$ [min] LC-MS Method | MS-data m/z [M + H]$^+$ |
|---|---|---|---|---|
| 227 | (±)-1-(2-Carboxymethoxy-5-chloro-phenyl)-3,4-dihydro-1H-isoquinoline-2-carboxylic acid 2-bromo-benzyl ester | C25H21NO5BrCl 530.80 | 1.22 LC-MS 1FA | 530.2 |
| 228 | (S)-1-(2-Carboxymethoxy-5-chloro-phenyl)-3,4-dihydro-1H-isoquinoline-2-carboxylic acid tert-butyl ester | C22H24NO5Cl 417.89 | 1.17 LC-MS 1FA | 418.3 |
| 229 | (S)-1-(2-Carboxymethoxy-5-chloro-phenyl)-5,6-difluoro-3,4-dihydro-1H-isoquinoline-2-carboxylic acid benzyl ester | C25H20NO5ClF2 487.89 | 1.19 LC-MS 1FA | 488.2 |
| 230 | (±)-1-(2-Carboxymethoxy-5-chloro-phenyl)-1,3-dihydro-isoindole-2-carboxylic acid benzyl ester | C24H20NO5Cl 437.88 | 1.09 LC-MS 1FA | 438.2 |
| 231 | 1-(2-Carboxymethoxy-5-chloro-phenyl)-1,3-dihydro-isoindole-2-carboxylic acid benzyl ester (enantiomer 1) | C24H20NO5Cl 437.88 | 1.09 LC-MS 1FA | 438.2 |
| 232 | {4-Chloro-2-[(S)-2-((1R,2R)-2-phenyl-cyclopropanecarbonyl)-1,2,3,4-tetrahydro-isoquinolin-1-yl]-phenoxy}-acetic acid | C27H24NO4Cl 461.94 | 0.94 LC-MS 3 | 462.0 |

Carbamate Formation and Saponification

Method A: To a solution of (±)-1-(5-chloro-2-ethoxycarbonylmethoxy-phenyl)-3,4-dihydro-1H-isoquinoline-2-carboxylic acid 4-nitro-phenyl ester (118 mg, 0.20 mmol, 1.0 eq.) and 2,4-dimethoxybenzyl alcohol (102 mg, 0.60 mmol, 3.0 eq.) in THF (4.5 mL), potassium tert-butoxide (67 mg, 0.60 mmol, 3.0 eq.) was added. The mixture was stirred at r.t. for 18 hours. The solvent was removed in vacuo (genevac). The residue was dissolved in MeCN/H$_2$O (1 mL, 1:1), formic acid (0.2 mL) was added followed by DMF (0.6 mL). The resulting solution was purified by prep. HPLC (column: Atlantis, 19×50 mm, 5 um, UV/MS, acidic conditions) to give the desired acid.

Listed in Table 18 below are examples of compounds of Formula (I), prepared according to the above-mentioned method with the corresponding 4-nitrophenol carbamate 7 and the corresponding alcohol as starting materials.

TABLE 18

| Example | Compound of Formula (I) | Formula MW | $t_R$ [min] LC-MS Method | MS-data m/z [M + H]$^+$ |
|---|---|---|---|---|
| 233 | (±)-1-(2-Carboxymethoxy-5-chloro-phenyl)-3,4-dihydro-1H-isoquinoline-2-carboxylic acid 2-methoxy-benzyl ester | C26H24NO6Cl 481.93 | 0.96 LC-MS 3 | 481.7 |
| 234 | (±)-1-(2-Carboxymethoxy-5-chloro-phenyl)-3,4-dihydro-1H-isoquinoline-2-carboxylic acid 2-fluoro-benzyl ester | C25H21NO5ClF 469.90 | 1.15 LC-MS 1FA | 470.2 |
| 235 | (±)-1-(2-Carboxymethoxy-5-chloro-phenyl)-3,4-dihydro-1H-isoquinoline-2-carboxylic acid 2-methyl-benzyl ester | C26H24NO5Cl 465.93 | 1.19 LC-MS 1FA | 466.2 |
| 236 | (±)-1-(2-Carboxymethoxy-5-chloro-phenyl)-3,4-dihydro-1H-isoquinoline-2-carboxylic acid 2-trifluoromethyl-benzyl ester | C26H21NO5ClF3 519.90 | 1.22 LC-MS 1FA | 520.2 |
| 237 | (±)-1-(2-Carboxymethoxy-5-chloro-phenyl)-3,4-dihydro-1H-isoquinoline-2-carboxylic acid 3-methoxy-benzyl ester | C26H24NO6Cl 481.93 | 1.14 LC-MS 1FA | 482.3 |
| 238 | (±)-1-(2-Carboxymethoxy-5-chloro-phenyl)-3,4-dihydro-1H-isoquinoline-2-carboxylic acid 3-fluoro-benzyl ester | C25H21NO5ClF 469.90 | 1.15 LC-MS 1FA | 470.2 |
| 239 | (±)-1-(2-Carboxymethoxy-5-chloro-phenyl)-3,4-dihydro-1H-isoquinoline-2-carboxylic acid 3-methyl-benzyl ester | C26H24NO5Cl 465.93 | 1.20 LC-MS 1FA | 466.3 |
| 240 | (±)-1-(2-Carboxymethoxy-5-chloro-phenyl)-3,4-dihydro-1H-isoquinoline-2-carboxylic acid 3-trifluoromethyl-benzyl ester | C26H21NO5ClF3 519.90 | 1.22 LC-MS 1FA | 520.2 |
| 241 | (±)-1-(2-Carboxymethoxy-5-chloro-phenyl)-3,4-dihydro-1H-isoquinoline-2-carboxylic acid 2,4-dichloro-benzyl ester | C25H20NO5Cl3 520.80 | 1.28 LC-MS 1FA | 520.1 |
| 242 | (±)-1-(2-Carboxymethoxy-5-chloro-phenyl)-3,4-dihydro-1H-isoquinoline-2-carboxylic acid 2,3-dichloro-benzyl ester | C25H20NO5Cl3 520.80 | 1.25 LC-MS 1FA | 520.1 |
| 243 | (±)-1-(2-Carboxymethoxy-5-chloro-phenyl)-3,4-dihydro-1H-isoquinoline-2-carboxylic acid 2,6-dichloro-benzyl ester | C25H20NO5Cl3 520.80 | 1.21 LC-MS 1FA | 520.2 |
| 244 | (±)-1-(2-Carboxymethoxy-5-chloro-phenyl)-3,4-dihydro-1H-isoquinoline-2-carboxylic acid 2,6-dimethoxy-benzyl ester | C27H26NO7Cl 511.96 | 1.14 LC-MS 1FA | 512.0 |
| 245 | (±)-1-(2-Carboxymethoxy-5-chloro-phenyl)-3,4-dihydro-1H-isoquinoline-2-carboxylic acid 2,4-dimethyl-benzyl ester | C27H26NO5Cl 479.96 | 1.24 LC-MS 1FA | 480.1 |
| 246 | (±)-1-(2-Carboxymethoxy-5-chloro-phenyl)-3,4-dihydro-1H-isoquinoline-2-carboxylic acid 2,3-dimethyl-benzyl ester | C27H26NO5Cl 479.96 | 1.23 LC-MS 1FA | 480.2 |
| 247 | (±)-1-(2-Carboxymethoxy-5-chloro-phenyl)-3,4-dihydro-1H-isoquinoline-2-carboxylic acid 2,6-dimethyl-benzyl ester | C27H26NO5Cl 479.96 | 1.21 LC-MS 1FA | 480.1 |
| 248 | (±)-1-(2-Carboxymethoxy-5-chloro-phenyl)-3,4-dihydro-1H-isoquinoline-2-carboxylic acid 2,4-difluoro-benzyl ester | C25H20NO5ClF2 487.89 | 1.17 LC-MS 1FA | 488.2 |

TABLE 18-continued

| Example | Compound of Formula (I) | Formula MW | $t_R$ [min] LC-MS Method | MS-data m/z [M + H]$^+$ |
|---|---|---|---|---|
| 249 | (±)-1-(2-Carboxymethoxy-5-chloro-phenyl)-3,4-dihydro-1H-isoquinoline-2-carboxylic acid 2,3-difluoro-benzyl ester | C25H20NO5ClF2 487.89 | 1.16 LC-MS 1FA | 488.2 |
| 250 | (±)-1-(2-Carboxymethoxy-5-chloro-phenyl)-3,4-dihydro-1H-isoquinoline-2-carboxylic acid 2,6-difluoro-benzyl ester | C25H20NO5ClF2 487.89 | 1.14 LC-MS 1FA | 488.2 |
| 251 | (±)-1-(2-Carboxymethoxy-5-chloro-phenyl)-3,4-dihydro-1H-isoquinoline-2-carboxylic acid 2,4,6-trimethyl-benzyl ester | C28H28NO5Cl 493.99 | 1.27 LC-MS 1FA | 494.2 |
| 252 | (±)-1-(2-Carboxymethoxy-5-chloro-phenyl)-3,4-dihydro-1H-isoquinoline-2-carboxylic acid 2-chloro-6-fluoro-benzyl ester | C25H20NO5Cl2F 504.34 | 1.18 LC-MS 1FA | 504.2 |
| 253 | (±)-1-(2-Carboxymethoxy-5-chloro-phenyl)-3,4-dihydro-1H-isoquinoline-2-carboxylic acid 2,5-dichloro-benzyl ester | C25H20NO5Cl3 520.80 | 1.26 LC-MS 1FA | 520.1 |
| 254 | (±)-1-(2-Carboxymethoxy-5-chloro-phenyl)-3,4-dihydro-1H-isoquinoline-2-carboxylic acid 2,4-dimethoxy-benzyl ester | C27H26NO7Cl 511.96 | 1.15 LC-MS 1FA | 512.0 |
| 255 | (±)-1-(2-Carboxymethoxy-5-chloro-phenyl)-3,4-dihydro-1H-isoquinoline-2-carboxylic acid 2,3-dimethoxy-benzyl ester | C27H26NO7Cl 511.96 | 1.14 LC-MS 1FA | 512.2 |
| 256 | (±)-1-(2-Carboxymethoxy-5-chloro-phenyl)-3,4-dihydro-1H-isoquinoline-2-carboxylic acid 2,6-dimethyl-pyridin-3-ylmethyl ester | C26H25N2O5Cl 480.95 | 0.73 LC-MS 1FA | 481.3 |
| 257 | (±)-1-(2-Carboxymethoxy-5-chloro-phenyl)-3,4-dihydro-1H-isoquinoline-2-carboxylic acid 3-cyano-benzyl ester | C26H21N2O5Cl 476.92 | 1.09 LC-MS 1FA | 477.2 |
| 258 | (±)-1-(2-Carboxymethoxy-5-chloro-phenyl)-3,4-dihydro-1H-isoquinoline-2-carboxylic acid 2,5-difluoro-benzyl ester | C25H20NO5ClF2 487.89 | 1.16 LC-MS 1FA | 488.2 |
| 259 | (±)-1-(2-Carboxymethoxy-5-chloro-phenyl)-3,4-dihydro-1H-isoquinoline-2-carboxylic acid 5-chloro-2-fluoro-benzyl ester | C25H20NO5Cl2F 504.34 | 1.21 LC-MS 1FA | 504.1 |
| 260 | (±)-1-(2-Carboxymethoxy-5-chloro-phenyl)-3,4-dihydro-1H-isoquinoline-2-carboxylic acid 2-chloro-5-fluoro-benzyl ester | C25H20NO5Cl2F 504.34 | 1.21 LC-MS 1FA | 504.2 |
| 261 | (S)-1-(2-Carboxymethoxy-5-chloro-phenyl)-3,4-dihydro-1H-isoquinoline-2-carboxylic acid (S)-1-phenyl-ethyl ester | C26H24NO5Cl 465.93 | 1.17 LC-MS 1FA | 466.3 |
| 262 | (±)-1-(2-Carboxymethoxy-5-chloro-phenyl)-3,4-dihydro-1H-isoquinoline-2-carboxylic acid cyclohexylmethyl ester | C25H28NO5Cl 457.95 | 1.29 LC-MS 1FA | 458.3 |
| 263 | (±)-1-(2-Carboxymethoxy-5-chloro-phenyl)-3,4-dihydro-1H-isoquinoline-2-carboxylic acid 1-methyl-1H-pyrazol-3-ylmethyl ester | C23H22N3O5Cl 455.90 | 0.97 LC-MS 1FA | 456.2 |
| 264 | (±)-1-(2-Carboxymethoxy-5-chloro-phenyl)-3,4-dihydro-1H-isoquinoline-2-carboxylic acid cyclopentylmethyl ester | C24H26NO5Cl 443.93 | 1.25 LC-MS 1FA | 444.3 |
| 265 | (±)-1-(2-Carboxymethoxy-5-chloro-phenyl)-3,4-dihydro-1H-isoquinoline-2-carboxylic acid isobutyl ester | C22H24NO5Cl 417.89 | 1.17 LC-MS 1FA | 418.2 |
| 266 | (±)-1-(2-Carboxymethoxy-5-chloro-phenyl)-3,4-dihydro-1H-isoquinoline-2-carboxylic acid butyl ester | C22H24NO5Cl 417.89 | 1.17 LC-MS 1FA | 418.2 |

TABLE 18-continued

| Example | Compound of Formula (I) | Formula MW | $t_R$ [min] LC-MS Method | MS-data m/z [M + H]+ |
|---|---|---|---|---|
| 267 | (±)-1-(2-Carboxymethoxy-5-chloro-phenyl)-3,4-dihydro-1H-isoquinoline-2-carboxylic acid 2-methoxy-ethyl ester | C21H22NO6Cl 419.86 | 0.99 LC-MS 1FA | 420.2 |
| 268 | (±)-1-(2-Carboxymethoxy-5-chloro-phenyl)-3,4-dihydro-1H-isoquinoline-2-carboxylic acid cyclopropylmethyl ester | C22H22NO5Cl 415.87 | 1.12 LC-MS 1FA | 416.2 |
| 269 | (±)-1-(2-Carboxymethoxy-5-chloro-phenyl)-3,4-dihydro-1H-isoquinoline-2-carboxylic acid 3,5-dimethyl-pyrazol-1-ylmethyl ester | C24H24N3O5Cl 469.92 | 1.03 LC-MS 1FA | 470.3 |
| 270 | (±)-1-(2-Carboxymethoxy-5-chloro-phenyl)-3,4-dihydro-1H-isoquinoline-2-carboxylic acid 5-methyl-isoxazol-3-ylmethyl ester | C23H21N2O6Cl 456.88 | 1.04 LC-MS 1FA | 457.2 |
| 271 | (±)-1-(2-Carboxymethoxy-5-chloro-phenyl)-3,4-dihydro-1H-isoquinoline-2-carboxylic acid 1,5-dimethyl-1H-pyrazol-3-ylmethyl ester | C24H24N3O5Cl 469.92 | 1.00 LC-MS 1FA | 470.3 |
| 272 | (±)-1-(2-Carboxymethoxy-5-chloro-phenyl)-3,4-dihydro-1H-isoquinoline-2-carboxylic acid 4-chloro-benzyl ester | C25H21NO5Cl2 486.35 | 1.21 LC-MS 1FA | 486.2 |
| 273 | (S)-1-(2-Carboxymethoxy-5-chloro-phenyl)-3,4-dihydro-1H-isoquinoline-2-carboxylic acid thiazol-2-ylmethyl ester | C22H19N2O5ClS 458.92 | 0.88 LC-MS 3 | 459.1 |
| 274 | (S)-1-(2-Carboxymethoxy-5-chloro-phenyl)-3,4-dihydro-1H-isoquinoline-2-carboxylic acid 2-(4-methyl-thiazol-5-yl)-ethyl ester | C24H23N2O5ClS 486.98 | 1.01 LC-MS 1FA | 487.2 |
| 275 | (S)-1-(2-Carboxymethoxy-5-chloro-phenyl)-3,4-dihydro-1H-isoquinoline-2-carboxylic acid 5-methyl-thiazol-2-ylmethyl ester | C23H21N2O5ClS 472.95 | 1.06 LC-MS 1FA | 473.2 |
| 276 | (S)-1-(2-Carboxymethoxy-5-chloro-phenyl)-3,4-dihydro-1H-isoquinoline-2-carboxylic acid 4-methyl-thiazol-2-ylmethyl ester | C23H21N2O5ClS 472.95 | 1.05 LC-MS 1FA | 473.2 |
| 277 | (S)-1-(2-Carboxymethoxy-5-chloro-phenyl)-3,4-dihydro-1H-isoquinoline-2-carboxylic acid 2-methyl-thiazol-5-ylmethyl ester | C23H21N2O5ClS 472.95 | 1.01 LC-MS 1FA | 473.2 |
| 278 | (S)-1-(2-Carboxymethoxy-5-chloro-phenyl)-3,4-dihydro-1H-isoquinoline-2-carboxylic acid 2-methyl-thiazol-4-ylmethyl ester | C23H21N2O5ClS 472.95 | 1.03 LC-MS 1FA | 473.2 |
| 279 | (S)-1-(2-Carboxymethoxy-5-chloro-phenyl)-3,4-dihydro-1H-isoquinoline-2-carboxylic acid 3-methyl-isoxazol-5-ylmethyl ester | C23H21N2O6Cl 456.88 | 1.02 LC-MS 1FA | 457.1 |
| 280 | (S)-1-(2-Carboxymethoxy-5-chloro-phenyl)-3,4-dihydro-1H-isoquinoline-2-carboxylic acid 4-methyl-isoxazol-3-ylmethyl ester | C23H21N2O6Cl 456.88 | 0.89 LC-MS 3 | 457.2 |
| 281 | (S)-1-(2-Carboxymethoxy-5-chloro-phenyl)-3,4-dihydro-1H-isoquinoline-2-carboxylic acid 3,5-dimethyl-isoxazol-4-ylmethyl ester | C24H23N2O6Cl 470.91 | 0.90 LC-MS 3 | 471.2 |
| 282 | (S)-1-(2-Carboxymethoxy-5-chloro-phenyl)-3,4-dihydro-1H-isoquinoline-2-carboxylic acid pyrazin-2-ylmethyl ester | C23H20N3O5Cl 453.88 | 0.85 LC-MS 3 | 454.2 |
| 283 | (S)-1-(2-Carboxymethoxy-5-chloro-phenyl)-3,4-dihydro-1H-isoquinoline-2-carboxylic acid pyrimidin-4-ylmethyl ester | C23H20N3O5Cl 453.88 | 0.85 LC-MS 3 | 454.2 |
| 284 | (S)-1-(2-Carboxymethoxy-5-chloro-phenyl)-3,4-dihydro-1H-isoquinoline-2-carboxylic acid pyrimidin-5-ylmethyl ester | C23H20N3O5Cl 453.88 | 0.85 LC-MS 3 | 454.2 |

TABLE 18-continued

| Example | Compound of Formula (I) | Formula MW | $t_R$ [min] LC-MS Method | MS-data m/z [M + H]+ |
|---|---|---|---|---|
| 285 | (S)-1-(2-Carboxymethoxy-5-chloro-phenyl)-3,4-dihydro-1H-isoquinoline-2-carboxylic acid phenethyl ester | C26H24NO5Cl 465.93 | 1.20 LC-MS 1FA | 466.3 |
| 286 | (S)-1-(2-Carboxymethoxy-5-chloro-phenyl)-3,4-dihydro-1H-isoquinoline-2-carboxylic acid 2-(3-fluoro-phenyl)-ethyl ester | C26H23NO5ClF 483.92 | 0.98 LC-MS 3 | 484.2 |
| 287 | (S)-1-(2-Carboxymethoxy-5-chloro-phenyl)-3,4-dihydro-1H-isoquinoline-2-carboxylic acid 2-methyl-2H-pyrazol-3-ylmethyl ester | C23H22N3O5Cl 455.90 | 0.96 LC-MS 1FA | 456.2 |
| 288 | (S)-1-(2-Carboxymethoxy-5-chloro-phenyl)-3,4-dihydro-1H-isoquinoline-2-carboxylic acid 2,5-dimethyl-2H-pyrazol-3-ylmethyl ester | C24H24N3O5Cl 469.92 | 0.99 LC-MS 1FA | 470.2 |
| 289 | (S)-1-(2-Carboxymethoxy-5-chloro-phenyl)-3,4-dihydro-1H-isoquinoline-2-carboxylic acid 2-(2-ethyl-5-methyl-2H-pyrazol-3-yl)-ethyl ester | C26H28N3O5Cl 497.98 | 0.84 LC-MS 3 | 498.0 |
| 290 | (S)-1-(2-Carboxymethoxy-5-chloro-phenyl)-3,4-dihydro-1H-isoquinoline-2-carboxylic acid 3-methyl-3H-imidazol-4-ylmethyl ester | C23H22N3O5Cl 455.90 | 0.69 LC-MS 3 | 456.2 |
| 291 | (S)-1-(2-Carboxymethoxy-5-chloro-phenyl)-3,4-dihydro-1H-isoquinoline-2-carboxylic acid 2-(3,5-dimethyl-pyrazol-1-yl)-ethyl ester | C25H26N3O5Cl 483.95 | 0.85 LC-MS 3 | 484.2 |
| 292 | (S)-1-(2-Carboxymethoxy-5-chloro-phenyl)-3,4-dihydro-1H-isoquinoline-2-carboxylic acid 4-methyl-pyrazol-1-ylmethyl ester | C23H22N3O5Cl 455.90 | 1.02 LC-MS 1FA | 456.2 |
| 293 | (S)-1-(2-Carboxymethoxy-5-chloro-phenyl)-3,4-dihydro-1H-isoquinoline-2-carboxylic acid 2-(2-methyl-benzoimidazol-1-yl)-ethyl ester | C28H26N3O5Cl 519.98 | 0.83 LC-MS 1TFA | 520.3 |
| 294 | (S)-1-(2-Carboxymethoxy-5-chloro-phenyl)-3,4-dihydro-1H-isoquinoline-2-carboxylic acid benzothiazol-2-ylmethyl ester | C26H21N2O5ClS 508.98 | 1.15 LC-MS 1FA | 509.2 |
| 295 | (S)-1-(2-Carboxymethoxy-5-chloro-phenyl)-3,4-dihydro-1H-isoquinoline-2-carboxylic acid benzooxazol-2-ylmethyl ester | C26H21N2O6Cl 492.91 | 0.93 LC-MS 3 | 493.2 |
| 296 | (S)-1-(2-Carboxymethoxy-5-chloro-phenyl)-3,4-dihydro-1H-isoquinoline-2-carboxylic acid 1-methyl-1H-indazol-3-ylmethyl ester | C27H24N3O5Cl 505.96 | 1.11 LC-MS 1FA | 506.3 |
| 297 | (S)-1-(2-Carboxymethoxy-5-chloro-phenyl)-3,4-dihydro-1H-isoquinoline-2-carboxylic acid indazol-1-ylmethyl ester | C26H22N3O5Cl 491.93 | 1.09 LC-MS 1FA | 492.2 |
| 298 | (S)-1-(2-Carboxymethoxy-5-chloro-phenyl)-3,4-dihydro-1H-isoquinoline-2-carboxylic acid benzo[d]isoxazol-3-ylmethyl ester | C26H21N2O6Cl 492.91 | 0.95 LC-MS 3 | 493.2 |
| 299 | (S)-1-(2-Carboxymethoxy-5-chloro-phenyl)-5,6-difluoro-3,4-dihydro-1H-isoquinoline-2-carboxylic acid thiazol-2-ylmethyl ester | C22H17N2O5ClF2S 494.90 | 1.05 LC-MS 1FA | 495.2 |
| 300 | (S)-1-(2-Carboxymethoxy-5-chloro-phenyl)-5,6-difluoro-3,4-dihydro-1H-isoquinoline-2-carboxylic acid 2-(4-methyl-thiazol-5-yl)-ethyl ester | C24H21N2O5ClF2S 522.96 | 0.90 LC-MS 3 | 523.1 |
| 301 | (S)-1-(2-Carboxymethoxy-5-chloro-phenyl)-5,6-difluoro-3,4-dihydro-1H-isoquinoline-2- | C23H19N2O5ClF2S 508.93 | 0.93 LC-MS 3 | 509.1 |

TABLE 18-continued

| Example | Compound of Formula (I) | Formula MW | $t_R$ [min] LC-MS Method | MS-data m/z [M + H]+ |
|---|---|---|---|---|
| | carboxylic acid 5-methyl-thiazol-2-ylmethyl ester | | | |
| 302 | (S)-1-(2-Carboxymethoxy-5-chloro-phenyl)-5,6-difluoro-3,4-dihydro-1H-isoquinoline-2-carboxylic acid 4-methyl-thiazol-2-ylmethyl ester | C23H19N2O5ClF2S 508.93 | 1.09 LC-MS 1FA | 509.2 |
| 303 | (S)-1-(2-Carboxymethoxy-5-chloro-phenyl)-5,6-difluoro-3,4-dihydro-1H-isoquinoline-2-carboxylic acid 2-methyl-thiazol-5-ylmethyl ester | C23H19N2O5ClF2S 508.93 | 0.92 LC-MS 3 | 509.1 |
| 304 | (S)-1-(2-Carboxymethoxy-5-chloro-phenyl)-5,6-difluoro-3,4-dihydro-1H-isoquinoline-2-carboxylic acid 2-methyl-thiazol-4-ylmethyl ester | C23H19N2O5ClF2S 508.93 | 1.07 LC-MS 1FA | 509.2 |
| 305 | (S)-1-(2-Carboxymethoxy-5-chloro-phenyl)-5,6-difluoro-3,4-dihydro-1H-isoquinoline-2-carboxylic acid 3-methyl-isoxazol-5-ylmethyl ester | C23H19N2O6ClF2 492.86 | 0.91 LC-MS 3 | 493.2 |
| 306 | (S)-1-(2-Carboxymethoxy-5-chloro-phenyl)-5,6-difluoro-3,4-dihydro-1H-isoquinoline-2-carboxylic acid 4-methyl-isoxazol-3-ylmethyl ester | C23H19N2O6ClF2 492.86 | 0.92 LC-MS 3 | 493.2 |
| 307 | (S)-1-(2-Carboxymethoxy-5-chloro-phenyl)-5,6-difluoro-3,4-dihydro-1H-isoquinoline-2-carboxylic acid 3,5-dimethyl-isoxazol-4-ylmethyl ester | C24H21N2O6ClF2 506.89 | 0.92 LC-MS 3 | 507.1 |
| 308 | (S)-1-(2-Carboxymethoxy-5-chloro-phenyl)-5,6-difluoro-3,4-dihydro-1H-isoquinoline-2-carboxylic acid pyrazin-2-ylmethyl ester | C23H18N3O5ClF2 489.86 | 0.88 LC-MS 3 | 490.2 |
| 309 | (S)-1-(2-Carboxymethoxy-5-chloro-phenyl)-5,6-difluoro-3,4-dihydro-1H-isoquinoline-2-carboxylic acid pyrimidin-4-ylmethyl ester | C23H18N3O5ClF2 489.86 | 0.89 LC-MS 3 | 490.2 |
| 310 | (S)-1-(2-Carboxymethoxy-5-chloro-phenyl)-5,6-difluoro-3,4-dihydro-1H-isoquinoline-2-carboxylic acid phenethyl ester | C26H22NO5ClF2 501.91 | 0.99 LC-MS 3 | 502.2 |
| 311 | (S)-1-(2-Carboxymethoxy-5-chloro-phenyl)-5,6-difluoro-3,4-dihydro-1H-isoquinoline-2-carboxylic acid 2-(3-fluoro-phenyl)-ethyl ester | C26H21NO5ClF3 519.90 | 0.99 LC-MS 3 | 520.1 |
| 312 | (S)-1-(2-Carboxymethoxy-5-chloro-phenyl)-5,6-difluoro-3,4-dihydro-1H-isoquinoline-2-carboxylic acid 2-methyl-2H-pyrazol-3-ylmethyl ester | C23H20N3O5ClF2 491.88 | 1.01 LC-MS 1FA | 492.2 |
| 313 | (S)-1-(2-Carboxymethoxy-5-chloro-phenyl)-5,6-difluoro-3,4-dihydro-1H-isoquinoline-2-carboxylic acid 2,5-dimethyl-2H-pyrazol-3-ylmethyl ester | C24H22N3O5ClF2 505.90 | 0.90 LC-MS 3 | 506.2 |
| 314 | (S)-1-(2-Carboxymethoxy-5-chloro-phenyl)-5,6-difluoro-3,4-dihydro-1H-isoquinoline-2-carboxylic acid 2-(2-ethyl-5-methyl-2H-pyrazol-3-yl)-ethyl ester | C26H26N3O5ClF2 533.96 | 1.06 LC-MS 1FA | 534.3 |
| 315 | (S)-1-(2-Carboxymethoxy-5-chloro-phenyl)-5,6-difluoro-3,4-dihydro-1H-isoquinoline-2-carboxylic acid 3-methyl-3H-imidazol-4-ylmethyl ester | C23H20N3O5ClF2 491.88 | 0.72 LC-MS 3 | 492.2 |
| 316 | (S)-1-(2-Carboxymethoxy-5-chloro-phenyl)-5,6-difluoro-3,4-dihydro-1H-isoquinoline-2-carboxylic acid 2-(3,5-dimethyl-pyrazol-1-yl)-ethyl ester | C25H24N3O5ClF2 519.93 | 0.87 LC-MS 3 | 520.2 |

TABLE 18-continued

| Example | Compound of Formula (I) | Formula MW | t_R [min] LC-MS Method | MS-data m/z [M + H]+ |
|---|---|---|---|---|
| 317 | (S)-1-(2-Carboxymethoxy-5-chloro-phenyl)-5,6-difluoro-3,4-dihydro-1H-isoquinoline-2-carboxylic acid 4-methyl-pyrazol-1-ylmethyl ester | C23H20N3O5ClF2 491.88 | 0.90 LC-MS 3 | 492.1 |
| 318 | (S)-1-(2-Carboxymethoxy-5-chloro-phenyl)-5,6-difluoro-3,4-dihydro-1H-isoquinoline-2-carboxylic acid 2-(2-methyl-benzoimidazol-1-yl)-ethyl ester | C28H24N3O5ClF2 555.96 | 0.86 LC-MS 1TFA | 556.3 |
| 319 | (S)-1-(2-Carboxymethoxy-5-chloro-phenyl)-5,6-difluoro-3,4-dihydro-1H-isoquinoline-2-carboxylic acid benzothiazol-2-ylmethyl ester | C26H19N2O5ClF2S 544.96 | 1.18 LC-MS 1FA | 545.1 |
| 320 | (S)-1-(2-Carboxymethoxy-5-chloro-phenyl)-5,6-difluoro-3,4-dihydro-1H-isoquinoline-2-carboxylic acid benzooxazol-2-ylmethyl ester | C26H19N2O6ClF2 528.89 | 0.95 LC-MS 3 | 529.0 |
| 321 | (S)-1-(2-Carboxymethoxy-5-chloro-phenyl)-5,6-difluoro-3,4-dihydro-1H-isoquinoline-2-carboxylic acid 1-methyl-1H-indazol-3-ylmethyl ester | C27H22N3O5ClF2 541.94 | 1.14 LC-MS 1FA | 542.3 |
| 322 | (S)-1-(2-Carboxymethoxy-5-chloro-phenyl)-5,6-difluoro-3,4-dihydro-1H-isoquinoline-2-carboxylic acid indazol-1-ylmethyl ester | C26H20N3O5ClF2 527.91 | 0.94 LC-MS 3 | 528.1 |
| 323 | (S)-1-(2-Carboxymethoxy-5-chloro-phenyl)-5,6-difluoro-3,4-dihydro-1H-isoquinoline-2-carboxylic acid benzo[d]isoxazol-3-ylmethyl ester | C26H19N2O6ClF2 528.89 | 0.96 LC-MS 3 | 529.0 |
| 324 | (S)-1-(2-Carboxymethoxy-5-chloro-phenyl)-6-fluoro-3,4-dihydro-1H-isoquinoline-2-carboxylic acid thiazol-2-ylmethyl ester | C22H18N2O5ClFS 476.91 | 1.02 LC-MS 1FA | 477.2 |
| 325 | (S)-1-(2-Carboxymethoxy-5-chloro-phenyl)-6-fluoro-3,4-dihydro-1H-isoquinoline-2-carboxylic acid 2-(4-methyl-thiazol-5-yl)-ethyl ester | C24H22N2O5ClFS 504.97 | 1.02 LC-MS 1FA | 505.2 |
| 326 | (S)-1-(2-Carboxymethoxy-5-chloro-phenyl)-6-fluoro-3,4-dihydro-1H-isoquinoline-2-carboxylic acid 5-methyl-thiazol-2-ylmethyl ester | C23H20N2O5ClFS 490.94 | 1.07 LC-MS 1FA | 491.2 |
| 327 | (S)-1-(2-Carboxymethoxy-5-chloro-phenyl)-6-fluoro-3,4-dihydro-1H-isoquinoline-2-carboxylic acid 4-methyl-thiazol-2-ylmethyl ester | C23H20N2O5ClFS 490.94 | 1.06 LC-MS 1FA | 491.2 |
| 328 | (S)-1-(2-Carboxymethoxy-5-chloro-phenyl)-6-fluoro-3,4-dihydro-1H-isoquinoline-2-carboxylic acid 2-methyl-thiazol-5-ylmethyl ester | C23H20N2O5ClFS 490.94 | 1.02 LC-MS 1FA | 491.2 |
| 329 | (S)-1-(2-Carboxymethoxy-5-chloro-phenyl)-6-fluoro-3,4-dihydro-1H-isoquinoline-2-carboxylic acid 2-methyl-thiazol-4-ylmethyl ester | C23H20N2O5ClFS 490.94 | 1.04 LC-MS 1FA | 491.2 |
| 330 | (S)-1-(2-Carboxymethoxy-5-chloro-phenyl)-6-fluoro-3,4-dihydro-1H-isoquinoline-2-carboxylic acid 3-methyl-isoxazol-5-ylmethyl ester | C23H20N2O6ClF 474.87 | 1.03 LC-MS 1FA | 475.2 |
| 331 | (S)-1-(2-Carboxymethoxy-5-chloro-phenyl)-6-fluoro-3,4-dihydro-1H-isoquinoline-2-carboxylic acid 4-methyl-isoxazol-3-ylmethyl ester | C23H20N2O6ClF 474.87 | 0.90 LC-MS 3 | 475.2 |

TABLE 18-continued

| Example | Compound of Formula (I) | Formula MW | $t_R$ [min] LC-MS Method | MS-data m/z $[M + H]^+$ |
|---|---|---|---|---|
| 332 | (S)-1-(2-Carboxymethoxy-5-chloro-phenyl)-6-fluoro-3,4-dihydro-1H-isoquinoline-2-carboxylic acid pyrazin-2-ylmethyl ester | C23H19N3O5ClF 471.87 | 0.96 LC-MS 1FA | 472.2 |
| 333 | (S)-1-(2-Carboxymethoxy-5-chloro-phenyl)-6-fluoro-3,4-dihydro-1H-isoquinoline-2-carboxylic acid pyrimidin-4-ylmethyl ester | C23H19N3O5ClF 471.87 | 0.94 LC-MS 1FA | 472.2 |
| 334 | (S)-1-(2-Carboxymethoxy-5-chloro-phenyl)-6-fluoro-3,4-dihydro-1H-isoquinoline-2-carboxylic acid pyrimidin-5-ylmethyl ester | C23H19N3O5ClF 471.87 | 0.86 LC-MS 3 | 472.2 |
| 335 | (S)-1-(2-Carboxymethoxy-5-chloro-phenyl)-6-fluoro-3,4-dihydro-1H-isoquinoline-2-carboxylic acid phenethyl ester | C26H23NO5ClF 483.92 | 1.20 LC-MS 1FA | 484.2 |
| 336 | (S)-1-(2-Carboxymethoxy-5-chloro-phenyl)-6-fluoro-3,4-dihydro-1H-isoquinoline-2-carboxylic acid 2-(3-fluoro-phenyl)-ethyl ester | C26H22NO5ClF2 501.91 | 0.98 LC-MS 3 | 502.2 |
| 337 | (S)-1-(2-Carboxymethoxy-5-chloro-phenyl)-6-fluoro-3,4-dihydro-1H-isoquinoline-2-carboxylic acid 2-methyl-2H-pyrazol-3-ylmethyl ester | C23H21N3O5ClF 473.89 | 0.98 LC-MS 1FA | 474.2 |
| 338 | (S)-1-(2-Carboxymethoxy-5-chloro-phenyl)-6-fluoro-3,4-dihydro-1H-isoquinoline-2-carboxylic acid 2,5-dimethyl-2H-pyrazol-3-ylmethyl ester | C24H23N3O5ClF 487.91 | 1.00 LC-MS 1FA | 488.3 |
| 339 | (S)-1-(2-Carboxymethoxy-5-chloro-phenyl)-6-fluoro-3,4-dihydro-1H-isoquinoline-2-carboxylic acid 2-(2-ethyl-5-methyl-2H-pyrazol-3-yl)-ethyl ester | C26H27N3O5ClF 515.97 | 0.85 LC-MS 3 | 516.2 |
| 340 | (S)-1-(2-Carboxymethoxy-5-chloro-phenyl)-6-fluoro-3,4-dihydro-1H-isoquinoline-2-carboxylic acid 3-methyl-3H-imidazol-4-ylmethyl ester | C23H21N3O5ClF 473.89 | 0.71 LC-MS 3 | 474.2 |
| 341 | (S)-1-(2-Carboxymethoxy-5-chloro-phenyl)-6-fluoro-3,4-dihydro-1H-isoquinoline-2-carboxylic acid 2-(3,5-dimethyl-pyrazol-1-yl)-ethyl ester | C25H25N3O5ClF 501.94 | 1.04 LC-MS 1FA | 502.3 |
| 342 | (S)-1-(2-Carboxymethoxy-5-chloro-phenyl)-6-fluoro-3,4-dihydro-1H-isoquinoline-2-carboxylic acid 4-methyl-pyrazol-1-ylmethyl ester | C23H21N3O5ClF 473.89 | 0.89 LC-MS 3 | 474.2 |
| 343 | (S)-1-(2-Carboxymethoxy-5-chloro-phenyl)-6-fluoro-3,4-dihydro-1H-isoquinoline-2-carboxylic acid 2-(2-methyl-benzoimidazol-1-yl)-ethyl ester | C28H25N3O5ClF 537.97 | 0.84 LC-MS 1TFA | 538.3 |
| 344 | (S)-1-(2-Carboxymethoxy-5-chloro-phenyl)-6-fluoro-3,4-dihydro-1H-isoquinoline-2-carboxylic acid benzothiazol-2-ylmethyl ester | C26H20N2O5ClFS 526.97 | 1.15 LC-MS 1FA | 527.2 |
| 345 | (S)-1-(2-Carboxymethoxy-5-chloro-phenyl)-6-fluoro-3,4-dihydro-1H-isoquinoline-2-carboxylic acid benzooxazol-2-ylmethyl ester | C26H20N2O6ClF 510.90 | 0.94 LC-MS 3 | 511.1 |
| 346 | (S)-1-(2-Carboxymethoxy-5-chloro-phenyl)-6-fluoro-3,4-dihydro-1H-isoquinoline-2-carboxylic acid 1-methyl-1H-indazol-3-ylmethyl ester | C27H23N3O5ClF 523.95 | 1.11 LC-MS 1FA | 524.3 |
| 347 | (S)-1-(2-Carboxymethoxy-5-chloro-phenyl)-6-fluoro-3,4- | C26H21N3O5ClF 509.92 | 0.93 LC-MS 3 | 510.1 |

TABLE 18-continued

| Example | Compound of Formula (I) | Formula MW | $t_R$ [min] LC-MS Method | MS-data m/z [M + H]$^+$ |
|---|---|---|---|---|
|  | dihydro-1H-isoquinoline-2-carboxylic acid indazol-1-ylmethyl ester |  |  |  |
| 348 | (S)-1-(2-Carboxymethoxy-5-chloro-phenyl)-6-fluoro-3,4-dihydro-1H-isoquinoline-2-carboxylic acid benzo[d]isoxazol-3-ylmethyl ester | C26H20N2O6ClF 510.90 | 0.95 LC-MS 3 | 511.1 |

Method B: To a solution of [4-chloro-2-((S)-5,6-difluoro-1,2,3,4-tetrahydro-isoquinolin-1-yl)-phenoxy]-acetic acid ethyl ester hydrochloride (91 mg, 0.21 mmol, 1 eq.) and DIPEA (90 µL, 0.53 mmol, 2.5 eq.) in DCM (3.3 mL), carbonic acid 2,5-dioxo-pyrrolidin-1-yl ester 2-fluoro-benzyl ester (70 mg, 0.25 mmol, 1.2 eq.) was added. The mixture was stirred at r.t. for 1 hour. The reaction was quenched with 1M aq. citric acid soln. (3.3 mL). The layers were separated. The aq. phase was extracted with DCM (3×5 mL). The comb. org. phases were concentrated in vacuo (genevac). To a solution of the residue in DMF (1 mL), 1M aq. NaOH (0.55 mL) was added. The solution was stirred at r.t. for 1 hour. Formic acid (0.1 mL) was added. The resulting acidic solution was purified by prep. HPLC (column: Waters XBridge, 30×75 mm, 10 um, UV/MS, acidic conditions) and evaporated (genevac) to give the desired acid.

Listed in Table 19 below are examples of compounds of Formula (I), prepared according to the above-mentioned method with the corresponding amine of Structure 2 and the corresponding carbonate 5 as starting materials.

TABLE 19

| Example | Compound of Formula (I) | Formula MW | $t_R$ [min] LC-MS Method | MS-data m/z [M + H]$^+$ |
|---|---|---|---|---|
| 349 | (S)-1-(2-Carboxymethoxy-5-chloro-phenyl)-5,6-difluoro-3,4-dihydro-1H-isoquinoline-2-carboxylic acid 2-fluoro-benzyl ester | C25H19NO5ClF3 505.88 | 1.19 LC-MS 1FA | 506.2 |
| 350 | (S)-1-(2-Carboxymethoxy-5-chloro-phenyl)-5,6-difluoro-3,4-dihydro-1H-isoquinoline-2-carboxylic acid 3-fluoro-benzyl ester | C25H19NO5ClF3 505.88 | 1.19 LC-MS 1FA | 506.1 |
| 351 | (S)-1-(2-Carboxymethoxy-5-chloro-phenyl)-5,6-difluoro-3,4-dihydro-1H-isoquinoline-2-carboxylic acid 2,3-difluoro-benzyl ester | C25H18NO5ClF4 523.87 | 1.19 LC-MS 1FA | 524.2 |
| 352 | (S)-1-(2-Carboxymethoxy-5-chloro-phenyl)-6-fluoro-3,4-dihydro-1H-isoquinoline-2-carboxylic acid 2-fluoro-benzyl ester | C25H20NO5ClF2 487.89 | 1.16 LC-MS 1FA | 488.2 |
| 353 | (S)-1-(2-Carboxymethoxy-5-chloro-phenyl)-6-fluoro-3,4-dihydro-1H-isoquinoline-2-carboxylic acid 3-fluoro-benzyl ester | C25H20NO5ClF2 487.89 | 1.16 LC-MS 1FA | 488.2 |
| 354 | (S)-1-(2-Carboxymethoxy-5-chloro-phenyl)-6-fluoro-3,4-dihydro-1H-isoquinoline-2-carboxylic acid 2,3-difluoro-benzyl ester | C25H19NO5ClF3 505.88 | 1.17 LC-MS 1FA | 506.2 |
| 355 | (S)-1-(2-Carboxymethoxy-5-chloro-phenyl)-3,4-dihydro-1H-isoquinoline-2-carboxylic acid 3-fluoro-benzyl ester | C25H21NO5ClF 469.90 | 1.15 LC-MS 1FA | 470.2 |
| 356 | (S)-1-(2-Carboxymethoxy-5-chloro-phenyl)-3,4-dihydro-1H-isoquinoline-2-carboxylic acid 2-methoxy-benzyl ester | C26H24NO6Cl 481.93 | 1.16 LC-MS 1FA | 482.1 |
| 357 | (S)-1-(2-Carboxymethoxy-5-chloro-phenyl)-3,4-dihydro-1H-isoquinoline-2-carboxylic acid 2-fluoro-benzyl ester | C25H21NO5ClF 469.90 | 1.15 LC-MS 1FA | 470.2 |
| 358 | (S)-1-(2-Carboxymethoxy-5-chloro-phenyl)-5-fluoro-3,4-dihydro-1H-isoquinoline-2- | C25H20NO5ClF2 487.89 | 1.17 LC-MS 1FA | 488.1 |

TABLE 19-continued

| Example | Compound of Formula (I) | Formula MW | t_R [min] LC-MS Method | MS-data m/z [M + H]+ |
|---|---|---|---|---|
| | carboxylic acid 3-fluoro-benzyl ester | | | |
| 359 | (S)-1-(2-Carboxymethoxy-5-chloro-phenyl)-5-fluoro-3,4-dihydro-1H-isoquinoline-2-carboxylic acid 2-fluoro-benzyl ester | C25H20NO5ClF2 487.89 | 1.17 LC-MS 1FA | 488.2 |
| 360 | (±)-1-(2-Carboxymethoxy-5-chloro-phenyl)-3,4-dihydro-1H-isoquinoline-2-carboxylic acid 4-methyl-benzyl ester | C26H24NO5Cl 465.93 | 1.20 LC-MS 1FA | 466.2 |
| 361 | (±)-1-(2-Carboxymethoxy-5-chloro-phenyl)-3,4-dihydro-1H-isoquinoline-2-carboxylic acid 4-methoxy-benzyl ester | C26H24NO6Cl 481.93 | 1.14 LC-MS 1FA | 482.2 |
| 362 | (±)-1-(2-Carboxymethoxy-5-chloro-phenyl)-3,4-dihydro-1H-isoquinoline-2-carboxylic acid 4-fluoro-benzyl ester | C25H21NO5ClF 469.90 | 1.15 LC-MS 1FA | 470.2 |
| 363 | (±)-1-(2-Carboxymethoxy-5-chloro-phenyl)-3,4-dihydro-1H-isoquinoline-2-carboxylic acid 4-trifluoromethyl-benzyl ester | C26H21NO5ClF3 519.90 | 1.23 LC-MS 1FA | 520.2 |
| 364 | (±)-1-(2-Carboxymethoxy-5-chloro-phenyl)-3,4-dihydro-1H-isoquinoline-2-carboxylic acid 3-chloro-benzyl ester | C25H21NO5Cl2 486.35 | 1.21 LC-MS 1FA | 486.2 |

Method C: To an-ice cooled solution of (±)-[4-chloro-2-(7-fluoro-1,2,3,4-tetrahydro-isoquinolin-1-yl)-phenoxy]-acetic acid ethyl ester hydrochloride (378 mg, 0.94 mmol, 1.0 eq.) and NEt₃ (0.39 mL, 2.83 mmol, 3.0 eq.) in DCM (10 mL), benzyl chloroformate (0.17 mL, 1.13 mmol, 1.2 eq.) was added. The solution was stirred at 0° C. for 1 hour and further at r.t. for 4 hours. The reaction was diluted with DCM (10 mL) and quenched with 1M aq. citric acid soln. (20 mL). The layers were separated. The aq. phase was extracted with DCM (3×10 mL). The comb. org. phases were dried over Na₂SO₄ and concentrated in vacuo. To a solution of the residue in DMF (3 mL), 1M aq. NaOH (1.5 mL) was added. The resulting mixture was stirred at r.t. for 18 hours. The reaction mixture was neutralized with formic acid (ca. 1.5 mL) and purified by prep. HPLC (column: Water X-Bridge, 30×75 mm, 10 um, UV/MS, acidic conditions) and concentrated in vacuo to give the desired acid.

Listed in Table 20 below are examples of compounds of Formula (I), prepared according to the above-mentioned method with the corresponding amine of Structure 2 as starting material.

Michael Addition and Subsequent Saponification

Potassium fluoride 40 wt. % on alumina (216 mg, 3.72 mmol, 17.2 eq.) was added to a mixture of (±)-[2-(2-acryloyl-1,2,3,4-tetrahydro-isoquinolin-1-yl)-4-chloro-phenoxy]-acetic acid ethyl ester (100 mg, 0.22 mmol, 1.0 eq.) and 5-fluoro-3-methylindole (33 mg, 0.22 mmol, 1.0 eq.) in MeCN (1 mL). The resulting suspension was stirred at 80° C. for 18 hours. Formic acid was added (0.2 mL). The reaction mixture was filtered and the filtrate purified by prep. HPLC (column: Atlantis, 30×75 mm, 10 um, UV/MS, acidic conditions) and concentrated in vacuo to give the desired product as a white foam.

Listed in Table 21 below are examples of compounds of Formula (I), prepared according to the above-mentioned method with the corresponding vinyl amide 8 and the corresponding heterocycle 9 as starting materials.

TABLE 20

| Example | Compound of Formula (I) | Formula MW | t_R [min] LC-MS Method | MS-data m/z [M + H]+ |
|---|---|---|---|---|
| 365 | (±)-1-(2-Carboxymethoxy-5-chloro-phenyl)-7-fluoro-3,4-dihydro-1H-isoquinoline-2-carboxylic acid benzyl ester | C25H21NO5ClF 469.90 | 1.15 LC-MS 1FA | 470.2 |
| 366 | (±)-1-(2-Carboxymethoxy-phenyl)-3,4-dihydro-1H-isoquinoline-2-carboxylic acid benzyl ester | C25H23NO5 417.46 | 1.09 LC-MS 1FA | 418.3 |
| 367 | (S)-1-(2-Carboxymethoxy-5-chloro-phenyl)-6-fluoro-3,4-dihydro-1H-isoquinoline-2-carboxylic acid benzyl ester | C25H21NO5ClF 469.90 | 1.16 LC-MS 1FA | 470.2 |

TABLE 21

| Example | Compound of Formula (I) | Formula MW | $t_R$ [min] LC-MS Method | MS-data m/z [M + H]+ |
|---|---|---|---|---|
| 368 | (±)-(4-Chloro-2-{2-[3-(5-fluoro-3-methyl-indol-1-yl)-propionyl]-1,2,3,4-tetrahydro-isoquinolin-1-yl}-phenoxy)-acetic acid | C29H26NO4ClF 520.99 | 1.19 LC-MS 1FA | 521.3 |
| 369 | (±)-{4-Chloro-2-[2-(3-pyrrolo[2,3-b]pyridin-1-yl-propionyl)-1,2,3,4-tetrahydro-isoquinolin-1-yl]-phenoxy}-acetic acid | C27H24N3O4Cl 489.96 | 1.01 LC-MS 1FA | 490.3 |
| 370 | (±)-(4-Chloro-2-{2-[3-(6-trifluoromethyl-indol-1-yl)-propionyl]-1,2,3,4-tetrahydro-isoquinolin-1-yl}-phenoxy)-acetic acid | C29H24N2O4ClF3 556.97 | 1.23 LC-MS 1FA | 557.1 |
| 371 | (±)-(4-Chloro-2-{2-[3-(5-cyano-indol-1-yl)-propionyl]-1,2,3,4-tetrahydro-isoquinolin-1-yl}-phenoxy)-acetic acid | C29H24N3O4Cl 513.98 | 1.06 LC-MS 1FA | 514.2 |
| 372 | (±)-{4-Chloro-2-[2-(3-pyrrolo[2,3-c]pyridin-1-yl-propionyl)-1,2,3,4-tetrahydro-isoquinolin-1-yl]-phenoxy}-acetic acid | C27H24N3O4Cl 489.96 | 0.70 LC-MS 1FA | 490.0 |
| 373 | (±)-(4-Chloro-2-{2-[3-(6-methoxy-pyrrolo[3,2-c]pyridin-1-yl)-propionyl]-1,2,3,4-tetrahydro-isoquinolin-1-yl}-phenoxy)-acetic acid | C28H26N3O5Cl 519.98 | 0.70 LC-MS 1FA | 520.3 |
| 374 | (±)-(4-Chloro-2-{2-[3-(6-methoxy-pyrrolo[2,3-b]pyridin-1-yl)-propionyl]-1,2,3,4-tetrahydro-isoquinolin-1-yl}-phenoxy)-acetic acid | C28H26N3O5Cl 519.98 | 1.15 LC-MS 1FA | 520.3 |
| 375 | (±)-(4-Chloro-2-{2-[3-(5-chloro-6-methoxy-indol-1-yl)-propionyl]-1,2,3,4-tetrahydro-isoquinolin-1-yl}-phenoxy)-acetic acid | C29H26N2O5Cl2 553.44 | 1.17 LC-MS 1FA | 553.1 |
| 376 | (±)-(4-Chloro-2-{2-[3-(4,6-dimethoxy-pyrrolo[2,3-b]pyridin-1-yl)-propionyl]-1,2,3,4-tetrahydro-isoquinolin-1-yl}-phenoxy)-acetic acid | C29H28N3O6Cl 550.01 | 1.12 LC-MS 1FA | 550.3 |
| 377 | (±)-(4-Chloro-2-{2-[3-(4,6-dimethoxy-indol-1-yl)-propionyl]-1,2,3,4-tetrahydro-isoquinolin-1-yl}-phenoxy)-acetic acid | C30H29N2O6Cl 549.02 | 1.11 LC-MS 1FA | 549.3 |
| 378 | (±)-{4-Chloro-2-[2-(3-indol-1-yl-propionyl)-1,2,3,4-tetrahydro-isoquinolin-1-yl]-phenoxy}-acetic acid | C28H25N2O4Cl 488.97 | 1.15 LC-MS 1FA | 489.3 |
| 379 | (±)-(4-Chloro-2-{2-[3-(5-fluoro-indol-1-yl)-propionyl]-1,2,3,4-tetrahydro-isoquinolin-1-yl}-phenoxy)-acetic acid | C28H24N2O4ClF 506.96 | 1.14 LC-MS 1FA | 507.3 |
| 380 | (±)-(4-Chloro-2-{2-[3-(7-chloro-indol-1-yl)-propionyl]-1,2,3,4-tetrahydro-isoquinolin-1-yl}-phenoxy)-acetic acid | C28H24N2O4Cl2 523.42 | 1.21 LC-MS 1FA | 523.1 |
| 381 | (±)-{4-Chloro-2-[2-(3-pyrrolo[3,2-b]pyridin-1-yl-propionyl)-1,2,3,4-tetrahydro-isoquinolin-1-yl]-phenoxy}-acetic acid | C27H24N3O4Cl 489.96 | 0.66 LC-MS 1FA | 490.3 |
| 382 | (±)-(4-Chloro-2-{2-[3-(4-methoxy-indol-1-yl)-propionyl]-1,2,3,4-tetrahydro-isoquinolin-1-yl}-phenoxy)-acetic acid | C29H27N2O5Cl 519.00 | 1.12 LC-MS 1FA | 519.3 |
| 383 | (±)-(4-Chloro-2-{2-[3-(3-chloro-indazol-1-yl)-propionyl]-1,2,3,4-tetrahydro-isoquinolin-1-yl}-phenoxy)-acetic acid | C27H23N3O4Cl2 524.40 | 1.16 LC-MS 1FA | 524.2 |
| 384 | (±)-(4-Chloro-2-{2-[3-(6-methyl-indol-1-yl)-propionyl]-1,2,3,4-tetrahydro-isoquinolin-1-yl}-phenoxy)-acetic acid | C29H27N2O4Cl 503.00 | 1.19 LC-MS 1FA | 503.3 |
| 385 | (±)-(4-Chloro-2-{2-[3-(5-chloro-indol-1-yl)-propionyl]-1,2,3,4-tetrahydro-isoquinolin-1-yl}-phenoxy)-acetic acid | C28H24N2O4Cl2 523.42 | 1.20 LC-MS 1FA | 523.1 |

TABLE 21-continued

| Example | Compound of Formula (I) | Formula MW | $t_R$ [min] LC-MS Method | MS-data m/z [M + H]$^+$ |
|---|---|---|---|---|
| 386 | (±)-(4-Chloro-2-{2-[3-(6-chloro-indol-1-yl)-propionyl]-1,2,3,4-tetrahydro-isoquinolin-1-yl}-phenoxy)-acetic acid | C28H24N2O4Cl2 523.42 | 1.20 LC-MS 1FA | 523.3 |
| 387 | (±)-(4-Chloro-2-{2-[3-(4-fluoro-indol-1-yl)-propionyl]-1,2,3,4-tetrahydro-isoquinolin-1-yl}-phenoxy)-acetic acid | C28H24N2O4ClF 506.96 | 1.15 LC-MS 1FA | 507.2 |
| 388 | (±)-(4-Chloro-2-{2-[3-(6-fluoro-indol-1-yl)-propionyl]-1,2,3,4-tetrahydro-isoquinolin-1-yl}-phenoxy)-acetic acid | C28H24N2O4ClF 506.96 | 1.15 LC-MS 1FA | 507.3 |
| 389 | (±)-(4-Chloro-2-{2-[3-(2,3-dimethyl-indol-1-yl)-propionyl]-1,2,3,4-tetrahydro-isoquinolin-1-yl}-phenoxy)-acetic acid | C30H29N2O4Cl 517.02 | 1.23 LC-MS 1FA | 517.3 |
| 390 | (±)-(4-Chloro-2-{2-[3-(6-methoxy-indol-1-yl)-propionyl]-1,2,3,4-tetrahydro-isoquinolin-1-yl}-phenoxy)-acetic acid | C29H27N2O5Cl 519.00 | 1.13 LC-MS 1FA | 519.3 |
| 391 | (4-Chloro-2-{(S)-6-fluoro-2-[3-(4-fluoro-3-methyl-indazol-1-yl)-propionyl]-1,2,3,4-tetrahydro-isoquinolin-1-yl}-phenoxy)-acetic acid | C28H24N3O4ClF2 539.97 | 1.11 LC-MS 1FA | 540.3 |
| 392 | (4-Chloro-2-{(S)-6-fluoro-2-[3-(7-fluoro-3-methyl-indazol-1-yl)-propionyl]-1,2,3,4-tetrahydro-isoquinolin-1-yl}-phenoxy)-acetic acid | C28H24N3O4ClF2 539.97 | 1.11 LC-MS 1FA | 540.3 |
| 393 | (4-Chloro-2-{(S)-6-fluoro-2-[3-(6-fluoro-3-methyl-indazol-1-yl)-propionyl]-1,2,3,4-tetrahydro-isoquinolin-1-yl}-phenoxy)-acetic acid | C28H24N3O4ClF2 539.97 | 1.10 LC-MS 1FA | 540.3 |
| 394 | (4-Chloro-2-{(S)-2-[3-(6-chloro-3-methyl-indazol-1-yl)-propionyl]-6-fluoro-1,2,3,4-tetrahydro-isoquinolin-1-yl}-phenoxy)-acetic acid | C28H24N3O4Cl2F 556.42 | 1.16 LC-MS 1FA | 556.2 |
| 395 | (4-Chloro-2-{(S)-6-fluoro-2-[3-(5-fluoro-indazol-1-yl)-propionyl]-1,2,3,4-tetrahydro-isoquinolin-1-yl}-phenoxy)-acetic acid | C27H22N3O4ClF2 525.94 | 1.07 LC-MS 1FA | 526.3 |
| 396 | (4-Chloro-2-{(S)-2-[3-(5-chloro-indazol-1-yl)-propionyl]-6-fluoro-1,2,3,4-tetrahydro-isoquinolin-1-yl}-phenoxy)-acetic acid | C27H22N3O4Cl2F 542.39 | 1.13 LC-MS 1FA | 542.2 |
| 397 | (4-Chloro-2-{(S)-6-fluoro-2-[3-(3-methyl-indazol-1-yl)propionyl]-1,2,3,4-tetrahydro-isoquinolin-1-yl}-phenoxy)-acetic acid | C28H25N3O4ClF 521.97 | 1.09 LC-MS 1FA | 522.3 |
| 398 | (4-Chloro-2-{(S)-6-fluoro-2-[3-(6-fluoro-indazol-1-yl)-propionyl]-1,2,3,4-tetrahydro-isoquinolin-1-yl}-phenoxy)-acetic acid | C27H22N3O4ClF2 525.94 | 1.08 LC-MS 1FA | 526.2 |
| 399 | (4-Chloro-2-{(S)-6-fluoro-2-[3-(4-fluoro-indazol-1-yl)-propionyl]-1,2,3,4-tetrahydro-isoquinolin-1-yl}-phenoxy)-acetic acid | C27H22N3O4ClF2 525.94 | 1.08 LC-MS 1FA | 526.2 |
| 400 | (4-Chloro-2-{(S)-2-[3-(7-chloro-indazol-1-yl)-propionyl]-6-fluoro-1,2,3,4-tetrahydro-isoquinolin-1-yl}-phenoxy)-acetic acid | C27H22N3O4Cl2F 542.39 | 1.09 LC-MS 1FA | 542.2 |
| 401 | (4-Chloro-2-{(S)-2-[3-(6-chloro-indazol-1-yl)-propionyl]-6-fluoro-1,2,3,4-tetrahydro-isoquinolin-1-yl}-phenoxy)-acetic acid | C27H22N3O4Cl2F 542.39 | 1.13 LC-MS 1FA | 542.2 |
| 402 | (4-Chloro-2-{(S)-2-[3-(4-chloro-indazol-1-yl)-propionyl]-6-fluoro-1,2,3,4-tetrahydro-isoquinolin-1-yl}-phenoxy)-acetic acid | C27H22N3O4Cl2F 542.39 | 1.13 LC-MS 1FA | 542.1 |
| 403 | (4-Chloro-2-{(S)-6-fluoro-2-[3-(7-fluoro-indazol-1-yl)-propionyl]-1,2,3,4-tetrahydro-isoquinolin-1-yl}-phenoxy)-acetic acid | C27H22N3O4ClF2 525.94 | 1.08 LC-MS 1FA | 526.3 |

TABLE 21-continued

| Example | Compound of Formula (I) | Formula MW | $t_R$ [min] LC-MS Method | MS-data m/z [M + H]$^+$ |
|---|---|---|---|---|
| 404 | (±)-(4-Chloro-2-{2-[3-(3-chloro-pyrrolo[2,3-b]pyrazin-5-yl)-propionyl]-1,2,3,4-tetrahydro-isoquinolin-1-yl}-phenoxy)-acetic acid | C26H22N4O4Cl2 525.39 | 1.04 LC-MS 1FA | 525.2 |
| 405 | (±)-(4-Chloro-2-{2-[3-(2-trifluoromethyl-indol-1-yl)-propionyl]-1,2,3,4-tetrahydro-isoquinolin-1-yl}-phenoxy)-acetic acid | C29H24N2O4ClF3 556.97 | 1.25 LC-MS 1FA | 557.1 |

Amide Coupling and Subsequent Saponification

Method A: To a solution of (2-methoxyphenoxy)acetic acid (22 mg, 0.12 mmol, 1.2 eq.) in DMF (0.3 mL), TBTU (39 mg, 0.12 mmol, 1.2 eq.) and Si-DEA (400 mg, 0.50 mmol, 5.0 eq.) were added. The resulting mixture was stirred at r.t. for 30 min. A solution of (±)-[4-chloro-2-(1,2,3,4-tetrahydro-iso-quinolin-1-yl)-phenoxy]-acetic acid ethyl ester hydrochloride (38 mg, 0.10 mmol, 1.0 eq.) in DCM/DMF 5:1 (0.6 mL) was added. The mixture was stirred at r.t. for 18 hours. The resulting suspension was filtered, the solids were rinsed with DCM (5 mL), and the filtrate was concentrated in vacuo. The residue was dissolved in THF (1 mL) and 1M aq. NaOH (1 mL) was added. The mixture was stirred at r.t. for 30 min. The mixture was acidified with 2M aq. HCl soln. and concentrated in vacuo. The residue was purified by prep. HPLC (column: Waters X-Bridge, 30×75 mm, 10 um, UV/MS, acidic conditions) and evaporated to give the desired acid as a white solid.

Listed in Table 22 below are examples of compounds of Formula (I), prepared according to the above-mentioned method with the corresponding amine of Structure 2 and the corresponding acid as starting materials.

TABLE 22

| Example | Compound of Formula (I) | Formula MW | $t_R$ [min] LC-MS Method | MS-data m/z [M + H]$^+$ |
|---|---|---|---|---|
| 406 | (±)-(4-Chloro-2-{2-[2-(2-methoxy-phenoxy)-acetyl]-1,2,3,4-tetrahydro-isoquinolin-1-yl}-phenoxy)-acetic acid | C26H24NO6Cl 481.93 | 1.28 LC-MS 5 | 482.1 |
| 407 | (±)-(4-Chloro-2-{2-[2-(4-fluoro-phenoxy)-acetyl]-1,2,3,4-tetrahydro-isoquinolin-1-yl}-phenoxy)-acetic acid | C25H21NO5ClF 469.90 | 1.07 LC-MS 1FA | 470.2 |
| 408 | (±)-(4-Chloro-2-{2-[3-(6-methyl-pyridin-2-yl)-propionyl]-1,2,3,4-tetrahydro-isoquinolin-1-yl}-phenoxy)-acetic acid | C26H25N2O4Cl 464.95 | 0.71 LC-MS 1FA | 465.3 |
| 409 | (±)-{4-Chloro-2-[2-(2-phenoxy-acetyl)-1,2,3,4-tetrahydro-isoquinolin-1-yl]-phenoxy}-acetic acid | C25H22N2O5Cl 451.91 | 1.06 LC-MS 1FA | 452.2 |
| 410 | (±)-(4-Chloro-2-{2-[2-(2-fluoro-phenoxy)-acetyl]-1,2,3,4-tetrahydro-isoquinolin-1-yl}-phenoxy)-acetic acid | C25H21NO5ClF 469.90 | 1.07 LC-MS 1FA | 470.2 |
| 411 | (±)-(4-Chloro-2-{2-[2-(quinolin-8-yloxy)-acetyl]-1,2,3,4-tetrahydro-isoquinolin-1-yl}-phenoxy)-acetic acid | C28H23N2O5Cl 502.95 | 0.80 LC-MS 1FA | 503.3 |
| 412 | (±)-(4-Chloro-2-{2-[2-(4-chloro-phenoxy)-acetyl]-1,2,3,4-tetrahydro-isoquinolin-1-yl}-phenoxy)-acetic acid | C25H21NO5Cl2 486.35 | 1.12 LC-MS 1FA | 486.2 |
| 413 | (±)-(4-Chloro-2-{2-[2-(3-chloro-phenoxy)-acetyl]-1,2,3,4-tetrahydro-isoquinolin-1-yl}-phenoxy)-acetic acid | C25H21NO5Cl2 486.35 | 1.12 LC-MS 1FA | 486.2 |
| 414 | (±)-{4-Chloro-2-[2-(2-p-tolyloxy-acetyl)-1,2,3,4-tetrahydro-isoquinolin-1-yl]-phenoxy}-acetic acid | C26H24NO5Cl 465.93 | 1.11 LC-MS 1FA | 466.2 |
| 415 | (±)-(4-Chloro-2-{2-[2-(4-methoxy-phenoxy)-acetyl]-1,2,3,4-tetrahydro-isoquinolin-1-yl}-phenoxy)-acetic acid | C26H24NO6Cl 481.93 | 1.05 LC-MS 1FA | 482.2 |
| 416 | (±)-(4-Chloro-2-{2-[2-(pyridin-3-yloxy)-acetyl]-1,2,3,4-tetrahydro- | C24H21N2O5Cl 452.89 | 0.70 LC-MS 1FA | 453.2 |

TABLE 22-continued

| Example | Compound of Formula (I) | Formula MW | t_R [min] LC-MS Method | MS-data m/z [M + H]⁺ |
|---|---|---|---|---|
| | isoquinolin-1-yl}-phenoxy)-acetic acid | | | |
| 417 | (±)-(4-Chloro-2-{2-[trans-2-(4-methoxy-phenyl)-cyclopropanecarbonyl]-1,2,3,4-tetrahydro-isoquinolin-1-yl}-phenoxy)-acetic acid | C28H26NO5Cl 491.97 | 1.10 LC-MS 1FA | 492.3 |
| 418 | (±)-(4-Chloro-2-{2-[trans-2-(4-fluoro-phenyl)-cyclopropanecarbonyl]-1,2,3,4-tetrahydro-isoquinolin-1-yl}-phenoxy)-acetic acid | C27H23NO4ClF 479.93 | 1.14 LC-MS 1FA | 480.3 |
| 419 | (±)-(4-Chloro-2-{2-[trans-2-(4-trifluoromethyl-phenyl)-cyclopropanecarbonyl]-1,2,3,4-tetrahydro-isoquinolin-1-yl}-phenoxy)-acetic acid | C28H23NO4ClF3 529.94 | 1.20 LC-MS 1FA | 530.2 |
| 420 | (±)-{4-Chloro-2-[2-(trans-2-p-tolyl-cyclopropanecarbonyl)-1,2,3,4-tetrahydro-isoquinolin-1-yl]-phenoxy}-acetic acid | C28H26NO4Cl 475.97 | 1.17 LC-MS 1FA | 476.3 |
| 421 | (±)-(4-Chloro-2-{2-[trans-2-(3-chloro-phenyl)-cyclopropanecarbonyl]-1,2,3,4-tetrahydro-isoquinolin-1-yl}-phenoxy)-acetic acid | C27H23NO4Cl2 496.39 | 1.17 LC-MS 1FA | 496.1 |
| 422 | (±)-{4-Chloro-2-[2-(trans-2-o-tolyl-cyclopropanecarbonyl)-1,2,3,4-tetrahydro-isoquinolin-1-yl]-phenoxy}-acetic acid | C28H26NO4Cl 475.97 | 1.15 LC-MS 1FA | 476.3 |
| 423 | (±)-(4-Chloro-2-{2-[trans-2-(2-trifluoromethyl-phenyl)-cyclopropanecarbonyl]-1,2,3,4-tetrahydro-isoquinolin-1-yl}-phenoxy)-acetic acid | C28H23NO4ClF3 529.94 | 1.17 LC-MS 1FA | 530.2 |
| 424 | (±)-(4-Chloro-2-{2-[trans-2-(3-fluoro-phenyl)-cyclopropanecarbonyl]-1,2,3,4-tetrahydro-isoquinolin-1-yl}-phenoxy)-acetic acid | C27H23NO4ClF 479.93 | 1.12 LC-MS 1FA | 480.2 |
| 425 | (±)-(4-Chloro-2-{2-[trans-2-(3-methoxy-phenyl)-cyclopropanecarbonyl]-1,2,3,4-tetrahydro-isoquinolin-1-yl}-phenoxy)-acetic acid | C28H26NO5Cl 491.97 | 1.11 LC-MS 1FA | 492.2 |
| 426 | (±)-(4-Chloro-2-{2-[trans-2-(3-trifluoromethyl-phenyl)-cyclopropanecarbonyl]-1,2,3,4-tetrahydro-isoquinolin-1-yl}-phenoxy)-acetic acid | C28H23NO4ClF3 529.94 | 1.19 LC-MS 1FA | 530.3 |
| 427 | (±)-{4-Chloro-2-[2-(trans-2-m-tolyl-cyclopropanecarbonyl)-1,2,3,4-tetrahydro-isoquinolin-1-yl]-phenoxy}-acetic acid | C28H26NO4Cl 475.97 | 1.18 LC-MS 1FA | 476.3 |
| 428 | (±)-{4-Chloro-2-[6-fluoro-2-(trans-2-phenyl-cyclopropanecarbonyl)-1,2,3,4-tetrahydro-isoquinolin-1-yl]-phenoxy}-acetic acid | C27H23NO4ClF 479.93 | 1.12 LC-MS 1FA | 480.2 |
| 429 | (±)-(4-Chloro-2-{6-fluoro-2-[trans-2-(2-trifluoromethyl-phenyl)-cyclopropanecarbonyl]-1,2,3,4-tetrahydro-isoquinolin-1-yl}-phenoxy)-acetic acid | C28H22NO4ClF4 547.93 | 1.17 LC-MS 1FA | 548.2 |
| 430 | (±)-(4-Chloro-2-{2-[2-(trans-2-chloro-phenyl)-cyclopropanecarbonyl]-6-fluoro-1,2,3,4-tetrahydro-isoquinolin-1-yl}-phenoxy)-acetic acid | C27H22NO4Cl2F 514.38 | 1.16 LC-MS 1FA | 514.2 |
| 431 | (±)-{4-Chloro-2-[6-fluoro-2-(trans-2-o-tolyl-cyclopropanecarbonyl)-1,2,3,4-tetrahydro-isoquinolin-1-yl]-phenoxy}-acetic acid | C28H25NO4ClF 493.96 | 1.16 LC-MS 1FA | 494.3 |
| 432 | (±)-(4-Chloro-2-{2-[2-(2,6-dimethyl-pyridin-3-yloxy)-acetyl]-6-fluoro-1,2,3,4-tetrahydro- | C26H24N2O5ClF 498.94 | 0.73 LC-MS 1FA | 499.3 |

TABLE 22-continued

| Example | Compound of Formula (I) | Formula MW | $t_R$ [min] LC-MS Method | MS-data m/z $[M + H]^+$ |
|---|---|---|---|---|
| | isoquinolin-1-yl}-phenoxy)-acetic acid | | | |
| 433 | (±)-(4-Chloro-2-{6-fluoro-2-[3-(5-methoxy-1H-indol-3-yl)-propionyl]-1,2,3,4-tetrahydro-isoquinolin-1-yl}-phenoxy)-acetic acid | C29H26N2O5ClF 536.99 | 1.05 LC-MS 1FA | 537.2 |
| 434 | (±)-(4-Chloro-2-{6-fluoro-2-[3-(1-methyl-1H-indol-3-yl)-propionyl]-1,2,3,4-tetrahydro-isoquinolin-1-yl}-phenoxy)-acetic acid | C29H26N2O4ClF 520.99 | 1.15 LC-MS 1FA | 521.3 |
| 435 | (±)-{4-Chloro-2-[6-fluoro-2-(3-o-tolyl-propionyl)-1,2,3,4-tetrahydro-isoquinolin-1-yl]-phenoxy}-acetic acid | C27H25NO4ClF 481.95 | 1.37 LC-MS 5 | 482.2 |
| 436 | (±)-(4-Chloro-2-{6-fluoro-2-[4-(2-fluoro-phenyl)-butyryl]-1,2,3,4-tetrahydro-isoquinolin-1-yl}-phenoxy)-acetic acid | C27H24NO4ClF2 499.94 | 1.16 LC-MS 1FA | 500.2 |
| 437 | (±)-(4-Chloro-2-{2-[2-(2-chloro-benzyloxy)-acetyl]-6-fluoro-1,2,3,4-tetrahydro-isoquinolin-1-yl}-phenoxy)-acetic acid | C26H22NO5Cl2F 518.37 | 1.13 LC-MS 1FA | 518.2 |
| 438 | (±)-(4-Chloro-2-{6-fluoro-2-[3-(4-fluoro-phenoxy)-propionyl]-1,2,3,4-tetrahydro-isoquinolin-1-yl}-phenoxy)-acetic acid | C26H22NO5ClF2 501.91 | 1.12 LC-MS 1FA | 502.2 |
| 439 | (±)-(4-Chloro-2-{2-[2-(methyl-phenyl-amino)-acetyl]-1,2,3,4-tetrahydro-isoquinolin-1-yl}-phenoxy)-acetic acid | C26H25N2O4Cl 464.95 | 1.09 LC-MS 1FA | 465.3 |
| 440 | (±)-(4-Chloro-2-{2-[4-(2-oxo-pyrrolidin-1-yl)-butyryl]-1,2,3,4-tetrahydro-isoquinolin-1-yl}-phenoxy)-acetic acid | C25H27N2O5Cl 470.95 | 0.89 LC-MS 1FA | 471.3 |
| 441 | (±)-{4-Chloro-2-[2-(3-2,3-dihydro-indol-1-yl-propionyl)-1,2,3,4-tetrahydro-isoquinolin-1-yl]-phenoxy}-acetic acid | C28H27N2O4Cl 490.99 | 1.13 LC-MS 1FA | 491.3 |
| 442 | (±)-(4-Chloro-2-{2-[3-(6-chloro-3-oxo-2,3-dihydro-benzo[1,4]oxazin-4-yl)-propionyl]-1,2,3,4-tetrahydro-isoquinolin-1-yl}-phenoxy)-acetic acid | C28H24N2O6Cl2 555.41 | 1.10 LC-MS 1FA | 555.0 |
| 443 | (±)-{4-Chloro-2-[2-(2-phenylamino-acetyl)-1,2,3,4-tetrahydro-isoquinolin-1-yl]-phenoxy}-acetic acid | C25H23N2O4Cl 450.92 | 1.06 LC-MS 1FA | 451.3 |
| 444 | (±)-{4-Chloro-2-[2-(2-1,3-dihydro-isoindol-2-yl-acetyl)-1,2,3,4-tetrahydro-isoquinolin-1-yl]-phenoxy}-acetic acid | C27H25N2O4Cl 476.96 | 0.83 LC-MS 1TFA | 477.2 |
| 445 | (±)-(4-Chloro-2-{2-[3-(1-oxo-1,3-dihydro-isoindol-2-yl)-propionyl]-1,2,3,4-tetrahydro-isoquinolin-1-yl}-phenoxy)-acetic acid | C28H25N2O5Cl 504.97 | 0.96 LC-MS 1FA | 505.3 |
| 446 | (±)-(4-Chloro-2-{2-[3-(2-methyl-indol-1-yl)-propionyl]-1,2,3,4-tetrahydro-isoquinolin-1-yl}-phenoxy)-acetic acid | C29H27N2O4Cl 503.00 | 1.18 LC-MS 1FA | 503.3 |
| 447 | (±)-(4-Chloro-2-{2-[3-(3-methyl-indol-1-yl)-propionyl]-1,2,3,4-tetrahydro-isoquinolin-1-yl}-phenoxy)-acetic acid | C29H27N2O4Cl 503.00 | 1.20 LC-MS 1FA | 503.3 |
| 448 | (±)-{4-Chloro-2-[2-(3-indazol-1-yl-propionyl)-1,2,3,4-tetrahydro-isoquinolin-1-yl]-phenoxy}-acetic acid | C27H24N3O4Cl 489.96 | 1.06 LC-MS 1TFA | 490.3 |
| 449 | (±)-{4-Chloro-2-[2-(3-3,4-dihydro-2H-quinolin-1-yl-propionyl)-1,2,3,4-tetrahydro-isoquinolin-1-yl]-phenoxy}-acetic acid | C29H29N2O4Cl 505.01 | 1.19 LC-MS 1FA | 505.3 |
| 450 | (±)-{4-Chloro-2-[2-(3-isobutoxy-propionyl)-1,2,3,4-tetrahydro-isoquinolin-1-yl]-phenoxy}-acetic acid | C24H28NO5Cl 445.94 | 1.12 LC-MS 1FA | 446.3 |

TABLE 22-continued

| Example | Compound of Formula (I) | Formula MW | $t_R$ [min] LC-MS Method | MS-data m/z $[M + H]^+$ |
|---|---|---|---|---|
| 451 | (±)-{2-[2-(3-Benzoimidazol-1-yl-propionyl)-1,2,3,4-tetrahydro-isoquinolin-1-yl]-4-chloro-phenoxy}-acetic acid | C27H24N3O4Cl 489.96 | 0.80 LC-MS 1TFA | 490.2 |
| 452 | (±)-(4-Chloro-2-{2-[3-(4-methyl-2-oxo-thiazol-3-yl)-propionyl]-1,2,3,4-tetrahydro-isoquinolin-1-yl}-phenoxy)-acetic acid | C24H23N2O5ClS 486.98 | 0.97 LC-MS 1FA | 487.2 |
| 453 | (±)-(4-Chloro-2-{2-[3-(2-oxo-thiazolidin-3-yl)-propionyl]-1,2,3,4-tetrahydro-isoquinolin-1-yl}-phenoxy)-acetic acid | C23H23N2O5ClS 474.96 | 0.92 LC-MS 1FA | 475.2 |

Method B: To a solution of 3-(2,4-dimethylphenyl)propionic acid (18 mg, 0.10 mmol, 1.0 eq.) and (±)-[4-chloro-2-(1,2,3,4-tetrahydro-isoquinolin-1-yl)-phenoxy]-acetic acid ethyl ester hydrochloride (41 mg, 0.10 mmol, 1.0 eq.) in DMF (1.2 mL), DMAP (49 mg, 0.40 mmol, 4.0 eq.) and N-(3-dimethylaminopropyl)-N'-ethylcarbodiimide hydrochloride (29 mg, 0.15 mmol, 1.5 eq.) were added. The resulting solution was stirred at r.t. for 18 hours. 1M aq. NaOH (0.6 mL) was added and the solution was stirred at r.t. during 2 hours. Formic acid (0.2 mL) was added. The crude mixture was purified by prep. HPLC (column: Atlantis, 19×50 mm, 5 um, UV/MS, acidic conditions) and evaporated (genevac) to give the desired acid.

Listed in Table 23 below are examples of compounds of Formula (I), prepared according to the above-mentioned method with the corresponding amine of Structure 2 and the corresponding acid as starting materials.

Method C: To a solution of (±)-trans-2-ethyl-cyclopropanecarboxylic acid (35 mg, 0.31 mmol, 1.3 eq.) in DMF (2 mL), DIPEA (4 eq.) and TBTU (98 mg, 0.31 mmol, 1.3 eq.) were added in sequence. The resulting solution was stirred at r.t. for 30 min. ((S)-4-Chloro-2-1,2,3,4-tetrahydro-isoquinolin-1-yl-phenoxy)-acetic acid ethyl ester hydrochloride (90 mg, 0.24 mmol, 1.0 eq.) was added and the resulting mixture was stirred at r.t. for 18 hours. The solution was neutralized with formic acid (1 mL) and then purified by prep. HPLC (column: Atlantis, 30×75 mm, 10 um, UV/MS, acidic conditions) and concentrated in vacuo (Genevac). To a solution of the ethyl ester derivative in DMF (1 mL), 1M aq. NaOH (0.5 mL) was added. The mixture was stirred at r.t. for 18 hours. The solution was neutralized with formic acid (1 mL) and then purified by prep. HPLC (column: Atlantis, 30×75 mm, 10 um, UV/MS, acidic conditions) and concentrated in vacuo (Genevac) to give the desired acid.

TABLE 23

| Example | Compound of Formula (I) | Formula MW | $t_R$ [min] LC-MS Method | MS-data m/z $[M + H]^+$ |
|---|---|---|---|---|
| 454 | (±)-(4-Chloro-2-{2-[3-(2,4-dimethyl-phenyl)-propionyl]-1,2,3,4-tetrahydro-isoquinolin-1-yl}-phenoxy)-acetic acid | C28H28NO4Cl 477.99 | 1.21 LC-MS 1FA | 478.3 |
| 455 | (±)-(4-Chloro-2-{2-[3-(2,6-dimethyl-pyridin-3-yl)-propionyl]-1,2,3,4-tetrahydro-isoquinolin-1-yl}-phenoxy)-acetic acid | C27H27N2O4Cl 478.97 | 0.69 LC-MS 1FA | 479.3 |
| 456 | (±)-(4-Chloro-2-{2-[2-(2,4-dimethyl-phenoxy)-acetyl]-1,2,3,4-tetrahydro-isoquinolin-1-yl}-phenoxy)-acetic acid | C27H26N2O5Cl 479.96 | 1.18 LC-MS 1FA | 480.3 |
| 457 | (±)-(4-Chloro-2-{2-[3-(1,2-dimethyl-1H-indol-3-yl)-propionyl]-1,2,3,4-tetrahydro-isoquinolin-1-yl}-phenoxy)-acetic acid | C30H29N2O4Cl 517.02 | 1.17 LC-MS 1FA | 517.3 |
| 458 | (±)-(4-Chloro-2-{2-[3-(5-methoxy-1-methyl-1H-indol-3-yl)-propionyl]-1,2,3,4-tetrahydro-isoquinolin-1-yl}-phenoxy)-acetic acid | C30H29N2O5Cl 533.02 | 1.12 LC-MS 1FA | 533.3 |
| 459 | (±)-(4-Chloro-2-{2-[3-(5-methoxy-indol-1-yl)-propionyl]-1,2,3,4-tetrahydro-isoquinolin-1-yl}-phenoxy)-acetic acid | C29H27N2O5Cl 519.00 | 1.11 LC-MS 1FA | 519.3 |

Listed in Table 24 below are examples of compounds of Formula (I), prepared according to the above-mentioned method with the corresponding amine of Structure 2 and the corresponding acid as starting materials.

TABLE 24

| Example | Compound of Formula (I) | Formula MW | $t_R$ [min] LC-MS Method | MS-data m/z $[M + H]^+$ |
|---|---|---|---|---|
| 460 | {4-Chloro-2-[(S)-2-(trans-2-ethyl-cyclopropanecarbonyl)-1,2,3,4-tetrahydro-isoquinolin-1-yl]-phenoxy}-acetic acid | C23H24NO4Cl 413.90 | 1.09 LC-MS 1FA | 414.2 |
| 461 | {4-Chloro-2-[(S)-2-(trans-2-ethoxy-cyclopropanecarbonyl)-1,2,3,4-tetrahydro-isoquinolin-1-yl]-phenoxy}-acetic acid | C23H24NO5Cl 429.90 | 1.01 LC-MS 1FA | 430.2 |
| 462 | {4-Chloro-2-[(S)-2-(trans-2-methyl-cyclopropanecarbonyl)-1,2,3,4-tetrahydro-isoquinolin-1-yl]-phenoxy}-acetic acid | C22H22NO4Cl 399.87 | 1.04 LC-MS 1FA | 400.2 |
| 463 | (±)-{4-Chloro-2-[2-(3-1H-indol-3-yl-propionyl)-1,2,3,4-tetrahydro-isoquinolin-1-yl]-phenoxy}-acetic acid | C28H25N2O4Cl 488.97 | 0.92 LC-MS 3 | 489.1 |

Example 464

{4-Chloro-2-[(S)-2-(trans-2-isopropyl-cyclopropanecarbonyl)-1,2,3,4-tetrahydro-isoquinolin-1-yl]-phenoxy}-acetic acid (diastereoisomer 1) (C24H26NO4Cl, MW=427.93) and Example 465

{4-Chloro-2-[(S)-2-(trans-2-isopropyl-cyclopropanecarbonyl)-1,2,3,4-tetrahydro-isoquinolin-1-yl]-phenoxy}-acetic acid (diastereoisomer 2) (C24H26NO4Cl, MW=427.93)

To a solution of (±)-trans-2-isopropyl-cyclopropanecarboxylic acid (39 mg, 0.31 mmol, 1.3 eq.) in DMF (2 mL), DIPEA (4 eq.) and TBTU (98 mg, 0.31 mmol, 1.3 eq.) were added in sequence. The resulting solution was stirred at r.t. for 30 min. ((S)-4-Chloro-2-1,2,3,4-tetrahydro-isoquinolin-1-yl-phenoxy)-acetic acid ethyl ester hydrochloride (90 mg, 0.24 mmol, 1.0 eq.) was added and the resulting mixture was stirred at r.t. for 18 hours. The solution was neutralized with formic acid (1 mL) and then purified by prep. HPLC (column: Atlantis, 30×75 mm, 10 um, UV/MS, acidic conditions) and concentrated in vacuo (Genevac). To a solution of the ethyl ester derivative in DMF (1 mL), 1M aq. NaOH (0.5 mL) was added. The mixture was stirred at r.t. for 18 hours. The solution was neutralized with formic acid (1 mL) and then purified by prep. HPLC (column: Waters XBridge, 19×50 mm, 5 um, UV/MS, acidic conditions) and concentrated in vacuo (Genevac) to give {4-Chloro-2-[(S)-2-(trans-2-isopropyl-cyclopropanecarbonyl)-1,2,3,4-tetrahydro-isoquinolin-1-yl]-phenoxy}-acetic acid (diastereoisomer 1) (LC-MS 1FA: $t_R$=1.13 min; [M+H]$^+$=428.3) and {4-Chloro-2-[(S)-2-(trans-2-isopropyl-cyclopropanecarbonyl)-1,2,3,4-tetrahydro-isoquinolin-1-yl]-phenoxy}-acetic acid (diastereoisomer 2) (LC-MS 1FA: $t_R$=1.15 min; [M+H]$^+$=428.3)

Example 466

(±)-{4-Chloro-2-[2-(2,2-dimethyl-cyclopropanecarbonyl)-1,2,3,4-tetrahydro-isoquinolin-1-yl]-phenoxy}-acetic acid (C23H24NO4Cl, MW=413.90)

To a solution of (±)-2,2-dimethyl-cyclopropanecarboxylic acid (26 mg, 0.20 mmol, 1.0 eq.) and (±)-[4-chloro-2-(1,2,3,4-tetrahydro-isoquinolin-1-yl)-phenoxy]-acetic acid ethyl ester (73 mg, 0.20 mmol, 1.0 eq.) in DMF (2.4 mL), DMAP (37 mg, 0.30 mmol, 1.5 eq.) and N-(3-dimethylaminopropyl)-N'-ethylcarbodiimide hydrochloride (58 mg, 0.30 mmol, 1.5 eq.) were added. The resulting solution was stirred at r.t. for 62 hours. 1M aq. NaOH soln. (1.2 mL) was added and the solution was stirred at r.t. for 3.5 hours. Formic acid (0.2 mL) was added. The crude mixture was purified by prep. HPLC (column: Waters XBridge, 19×50 mm, 5 um, UV/MS, acidic conditions). The two racemic diastereoisomers were separated (LC-MS 3: $t_R$ (±)-dia1=0.91 and $t_R$ (±)-dia2=0.93). The title compound showed: $t_R$=0.93.

LC-MS 1FA: $t_R$=1.09 min; [M+H]$^+$=414.3

Example 467

(±)-(4-Chloro-2-{2-[2-(2,4-dimethyl-thiazol-5-yl)-cyclopropanecarbonyl]-1,2,3,4-tetrahydro-isoquinolin-1-yl}-phenoxy)-acetic acid (C26H25N2O4ClS, MW=497.01)

To a solution of (±)-trans-2-(2,4-dimethyl-thiazol-5-yl)cyclopropanecarboxylic acid (42 mg, 0.20 mmol, 1.0 eq.) and (±)-[4-chloro-2-(1,2,3,4-tetrahydro-isoquinolin-1-yl)-phenoxy]-acetic acid ethyl ester (73 mg, 0.20 mmol, 1.0 eq.) in DMF (2.4 mL), DMAP (37 mg, 0.30 mmol, 1.5 eq.) and N-(3-dimethylaminopropyl)-N'-ethylcarbodiimide hydrochloride (58 mg, 0.30 mmol, 1.5 eq.) were added. The resulting solution was stirred at r.t. for 62 hours. 1M aq. NaOH soln. (1.2 mL) was added and the solution was stirred at r.t. for 3.5 hours. Formic acid (0.2 mL) was added. The crude mixture was purified by prep. HPLC (column: Waters XBridge, 19×50 mm, 5 um, UV/MS, acidic conditions). The two racemic diastereoisomers were separated (LC-MS 3: $t_R$ (±)-dia1=0.81 and $t_R$ (±)-dia2=0.82). The title compound showed: $t_R$=0.82.

LC-MS 1 FA: $t_R$=0.99 min; [M+H]$^+$=497.3

Alcohol Alkylation and Subsequent Saponification

Method A: To a mixture of 3-hydroxy-6-methylpyridine (13 mg, 0.12 mmol, 1.2 eq.) and potassium carbonate (22 mg, 0.16 mmol, 1.6 eq.) in MeCN (0.8 mL) at 75° C., a solution of (±)-{2-[2-(2-bromo-acetyl)-1,2,3,4-tetrahydro-isoquinolin-1-yl]-4-chloro-phenoxy}-acetic acid ethyl ester (47 mg, 0.10 mmol, 1.0 eq.) in MeCN (0.2 mL) was added. The reaction mixture was stirred at 75° C. for 2 hours and further at r.t. for 18 hours. 1M aq. NaOH soln. (1 mL) was added and the mixture was stirred at r.t. for 1 hour. The mixture was acidified with 2M aq. HCl soln. and purified by prep. HPLC (column: Waters X-Bridge, 30×75 mm, 10 um, UV/MS, acidic conditions) and evaporated to give the desired acid as a white solid.

Listed in Table 25 below are examples of compounds of Formula (I), prepared according to the above-mentioned method with the corresponding alcohol as starting material.

TABLE 25

| | Example Compound of Formula (I) | Formula MW | $t_R$ [min] LC-MS Method | MS-data m/z [M + H]$^+$ |
|---|---|---|---|---|
| 468 | (±)-(4-Chloro-2-{2-[2-(6-methyl-pyridin-3-yloxy)-acetyl]-1,2,3,4-tetrahydro-isoquinolin-1-yl}-phenoxy)-acetic acid | C25H23N2O5Cl 466.92 | 0.74 LC-MS 1FA | 467.3 |
| 469 | (±)-(4-Chloro-2-{2-[2-(2-methyl-pyridin-3-yloxy)-acetyl]-1,2,3,4-tetrahydro-isoquinolin-1-yl}-phenoxy)-acetic acid | C25H23N2O5Cl 466.92 | 0.72 LC-MS 1FA | 467.3 |
| 470 | (±)-(4-Chloro-2-{2-[2-(5-chloro-pyridin-3-yloxy)-acetyl]-1,2,3,4-tetrahydro-isoquinolin-1-yl}-phenoxy)-acetic acid | C24H20N2O5Cl2 487.34 | 1.00 LC-MS 1FA | 487.2 |
| 471 | (±)-(4-Chloro-2-{2-[2-(2-chloro-pyridin-3-yloxy)-acetyl]-1,2,3,4-tetrahydro-isoquinolin-1-yl}-phenoxy)-acetic acid | C24H20N2O5Cl2 487.34 | 0.99 LC-MS 1FA | 487.2 |
| 472 | (±)-(4-Chloro-2-{2-[2-(6-chloro-pyridin-3-yloxy)-acetyl]-1,2,3,4-tetrahydro-isoquinolin-1-yl}-phenoxy)-acetic acid | C24H20N2O5Cl2 487.34 | 1.01 LC-MS 1FA | 487.2 |
| 473 | (±)-(4-Chloro-2-{2-[2-(2,6-dichloro-pyridin-4-yloxy)-acetyl]-1,2,3,4-tetrahydro-isoquinolin-1-yl}-phenoxy)-acetic acid | C24H19N2O5Cl3 521.78 | 1.09 LC-MS 1FA | 521.1 |

Method B: To a solution of 3-hydroxy-5-methylpyridine (12 mg, 0.10 mmol, 1.0 eq.) in DMF (1.0 mL), 60% sodium hydride in mineral oil (4.4 mg, 0.11 mmol, 1.1 eq.) was added. The mixture was stirred at r.t. for 10 min. A solution of (±)-{2-[2-(2-bromo-acetyl)-1,2,3,4-tetrahydro-isoquinolin-1-yl]-4-chloro-phenoxy}-acetic acid ethyl ester (47 mg, 0.10 mmol, 1.0 eq.) in DMF (0.3 mL) was added and the reaction mixture was stirred at r.t. for 4 hours. 1M aq. NaOH soln. (1.0 mL) was added. The solution was stirred at r.t. for 30 min. The reaction mixture was acidified with 2M aq. HCl soln. (1.0 mL) and concentrated in vacuo. The residue, redissolved in DMF (1.2 mL), was purified by prep. HPLC (column: Atlantis, 19×50 mm, 5 um, UV/MS, acidic conditions) to give the desired acid.

Listed in Table 26 below are examples of compounds of Formula (I), prepared according to the above-mentioned method with the corresponding alcohol as starting material.

TABLE 26

| | Example Compound of Formula (I) | Formula MW | $t_R$ [min] LC-MS Method | MS-data m/z [M + H]$^+$ |
|---|---|---|---|---|
| 474 | (±)-(4-Chloro-2-{2-[2-(5-methyl-pyridin-3-yloxy)-acetyl]-1,2,3,4-tetrahydro-isoquinolin-1-yl}-phenoxy)-acetic acid | C25H23N2O5Cl 466.92 | 0.78 LC-MS 1FA | 467.3 |
| 475 | (±)-[4-Chloro-2-(2-{2-[2-(2-hydroxy-ethoxy)-pyridin-3-yloxy]-acetyl}-1,2,3,4-tetrahydro- | C26H25N2O7Cl 512.95 | 0.90 LC-MS 1FA | 513.2 |

TABLE 26-continued

| | Example Compound of Formula (I) | Formula MW | $t_R$ [min] LC-MS Method | MS-data m/z [M + H]+ |
|---|---|---|---|---|
| | isoquinolin-1-yl)-phenoxy]-acetic acid | | | |
| 476 | (±)-(4-Chloro-2-{2-[2-(2,6-dimethoxy-pyridin-3-yloxy)-acetyl]-1,2,3,4-tetrahydro-isoquinolin-1-yl}-phenoxy)-acetic acid | C26H25N2O7Cl 512.95 | 1.07 LC-MS 1FA | 513.2 |
| 477 | (±)-(4-Chloro-2-{2-[2-(5-methoxy-pyridin-3-yloxy)-acetyl]-1,2,3,4-tetrahydro-isoquinolin-1-yl}-phenoxy)-acetic acid | C25H23N2O6Cl 482.92 | 0.87 LC-MS 1FA | 483.3 |
| 478 | (±)-(4-Chloro-2-{2-[2-(5-fluoro-pyridin-3-yloxy)-acetyl]-1,2,3,4-tetrahydro-isoquinolin-1-yl}-phenoxy)-acetic acid | C24H20N2O5ClF 470.88 | 0.95 LC-MS 1FA | 471.2 |
| 479 | (±)-(2-{2-[2-(2-Carbamoyl-pyridin-3-yloxy)-acetyl]-1,2,3,4-tetrahydro-isoquinolin-1-yl}-4-chloro-phenoxy)-acetic acid | C25H22N3O6Cl 495.92 | 0.82 LC-MS 1FA | 496.2 |
| 480 | (±)-(4-Chloro-2-{2-[2-(2-cyano-pyridin-3-yloxy)-acetyl]-1,2,3,4-tetrahydro-isoquinolin-1-yl}-phenoxy)-acetic acid | C25H20N3O5Cl 477.90 | 0.95 LC-MS 1FA | 478.2 |
| 481 | (±)-(4-Chloro-2-{2-[2-(6-trifluoromethyl-pyridin-3-yloxy)-acetyl]-1,2,3,4-tetrahydro-isoquinolin-1-yl}-phenoxy)-acetic acid | C25H20N2O5ClF3 520.89 | 1.06 LC-MS 1FA | 521.2 |
| 482 | (±)-(4-Chloro-2-{2-[2-(2-fluoro-pyridin-3-yloxy)-acetyl]-1,2,3,4-tetrahydro-isoquinolin-1-yl}-phenoxy)-acetic acid | C24H20N2O5ClF 470.88 | 0.97 LC-MS 1FA | 471.2 |
| 483 | (±)-(4-Chloro-2-{2-[2-(3-methyl-3H-imidazo[4,5-b]pyridin-6-yloxy)-acetyl]-1,2,3,4-tetrahydro-isoquinolin-1-yl}-phenoxy)-acetic acid | C26H23N4O5Cl 506.95 | 0.90 LC-MS 5 | 507.2 |
| 484 | (±)-(4-Chloro-2-{2-[2-(2-methoxy-5-methyl-pyridin-3-yloxy)-acetyl]-1,2,3,4-tetrahydro-isoquinolin-1-yl}-phenoxy)-acetic acid | C26H25N2O6Cl 496.95 | 1.02 LC-MS 1FA | 497.3 |
| 485 | (±)-(4-Chloro-2-{2-[2-(5,6-dimethoxy-pyridin-3-yloxy)-acetyl]-1,2,3,4-tetrahydro-isoquinolin-1-yl}-phenoxy)-acetic acid | C26H25N2O7Cl 512.95 | 0.98 LC-MS 1FA | 513.3 |
| 486 | (±)-(4-Chloro-2-{2-[2-(6-methoxy-pyridin-3-yloxy)-acetyl]-1,2,3,4-tetrahydro-isoquinolin-1-yl}-phenoxy)-acetic acid | C25H23N2O6Cl 482.92 | 0.99 LC-MS 1FA | 483.3 |
| 487 | (±)-(4-Chloro-2-{2-[2-(4-chloro-pyridin-3-yloxy)-acetyl]-1,2,3,4-tetrahydro-isoquinolin-1-yl}-phenoxy)-acetic acid | C24H20N2O5Cl2 487.34 | 0.97 LC-MS 1FA | 487.2 |

Alkylation and Subsequent Saponification

To a solution of (±)-{2-[2-(2-bromo-acetyl)-1,2,3,4-tetrahydro-isoquinolin-1-yl]-4-chloro-phenoxy}-acetic acid ethyl ester (47 mg, 0.10 mmol, 1.0 eq.) and cesium carbonate (65 mg, 0.20 mmol, 2.0 eq.) in DMF (0.8 mL), 3-methylindole (13 mg, 0.10 mmol, 1.0 eq.) was added. The mixture was stirred at 80° C. for 17 hours. The mixture was allowed to cool to r.t. 1M aq. NaOH soln. (0.2 mL) was added. The mixture was stirred at r.t. for 4 hours. The mixture was neutralized with formic acid (ca. 0.2 mL) and purified by prep. HPLC (column: Water X-Bridge, 30×75 mm, 10 um, UV/MS, acidic conditions) and concentrated in vacuo (Genevac) to give the desired acid.

Listed in Table 27 below are examples of compounds of Formula (I), prepared according to the above-mentioned method with the corresponding indole as starting material.

TABLE 27

| | Example Compound of Formula (I) | Formula MW | $t_R$ [min] LC-MS Method | MS-data m/z [M + H]+ |
|---|---|---|---|---|
| 488 | (±)-(4-Chloro-2-{2-[2-(3-methyl-indol-1-yl)-acetyl]-1,2,3,4-tetrahydro-isoquinolin-1-yl}-phenoxy)-acetic acid | C28H25N2O4Cl 488.97 | 1.15 LC-MS 1FA | 489.3 |

TABLE 27-continued

| Example | Compound of Formula (I) | Formula MW | $t_R$ [min] LC-MS Method | MS-data m/z [M + H]$^+$ |
|---|---|---|---|---|
| 489 | (±)-(4-Chloro-2-{2-[2-(5-methoxy-indol-1-yl)-acetyl]-1,2,3,4-tetrahydro-isoquinolin-1-yl}-phenoxy)-acetic acid | C28H25N2O5Cl 504.97 | 1.07 LC-MS 1FA | 505.2 |

Urea Formation and Subsequent Saponification

To a solution of (±)-[4-chloro-2-(1,2,3,4-tetrahydro-isoquinolin-1-yl)-phenoxy]-acetic acid ethyl ester hydrochloride (50 mg, 0.13 mmol, 1.00 eq.) and NEt$_3$ (55 µL, 0.39 mmol, 3.00 eq.) in MeCN (1 mL), 2-chlorobenzyl isocyanate (23 mg, 0.14 mmol, 1.05 eq.) in MeCN (1 mL) was added. The mixture was stirred at r.t. for 18 hours. 1M aq. NaOH (0.5 mL) was added. The mixture was stirred at r.t. for 18 hours. The solution was neutralized with formic acid and purified by prep. HPLC (column: Atlantis, 30×75 mm, 10 um, UV/MS, acidic conditions) and concentrated in vacuo (Genevac) to give the desired acid.

Listed in Table 28 below are examples of compounds of Formula (I), prepared according to the above-mentioned method with the corresponding amine of Structure 2 and the corresponding isocyanate as starting materials.

TABLE 28

| Example | Compound of Formula (I) | Formula MW | $t_R$ [min] LC-MS Method | MS-data m/z [M + H]$^+$ |
|---|---|---|---|---|
| 490 | (±)-{4-Chloro-2-[2-(2-chloro-benzylcarbamoyl)-1,2,3,4-tetrahydro-isoquinolin-1-yl]-phenoxy}-acetic acid | C25H22N2O4Cl2 485.37 | 1.08 LC-MS 1FA | 485.2 |
| 491 | (±)-{4-Chloro-2-[2-(3-fluoro-benzylcarbamoyl)-1,2,3,4-tetrahydro-isoquinolin-1-yl]-phenoxy}-acetic acid | C25H22N2O4ClF 468.91 | 1.05 LC-MS 1FA | 469.2 |
| 492 | (±)-[2-(2-Benzylcarbamoyl-1,2,3,4-tetrahydro-isoquinolin-1-yl)-4-chloro-phenoxy]-acetic acid | C25H23N2O4Cl 450.92 | 1.04 LC-MS 1FA | 451.2 |
| 493 | (±)-[4-Chloro-2-(2-phenethylcarbamoyl-1,2,3,4-tetrahydro-isoquinolin-1-yl)-phenoxy]-acetic acid | C26H25N2O4Cl 464.95 | 1.08 LC-MS 1FA | 465.3 |
| 494 | (±)-{4-Chloro-2-[2-(4-fluoro-benzylcarbamoyl)-1,2,3,4-tetrahydro-isoquinolin-1-yl]-phenoxy}-acetic acid | C25H22N2O4ClF 468.91 | 1.05 LC-MS 1FA | 469.2 |
| 495 | (±)-{4-Chloro-2-[2-(2-fluoro-benzylcarbamoyl)-1,2,3,4-tetrahydro-isoquinolin-1-yl]-phenoxy}-acetic acid | C25H22N2O4ClF 468.91 | 1.05 LC-MS 1FA | 469.2 |
| 496 | (±)-[2-(2-Butylcarbamoyl-1,2,3,4-tetrahydro-isoquinolin-1-yl)-4-chloro-phenoxy]-acetic acid | C22H25N2O4Cl 416.90 | 1.04 LC-MS 1FA | 417.3 |

Suzuki Cross-coupling and Subsequent Saponification

To a mixture under N2 of (±)-7-bromo-1-(2-ethoxycarbonylmethoxy-5-fluoro-phenyl)-3,4-dihydro-1H-isoquinoline-2-carboxylic acid benzyl ester (113 mg, 0.20 mmol, 1.00 eq.), 4-fluorobenzeneboronic acid (29 mg, 0.20 mmol, 1.00 eq.) and sodium carbonate (85 mg, 0.80 mmol, 4.00 eq.) in toluene/MeOH/water 20:4:1 (4 mL), tetrakis(triphenylphosphine) palladium (0) (12 mg, 0.01 mmol, 0.05 eq.) was added and the mixture was stirred at 100° C. in a sealed vial for 18 hours. The mixture was allowed to cool to r.t. and concentrated in vacuo. To a solution of the residue in DMF (0.9 mL), 1M aq. NaOH solution (0.25 mL) was added. The solution was stirred at r.t. for 18 hours, then acidified with formic acid (0.25 mL). The crude mixture was filtered over celite and purified by prep. HPLC (column: Atlantis, 19×50 mm, 5 um, UV/MS, acidic conditions) and evaporated (genevac) to give the desired acid.

Listed in Table 29 below are examples of compounds of Formula (I), prepared according to the above-mentioned method with the corresponding boronic acid as starting material.

TABLE 29

| Example | Compound of Formula (I) | Formula MW | $t_R$ [min] LC-MS Method | MS-data m/z [M + H]$^+$ |
|---|---|---|---|---|
| 497 | (±)-1-(2-Carboxymethoxy-5-fluoro-phenyl)-7-(4-fluoro-phenyl)-3,4-dihydro-1H-isoquinoline-2-carboxylic acid benzyl ester | C31H25NO5F2 529.54 | 1.24 LC-MS 1FA | 530.3 |
| 498 | (±)-1-(2-Carboxymethoxy-5-fluoro-phenyl)-7-pyrimidin-5-yl-3,4-dihydro-1H-isoquinoline-2-carboxylic acid benzyl ester | C29H24N3O5F 513.52 | 1.00 LC-MS 1FA | 514.3 |

Phenol Alkylation and Subsequent Saponification

To a suspension of (±)-1-(5-fluoro-2-hydroxy-phenyl)-1,3-dihydro-isoindole-2-carboxylic acid benzyl ester (14 mg, 0.038 mmol, 1.0 eq.) and cesium carbonate (37 mg, 0.115 mmol, 3.0 eq.) in DMF (1 mL), ethyl bromoacetate (6 µL, 0.057 mmol, 1.5 eq.) was added. The reaction mixture was stirred at r.t. for 18 hours. The reaction mixture was diluted with water (25 mL) and AcOEt (30 mL). The layers were separated. The aq. phase was extracted with AcOEt (2×15 mL). The comb. org. phases were washed with water (1×10 mL), sat. aq. NaCl soln. (1×10 mL), dried over MgSO$_4$, and concentrated in vacuo. The residue was dissolved in DMF (1 mL), 1M aq. NaOH (1 mL) was added. The resulting solution was stirred at r.t. for 18 hours. The solution was neutralized with formic acid (1.00 mL), filtered and then purified by prep. HPLC (column: Atlantis, 30×75 mm, 10 um, UV/MS, acidic conditions) and concentrated in vacuo to give the desired acid.

Listed in Table 30 below are examples of compounds of Formula (I), prepared according to the above-mentioned method with the corresponding phenol 30 as starting material.

TABLE 30

| Example | Compound of Formula (I) | Formula MW | $t_R$ [min] LC-MS Method | MS-data m/z [M + H]$^+$ |
|---|---|---|---|---|
| 499 | (±)-1-(2-Carboxymethoxy-5-fluoro-phenyl)-1,3-dihydro-isoindole-2-carboxylic acid benzyl ester | C24H20NO5F 421.42 | 0.89 LC-MS 3 | 422.0 |
| 500 | (±)-1-(2-Carboxymethoxy-5-chloro-phenyl)-5-fluoro-1,3-dihydro-isoindole-2-carboxylic acid benzyl ester | C24H19NO5ClF 455.87 | 1.10 LC-MS 1FA | 456.2 |
| 501 | (±)-1-(2-Carboxymethoxy-5-chloro-phenyl)-4-fluoro-1,3-dihydro-isoindole-2-carboxylic acid benzyl ester | C24H19NO5ClF 455.87 | 1.12 LC-MS 1FA | 456.2 |

Amide Coupling and Subsequent Saponification

To a solution of (2-methoxyphenoxy)acetic acid (22 mg, 0.12 mmol, 1.2 eq.) in DMF (1 mL), TBTU (39 mg, 0.12 mmol, 1.2 eq.) and DIPEA (51 µL, 0.30 mmol, 3.0 eq.) were added. The resulting mixture was stirred at r.t. for 30 min. A solution of (±)-[4-chloro-2-(2,3-dihydro-1H-isoindol-1-yl)-phenoxy]-acetic acid ethyl ester hydrochloride (37 mg, 0.10 mmol, 1.0 eq.) in DMF (0.5 mL) was added. The mixture was stirred at r.t. for 1 hour. 1M aq. NaOH (1 mL) was added and the mixture was stirred at r.t. for 30 min, then concentrated in vacuo. The residue was purified by prep. HPLC (column: Waters X-Bridge, 30×75 mm, 10 um, UV/MS, acidic conditions) and evaporated to give the desired acid as a white solid.

Listed in Table 31 below are examples of compounds of Formula (I), prepared according to the above-mentioned method with the corresponding amine of Structure 2 and the corresponding acid as starting materials.

TABLE 31

| Example | Compound of Formula (I) | Formula MW | $t_R$ [min] LC-MS Method | MS-data m/z [M + H]$^+$ |
|---|---|---|---|---|
| 502 | (±)-(4-Chloro-2-{2-[2-(2-methoxy-phenoxy)-acetyl]-2,3-dihydro-1H-isoindol-1-yl}-phenoxy)-acetic acid | C25H22NO6Cl 467.90 | 0.97 LC-MS 1FA | 468.2 |

TABLE 31-continued

| Example | Compound of Formula (I) | Formula MW | $t_R$ [min] LC-MS Method | MS-data m/z [M + H]$^+$ |
|---|---|---|---|---|
| 503 | {4-Chloro-2-[2-trans-(2-phenyl-cyclopropanecarbonyl)-2,3-dihydro-1H-isoindol-1-yl]-phenoxy}-acetic acid | C26H22NO4Cl 447.92 | 1.03 LC-MS 1FA | 448.2 |
| 504 | (±)-(4-Chloro-2-{2-[2-(4-fluoro-phenoxy)-acetyl]-2,3-dihydro-1H-isoindol-1-yl}-phenoxy)-acetic acid | C24H19NO5ClF 455.87 | 1.00 LC-MS 1FA | 456.2 |
| 505 | (±)-{4-Chloro-2-[2-(3-pyridin-3-yl-propionyl)-2,3-dihydro-1H-isoindol-1-yl]-phenoxy}-acetic acid | C24H21N2O4Cl 436.89 | 0.65 LC-MS 1FA | 437.3 |
| 506 | (±)-{4-Chloro-2-[2-(3-o-tolyl-propionyl)-2,3-dihydro-1H-isoindol-1-yl]-phenoxy}-acetic acid | C26H24NO4Cl 449.93 | 1.08 LC-MS 1FA | 450.2 |
| 507 | (±)-{4-Chloro-2-[2-(2-indol-1-yl-acetyl)-2,3-dihydro-1H-isoindol-1-yl]-phenoxy}-acetic acid | C26H21N2O4Cl 460.92 | 1.28 LC-MS 5 | 461.2 |
| 508 | (±)-(4-Chloro-2-{2-[3-(1-ethyl-2-methyl-1H-indol-3-yl)-propionyl]-2,3-dihydro-1H-isoindol-1-yl}-phenoxy)-acetic acid | C30H29N2O4Cl 517.02 | 1.13 LC-MS 1FA | 517.3 |
| 509 | (±)-(4-Chloro-2-{2-[2-(quinolin-8-yloxy)-acetyl]-2,3-dihydro-1H-isoindol-1-yl}-phenoxy)-acetic acid | C27H21N2O5Cl 488.93 | 0.75 LC-MS 1FA | 489.2 |
| 510 | (±)-(4-Chloro-2-{2-[3-(2-methyl-1H-indol-3-yl)-propionyl]-2,3-dihydro-1H-isoindol-1-yl}-phenoxy)-acetic acid | C28H25N2O4Cl 488.97 | 1.01 LC-MS 1FA | 489.3 |
| 511 | (±)-(4-Chloro-2-{2-[3-(5-methoxy-1H-indol-3-yl)-propionyl]-2,3-dihydro-1H-isoindol-1-yl}-phenoxy)-acetic acid | C28H25N2O5Cl 504.97 | 0.96 LC-MS 1FA | 505.3 |
| 512 | (±)-(4-Chloro-2-{2-[2-(2,6-dimethyl-pyridin-3-yloxy)-acetyl]-2,3-dihydro-1H-isoindol-1-yl}-phenoxy)-acetic acid | C25H23N2O5Cl 466.92 | 0.66 LC-MS 1FA | 467.3 |
| 513 | (±)-(4-Chloro-2-{2-[3-(1-methyl-1H-indol-3-yl)-propionyl]-2,3-dihydro-1H-isoindol-1-yl}-phenoxy)-acetic acid | C28H25N2O4Cl 488.97 | 1.07 LC-MS 1FA | 489.2 |
| 514 | (±)-{4-Chloro-2-[2-(3-2,3-dihydro-indol-1-yl-propionyl)-2,3-dihydro-1H-isoindol-1-yl]-phenoxy}-acetic acid | C27H25N2O4Cl 476.96 | 1.05 LC-MS 1FA | 477.3 |
| 515 | (±)-{4-Chloro-2-[2-(3-3,4-dihydro-2H-quinolin-1-yl-propionyl)-2,3-dihydro-1H-isoindol-1-yl]-phenoxy}-acetic acid | C28H27N2O4Cl 490.99 | 1.10 LC-MS 1FA | 491.3 |
| 516 | (±)-{4-Chloro-2-[2-(3-indazol-1-yl-propionyl)-2,3-dihydro-1H-isoindol-1-yl]-phenoxy}-acetic acid | C26H22N3O4Cl 475.93 | 0.99 LC-MS 1FA | 476.3 |
| 517 | (±)-(4-Chloro-2-{2-[3-(3-fluoro-phenoxy)-propionyl]-2,3-dihydro-1H-isoindol-1-yl}-phenoxy)-acetic acid | C25H21NO5ClF 469.90 | 1.30 LC-MS 5 | 469.8 |
| 518 | (±)-(4-Chloro-2-{2-[2-(5-methoxy-benzo[d]isoxazol-3-yl)-acetyl]-2,3-dihydro-1H-isoindol-1-yl}-phenoxy)-acetic acid | C26H21N2O6Cl 492.91 | 0.99 LC-MS 1FA | 493.2 |
| 519 | (±)-(4-Chloro-2-{2-[3-(3-methyl-indol-1-yl)-propionyl]-2,3-dihydro-1H-isoindol-1-yl}-phenoxy)-acetic acid | C28H25N2O4Cl 488.97 | 1.12 LC-MS 1FA | 489.3 |
| 520 | (±)-(4-Chloro-2-{2-[3-(4-fluoro-phenoxy)-propionyl]-2,3-dihydro-1H-isoindol-1-yl}-phenoxy)-acetic acid | C25H21NO5ClF 469.90 | 1.29 LC-MS 5 | 469.8 |
| 521 | (±)-(4-Chloro-2-{2-[2-(2-chloro-benzyloxy)-acetyl]-2,3-dihydro-1H-isoindol-1-yl}-phenoxy)-acetic acid | C25H21N2O5Cl2 486.35 | 1.06 LC-MS 1FA | 486.2 |
| 522 | (±)-(4-Chloro-2-{2-[3-(2-fluoro-phenoxy)-propionyl]-2,3-dihydro-1H-isoindol-1-yl}-phenoxy)-acetic acid | C25H21NO5ClF 469.90 | 1.03 LC-MS 1FA | 470.2 |

TABLE 31-continued

| Example Compound of Formula (I) | Formula MW | $t_R$ [min] LC-MS Method | MS-data m/z [M + H]+ |
|---|---|---|---|
| 523 (4-Chloro-2-{2-trans-[2-(3-fluoro-phenyl)-cyclopropanecarbonyl]-2,3-dihydro-1H-isoindol-1-yl}-phenoxy)-acetic acid | C26H21NO4ClF 465.91 | 1.03 LC-MS 1FA | 466.2 |
| 524 (4-Chloro-2-{2-trans-[2-(3-chloro-phenyl)-cyclopropanecarbonyl]-2,3-dihydro-1H-isoindol-1-yl}-phenoxy)-acetic acid | C26H21NO4Cl2 482.36 | 1.08 LC-MS 1FA | 482.1 |
| 525 (4-Chloro-2-{2-trans-[2-(2-fluoro-phenyl)-cyclopropanecarbonyl]-2,3-dihydro-1H-isoindol-1-yl}-phenoxy)-acetic acid | C26H21NO4ClF 465.91 | 1.03 LC-MS 1FA | 466.2 |

Example 526

(±)-{4-Chloro-2-[5-fluoro-2-(3-indazol-1-yl-propionyl)-2,3-dihydro-1H-isoindol-1-yl]-phenoxy}-acetic acid (C26H21N3O4ClF, MW=493.92)

To a solution of 3-indazol-1-yl-propionic acid (34 mg, 0.17 mmol, 1.2 eq.) in DMF (4 mL), DIPEA (0.12 mL, 0.70 mmol, 5.0 eq.) and TBTU (54 mg, 0.17 mmol, 1.2 eq.) were added in sequence. The resulting solution was stirred at r.t. for 30 min. (±)-[4-Chloro-2-(5-fluoro-2,3-dihydro-1H-isoindol-1-yl)-phenoxy]-acetic acid ethyl ester hydrochloride (60 mg, 0.14 mmol, 1.0 eq.) in DMF (1 mL) was added and the resulting mixture was stirred at r.t. for 18 hours. The reaction mixture was concentrated in vacuo. The residue was purified by prep. HPLC (column: Atlantis, 30×75 mm, 10 um, UV/MS, acidic conditions) and concentrated in vacuo. The resulting ester derivative was dissolved in DMF (0.50 mL) and 1M aq. NaOH (0.50 mL) was added. The resulting solution was stirred at r.t. for 18 hours. The solution was acidified with formic acid (1.0 mL), filtered, and then purified by prep. HPLC (column: Atlantis, 30×75 mm, 10 um, UV/MS, acidic conditions) and concentrated in vacuo to give the desired acid.

LC-MS 1 FA: $t_R$=1.00 min; [M+H]+=494.2

Michael Addition

Potassium fluoride 40 wt. % on alumina (218 mg, 3.75 mmol, 25 eq.) was added to a mixture of [2-((S)-2-acryloyl-2,3-dihydro-1H-isoindol-1-yl)-4-chloro-phenoxy]-acetic acid ethyl ester (58 mg, 0.15 mmol, 1.0 eq.) and 5-fluoro-1H-indazole (25 mg, 0.18 mmol, 1.2 eq.) in MeCN (1 mL). The resulting suspension was stirred at 80° C. for 18 hours. Formic acid was added (0.2 mL). The reaction mixture was filtered and the filtrate was concentrated in vacuo. The residue was purified by prep. HPLC (column: Atlantis, 30×75 mm, 10 um, UV/MS, acidic conditions) and concentrated in vacuo to give the desired product as a white foam.

Listed in Table 32 below are examples of compounds of Formula (I), prepared according to the above-mentioned method with the corresponding vinyl amide 8 and the corresponding heterocycle 9 as starting materials.

TABLE 32

| Example Compound of Formula (I) | Formula MW | $t_R$ [min] LC-MS Method | MS-data m/z [M + H]+ |
|---|---|---|---|
| 527 (4-Chloro-2-{2-[3-(5-fluoro-indazol-1-yl)-propionyl]-2,3-dihydro-1H-isoindol-1-yl}-phenoxy)-acetic acid (enantiomer 1) | C26H21N3O4ClF 493.92 | 1.00 LC-MS 1FA | 494.2 |
| 528 (4-Chloro-2-{2-[3-(4-fluoro-3-methyl-indazol-1-yl)-propionyl]-2,3-dihydro-1H-isoindol-1-yl}-phenoxy)-acetic acid (enantiomer 1) | C27H23N3O4ClF 507.95 | 1.05 LC-MS 1FA | 508.3 |
| 529 (4-Chloro-2-{2-[3-(4-chloro-3-methyl-indazol-1-yl)-propionyl]-2,3-dihydro-1H-isoindol-1-yl}-phenoxy)-acetic acid (enantiomer 1) | C27H23N3O4Cl2 524.40 | 1.11 LC-MS 1FA | 524.2 |
| 530 (4-Chloro-2-{2-[3-(7-fluoro-3-methyl-indazol-1-yl)-propionyl]-2,3-dihydro-1H-isoindol-1-yl}-phenoxy)-acetic acid (enantiomer 1) | C27H23N3O4ClF 507.95 | 1.04 LC-MS 1FA | 508.2 |
| 531 (4-Chloro-2-{2-[3-(6-fluoro-3-methyl-indazol-1-yl)-propionyl]-2,3-dihydro-1H-isoindol-1-yl}-phenoxy)-acetic acid (enantiomer 1) | C27H23N3O4ClF 507.95 | 1.03 LC-MS 1FA | 508.2 |
| 532 (4-Chloro-2-{2-[3-(6-chloro-3-methyl-indazol-1-yl)-propionyl]-2,3-dihydro-1H-isoindol-1-yl}-phenoxy)-acetic acid (enantiomer 1) | C27H23N3O4Cl2 524.40 | 1.09 LC-MS 1FA | 524.2 |
| 533 (4-Chloro-2-{2-[3-(3-methyl-indazol-1-yl)-propionyl]-2,3-dihydro-1H-isoindol-1-yl}-phenoxy)-acetic acid (enantiomer 1) | C27H24N3O4Cl 489.96 | 1.02 LC-MS 1FA | 490.3 |

TABLE 32-continued

| Example | Compound of Formula (I) | Formula MW | $t_R$ [min] LC-MS Method | MS-data m/z [M + H]+ |
|---|---|---|---|---|
| 534 | (4-Chloro-2-{2-[3-(6-fluoro-indazol-1-yl)-propionyl]-2,3-dihydro-1H-isoindol-1-yl}-phenoxy)-acetic acid (enantiomer 1) | C26H21N3O4ClF 493.92 | 1.00 LC-MS 1FA | 494.2 |
| 535 | (4-Chloro-2-{2-[3-(4-fluoro-indazol-1-yl)-propionyl]-2,3-dihydro-1H-isoindol-1-yl}-phenoxy)-acetic acid (enantiomer 1) | C26H21N3O4ClF 493.92 | 1.02 LC-MS 1FA | 494.3 |
| 536 | (4-Chloro-2-{2-[3-(7-chloro-indazol-1-yl)-propionyl]-2,3-dihydro-1H-isoindol-1-yl}-phenoxy)-acetic acid (enantiomer 1) | C26H21N3O4Cl2 510.38 | 1.02 LC-MS 1FA | 510.2 |
| 537 | (4-Chloro-2-{2-[3-(7-fluoro-indazol-1-yl)-propionyl]-2,3-dihydro-1H-isoindol-1-yl}-phenoxy)-acetic acid (enantiomer 1) | C26H21N3O4ClF 493.92 | 1.01 LC-MS 1FA | 494.2 |
| 538 | (4-Chloro-2-{2-[3-(4-fluoro-3-methyl-indazol-1-yl)-propionyl]-2,3-dihydro-1H-isoindol-1-yl}-phenoxy)-acetic acid (enantiomer 2) | C27H23N3O4ClF 507.95 | 1.05 LC-MS 1FA | 508.3 |
| 539 | (4-Chloro-2-{2-[3-(4-chloro-3-methyl-indazol-1-yl)-propionyl]-2,3-dihydro-1H-isoindol-1-yl}-phenoxy)-acetic acid (enantiomer 2) | C27H23N3O4Cl2 524.40 | 1.11 LC-MS 1FA | 524.2 |
| 540 | (4-Chloro-2-{2-[3-(7-fluoro-3-methyl-indazol-1-yl)-propionyl]-2,3-dihydro-1H-isoindol-1-yl}-phenoxy)-acetic acid (enantiomer 2) | C27H23N3O4ClF 507.95 | 1.04 LC-MS 1FA | 508.2 |
| 541 | (4-Chloro-2-{2-[3-(6-fluoro-3-methyl-indazol-1-yl)-propionyl]-2,3-dihydro-1H-isoindol-1-yl}-phenoxy)-acetic acid (enantiomer 2) | C27H23N3O4ClF 507.95 | 1.03 LC-MS 1FA | 508.2 |
| 542 | (4-Chloro-2-{2-[3-(6-chloro-3-methyl-indazol-1-yl)-propionyl]-2,3-dihydro-1H-isoindol-1-yl}-phenoxy)-acetic acid (enantiomer 2) | C27H23N3O4Cl2 524.40 | 1.09 LC-MS 1FA | 524.2 |
| 543 | (4-Chloro-2-{2-[3-(5-fluoro-indazol-1-yl)-propionyl]-2,3-dihydro-1H-isoindol-1-yl}-phenoxy)-acetic acid (enantiomer 2) | C26H21N3O4ClF 493.92 | 1.00 LC-MS 1FA | 494.2 |
| 544 | (4-Chloro-2-{2-[3-(5-chloro-indazol-1-yl)-propionyl]-2,3-dihydro-1H-isoindol-1-yl}-phenoxy)-acetic acid (enantiomer 2) | C26H21N3O4Cl2 510.38 | 1.06 LC-MS 1FA | 510.2 |
| 545 | (4-Chloro-2-{2-[3-(3-methyl-indazol-1-yl)-propionyl]-2,3-dihydro-1H-isoindol-1-yl}-phenoxy)-acetic acid (enantiomer 2) | C27H24N3O4Cl 489.96 | 1.02 LC-MS 1FA | 490.3 |
| 546 | (4-Chloro-2-{2-[3-(6-fluoro-indazol-1-yl)-propionyl]-2,3-dihydro-1H-isoindol-1-yl}-phenoxy)-acetic acid (enantiomer 2) | C26H21N3O4ClF 493.92 | 1.00 LC-MS 1FA | 494.2 |
| 547 | (4-Chloro-2-{2-[3-(4-fluoro-indazol-1-yl)-propionyl]-2,3-dihydro-1H-isoindol-1-yl}-phenoxy)-acetic acid (enantiomer 2) | C26H21N3O4ClF 493.92 | 1.02 LC-MS 1FA | 494.2 |
| 548 | (4-Chloro-2-{2-[3-(7-chloro-indazol-1-yl)-propionyl]-2,3-dihydro-1H-isoindol-1-yl}-phenoxy)-acetic acid (enantiomer 2) | C26H21N3O4Cl2 510.38 | 1.02 LC-MS 1FA | 510.2 |
| 549 | (4-Chloro-2-{2-[3-(6-chloro-indazol-1-yl)-propionyl]-2,3-dihydro-1H-isoindol-1-yl}-phenoxy)-acetic acid (enantiomer 2) | C26H21N3O4Cl2 510.38 | 1.06 LC-MS 1FA | 510.2 |
| 550 | (4-Chloro-2-{2-[3-(4-chloro-indazol-1-yl)-propionyl]-2,3-dihydro-1H-isoindol-1-yl}-phenoxy)-acetic acid (enantiomer 2) | C26H21N3O4Cl2 510.38 | 1.07 LC-MS 1FA | 510.2 |
| 551 | (4-Chloro-2-{2-[3-(7-fluoro-indazol-1-yl)-propionyl]-2,3-dihydro-1H-isoindol-1-yl}-phenoxy)-acetic acid (enantiomer 2) | C26H21N3O4ClF 493.92 | 1.01 LC-MS 1FA | 494.2 |

Urea Formation and Subsequent Saponification

To a solution of (±)-[4-chloro-2-(2,3-dihydro-1H-isoindol-1-yl)-phenoxy]-acetic acid ethyl ester hydrochloride (40 mg, 0.11 mmol, 1.00 eq.) and NEt$_3$ (45 µL, 0.33 mmol, 3.00 eq.) in MeCN (1 mL), a solution of 2-fluorobenzyl isocyanate (17 mg, 0.11 mmol, 1.05 eq.) in MeCN (1 mL) was added. The mixture was stirred at r.t. for 18 hours. 1M aq. NaOH (0.50 mL) was added and the solution was stirred at r.t. for 18 hours. The solution was neutralized with formic acid (ca. 1 mL) and then purified by prep. HPLC (column: Atlantis, 30×75 mm, 10 um, UV/MS, acidic conditions) and concentrated in vacuo (Genevac) to give the desired acid.

Listed in Table 33 below are examples of compounds of Formula (I), prepared according to the above-mentioned method with the corresponding amine of Structure 2 and the corresponding isocyanate as starting materials.

TABLE 33

| Example | Compound of Formula (I) | Formula MW | $t_R$ [min] LC-MS Method | MS-data m/z [M + H]$^+$ |
|---|---|---|---|---|
| 552 | (±)-{4-Chloro-2-[2-(2-fluoro-benzylcarbamoyl)-2,3-dihydro-1H-isoindol-1-yl]-phenoxy}-acetic acid | C24H20N2O4ClF 454.88 | 0.97 LC-MS 1FA | 455.2 |
| 553 | (±)-{4-Chloro-2-[2-(3-fluoro-benzylcarbamoyl)-2,3-dihydro-1H-isoindol-1-yl]-phenoxy}-acetic acid | C24H20N2O4ClF 454.88 | 0.98 LC-MS 1FA | 455.2 |
| 554 | (±)-{4-Chloro-2-[2-(4-fluoro-benzylcarbamoyl)-2,3-dihydro-1H-isoindol-1-yl]-phenoxy}-acetic acid | C24H20N2O4ClF 454.88 | 0.98 LC-MS 1FA | 455.2 |
| 555 | (±)-[2-(2-Benzylcarbamoyl-2,3-dihydro-1H-isoindol-1-yl)-4-chloro-phenoxy]-acetic acid | C24H21N2O4Cl 436.89 | 0.97 LC-MS 1FA | 437.2 |
| 556 | (±)-[4-Chloro-2-(2-phenethylcarbamoyl-2,3-dihydro-1H-isoindol-1-yl)-phenoxy]-acetic acid | C25H23N2O4Cl 450.92 | 1.00 LC-MS 1FA | 451.2 |
| 557 | (±)-{4-Chloro-2-[2-(2-chloro-benzylcarbamoyl)-2,3-dihydro-1H-isoindol-1-yl]-phenoxy}-acetic acid | C24H20N2O4Cl2 471.34 | 1.01 LC-MS 1FA | 471.2 |

Phenol Alkylation and Subsequent Saponification

To a solution of (±)-4,5-dichloro-1-(5-chloro-2-hydroxy-phenyl)-1,3-dihydro-isoindole-2-carboxylic acid benzyl ester (25 mg, 0.06 mmol, 1.0 eq.) and cesium carbonate (37 mg, 0.11 mmol, 2.0 eq.) in DMF (1.0 mL), ethyl bromoacetate (7.5 µL, 0.07 mmol, 1.2 eq.) was added. The resulting solution was stirred at r.t. for 18 hours. 1M aq. NaOH (0.50 mL) was added. The mixture was stirred at r.t. for 2 hours. The solution was neutralized with formic acid (0.50 mL) and then purified by prep. HPLC (column: Atlantis, 18×50 mm, 10 um, UV/MS, acidic conditions) and concentrated in vacuo to give the desired acid.

Listed in Table 34 below are examples of compounds of Formula (I), prepared according to the above-mentioned method with the corresponding phenols 30 as starting materials.

TABLE 34

| Example | Compound of Formula (I) | Formula MW | $t_R$ [min] LC-MS Method | MS-data m/z [M + H]$^+$ |
|---|---|---|---|---|
| 558 | (±)-1-(2-Carboxymethoxy-5-chloro-phenyl)-4,5-dichloro-1,3-dihydro-isoindole-2-carboxylic acid benzyl ester | C24H18NO5Cl3 506.77 | 1.24 LC-MS 1FA | 506.1 |
| 559 | (±)-1-(2-Carboxymethoxy-5-chloro-phenyl)-4,5-difluoro-1,3-dihydro-isoindole-2-carboxylic acid benzyl ester | C24H18NO5ClF2 473.86 | 1.14 LC-MS 1FA | 474.1 |

Example 560

{4-Chloro-2-[(S)-2-((1R,2R)-2-o-tolyl-cyclopropanecarbonyl)-1,2,3,4-tetrahydro-isoquinolin-1-yl]-phenoxy}-acetic acid (C28H26NO4Cl, MW=475.97) and

Example 561

{4-Chloro-2-[(S)-2-((1S,2S)-2-o-tolyl-cyclopropanecarbonyl)-1,2,3,4-tetrahydro-isoquinolin-1-yl]-phenoxy}-acetic acid (C28H26NO4Cl, MW=475.97)

{4-Chloro-2-[(S)-2-(trans-2-o-tolyl-cyclopropanecarbonyl)-1,2,3,4-tetrahydro-isoquinolin-1-yl]-phenoxy}-acetic acid (mixture of 2 diastereoisomers) was separated by chiral prep. HPLC (column: (R,R)-Whelk-01, 5 um, 21.1×250 mm, Hept/EtOH+0.1% TFA 6:4, flow 16 mL/min) to give {4-chloro-2-[(S)-2-((1R,2R)-2-o-tolyl-cyclopropanecarbonyl)-1,2,3,4-tetrahydro-isoquinolin-1-yl]-phenoxy}-acetic acid (LC-MS 1FA: $t_R$=1.15 min; [M+H]$^+$=476.3) and {4-chloro-2-[(S)-2-((1S,2S)-2-o-tolyl-cyclopropanecarbonyl)-1,2,3,4-tetrahydro-isoquinolin-1-yl]-phenoxy}-acetic acid (LC-MS 1FA: $t_R$=1.18 min; [M+H]$^+$=476.3).

Example 562

(4-Chloro-2-{(S)-2-[(1R,2R)-2-(2-trifluoromethyl-phenyl)-cyclopropanecarbonyl]-1,2,3,4-tetrahydro-isoquinolin-1-yl}-phenoxy)-acetic acid (C28H23NO4ClF3, MW=529.94) and

Example 563

(4-Chloro-2-{(S)-2-[(1S,2S)-2-(2-trifluoromethyl-phenyl)-cyclopropanecarbonyl]-1,2,3,4-tetrahydro-isoquinolin-1-yl}-phenoxy)-acetic acid (C28H23NO4ClF3, MW=529.94)

(4-Chloro-2-{(S)-2-[trans-2-(2-trifluoromethyl-phenyl)-cyclopropanecarbonyl]-1,2,3,4-tetrahydro-isoquinolin-1-yl}-phenoxy)-acetic acid (mixture of 2 diastereoisomers) was separated by chiral prep. HPLC (column: (R,R)-Whelk-01, 5 um, 21.1×250 mm, Hept/EtOH+0.1% TFA 7:3, flow 16 mL/min) to give (4-chloro-2-{(S)-2-[(1R,2R)-2-(2-trifluoromethyl-phenyl)-cyclopropanecarbonyl]-1,2,3,4-tetrahydro-isoquinolin-1-yl}-phenoxy)-acetic acid (LC-MS 1FA: $t_R$=1.17 min; [M+H]$^+$=530.3) and (4-chloro-2-{(S)-2-[(1S,2S)-2-(2-trifluoromethyl-phenyl)-cyclopropanecarbonyl]-1,2,3,4-tetrahydro-isoquinolin-1-yl}-phenoxy)-acetic acid (LC-MS 1FA: $t_R$=1.19 min; [M+H]$^+$=530.3).

Example 564

(4-Chloro-2-{(S)-2-[(1R,2R)-2-(3-chloro-phenyl)-cyclopropanecarbonyl]-1,2,3,4-tetrahydro-isoquinolin-1-yl}-phenoxy)-acetic acid (C27H23NO4Cl2, MW=496.39)

(4-Chloro-2-{(S)-2-[trans-2-(3-chloro-phenyl)-cyclopropanecarbonyl]-1,2,3,4-tetrahydro-isoquinolin-1-yl}-phenoxy)-acetic acid (mixture of 2 diastereoisomers) was separated by chiral prep. HPLC (column: Daicel, ChiralPak IA, 5 um, 20×250 mm, Hept/EtOH+0.1% TFA 85:15, flow 16 mL/min) to give (4-chloro-2-{(S)-2-[(1R,2R)-2-(3-chloro-phenyl)-cyclopropanecarbonyl]-1,2,3,4-tetrahydro-isoquinolin-1-yl}-phenoxy)-acetic acid (LC-MS 1FA: $t_R$=1.17 min; [M+H]$^+$=496.2).

Example 565

(4-Chloro-2-{(S)-2-[(1R,2R)-2-(3-fluoro-phenyl)-cyclopropanecarbonyl]-1,2,3,4-tetrahydro-isoquinolin-1-yl}-phenoxy)-acetic acid (C27H23NO4ClF, MW=479.93)

(4-Chloro-2-{(S)-2-[trans-2-(3-fluoro-phenyl)-cyclopropanecarbonyl]-1,2,3,4-tetrahydro-isoquinolin-1-yl}-phenoxy)-acetic acid (mixture of 2 diastereoisomers) was separated by chiral prep. HPLC (column: Daicel, ChiralPak IA, 5 um, 20×250 mm, Hept/EtOH+0.1% TFA 8:2, flow mL/min) to give (4-chloro-2-{(S)-2-[(1R,2R)-2-(3-fluoro-phenyl)-cyclopropanecarbonyl]-1,2,3,4-tetrahydro-isoquinolin-1-yl}-phenoxy)-acetic acid (LC-MS 1FA: $t_R$=1.12 min; [M+H]$^+$=480.3).

Example 566

(4-Chloro-2-{(S)-2-[(1R,2R)-2-(4-fluoro-phenyl)-cyclopropanecarbonyl]-1,2,3,4-tetrahydro-isoquinolin-1-yl}-phenoxy)-acetic acid (C27H23NO4ClF, MW=479.93)

(4-Chloro-2-{(S)-2-[trans-2-(4-fluoro-phenyl)-cyclopropanecarbonyl]-1,2,3,4-tetrahydro-isoquinolin-1-yl}-phenoxy)-acetic acid (mixture of 2 diastereoisomers) was separated by chiral prep. HPLC (column: Daicel, ChiralPak IA, 5 um, 20×250 mm, Hept/EtOH+0.1% TFA 75:25, flow 16 mL/min) to give (4-chloro-2-{(S)-2-[(1R,2R)-2-(4-fluoro-phenyl)-cyclopropanecarbonyl]-1,2,3,4-tetrahydro-isoquinolin-1-yl}-phenoxy)-acetic acid (LC-MS 1FA: $t_R$=1.12 min; [M+H]$^+$=480.3).

Example 567

(S)-benzyl 1-(5-chloro-2-(2-cyanamido-2-oxoethoxy)phenyl)-3,4-dihydroisoquinoline-2(1H)-carboxylate (C26H22N3O4Cl, MW=475.93)

To a solution of (S)-1-(2-carboxymethoxy-5-chloro-phenyl)-3,4-dihydro-1H-isoquinoline-2-carboxylic acid benzyl ester (138 mg, 0.30 mmol, 1.0 eq.), cyanamide (16 mg, 0.36 mmol, 1.2 eq.), and NEt$_3$ (84 µL, 0.60 mmol, 2 eq.) in DMF (3.3 mL), HATU (137 mg, 0.36 mmol, 1.2 eq.) was added. The reaction mixture was stirred at r.t. for 1 hour. The mixture was purified by prep. HPLC (column: Waters XBridge, 30×75 mm, 10 um, UV/MS, basic conditions) and evaporated to give a pale yellow oil, contaminated with NEt$_3$. The contaminated product was redissolved in AcOEt and washed with 1M aq. HCl soln. and sat. aq. NaCl soln. The org. phase was dried over MgSO$_4$, filtered and concentrated in vacuo to give the desired product as a pale yellow oil.

LC-MS 1FA: $t_R$=1.27 min; [M+H]$^+$=476.1

Example 568

(S)-1-[5-Chloro-2-(2-oxo-2-trifluoromethanesulfonylamino-ethoxy)-phenyl]-3,4-dihydro-1H-isoquinoline-2-carboxylic acid benzyl ester (C26H22N2O6ClF3S, MW=582.98)

To a solution of (S)-1-(2-carboxymethoxy-5-chloro-phenyl)-3,4-dihydro-1H-isoquinoline-2-carboxylic acid benzyl ester (138 mg, 0.30 mmol, 1.0 eq.) in DMF (1.2 mL), trifluoromethanesulfonamide (47 mg, 0.30 mmol, 1.0 eq.), HATU (125 mg, 0.33 mmol, 1.1 eq.), DIPEA (103 µL, 0.60 mmol, 2.0 eq.), and DMAP (spatula tip) were added. The resulting mixture was stirred at 50° C. for 18 hours. The mixture was then purified by prep. HPLC (column: Waters XBridge, 30×75 mm, 10 um, UV/MS, basic conditions) and evaporated to give a white-off solid, contaminated with some DIPEA. The contaminated product was redissolved in AcOEt and washed with 1M aq. HCl soln. and sat. aq. NaCl soln. The org. phase was dried over MgSO$_4$, filtered, and concentrated in vacuo to give the desired product as a white-off solid.

LC-MS 1FA: $t_R$=1.19 min; [M+H]$^+$=583.1

Example 569

(S)-1-(5-Chloro-2-hydroxycarbamoylmethoxy-phenyl)-3,4-dihydro-1H-isoquinoline-2-carboxylic acid benzyl ester (C25H23N2O5Cl, MW=466.92)

To an ice-cooled solution of (S)-1-(5-chloro-2-ethoxycarbonylmethoxy-phenyl)-3,4-dihydro-1H-isoquinoline-2-carboxylic acid benzyl ester (144 mg, 0.30 mmol, 1.0 eq.) in isopropanol (1.5 mL), hydroxylamine (50% w/w aqueous solution, 1.5 mL) was added. The ice bath was removed and the reaction mixture was stirred at r.t. for 18 hours. The reaction mixture was concentrated to half and water (5 mL) was added. The resulting suspension was filtered, washed with water and dried under hv to give the desired product as a white solid.

LC-MS 1FA: $t_R$=1.13 min; [M+H]$^+$=467.3

Example 570

(γ)-1-[5-Chloro-2-(1H-tetrazol-5-ylmethoxy)-phenyl]-3,4-dihydro-1H-isoquinoline-2-carboxylic acid benzyl ester (C25H22N5O3Cl, MW=475.94)

Sodium azide (49 mg, 0.75 mmol, 3 eq.) was added to a solution of (±)-1-(5-chloro-2-cyanomethoxy-phenyl)-3,4-dihydro-1H-isoquinoline-2-carboxylic acid benzyl ester (108 mg, 0.25 mmol, 1 eq.) in DMF (4.6 mL). The reaction mixture was heated up to 100° C. and stirred at that temperature for 18 hours. The mixture was allowed to cool to r.t. and purified by prep. HPLC (column: Waters XBridge, 30×75 mm, 10 um, UV/MS, basic conditions) and evaporated (genevac) to give the desired product as a white solid.

LC-MS 1 FA: $t_R$=1.21 min; [M+H]$^+$=476.3

Example 571

(S)-1-[5-Chloro-2-(5-oxo-4,5-dihydro-[1,3,4]oxadiazol-2-ylmethoxy)-phenyl]-3,4-dihydro-1H-isoquinoline-2-carboxylic acid benzyl ester (C26H22N3O5Cl, MW=491.93)

To an ice-cooled solution of (S)-1-(5-chloro-2-hydrazinocarbonylmethoxy-phenyl)-3,4-dihydro-1H-isoquinoline-2-carboxylic acid benzyl ester (137 mg, 0.29 mmol, 1.0 eq.) and NEt$_3$ (82 µL, 0.59 mmol, 2.0 eq.) in THF (3 mL), 1,1'-carbonyldiimidazole (72 mg, 0.44 mmol, 1.5 eq.) was added. The reaction mixture was stirred at r.t. for 1 hour. The solvent was removed in vacuo. The residue, redissolved in DMF (2.4 mL), was purified by prep. HPLC (column: Waters X-Bridge, 30×75 mm, 10 um, UV/MS, acidic conditions) and evaporated to give the desired product as a white foam.

LC-MS 1FA: $t_R$=1.14 min; [M+H]$^+$=492.3

Example 572

(±)-1-[5-Chloro-2-(5-oxo-4,5-dihydro-[1,2,4]oxadiazol-3-ylmethoxy)-phenyl]-3,4-dihydro-1H-isoquinoline-2-carboxylic acid benzyl ester (C26H22N3O5Cl, MW=491.93)

A solution of (±)-1-[5-chloro-2-(N-hydroxycarbamimidoylmethoxy)-phenyl]-3,4-dihydro-1H-isoquinoline-2-carboxylic acid benzyl ester (93 mg, 0.20 mmol, 1.0 eq.), 1,1'-carbonyldiimidazole (39 mg, 0.24 mmol, 1.2 eq.) and 1,8-diazabicyclo[5.4.0]undec-7-ene (33 µL, 0.22 mmol, 1.1 eq.) in THF (2.7 mL) was heated at 120° C. under microwave irradiation for 20 min. The mixture was allowed to cool to r.t. and partitioned between AcOEt and 0.5M aq. HCl soln. The org. phase was washed with 0.5M aq. HCl soln. and sat. aq. NaCl soln., dried over MgSO$_4$, filtered, and concentrated in vacuo. The residue was purified by prep. HPLC (column: Waters XBridge, 30×75 mm, 10 um, UV/MS, acidic conditions) and concentrated in vacuo to give the desired product as a white solid.

LC-MS 1 FA: $t_R$=1.21 min; [M+H]$^+$=492.3

Example 573

(±)-1-[5-Chloro-2-(3-hydroxy-isoxazol-5-ylmethoxy)-phenyl]-3,4-dihydro-1H-isoquinoline-2-carboxylic acid benzyl ester (C27H23N2O5Cl, MW=490.94)

To an ice-cooled solution of (±)-5-[4-chloro-2-(1,2,3,4-tetrahydro-isoquinolin-1-yl)-phenoxymethyl]-isoxazol-3-ol (49 mg, 0.138 mmol, 1.0 eq.) and NEt$_3$ (58 µL, 0.414 mmol, 3.0 eq.) in DCM (3.8 mL), benzyl chloroformate (23 µL, 0.152 mmol, 1.1 eq.) was added dropwise. Upon completion of the addition, the cooling bath was removed and the suspension was stirred at r.t. for 4 hours. The reaction was quenched with 1M aq. citric acid soln. (3.8 mL). The layers were separated. The aq. phase was extracted with DCM (3×). The comb. org. phases were concentrated in vacuo. The residue, redissolved in DMF, was purified by prep. HPLC (column: Waters XBridge, 30×75 mm, 10 um, UV/MS, acidic conditions) and evaporated (genevac) to give the desired product as a pale yellow solid.

LC-MS 1TFA: $t_R$=1.16 min; [M+H]$^+$=491.2

Synthesis of Precursors and Intermediates

General Method for the Synthesis of the Nitrostyrenes 22

A benzaldehyde 23 (40.00 mmol, 1 eq.) was dissolved in nitromethane (23.8 mL). Molecular sieves 4A (766 mg), butylamine (0.47 mL, 4.72 mmol, 0.12 eq.) and acetic acid (0.47 ml, 8.16 mmol, 0.20 eq.) were added and the mixture was heated to 95° C. for 1 hour. The mixture was transferred into a new flask to remove the molecular sieves. The solvent was removed in vacuo. The residue was purified by CC (SiO$_2$, eluent: Hept/AcOEt) to give the desired nitrostyrene.

Listed in Table 35 below are nitrostyrenes 22, prepared according to the above-mentioned method, with corresponding benzaldehyde 23 as starting material.

TABLE 35

| Nitrostyrene 22 | Formula MW | $t_R$ [min] LC-MS Method | MS-data m/z [M + H]+ |
|---|---|---|---|
| 1,2-Difluoro-4-((E)-2-nitro-vinyl)-benzene | C8H5NO2F2 185.13 | 0.86 LC-MS 2 | no ionization |
| 2-Bromo-1-fluoro-3-((E)-2-nitro-vinyl)-benzene | C8H5NO2BrF 246.04 | 0.78 LC-MS 3 | no ionization |
| 1,2-Difluoro-3-((E)-2-nitro-vinyl)-benzene | C8H5NO2F2 185.13 | 0.76 LC-MS 2 | no ionization |
| 2,4-Difluoro-1-((E)-2-nitro-vinyl)-benzene | C8H5NO2F2 185.13 | 0.84 LC-MS 3 | no ionization |

General Method for the Preparation of the phenethylamines (or the Corresponding Hydrochloride Salt) 21

$H_2SO_4$ (2.870 mL) was added dropwise to a stirred suspension of $LiAlH_4$ (4.30 g, 107.6 mmol, 4.46 eq.) in THF (162 mL) under ice-cooling. After stirring for 20 min, a solution of a nitrostyrene 22 (24.1 mmol, 1.00 eq.) in THF (17 mL) was added dropwise within 20 min under ice-cooling. After 10 min the cooling bath was removed and the mixture was warmed up gently by using a heat gun until the mixture gently boiled. After 5 min the mixture was again cooled to 0° C. The reaction was carefully quenched by the dropwise addition of iPrOH (18 mL), followed by 2M aq. NaOH (13 mL). The resulting suspension was filtered off and the filter cake was rinsed with THF. The fitrate was concentrated in vacuo to give the desired phenethylamine. The free amine was dissolved in $Et_2O$ (88 mL) containing iPrOH (3 mL) and acidified with 2M HCl in $Et_2O$ soln. (46 mL). The resulting suspension was filtered off. The white solids were rinsed with $Et_2O$ and dried under high vacuum. The desired phenethylamine salt was used without further purification.

Listed in Table 36 below are phenethylamines 21 and phenethylamine hydrochlorides 21, prepared according to the above-mentioned method, with corresponding nitrostyrenes 22 as starting material.

TABLE 36

| Intermediates 21 | Formula MW | $t_R$ [min] LC-MS Method | MS-data m/z [M + H]+ |
|---|---|---|---|
| 2-(3,4-Difluoro-phenyl)-ethylamine hydrochloride | C8H9NF2 157.07 | 0.40 LC-MS 2 | no ionization |
| 2-(2-Bromo-3-fluoro-phenyl)-ethylamine | C8H9NBrF 218.07 | 0.40 LC-MS 3 | 218.1 |
| 2-(2,3-Difluoro-phenyl)-ethylamine hydrochloride | C8H9NF2 157.07 | 0.37 LC-MS 2 | 158.2 |
| 2-(2,4-Difluoro-phenyl)-ethylamine hydrochloride | C8H9NF2 157.07 | 0.43 LC-MS 3 | 158.0 |

Synthesis of 2-methyl-2-phenyl-propylamine
(C10H15N, MW=149.24)

Step 1: To a suspension of benzyl cyanide (2.34 mL, 20.0 mmol, 1.0 eq.) and NaOH (3.22 g, 80.5 mmol, 4.0 eq.) in a mixture of DMSO (19 mL) and water (3.2 mL), methyl iodide (5.0 mL, 80.0 mmol, 4.0 eq.) was added dropwise at 0° C. The resulting mixture was stirred at r.t. for 18 hours. The mixture was partitioned between $Et_2O$ (125 mL) and water (125 mL). The layers were separated and the aq. phase was extracted with $Et_2O$ (2×50 mL). The comb. org. phases were washed with sat. aq. NaCl soln. (1×25 mL), dried over $MgSO_4$, and concentrated in vacuo to give 2-methyl-2-phenyl-propionitrile. The product was used without further purification.

Step 2: To an ice-cooled suspension of LAH (1.43 g, 35.7 mmol, 1.5 eq.) in dry $Et_2O$ (70.0 mL) under $N_2$, a solution of 2-methyl-2-phenyl-propionitrile (3.46 g, 23.8 mmol, 1.0 eq.) in dry $Et_2O$ (3.0 mL) was added dropwise over 30 min. After 30 min the cooling bath was removed and the mixture was stirred at r.t. for 3 hours. The mixture was again cooled to 0° C. and carefully quenched by the dropwise addition of iPrOH (35 mL) and then 2M aq. NaOH (20 mL). The resulting suspension was filtered through celite and the filter cake was rinsed with THF. The fitrate was concentrated in vacuo. The residue was partitioned between DCM (125 mL) and 1M aq. NaOH (125 mL). The layers were separated and the aq. phase was extracted with DCM (2×50 mL). The comb. org. phases were washed with sat. aq. NaCl soln. (1×25 mL), dried over $MgSO_4$, and concentrated in vacuo. The resulting 2-methyl-2-phenyl-propylamine was used without further purification.

LC-MS 2: $t_R$=0.39 min; [M+H]+=150.2 (Waters X-bridge)

General Method for the Synthesis of the 3,4-dihydroisoquinolines 11

Method A: A mixture of a phenethylamine hydrochloride 21 (12.45 mmol, 1.0 eq.), triethylamine (3.47 mL, 24.89 mmol, 2.0 eq.) and ethyl formiate (1.01 g, 13.69 mmol, 1.1 eq.) was stirred at 70° C. for 4 hours. The reaction mixture was allowed to cool to r.t. and partitioned between AcOEt (65 mL) and water (65 mL). The layers were separated. The org. phase was washed with water (1×65 mL), sat. aq. NaCl soln. (1×65 mL), dried over $MgSO_4$, and concentrated in vacuo to give the corresponding formamide. The formamide was dissolved in DCM (125 mL). Oxalyl chloride (1.18 mL, 13.69 mmol, 1.1 eq.) was added. The mixture was stirred at r.t. for 30 min, then cooled to −10° C. Iron(III) chloride anhydrous (2.42 g, 14.94 mmol, 1.2 eq.) was added to the cold mixture. The resulting mixture was allowed to slowly warm to r.t. and stirred at r.t. for 18 hours. The reaction was quenched with 2M aq. HCl soln. (125 mL) and the biphasic system was stirred at r.t. for 1 hour. The layers were separated. The aq. phase was extracted with DCM (1×65 mL). The comb. org. phases were washed with sat. aq. NaCl soln. (1×65 mL), dried over $MgSO_4$, and concentrated in vacuo to give the oxazolo intermediate. The oxazolo intermediate was dissolved in MeOH (142 mL) and conc. $H_2SO_4$ (7.5 mL). The resulting mixture was refluxed during 3 hours. The mixture was allowed to cool to r.t. and concentrated in vacuo. The residue was partitioned between water (65 mL) and AcOEt (65 mL). The layers were separated. The org. phase was extracted with 2M aq. HCl (2×30 mL). The three comb. acidic aq. phases were basified with 25% $NH_3$ and extracted with DCM (3×65 mL). The comb. org. phases were washed with sat. aq. NaCl soln. (1×65 mL), dried over $MgSO_4$ and concentrated in vacuo to give the desired 3,4-dihydro-isoquinoline as a yellow solid. The residue was used without further purification.

Listed in Table 37 below are 3,4-dihydroisoquinolines 11, prepared according to the above-mentioned method, with corresponding phenethylamines (or the corresponding hydrochloride salt) 21 as starting material.

TABLE 37

| Intermediates 11 | Formula MW | $t_R$ [min] LC-MS Method | MS-data m/z [M + H]+ |
|---|---|---|---|
| 7-Bromo-3,4-dihydro-isoquinoline | C9H8NBr 210.07 | 0.44 LC-MS 2 | 212.3 |
| 5-Bromo-3,4-dihydro- | C9H8NBr | 0.45 | 212.2 |

TABLE 37-continued

| Intermediates 11 | Formula MW | $t_R$ [min] LC-MS Method | MS-data m/z [M + H]$^+$ |
|---|---|---|---|
| isoquinoline | 210.07 | LC-MS 2 | |
| 6,7-Difluoro-3,4-dihydro-isoquinoline | C9H7NF2 167.16 | 0.31 LC-MS 2 | 168.0 |
| 5-Methoxy-3,4-dihydro-isoquinoline | C10H11NO 161.20 | 0.41 LC-MS 3 | 162.1 |
| 5-Fluoro-3,4-dihydro-isoquinoline | C9H8NF 149.17 | 0.26 LC-MS 2 | 150.2 |
| 6,7-Dimethoxy-3,4-dihydro-isoquinoline | C11H13NO2 191.23 | 0.42 LC-MS 3 | 192.5 |
| 7-Methoxy-3,4-dihydro-isoquinoline | C10H11NO 161.20 | 0.40 LC-MS 3 | 161.9 |
| 5-Chloro-3,4-dihydro-isoquinoline | C9H8NCl 165.62 | 0.37 LC-MS 3 | 166.0 |
| 5-Methyl-3,4-dihydro-isoquinoline | C10H11N 145.20 | 0.36 LC-MS 3 | 146.1 |
| 5-Trifluoromethyl-3,4-dihydro-isoquinoline | C10H8NF3 199.18 | 0.40 LC-MS 2 | 200.3 |
| 7-Fluoro-3,4-dihydro-isoquinoline | C9H8NF 149.17 | 0.24 LC-MS 3 | 150.1 |
| 5-Bromo-6-fluoro-3,4-dihydro-isoquinoline | C9H7NBrF 228.06 | 0.38 LC-MS 3 | 228.0 |
| 5,6-Difluoro-3,4-dihydro-isoquinoline | C9H7NF2 167.16 | 0.32 LC-MS 2 | 168.0 |
| 5,7-Difluoro-3,4-dihydro-isoquinoline | C9H7NF2 167.16 | 0.38 LC-MS 3 | 168.0 |
| 4,4-Dimethyl-3,4-dihydro-isoquinoline | C11H13N 159.23 | 0.45 LC-MS 3 | 160.1 |
| 6-Fluoro-3,4-dihydro-isoquinoline | C9H8NF 149.17 | 0.36 LC-MS 3 | 150.2 |

Method B: Synthesis of 3,4-dihydro-isoquinoline (C9H9N, MW=131.18): N-Bromosuccinimide (9.89 g, 55.0 mmol, 1.1 eq.) was added cautiously and portionwise over 20 min to a solution of 1,2,3,4-tetrahydroisoquinoline (6.34 mL, 50.0 mmol, 1.0 eq.) in DCM (130 mL) at r.t. The mixture was stirred at r.t. for 1.5 hour. 30% aq. NaOH (35 mL) was added and the mixture was stirred at r.t. for 2 hours. The organic layer was separated and washed with water (1×70 mL). The product was extracted with 10% aq. HCl (2×80 mL). The combined acidic extracts were washed with DCM (1×80 mL) and basified with 25% NH$_3$. The resulting mixture was extracted with DCM (2×80 mL). The comb. org. extracts were dried over MgSO$_4$, filtered and concentrated in vacuo to yield the 3,4-dihydroisoquinoline as an orange oil. The product was used without further purification.

LC-MS 2: $t_R$=0.23 min; [M+H]$^+$=132.1

General Method for the Synthesis of the tetrahydroisoquinolines 13

Method A: Benzyl chloroformate (0.33 mL, 2.17 mmol, 1.0 eq.) was added to a solution of a 3,4-dihydroisoquinoline 11 (2.17 mmol, 1.0 eq.) in MeCN (4 mL) at r.t. under an argon atmosphere. After 30 min of stirring, a phenol 12 (2.17 mmol, 1.0 eq.) was added and the mixture was stirred at 70° C. for 4 days. The reaction mixture was allowed to cool to r.t., diluted with AcOEt, washed with 2M aq. HCl, water, and sat. aq. NaCl soln., dried over MgSO$_4$, filtered and concentrated in vacuo. The product was purified by flash master (Hept/AcOEt) to yield the desired tetrahydroisoquinoline 13 as a white foam.

Listed in Table 38 below are tetrahydroisoquinolines 13, prepared according to the above-mentioned method, with corresponding 3,4-dihydroisoquinolines 11 and phenol 12 as starting materials.

TABLE 38

| Intermediates 13 | Formula MW | $t_R$ [min] LC-MS Method | MS-data m/z [M + H]$^+$ |
|---|---|---|---|
| (±)-1-(5-Fluoro-2-hydroxy-phenyl)-3,4-dihydro-1H-isoquinoline-2-carboxylic acid benzyl ester | C23H20NO3F 377.41 | 1.07 LC-MS 2 | 378.1 |
| (±)-1-(5-Chloro-2-hydroxy-phenyl)-3,4-dihydro-1H-isoquinoline-2-carboxylic acid benzyl ester | C23H20NO3Cl 393.87 | 1.11 LC-MS 2 | 394.0 |
| (±)-1-(5-Bromo-2-hydroxy-phenyl)-3,4-dihydro-1H-isoquinoline-2-carboxylic acid benzyl ester | C23H20NO3Br 438.32 | 1.12 LC-MS 2 | 439.8 |
| (±)-1-(2-Hydroxy-5-trifluoromethyl-phenyl)-3,4-dihydro-1H-isoquinoline-2-carboxylic acid benzyl ester | C24H20NO3F3 427.42 | 1.10 LC-MS 2 | 428.1 |
| (±)-1-(2-Hydroxy-5-methoxy-phenyl)-3,4-dihydro-1H-isoquinoline-2-carboxylic acid benzyl ester | C24H23NO4 389.45 | 1.04 LC-MS 2 | 390.1 |
| (±)-1-(2-Hydroxy-5-methyl-phenyl)-3,4-dihydro-1H-isoquinoline-2-carboxylic acid benzyl ester | C24H23NO3 373.45 | 1.09 LC-MS 2 | 374.1 |
| (±)-1-(2-Hydroxy-5-isopropyl-phenyl)-3,4-dihydro-1H-isoquinoline-2-carboxylic acid benzyl ester | C26H27NO3 401.50 | 1.16 LC-MS 2 | 401.7 |
| (±)-1-(6-Hydroxy-benzo[1,3]dioxol-5-yl)-3,4-dihydro-1H-isoquinoline-2-carboxylic acid benzyl ester | C24H21NO5 403.43 | 1.05 LC-MS 2 | 404.0 |
| (±)-7-Bromo-1-(5-fluoro-2-hydroxy-phenyl)-3,4-dihydro-1H-isoquinoline-2-carboxylic acid benzyl ester | C23H19NO3BrF 456.31 | 1.11 LC-MS 2 | 456.0 |
| (±)-1-(4,5-Difluoro-2-hydroxy-phenyl)-3,4-dihydro-1H-isoquinoline-2-carboxylic acid benzyl ester | C23H19NO3F2 395.40 | 1.10 LC-MS 2 | 396.0 |
| (±)-5-Fluoro-1-(5-fluoro-2-hydroxy-phenyl)-3,4-dihydro-1H-isoquinoline-2-carboxylic acid benzyl ester | C23H19NO3F2 395.40 | 0.98 LC-MS 3 | 396.0 |
| (±)-1-(5-Fluoro-2-hydroxy-phenyl)-5- | C24H22NO4F | 0.99 | 407.9 |

TABLE 38-continued

| Intermediates 13 | Formula MW | $t_R$ [min] LC-MS Method | MS-data m/z [M + H]⁺ |
|---|---|---|---|
| methoxy-3,4-dihydro-1H-isoquinoline-2-carboxylic acid benzyl ester | 407.44 | LC-MS 3 | |
| (±)-1-(5-Fluoro-2-hydroxy-phenyl)-6,7-dimethoxy-3,4-dihydro-1H-isoquinoline-2-carboxylic acid benzyl ester | C25H24NO5F 437.47 | 0.95 LC-MS 3 | 438.2 |
| (±)-1-(5-Fluoro-2-hydroxy-phenyl)-7-methoxy-3,4-dihydro-1H-isoquinoline-2-carboxylic acid benzyl ester | C24H22NO4F 407.44 | 0.97 LC-MS 3 | 408.0 |
| (±)-1-(5-Cyano-2-hydroxy-phenyl)-3,4-dihydro-1H-isoquinoline-2-carboxylic acid benzyl ester | C24H20N2O3 384.43 | 0.90 LC-MS 2 | 385.3 |
| (±)-1-(5-Fluoro-2-hydroxy-phenyl)-5-methyl-3,4-dihydro-1H-isoquinoline-2-carboxylic acid benzyl ester | C24H22NO3F 391.44 | 1.08 LC-MS 4 | 392.0 |
| (±)-5-Chloro-1-(5-fluoro-2-hydroxy-phenyl)-3,4-dihydro-1H-isoquinoline-2-carboxylic acid benzyl ester | C23H19NO3ClF 411.86 | 1.09 LC-MS 4 | 412.0 |
| (±)-1-(5-Bromo-2-hydroxy-phenyl)-6,7-difluoro-3,4-dihydro-1H-isoquinoline-2-carboxylic acid benzyl ester | C23H18NO3BrF2 474.30 | 1.02 LC-MS 2 | 473.8 |
| (±)-6,7-Difluoro-1-(5-fluoro-2-hydroxy-phenyl)-3,4-dihydro-1H-isoquinoline-2-carboxylic acid benzyl ester | C23H18NO3F3 413.39 | 0.97 LC-MS 2 | 413.9 |
| (±)-5-Bromo-1-(5-fluoro-2-hydroxy-phenyl)-3,4-dihydro-1H-isoquinoline-2-carboxylic acid benzyl ester | C23H19NO3BrF 456.31 | 1.15 LC-MS 2 | 455.8 |
| (±)-7-Fluoro-1-(5-fluoro-2-hydroxy-phenyl)-3,4-dihydro-1H-isoquinoline-2-carboxylic acid benzyl ester | C23H19NO3F2 395.40 | 0.89 LC-MS 3 | 395.9 |
| (±)-1-(5-Cyano-2-hydroxy-phenyl)-5,6-difluoro-3,4-dihydro-1H-isoquinoline-2-carboxylic acid benzyl ester | C24H18N2O3F2 420.41 | 0.93 LC-MS 2 | 421.6 |
| (±)-1-(5-Dimethylsulfamoyl-2-hydroxy-phenyl)-3,4-dihydro-1H-isoquinoline-2-carboxylic acid benzyl ester | C25H26N2O5S 466.56 | 0.90 LC-MS 2 | 467.2 |
| (±)-1-(5-Fluoro-2-hydroxy-phenyl)-5-trifluoromethyl-3,4-dihydro-1H-isoquinoline-2-carboxylic acid benzyl ester | C24H19NO3F4 445.41 | 1.02 LC-MS 2 | 446.0 |
| (±)-5-Bromo-6-fluoro-1-(5-fluoro-2-hydroxy-phenyl)-3,4-dihydro-1H-isoquinoline-2-carboxylic acid benzyl ester | C23H18NO3BrF2 474.30 | 0.93 LC-MS 3 | no ionization |
| (±)-1-(5-Chloro-2-hydroxy-phenyl)-5-fluoro-3,4-dihydro-1H-isoquinoline-2-carboxylic acid benzyl ester | C23H19NO3ClF 411.86 | 1.03 LC-MS 2 | 412.2 |
| (±)-1-(5-Cyano-2-hydroxy-phenyl)-5-fluoro-3,4-dihydro-1H-isoquinoline-2-carboxylic acid benzyl ester | C24H19N2O3F 402.42 | 0.92 LC-MS 2 | 403.3 |
| (±)-5,6-Difluoro-1-(5-fluoro-2-hydroxy-phenyl)-3,4-dihydro-1H-isoquinoline-2-carboxylic acid benzyl ester | C23H18NO3F3 413.39 | 0.99 LC-MS 2 | 414.2 |
| (±)-1-(5-Chloro-2-hydroxy-phenyl)-5,6-difluoro-3,4-dihydro-1H-isoquinoline-2-carboxylic acid benzyl ester | C23H18NO3ClF2 429.85 | 1.03 LC-MS 2 | 430.8 |
| (±)-1-(3,5-Difluoro-2-hydroxy-phenyl)-3,4-dihydro-1H-isoquinoline-2-carboxylic acid benzyl ester | C23H19NO3F2 395.40 | 0.99 LC-MS 2 | 396.2 |
| (±)-5,7-Difluoro-1-(5-fluoro-2-hydroxy-phenyl)-3,4-dihydro-1H-isoquinoline-2-carboxylic acid benzyl ester | C23H18NO3F3 413.39 | 0.99 LC-MS 3 | 414.1 |
| (±)-1-(5-Chloro-2-hydroxy-phenyl)-5,7-difluoro-3,4-dihydro-1H-isoquinoline-2-carboxylic acid benzyl ester | C23H18NO3ClF2 429.85 | 1.01 LC-MS 3 | 430.0 |
| (±)-1-(5-Cyano-2-hydroxy-phenyl)-5,7-difluoro-3,4-dihydro-1H-isoquinoline-2-carboxylic acid benzyl ester | C24H18N2O3F2 420.41 | 0.99 LC-MS 4 | 421.2 |
| (±)-5-Bromo-1-(5-chloro-2-hydroxy-phenyl)-6-fluoro-3,4-dihydro-1H-isoquinoline-2-carboxylic acid benzyl ester | C23H18NO3BrClF 490.76 | 1.04 LC-MS 3 | 492.0 |

Method B: To a solution of a 3,4-dihydroisoquinoline 11 (5.0 mmol, 1.0 eq.) in MeCN (15 mL), di-tert-butyl dicarbonate (1.09 g, 5.0 mmol, 1.0 eq.) was added. The resulting solution was stirred at r.t. for 2 hours. A phenol 12 (5.0 mmol, 1 eq.) was added and the mixture was stirred at 60° C. for 6 days. The reaction mixture was concentrated in vacuo. The residue was diluted with AcOEt (50 mL) and washed with 10% aq. HCl (1×25 mL), sat. aq. NaHCO$_3$ (1×25 mL), water (2×25 mL), sat. aq. NaCl soln. (1×25 mL), dried over MgSO$_4$, and concentrated in vacuo. The residue was purified by flash master (column: 100 g, flow: 40 mL/min, Heptane to Heptane+AcOEt) to yield the desired tetrahydroisoquinoline 13 as a white foam.

Listed in Table 39 below are tetrahydroisoquinolines 13, prepared according to the above-mentioned method, with corresponding 3,4-dihydroisoquinolines 11 and phenol 12 as starting materials.

Synthesis of (±)-1-(2-Allyloxy-4-fluoro-phenyl)-3,4-dihydro-1H-isoquinoline-2-carboxylic acid benzyl ester (C26H24NO3F, MW=417.48) and (±)-1-(2-Allyloxy-6-fluoro-phenyl)-3,4-dihydro-1H-isoquinoline-2-carboxylic acid benzyl ester (C26H24NO3F, MW=417.48)

To a solution under N$_2$ of 2-allyloxy-1-bromo-4-fluoro-benzene (462 mg, 2.00 mmol, 2.0 eq.) in THF (2 mL) cooled at −20° C., Isopropylmagnesium chloride—lithium chloride complex in THF (1:1), ca.14% in THF (320 mg, 2.20 mmol, 2.2 eq.) was added dropwise. The mixture was stirred at −20° C. for 30 min and further at 0° C. for 2 h and further at r.t. for 6 h.→Grignard Solution A To a solution of 3,4-dihydro-isoquinoline (131 mg, 1.00 mmol, 1.0 eq.) in THF (5 mL), benzyl chloroformate (0.15 mL, 1.00 mmol, 1.0 eq.) was added. The mixture was stirred

TABLE 39

| Intermediates 13 | Formula MW | $t_R$ [min] LC-MS Method | MS-data m/z [M + H]$^+$ |
|---|---|---|---|
| (±)-1-(5-Chloro-2-hydroxy-phenyl)-3,4-dihydro-1H-isoquinoline-2-carboxylic acid tert-butyl ester | C20H22NO3Cl 359.85 | 1.06 LC-MS 2 | 360.2 |
| (±)-1-(5-Chloro-2-hydroxy-phenyl)-5-fluoro-3,4-dihydro-1H-isoquinoline-2-carboxylic acid tert-butyl ester | C20H21NO3ClF 377.84 | 1.03 LC-MS 3 | 378.3 |
| (±)-1-(5-Chloro-2-hydroxy-phenyl)-4,4-dimethyl-3,4-dihydro-1H-isoquinoline-2-carboxylic acid tert-butyl ester | C22H26NO3Cl 387.91 | 1.09 LC-MS 3 | 388.3 |
| (±)-1-(5-Chloro-2-hydroxy-phenyl)-6-fluoro-3,4-dihydro-1H-isoquinoline-2-carboxylic acid tert-butyl ester | C20H21NO3ClF 377.84 | 1.02 LC-MS 3 | 378.2 |
| (±)-1-(5-Chloro-2-hydroxy-phenyl)-7-fluoro-3,4-dihydro-1H-isoquinoline-2-carboxylic acid tert-butyl ester | C20H21NO3ClF 377.84 | 1.03 LC-MS 2 | 378.2 |
| (±)-1-(5-Chloro-2-hydroxy-phenyl)-5,6-difluoro-3,4-dihydro-1H-isoquinoline-2-carboxylic acid tert-butyl ester | C20H20NO3ClF2 395.83 | 1.03 LC-MS 3 | 396.1 |
| (±)-5-Bromo-1-(5-chloro-2-hydroxy-phenyl)-6-fluoro-3,4-dihydro-1H-isoquinoline-2-carboxylic acid tert-butyl ester | C20H20NO3BrClF 456.74 | 1.06 LC-MS 3 | 457.7 |

Synthesis of 2-allyloxy-1-bromo-4-fluoro-benzene (C9H8OBrF, MW=231.06) and 1-allyloxy-2-bromo-3-fluoro-benzene (C9H8OBrF, MW=231.06)

To a mixture of 2-bromo-5-fluorophenol (2.01 g, 10.5 mmol, 1.00 eq.) and potassium carbonate anhydrous (1.60 g, 11.6 mmol, 1.10 eq.) in acetone (25 mL), allyl bromide (0.97 mL, 11.1 mmol, 1.05 eq.) was added. The mixture was heated to reflux for 4 hours. The reaction mixture was allowed to cool to r.t. and poured in water (150 mL). The mixture was extracted with DCM (2×200 mL). The comb. org. phases were dried over MgSO$_4$ and concentrated in vacuo. The residue was purified by flash master (flow: 40 mL/min, heptane to Heptane+AcOEt) to yield the protected phenol as a colorless oil.

LC-MS 3: $t_R$=0.92 min; [M+H]$^+$=no ionization

Following the same procedure, but starting from 2-bromo-3-fluorophenol, 1-allyloxy-2-bromo-3-fluoro-benzene was obtained.

LC-MS 3: $t_R$=0.92 min; [M+H]$^+$=no ionization at r.t. for 30 min. The reaction was cooled to 0° C. and the Grignard solution A was added dropwise. The mixture was stirred at 0° C. for 1 hour and further at r.t. for 18 hours. The reaction was carefully quenched with 1M aq. NH$_4$Cl (50 mL) and with AcOEt (50 mL). The resulting suspension was filtered through celite and the filter cake was rinsed with water and AcOEt. The layers were separated and the aq. phase was extracted with AcOEt (2×50 mL). The comb. org. phases were washed with sat. aq. NaCl soln. (1×50 mL), dried over MgSO$_4$, and concentrated in vacuo.

The residue was purified by prep. HPLC (column Water X-bridge, 30×75 mm, 10 um, UV/MS, basic conditions) and concentrated in vacuo.

LC-MS 2: $t_R$=1.05 min; [M+H]$^+$=417.8

Following the same procedure, but starting from 1-allyloxy-2-bromo-3-fluoro-benzene, (±)-1-(2-allyloxy-6-fluoro-phenyl)-3,4-dihydro-1H-isoquinoline-2-carboxylic acid benzyl ester was obtained.

LC-MS 3: $t_R$=1.04 min; [M+H]$^+$=417.9

Synthesis of (±)-1-(5-Cyano-2-ethoxycarbonyl-methoxy-phenyl)-6,7-difluoro-3,4-dihydro-1H-isoquinoline-2-carboxylic acid benzyl ester (C28H24N2O5F2, MW=506.50)

To a solution of (±)-1-(5-bromo-2-ethoxycarbonyl-methoxy-phenyl)-6,7-difluoro-3,4-dihydro-1H-isoquinoline-2-carboxylic acid benzyl ester (126 mg, 0.23 mmol, 1.00 eq.) in N,N-dimethylacetamide (0.45 mL) was added poly(methylhydrosiloxane) (5 µL) at r.t. The reaction mixture was heated to 120° C. and tris(dibenzylideneacetone) dipalladium (0) (4.5 mg, 0.005 mmol, 0.002 eq) then 1,1'-bis-(diphenylphosphino)-ferrocene (3.4 mg, 0.006 mmol, 0.027 eq.) were added. Afterwards, zinc cyanide (6.6 mg, 0.056 mmol, 0.25 eq.) was added. The resulting mixture was stirred at 150° C. during 25 min in a microwave. Zinc cyanide (3.3 mg, 0.028 mmol, 0.13 eq.), tris(dibenzylideneacetone) dipalladium(0) (2.3 mg, 0.002 mmol, 0.001 eq.) and 1,1'-bis-(diphenylphosphino)-ferrocene (1.7 mg, 0.003 mmol, 0.014 eq.) were added again. The resulting mixture was stirred at 150° C. during 25 min in a microwave. The reaction mixture was diluted with AcOEt and filtered over celite. The filtrate was washed with water, dried over MgSO$_4$, filtered and concentrated in vacuo. The residue was purified by CC (SiO$_2$, eluent:Hept/AcOEt) to yield the nitrile derivative as a pale yellow oil.

LC-MS 2: $t_R$=0.97 min; $[M+H]^+$=507.3

General Method for the Synthesis of Esters of Structure 10

Ethyl bromoacetate (0.44 mL, 3.97 mmol, 1.5 eq.) was added to a solution of a phenol 13 (2.65 mmol, 1.0 eq.) and K$_2$CO$_3$ (1.10 g, 7.95 mmol, 3.0 eq.) in DMF (9 mL) at r.t. The mixture was stirred at r.t. for 2 hours. The reaction mixture was diluted with AcOEt and water. The layers were separated and the aq. phase was extracted with AcOEt (2×). The comb. org. phases were washed with water and sat. aq. NaCl, dried over MgSO$_4$, filtered, and concentrated in vacuo. The crude product was purified by CC (SiO$_2$, Hept./AcOEt) to yield the desired ethyl ester.

Listed in Table 40 below are esters of Structure 10, prepared according to the above-mentioned method, with corresponding tetrahydroisoquinolines 13 as starting material.

TABLE 40

| Intermediates of Structure 10 | Formula MW | $t_R$ [min] LC-MS Method | MS-data m/z $[M + H]^+$ |
|---|---|---|---|
| (±)-1-(2-Ethoxycarbonylmethoxy-5-fluoro-phenyl)-3,4-dihydro-1H-isoquinoline-2-carboxylic acid benzyl ester | C27H26NO5F 463.50 | 0.99 LC-MS 2 | 464.0 |
| (±)-1-(2-Ethoxycarbonylmethoxy-5-methyl-phenyl)-3,4-dihydro-1H-isoquinoline-2-carboxylic acid benzyl ester | C28H29NO5 459.54 | 1.11 LC-MS 2 | 460.1 |
| (±)-1-(2-Ethoxycarbonylmethoxy-5-methoxy-phenyl)-3,4-dihydro-1H-isoquinoline-2-carboxylic acid benzyl ester | C28H29NO6 475.54 | 1.07 LC-MS 2 | 476.0 |
| (±)-1-(2-Ethoxycarbonylmethoxy-5-trifluoromethyl-phenyl)-3,4-dihydro-1H-isoquinoline-2-carboxylic acid benzyl ester | C28H26NO5F3 513.51 | 1.12 LC-MS 2 | 513.5 |
| (±)-1-(5-Bromo-2-ethoxycarbonylmethoxy-phenyl)-3,4-dihydro-1H-isoquinoline-2-carboxylic acid benzyl ester | C27H26NO5Br 524.41 | 1.13 LC-MS 2 | 525.9 |
| (±)-1-(2-Ethoxycarbonylmethoxy-5-isopropyl-phenyl)-3,4-dihydro-1H-isoquinoline-2-carboxylic acid benzyl ester | C30H33NO5 487.59 | 1.17 LC-MS 2 | 488.2 |
| (±)-1-(6-Ethoxycarbonylmethoxy-benzo[1,3]dioxol-5-yl)-3,4-dihydro-1H-isoquinoline-2-carboxylic acid benzyl ester | C28H27NO7 489.52 | 1.06 LC-MS 2 | 490.1 |
| (±)-1-(5-Chloro-2-ethoxycarbonylmethoxy-phenyl)-3,4-dihydro-1H-isoquinoline-2-carboxylic acid benzyl ester | C27H26NO5Cl 479.96 | 1.04 LC-MS 2 | 480.1 |
| (±)-1-(2-Ethoxycarbonylmethoxy-4,5-difluoro-phenyl)-3,4-dihydro-1H-isoquinoline-2-carboxylic acid benzyl ester | C27H25NO5F2 481.49 | 1.10 LC-MS 2 | 481.5 |
| (±)-5-Bromo-1-(2-ethoxycarbonylmethoxy-5-fluoro-phenyl)-3,4-dihydro-1H-isoquinoline-2-carboxylic acid benzyl ester | C27H25NO5BrF 542.40 | 1.16 LC-MS 2 | 541.9 |
| (±)-1-(2-Ethoxycarbonylmethoxy-5-fluoro-phenyl)-6,7-difluoro-3,4-dihydro-1H-isoquinoline-2-carboxylic acid benzyl ester | C27H24NO5F3 499.48 | 1.01 LC-MS 2 | 500.2 |
| (±)-1-(5-Cyano-2-ethoxycarbonylmethoxy-phenyl)-3,4-dihydro-1H-isoquinoline-2-carboxylic acid benzyl ester | C28H26N2O5 470.52 | 0.94 LC-MS 2 | 471.0 |
| (±)-7-Bromo-1-(2-ethoxycarbonylmethoxy-5-fluoro-phenyl)-3,4-dihydro-1H-isoquinoline-2-carboxylic acid benzyl ester | C27H25NO5BrF 542.39 | 1.14 LC-MS 2 | 541.9 |
| (±)-1-(5-Bromo-2-ethoxycarbonylmethoxy-phenyl)-6,7-difluoro-3,4-dihydro-1H-isoquinoline-2-carboxylic acid benzyl ester | C27H24NO5BrF2 560.38 | 1.06 LC-MS 2 | 559.8 |
| (±)-1-(2-Ethoxycarbonylmethoxy-5-fluoro-phenyl)-5-trifluoromethyl-3,4-dihydro-1H-isoquinoline-2-carboxylic acid benzyl ester | C28H25NO5F4 531.50 | 1.05 LC-MS 2 | 532.1 |
| (±)-1-(2-Ethoxycarbonylmethoxy-5-fluoro-phenyl)-5,6-difluoro-3,4-dihydro-1H-isoquinoline-2-carboxylic acid benzyl ester | C27H24NO5F3 499.48 | 1.03 LC-MS 2 | 500.2 |

TABLE 40-continued

| Intermediates of Structure 10 | Formula MW | $t_R$ [min] LC-MS Method | MS-data m/z [M + H]$^+$ |
|---|---|---|---|
| (±)-1-(5-Chloro-2-ethoxycarbonylmethoxy-phenyl)-5,6-difluoro-3,4-dihydro-1H-isoquinoline-2-carboxylic acid benzyl ester | C27H24NO5ClF2 515.94 | 1.06 LC-MS 2 | 516.2 |
| (±)-1-(5-Cyano-2-ethoxycarbonylmethoxy-phenyl)-5,6-difluoro-3,4-dihydro-1H-isoquinoline-2-carboxylic acid benzyl ester | C28H24N2O5F2 506.50 | 0.98 LC-MS 2 | 507.5 |
| (±)-1-(5-Dimethylsulfamoyl-2-ethoxycarbonylmethoxy-phenyl)-3,4-dihydro-1H-isoquinoline-2-carboxylic acid benzyl ester | C29H32N2O7S 552.65 | 0.94 LC-MS 2 | 553.5 |
| (±)-1-(5-Chloro-2-ethoxycarbonylmethoxy-phenyl)-5-fluoro-3,4-dihydro-1H-isoquinoline-2-carboxylic acid benzyl ester | C27H25NO5ClF 497.95 | 1.05 LC-MS 2 | 498.0 |
| (±)-1-(5-Cyano-2-ethoxycarbonylmethoxy-phenyl)-5-fluoro-3,4-dihydro-1H-isoquinoline-2-carboxylic acid benzyl ester | C28H25N2O5F 488.51 | 0.96 LC-MS 2 | 489.3 |
| (±)-1-(5-Chloro-2-ethoxycarbonylmethoxy-phenyl)-3,4-dihydro-1H-isoquinoline-2-carboxylic acid tert-butyl ester | C24H28NO5Cl 445.94 | 1.05 LC-MS 2 | 446.2 |
| (±)-1-(5-Chloro-2-ethoxycarbonylmethoxy-phenyl)-5-fluoro-3,4-dihydro-1H-isoquinoline-2-carboxylic acid tert-butyl ester | C24H27NO5ClF 463.93 | 1.05 LC-MS 3 | 464.1 |
| (±)-1-(5-Chloro-2-ethoxycarbonylmethoxy-phenyl)-4,4-dimethyl-3,4-dihydro-1H-isoquinoline-2-carboxylic acid tert-butyl ester | C26H32NO5Cl 474.00 | 1.09 LC-MS 3 | 474.3 |
| (±)-1-(5-Chloro-2-ethoxycarbonylmethoxy-phenyl)-6-fluoro-3,4-dihydro-1H-isoquinoline-2-carboxylic acid tert-butyl ester | C24H27NO5ClF 463.93 | 1.04 LC-MS 3 | 464.3 |
| (±)-1-(5-Chloro-2-ethoxycarbonylmethoxy-phenyl)-5,6-difluoro-3,4-dihydro-1H-isoquinoline-2-carboxylic acid tert-butyl ester | C24H26NO5ClF2 481.92 | 1.05 LC-MS 3 | 482.1 |
| (±)-1-(5-Chloro-2-ethoxycarbonylmethoxy-phenyl)-7-fluoro-3,4-dihydro-1H-isoquinoline-2-carboxylic acid tert-butyl ester | C24H27NO5ClF 463.93 | 1.05 LC-MS 2 | 464.3 |

(±)-1-(5-Chloro-2-ethoxycarbonylmethoxy-phenyl)-6-fluoro-3,4-dihydro-1H-isoquinoline-2-carboxylic acid benzyl ester (C27H25NO5ClF, MW=497.95)

To an-ice cooled solution of (±)-[4-chloro-2-(6-fluoro-1,2,3,4-tetrahydro-isoquinolin-1-yl)-phenoxy]-acetic acid ethyl ester hydrochloride (900 mg, 2.25 mmol, 1.0 eq.) and DIPEA (1.16 mL, 6.75 mmol, 3.0 eq.) in DCM (30 mL), benzyl chloroformate (0.43 mL, 2.92 mmol, 1.3 eq.) was added dropwise. Upon completion of the addition, the cooling bath was removed and the solution was stirred at r.t. for 3 hours. The reaction was quenched with 1M aq. citric acid soln. (25 mL). The layers were separated. The aq. phase was extracted with DCM (3×50 mL). The comb. org. phases were dried over MgSO$_4$ and concentrated in vacuo. The residue was purified by flash master (column: 50 g, flow: 40 mL/min, Heptane+ 10% EtOAc to Heptane+50% EtOAc) to yield the title compound.

LC-MS 3: $t_R$=1.05 min; [M+H]$^+$=498.4

General Method for the Synthesis of Esters of Structure 10

Step 1: (S)-2-(Toluene-4-sulfonyloxy)-propionic acid methyl ester (C11H14O5S, MW=258.29)

To an ice-cooled solution of methyl (S)-(−)-lactate (4.6 mL, 47.07 mmol, 1.0 eq.) in MeCN (25 mL), trimethylamine hydrochloride (450 mg, 4.71 mmol, 0.1 eq.) and triethylamine (7.35 mL, 52.81 mmol, 1.1 eq.) were added. A solution of p-toluenesulfonyl chloride (9.06 g, 47.07 mmol, 1.0 eq.) in MeCN (25 mL) was slowly added over 40 min at 0° C. The reaction mixture was stirred under N$_2$ at 0° C. for 1 hour. The mixture was filtered through celite and washed with MeCN. The filtrate was concentrated in vacuo then diluted with water (30 mL) and extracted with Et$_2$O (3×60 mL). The comb. org. layers were dried over MgSO$_4$, filtered and concentrated in vacuo to give the tosylate as a yellow liquid. The product was used crude for the next step.

LC-MS 2: $t_R$=0.84 min; [M+H]$^+$=259.1

Starting from methyl (R)-(+)-lactate, (R)-2-(Toluene-4-sulfonyloxy)-propionic acid methyl ester (C11H14O5S, MW=258.29) was obtained.

Step 2: To a solution of (±)-1-(5-fluoro-2-hydroxy-phenyl)-3,4-dihydro-1H-isoquinoline-2-carboxylic acid benzyl ester (500 mg, 1.33 mmol, 1.0 eq.) in MeCN (5 mL), a tosylate (1.33 mmol, 1.0 eq.) and potassium carbonate anhydrous (366 mg, 2.65 mmol, 2.0 eq.) were added and the mixture was heated to 65° C. for 18 hours. The mixture was cooled to r.t. and extracted with Et$_2$O (2×), dried over MgSO$_4$, filtered, and concentrated in vacuo. The crude product was purified by FC (SiO$_2$, eluent: Hept/AcOEt) to yield the ester as a mixture of 2 diastereoisomers.

Listed in Table 41 below are esters of Structure 10, prepared according to the above-mentioned method, with corresponding tetrahydroisoquinolines 13 and the corresponding tosylate as starting materials.

TABLE 41

| Intermediates of Structure 10 | Formula MW | $t_R$ [min] LC-MS Method | MS-data m/z [M + H]+ |
|---|---|---|---|
| 1-[5-Fluoro-2-((R)-1-methoxycarbonyl-ethoxy)-phenyl]-3,4-dihydro-1H-isoquinoline-2-carboxylic acid benzyl ester | C27H26NO5F 463.50 | 0.99 LC-MS 2 | 464.0 |
| 1-[5-Fluoro-2-((S)-1-methoxycarbonyl-ethoxy)-phenyl]-3,4-dihydro-1H-isoquinoline-2-carboxylic acid benzyl ester | C27H26NO5F 463.50 | 1.08 LC-MS 2 | 464.2 |
| 1-[5-Cyano-2-((R)-1-methoxycarbonyl-ethoxy)-phenyl]-3,4-dihydro-1H-isoquinoline-2-carboxylic acid benzyl ester | C28H26N2O5 470.52 | 0.94 LC-MS 2 | 471.2 |

General Method for the Synthesis of Amines of Structure 2 or of the Corresponding Hydrochloride Salt Method A: To a solution of (±)-1-(2-ethoxycarbonyl-methoxy-5-fluoro-phenyl)-3,4-dihydro-1H-isoquinoline-2-carboxylic acid benzyl ester (760 mg, 1.64 mmol, 1.0 eq.) in EtOH under $N_2$, palladium on activated carbon (10 wt. %, 76 mg) was added. The flask was carefully evacuated and refilled with $H_2$ (3×). The black suspension was stirred at r.t. under an $H_2$-atmosphere for 18 hours. The black suspension was filtered through Celite. The Celite was rinsed with EtOH. The filtrate was concentrated in vacuo. The crude mixture was dissolved in 4M HCl in dioxane (10 mL). The resulting solution was stirred at r.t. during 30 min, then concentrated in vacuo. The new crude salt was dissolved in EtOH and concentrated in vacuo (3 times) to afford the desired salt.

Listed in Table 42 below are hydrochloride salts of Structure 2, prepared according to the above-mentioned method, with corresponding Cbz-protected tetrahydroisoquinolines of Structure 10 as starting material.

TABLE 42

| Intermediates of Structure 2 | Formula MW | $t_R$ [min] LC-MS Method | MS-data m/z [M + H]+ |
|---|---|---|---|
| (±)-[4-Fluoro-2-(1,2,3,4-tetrahydro-isoquinolin-1-yl)-phenoxy]-acetic acid ethyl ester hydrochloride | C19H20NO3F 329.14 | 0.59 LC-MS 2 | 330.4 |
| ((S)-4-Fluoro-2-1,2,3,4-tetrahydro-isoquinolin-1-yl-phenoxy)-acetic acid ethyl ester hydrochloride | C19H20NO3F 329.14 | 0.60 LC-MS 2 | 330.3 |

Method B: To an ice-cooled solution of (±)-1-(5-chloro-2-ethoxycarbonylmethoxy-phenyl)-3,4-dihydro-1H-isoquinoline-2-carboxylic acid tert-butyl ester (1.27 g, 2.84 mmol, 1.0 eq.) in DCM (5 mL), 4M HCl in dioxane (12 mL) was added. The resulting solution was stirred at r.t. for 7 hours. The reaction mixture was concentrated in vacuo. The residue was coevaporated with EtOH (3×). The product was triturated with $Et_2O$/pentane to afford the title salt.

Listed in Table 43 below are hydrochloride salts of Structure 2, prepared according to the above-mentioned method, with corresponding Boc-protected tetrahydroisoquinolines of Structure 10 as starting material.

TABLE 43

| Intermediates of Structure 2 | Formula MW | $t_R$ [min] LC-MS Method | MS-data m/z [M + H]+ |
|---|---|---|---|
| (±)-[4-Chloro-2-(1,2,3,4-tetrahydro-isoquinolin-1-yl)-phenoxy]-acetic acid ethyl ester hydrochloride | C19H20NO3Cl 345.11 | 0.64 LC-MS 2 | 346.1 |
| (±)-[4-Chloro-2-(7-fluoro-1,2,3,4-tetrahydro-isoquinolin-1-yl)-phenoxy]-acetic acid ethyl ester hydrochloride | C19H19NO3ClF 363.10 | 0.64 LC-MS 2 | 364.2 |
| [4-Chloro-2-((S)-5-fluoro-1,2,3,4-tetrahydro-isoquinolin-1-yl)-phenoxy]-acetic acid ethyl ester hydrochloride | C19H19NO3ClF 363.10 | 0.74 LC-MS 3 | 364.0 |
| (±)-[4-Chloro-2-(6-fluoro-1,2,3,4-tetrahydro-isoquinolin-1-yl)-phenoxy]-acetic acid ethyl ester hydrochloride | C19H19NO3ClF 363.10 | 0.74 LC-MS 3 | 363.8 |

TABLE 43-continued

| Intermediates of Structure 2 | Formula MW | $t_R$ [min] LC-MS Method | MS-data m/z [M + H]$^+$ |
|---|---|---|---|
| [4-Chloro-2-((S)-6-fluoro-1,2,3,4-tetrahydro-isoquinolin-1-yl)-phenoxy]-acetic acid ethyl ester hydrochloride | C19H19NO3ClF 363.10 | 0.72 LC-MS 3 | 364.2 |
| [4-Chloro-2-((S)-5,6-difluoro-1,2,3,4-tetrahydro-isoquinolin-1-yl)-phenoxy]-acetic acid ethyl ester hydrochloride | C19H18NO3ClF2 381.09 | 0.73 LC-MS 3 | 382.2 |

Method C: To a solution of Cbz-protected tetrahydroisoquinoline of Structure 10 (1.04 mmol, 1.0 eq.) in AcOH (10 mL), 33% hydrobromic acid in acetic acid (2.5 mL) was added. The mixture was stirred at r.t. for 1 hour. The reaction mixture was concentrated in vacuo. The residue was purified by flash master (column: 100 g, flow: 45 mL/min, Heptane to AcOEt with 10% of NEt$_3$). The resulting amine was dissolved in EtOH (20 mL) and acetyl chloride (0.11 mL, 1.48 mmol, 1.4 eq.) was added. The resulting solution was refluxed for 2 hours, then allowed to cool to r.t., and concentrated in vacuo to give the desired hydrochloride salt.

Listed in Table 44 below are hydrochloride salts of Structure 2, prepared according to the above-mentioned method, with corresponding Cbz-protected tetrahydroisoquinolines of Structure 10 as starting material.

TABLE 44

| Intermediates of Structure 2 | Formula MW | $t_R$ [min] LC-MS Method | MS-data m/z [M + H]$^+$ |
|---|---|---|---|
| (±)-[4-Chloro-2-(5-fluoro-1,2,3,4-tetrahydro-isoquinolin-1-yl)-phenoxy]-acetic acid ethyl ester hydrochloride | C19H19NO3ClF 363.10 | 0.71 LC-MS 3 | 364.1 |
| ((S)-4-Chloro-2-1,2,3,4-tetrahydro-isoquinolin-1-yl-phenoxy)-acetic acid ethyl ester hydrochloride | C19H20NO3Cl 345.11 | 0.71 LC-MS 3 | 346.1 |
| (±)-[4-Chloro-2-(1,2,3,4-tetrahydro-isoquinolin-1-yl)-phenoxy]-acetic acid ethyl ester hydrochloride | C19H20NO3Cl 345.11 | 0.64 LC-MS 2 | 346.1 |

Method D: (±)-[4-Chloro-2-(1,2,3,4-tetrahydro-isoquinolin-1-yl)-phenoxy]-acetic acid ethyl ester (C19H20NO3Cl, MW=345.83): To a solution of (±)-1-(5-chloro-2-ethoxycarbonylmethoxy-phenyl)-3,4-dihydro-1H-isoquinoline-2-carboxylic acid benzyl ester (1.03 g, 2.15 mmol, 1.0 eq.) in AcOH (30 mL), 33% hydrobromic acid in acetic acid (7.5 mL) was added. The mixture was stirred at r.t. for 1 hour. The reaction mixture was concentrated in vacuo. The residue was purified by flash master (column: 100 g, flow: 45 mL/min, Heptane to AcOEt with 10% of NEt$_3$) to yield the title amine.

LC-MS 3: $t_R$=0.71 min; [M+H]$^+$=346.3

Method E: (±)-[4-Fluoro-2-(6-fluoro-1,2,3,4-tetrahydro-isoquinolin-1-yl)-phenoxy]-acetic acid ethyl ester (C19H19NO3F2, MW=347.36): To a solution of (±)-5-bromo-6-fluoro-1-(5-fluoro-2-hydroxy-phenyl)-3,4-dihydro-1H-isoquinoline-2-carboxylic acid benzyl ester (50 mg, 0.11 mmol, 1.0 eq.) and Cs$_2$CO$_3$ (104 mg, 0.32 mmol, 3.0 eq.) in DMF (1 mL), ethyl bromoacetate (18 μL, 0.16 mmol, 1.5 eq.) was added. The resulting solution was stirred at r.t. for 18 hours. The solvent was evaporated and the mixture was poured into water and extracted with DCM (3×). The combined extracts were washed with water and dried over MgSO$_4$. To a solution under N$_2$ of the residue in EtOH (4 mL), palladium on activated carbon (10 wt. %, 10 mg) was added. The flask was evacuated and backfilled with H$_2$ (3×). The black suspension was stirred at r.t. under an H$_2$-atmosphere for 18 hours. The suspension was filtered through Celite, the Celite rinsed with EtOH, and the filtrate was concentrated in vacuo. The residue was purified by prep. HPLC (column: Waters X-bridge, 19×50 mm, 10 um, UV/MS, basic conditions) to give the title amine.

LC-MS 3: $t_R$=0.62 min; [M+H]$^+$=348.2

Synthesis of ((S)-4-Chloro-2-1,2,3,4-tetrahydro-isoquinolin-1-yl-phenoxy)-acetic acid ethyl ester (C19H20NO3Cl, MW=345.83)

To an ice-cooled solution of (S)-1-(5-chloro-2-ethoxycarbonylmethoxy-phenyl)-3,4-dihydro-1H-isoquinoline-2-carboxylic acid tert-butyl ester (790 mg, 1.77 mmol, 1.0 eq.) in DCM (3 mL), 4M HCl in dioxane (7.4 mL) was added. The resulting solution was stirred at r.t. for 1.5 hours. The reaction mixture was concentrated in vacuo. The residue was coevaporated with EtOH (3×). To a solution of the residue in EtOH (2 mL), conc. H$_2$SO$_4$ (0.18 mL) was added. The solution was stirred at r.t. for 18 hours. Water and 5% aq. NaOH soln. were added and the mixture was extracted with Et$_2$O (3×10 mL). The comb. org. phases were dried over MgSO$_4$, filtered, and concentrated in vacuo to give the desired product.

LC-MS 3: $t_R$=0.67 min; [M+H]$^+$=346.1

Synthesis of [4-Chloro-2-((S)-6-fluoro-1,2,3,4-tetrahydro-isoquinolin-1-yl)-phenoxy]-acetic acid ethyl ester (C19H19NO3ClF, MW=363.82)

To an ice-cooled solution of (S)-1-(5-chloro-2-ethoxycarbonylmethoxy-phenyl)-6-fluoro-3,4-dihydro-1H-isoquinoline-2-carboxylic acid tert-butyl ester (640 mg, 1.38 mmol, 1 eq.) in EtOH (2.5 mL), 4M HCl in dioxane (5.5 mL) was added. The resulting solution was stirred at r.t. for 3 hours. The reaction mixture was concentrated in vacuo. The residue was partitioned between AcOEt and a sat. aq. NaHCO$_3$ soln. The layers were separated and the aq. phase was extracted with AcOEt. The comb. org. phases were concentrated in vacuo to give the free amine.

LC-MS 3: $t_R$=0.73 min; [M+H]$^+$=364.2

Synthesis of (±)-[2-(1,2,3,4-Tetrahydro-isoquinolin-1-yl)-phenoxy]-acetic acid ethyl ester (C19H21NO3, MW=311.15)

To a solution of (±)-1-(5-chloro-2-ethoxycarbonylmethoxy-phenyl)-3,4-dihydro-1H-isoquinoline-2-carboxylic acid tert-butyl ester (446 mg, 1.0 mmol, 1.0 eq.) in EtOH (4.8 mL) under N$_2$, palladium on activated carbon (10 wt. %, 106 mg) was added. The flask was carefully evacuated and refilled with H$_2$ (3×). The black suspension was stirred at 50°

C. under an H$_2$-atmosphere for 48 hours. The black suspension was filtered through Celite. The Celite was rinsed with EtOH. The filtrate was concentrated in vacuo. To an ice-cooled solution of the residue in DCM (1.8 mL), 4M HCl in dioxane (2.6 mL) was added. The resulting solution was stirred at r.t. for 18 hours. The reaction mixture was concentrated in vacuo. The residue was coevaporated with EtOH (3×). The residue, redissolved in DMF (2 mL), was purified by prep. HPLC (column: Atlantis, 19×30 mm, 5 um, UV/MS, acidic conditions) and evaporated to give the desired amine as a yellow oil.

LC-MS 3: $t_R$=0.69 min; [M+H]$^+$=312.1

Synthesis of (±)-1-(2-Allyloxy-5-chloro-phenyl)-6-fluoro-3,4-dihydro-1H-isoquinoline-2-carboxylic acid benzyl ester (C26H23NO3ClF, MW=451.92)

Step 1: To a mixture of (±)-5-bromo-1-(5-chloro-2-hydroxy-phenyl)-6-fluoro-3,4-dihydro-1H-isoquinoline-2-carboxylic acid benzyl ester (150 mg, 0.28 mmol, 1.00 eq.) and K$_2$CO$_3$ (43 mg, 0.31 mmol, 1.10 eq.) in acetone (0.7 mL), allyl bromide (26 µL, 0.29 mmol, 1.05 eq.) was added. The mixture was heated to 60° C. in a sealed vial for 18 hours. The reaction mixture was allowed to cool to r.t. and poured in water (4 mL). The mixture was extracted with DCM (2×5 mL). The comb. org. phases were dried over MgSO$_4$, filtered, and concentrated in vacuo. The residue was partially purified by flash master (column: 10 g, flow: 15 mL/min, Heptane to Heptane+10% AcOEt) to yield (±)-1-(2-allyloxy-5-chloro-phenyl)-5-bromo-6-fluoro-3,4-dihydro-1H-isoquinoline-2-carboxylic acid benzyl ester as a colorless oil.

Step 2: To a solution under N$_2$ of (±)-1-(2-allyloxy-5-chloro-phenyl)-5-bromo-6-fluoro-3,4-dihydro-1H-isoquinoline-2-carboxylic acid benzyl ester (90 mg, 0.14 mmol, 1.00 eq.) in THF (0.28 mL) cooled at −20° C., isopropylmagnesium chloride—lithium chloride complex 14% in THF (0.32 mL, 0.14 mmol, 1.00 eq.) was added dropwise. The mixture was stirred at 0° C. and slowly warmed to r.t. over 2.5 hours. The reaction was carefully quenched with 1M aq. NH$_4$Cl soln. (10 mL) and with AcOEt (10 mL). The resulting suspension was filtered through celite and the filter cake was rinsed with water and AcOEt. The layers were separated and the aq. phase was extracted with AcOEt (2×10 mL). The comb. org. phases were washed with sat. aq. NaCl soln. (1×10 mL), dried over MgSO$_4$, filtered and concentrated in vacuo. The residue was purified by flash master (column: 10 g, flow: 15 mL/min, Heptane to Heptane+10% AcOEt) to yield (±)-1-(2-allyloxy-5-chloro-phenyl)-6-fluoro-3,4-dihydro-1H-isoquinoline-2-carboxylic acid benzyl ester as a colorless oil.

LC-MS 3: $t_R$=1.07 min; [M+H]$^+$=452.1

Synthesis of (±)-1-(5-Chloro-2-ethoxycarbonyl-methoxy-phenyl)-3,4-dihydro-1H-isoquinoline-2-carboxylic acid 2-bromo-benzyl ester (C27H25NO5BrCl, MW=558.85)

To a solution of (±)-[4-chloro-2-(1,2,3,4-tetrahydro-isoquinolin-1-yl)-phenoxy]-acetic acid ethyl ester hydrochloride (836 mg, 2.00 mmol, 1.0 eq.) and DIPEA (0.86 mL, 5.00 mmol, 2.5 eq.) in DCM (30 mL), carbonic acid 2-bromo-benzyl ester 2,5-dioxo-pyrrolidin-1-yl ester (787 mg, 2.40 mmol, 1.2 eq.) was added. The mixture was stirred at r.t. during 2 hours. The reaction was quenched with 1M aq. citric acid soln. (30 mL). The layers were separated. The aq. phase was extracted with DCM (3×). The comb. org. phases were dried over MgSO$_4$, filtered, and concentrated in vacuo. To a solution of the previous mixture in EtOH (1.1 mL), conc. H$_2$SO$_4$ (0.10 mL) was added. The solution was stirred at r.t. during 3 hours. Water and 5% aq. NaOH soln. were added and the mixture was extracted with DCM (3×). The comb. org. phases were dried over MgSO$_4$, filtered and concentrated in vacuo to give the desired product as a pale yellow oil.

LC-MS 3: $t_R$=1.06 min; [M+H]$^+$=560.0

General Synthesis of Vinyl Amide 8

To an ice-cooled solution of (±)-[4-chloro-2-(1,2,3,4-tetrahydro-isoquinolin-1-yl)-phenoxy]-acetic acid ethyl ester hydrochloride (4.57 g, 10.6 mmol, 1.0 eq.) in DCM (43 mL), acryloyl chloride (0.98 mL, 11.7 mmol, 1.1 eq.) and DIPEA (3.99 mL, 23.3 mmol, 2.2 eq.) were added in sequence. The mixture was stirred at 0° C. for 1 hour. The reaction was diluted with DCM (200 mL) and 1M aq. citric acid soln. (1×200 mL). The layers were separated. The aq. phase was extracted with DCM (2×200 mL). The comb. org. phases were washed with sat. aq. NaCl soln. (1×200 mL), dried over MgSO$_4$, filtered and concentrated in vacuo. The residue was purified by flash master (column: 100 g, flow: 45 mL/min, Heptane+20% AcOEt to Heptane+52% AcOEt) to yield the desired vinyl amide derivative.

Listed in Table 45 below are vinyl amides 8, prepared according to the above-mentioned method, with corresponding amine of Structure 2 as starting materials.

TABLE 45

| Vinyl amides 8 | Formula MW | $t_R$ [min] LC-MS Method | MS-data m/z [M + H]$^+$ |
|---|---|---|---|
| (±)-[2-(2-Acryloyl-1,2,3,4-tetrahydro-isoquinolin-1-yl)-4-chloro-phenoxy]-acetic acid ethyl ester | C22H22NO4Cl 399.87 | 0.93 LC-MS 3 | 400.3 |
| [2-((S)-2-Acryloyl-6-fluoro-1,2,3,4-tetrahydro-isoquinolin-1-yl)-4-chloro-phenoxy]-acetic acid ethyl ester | C22H21NO4ClF 417.86 | 0.95 LC-MS 3 | 417.9 |

General Method for the Synthesis of Carbonate 5

To a solution of 2-bromobenzyl alcohol (2.83 g, 15.0 mmol, 1.0 eq.) and DMAP (916 mg, 7.5 mmol, 0.5 eq.) in MeCN/DCM 1:1 (45 mL), N,N'-disuccinimidyl carbonate (3.84 g, 15.0 mmol, 1.0 eq.) was added. The mixture was stirred at r.t. for 18 hours. The mixture was washed with H$_2$O (1×45 mL), sat. aq. NaCl soln. (1×45 mL), dried over MgSO$_4$, filtered and concentrated in vacuo. The residue was recrystallized from iPrOH.

Listed in Table 46 below are carbonates 5, prepared according to the above-mentioned method, with corresponding benzyl alcohols 6 as starting materials.

TABLE 46

| Carbonates 5 | Formula MW | $t_R$ [min] LC-MS Method | MS-data m/z [M + H]$^+$ |
|---|---|---|---|
| Carbonic acid 2-bromo-benzyl ester 2,5-dioxo-pyrrolidin-1-yl ester | C12H10NO5Br 328.12 | 0.82 LC-MS 3 | No ionization |

TABLE 46-continued

| Carbonates 5 | Formula MW | $t_R$ [min] LC-MS Method | MS-data m/z [M + H]+ |
|---|---|---|---|
| Carbonic acid 2,5-dioxo-pyrrolidin-1-yl ester 4-methoxy-benzyl ester | C13H13NO6 279.25 | 0.56 LC-MS 2 | No ionization |
| Carbonic acid 2,5-dioxo-pyrrolidin-1-yl ester 4-fluoro-benzyl ester | C12H10NO5F 267.21 | 0.69 LC-MS 2 | No ionization |
| Carbonic acid 2,5-dioxo-pyrrolidin-1-yl ester 4-trifluoromethyl-benzyl ester | C13H10NO5F3 317.22 | 0.78 LC-MS 2 | No ionization |
| Carbonic acid 3-chloro-benzyl ester 2,5-dioxo-pyrrolidin-1-yl ester | C12H10NO5Cl 283.67 | 0.74 LC-MS 2 | No ionization |
| Carbonic acid 2,5-dioxo-pyrrolidin-1-yl ester 4-methyl-benzyl ester | C13H13NO5 263.25 | 0.73 LC-MS 2 | No ionization |
| Carbonic acid 2,3-difluoro-benzyl ester 2,5-dioxo-pyrrolidin-1-yl ester | C12H9NO5F2 285.20 | 0.78 LC-MS 3 | No ionization |
| Carbonic acid 2,5-dioxo-pyrrolidin-1-yl ester 3-fluoro-benzyl ester | C12H10NO5F 267.21 | 0.78 LC-MS 3 | No ionization |
| Carbonic acid 2,5-dioxo-pyrrolidin-1-yl ester 2-fluoro-benzyl ester | C12H10NO5F 267.21 | 0.78 LC-MS 3 | No ionization |
| Carbonic acid 2,5-dioxo-pyrrolidin-1-yl ester 2-methoxy-benzyl ester | C13H13NO6 279.25 | 0.80 LC-MS 3 | No ionization |

General Method for the Synthesis of isoindoline 28

To a solution of 2-bromobenzyl chloride (424 mg, 2.0 mmol, 1.0 eq.) in THF (15 mL) cooled at −78° C., 2.5M butyllithium solution in hexanes (0.80 mL, 2.0 mmol, 1.0 eq.) was added. The resulting yellow solution was stirred at −78° C. for 20 min. A solution of (±)-2-methyl-propane-2-sulfinic acid 1-(2-allyloxy-5-chloro-phenyl)-methylideneamide (600 mg, 2.0 mmol, 1.0 eq.) in THF (5 mL) was added dropwise at −78° C. The dark yellow solution was stirred at −78° C. for 1 hour and further at r.t. for 1 hour. H$_2$O (20 mL) was added and the layers were separated. The aq. layer was extracted with Et$_2$O (3×20 mL). The comb. org. phases were washed with sat. aq. NaCl soln. (1×20 mL), dried over MgSO$_4$ and concentrated in vacuo. The residue was purified by flashmaster (column: 100 g, flow: 45 mL/min, heptane to heptane+30% AcOEt) to yield the desired isoindoline 28 as a beige solid.

Listed in Table 47 below are isoindolines 28, prepared according to the above-mentioned method, with corresponding 2-bromobenzyl chloride derivatives 26 as starting materials.

TABLE 47

| Isoindolines 28 | Formula MW | $t_R$ [min] LC-MS Method | MS-data m/z [M + H]+ |
|---|---|---|---|
| 1-(2-Allyloxy-5-chloro-phenyl)-2-(2-methyl-propane-2-sulfinyl)-2,3-dihydro-1H-isoindole | C21H24NO2ClS 389.95 | 0.99 LC-MS 2 | 390.2 |
| 1-(2-Allyloxy-5-chloro-phenyl)-5-fluoro-2-(2-methyl-propane-2-sulfinyl)-2,3-dihydro-1H-isoindole | C21H23NO2ClFS 407.94 | 0.99 LC-MS 3 | 408.3 |
| 1-(2-Allyloxy-5-chloro-phenyl)-4-fluoro-2-(2-methyl-propane-2-sulfinyl)-2,3-dihydro-1H-isoindole | C21H23NO2ClFS 407.94 | 1.00 LC-MS 3 | 408.3 |
| 1-(2-Allyloxy-5-chloro-phenyl)-4,5-difluoro-2-(2-methyl-propane-2-sulfinyl)-2,3-dihydro-1H-isoindole | C21H22NO2ClF2S 425.93 | 1.02 LC-MS 3 | 426.1 |
| 1-(2-Allyloxy-5-chloro-phenyl)-4,5-dichloro-2-(2-methyl-propane-2-sulfinyl)-2,3-dihydro-1H-isoindole | C21H22NO2Cl3S 458.84 | 1.07 LC-MS 3 | 458.2 |

Synthesis of (±)-2-methyl-propane-2-sulfinic acid 1-(2-allyloxy-5-chloro-phenyl)-methylideneamide (C14H18NO2ClS, MW=299.82)

Step 1: To a mixture of 5-chlorosalicylaldehyde (8.20 g, 52.37 mmol, 1.00 eq.) and potassium carbonate anhydrous (8.69 g, 62.85 mmol, 1.20 eq.) in DMF (100 mL), allyl bromide (4.7 mL, 54.99 mmol, 1.05 eq.) was added. The mixture was heated at 50° C. for 18 hours. The reaction mixture was allowed to cool to r.t. and poured in water (150 mL). The mixture was extracted with DCM (2×200 mL). The comb. org. phases were dried over MgSO$_4$ and concentrated in vacuo to give 2-allyloxy-5-chloro-benzaldehyde. The product was used without further purification.

Step 2: To a mixture of 2-allyloxy-5-chloro-benzaldehyde (8.55 g, 43.48 mmol, 1.0 eq.) and 2-methyl-2-propanesulfinamide (6.86 g, 56.64 mmol, 1.3 eq.) in THF (200 mL), titanium (IV) ethoxide (52.3 mL, 49.84 mmol, 1.1 eq.) was added dropwise. The reaction mixture was stirred at r.t. for 18 hours. The reaction mixture was diluted with water (1000 mL) and DCM (300 mL).The reaction mixture was filtered. The layers were separated. The aq. phase was extracted with DCM (2×200 mL). The comb. org. phases were washed with water (1×250 mL), sat. aq. NaCl soln. (1×150 mL), dried over MgSO$_4$, and concentrated in vacuo. The residue was used without further purification.

LC-MS 3: $t_R$=0.98 min; [M+H]+=300.0

General Method for the Synthesis of isoindoline 29

To a solution of 1-(2-allyloxy-5-chloro-phenyl)-5-fluoro-2-(2-methyl-propane-2-sulfinyl)-2,3-dihydro-1H-isoindole (230 mg, 0.56 mmol, 1.0 eq.) in MeOH (10 mL), 4M HCl in dioxane (2 mL) was added. The mixture was stirred at r.t. for 2 hours. The reaction mixture was concentrated in vacuo. To a solution of the residue and DIPEA (0.30 mL, 1.69 mmol, 3.0 eq.) in DCM (10 mL), benzyl chloroformate (0.10 mL, 0.68 mmol, 1.2 eq.) was added. The mixture was stirred at r.t. for 4 hours. The reaction mixture was diluted with 1M aq. citric acid soln. (10 mL). The layers were separated. The aq. phase was extracted with DCM (2×10 mL). The comb. org. phases were washed with sat. aq. NaCl soln. (1×10 mL), dried over MgSO$_4$, and concentrated in vacuo. The residue was purified by prep. HPLC (column: Atlantis, 30×75 mm, 10 um, UV/MS, acidic conditions) and concentrated in vacuo to give the desired isoindoline.

Listed in Table 48 below are isoindolines 29, prepared according to the above-mentioned method, with corresponding isoindoline derivatives 28 as starting materials.

TABLE 48

| Isoindolines 29 | Formula MW | $t_R$ [min] LC-MS Method | MS-data m/z [M + H]+ |
|---|---|---|---|
| (±)-1-(2-Allyloxy-5-chloro-phenyl)-5-fluoro-1,3-dihydro-isoindole-2-carboxylic acid benzyl ester | C25H21NO3ClF 437.90 | 1.06 LC-MS 3 | 438.2 |
| (±)-1-(2-Allyloxy-5-chloro-phenyl)-4-fluoro-1,3-dihydro-isoindole-2-carboxylic acid benzyl ester | C25H21NO3ClF 437.90 | 1.06 LC-MS 3 | 438.2 |
| (±)-1-(2-Allyloxy-5-chloro-phenyl)-4,5-dichloro-1,3-dihydro-isoindole-2-carboxylic acid benzyl ester | C25H20NO3Cl3 488.80 | 1.11 LC-MS 3 | 488.1 |
| (±)-1-(2-Allyloxy-5-chloro-phenyl)-4,5-difluoro-1,3-dihydro-isoindole-2-carboxylic acid benzyl ester | C25H20NO3ClF2 455.89 | 1.07 LC-MS 3 | 456.1 |

TABLE 49

| Isoindolines 30 | Formula MW | $t_R$ [min] LC-MS Method | MS-data m/z [M + H]+ |
|---|---|---|---|
| (±)-1-(5-Chloro-2-hydroxy-phenyl)-1,3-dihydro-isoindole-2-carboxylic acid tert-butyl ester | C19H20NO3Cl 345.85 | 0.93 LC-MS 3 | 346.3 |
| (±)-1-(5-Chloro-2-hydroxy-phenyl)-5-fluoro-1,3-dihydro-isoindole-2-carboxylic acid benzyl ester | C22H17NO3ClF 397.83 | 0.96 LC-MS 3 | 398.2 |
| (±)-1-(5-Chloro-2-hydroxy-phenyl)-4-fluoro-1,3-dihydro-isoindole-2-carboxylic acid benzyl ester | C22H17NO3ClF 397.83 | 0.95 LC-MS 3 | 398.2 |
| (±)-4,5-Dichloro-1-(5-chloro-2-hydroxy-phenyl)-1,3-dihydro-isoindole-2-carboxylic acid benzyl ester | C22H16NO3Cl3 448.73 | 1.01 LC-MS 3 | 449.6 |
| (±)-1-(5-Chloro-2-hydroxy-phenyl)-4,5-difluoro-1,3-dihydro-isoindole-2-carboxylic acid benzyl ester | C22H16NO3ClF2 415.82 | 0.97 LC-MS 3 | 416.0 |

Synthesis of (±)-1-(2-Allyloxy-5-chloro-phenyl)-1,3-dihydro-isoindole-2-carboxylic acid tert-butyl ester (C22H24NO3Cl, MW=385.89)

To a solution of (±)-1-(2-allyloxy-5-chloro-phenyl)-2-(2-methyl-propane-2-sulfinyl)-2,3-dihydro-1H-isoindole (10.77 g, 27.6 mmol, 1.0 eq.) in MeOH (300 mL), 4M HCl in dioxane (40.0 mL) was added. The mixture was stirred at r.t. for 2 hours. The reaction mixture was concentrated in vacuo. To a solution of the residue and DIPEA (14.5 mL, 82.9 mmol, 3.0 eq.) in DCM (300 mL), di-tert-butyl dicarbonate (7.23 g, 33.1 mmol, 1.2 eq.) was added. The mixture was stirred at r.t. for 4 hours. The reaction mixture was diluted 1M aq. citric acid (100 mL). The layers were separated. The aq. phase was extracted with DCM (2×100 mL). The comb. org. phases were washed with sat. aq. NaCl soln. (1×100 mL), dried over MgSO4, and concentrated in vacuo. The residue was purified by flashmaster (column: 340 g, flow: 90 mL/min, Heptane to Heptane+20% AcOEt) to yield the desired product as a white foam.

LC-MS 3: $t_R$=1.04 min; [M+H]+=386.1

General Method for the Synthesis of isoindoline 30

A mixture under N2 of (±)-1-(2-allyloxy-5-chloro-phenyl)-1,3-dihydro-isoindole-2-carboxylic acid tert-butyl ester (10.35 g, 26.8 mmol, 1.00 eq.), 1,3-dimethylbarbituric acid (8.38 g, 53.6 mmol, 2.00 eq.) and tetrakis(triphenylphosphine) palladium (0) (1.55 g, 1.34 mmol, 0.05 eq.) in MeOH (300 mL) was stirred at r.t. for 5 hours. The mixture was partitioned between AcOEt (250 mL) and water (250 mL). The layers were separated and the aq. phase was extracted with AcOEt (2×100 mL). The comb. org. phases were washed with sat. aq. NaCl soln. (1×250 mL), dried over MgSO4, and concentrated in vacuo. The residue was purified by flash master (column: 340 g, flow: 90 mL/min, Heptane to Heptane+50% AcOEt) to give the desired phenol 30.

Listed in Table 49 below are isoindolines 30, prepared according to the above-mentioned method, with corresponding isoindoline derivatives 29 as starting materials.

General Synthesis of isoindoline of Structure 10

To a mixture of (±)-1-(5-chloro-2-hydroxy-phenyl)-1,3-dihydro-isoindole-2-carboxylic acid tert-butyl ester (7.47 g, 21.6 mmol, 1.0 eq.) and potassium carbonate anhydrous (4.48 g, 32.4 mmol, 1.5 eq.) in acetone (400 mL), ethyl bromoacetate (2.63 mL, 23.8 mmol, 1.1 eq.) was added. The mixture was stirred at r.t. for 18 hours. The reaction mixture was poured in water (150 mL). The mixture was extracted with AcOEt (2×200 mL). The comb. org. phases were dried over MgSO4 and concentrated in vacuo. The residue was purified by flash master (column: 340 g, flow: 90 mL/min, Heptane to Heptane+50% EtOAc) to yield the title product as an yellow oil.

Listed in Table 50 below are isoindolines of Structure 10, prepared according to the above-mentioned method, with corresponding isoindoline derivatives 30 as starting materials.

TABLE 50

| Isoindolines of Structure 10 | Formula MW | $t_R$ [min] LC-MS Method | MS-data m/z [M + H]+ |
|---|---|---|---|
| (±)-1-(5-Chloro-2-ethoxycarbonylmethoxy-phenyl)-1,3-dihydro-isoindole-2-carboxylic acid tert-butyl ester | C23H26NO5Cl 431.91 | 1.01 LC-MS 3 | 432.3 |
| (±)-1-(5-Chloro-2-ethoxycarbonylmethoxy-phenyl)-5-fluoro-1,3-dihydro-isoindole-2-carboxylic acid benzyl ester | C26H23NO5ClF 483.92 | 1.02 LC-MS 3 | 484.3 |

Synthesis of [2-(2-Acryloyl-2,3-dihydro-1H-isoindol-1-yl)-4-chloro-phenoxy]-acetic acid ethyl ester (enantiomer 1) (C21H20NO4Cl, MW=385.85)

To an ice-cooled solution of (S)-1-(5-chloro-2-ethoxycarbonylmethoxy-phenyl)-1,3-dihydro-isoindole-2-carboxylic acid tert-butyl ester (2.16 g, 5.0 mmol, 1.0 eq.) in DCM (100 mL), 4M HCl in dioxane (25 mL) was added. The resulting solution was stirred at r.t. for 18 hours. The reaction mixture was concentrated in vacuo. To a solution of the residue and NEt₃ (3.48 mL, 25 mmol, 5.0 eq.) in DCM (100 mL), acryloyl chloride (0.45 mL, 5.5 mmol, 1.1 eq.) was added. The resulting solution was stirred at r.t. for 2 hours. The reaction mixture was concentrated in vacuo. The residue was purified by flash master (column: 100 g, flow: 45 mL/min, Heptane+20% AcOEt to Heptane+70% AcOEt) to give the title compound.

LC-MS 3: $t_R$=0.92 min; [M+H]⁺=385.9

Following the same procedure, but starting from 1-(5-chloro-2-ethoxycarbonylmethoxy-phenyl)-1,3-dihydro-isoindole-2-carboxylic acid tert-butyl ester (enantiomer 2), [2-(2-acryloyl-2,3-dihydro-1H-isoindol-1-yl)-4-chloro-phenoxy]-acetic acid ethyl ester (enantiomer 2) was prepared.

LC-MS 3: $t_R$=0.92 min; [M+H]⁺=385.9

Synthesis of (S)-1-(5-Chloro-2-ethoxycarbonyl-methoxy-phenyl)-1,3-dihydro-isoindole-2-carboxylic acid benzyl ester (C26H24NO5Cl, MW=465.93)

To an ice-cooled solution of (S)-1-(5-chloro-2-ethoxycarbonylmethoxy-phenyl)-1,3-dihydro-isoindole-2-carboxylic acid tert-butyl ester (86 mg, 0.2 mmol, 1.00 eq.) in DCM (5 mL), 4M HCl in dioxane (5 mL) was added. The resulting solution was stirred at r.t. for 18 hours. The reaction mixture was concentrated in vacuo. To a solution of the residue and NEt₃ (0.14 mL, 1.0 mmol, 5.00 eq.) in DCM (5 mL), benzyl chloroformate (30 μL, 0.21 mmol, 1.05 eq.) was added. The resulting solution was stirred at r.t. for 18 hours. The reaction mixture was concentrated in vacuo. The residue was purified by prep. HPLC (column: Atlantis, 18×50 mm, 10 um, UV/MS, acidic conditions) and concentrated in vacuo.

LC-MS 3: $t_R$=1.03 min; [M+H]⁺=465.9

Following the same procedure, but starting from (±)-1-(5-chloro-2-ethoxycarbonylmethoxy-phenyl)-1,3-dihydro-isoindole-2-carboxylic acid tert-butyl ester, (±)-1-(5-chloro-2-ethoxycarbonylmethoxy-phenyl)-1,3-dihydro-isoindole-2-carboxylic acid benzyl ester was prepared.

LC-MS 3: $t_R$=1.03 min; [M+H]⁺=466.9

Synthesis of (±)-[4-Chloro-2-(2,3-dihydro-1H-isoindol-1-yl)-phenoxy]-acetic acid ethyl ester hydrochloride (C18H18NO3Cl, MW=331.10)

To an ice-cooled solution of (±)-1-(5-chloro-2-ethoxycarbonylmethoxy-phenyl)-1,3-dihydro-isoindole-2-carboxylic acid tert-butyl ester (2.26 g, 5.23 mmol, 1.0 eq.) in EtOH (100 mL), 4M HCl in dioxane (25 mL) was added. The resulting solution was stirred at r.t. for 18 hours. The reaction mixture was concentrated in vacuo. The residue was triturated with cold methyl tert-butyl ether (50 mL), filtered, and rinsed with cold methyl tert-butyl ether (20 mL) to give the desired salt as a white solid.

LC-MS 3: $t_R$=0.70 min; [M+H]⁺=332.2

Synthesis of (±)-[4-Chloro-2-(5-fluoro-2,3-dihydro-1H-isoindol-1-yl)-phenoxy]-acetic acid ethyl ester hydrochloride (C18H17NO3ClF, MW=349.09)

To a solution of (±)-1-(5-chloro-2-ethoxycarbonylmethoxy-phenyl)-5-fluoro-1,3-dihydro-isoindole-2-carboxylic acid benzyl ester (165 mg, 0.34 mmol, 1.0 eq.) in AcOH (3.0 mL), 33% hydrobromic acid in acetic acid (3.0 mL) was added. The mixture was stirred at r.t. for 2 hours. The reaction mixture was concentrated in vacuo. The residue was stirred in 1.25M HCl in ethanol (5.0 mL) at r.t. for 18 hours. The reaction mixture was concentrated in vacuo to give the desired salt as a colorless oil.

LC-MS 3: $t_R$=0.71 min; [M+H]⁺=350.1

Synthesis of (±)-1-(5-Fluoro-2-hydroxy-phenyl)-1,3-dihydro-isoindole-2-carboxylic acid benzyl ester (C22H18NO3F, MW 363.39)

Step 1: To a mixture of 5-fluoro-2-hydroxybenzaldehyde (5.0 g, 35.69 mmol, 1.00 eq.) and potassium carbonate (7.97 g, 57.10 mmol, 1.60 eq.) in DMF (60 mL), benzyl bromide (4.54 mL, 37.47 mmol, 1.05 eq.) was added dropwise. The reaction mixture was refluxed for 2 hours, then allowed to cool to r.t. and poured into 100 mL of cold water and extracted with AcOEt. The organic extract was washed with 10% aq. NaOH soln. and sat. aq. NaCl soln., dried over MgSO₄ and concentrated in vacuo. The residue was purified by flash master (column: 100 g, flow: 45 mL/min, Heptane to Heptane+30% AcOEt) to yield 2-benzyloxy-5-fluoro-benzaldehyde as an yellow oil.

Step 2: To a solution under N₂ of methyl 2-iodobenzoate (1.0 g, 3.82 mmol) in THF (20 mL) cooled at –78° C., iso-propylmagnesium chloride—lithium chloride complex in THF (1:1), ca. 14% in THF (554 mg, 3.82 mmol, 1.0 eq.) was added dropwise. The mixture was stirred at –78° C. for 1 hour and further at r.t. for 1 hour.==>Grignard Solution A To the Grignard Solution A cooled to –78° C., a solution of 2-benzyloxy-5-fluoro-benzaldehyde (879 mg, 3.82 mmol, 1.0 eq.) in THF (10 mL) was added dropwise. The mixture was stirred at –78° C. for 1 hour and further at r.t. for 18 hours. The reaction was carefully quenched with 1M aq. NH₄Cl soln. (50 mL) and AcOEt (100 mL) was added. The resulting suspension was filtered through celite and the filter cake was rinsed with water and AcOEt. The layers were separated and the aq. phase was extracted with AcOEt (2×150 mL). The comb. org. phases were washed with sat. aq. NaCl soln. (1×100 mL), dried over MgSO₄, and concentrated in vacuo. The residue was purified by flash master (column: 100 g, flow: 45 mL/min, Heptane to Heptane+45% AcOEt) to yield (±)-3-(2-benzyloxy-5-fluoro-phenyl)-3H-isobenzofuran-1-one as a white solid.

Step 3: To an ice-cooled and stirred suspension of lithium aluminum hydride (170 mg, 4.49 mmol, 1.5 eq.) in THF (30 mL), (±)-3-(2-benzyloxy-5-fluoro-phenyl)-3H-isobenzofuran-1-one (1.0 g, 2.99 mmol, 1.0 eq.) in THF (20 mL) was added dropwise. The mixture was stirred at 0° C. for 30 min and further at r.t. for 1 hour. The mixture was again cooled to 0° C. and carefully hydrolyzed by the dropwise addition of iPrOH (15 mL) and 2M aq. NaOH (6 mL). The resulting suspension was filtered through celite and the filter cake was rinsed with THF. The fitrate was concentrated in vacuo. The residue was diluted with 2M aq. HCl soln. (150 mL) and DCM (150 mL). The layers were separated. The aq. phase was extracted with DCM (2×50 mL). The comb. org. phases were washed with water (1×150 mL), sat. aq. NaCl soln. (1×50 mL), dried over MgSO₄, and concentrated in vacuo to give (±)-(2-benzyloxy-5-fluoro-phenyl)-(2-hydroxymethyl-phenyl)-methanol as a colorless oil.

Step 4: To an ice-cooled solution of (±)-(2-benzyloxy-5-fluoro-phenyl)-(2-hydroxymethyl-phenyl)-methanol (500 mg, 1.48 mmol, 1.00 eq.) and DMAP (9 mg, 0.07 mmol, 0.05 eq.) in DCM (30 mL), NEt₃ (0.82 mL, 5.91 mmol, 4.00 eq.) and methanesulfonyl chloride (0.24 mL, 3.10 mmol, 2.10 eq.) were added dropwise. The mixture was stirred at 0° C. for 1 hour and further at r.t. for 2 hours. The reaction mixture was diluted with H₂O (50 mL) and DCM (50 mL). The layers were separated. The aq. phase was extracted with DCM (2×50 mL). The comb. org. phases were washed with water (1×150 mL), sat. aq. NaCl soln. (1×50 mL), dried over MgSO₄, and concentrated in vacuo to give (±)-methanesulfonic acid 2-[(2-benzyloxy-5-fluoro-phenyl)-methanesulfonyloxy-methyl]-benzyl ester.

Step 5: To a solution of (±)-methanesulfonic acid 2-[(2-benzyloxy-5-fluoro-phenyl)-methanesulfonyloxy-methyl]-benzyl ester (650 mg, 1.31 mmol, 1.0 eq.) in DMF (15 mL), benzylamine (0.19 mL, 1.71 mmol, 1.3 eq.) and DIPEA (0.69 mL, 3.94 mmol, 3.0 eq.) were added in sequence. The mixture was heated at 70° C. for 2 days. The reaction mixture was allowed to cool to r.t. and concentrated in vacuo. The residue was filtered and then purified by prep. HPLC (column: Water X-Bridge, 30×75 mm, 10 um, UV/MS, basic conditions) and concentrated in vacuo to give (±)-2-benzyl-1-(2-benzyloxy-5-fluoro-phenyl)-2,3-dihydro-1H-isoindole.

Step 6: To a solution under $N_2$ of (±)-2-benzyl-1-(2-benzyloxy-5-fluoro-phenyl)-2,3-dihydro-1H-isoindole (181 mg, 0.44 mmol, 1.0 eq.) in EtOH (20 mL), palladium on activated carbon (10 wt. %, 60 mg) was added. The flask was evacuated and backfilled with $H_2$ (3×). The black suspension was stirred at r.t. under an $H_2$-atmosphere for 18 hours. The suspension was filtered through Celite, the Celite rinsed with EtOH. The filtrate was concentrated in vacuo. The residue was filtered and then purified by prep. HPLC (column: Atlantis, 30×75 mm, 10 um, UV/MS, acidic conditions) and concentrated in vacuo to give (±)-2-(2,3-dihydro-1H-isoindol-1-yl)-4-fluoro-phenol.

Step 7: To an ice cooled solution of (±)-2-(2,3-dihydro-1H-isoindol-1-yl)-4-fluoro-phenol (13 mg, 0.055 mmol, 1.00 eq.) and DIPEA (37 µL, 0.218 mmol, 4.00 eq.) in DCM (2 mL), benzyl chloroformate (8 µL, 0.057 mmol, 1.05 eq.) was added dropwise. Upon completion of the addition, the cooling bath was removed and the solution was stirred at r.t. for 3 hours. The reaction was quenched with 1M aq. citric acid soln. (5 mL). The layers were separated. The aq. phase was extracted with DCM (3×2 mL). The comb. org. phases were dried over $MgSO_4$ and concentrated in vacuo. The residue was purified by prep. HPLC (column: Atlantis, 30×75 mm, 10 um, UV/MS, acidic conditions) and concentrated in vacuo to give (±)-1-(5-fluoro-2-hydroxy-phenyl)-1,3-dihydro-isoindole-2-carboxylic acid benzyl ester.

LC-MS 3: $t_R$=0.92 min; $[M+H]^+$=364.1

Synthesis of (±)-1-(5-Chloro-2-cyanomethoxy-Phenyl)-3,4-dihydro-1H-isoquinoline-2-carboxylic acid benzyl ester (C25H21N2O3 Cl, MW=432.91)

A mixture of (±)-1-(5-chloro-2-hydroxy-phenyl)-3,4-dihydro-1H-isoquinoline-2-carboxylic acid benzyl ester (1.9 g, 5.00 mmol, 1.00 eq.) and chloroacetonitrile (0.34 mL, 5.19 mmol, 1.04 eq.) in DMSO (1.5 mL) was added to a suspension of potassium carbonate (980 mg, 7.09 mmol, 1.42 eq.) in DMSO (1.5 mL) (exothermic). The mixture was heated up to 80° C. and stirred at that temperature for 1 hour. The reaction mixture was poured onto ice. After the ice melted, the mixture was filtered and the filter cake was rinsed with water. The resulting yellow gum was dried under hv The product was used without further purification.

LC-MS 3: $t_R$=1.00 min; $[M+H]^+$=433.1

Synthesis of (S)-1-(5-Chloro-2-hydrazinocarbonylmethoxy-phenyl)-3,4-dihydro-1H-isoquinoline-2-carboxylic acid benzyl ester (C25H24N3O4Cl, MW=465.94)

To a solution of (S)-1-(2-carboxymethoxy-5-chloro-phenyl)-3,4-dihydro-1H-isoquinoline-2-carboxylic acid benzyl ester (165 mg, 0.36 mmol, 1.0 eq.) in DMF (0.9 mL), TBTU (138 mg, 0.43 mmol, 1.2 eq.) and DIPEA (0.19 mL, 1.08 mmol, 3.0 eq.) were added in sequence. The resulting reaction mixture was stirred at r.t. for 15 min. Then 1M hydrazine in anhydrous THF (1.99 mL, 1.99 mmol, 5.6 eq.) was added at 0° C. (exothermic). The resulting mixture was stirred at r.t. for 18 hours. The reaction mixture was diluted with DCM and then washed with sat. aq. $NaHCO_3$ soln. The aq. phase was extracted once with DCM. The comb. org. phases were dried over $MgSO_4$, filtered, and concentrated in vacuo. The residue was purified by prep. HPLC (column: Waters XBridge, 30×75 mm, 10 um, UV/MS, basic conditions) and evaporated to give the desired product as a brown foam.

LC-MS 3: $t_R$=0.92 min; $[M+H]^+$=466.3

Synthesis of (±)-1-[5-Chloro-2-(N-hydroxycarbamimidoylmethoxy)-phenyl]-3,4-dihydro-1H-isoquinoline-2-carboxylic acid benzyl ester (C25H24N3O4Cl, MW=465.94)

To a solution of (±)-1-(5-chloro-2-cyanomethoxy-phenyl)-3,4-dihydro-1H-isoquinoline-2-carboxylic acid benzyl ester (866 mg, 2.0 mmol, 1.0 eq.) in EtOH (25 mL), water (6 mL), hydroxylamine hydrochloride (542 mg, 7.6 mmol, 3.8 eq.) and potassium carbonate (485 mg, 3.5 mmol, 1.8 eq.) were added in sequence. The mixture was heated to reflux for 1 hour. The mixture was allowed to cool to r.t. and the solvent was removed in vacuo. The residue was partitioned between water and DCM. The layers were separated and the aq. layer was extracted with DCM (3×). The comb. org. layers were dried over $MgSO_4$, filtered, and concentrated in vacuo. The residue, redissolved in DMF (5 mL), was purified by prep. HPLC (column: Waters XBridge, 30×75 mm, 10 um, UV/MS, basic conditions) and evaporated to give the title product as a white foam.

LC-MS 3: $t_R$=0.84 min; $[M+H]^+$=466.2

Synthesis of (±)-5-[4-Chloro-2-(1,2,3,4-tetrahydroisoquinolin-1-yl)-phenoxymethyl]-isoxazol-3-ol (C19H17N2O3Cl, MW=356.81)

Step 1: To an ice-cooled solution of (3-benzyloxy-isoxazol-5-yl)-methanol (500 mg, 2.44 mmol, 1.00 eq., prepared as described by R. Riess et al. Eur. J. Org. Chem. 1998, 473-479) in DCM (5.1 mL), $NEt_3$ (0.39 mL, 2.8 mmol, 1.15 eq.), DMAP (3 mg, 0.02 mmol, 0.01 eq.), and methasulfonyl chloride (0.22 mL, 2.8 mmol, 1.15 eq.) were added in sequence. The reaction mixture was stirred at 0° C. for 2.5 hours, then was concentrated in vacuo to afford methanesulfonic acid 3-benzyloxy-isoxazol-5-ylmethyl ester. The product was used for the next step without further purification.

Step 2: To a solution of (±)-1-(5-chloro-2-hydroxy-phenyl)-3,4-dihydro-1H-isoquinoline-2-carboxylic acid benzyl ester (159 mg, 0.4 mmol, 1 eq.) in MeCN (0.8 mL), potassium carbonate (166 mg, 1.2 mmol, 3 eq.) and methanesulfonic acid 3-benzyloxy-isoxazol-5-ylmethyl ester (113 mg, 0.4 mmol, 1 eq.) were added. The reaction mixture was stirred at 80° C. for 18 hours. The mixture was diluted with MeCN/$H_2O$ 1:1 (1 mL) and purified by prep. HPLC (column: Atlantis, 30×75 mm, 10 um, UV/MS, acidic conditions) and concentrated in vacuo to give (±)-1-[2-(3-benzyloxy-isoxazol-5-ylmethoxy)-5-chloro-phenyl]-3,4-dihydro-1H-isoquinoline-2-carboxylic acid benzyl ester.

Step 3: A solution of (±)-1-[2-(3-benzyloxy-isoxazol-5-ylmethoxy)-5-chloro-phenyl]-3,4-dihydro-1H-isoquinoline-2-carboxylic acid benzyl ester (70 mg, 0.12 mmol, 1 eq.) in 33% hydrobromic acid in acetic acid (0.64 mL) was stirred at r.t. for 1.5 hours. The solvent was removed in vacuo. The residue, redissolved in MeCN/MeOH, was purified by prep. HPLC (column: Waters XBridge, 30×75 mm, 10 um, UV/MS, acidic conditions) and evaporated (genevac) to give (±)-5-[4-chloro-2-(1,2,3,4-tetrahydro-isoquinolin-1-yl)-phenoxymethyl]-isoxazol-3-ol.

LC-MS 3: $t_R$=0.66 min; $[M+H]^+$=357.2

General Method for the Synthesis of phenyl butyric acid 45

To a solution under $N_2$ of a bromobenzene 43 (5.00 mmol, 1.00 eq.) and tetrakis(triphenylphosphine) palladium (0) (289 mg, 0.25 mmol, 0.05 eq.) in THF (10 mL), 4-ethoxy-4-oxobutylzinc bromide 0.5N in THF (20 mL, 10.00 mmol, 2.00 eq.) was added. The mixture was stirred at 50° C. for 18 hours. The mixture was allowed to cool to r.t. and concentrated in vacuo. The residue was purified by flashmaster (column: 100 g, flow: 45 mL/min, Heptane to Heptane+AcOEt) to yield the desired phenyl propionic ester. To a solution of the ester in THF (8 mL) and MeOH (2 mL), 1M aq. NaOH (4 mL) was added. The pale yellow solution was stirred at 50° C. for 18 hours, then the org. solvents were removed in vacuo. The resulting aq. layer was carefully acidified with 2N aq. HCl. The mixture was extracted with DCM (3×20 mL). The comb. org. phases were dried over $MgSO_4$ and concentrated in vacuo to give the desired acid. The product was used without further purification.

Listed in Table 51 below are phenyl butyric acids 45, prepared according to the above-mentioned method, with the corresponding bromobenzene 43 as starting material.

TABLE 51

| Intermediates 45 | Formula MW | $t_R$ [min] LC-MS Method | MS-data m/z $[M + H]^+$ |
|---|---|---|---|
| 4-(2-Fluoro-phenyl)-butyric acid | C10H11O2F 182.19 | 0.71 LC-MS 4 | No ionization |
| 4-(3-Methoxy-phenyl)-butyric acid | C11H14O3 194.23 | 0.73 LC-MS 3 | No ionization |
| 4-(2-Chloro-phenyl)-butyric acid | C10H11O2Cl 198.65 | 0.78 LC-MS 3 | No ionization |
| 4-(3-Chloro-phenyl)-butyric acid | C10H11O2Cl 198.65 | 0.77 LC-MS 3 | No ionization |
| 4-o-Tolyl-butyric acid | C11H14O2 178.23 | 0.75 LC-MS 3 | No ionization |
| 4-m-Tolyl-butyric acid | C11H14O2 178.23 | 0.76 LC-MS 3 | No ionization |
| 4-(2,3-Dichloro-phenyl)-butyric acid | C10H10O2Cl2 233.09 | 0.81 LC-MS 3 | No ionization |
| 4-(3-Fluoro-phenyl)-butyric acid | C10H11O2F 182.19 | 0.73 LC-MS 3 | No ionization |

General Method for the Synthesis of cyclopropanecarboxylic acid Derivatives 49

Step 1: A solution of 2-chlorocinnamic acid (1.84 g, 10.0 mmol, 1.0 eq.) and N,O-dimethylhydroxylamine hydrochloride (995 mg, 10.0 mmol, 1.0 eq.) in DMF (60 mL) was treated with 4-(dimethylamino)pyridine (4.89 g, 40.0 mmol, 4.0 eq.) and N-(3-dimethylaminopropyl)-N'-ethylcarbodiimide hydrochloride (2.88 g, 15.0 mmol, 1.5 eq.) and the resulting solution was stirred at r.t. for 62 hours. The reaction mixture was diluted with AcOEt (1 L). The diluted solution was washed with 1N aq. HCl soln. (3×400 mL), sat. aq. $NaHCO_3$ soln. (3×400 mL), sat. aq. NaCl soln. (1×400 mL), dried over $MgSO_4$, and concentrated in vacuo to give the desired amide as a pale yellow oil. The product was used without further purification.

LC-MS 3: $t_R$=0.80 min; $[M+H]^+$=226.2

Step 2: To a solution under $N_2$ of trimethylsulfoxonium (2.20 g,10.0 mmol, 2.0 eq.) in DMSO (10 mL) maintained at r.t. with a water bath, sodium hydride (60% dispersion in mineral oil, 400 mg, 10.0 mmol, 2.0 eq.) was added portionwise over 10 min. The resulting mixture was stirred at r.t. for 1 hour. A solution of (E)-3-(2-chloro-phenyl)-N-methoxy-N-methyl-acrylamide (1.14 g g, 5.0 mmol, 1.0 eq.) in DMSO (5 mL) was added and the reaction mixture was stirred at r.t. for 19 hours. The reaction mixture was poured in sat. aq. $NH_4Cl$ soln. (50 mL) and extracted with DCM (3×50 mL). The comb. org. phases were washed with sat. aq. NaCl soln. (1×50 mL), dried over $MgSO_4$, and concentrated in vacuo. The residue was purified by CC ($SiO_2$, Hept/AcOEt) to give the desired cyclopropyl as a colorless oil.

LC-MS 2: $t_R$=0.75 min; $[M+H]^+$=240.2

Step 3: To a solution of (±)-(trans)-2-(2-chloro-phenyl)-cyclopropanecarboxylic acid methoxy-methyl-amide (1.00 g, 4.20 mmol, 1.0 eq.) in $Et_2O$ (30 mL), tert-butoxide (2.54 g, 22.66 mmol, 5.4 eq.) and $H_2O$ (0.15 mL) were added. The mixture was stirred at r.t. for 18 hours. The reaction mixture was concentrated in vacuo. The residue was dissolved in $H_2O$ and the solution was carefully acidified with conc. HCl. The mixture was extracted with DCM (3×20 mL). The comb. org. phases were dried over $MgSO_4$, filtered and concentrated in vacuo to give the desired acid as a colorless oil that solidifies upon standing. The residue was used without further purification.

Listed in Tables 52a and 52b below are cyclopropyl acids 49, prepared according to the above-mentioned method, with the corresponding α,β-unsaturated acid 46 as starting material.

TABLE 52a

| Intermediates 49 | Formula MW | $t_R$ [min] LC-MS Method | MS-data m/z $[M + H]^+$ |
|---|---|---|---|
| (±)-(trans)-2-(2-Chloro-phenyl)-cyclopropanecarboxylic acid | C10H9O2Cl 196.63 | 0.67 LC-MS 2 | No ionization |
| (±)-(trans)-2-(2-Fluoro-phenyl)-cyclopropanecarboxylic acid | C10H9O2F 180.18 | 0.71 LC-MS 3 | No ionization |
| (±)-(trans)-2-(2-Trifluoromethyl-phenyl)-cyclopropanecarboxylic acid | C11H9O2F3 230.18 | 0.78 LC-MS 3 | No ionization |
| (±)-(trans)-2-o-Tolyl-cyclopropanecarboxylic acid | C11H12O2 176.21 | 0.73 LC-MS 3 | No ionization |
| (±)-(trans)-2-(2-Methoxy-phenyl)-cyclopropanecarboxylic acid | C11H12O3 192.21 | 0.71 LC-MS 3 | No ionization |
| (±)-(trans)-2-(2,4-Dichloro-phenyl)-cyclopropanecarboxylic acid | C10H8O2Cl2 231.08 | 0.80 LC-MS 3 | No ionization |
| (±)-(trans)-2-(4-Chloro-phenyl)-cyclopropanecarboxylic acid | C10H9O2Cl 196.63 | 0.76 LC-MS 3 | No ionization |
| (±)-(trans)-2-(3-Chloro-phenyl)-cyclopropanecarboxylic acid | C10H9O2Cl 196.63 | 0.76 LC-MS 3 | No ionization |
| (±)-(trans)-2-(3-Fluoro-phenyl)-cyclopropanecarboxylic acid | C10H9O2F 180.18 | 0.71 LC-MS 3 | No ionization |
| (±)-(trans)-2-(3-Methoxy-phenyl)-cyclopropanecarboxylic acid | C11H12O3 192.21 | 0.70 LC-MS 3 | No ionization |
| (±)-(trans)-2-(3-Trifluoromethyl-phenyl)-cyclopropanecarboxylic acid | C11H9O2F3 230.18 | 0.80 LC-MS 3 | No ionization |
| (±)-(trans)-2-(4-Methoxy-phenyl)-cyclopropanecarboxylic acid | C11H12O3 192.21 | 0.61 LC-MS 2 | No ionization |
| (±)-(trans)-2-(4-Fluoro-phenyl)-cyclopropanecarboxylic acid | C10H9O2F 180.18 | 0.63 LC-MS 2 | No ionization |
| (±)-(trans)-2-(4-Trifluoromethyl-phenyl)-cyclopropanecarboxylic acid | C11H9O2F3 230.18 | 0.74 LC-MS 2 | No ionization |
| (±)-(trans)-2-p-Tolyl-cyclopropanecarboxylic acid | C11H12O2 176.21 | 0.69 LC-MS 2 | No ionization |
| (±)-(trans)-2-m-Tolyl- | C11H12O2 | 0.74 | No |

TABLE 52a-continued

| Intermediates 49 | Formula MW | $t_R$ [min] LC-MS Method | MS-data m/z [M + H]⁺ |
|---|---|---|---|
| cyclopropanecarboxylic acid | 176.21 | LC-MS 3 | ionization |
| (±)-2,2-Dimethyl-cyclopropanecarboxylic acid | C6H10O2 114.14 | 0.44 LC-MS 3 | 114.1 |
| (±)-(trans)-2-(2,4-Dimethyl-thiazol-5-yl)-cyclopropanecarboxylic acid | C9H11NO2S 197.26 | 0.33 LC-MS 2 | 198.1 |

TABLE 52b

| Intermediates 49 | Formula MW | ¹H-NMR (300 MHz, CDCl₃) |
|---|---|---|
| (±)-(trans)-2-Ethyl-cyclopropanecarboxylic acid | C6H10O2 114.14 | 0.76 (ddd, J = 8.1, 6.0, 3.9, 1H); 0.97 (t, J = 7.3, 3H); 1.16-1.45 (m, 5H) |
| (±)-(trans)-2-Ethoxy-cyclopropanecarboxylic acid | C6H10O3 130.14 | 0.80-0.92 (m, 1H); 1.24-1.31 (m, 5H); 1.70-1.76 (m, 1H); 3.60-3.64 (m, 2H) |
| (±)-(trans)-2-Isopropyl-cyclopropanecarboxylic acid | C7H12O2 128.17 | 0.80 (ddd, J = 8.1, 6.4, 3.2, 1H); 0.96-0.99 (m, 6H); 0.99-1.09 (m, 1H); 1.15-1.21 (m, 1H); 1.23-1.32 (m, 1H); 1.35-1.41 (m, 1H) |
| (±)-(trans)-2-Methyl-cyclopropanecarboxylic acid | C5H8O2 100.12 | 0.73 (ddd, J = 8.0, 6.4, 4.0, 1H); 1.11 (d, J = 6.0, 3H); 1.18-1.25 (m, 1H); 1.28-1.34 (m, 1H); 1.38-1.49 (m, 1H) |

Synthesis of {4-Chloro-2-[(S)-2-(trans-2-phenyl-cyclopropanecarbonyl)-1,2,3,4-tetrahydro-isoquinolin-1-yl]-phenoxy}-acetic acid ethyl ester (C29H28NO4Cl, MW=490.00)

A solution of the amine ((S)-4-chloro-2-1,2,3,4-tetrahydro-isoquinolin-1-yl-phenoxy)-acetic acid ethyl ester (456 mg, 1.31 mmol, 1.0 eq.) and (±)-(trans)-2-phenylcyclopropane-1-carboxylic acid (219 mg, 1.31 mmol, 1.0 eq.) in DMF (8 mL) was treated with DMAP (240 mg, 1.97 mmol, 1.5 eq.) and N-(3-dimethylaminopropyl)-N'-ethylcarbodiimide hydrochloride (377 mg, 1.97 mmol, 1.5 eq.) and the resulting solution was stirred at r.t. for 18 hours. The reaction mixture was diluted with AcOEt (150 mL). The diluted solution was washed with 1N aq. HCl (3×50 mL), sat. aq. NaHCO₃ soln. (3×50 mL), sat. aq. NaCl soln. (1×50 mL), dried over MgSO₄, filtered, and concentrated in vacuo to give the desired amide.
LC-MS 3: $t_R$=1.04 min; [M+H]⁺=490.0

General Method for the Amide Coupling Between a cyclopropanecarboxylic acid 49 and ((S)-4-Chloro-2-1,2,3,4-tetrahydro-isoquinolin-1-yl-phenoxy)-acetic acid ethyl ester hydrochloride and Subsequent Saponification A solution of the amine ((S)-4-chloro-2-1,2,3,4-tetrahydro-isoquinolin-1-yl-phenoxy)-acetic acid ethyl ester hydrochloride (210 mg, 0.50 mmol, 1.0 eq.) and (±)-(trans)-2-(2-trifluoromethyl-phenyl)-cyclopropanecarboxylic acid (116 mg, 0.50 mmol, 1.0 eq.) in DMF (3 mL) was treated with DMAP (490 mg, 4.00 mmol, 8.0 eq.) and N-(3-dimethylaminopropyl)-N'-ethylcarbodiimide hydrochloride (288 mg, 1.50 mmol, 3.0 eq.) and the resulting solution was stirred at r.t. for 96 hours. The reaction mixture was diluted with AcOEt (50 mL). The diluted solution was washed with 1N aq. HCl (3×20 mL), sat. aq. NaHCO₃ soln. (3×20 mL), sat. aq. NaCl soln. (1×20 mL), dried over MgSO₄, filtered and concentrated in vacuo. To a solution of the residue in THF (2 mL), 1M aq. NaOH (0.64 mL) was added. The solution was stirred at r.t. for 18 hours. The reaction mixture was concentrated in vacuo. The residue was diluted with water and washed with AcOEt. The aq. phase was acidified with 2N aq. HCl. The mixture was extracted with DCM. The comb. org. phases were dried over MgSO₄, filtered and concentrated in vacuo to give the desired acid.

Listed in Table 53 below are examples of compounds of Formula (I), prepared according to the above-mentioned method with the corresponding acid as starting material.

TABLE 53

| Compounds of Formula I | Formula MW | $t_R$ [min] LC-MS Method | MS-data m/z [M + H]⁺ |
|---|---|---|---|
| (4-Chloro-2-{(S)-2-[trans-2-(2-trifluoromethyl-phenyl)-cyclopropanecarbonyl]-1,2,3,4-tetrahydro-isoquinolin-1-yl}-phenoxy)-acetic acid | C28H23NO4ClF3 529.94 | 0.98 LC-MS 3 | 531.1 |
| {4-Chloro-2-[(S)-2-(trans-2-o-tolyl-cyclopropanecarbonyl)-1,2,3,4-tetrahydro-isoquinolin-1-yl]-phenoxy}-acetic acid | C28H26NO4Cl 475.97 | 0.97 LC-MS 3 | 476.1 |
| (4-Chloro-2-{(S)-2-[trans-2-(3-fluoro-phenyl)-cyclopropanecarbonyl]-1,2,3,4-tetrahydro-isoquinolin-1-yl}-phenoxy)-acetic acid | C27H23NO4ClF 479.93 | 0.95 LC-MS 3 | 480.3 |
| (4-Chloro-2-{(S)-2-[trans-2-(3-chloro-phenyl)-cyclopropanecarbonyl]-1,2,3,4-tetrahydro-isoquinolin-1-yl}-phenoxy)-acetic acid | C27H23NO4Cl2 496.39 | 0.97 LC-MS 3 | 496.3 |
| (4-Chloro-2-{(S)-2-[trans-2-(4-fluoro-phenyl)-cyclopropanecarbonyl]-1,2,3,4-tetrahydro-isoquinolin-1-yl}-phenoxy)-acetic acid | C27H23NO4ClF 479.93 | 0.95 LC-MS 3 | 480.3 |

Synthesis of (±)-{2-[2-(2-Bromo-acetyl)-1,2,3,4-tetrahydro-isoquinolin-1-yl]-4-fluoro-phenoxyl}-acetic acid ethyl ester (C21H21NO4BrF, MW=450.30)

To an ice-cooled solution under $N_2$ of (±)-[4-fluoro-2-(1,2,3,4-tetrahydro-isoquinolin-1-yl)-phenoxy]-acetic acid ethyl ester hydrochloride (2.0 g, 5.2 mmol, 1.0 eq.) in DCM (13 mL), N-ethyldiisopropylamine (2.7 mL, 15.6 mmol, 3.0 eq.) was added. A solution of bromoacetyl bromide (0.5 mL, 5.7 mmol, 1.1 eq.) in DCM (5 mL) was added dropwise. The cooling bath was removed and the brown solution stirred at r.t. for 2 hours. The solution was diluted with AcOEt (170 mL), washed with sat. aq. $NaHCO_3$ soln. (1×90 mL), with sat. aq. NaCl soln. (1×90 mL), dried over $MgSO_4$, and concentrated in vacuo. The residue was purified by flash master (column: 100 g, flow: 35 mL/min, heptane to heptane+AcOEt) to yield the title compound as a brown oil.

LC-MS 2: $t_R$=0.86 min; $[M+H]^+$=449.6

Synthesis of (±)-{2-[2-(2-Benzyloxycarbonylamino-acetyl)-1,2,3,4-tetrahydro-isoquinolin-1-yl]-4-fluoro-phenoxy}-acetic acid ethyl ester (C29H29N2O6F, MW=520.56)

A solution of N-carbobenzyloxyglycine (1.07 g, 5.00 mmol, 1.0 eq.) and (±)-[4-fluoro-2-(1,2,3,4-tetrahydro-isoquinolin-1-yl)-phenoxy]-acetic acid ethyl ester hydrochloride (1.93 g, 5.00 mmol, 1.0 eq.) in DMF (30 mL) was treated with 4-(dimethylamino)pyridine (2.44 g, 20.00 mmol, 4.0 eq.) and N-(3-dimethylaminopropyl)-N'-ethylcarbodiimide hydrochloride (1.44 g, 7.50 mmol, 1.5 eq.) and the resulting solution was stirred at r.t. for 18 hours. The reaction mixture was diluted with AcOEt (500 mL). The diluted solution was washed with 1N aq. HCl soln. (3×200 mL), sat. aq. $NaHCO_3$ soln. (3×200 mL), sat. aq. NaCl soln. (1×200 mL), dried over $MgSO_4$, and concentrated in vacuo. The crude product was purified by flash master (column: 100 g, flow: 35 mL/min, heptane to heptane+AcOEt) to yield the title product as a white foam.

LC-MS 2: $t_R$=0.92 min; $[M+H]^+$=521.1

Synthesis of (±)-{2-[2-(2-Amino-acetyl)-1,2,3,4-tetrahydro-isoquinolin-1-yl]-4-fluoro-phenoxy}-acetic acid ethyl ester hydrochloride (C21H24N2O4ClF, MW=422.88)

To a solution under $N_2$ of (±)-{2-[2-(2-benzyloxycarbonylamino-acetyl)-1,2,3,4-tetrahydro-isoquinolin-1-yl]-4-fluoro-phenoxy}-acetic acid ethyl ester (1.81 g, 3.48 mmol, 1.0 eq.) in EtOH (17 mL), palladium on activated carbon (10% wt., 181 mg) was added. The flask was carefully evacuated and backfilled with $H_2$ (3×). The black suspension was stirred at r.t. under an $H_2$-atmosphere for 18 hours. The black suspension was filtered through Celite. The Celite was rinsed with EtOH. The filtrate was concentrated in vacuo. The residue was dissolved in 4M HCl in dioxane (20 mL). The resulting solution was stirred at r.t. during 30 min, then concentrated in vacuo. The crude salt was dissolved in EtOH and concentrated in vacuo (3 times) to afford the title salt as a pale yellow foam.

LC-MS 2: $t_R$=0.64 min; $[M+H]^+$=387.2

General Method for the Synthesis of indazoles 9

To a solution of 4'-chloro-2'-fluoroacetophenone (0.7 mL, 5 mmol, 1 eq.) in DME (5 mL), hydrazine monohydrate (5 mL, 5 mmol, 1 eq.) was added at r.t. over 5 min. The reaction mixture was then refluxed in a sealed microwave vial for 24 hours. The mixture was cooled down to r.t. and the solvent was removed in vacuo. Water was added. The resulting suspension was filtered off and the solids were purified by prep. HPLC (column: Waters XBridge, 30×75 mm, 10 um, UV/MS, acidic conditions) and evaporated to give the desired indazole as a white solid.

Listed in Table 54 below are indazoles 9, prepared according to the above-mentioned method, with the corresponding 2'-fluoroacetophenone as starting material.

TABLE 54

| Intermediates 27 | Formula MW | $t_R$ [min] LC-MS Method | MS-data m/z $[M + H]^+$ |
|---|---|---|---|
| 6-Chloro-3-methyl-1H-indazole | C8H7N2Cl 166.61 | 0.74 LC-MS 3 | 167.1 |
| 4-Chloro-3-methyl-1H-indazole | C8H7N2Cl 166.61 | 0.75 LC-MS 3 | 167.1 |
| 7-Fluoro-3-methyl-1H-indazole | C8H7N2F 150.16 | 0.68 LC-MS 3 | 151.2 |
| 4-Fluoro-3-methyl-1H-indazole | C8H7N2F 150.16 | 0.70 LC-MS 3 | 151.2 |
| 6-Fluoro-3-methyl-1H-indazole | C8H7N2F 150.16 | 0.68 LC-MS 3 | 151.2 |

Chiral Separation

Listed in table 55 are enantiomers or diastereoisomers which were separated by prep. HPLC over a chiral stationary phase. Conditions for the separation are:

Method CS1: Column DaiCel ChiralPak IB (20×250 mm, 5 μm), eluent A 90% Heptane and eluent B 10% EtOH, flow 16 mL/min.

Method CS2: Column DaiCel ChiralPak IB (20×250 mm, 5 μm), eluent A 95% Heptane and eluent B 15% EtOH, flow 16 mL/min.

Method CS3: Column DaiCel ChiralPak OD (20×250 mm, 10 μm), eluent A 95% Heptane and eluent B 5% EtOH, flow 16 mL/min.

Method CS4: Column DaiCel ChiralPak AD-H (20×250 mm, 5 μm), eluent A 60% Heptane and eluent B 40% EtOH, flow 16 mL/min.

Method CS5: Column DaiCel ChiralPak AD-H (20×250 mm, 5 μm), eluent A 95% Heptane and eluent B 5% EtOH, flow 16 mL/min.

Method CS6: Column DaiCel ChiralPak OD-H (20×250 mm, 5 μm), eluent A 85% Heptane and eluent B 15% EtOH, flow 16 mL/min.

Method CS7: Column DaiCel ChiralPak AD-H (20×250 mm, 5 μm), eluent A 85% Heptane and eluent B 15% EtOH, flow 16 mL/min.

Method CS8: Column DaiCel ChiralPak AD-H (20×250 mm, 5 μm), eluent A 80% Heptane and eluent B 20% EtOH, flow 16 mL/min.

Method CS9: Column DaiCel ChiralPak AD-H (30×250 mm, 5 μm), eluent A 90% Heptane and eluent B 10% EtOH, flow 34 mL/min.

TABLE 55

| Optically pure intermediates | Formula MW HPLC Method | $t_R$ [min] LC-MS Method | MS-data m/z [M + H]+ |
|---|---|---|---|
| (S)-1-(5-Cyano-2-ethoxy-carbonyl-methoxy-phenyl)-3,4-dihydro-1H-isoquinoline-2-carboxylic acid benzyl ester | C28H26N2O5 470.52 CS1 | 0.94 LC-MS 2 | 471.1 |
| (S)-1-(2-Ethoxycarbonyl-methoxy-5-fluoro-phenyl)-3,4-dihydro-1H-isoquinoline-2-carboxylic acid benzyl ester | C27H26NO5F 463.50 CS2 | 0.99 LC-MS 2 | 464.0 |
| (S)-1-(5-Chloro-2-ethoxy-carbonyl-methoxy-phenyl)-3,4-dihydro-1H-isoquinoline-2-carboxylic acid benzyl ester | C27H26NO5Cl 479.96 CS2 | 1.04 LC-MS 2 | 480.1 |
| (S)-1-[5-Fluoro-2-((S)-1-methoxy-carbonyl-ethoxy)-phenyl]-3,4-dihydro-1H-isoquinoline-2-carboxylic acid benzyl ester | C27H26NO5F 463.50 CS3 | 1.08 LC-MS 2 | 464.2 |
| (S)-1-[5-Fluoro-2-((R)-1-methoxy-carbonyl-ethoxy)-phenyl]-3,4-dihydro-1H-isoquinoline-2-carboxylic acid benzyl ester | C27H26NO5F 463.50 CS3 | 1.09 LC-MS 2 | 464.1 |
| (S)-1-(5-Chloro-2-ethoxy-carbonyl-methoxy-phenyl)-5-fluoro-3,4-dihydro-1H-isoquinoline-2-carboxylic acid benzyl ester | C27H25NO5ClF 497.95 CS4 | 1.06 LC-MS 3 | 498.1 |
| {4-Fluoro-2-[(S)-2-((trans)-2-phenyl-cyclopropanecarbonyl)-1,2,3,4-tetrahydro-isoquinolin-1-yl]-phenoxy}-acetic acid ethyl ester (diastereoisomer 1) | C29H28NO4F 473.54 CS1 | 0.97 LC-MS 2 | 474.1 |
| {4-Fluoro-2-[(S)-2-((trans)-2-phenyl-cyclopropanecarbonyl)-1,2,3,4-tetrahydro-isoquinolin-1-yl]-phenoxy}-acetic acid ethyl ester (diastereoisomer 2) | C29H28NO4F 473.54 CS1 | 0.97 LC-MS 2 | 474.1 |
| (S)-1-(2-Carboxymethoxy-5-cyano-phenyl)-5-fluoro-3,4-dihydro-1H-isoquinoline-2-carboxylic acid benzyl ester | C26H21N2O5F 460.46 CS5 | 0.90 LC-MS 3 | 461.1 |
| (S)-1-(5-Chloro-2-ethoxy-carbonyl-methoxy-phenyl)-5-fluoro-3,4-dihydro-1H-isoquinoline-2-carboxylic acid tert-butyl ester | C24H27NO5ClF 463.93 CS5 | 1.04 LC-MS 3 | 464.1 |
| (S)-1-(5-Chloro-2-ethoxy-carbonyl-methoxy-phenyl)-3,4-dihydro-1H-isoquinoline-2-carboxylic acid tert-butyl ester | C24H28NO5Cl 445.94 CS6 | 1.04 LC-MS 3 | 446.0 |
| (S)-1-(5-Chloro-2-ethoxy-carbonyl-methoxy-phenyl)-5,6-difluoro-3,4-dihydro-1H-isoquinoline-2-carboxylic acid tert-butyl ester | C24H26NO5ClF2 481.92 CS7 | 1.05 LC-MS 3 | 482.1 |
| (S)-1-(5-Chloro-2-ethoxy-carbonyl-methoxy-phenyl)-6-fluoro-3,4-dihydro-1H-isoquinoline-2-carboxylic acid tert-butyl ester | C24H27NO5ClF 463.93 CS7 | 1.04 LC-MS 3 | 464.3 |
| (S)-1-(5-Chloro-2-ethoxy-carbonyl-methoxy-phenyl)-5,6-difluoro-3,4-dihydro-1H-isoquinoline-2-carboxylic acid benzyl ester | C27H24NO5ClF2 515.94 CS8 | 1.05 LC-MS 3 | 516.1 |
| (S)-1-(5-Chloro-2-ethoxy-carbonyl-methoxy-phenyl)-6-fluoro-3,4-dihydro-1H-isoquinoline-2-carboxylic acid benzyl ester | C27H25NO5ClF 497.95 CS8 | 1.05 LC-MS 3 | 497.6 |
| 1-(5-Chloro-2-ethoxycarbonyl-methoxy-phenyl)-1,3-dihydro-isoindole-2-carboxylic acid tert-butyl ester (enantiomer 1) | C23H26NO5Cl 431.91 CS9 | 1.01 LC-MS 3 | 432.3 |
| 1-(5-Chloro-2-ethoxycarbonyl-methoxy-phenyl)-1,3-dihydro-isoindole-2-carboxylic acid tert-butyl ester (enantiomer 2) | C23H26NO5Cl 431.91 CS9 | 1.01 LC-MS 3 | 432.3 |
| {4-Chloro-2-[(S)-2-((1R,2R)-2-phenyl-cyclopropanecarbonyl)-1,2,3,4-tetrahydro-isoquinolin-1-yl]-phenoxy}-acetic acid ethyl ester | C29H28NO4Cl 490.00 CS1 | 1.04 LC-MS 3 | 490.0 |

Determination of the Stereochemistry

The assessment of the absolute configuration on the tetrahydroisoquinoline was done by X-ray analysis of compound 50 which was obtained according to the procedure as described in Scheme 20. The racemic phenol 51 was subjected to an alkylation with the enantiopure tosylate 52 (obtained upon treatment of the corresponding commercially available alcohol with tosyl chloride in the presence of NEt$_3$ and triethylamine hydrochloride), with the assumption that the alkylation goes via inversion. The resulting mixture of diastereoisomers 53 was separated by chiral prep. HPLC (Conditions: Column Daicel ChiralPak OD (20×250 mm, 10 µm), eluent A 95% Heptane and eluent B 5% EtOH, flow 16 mL/min) to afford the two enantiomerically pure esters, which were saponified to the acids 50 and 54. The acid 50 was more active in the CRTH2 binding assay; it has been crystallized by slow evaporation of a solution in DCM and used for X-ray analysis.

Scheme 20. Determination of the absolute stereochemistry on the tetrahydroisoquinoline.

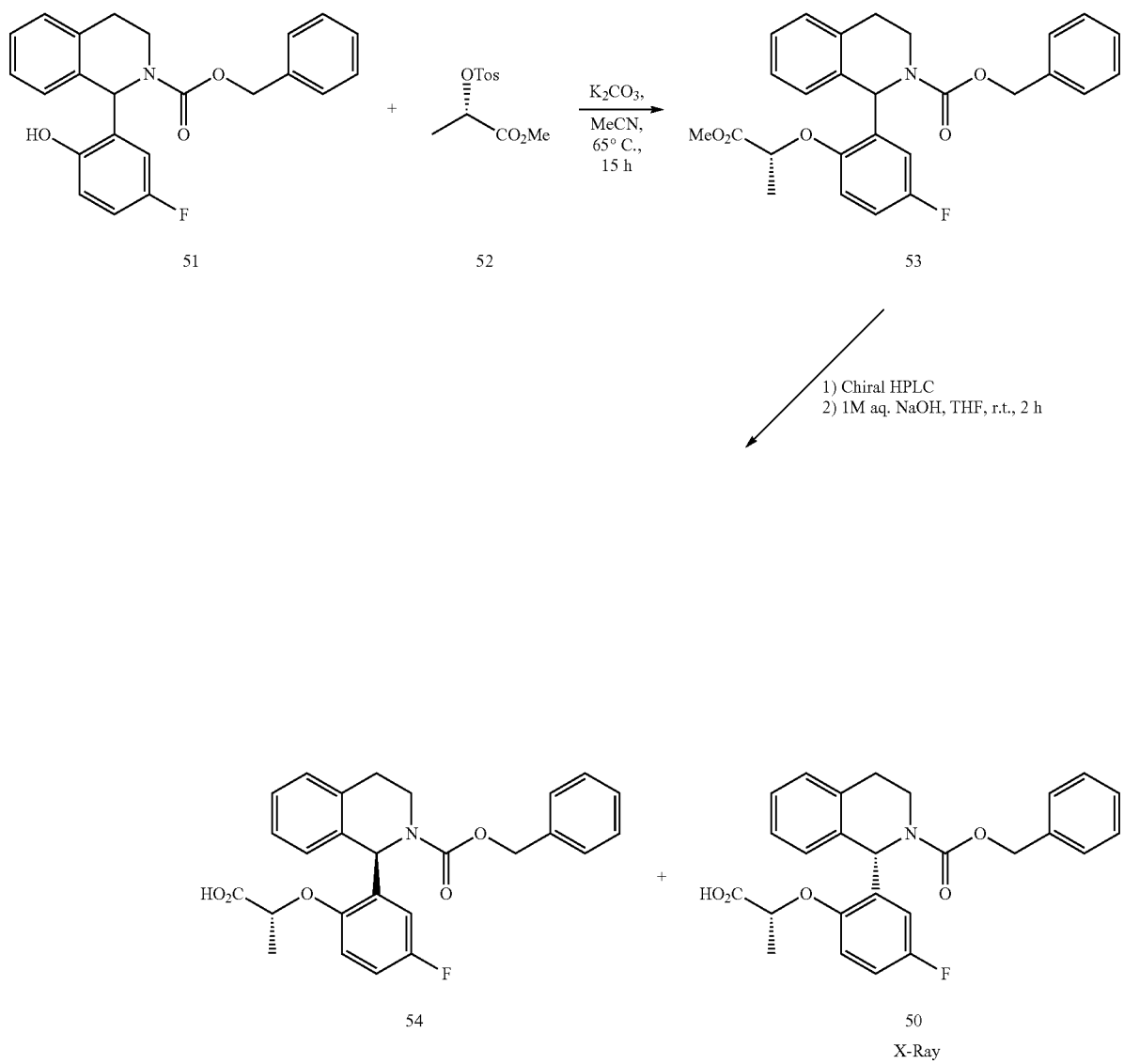

The assessment of the absolute configuration on the phenylcyclopropyl ring was done by following the asymmetric synthesis developed by Charette et al. (JACS1998, 120, 11943-11952). The commercially available cinnamic acid 55 was esterified and reduced to give the homoallylic alcohol 56, which undergoes an asymmetric Simmons-Smith cyclopropanation in the presence of a stoichiometric amount of the ligand 57. The resulting alcohol was then oxidized to give the desired acid 58. The acid 58 was obtained with an ee of 88% and the (S,S)-assignment was confirmed by comparison with published data (S. J. Cho et al. J. Med. Chem. 2009, 52, 1885-1902). Amide coupling between acid 58 and amine 59 in the presence of EDC as activating agent and DMAP as a base, followed by saponification afforded the final compound 60. Compound 60 has been obtained with an ee of 96% and was measured to have an antagonistic activity in the radioligand displacement assay (described below) of $IC_{50}=215$ nM.

By comparison, separation of the diasteroisomeric mixture 61 by prep. HPLC over a chiral stationary phase (Conditions: Column Daicel ChiralPak IB (20×250 mm, 5 μm), eluent A 90% Heptane and eluent B 10% EtOH, flow 16 mL/min) afforded two enantiomerically pure esters. The resulting two esters were saponified in the presence of 1M aq. NaOH to give the two optically pure acids 62 and 60; the thus obtained acid 60 has the same retention time as the acid obtained from intermediates 58 and 59 and was shown to be the less active isomer in the radioligand displacement assay (62: $IC_{50}=1.39$ nM; 60: $IC_{50}=1000$ nM). The stereochemistry of other examples containing a phenyl-cyclopropyl-carbonyl moiety, which were obtained by chiral chromatography, has been assigned in analogy, meaning that the more active isomer was assumed to have (R,R)-configuration at the two stereocenters of the cyclopropyl ring.

Scheme 21. Determination of the absolute stereochemistry of the phenylcyclopropyl moiety.
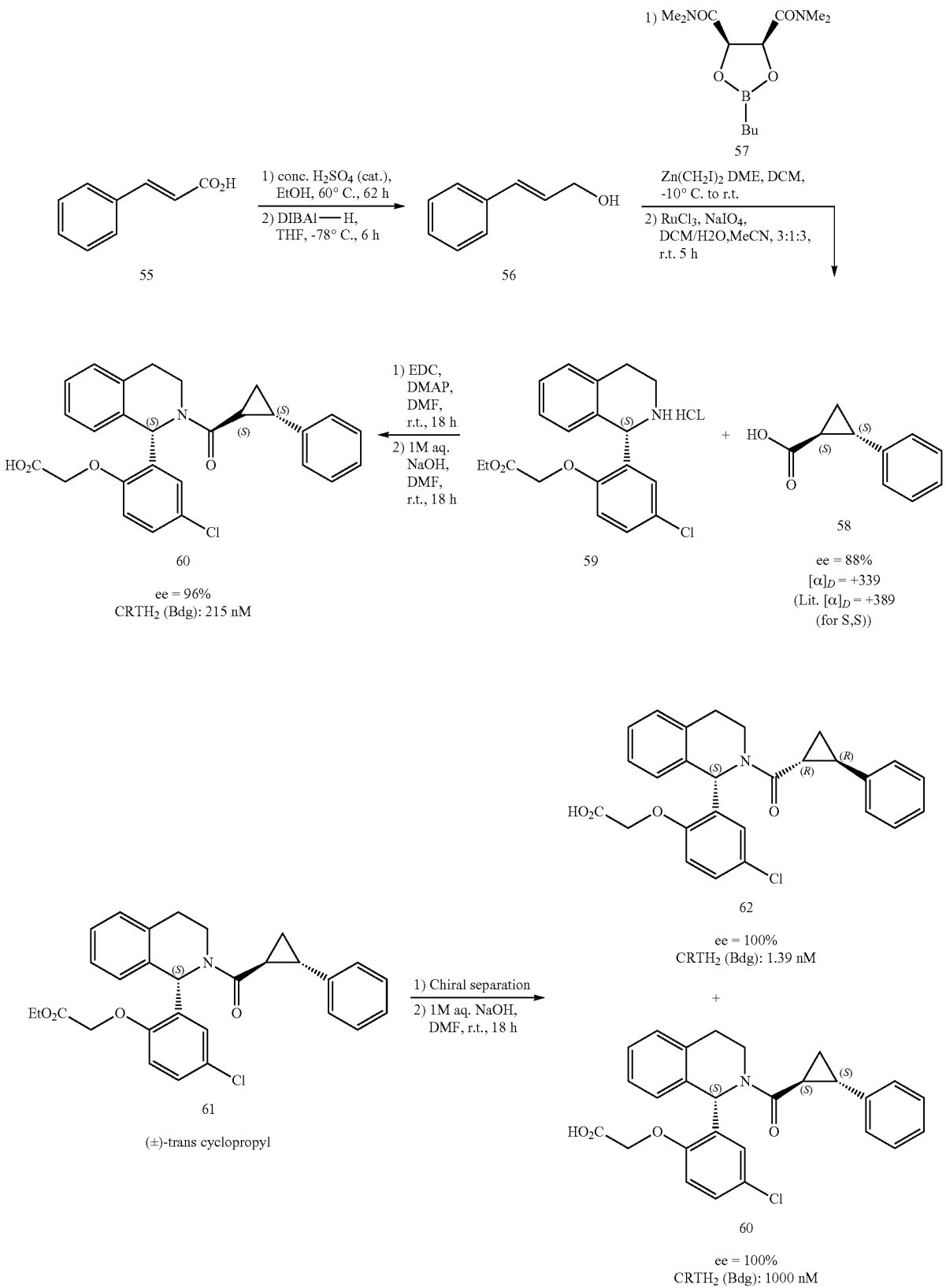

Biological Assays:
Preparation of hCRTH2 Receptor Membranes and Radioligand Displacement Assay:

First, recombinant HEK293-hCRTH$_2$ cells were detached from culture plates into 5 ml buffer A/plate (Buffer A: 5 mM Tris, 1 mM MgCl$_2$-6H$_2$O pH=7.4) using a rubber policeman. Cells were then transferred into centrifugation tubes and centrifuged for 5 min at 400 g. The cell pellet was resuspended in the same buffer and tubes were frozen at −80° C. Cells were thawed and membrane fragments were generated by homogenization using a polytron homogenizer (30 seconds). The membrane fragments were then centrifuged at 3000 g for 20 minutes and resuspended in buffer C (Buffer C: 75 mM Tris, 25 mM MgCl$_2$, 250 mM Saccharose pH 7.4). Aliquots of membrane fragments were stored at −20° C.

Binding assay was performed in a final assay volume of 250 μl. First, 25 μl of test compound, previously diluted in Binding-Buffer (Binding-Buffer: 50 mM Tris-Base, 100 mM NaCl, 1 mM EDTA, 0.1% BSA (protease free), 0.01% NaN$_3$, 10 mM MnCl$_2$, pH 7.0) was placed into each well. After addition of 75 μl Binding-Buffer, 50 μl of the radioligand $^3$H-PGD$_2$ (at 2.5 nM (220.000 dpm/well) from ANAWA ART0662) was added to each well. Binding assay was started by addition of 100 μl CRTH$_2$ membrane fragments, reaching a final concentration of 20 μg/well. For non-specific binding, PGD$_2$ was added to the reaction mixture to 10 mM final concentration.

This assay mix was incubated for 90 minutes at room temperature and then filtered through a GF/C filter 96-well plate which was pre-soaked for 3 hours in 0.5% polyethyleneimine (PEI). The filter-wells were washed three times with ice cold Binding-Buffer. Then, 40 μl of Microscint-40 (Packard) was added to each well and the retained radioactivity quantified in a Topcount (Packard).

Antagonistic activities of exemplified compounds are displayed in the following Table:

| Example | Name | IC$_{50}$ [nM] |
|---|---|---|
| 1 | (±)-1-(2-Carboxymethoxy-5-fluoro-phenyl)-3,4-dihydro-1H-isoquinoline-2-carboxylic acid benzyl ester | 7.6 |
| 2 | 1-[2-((S)-1-Carboxy-ethoxy)-5-fluoro-phenyl]-3,4-dihydro-1H-isoquinoline-2-carboxylic acid benzyl ester | 499 |
| 3 | (±)-1-(2-Carboxymethoxy-5-methyl-phenyl)-3,4-dihydro-1H-isoquinoline-2-carboxylic acid benzyl ester | 62.7 |
| 4 | (±)-1-(5-Bromo-2-carboxymethoxy-phenyl)-3,4-dihydro-1H-isoquinoline-2-carboxylic acid benzyl ester | 10.5 |
| 5 | (±)-7-Bromo-1-(2-carboxymethoxy-5-fluoro-phenyl)-3,4-dihydro-1H-isoquinoline-2-carboxylic acid benzyl ester | 81.2 |
| 6 | (±)-1-(2-Carboxymethoxy-4,5-difluoro-phenyl)-3,4-dihydro-1H-isoquinoline-2-carboxylic acid benzyl ester | 30.1 |
| 7 | (±)-5-Bromo-1-(2-carboxymethoxy-5-fluoro-phenyl)-3,4-dihydro-1H-isoquinoline-2-carboxylic acid benzyl ester | 7.9 |
| 8 | 1-[2-((R)-1-Carboxy-ethoxy)-5-fluoro-phenyl]-3,4-dihydro-1H-isoquinoline-2-carboxylic acid benzyl ester | 39.5 |
| 9 | (±)-1-(2-Carboxymethoxy-5-fluoro-phenyl)-6,7-difluoro-3,4-dihydro-1H-isoquinoline-2-carboxylic acid benzyl ester | 35.5 |
| 10 | (±)-1-(5-Bromo-2-carboxymethoxy-phenyl)-6,7-difluoro-3,4-dihydro-1H-isoquinoline-2-carboxylic acid benzyl ester | 74 |
| 11 | (±)-1-(2-Carboxymethoxy-5-cyano-phenyl)-6,7-difluoro-3,4-dihydro-1H-isoquinoline-2-carboxylic acid benzyl ester | 13.3 |
| 12 | (±)-1-(2-Carboxymethoxy-5-fluoro-phenyl)-5-trifluoromethyl-3,4-dihydro-1H-isoquinoline-2-carboxylic acid benzyl ester | 4.59 |
| 13 | 1-[2-((R)-1-Carboxy-ethoxy)-5-cyano-phenyl]-3,4-dihydro-1H-isoquinoline-2-carboxylic acid benzyl ester | 11 |
| 14 | (±)-1-(2-Carboxymethoxy-5-fluoro-phenyl)-5,6-difluoro-3,4-dihydro-1H-isoquinoline-2-carboxylic acid benzyl ester | 18.8 |
| 15 | (±)-1-(2-Carboxymethoxy-5-chloro-phenyl)-5,6-difluoro-3,4-dihydro-1H-isoquinoline-2-carboxylic acid benzyl ester | 10.1 |
| 16 | (±)-1-(2-Carboxymethoxy-5-cyano-phenyl)-5,6-difluoro-3,4-dihydro-1H-isoquinoline-2-carboxylic acid benzyl ester | 4.34 |
| 17 | (±)-1-(2-Carboxymethoxy-5-dimethylsulfamoyl-phenyl)-3,4-dihydro-1H-isoquinoline-2-carboxylic acid benzyl ester | 889 |
| 18 | (±)-1-(2-Carboxymethoxy-5-chloro-phenyl)-5-fluoro-3,4-dihydro-1H-isoquinoline-2-carboxylic acid benzyl ester | 5.43 |
| 19 | (±)-1-(2-Carboxymethoxy-5-cyano-phenyl)-5-fluoro-3,4-dihydro-1H-isoquinoline-2-carboxylic acid benzyl ester | 9.38 |
| 20 | (±)-1-(2-Carboxymethoxy-5-trifluoromethyl-phenyl)-3,4-dihydro-1H-isoquinoline-2-carboxylic acid benzyl ester | 50.7 |
| 21 | (±)-1-(2-Carboxymethoxy-5-chloro-phenyl)-3,4-dihydro-1H-isoquinoline-2-carboxylic acid benzyl ester | 6.87 |
| 22 | (±)-1-(2-Carboxymethoxy-5-isopropyl-phenyl)-3,4-dihydro-1H-isoquinoline-2-carboxylic acid benzyl ester | 483 |
| 23 | (±)-1-(6-Carboxymethoxy-benzo[1,3]dioxol-5-yl)-3,4-dihydro-1H-isoquinoline-2-carboxylic acid benzyl ester | 227 |
| 24 | (±)-1-(2-Carboxymethoxy-5-methoxy-phenyl)-3,4-dihydro-1H-isoquinoline-2-carboxylic acid benzyl ester | 83.7 |
| 25 | (S)-1-(2-Carboxymethoxy-5-cyano-phenyl)-3,4-dihydro-1H-isoquinoline-2-carboxylic acid benzyl ester | 2.52 |
| 26 | (S)-1-(2-Carboxymethoxy-5-chloro-phenyl)-3,4-dihydro-1H-isoquinoline-2-carboxylic acid benzyl ester | 4.52 |
| 27 | (S)-1-[2-((R)-1-Carboxy-ethoxy)-5-fluoro-phenyl]-3,4-dihydro-1H-isoquinoline-2-carboxylic acid benzyl ester | 12.1 |
| 28 | (S)-1-[2-((S)-1-Carboxy-ethoxy)-5-fluoro-phenyl]-3,4-dihydro-1H-isoquinoline-2-carboxylic acid benzyl ester | 443 |
| 29 | {4-Fluoro-2-[(S)-2-((trans)-2-phenyl-cyclopropanecarbonyl)-1,2,3,4-tetrahydro-isoquinolin-1-yl]-phenoxy}-acetic acid (diastereoisomer 1) | 7.72 |
| 30 | {4-Fluoro-2-[(S)-2-((trans)-2-phenyl-cyclopropanecarbonyl)-1,2,3,4-tetrahydro-isoquinolin-1-yl]-phenoxy}-acetic acid (diastereoisomer 2) | 912 |
| 31 | (S)-1-(2-Carboxymethoxy-5-chloro-phenyl)-5-fluoro-3,4-dihydro-1H-isoquinoline-2-carboxylic acid benzyl ester | 1.41 |
| 32 | (S)-1-(2-Carboxymethoxy-5-cyano-phenyl)-5-fluoro-3,4-dihydro-1H-isoquinoline-2-carboxylic acid benzyl ester | 1.99 |
| 33 | (±)-1-(2-Carboxymethoxy-3,5-difluoro-phenyl)-3,4-dihydro-1H-isoquinoline-2-carboxylic acid benzyl ester | 196 |
| 34 | (±)-1-(2-Carboxymethoxy-5-fluoro-phenyl)-5-fluoro-3,4-dihydro-1H-isoquinoline-2-carboxylic acid benzyl ester | 7.22 |
| 35 | (±)-1-(2-Carboxymethoxy-5-fluoro-phenyl)-5-methoxy-3,4-dihydro-1H-isoquinoline-2-carboxylic acid benzyl ester | 19.7 |
| 36 | (±)-1-(2-Carboxymethoxy-5-fluoro-phenyl)-6,7-dimethoxy-3,4-dihydro-1H-isoquinoline-2-carboxylic acid benzyl ester | 57.1 |
| 37 | (±)-1-(2-Carboxymethoxy-5-fluoro-phenyl)-7-methoxy-3,4-dihydro-1H-isoquinoline-2-carboxylic acid benzyl ester | 19.9 |
| 38 | (±)-1-(2-Carboxymethoxy-5-fluoro-phenyl)-5-chloro-3,4-dihydro-1H-isoquinoline-2-carboxylic acid benzyl ester | 20.8 |
| 39 | (±)-1-(2-Carboxymethoxy-5-fluoro-phenyl)-5-methyl-3,4-dihydro-1H-isoquinoline-2-carboxylic acid benzyl ester | 22.2 |
| 40 | (±)-5-Bromo-1-(2-carboxymethoxy-5-fluoro-phenyl)-6-fluoro-3,4-dihydro-1H-isoquinoline-2-carboxylic acid benzyl ester | 23 |

-continued

| Example | Name | IC$_{50}$ [nM] |
|---|---|---|
| 41 | (±)-1-(2-Carboxymethoxy-5-fluoro-phenyl)-7-fluoro-3,4-dihydro-1H-isoquinoline-2-carboxylic acid benzyl ester | 24.8 |
| 42 | (±)-1-(2-Carboxymethoxy-5-fluoro-phenyl)-5,7-difluoro-3,4-dihydro-1H-isoquinoline-2-carboxylic acid benzyl ester | 6.84 |
| 43 | (±)-1-(2-Carboxymethoxy-5-chloro-phenyl)-5,7-difluoro-3,4-dihydro-1H-isoquinoline-2-carboxylic acid benzyl ester | 4.94 |
| 44 | (±)-1-(2-Carboxymethoxy-5-cyano-phenyl)-5,7-difluoro-3,4-dihydro-1H-isoquinoline-2-carboxylic acid benzyl ester | 8.34 |
| 45 | (±)-{2-[2-(2-Benzo[d]isoxazol-3-yl-acetyl)-1,2,3,4-tetrahydro-isoquinolin-1-yl]-4-fluoro-phenoxy}-acetic acid | 369 |
| 46 | (±)-{4-Fluoro-2-[2-(3-methyl-3-phenyl-butyryl)-1,2,3,4-tetrahydro-isoquinolin-1-yl]-phenoxy}-acetic acid | 916 |
| 47 | (±)-{4-Fluoro-2-[2-(2-naphthalen-1-yl-acetyl)-1,2,3,4-tetrahydro-isoquinolin-1-yl]-phenoxy}-acetic acid | 198 |
| 48 | (±)-{4-Fluoro-2-[2-(2-quinolin-7-yl-acetyl)-1,2,3,4-tetrahydro-isoquinolin-1-yl]-phenoxy}-acetic acid | 287 |
| 49 | (±)-{4-Fluoro-2-[2-(2-quinolin-6-yl-acetyl)-1,2,3,4-tetrahydro-isoquinolin-1-yl]-phenoxy}-acetic acid | 35.7 |
| 50 | (±)-{2-[2-(2-2,3-Dihydro-benzo[1,4]dioxin-6-yl-acetyl)-1,2,3,4-tetrahydro-isoquinolin-1-yl]-4-fluoro-phenoxy}-acetic acid | 182 |
| 51 | (±)-{4-Fluoro-2-[2-(3-1H-indol-3-yl-propionyl)-1,2,3,4-tetrahydro-isoquinolin-1-yl]-phenoxy}-acetic acid | 30.1 |
| 52 | (±)-(2-{2-[3-(1-Ethyl-2-methyl-1H-indol-3-yl)-propionyl]-1,2,3,4-tetrahydro-isoquinolin-1-yl}-4-fluoro-phenoxy)-acetic acid | 600 |
| 53 | (±)-(2-{2-[3-(2,6-Dichloro-phenyl)-propionyl]-1,2,3,4-tetrahydro-isoquinolin-1-yl}-4-fluoro-phenoxy)-acetic acid | 877 |
| 54 | (±)-(4-Fluoro-2-{2-[3-(2-fluoro-phenoxy)-propionyl]-1,2,3,4-tetrahydro-isoquinolin-1-yl}-phenoxy)-acetic acid | 32.2 |
| 55 | (±)-[4-Fluoro-2-(2-{2-[4-(5-methyl-tetrazol-1-yl)-phenyl]-acetyl}-1,2,3,4-tetrahydro-isoquinolin-1-yl)-phenoxy]-acetic acid | 800 |
| 56 | (±)-(2-{2-[3-(6-Chloro-3-oxo-2,3-dihydro-benzo[1,4]oxazin-4-yl)-propionyl]-1,2,3,4-tetrahydro-isoquinolin-1-yl}-4-fluoro-phenoxy)-acetic acid | 735 |
| 57 | (±)-(4-Fluoro-2-{2-[2-(2-methyl-thiazol-4-yl)-acetyl]-1,2,3,4-tetrahydro-isoquinolin-1-yl}-phenoxy)-acetic acid | 730 |
| 58 | (±)-{2-[2-(2-Benzo[b]thiophen-3-yl-acetyl)-1,2,3,4-tetrahydro-isoquinolin-1-yl]-4-fluoro-phenoxy}-acetic acid | 123 |
| 59 | (±)-{2-[2-(3-Benzothiazol-2-yl-propionyl)-1,2,3,4-tetrahydro-isoquinolin-1-yl]-4-fluoro-phenoxy}-acetic acid | 794 |
| 60 | (±)-{2-[2-(2-Biphenyl-4-yl-acetyl)-1,2,3,4-tetrahydro-isoquinolin-1-yl]-4-fluoro-phenoxy}-acetic acid | 577 |
| 61 | (±)-{4-Fluoro-2-[2-(2-indol-1-yl-acetyl)-1,2,3,4-tetrahydro-isoquinolin-1-yl]-phenoxy}-acetic acid | 846 |
| 62 | (±)-{2-[2-(2-1H-Benzoimidazol-2-yl-acetyl)-1,2,3,4-tetrahydro-isoquinolin-1-yl]-4-fluoro-phenoxy}-acetic acid | 794 |
| 63 | (±)-{2-[2-(2-1,3-Dihydro-isoindol-2-yl-acetyl)-1,2,3,4-tetrahydro-isoquinolin-1-yl]-4-fluoro-phenoxy}-acetic acid | 871 |
| 64 | (±)-(4-Fluoro-2-{2-[3-(5-methoxy-1H-indol-3-yl)-propionyl]-1,2,3,4-tetrahydro-isoquinolin-1-yl}-phenoxy)-acetic acid | 49.7 |
| 65 | (±)-(4-Fluoro-2-{2-[3-(2-methyl-1H-indol-3-yl)-propionyl]-1,2,3,4-tetrahydro-isoquinolin-1-yl}-phenoxy)-acetic acid | 191 |
| 66 | (±)-(4-Fluoro-2-{2-[3-(1-methyl-1H-indol-3-yl)-propionyl]-1,2,3,4-tetrahydro-isoquinolin-1-yl}-phenoxy)-acetic acid | 27.5 |
| 67 | {4-Fluoro-2-[2-(trans-2-phenyl-cyclopropanecarbonyl)-1,2,3,4-tetrahydro-isoquinolin-1-yl]-phenoxy}-acetic acid | 15.5 |
| 68 | (±)-{4-Chloro-2-[2-(2-cyclopropyl-acetyl)-1,2,3,4-tetrahydro-isoquinolin-1-yl]-phenoxy}-acetic acid | 508 |
| 69 | (±)-{4-Chloro-2-[2-(2H-chromene-3-carbonyl)-1,2,3,4-tetrahydro-isoquinolin-1-yl]-phenoxy}-acetic acid | 377 |
| 70 | (±)-{4-Chloro-2-[2-(3-methoxy-propionyl)-1,2,3,4-tetrahydro-isoquinolin-1-yl]-phenoxy}-acetic acid | 139 |
| 71 | (±)-(4-Chloro-2-{2-[2-(2-chloro-phenyl)-acetyl]-1,2,3,4-tetrahydro-isoquinolin-1-yl}-phenoxy)-acetic acid | 291 |
| 72 | (±)-{4-Chloro-2-[2-(2-indol-1-yl-acetyl)-1,2,3,4-tetrahydro-isoquinolin-1-yl]-phenoxy}-acetic acid | 44 |
| 73 | (±)-(4-Chloro-2-{2-[3-(2-methyl-1H-indol-3-yl)-propionyl]-1,2,3,4-tetrahydro-isoquinolin-1-yl}-phenoxy)-acetic acid | 4.13 |
| 74 | (±)-(4-Chloro-2-{2-[3-(5-methoxy-1H-indol-3-yl)-propionyl]-1,2,3,4-tetrahydro-isoquinolin-1-yl}-phenoxy)-acetic acid | 1.42 |
| 75 | (±)-(4-Chloro-2-{2-[2-(2,6-dimethyl-pyridin-3-yloxy)-acetyl]-1,2,3,4-tetrahydro-isoquinolin-1-yl}-phenoxy)-acetic acid | 3.68 |
| 76 | (±)-(4-Chloro-2-{2-[3-(1-methyl-1H-indol-3-yl)-propionyl]-1,2,3,4-tetrahydro-isoquinolin-1-yl}-phenoxy)-acetic acid | 4.46 |
| 77 | {4-Chloro-2-[2-(1,2,3,4-tetrahydro-naphthalene-2-carbonyl)-1,2,3,4-tetrahydro-isoquinolin-1-yl]-phenoxy}-acetic acid | 134 |
| 78 | (±)-{2-[2-(2-Benzoimidazol-1-yl-acetyl)-1,2,3,4-tetrahydro-isoquinolin-1-yl]-4-chloro-phenoxy}-acetic acid | 51.1 |
| 79 | (±)-{4-Chloro-2-[2-(2-3,4-dihydro-2H-quinolin-1-yl-acetyl)-1,2,3,4-tetrahydro-isoquinolin-1-yl]-phenoxy}-acetic acid | 62.9 |
| 80 | (±)-{4-Chloro-2-[2-(2-indazol-2-yl-acetyl)-1,2,3,4-tetrahydro-isoquinolin-1-yl]-phenoxy}-acetic acid | 46.9 |
| 81 | (±)-(4-Chloro-2-{2-[3-(3-trifluoromethyl-phenyl)-propionyl]-1,2,3,4-tetrahydro-isoquinolin-1-yl}-phenoxy)-acetic acid | 27.5 |
| 82 | (4-Chloro-2-{2-trans-[2-(2-chloro-phenyl)-cyclopropanecarbonyl]-1,2,3,4-tetrahydro-isoquinolin-1-yl}-phenoxy)-acetic acid | 4.8 |
| 83 | (±)-(4-Chloro-2-{2-[3-(1-phenyl-1H-imidazol-2-yl)-propionyl]-1,2,3,4-tetrahydro-isoquinolin-1-yl}-phenoxy)-acetic acid | 422 |
| 84 | (4-Chloro-2-{2-[3-(4-oxo-2-phenyl-thiazolidin-3-yl)-propionyl]-1,2,3,4-tetrahydro-isoquinolin-1-yl}-phenoxy)-acetic acid | 28.4 |
| 85 | (±)-[4-Chloro-2-(2-{3-[3-(2,3-dimethyl-phenyl)-3H-imidazol-4-yl]-propionyl}-1,2,3,4-tetrahydro-isoquinolin-1-yl)-phenoxy]-acetic acid | 18.9 |
| 86 | (±)-(2-{2-[2-(Biphenyl-2-yloxy)-acetyl]-1,2,3,4-tetrahydro-isoquinolin-1-yl}-4-chloro-phenoxy)-acetic acid | 422 |
| 87 | (±)-(4-Chloro-2-{2-[3-(3-fluoro-phenoxy)-propionyl]-1,2,3,4-tetrahydro-isoquinolin-1-yl}-phenoxy)-acetic acid | 17.8 |
| 88 | (±)-{4-Chloro-2-[2-(3-p-tolyloxy-propionyl)-1,2,3,4-tetrahydro-isoquinolin-1-yl]-phenoxy}-acetic acid | 148 |
| 89 | (±)-(4-Chloro-2-{2-[3-(4-chloro-phenoxy)-propionyl]-1,2,3,4-tetrahydro-isoquinolin-1-yl}-phenoxy)-acetic acid | 37.9 |
| 90 | (±)-(4-Chloro-2-{2-[3-(2-trifluoromethyl-phenyl)-propionyl]-1,2,3,4-tetrahydro-isoquinolin-1-yl}-phenoxy)-acetic acid | 45.8 |
| 91 | (±)-(4-Chloro-2-{2-[2-(5-fluoro-1H-indol-3-yl)-acetyl]-1,2,3,4-tetrahydro-isoquinolin-1-yl}-phenoxy)-acetic acid | 113 |
| 92 | (±)-(4-Chloro-2-{2-[2-(6-methoxy-benzofuran-3-yl)-acetyl]-1,2,3,4-tetrahydro-isoquinolin-1-yl}-phenoxy)-acetic acid | 2.86 |
| 93 | (±)-(4-Chloro-2-{2-[4-(4-chloro-phenyl)-butyryl]-1,2,3,4-tetrahydro-isoquinolin-1-yl}-phenoxy)-acetic acid | 12.9 |
| 94 | (±)-{4-Chloro-2-[2-(3-m-tolyloxy-propionyl)-1,2,3,4-tetrahydro-isoquinolin-1-yl]-phenoxy}-acetic acid | 16.2 |
| 95 | (±)-(4-Chloro-2-{2-[3-(3-chloro-phenoxy)-propionyl]-1,2,3,4-tetrahydro-isoquinolin-1-yl}-phenoxy)-acetic acid | 27.5 |

| Example | Name | IC$_{50}$ [nM] |
|---|---|---|
| 96 | (±)-(4-Chloro-2-{2-[2-(5-chloro-1H-indol-3-yl)-acetyl]-1,2,3,4-tetrahydro-isoquinolin-1-yl}-phenoxy)-acetic acid | 172 |
| 97 | (±)-{4-Chloro-2-[2-(4-p-tolyl-butyryl)-1,2,3,4-tetrahydro-isoquinolin-1-yl]-phenoxy}-acetic acid | 9.7 |
| 98 | (±)-(4-Chloro-2-{2-[2-(5-chloro-benzo[b]thiophen-3-yl)-acetyl]-1,2,3,4-tetrahydro-isoquinolin-1-yl}-phenoxy)-acetic acid | 124 |
| 99 | (±)-(4-Chloro-2-{2-[2-(5-methoxy-1H-indol-2-yl)-acetyl]-1,2,3,4-tetrahydro-isoquinolin-1-yl}-phenoxy)-acetic acid | 296 |
| 100 | (±)-(4-Chloro-2-{2-[2-(5-methyl-benzo[d]isoxazol-3-yl)-acetyl]-1,2,3,4-tetrahydro-isoquinolin-1-yl}-phenoxy)-acetic acid | 205 |
| 101 | (±)-(4-Chloro-2-{2-[2-(5-methoxy-benzo[d]isoxazol-3-yl)-acetyl]-1,2,3,4-tetrahydro-isoquinolin-1-yl}-phenoxy)-acetic acid | 19.6 |
| 102 | (±)-(4-Chloro-2-{2-[3-(4-fluoro-phenoxy)-propionyl]-1,2,3,4-tetrahydro-isoquinolin-1-yl}-phenoxy)-acetic acid | 7.53 |
| 103 | (±)-(4-Chloro-2-{2-[4-(4-fluoro-phenyl)-butyryl]-1,2,3,4-tetrahydro-isoquinolin-1-yl}-phenoxy)-acetic acid | 11.2 |
| 104 | (±)-{4-Chloro-2-[2-(3-o-tolyl-propionyl)-1,2,3,4-tetrahydro-isoquinolin-1-yl]-phenoxy}-acetic acid | 28.6 |
| 105 | (±)-{2-[2-(2-Benzyloxy-acetyl)-1,2,3,4-tetrahydro-isoquinolin-1-yl]-4-chloro-phenoxy}-acetic acid | 9.95 |
| 106 | (±)-(4-Chloro-2-{2-[2-(2-chloro-benzyloxy)-acetyl]-1,2,3,4-tetrahydro-isoquinolin-1-yl}-phenoxy)-acetic acid | 4.06 |
| 107 | (±)-{4-Chloro-2-[2-(4-phenyl-butyryl)-1,2,3,4-tetrahydro-isoquinolin-1-yl]-phenoxy}-acetic acid | 20.6 |
| 108 | (±)-(4-Chloro-2-{2-[4-(3-fluoro-phenyl)-butyryl]-1,2,3,4-tetrahydro-isoquinolin-1-yl}-phenoxy)-acetic acid | 35.9 |
| 109 | (±)-(4-Chloro-2-{2-[4-(2,3-dichloro-phenyl)-butyryl]-1,2,3,4-tetrahydro-isoquinolin-1-yl}-phenoxy)-acetic acid | 16.9 |
| 110 | (±)-{4-Chloro-2-[2-(4-m-tolyl-butyryl)-1,2,3,4-tetrahydro-isoquinolin-1-yl]-phenoxy}-acetic acid | 41.2 |
| 111 | (±)-{4-Chloro-2-[2-(4-o-tolyl-butyryl)-1,2,3,4-tetrahydro-isoquinolin-1-yl]-phenoxy}-acetic acid | 45 |
| 112 | (±)-(4-Chloro-2-{2-[4-(3-chloro-phenyl)-butyryl]-1,2,3,4-tetrahydro-isoquinolin-1-yl}-phenoxy)-acetic acid | 23.4 |
| 113 | (±)-(4-Chloro-2-{2-[4-(2-chloro-phenyl)-butyryl]-1,2,3,4-tetrahydro-isoquinolin-1-yl}-phenoxy)-acetic acid | 25.5 |
| 114 | (±)-(4-Chloro-2-{2-[4-(3-methoxy-phenyl)-butyryl]-1,2,3,4-tetrahydro-isoquinolin-1-yl}-phenoxy)-acetic acid | 34.5 |
| 115 | (±)-(4-Chloro-2-{2-[4-(2-fluoro-phenyl)-butyryl]-1,2,3,4-tetrahydro-isoquinolin-1-yl}-phenoxy)-acetic acid | 27 |
| 116 | {4-Chloro-2-[2-(trans-2-phenyl-cyclopropanecarbonyl)-1,2,3,4-tetrahydro-isoquinolin-1-yl]-phenoxy}-acetic acid | 5.42 |
| 117 | {4-Chloro-2-[5-fluoro-2-(trans-2-phenyl-cyclopropanecarbonyl)-1,2,3,4-tetrahydro-isoquinolin-1-yl]-phenoxy}-acetic acid | 32.5 |
| 118 | (±)-{4-Chloro-2-[5-fluoro-2-(3-o-tolyl-propionyl)-1,2,3,4-tetrahydro-isoquinolin-1-yl]-phenoxy}-acetic acid | 95.4 |
| 119 | (±)-{2-[2-(2-Benzyloxy-acetyl)-5-fluoro-1,2,3,4-tetrahydro-isoquinolin-1-yl]-4-chloro-phenoxy}-acetic acid | 30.9 |
| 120 | (±)-(4-Chloro-2-{2-[2-(2-chloro-benzyloxy)-acetyl]-5-fluoro-1,2,3,4-tetrahydro-isoquinolin-1-yl}-phenoxy)-acetic acid | 33.3 |
| 121 | (±)-{4-Chloro-2-[5-fluoro-2-(4-phenyl-butyryl)-1,2,3,4-tetrahydro-isoquinolin-1-yl]-phenoxy}-acetic acid | 52.3 |
| 122 | (±)-{4-Chloro-2-[5-fluoro-2-(3-phenyl-propynoyl)-1,2,3,4-tetrahydro-isoquinolin-1-yl]-phenoxy}-acetic acid | 196 |
| 123 | (±)-{4-Fluoro-2-[2-(3-phenyl-propionyl)-1,2,3,4-tetrahydro-isoquinolin-1-yl]-phenoxy}-acetic acid | 152 |
| 124 | (±)-[4-Fluoro-2-(2-phenylacetyl-1,2,3,4-tetrahydro-isoquinolin-1-yl)-phenoxy]-acetic acid | 417 |
| 125 | (±)-{4-Fluoro-2-[2-(2-phenoxy-acetyl)-1,2,3,4-tetrahydro-isoquinolin-1-yl]-phenoxy}-acetic acid | 175 |
| 126 | (±)-{2-[2-(2-Benzyloxy-acetyl)-1,2,3,4-tetrahydro-isoquinolin-1-yl]-4-fluoro-phenoxy}-acetic acid | 20 |
| 127 | (±)-{4-Fluoro-2-[2-(4-phenyl-butyryl)-1,2,3,4-tetrahydro-isoquinolin-1-yl]-phenoxy}-acetic acid | 29 |
| 128 | (±)-(4-Fluoro-2-{2-[3-(2-methoxy-phenyl)-propionyl]-1,2,3,4-tetrahydro-isoquinolin-1-yl}-phenoxy)-acetic acid | 69 |
| 129 | (±)-(4-Fluoro-2-{2-[3-(3-methoxy-phenyl)-propionyl]-1,2,3,4-tetrahydro-isoquinolin-1-yl}-phenoxy)-acetic acid | 280 |
| 130 | (±)-(4-Fluoro-2-{2-[3-(4-methoxy-phenyl)-propionyl]-1,2,3,4-tetrahydro-isoquinolin-1-yl}-phenoxy)-acetic acid | 270 |
| 131 | (±)-(2-{2-[3-(2-Chloro-phenyl)-propionyl]-1,2,3,4-tetrahydro-isoquinolin-1-yl}-4-fluoro-phenoxy)-acetic acid | 48 |
| 132 | (±)-(2-{2-[3-(3-Chloro-phenyl)-propionyl]-1,2,3,4-tetrahydro-isoquinolin-1-yl}-4-fluoro-phenoxy)-acetic acid | 86 |
| 133 | (±)-(2-{2-[3-(4-Chloro-phenyl)-propionyl]-1,2,3,4-tetrahydro-isoquinolin-1-yl}-4-fluoro-phenoxy)-acetic acid | 126 |
| 134 | (±)-{4-Fluoro-2-[2-(3-o-tolyl-propionyl)-1,2,3,4-tetrahydro-isoquinolin-1-yl]-phenoxy}-acetic acid | 31 |
| 135 | (±)-{4-Fluoro-2-[2-(2-naphthalen-2-yl-acetyl)-1,2,3,4-tetrahydro-isoquinolin-1-yl]-phenoxy}-acetic acid | 42.2 |
| 136 | (±)-{4-Fluoro-2-[2-(2-o-tolyloxy-acetyl)-1,2,3,4-tetrahydro-isoquinolin-1-yl]-phenoxy}-acetic acid | 119 |
| 137 | (±)-(4-Fluoro-2-{2-[2-(1-methyl-1H-indol-3-yl)-acetyl]-1,2,3,4-tetrahydro-isoquinolin-1-yl}-phenoxy)-acetic acid | 314 |
| 138 | (±)-(2-{2-[2-(2-Chloro-phenoxy)-acetyl]-1,2,3,4-tetrahydro-isoquinolin-1-yl}-4-fluoro-phenoxy)-acetic acid | 101 |
| 139 | (±)-(4-Fluoro-2-{2-[3-(2-fluoro-phenyl)-propionyl]-1,2,3,4-tetrahydro-isoquinolin-1-yl}-phenoxy)-acetic acid | 233 |
| 140 | (±)-{4-Fluoro-2-[2-(2-indan-2-yl-acetyl)-1,2,3,4-tetrahydro-isoquinolin-1-yl]-phenoxy}-acetic acid | 36.4 |
| 141 | (±)-(4-Fluoro-2-{2-[(E)-3-(2-fluoro-phenyl)-acryloyl]-1,2,3,4-tetrahydro-isoquinolin-1-yl}-phenoxy)-acetic acid | 835 |
| 142 | (±)-{4-Fluoro-2-[2-((E)-3-o-tolyl-acryloyl)-1,2,3,4-tetrahydro-isoquinolin-1-yl]-phenoxy}-acetic acid | 349 |
| 143 | (±)-{4-Fluoro-2-[2-(5-phenyl-pentanoyl)-1,2,3,4-tetrahydro-isoquinolin-1-yl]-phenoxy}-acetic acid | 395 |
| 144 | (±)-{4-Fluoro-2-[2-(3-phenoxy-propionyl)-1,2,3,4-tetrahydro-isoquinolin-1-yl]-phenoxy}-acetic acid | 73.9 |
| 145 | (±)-(4-Fluoro-2-{2-[3-(4-methanesulfonyl-phenyl)-propionyl]-1,2,3,4-tetrahydro-isoquinolin-1-yl}-phenoxy)-acetic acid | 983 |
| 146 | (±)-{2-[2-(3-(2,3-Dihydro-indol-1-yl-propionyl)-1,2,3,4-tetrahydro-isoquinolin-1-yl]-4-fluoro-phenoxy}-acetic acid | 61.3 |
| 147 | (±)-{4-Fluoro-2-[2-(3-o-tolyloxy-propionyl)-1,2,3,4-tetrahydro-isoquinolin-1-yl]-phenoxy}-acetic acid | 57.6 |
| 148 | (±)-(4-Fluoro-2-{2-[2-(2-fluoro-phenoxy)-acetyl]-1,2,3,4-tetrahydro-isoquinolin-1-yl}-phenoxy)-acetic acid | 132 |
| 149 | (±)-(4-Fluoro-2-{2-[4-(2-methoxy-phenyl)-butyryl]-1,2,3,4-tetrahydro-isoquinolin-1-yl}-phenoxy)-acetic acid | 42.7 |
| 150 | (±)-(2-{2-[2-(2-Chloro-benzyloxy)-acetyl]-1,2,3,4-tetrahydro-isoquinolin-1-yl}-4-fluoro-phenoxy)-acetic acid | 6.16 |
| 151 | (±)-(4-Chloro-2-{2-[(trans)-2-(3-chloro-phenyl)-cyclopropanecarbonyl]-1,2,3,4-tetrahydro-isoquinolin-1-yl}-phenoxy)-acetic acid (diastereoisomer 1) | 264 |
| 152 | (±)-(4-Chloro-2-{2-[(trans)-2-(3-chloro-phenyl)-cyclopropanecarbonyl]-1,2,3,4-tetrahydro-isoquinolin-1-yl}-phenoxy)-acetic acid (diastereoisomer 2) | 33.4 |

-continued

| Example | Name | IC$_{50}$ [nM] |
|---|---|---|
| 153 | (±)-{4-Chloro-2-[2-((trans)-2-o-tolyl-cyclopropanecarbonyl)-1,2,3,4-tetrahydro-isoquinolin-1-yl]-phenoxy}-acetic acid (diastereoisomer 1) | 123 |
| 154 | (±)-{4-Chloro-2-[2-((trans)-2-o-tolyl-cyclopropanecarbonyl)-1,2,3,4-tetrahydro-isoquinolin-1-yl]-phenoxy}-acetic acid (diastereoisomer 2) | 4.83 |
| 155 | (±)-(4-Chloro-2-{2-[(trans)-2-(2-trifluoromethyl-phenyl)-cyclopropanecarbonyl]-1,2,3,4-tetrahydro-isoquinolin-1-yl}-phenoxy)-acetic acid (diatereoisomer 1) | 166 |
| 156 | (±)-(4-Chloro-2-{2-[(trans)-2-(2-trifluoromethyl-phenyl)-cyclopropanecarbonyl]-1,2,3,4-tetrahydro-isoquinolin-1-yl}-phenoxy)-acetic acid (diatereoisomer 2) | 14.2 |
| 157 | (±)-(4-Chloro-2-{2-[trans-2-(4-chloro-phenyl)-cyclopropanecarbonyl]-1,2,3,4-tetrahydro-isoquinolin-1-yl}-phenoxy)-acetic acid | 45.3 |
| 158 | (±)-(4-Chloro-2-{2-[trans-2-(2,4-dichloro-phenyl)-cyclopropanecarbonyl]-1,2,3,4-tetrahydro-isoquinolin-1-yl}-phenoxy)-acetic acid | 37.6 |
| 159 | (±)-(4-Chloro-2-{2-[trans-2-(2-methoxy-phenyl)-cyclopropanecarbonyl]-1,2,3,4-tetrahydro-isoquinolin-1-yl}-phenoxy)-acetic acid | 21.2 |
| 160 | (±)-(4-Chloro-2-{2-[trans-2-(2-fluoro-phenyl)-cyclopropanecarbonyl]-1,2,3,4-tetrahydro-isoquinolin-1-yl}-phenoxy)-acetic acid | 16.4 |
| 161 | (±)-(4-Chloro-2-{2-[3-(3-phenyl-3H-[1,2,3]triazol-4-yl)-propionyl]-1,2,3,4-tetrahydro-isoquinolin-1-yl}-phenoxy)-acetic acid | 116 |
| 162 | (±)-(4-Chloro-2-{2-[2-(3-phenyl-3H-[1,2,3]triazol-4-ylsulfanyl)-acetyl]-1,2,3,4-tetrahydro-isoquinolin-1-yl}-phenoxy)-acetic acid | 115 |
| 163 | (±)-1-(2-Carboxymethoxy-5-fluoro-phenyl)-6-fluoro-3,4-dihydro-1H-isoquinoline-2-carboxylic acid benzyl ester | 4.21 |
| 164 | (±)-1-(2-Carboxymethoxy-5-chloro-phenyl)-3,4-dihydro-1H-isoquinoline-2-carboxylic acid 2-chloro-benzyl ester | 0.94 |
| 165 | (±)-1-(2-Carboxymethoxy-5-fluoro-phenyl)-3,4-dihydro-1H-isoquinoline-2-carboxylic acid 2-chloro-benzyl ester | 5 |
| 166 | (±)-1-(2-Carboxymethoxy-5-fluoro-phenyl)-3,4-dihydro-1H-isoquinoline-2-carboxylic acid 2,2-dimethyl-propyl ester | 120 |
| 167 | (±)-1-(2-Carboxymethoxy-5-fluoro-phenyl)-3,4-di-hydro-1H-isoquinoline-2-carboxylic acid butyl ester | 42 |
| 168 | (±)-1-(2-Carboxymethoxy-5-fluoro-phenyl)-3,4-dihydro-1H-isoquinoline-2-carboxylic acid 2-methoxy-phenyl ester | 109 |
| 169 | (±)-1-(2-Carboxymethoxy-5-fluoro-phenyl)-3,4-di-hydro-1H-isoquinoline-2-carboxylic acid phenyl ester | 451 |
| 170 | (±)-1-(2-Carboxymethoxy-5-fluoro-phenyl)-3,4-dihydro-1H-isoquinoline-2-carboxylic acid 2-chloro-phenyl ester | 169 |
| 171 | (±)-1-(2-Carboxymethoxy-5-fluoro-phenyl)-3,4-di-hydro-1H-isoquinoline-2-carboxylic acid isobutyl ester | 47.7 |
| 172 | (±)-1-(2-Carboxymethoxy-5-fluoro-phenyl)-3,4-dihydro-1H-isoquinoline-2-carboxylic acid 2-methoxy-ethyl ester | 59.8 |
| 173 | (±)-1-(2-Carboxymethoxy-5-fluoro-phenyl)-3,4-dihydro-1H-isoquinoline-2-carboxylic acid 4-methoxy-phenyl ester | 102 |
| 174 | (S)-1-(2-Carboxymethoxy-5-chloro-phenyl)-3,4-dihydro-1H-isoquinoline-2-carboxylic acid 2-chloro-benzyl ester | 5.75 |
| 175 | (±)-1-(2-Carboxymethoxy-5-chloro-phenyl)-5-fluoro-3,4-dihydro-1H-isoquinoline-2-carboxylic acid 2-chloro-benzyl ester | 8.75 |
| 176 | (±)-1-(2-Carboxymethoxy-5-chloro-phenyl)-3,4-dihydro-1H-isoquinoline-2-carboxylic acid 2-(2-chloro-phenyl)-ethyl ester | 10.4 |
| 177 | (±)-1-(2-Carboxymethoxy-5-fluoro-phenyl)-3,4-dihydro-1H-isoquinoline-2-carboxylic acid 2-(2-chloro-phenyl)-ethyl ester | 27.5 |
| 178 | (±)-1-(2-Carboxymethoxy-5-fluoro-phenyl)-3,4-dihydro-1H-isoquinoline-2-carboxylic acid 3-chloro-phenyl ester | 687 |
| 179 | (±)-1-(2-Carboxymethoxy-5-chloro-phenyl)-5-fluoro-3,4-dihydro-1H-isoquinoline-2-carboxylic acid 2-(2-chloro-phenyl)-ethyl ester | 39.5 |
| 180 | (±)-1-(2-Carboxymethoxy-5-chloro-phenyl)-4,4-dimethyl-3,4-dihydro-1H-isoquinoline-2-carboxylic acid benzyl ester | 151 |
| 181 | (±)-1-(2-Carboxymethoxy-5-fluoro-phenyl)-7-ethanesulfonyl-3,4-dihydro-1H-isoquinoline-2-carboxylic acid benzyl ester | 572 |
| 182 | (±)-1-(2-Carboxymethoxy-5-methanesulfonyl-phenyl)-3,4-dihydro-1H-isoquinoline-2-carboxylic acid benzyl ester | 308 |
| 183 | (±)-1-(5-Benzenesulfonyl-2-carboxymethoxy-phenyl)-3,4-dihydro-1H-isoquinoline-2-carboxylic acid benzyl ester | 64 |
| 184 | (±)-1-(2-Carboxymethoxy-5-ethanesulfonyl-phenyl)-3,4-dihydro-1H-isoquinoline-2-carboxylic acid benzyl ester | 346 |
| 185 | (±)-1-(2-Carboxymethoxy-5-fluoro-phenyl)-5-methanesulfonyl-3,4-dihydro-1H-isoquinoline-2-carboxylic acid benzyl ester | 78.7 |
| 186 | (±)-1-(2-Carboxymethoxy-5-fluoro-phenyl)-5-ethanesulfonyl-3,4-dihydro-1H-isoquinoline-2-carboxylic acid benzyl ester | 311 |
| 187 | (±)-5-Benzenesulfonyl-1-(2-carboxymethoxy-5-fluoro-phenyl)-3,4-dihydro-1H-isoquinoline-2-carboxylic acid benzyl ester | 241 |
| 188 | (±)-1-(2-Carboxymethoxy-5-pyrimidin-5-yl-phenyl)-3,4-dihydro-1H-isoquinoline-2-carboxylic acid benzyl ester | 89.4 |
| 189 | (±)-1-(4-Carboxymethoxy-4'-fluoro-biphenyl-3-yl)-3,4-dihydro-1H-isoquinoline-2-carboxylic acid benzyl ester | 23.3 |
| 190 | (±)-(2-{2-[2-(3-Chloro-benzyloxy)-acetyl]-1,2,3,4-tetrahydro-isoquinolin-1-yl}-4-fluoro-phenoxy)-acetic acid | 16.9 |
| 191 | (±)-(2-{2-[2-(4-Chloro-benzyloxy)-acetyl]-1,2,3,4-tetrahydro-isoquinolin-1-yl}-4-fluoro-phenoxy)-acetic acid | 33.3 |
| 192 | (±)-(4-Fluoro-2-{2-[2-(2-methyl-benzyloxy)-acetyl]-1,2,3,4-tetrahydro-isoquinolin-1-yl}-phenoxy)-acetic acid | 11.1 |
| 193 | (±)-(4-Fluoro-2-{2-[2-(3-methyl-benzyloxy)-acetyl]-1,2,3,4-tetrahydro-isoquinolin-1-yl}-phenoxy)-acetic acid | 27.7 |
| 194 | (±)-(4-Fluoro-2-{2-[2-(4-methyl-benzyloxy)-acetyl]-1,2,3,4-tetrahydro-isoquinolin-1-yl}-phenoxy)-acetic acid | 90.2 |
| 195 | (±)-(4-Fluoro-2-{2-[2-(3-methoxy-benzyloxy)-acetyl]-1,2,3,4-tetrahydro-isoquinolin-1-yl}-phenoxy)-acetic acid | 36.3 |
| 196 | (±)-(4-Fluoro-2-{2-[2-(4-methoxy-benzyloxy)-acetyl]-1,2,3,4-tetrahydro-isoquinolin-1-yl}-phenoxy)-acetic acid | 146 |
| 197 | (±)-(4-Fluoro-2-{2-[2-(1-methyl-1H-pyrazol-3-ylmethoxy)-acetyl]-1,2,3,4-tetrahydro-isoquinolin-1-yl}-phenoxy)-acetic acid | 323 |
| 198 | (±)-(4-Fluoro-2-{2-[2-(2-methoxy-benzyloxy)-acetyl]-1,2,3,4-tetrahydro-isoquinolin-1-yl}-phenoxy)-acetic acid | 19 |
| 199 | (±)-[2-(2-Benzylcarbamoyl-1,2,3,4-tetrahydro-isoquinolin-1-yl)-4-fluoro-phenoxy]-acetic acid | 54 |
| 200 | (±)-[4-Fluoro-2-(2-phenethylcarbamoyl-1,2,3,4-tetrahydro-isoquinolin-1-yl)-phenoxy]-acetic acid | 31 |
| 201 | (±)-{4-Fluoro-2-[2-(2-methoxy-benzylcarbamoyl)-1,2,3,4-tetrahydro-isoquinolin-1-yl]-phenoxy}-acetic acid | 21 |
| 202 | (±)-{4-Chloro-2-[2-(2-methoxy-benzylcarbamoyl)-1,2,3,4-tetrahydro-isoquinolin-1-yl]-phenoxy}-acetic acid | 7.29 |
| 203 | (±)-{2-[2-(2-Chloro-benzylcarbamoyl)-1,2,3,4-tetrahydro-isoquinolin-1-yl]-4-fluoro-phenoxy}-acetic acid | 27.9 |
| 204 | (±)-(2-{2-[2-(2-Chloro-phenyl)-ethylcarbamoyl]-1,2,3,4-tetrahydro-isoquinolin-1-yl}-4-fluoro-phenoxy)-acetic acid | 83 |

| Example | Name | IC$_{50}$ [nM] |
|---|---|---|
| 205 | (±)-{2-[2-(2-Benzenesulfonylamino-acetyl)-1,2,3,4-tetrahydro-isoquinolin-1-yl]-4-fluoro-phenoxy}-acetic acid | 928 |
| 206 | (±)-(2-{2-[2-(3,5-Dimethyl-isoxazole-4-sulfonylamino)-acetyl]-1,2,3,4-tetrahydro-isoquinolin-1-yl}-4-fluoro-phenoxy)-acetic acid | 819 |
| 207 | (±)-(4-Fluoro-2-{2-[2-(3-fluoro-benzenesulfonylamino)-acetyl]-1,2,3,4-tetrahydro-isoquinolin-1-yl}-phenoxy)-acetic acid | 347 |
| 208 | (±)-(4-Fluoro-2-{2-[2-(2-fluoro-benzenesulfonylamino)-acetyl]-1,2,3,4-tetrahydro-isoquinolin-1-yl}-phenoxy)-acetic acid | 983 |
| 209 | (±)-(2-{2-[2-(3,4-Difluoro-benzenesulfonylamino)-acetyl]-1,2,3,4-tetrahydro-isoquinolin-1-yl}-4-fluoro-phenoxy)-acetic acid | 644 |
| 210 | (±)-(2-{2-[2-(N-Benzenesulfonyl-N-methyl-amino)-acetyl]-1,2,3,4-tetrahydro-isoquinolin-1-yl}-4-fluoro-phenoxy)-acetic acid | 423 |
| 211 | (±)-[4-Fluoro-2-(2-{2-[N-(3-fluoro-benzenesulfonyl)-N-methyl-amino]-acetyl}-1,2,3,4-tetrahydro-isoquinolin-1-yl)-phenoxy]-acetic acid | 261 |
| 212 | (±)-[2-(2-{2-[N-(3,4-Difluoro-benzenesulfonyl)-N-methyl-amino]-acetyl}-1,2,3,4-tetrahydro-isoquinolin-1-yl)-4-fluoro-phenoxy]-acetic acid | 920 |
| 213 | (±)-1-(5-Carbamoyl-2-carboxymethoxy-phenyl)-3,4-dihydro-1H-isoquinoline-2-carboxylic acid benzyl ester | 344 |
| 214 | (±)-1-[2-Carboxymethoxy-5-(5-thioxo-4,5-dihydro-[1,2,4]oxadiazol-3-yl)-phenyl]-3,4-dihydro-1H-isoquinoline-2-carboxylic acid benzyl ester | 147 |
| 215 | (±)-1-(2-Carboxymethoxy-4-fluoro-phenyl)-3,4-dihydro-1H-isoquinoline-2-carboxylic acid benzyl ester | 27 |
| 216 | (±)-1-(2-Carboxymethoxy-6-fluoro-phenyl)-3,4-dihydro-1H-isoquinoline-2-carboxylic acid benzyl ester | 182 |
| 217 | (±)-1-[2-(3-Carboxy-propoxy)-5-fluoro-phenyl]-3,4-dihydro-1H-isoquinoline-2-carboxylic acid benzyl ester | 110 |
| 218 | (±)-{4-Cyano-2-[2-(trans-2-phenyl-cyclopropanecarbonyl)-1,2,3,4-tetrahydro-isoquinolin-1-yl]-phenoxy}-acetic acid | 13.4 |
| 219 | (±)-1-(2-Carboxymethoxy-5-cyano-phenyl)-3,4-dihydro-1H-isoquinoline-2-carboxylic acid benzyl ester | 4.72 |
| 220 | (R)-1-[2-(1-Carboxy-ethoxy)-5-chloro-phenyl]-3,4-dihydro-1H-isoquinoline-2-carboxylic acid benzyl ester | 21 |
| 221 | (S)-1-(2-Carboxymethoxy-5-fluoro-phenyl)-3,4-dihydro-1H-isoquinoline-2-carboxylic acid benzyl ester | 2.91 |
| 222 | (±)-1-(2-Carboxymethoxy-5-fluoro-phenyl)-5-methanesulfonylamino-3,4-dihydro-1H-isoquinoline-2-carboxylic acid benzyl ester | 141 |
| 223 | (±)-1-(2-Carboxymethoxy-5-[1,2,3]triazol-1-yl-phenyl)-3,4-dihydro-1H-isoquinoline-2-carboxylic acid benzyl ester | 7.01 |
| 224 | (±)-1-(2-Carboxymethoxy-5-[1,2,3]triazol-2-yl-phenyl)-3,4-dihydro-1H-isoquinoline-2-carboxylic acid benzyl ester | 12.7 |
| 225 | (±)-{4-Chloro-2-[2-(2-methoxy-benzylthiocarbamoyl)-1,2,3,4-tetrahydro-isoquinolin-1-yl]-phenoxy}-acetic acid | 76.5 |
| 226 | (±)-1-(2-Carboxymethoxy-5-chloro-phenyl)-6-fluoro-3,4-dihydro-1H-isoquinoline-2-carboxylic acid benzyl ester | 5.23 |
| 227 | (±)-1-(2-Carboxymethoxy-5-chloro-phenyl)-3,4-dihydro-1H-isoquinoline-2-carboxylic acid 2-bromo-benzyl ester | 7.21 |
| 228 | (S)-1-(2-Carboxymethoxy-5-chloro-phenyl)-3,4-dihydro-1H-isoquinoline-2-carboxylic acid tert-butyl ester | 71.3 |
| 229 | (S)-1-(2-Carboxymethoxy-5-chloro-phenyl)-5,6-difluoro-3,4-dihydro-1H-isoquinoline-2-carboxylic acid benzyl ester | 4.95 |
| 230 | (±)-1-(2-Carboxymethoxy-5-chloro-phenyl)-1,3-dihydro-isoindole-2-carboxylic acid benzyl ester | 12.8 |
| 231 | 1-(2-Carboxymethoxy-5-chloro-phenyl)-1,3-dihydro-isoindole-2-carboxylic acid benzyl ester (enantiomer 1) | 2.65 |
| 232 | {4-Chloro-2-[(S)-2-((1R,2R)-2-phenyl-cyclopropanecarbonyl)-1,2,3,4-tetrahydro-isoquinolin-1-yl]-phenoxy}-acetic acid | 1.39 |
| 233 | (±)-1-(2-Carboxymethoxy-5-chloro-phenyl)-3,4-dihydro-1H-isoquinoline-2-carboxylic acid 2-methoxy-benzyl ester | 4.55 |
| 234 | (±)-1-(2-Carboxymethoxy-5-chloro-phenyl)-3,4-dihydro-1H-isoquinoline-2-carboxylic acid 2-fluoro-benzyl ester | 3.61 |
| 235 | (±)-1-(2-Carboxymethoxy-5-chloro-phenyl)-3,4-dihydro-1H-isoquinoline-2-carboxylic acid 2-methyl-benzyl ester | 5.62 |
| 236 | (±)-1-(2-Carboxymethoxy-5-chloro-phenyl)-3,4-dihydro-1H-isoquinoline-2-carboxylic acid 2-trifluoromethyl-benzyl ester | 5.59 |
| 237 | (±)-1-(2-Carboxymethoxy-5-chloro-phenyl)-3,4-dihydro-1H-isoquinoline-2-carboxylic acid 3-methoxy-benzyl ester | 4.02 |
| 238 | (±)-1-(2-Carboxymethoxy-5-chloro-phenyl)-3,4-dihydro-1H-isoquinoline-2-carboxylic acid 3-fluoro-benzyl ester | 12.6 |
| 239 | (±)-1-(2-Carboxymethoxy-5-chloro-phenyl)-3,4-dihydro-1H-isoquinoline-2-carboxylic acid 3-methyl-benzyl ester | 17.7 |
| 240 | (±)-1-(2-Carboxymethoxy-5-chloro-phenyl)-3,4-dihydro-1H-isoquinoline-2-carboxylic acid 3-trifluoromethyl-benzyl ester | 18.6 |
| 241 | (±)-1-(2-Carboxymethoxy-5-chloro-phenyl)-3,4-dihydro-1H-isoquinoline-2-carboxylic acid 2,4-dichloro-benzyl ester | 0.96 |
| 242 | (±)-1-(2-Carboxymethoxy-5-chloro-phenyl)-3,4-dihydro-1H-isoquinoline-2-carboxylic acid 2,3-dichloro-benzyl ester | 1.07 |
| 243 | (±)-1-(2-Carboxymethoxy-5-chloro-phenyl)-3,4-dihydro-1H-isoquinoline-2-carboxylic acid 2,6-dichloro-benzyl ester | 6.48 |
| 244 | (±)-1-(2-Carboxymethoxy-5-chloro-phenyl)-3,4-dihydro-1H-isoquinoline-2-carboxylic acid 2,6-dimethoxy-benzyl ester | 7.67 |
| 245 | (±)-1-(2-Carboxymethoxy-5-chloro-phenyl)-3,4-dihydro-1H-isoquinoline-2-carboxylic acid 2,4-dimethyl-benzyl ester | 2.87 |
| 246 | (±)-1-(2-Carboxymethoxy-5-chloro-phenyl)-3,4-dihydro-1H-isoquinoline-2-carboxylic acid 2,3-dimethyl-benzyl ester | 3.43 |
| 247 | (±)-1-(2-Carboxymethoxy-5-chloro-phenyl)-3,4-dihydro-1H-isoquinoline-2-carboxylic acid 2,6-dimethyl-benzyl ester | 17.3 |
| 248 | (±)-1-(2-Carboxymethoxy-5-chloro-phenyl)-3,4-dihydro-1H-isoquinoline-2-carboxylic acid 2,4-difluoro-benzyl ester | 3.3 |
| 249 | (±)-1-(2-Carboxymethoxy-5-chloro-phenyl)-3,4-dihydro-1H-isoquinoline-2-carboxylic acid 2,3-difluoro-benzyl ester | 3.86 |
| 250 | (±)-1-(2-Carboxymethoxy-5-chloro-phenyl)-3,4-dihydro-1H-isoquinoline-2-carboxylic acid 2,6-difluoro-benzyl ester | 6.84 |
| 251 | (±)-1-(2-Carboxymethoxy-5-chloro-phenyl)-3,4-dihydro-1H-isoquinoline-2-carboxylic acid 2,4,6-trimethyl-benzyl ester | 12.3 |
| 252 | (±)-1-(2-Carboxymethoxy-5-chloro-phenyl)-3,4-dihydro-1H-isoquinoline-2-carboxylic acid 2-chloro-6-fluoro-benzyl ester | 3.98 |
| 253 | (±)-1-(2-Carboxymethoxy-5-chloro-phenyl)-3,4-dihydro-1H-isoquinoline-2-carboxylic acid 2,5-dichloro-benzyl ester | 6.52 |
| 254 | (±)-1-(2-Carboxymethoxy-5-chloro-phenyl)-3,4-dihydro-1H-isoquinoline-2-carboxylic acid 2,4-dimethoxy-benzyl ester | 16 |
| 255 | (±)-1-(2-Carboxymethoxy-5-chloro-phenyl)-3,4-dihydro-1H-isoquinoline-2-carboxylic acid 2,3-dimethoxy-benzyl ester | 4.9 |
| 256 | (±)-1-(2-Carboxymethoxy-5-chloro-phenyl)-3,4-dihydro-1H-isoquinoline-2-carboxylic acid 2,6-dimethyl-pyridin-3-ylmethyl ester | 14.1 |

| Example | Name | IC$_{50}$ [nM] |
|---|---|---|
| 257 | (±)-1-(2-Carboxymethoxy-5-chloro-phenyl)-3,4-dihydro-1H-isoquinoline-2-carboxylic acid 3-cyano-benzyl ester | 5.72 |
| 258 | (±)-1-(2-Carboxymethoxy-5-chloro-phenyl)-3,4-dihydro-1H-isoquinoline-2-carboxylic acid 2,5-difluoro-benzyl ester | 7.54 |
| 259 | (±)-1-(2-Carboxymethoxy-5-chloro-phenyl)-3,4-dihydro-1H-isoquinoline-2-carboxylic acid 5-chloro-2-fluoro-benzyl ester | 5.29 |
| 260 | (±)-1-(2-Carboxymethoxy-5-chloro-phenyl)-3,4-dihydro-1H-isoquinoline-2-carboxylic acid 2-chloro-5-fluoro-benzyl ester | 15.1 |
| 261 | (S)-1-(2-Carboxymethoxy-5-chloro-phenyl)-3,4-dihydro-1H-isoquinoline-2-carboxylic acid (S)-1-phenyl-ethyl ester | 97.1 |
| 262 | (±)-1-(2-Carboxymethoxy-5-chloro-phenyl)-3,4-dihydro-1H-isoquinoline-2-carboxylic acid cyclohexylmethyl ester | 9.43 |
| 263 | (±)-1-(2-Carboxymethoxy-5-chloro-phenyl)-3,4-dihydro-1H-isoquinoline-2-carboxylic acid 1-methyl-1H-pyrazol-3-ylmethyl ester | 7.91 |
| 264 | (±)-1-(2-Carboxymethoxy-5-chloro-phenyl)-3,4-dihydro-1H-isoquinoline-2-carboxylic acid cyclopentylmethyl ester | 13.1 |
| 265 | (±)-1-(2-Carboxymethoxy-5-chloro-phenyl)-3,4-dihydro-1H-isoquinoline-2-carboxylic acid isobutyl ester | 37.6 |
| 266 | (±)-1-(2-Carboxymethoxy-5-chloro-phenyl)-3,4-dihydro-1H-isoquinoline-2-carboxylic acid butyl ester | 24.5 |
| 267 | (±)-1-(2-Carboxymethoxy-5-chloro-phenyl)-3,4-dihydro-1H-isoquinoline-2-carboxylic acid 2-methoxy-ethyl ester | 21.2 |
| 268 | (±)-1-(2-Carboxymethoxy-5-chloro-phenyl)-3,4-dihydro-1H-isoquinoline-2-carboxylic acid cyclopropylmethyl ester | 27.7 |
| 269 | (±)-1-(2-Carboxymethoxy-5-chloro-phenyl)-3,4-dihydro-1H-isoquinoline-2-carboxylic acid 3,5-dimethyl-pyrazol-1-ylmethyl ester | 4.95 |
| 270 | (±)-1-(2-Carboxymethoxy-5-chloro-phenyl)-3,4-dihydro-1H-isoquinoline-2-carboxylic acid 5-methyl-isoxazol-3-ylmethyl ester | 8.31 |
| 271 | (±)-1-(2-Carboxymethoxy-5-chloro-phenyl)-3,4-dihydro-1H-isoquinoline-2-carboxylic acid 1,5-dimethyl-1H-pyrazol-3-ylmethyl ester | 12 |
| 272 | (±)-1-(2-Carboxymethoxy-5-chloro-phenyl)-3,4-dihydro-1H-isoquinoline-2-carboxylic acid 4-chloro-benzyl ester | 17.1 |
| 273 | (S)-1-(2-Carboxymethoxy-5-chloro-phenyl)-3,4-dihydro-1H-isoquinoline-2-carboxylic acid thiazol-2-ylmethyl ester | 2.04 |
| 274 | (S)-1-(2-Carboxymethoxy-5-chloro-phenyl)-3,4-dihydro-1H-isoquinoline-2-carboxylic acid 2-(4-methyl-thiazol-5-yl)-ethyl ester | 2.42 |
| 275 | (S)-1-(2-Carboxymethoxy-5-chloro-phenyl)-3,4-dihydro-1H-isoquinoline-2-carboxylic acid 5-methyl-thiazol-2-ylmethyl ester | 5.01 |
| 276 | (S)-1-(2-Carboxymethoxy-5-chloro-phenyl)-3,4-dihydro-1H-isoquinoline-2-carboxylic acid 4-methyl-thiazol-2-ylmethyl ester | 1.82 |
| 277 | (S)-1-(2-Carboxymethoxy-5-chloro-phenyl)-3,4-dihydro-1H-isoquinoline-2-carboxylic acid 2-methyl-thiazol-5-ylmethyl ester | 0.77 |
| 278 | (S)-1-(2-Carboxymethoxy-5-chloro-phenyl)-3,4-dihydro-1H-isoquinoline-2-carboxylic acid 2-methyl-thiazol-4-ylmethyl ester | 1.28 |
| 279 | (S)-1-(2-Carboxymethoxy-5-chloro-phenyl)-3,4-dihydro-1H-isoquinoline-2-carboxylic acid 3-methyl-isoxazol-5-ylmethyl ester | 0.87 |
| 280 | (S)-1-(2-Carboxymethoxy-5-chloro-phenyl)-3,4-dihydro-1H-isoquinoline-2-carboxylic acid 4-methyl-isoxazol-3-ylmethyl ester | 0.35 |
| 281 | (S)-1-(2-Carboxymethoxy-5-chloro-phenyl)-3,4-dihydro-1H-isoquinoline-2-carboxylic acid 3,5-dimethyl-isoxazol-4-ylmethyl ester | 4.8 |
| 282 | (S)-1-(2-Carboxymethoxy-5-chloro-phenyl)-3,4-dihydro-1H-isoquinoline-2-carboxylic acid pyrazin-2-ylmethyl ester | 3.96 |
| 283 | (S)-1-(2-Carboxymethoxy-5-chloro-phenyl)-3,4-dihydro-1H-isoquinoline-2-carboxylic acid pyrimidin-4-ylmethyl ester | 7.56 |
| 284 | (S)-1-(2-Carboxymethoxy-5-chloro-phenyl)-3,4-dihydro-1H-isoquinoline-2-carboxylic acid pyrimidin-5-ylmethyl ester | 0.86 |
| 285 | (S)-1-(2-Carboxymethoxy-5-chloro-phenyl)-3,4-dihydro-1H-isoquinoline-2-carboxylic acid phenethyl ester | 3.17 |
| 286 | (S)-1-(2-Carboxymethoxy-5-chloro-phenyl)-3,4-dihydro-1H-isoquinoline-2-carboxylic acid 2-(3-fluoro-phenyl)-ethyl ester | 2.67 |
| 287 | (S)-1-(2-Carboxymethoxy-5-chloro-phenyl)-3,4-dihydro-1H-isoquinoline-2-carboxylic acid 2-methyl-2H-pyrazol-3-ylmethyl ester | 0.20 |
| 288 | (S)-1-(2-Carboxymethoxy-5-chloro-phenyl)-3,4-dihydro-1H-isoquinoline-2-carboxylic acid 2,5-dimethyl-2H-pyrazol-3-ylmethyl ester | 0.41 |
| 289 | (S)-1-(2-Carboxymethoxy-5-chloro-phenyl)-3,4-dihydro-1H-isoquinoline-2-carboxylic acid 2-(2-ethyl-5-methyl-2H-pyrazol-3-yl)-ethyl ester | 2.94 |
| 290 | (S)-1-(2-Carboxymethoxy-5-chloro-phenyl)-3,4-dihydro-1H-isoquinoline-2-carboxylic acid 3-methyl-3H-imidazol-4-ylmethyl ester | 0.48 |
| 291 | (S)-1-(2-Carboxymethoxy-5-chloro-phenyl)-3,4-dihydro-1H-isoquinoline-2-carboxylic acid 2-(3,5-dimethyl-pyrazol-1-yl)-ethyl ester | 8.92 |
| 292 | (S)-1-(2-Carboxymethoxy-5-chloro-phenyl)-3,4-dihydro-1H-isoquinoline-2-carboxylic acid 4-methyl-pyrazol-1-ylmethyl ester | 2.08 |
| 293 | (S)-1-(2-Carboxymethoxy-5-chloro-phenyl)-3,4-dihydro-1H-isoquinoline-2-carboxylic acid 2-(2-methyl-benzoimidazol-1-yl)-ethyl ester | 98.1 |
| 294 | (S)-1-(2-Carboxymethoxy-5-chloro-phenyl)-3,4-dihydro-1H-isoquinoline-2-carboxylic acid benzothiazol-2-ylmethyl ester | 1.94 |
| 295 | (S)-1-(2-Carboxymethoxy-5-chloro-phenyl)-3,4-dihydro-1H-isoquinoline-2-carboxylic acid benzooxazol-2-ylmethyl ester | 7.41 |
| 296 | (S)-1-(2-Carboxymethoxy-5-chloro-phenyl)-3,4-dihydro-1H-isoquinoline-2-carboxylic acid 1-methyl-1H-indazol-3-ylmethyl ester | 1.72 |
| 297 | (S)-1-(2-Carboxymethoxy-5-chloro-phenyl)-3,4-dihydro-1H-isoquinoline-2-carboxylic acid indazol-1-ylmethyl ester | 1.06 |
| 298 | (S)-1-(2-Carboxymethoxy-5-chloro-phenyl)-3,4-dihydro-1H-isoquinoline-2-carboxylic acid benzo[d]isoxazol-3-ylmethyl ester | 2.49 |
| 299 | (S)-1-(2-Carboxymethoxy-5-chloro-phenyl)-5,6-difluoro-3,4-dihydro-1H-isoquinoline-2-carboxylic acid thiazol-2-ylmethyl ester | 6.83 |
| 300 | (S)-1-(2-Carboxymethoxy-5-chloro-phenyl)-5,6-difluoro-3,4-dihydro-1H-isoquinoline-2-carboxylic acid 2-(4-methyl-thiazol-5-yl)-ethyl ester | 6.39 |
| 301 | (S)-1-(2-Carboxymethoxy-5-chloro-phenyl)-5,6-difluoro-3,4-dihydro-1H-isoquinoline-2-carboxylic acid 5-methyl-thiazol-2-ylmethyl ester | 4.55 |
| 302 | (S)-1-(2-Carboxymethoxy-5-chloro-phenyl)-5,6-difluoro-3,4-dihydro-1H-isoquinoline-2-carboxylic acid 4-methyl-thiazol-2-ylmethyl ester | 5.7 |
| 303 | (S)-1-(2-Carboxymethoxy-5-chloro-phenyl)-5,6-difluoro-3,4-dihydro-1H-isoquinoline-2-carboxylic acid 2-methyl-thiazol-5-ylmethyl ester | 5.05 |
| 304 | (S)-1-(2-Carboxymethoxy-5-chloro-phenyl)-5,6-difluoro-3,4-dihydro-1H-isoquinoline-2-carboxylic acid 2-methyl-thiazol-4-ylmethyl ester | 5.39 |
| 305 | (S)-1-(2-Carboxymethoxy-5-chloro-phenyl)-5,6-difluoro-3,4-dihydro-1H-isoquinoline-2-carboxylic acid 3-methyl-isoxazol-5-ylmethyl ester | 2.13 |
| 306 | (S)-1-(2-Carboxymethoxy-5-chloro-phenyl)-5,6-difluoro-3,4-dihydro-1H-isoquinoline-2-carboxylic acid 4-methyl-isoxazol-3-ylmethyl ester | 3.12 |
| 307 | (S)-1-(2-Carboxymethoxy-5-chloro-phenyl)-5,6-difluoro-3,4-dihydro-1H-isoquinoline-2-carboxylic acid 3,5-dimethyl-isoxazol-4-ylmethyl ester | 3.34 |

| Example | Name | IC$_{50}$ [nM] |
|---|---|---|
| 308 | (S)-1-(2-Carboxymethoxy-5-chloro-phenyl)-5,6-difluoro-3,4-dihydro-1H-isoquinoline-2-carboxylic acid pyrazin-2-ylmethyl ester | 1.69 |
| 309 | (S)-1-(2-Carboxymethoxy-5-chloro-phenyl)-5,6-difluoro-3,4-dihydro-1H-isoquinoline-2-carboxylic acid pyrimidin-4-ylmethyl ester | 4.77 |
| 310 | (S)-1-(2-Carboxymethoxy-5-chloro-phenyl)-5,6-difluoro-3,4-dihydro-1H-isoquinoline-2-carboxylic acid phenethyl ester | 5.14 |
| 311 | (S)-1-(2-Carboxymethoxy-5-chloro-phenyl)-5,6-difluoro-3,4-dihydro-1H-isoquinoline-2-carboxylic acid 2-(3-fluoro-phenyl)-ethyl ester | 11 |
| 312 | (S)-1-(2-Carboxymethoxy-5-chloro-phenyl)-5,6-difluoro-3,4-dihydro-1H-isoquinoline-2-carboxylic acid 2-methyl-2H-pyrazol-3-ylmethyl ester | 4.65 |
| 313 | (S)-1-(2-Carboxymethoxy-5-chloro-phenyl)-5,6-difluoro-3,4-dihydro-1H-isoquinoline-2-carboxylic acid 2,5-dimethyl-2H-pyrazol-3-ylmethyl ester | 2.37 |
| 314 | (S)-1-(2-Carboxymethoxy-5-chloro-phenyl)-5,6-difluoro-3,4-dihydro-1H-isoquinoline-2-carboxylic acid 2-(2-ethyl-5-methyl-2H-pyrazol-3-yl)-ethyl ester | 9.8 |
| 315 | (S)-1-(2-Carboxymethoxy-5-chloro-phenyl)-5,6-difluoro-3,4-dihydro-1H-isoquinoline-2-carboxylic acid 3-methyl-3H-imidazol-4-ylmethyl ester | 2.82 |
| 316 | (S)-1-(2-Carboxymethoxy-5-chloro-phenyl)-5,6-difluoro-3,4-dihydro-1H-isoquinoline-2-carboxylic acid 2-(3,5-dimethyl-pyrazol-1-yl)-ethyl ester | 5.07 |
| 317 | (S)-1-(2-Carboxymethoxy-5-chloro-phenyl)-5,6-difluoro-3,4-dihydro-1H-isoquinoline-2-carboxylic acid 4-methyl-pyrazol-1-ylmethyl ester | 14.7 |
| 318 | (S)-1-(2-Carboxymethoxy-5-chloro-phenyl)-5,6-difluoro-3,4-dihydro-1H-isoquinoline-2-carboxylic acid 2-(2-methyl-benzoimidazol-1-yl)-ethyl ester | 138 |
| 319 | (S)-1-(2-Carboxymethoxy-5-chloro-phenyl)-5,6-difluoro-3,4-dihydro-1H-isoquinoline-2-carboxylic acid benzothiazol-2-ylmethyl ester | 1.44 |
| 320 | (S)-1-(2-Carboxymethoxy-5-chloro-phenyl)-5,6-difluoro-3,4-dihydro-1H-isoquinoline-2-carboxylic acid benzooxazol-2-ylmethyl ester | 0.52 |
| 321 | (S)-1-(2-Carboxymethoxy-5-chloro-phenyl)-5,6-difluoro-3,4-dihydro-1H-isoquinoline-2-carboxylic acid 1-methyl-1H-indazol-3-ylmethyl ester | 1.84 |
| 322 | (S)-1-(2-Carboxymethoxy-5-chloro-phenyl)-5,6-difluoro-3,4-dihydro-1H-isoquinoline-2-carboxylic acid indazol-1-ylmethyl ester | 0.53 |
| 323 | (S)-1-(2-Carboxymethoxy-5-chloro-phenyl)-5,6-difluoro-3,4-dihydro-1H-isoquinoline-2-carboxylic acid benzo[d]isoxazol-3-ylmethyl ester | 1.2 |
| 324 | (S)-1-(2-Carboxymethoxy-5-chloro-phenyl)-6-fluoro-3,4-dihydro-1H-isoquinoline-2-carboxylic acid thiazol-2-ylmethyl ester | 6.26 |
| 325 | (S)-1-(2-Carboxymethoxy-5-chloro-phenyl)-6-fluoro-3,4-dihydro-1H-isoquinoline-2-carboxylic acid 2-(4-methyl-thiazol-5-yl)-ethyl ester | 21.3 |
| 326 | (S)-1-(2-Carboxymethoxy-5-chloro-phenyl)-6-fluoro-3,4-dihydro-1H-isoquinoline-2-carboxylic acid 5-methyl-thiazol-2-ylmethyl ester | 8.67 |
| 327 | (S)-1-(2-Carboxymethoxy-5-chloro-phenyl)-6-fluoro-3,4-dihydro-1H-isoquinoline-2-carboxylic acid 4-methyl-thiazol-2-ylmethyl ester | 3.38 |
| 328 | (S)-1-(2-Carboxymethoxy-5-chloro-phenyl)-6-fluoro-3,4-dihydro-1H-isoquinoline-2-carboxylic acid 2-methyl-thiazol-5-ylmethyl ester | 3.2 |
| 329 | (S)-1-(2-Carboxymethoxy-5-chloro-phenyl)-6-fluoro-3,4-dihydro-1H-isoquinoline-2-carboxylic acid 2-methyl-thiazol-4-ylmethyl ester | 5.9 |
| 330 | (S)-1-(2-Carboxymethoxy-5-chloro-phenyl)-6-fluoro-3,4-dihydro-1H-isoquinoline-2-carboxylic acid 3-methyl-isoxazol-5-ylmethyl ester | 10.6 |
| 331 | (S)-1-(2-Carboxymethoxy-5-chloro-phenyl)-6-fluoro-3,4-dihydro-1H-isoquinoline-2-carboxylic acid 4-methyl-isoxazol-3-ylmethyl ester | 7.29 |
| 332 | (S)-1-(2-Carboxymethoxy-5-chloro-phenyl)-6-fluoro-3,4-dihydro-1H-isoquinoline-2-carboxylic acid pyrazin-2-ylmethyl ester | 7.65 |
| 333 | (S)-1-(2-Carboxymethoxy-5-chloro-phenyl)-6-fluoro-3,4-dihydro-1H-isoquinoline-2-carboxylic acid pyrimidin-4-ylmethyl ester | 45.7 |
| 334 | (S)-1-(2-Carboxymethoxy-5-chloro-phenyl)-6-fluoro-3,4-dihydro-1H-isoquinoline-2-carboxylic acid pyrimidin-5-ylmethyl ester | 4.95 |
| 335 | (S)-1-(2-Carboxymethoxy-5-chloro-phenyl)-6-fluoro-3,4-dihydro-1H-isoquinoline-2-carboxylic acid phenethyl ester | 13.3 |
| 336 | (S)-1-(2-Carboxymethoxy-5-chloro-phenyl)-6-fluoro-3,4-dihydro-1H-isoquinoline-2-carboxylic acid 2-(3-fluoro-phenyl)-ethyl ester | 11.5 |
| 337 | (S)-1-(2-Carboxymethoxy-5-chloro-phenyl)-6-fluoro-3,4-dihydro-1H-isoquinoline-2-carboxylic acid 2-methyl-2H-pyrazol-3-ylmethyl ester | 3.61 |
| 338 | (S)-1-(2-Carboxymethoxy-5-chloro-phenyl)-6-fluoro-3,4-dihydro-1H-isoquinoline-2-carboxylic acid 2,5-dimethyl-2H-pyrazol-3-ylmethyl ester | 3.13 |
| 339 | (S)-1-(2-Carboxymethoxy-5-chloro-phenyl)-6-fluoro-3,4-dihydro-1H-isoquinoline-2-carboxylic acid 2-(2-ethyl-5-methyl-2H-pyrazol-3-yl)-ethyl ester | 11.5 |
| 340 | (S)-1-(2-Carboxymethoxy-5-chloro-phenyl)-6-fluoro-3,4-dihydro-1H-isoquinoline-2-carboxylic acid 3-methyl-3H-imidazol-4-ylmethyl ester | 5.17 |
| 341 | (S)-1-(2-Carboxymethoxy-5-chloro-phenyl)-6-fluoro-3,4-dihydro-1H-isoquinoline-2-carboxylic acid 2-(3,5-dimethyl-pyrazol-1-yl)-ethyl ester | 11.1 |
| 342 | (S)-1-(2-Carboxymethoxy-5-chloro-phenyl)-6-fluoro-3,4-dihydro-1H-isoquinoline-2-carboxylic acid 4-methyl-pyrazol-1-ylmethyl ester | 17.9 |
| 343 | (S)-1-(2-Carboxymethoxy-5-chloro-phenyl)-6-fluoro-3,4-dihydro-1H-isoquinoline-2-carboxylic acid 2-(2-methyl-benzoimidazol-1-yl)-ethyl ester | 266 |
| 344 | (S)-1-(2-Carboxymethoxy-5-chloro-phenyl)-6-fluoro-3,4-dihydro-1H-isoquinoline-2-carboxylic acid benzothiazol-2-ylmethyl ester | 37.8 |
| 345 | (S)-1-(2-Carboxymethoxy-5-chloro-phenyl)-6-fluoro-3,4-dihydro-1H-isoquinoline-2-carboxylic acid benzooxazol-2-ylmethyl ester | 12.4 |
| 346 | (S)-1-(2-Carboxymethoxy-5-chloro-phenyl)-6-fluoro-3,4-dihydro-1H-isoquinoline-2-carboxylic acid 1-methyl-1H-indazol-3-ylmethyl ester | 1.16 |
| 347 | (S)-1-(2-Carboxymethoxy-5-chloro-phenyl)-6-fluoro-3,4-dihydro-1H-isoquinoline-2-carboxylic acid indazol-1-ylmethyl ester | 0.87 |
| 348 | (S)-1-(2-Carboxymethoxy-5-chloro-phenyl)-6-fluoro-3,4-dihydro-1H-isoquinoline-2-carboxylic acid benzo[d]isoxazol-3-ylmethyl ester | 0.40 |
| 349 | (S)-1-(2-Carboxymethoxy-5-chloro-phenyl)-5,6-difluoro-3,4-dihydro-1H-isoquinoline-2-carboxylic acid 2-fluoro-benzyl ester | 8.99 |
| 350 | (S)-1-(2-Carboxymethoxy-5-chloro-phenyl)-5,6-difluoro-3,4-dihydro-1H-isoquinoline-2-carboxylic acid 3-fluoro-benzyl ester | 3.38 |
| 351 | (S)-1-(2-Carboxymethoxy-5-chloro-phenyl)-5,6-difluoro-3,4-dihydro-1H-isoquinoline-2-carboxylic acid 2,3-difluoro-benzyl ester | 3.27 |
| 352 | (S)-1-(2-Carboxymethoxy-5-chloro-phenyl)-6-fluoro-3,4-dihydro-1H-isoquinoline-2-carboxylic acid 2-fluoro-benzyl ester | 1.87 |
| 353 | (S)-1-(2-Carboxymethoxy-5-chloro-phenyl)-6-fluoro-3,4-dihydro-1H-isoquinoline-2-carboxylic acid 3-fluoro-benzyl ester | 2.79 |
| 354 | (S)-1-(2-Carboxymethoxy-5-chloro-phenyl)-6-fluoro-3,4-dihydro-1H-isoquinoline-2-carboxylic acid 2,3-difluoro-benzyl ester | 7.72 |
| 355 | (S)-1-(2-Carboxymethoxy-5-chloro-phenyl)-3,4-dihydro-1H-isoquinoline-2-carboxylic acid 3-fluoro-benzyl ester | 2.01 |
| 356 | (S)-1-(2-Carboxymethoxy-5-chloro-phenyl)-3,4-dihydro-1H-isoquinoline-2-carboxylic acid 2-methoxy-benzyl ester | 3.58 |
| 357 | (S)-1-(2-Carboxymethoxy-5-chloro-phenyl)-3,4-dihydro-1H-isoquinoline-2-carboxylic acid 2-fluoro-benzyl ester | 1.23 |

| Example | Name | IC$_{50}$ [nM] |
|---|---|---|
| 358 | (S)-1-(2-Carboxymethoxy-5-chloro-phenyl)-5-fluoro-3,4-dihydro-1H-isoquinoline-2-carboxylic acid 3-fluoro-benzyl ester | 2.84 |
| 359 | (S)-1-(2-Carboxymethoxy-5-chloro-phenyl)-5-fluoro-3,4-dihydro-1H-isoquinoline-2-carboxylic acid 2-fluoro-benzyl ester | 1.79 |
| 360 | (±)-1-(2-Carboxymethoxy-5-chloro-phenyl)-3,4-dihydro-1H-isoquinoline-2-carboxylic acid 4-methyl-benzyl ester | 18.8 |
| 361 | (±)-1-(2-Carboxymethoxy-5-chloro-phenyl)-3,4-dihydro-1H-isoquinoline-2-carboxylic acid 4-methoxy-benzyl ester | 22.8 |
| 362 | (±)-1-(2-Carboxymethoxy-5-chloro-phenyl)-3,4-dihydro-1H-isoquinoline-2-carboxylic acid 4-fluoro-benzyl ester | 14.3 |
| 363 | (±)-1-(2-Carboxymethoxy-5-chloro-phenyl)-3,4-dihydro-1H-isoquinoline-2-carboxylic acid 4-trifluoromethyl-benzyl ester | 34.1 |
| 364 | (±)-1-(2-Carboxymethoxy-5-chloro-phenyl)-3,4-dihydro-1H-isoquinoline-2-carboxylic acid 3-chloro-benzyl ester | 16.5 |
| 365 | (±)-1-(2-Carboxymethoxy-5-chloro-phenyl)-7-fluoro-3,4-dihydro-1H-isoquinoline-2-carboxylic acid benzyl ester | 37.8 |
| 366 | (±)-1-(2-Carboxymethoxy-phenyl)-3,4-dihydro-1H-isoquinoline-2-carboxylic acid benzyl ester | 41.5 |
| 367 | (S)-1-(2-Carboxymethoxy-5-chloro-phenyl)-6-fluoro-3,4-dihydro-1H-isoquinoline-2-carboxylic acid benzyl ester | 4.89 |
| 368 | (±)-(4-Chloro-2-{2-[3-(5-fluoro-3-methyl-indol-1-yl)-propionyl]-1,2,3,4-tetrahydro-isoquinolin-1-yl}-phenoxy)-acetic acid | 20.7 |
| 369 | (±)-{4-Chloro-2-[2-(3-pyrrolo[2,3-b]pyridin-1-yl-propionyl)-1,2,3,4-tetrahydro-isoquinolin-1-yl]-phenoxy}-acetic acid | 195 |
| 370 | (±)-(4-Chloro-2-{2-[3-(6-trifluoromethyl-indol-1-yl)-propionyl]-1,2,3,4-tetrahydro-isoquinolin-1-yl}-phenoxy)-acetic acid | 80.6 |
| 371 | (±)-(4-Chloro-2-{2-[3-(5-cyano-indol-1-yl)-propionyl]-1,2,3,4-tetrahydro-isoquinolin-1-yl}-phenoxy)-acetic acid | 53.1 |
| 372 | (±)-{4-Chloro-2-[2-(3-pyrrolo[2,3-c]pyridin-1-yl-propionyl)-1,2,3,4-tetrahydro-isoquinolin-1-yl]-phenoxy}-acetic acid | 596 |
| 373 | (±)-(4-Chloro-2-{2-[3-(6-methoxy-pyrrolo[3,2-c]pyridin-1-yl)-propionyl]-1,2,3,4-tetrahydro-isoquinolin-1-yl}-phenoxy)-acetic acid | 433 |
| 374 | (±)-(4-Chloro-2-{2-[3-(6-methoxy-pyrrolo[2,3-b]pyridin-1-yl)-propionyl]-1,2,3,4-tetrahydro-isoquinolin-1-yl}-phenoxy)-acetic acid | 12.3 |
| 375 | (±)-(4-Chloro-2-{2-[3-(5-chloro-6-methoxy-indol-1-yl)-propionyl]-1,2,3,4-tetrahydro-isoquinolin-1-yl}-phenoxy)-acetic acid | 81.8 |
| 376 | (±)-(4-Chloro-2-{2-[3-(4,6-dimethoxy-pyrrolo[2,3-b]pyridin-1-yl)-propionyl]-1,2,3,4-tetrahydro-isoquinolin-1-yl}-phenoxy)-acetic acid | 32.5 |
| 377 | (±)-(4-Chloro-2-{2-[3-(4,6-dimethoxy-indol-1-yl)-propionyl]-1,2,3,4-tetrahydro-isoquinolin-1-yl}-phenoxy)-acetic acid | 9.71 |
| 378 | (±)-{4-Chloro-2-[2-(3-indol-1-yl-propionyl)-1,2,3,4-tetrahydro-isoquinolin-1-yl]-phenoxy}-acetic acid | 11.6 |
| 379 | (±)-(4-Chloro-2-{2-[3-(5-fluoro-indol-1-yl)-propionyl]-1,2,3,4-tetrahydro-isoquinolin-1-yl}-phenoxy)-acetic acid | 16.8 |
| 380 | (±)-(4-Chloro-2-{2-[3-(7-chloro-indol-1-yl)-propionyl]-1,2,3,4-tetrahydro-isoquinolin-1-yl}-phenoxy)-acetic acid | 24.3 |
| 381 | (±)-{4-Chloro-2-[2-(3-pyrrolo[3,2-b]pyridin-1-yl-propionyl)-1,2,3,4-tetrahydro-isoquinolin-1-yl]-phenoxy}-acetic acid | 31.6 |
| 382 | (±)-(4-Chloro-2-{2-[3-(4-methoxy-indol-1-yl)-propionyl]-1,2,3,4-tetrahydro-isoquinolin-1-yl}-phenoxy)-acetic acid | 20.7 |
| 383 | (±)-(4-Chloro-2-{2-[3-(3-chloro-indazol-1-yl)-propionyl]-1,2,3,4-tetrahydro-isoquinolin-1-yl}-phenoxy)-acetic acid | 8.5 |
| 384 | (±)-(4-Chloro-2-{2-[3-(6-methyl-indol-1-yl)-propionyl]-1,2,3,4-tetrahydro-isoquinolin-1-yl}-phenoxy)-acetic acid | 14.8 |
| 385 | (±)-(4-Chloro-2-{2-[3-(5-chloro-indol-1-yl)-propionyl]-1,2,3,4-tetrahydro-isoquinolin-1-yl}-phenoxy)-acetic acid | 51.2 |
| 386 | (±)-(4-Chloro-2-{2-[3-(6-chloro-indol-1-yl)-propionyl]-1,2,3,4-tetrahydro-isoquinolin-1-yl}-phenoxy)-acetic acid | 11.6 |
| 387 | (±)-(4-Chloro-2-{2-[3-(4-fluoro-indol-1-yl)-propionyl]-1,2,3,4-tetrahydro-isoquinolin-1-yl}-phenoxy)-acetic acid | 36.7 |
| 388 | (±)-(4-Chloro-2-{2-[3-(6-fluoro-indol-1-yl)-propionyl]-1,2,3,4-tetrahydro-isoquinolin-1-yl}-phenoxy)-acetic acid | 25.7 |
| 389 | (±)-(4-Chloro-2-{2-[3-(2,3-dimethyl-indol-1-yl)-propionyl]-1,2,3,4-tetrahydro-isoquinolin-1-yl}-phenoxy)-acetic acid | 70.4 |
| 390 | (±)-(4-Chloro-2-{2-[3-(6-methoxy-indol-1-yl)-propionyl]-1,2,3,4-tetrahydro-isoquinolin-1-yl}-phenoxy)-acetic acid | 7.52 |
| 391 | (4-Chloro-2-{(S)-6-fluoro-2-[3-(4-fluoro-3-methyl-indazol-1-yl)-propionyl]-1,2,3,4-tetrahydro-isoquinolin-1-yl}-phenoxy)-acetic acid | 158 |
| 392 | (4-Chloro-2-{(S)-6-fluoro-2-[3-(7-fluoro-3-methyl-indazol-1-yl)-propionyl]-1,2,3,4-tetrahydro-isoquinolin-1-yl}-phenoxy)-acetic acid | 273 |
| 393 | (4-Chloro-2-{(S)-6-fluoro-2-[3-(6-fluoro-3-methyl-indazol-1-yl)-propionyl]-1,2,3,4-tetrahydro-isoquinolin-1-yl}-phenoxy)-acetic acid | 154 |
| 394 | (4-Chloro-2-{(S)-2-[3-(6-chloro-3-methyl-indazol-1-yl)-propionyl]-6-fluoro-1,2,3,4-tetrahydro-isoquinolin-1-yl}-phenoxy)-acetic acid | 185 |
| 395 | (4-Chloro-2-{(S)-6-fluoro-2-[3-(5-fluoro-indazol-1-yl)-propionyl]-1,2,3,4-tetrahydro-isoquinolin-1-yl}-phenoxy)-acetic acid | 28.4 |
| 396 | (4-Chloro-2-{(S)-2-[3-(5-chloro-indazol-1-yl)-propionyl]-6-fluoro-1,2,3,4-tetrahydro-isoquinolin-1-yl}-phenoxy)-acetic acid | 152 |
| 397 | (4-Chloro-2-{(S)-6-fluoro-2-[3-(3-methyl-indazol-1-yl)-propionyl]-1,2,3,4-tetrahydro-isoquinolin-1-yl}-phenoxy)-acetic acid | 32.1 |
| 398 | (4-Chloro-2-{(S)-6-fluoro-2-[3-(6-fluoro-indazol-1-yl)-propionyl]-1,2,3,4-tetrahydro-isoquinolin-1-yl}-phenoxy)-acetic acid | 64.7 |
| 399 | (4-Chloro-2-{(S)-6-fluoro-2-[3-(4-fluoro-indazol-1-yl)-propionyl]-1,2,3,4-tetrahydro-isoquinolin-1-yl}-phenoxy)-acetic acid | 144 |
| 400 | (4-Chloro-2-{(S)-2-[3-(7-chloro-indazol-1-yl)-propionyl]-6-fluoro-1,2,3,4-tetrahydro-isoquinolin-1-yl}-phenoxy)-acetic acid | 678 |
| 401 | (4-Chloro-2-{(S)-2-[3-(6-chloro-indazol-1-yl)-propionyl]-6-fluoro-1,2,3,4-tetrahydro-isoquinolin-1-yl}-phenoxy)-acetic acid | 46.9 |
| 402 | (4-Chloro-2-{(S)-2-[3-(4-chloro-indazol-1-yl)-propionyl]-6-fluoro-1,2,3,4-tetrahydro-isoquinolin-1-yl}-phenoxy)-acetic acid | 170 |
| 403 | (4-Chloro-2-{(S)-6-fluoro-2-[3-(7-fluoro-indazol-1-yl)-propionyl]-1,2,3,4-tetrahydro-isoquinolin-1-yl}-phenoxy)-acetic acid | 79.1 |
| 404 | (±)-(4-Chloro-2-{2-[3-(3-chloro-pyrrolo[2,3-b]pyrazin-5-yl)-propionyl]-1,2,3,4-tetrahydro-isoquinolin-1-yl}-phenoxy)-acetic acid | 42.6 |
| 405 | (±)-(4-Chloro-2-{2-[3-(2-trifluoromethyl-indol-1-yl)-propionyl]-1,2,3,4-tetrahydro-isoquinolin-1-yl}-phenoxy)-acetic acid | 451 |
| 406 | (±)-(4-Chloro-2-{2-[2-(2-methoxy-phenoxy)-acetyl]-1,2,3,4-tetrahydro-isoquinolin-1-yl}-phenoxy)-acetic acid | 26.8 |
| 407 | (±)-(4-Chloro-2-{2-[2-(4-fluoro-phenoxy)-acetyl]-1,2,3,4-tetrahydro-isoquinolin-1-yl}-phenoxy)-acetic acid | 34.9 |
| 408 | (±)-(4-Chloro-2-{2-[3-(6-methyl-pyridin-2-yl)-propionyl]-1,2,3,4-tetrahydro-isoquinolin-1-yl}-phenoxy)-acetic acid | 177 |
| 409 | (±)-{4-Chloro-2-[2-(2-phenoxy-acetyl)-1,2,3,4-tetrahydro-isoquinolin-1-yl]-phenoxy}-acetic acid | 74 |

-continued

| Example | Name | IC$_{50}$ [nM] |
|---|---|---|
| 410 | (±)-(4-Chloro-2-{2-[2-(2-fluoro-phenoxy)-acetyl]-1,2,3,4-tetrahydro-isoquinolin-1-yl}-phenoxy)-acetic acid | 70.7 |
| 411 | (±)-(4-Chloro-2-{2-[2-(quinolin-8-yloxy)-acetyl]-1,2,3,4-tetrahydro-isoquinolin-1-yl}-phenoxy)-acetic acid | 25.7 |
| 412 | (±)-(4-Chloro-2-{2-[2-(4-chloro-phenoxy)-acetyl]-1,2,3,4-tetrahydro-isoquinolin-1-yl}-phenoxy)-acetic acid | 40.2 |
| 413 | (±)-(4-Chloro-2-{2-[2-(3-chloro-phenoxy)-acetyl]-1,2,3,4-tetrahydro-isoquinolin-1-yl}-phenoxy)-acetic acid | 70.5 |
| 414 | (±)-{4-Chloro-2-[2-(2-p-tolyloxy-acetyl)-1,2,3,4-tetrahydro-isoquinolin-1-yl]-phenoxy}-acetic acid | 126 |
| 415 | (±)-(4-Chloro-2-{2-[2-(4-methoxy-phenoxy)-acetyl]-1,2,3,4-tetrahydro-isoquinolin-1-yl}-phenoxy)-acetic acid | 210 |
| 416 | (±)-(4-Chloro-2-{2-[2-(pyridin-3-yloxy)-acetyl]-1,2,3,4-tetrahydro-isoquinolin-1-yl}-phenoxy)-acetic acid | 215 |
| 417 | (±)-(4-Chloro-2-{2-[trans-2-(4-methoxy-phenyl)-cyclopropanecarbonyl]-1,2,3,4-tetrahydro-isoquinolin-1-yl]-phenoxy)-acetic acid | 187 |
| 418 | (±)-(4-Chloro-2-{2-[trans-2-(4-fluoro-phenyl)-cyclopropanecarbonyl]-1,2,3,4-tetrahydro-isoquinolin-1-yl]-phenoxy)-acetic acid | 16.3 |
| 419 | (±)-(4-Chloro-2-{2-[trans-2-(4-trifluoromethyl-phenyl)-cyclopropanecarbonyl]-1,2,3,4-tetrahydro-isoquinolin-1-yl]-phenoxy)-acetic acid | 958 |
| 420 | (±)-{4-Chloro-2-[2-(trans-p-tolyl-cyclopropanecarbonyl)-1,2,3,4-tetrahydro-isoquinolin-1-yl]-phenoxy}-acetic acid | 103 |
| 421 | (±)-(4-Chloro-2-{2-[trans-2-(3-chloro-phenyl)-cyclopropanecarbonyl]-1,2,3,4-tetrahydro-isoquinolin-1-yl]-phenoxy)-acetic acid | 24 |
| 422 | (±)-{4-Chloro-2-[2-(trans-2-o-tolyl-cyclopropanecarbonyl)-1,2,3,4-tetrahydro-isoquinolin-1-yl]-phenoxy}-acetic acid | 5.58 |
| 423 | (±)-(4-Chloro-2-{2-[trans-2-(2-trifluoromethyl-phenyl)-cyclopropanecarbonyl]-1,2,3,4-tetrahydro-isoquinolin-1-yl]-phenoxy)-acetic acid | 6.62 |
| 424 | (±)-(4-Chloro-2-{2-[trans-2-(3-fluoro-phenyl)-cyclopropanecarbonyl]-1,2,3,4-tetrahydro-isoquinolin-1-yl]-phenoxy)-acetic acid | 12 |
| 425 | (±)-(4-Chloro-2-{2-[trans-2-(3-methoxy-phenyl)-cyclopropanecarbonyl]-1,2,3,4-tetrahydro-isoquinolin-1-yl]-phenoxy)-acetic acid | 30.6 |
| 426 | (±)-(4-Chloro-2-{2-[trans-2-(3-trifluoromethyl-phenyl)-cyclopropanecarbonyl]-1,2,3,4-tetrahydro-isoquinolin-1-yl]-phenoxy)-acetic acid | 93.8 |
| 427 | (±)-{4-Chloro-2-[2-(trans-2-m-tolyl-cyclopropanecarbonyl)-1,2,3,4-tetrahydro-isoquinolin-1-yl]-phenoxy}-acetic acid | 46.6 |
| 428 | (±)-{4-Chloro-2-[6-fluoro-2-(trans-2-phenyl-cyclopropanecarbonyl)-1,2,3,4-tetrahydro-isoquinolin-1-yl]-phenoxy}-acetic acid | 1.33 |
| 429 | (±)-(4-Chloro-2-{6-fluoro-2-[trans-2-(2-trifluoro-methyl-phenyl)-cyclopropanecarbonyl]-1,2,3,4-tetrahydro-isoquinolin-1-yl]-phenoxy)-acetic acid | 2.21 |
| 430 | (±)-(4-Chloro-2-{2-[2-(trans-2-chloro-phenyl)-cyclopropanecarbonyl]-6-fluoro-1,2,3,4-tetrahydro-isoquinolin-1-yl]-phenoxy)-acetic acid | 9.37 |
| 431 | (±)-{4-Chloro-2-[6-fluoro-2-(trans-2-o-tolyl-cyclopropanecarbonyl)-1,2,3,4-tetrahydro-isoquinolin-1-yl]-phenoxy}-acetic acid | 3.56 |
| 432 | (±)-(4-Chloro-2-{2-[2-(2,6-dimethyl-pyridin-3-yloxy)-acetyl]-6-fluoro-1,2,3,4-tetrahydro-isoquinolin-1-yl]-phenoxy)-acetic acid | 40.6 |
| 433 | (±)-(4-Chloro-2-{6-fluoro-2-[3-(5-methoxy-1H-indol-3-yl)-propionyl]-1,2,3,4-tetrahydro-isoquinolin-1-yl}-phenoxy)-acetic acid | 90.1 |
| 434 | (±)-(4-Chloro-2-{6-fluoro-2-[3-(1-methyl-1H-indol-3-yl)-propionyl]-1,2,3,4-tetrahydro-isoquinolin-1-yl}-phenoxy)-acetic acid | 33.3 |
| 435 | (±)-{4-Chloro-2-[6-fluoro-2-(3-o-tolyl-propionyl)-1,2,3,4-tetrahydro-isoquinolin-1-yl]-phenoxy}-acetic acid | 46.5 |
| 436 | (±)-(4-Chloro-2-{6-fluoro-2-[4-(2-fluoro-phenyl)-butyryl]-1,2,3,4-tetrahydro-isoquinolin-1-yl}-phenoxy)-acetic acid | 5.73 |
| 437 | (±)-(4-Chloro-2-{2-[2-(2-chloro-benzyloxy)-acetyl]-6-fluoro-1,2,3,4-tetrahydro-isoquinolin-1-yl}-phenoxy)-acetic acid | 5.23 |
| 438 | (±)-(4-Chloro-2-{6-fluoro-2-[3-(4-fluoro-phenoxy)-propionyl]-1,2,3,4-tetrahydro-isoquinolin-1-yl}-phenoxy)-acetic acid | 91.1 |
| 439 | (±)-(4-Chloro-2-{2-[2-(methyl-phenyl-amino)-acetyl]-1,2,3,4-tetrahydro-isoquinolin-1-yl}-phenoxy)-acetic acid | 379 |
| 440 | (±)-(4-Chloro-2-{2-[4-(2-oxo-pyrrolidin-1-yl)-butyryl]-1,2,3,4-tetrahydro-isoquinolin-1-yl}-phenoxy)-acetic acid | 55.7 |
| 441 | (±)-{4-Chloro-2-[2-(3-2,3-dihydro-indol-1-yl-propionyl)-1,2,3,4-tetrahydro-isoquinolin-1-yl]-phenoxy}-acetic acid | 12.7 |
| 442 | (±)-(4-Chloro-2-{2-[3-(6-chloro-3-oxo-2,3-dihydro-benzo[1,4]oxazin-4-yl)-propionyl]-1,2,3,4-tetrahydro-isoquinolin-1-yl}-phenoxy)-acetic acid | 347 |
| 443 | (±)-(4-Chloro-2-{2-[2-(2-phenylamino-acetyl)-1,2,3,4-tetrahydro-isoquinolin-1-yl}-phenoxy}-acetic acid | 855 |
| 444 | (±)-{4-Chloro-2-[2-(2-1,3-dihydro-isoindol-2-yl-acetyl)-1,2,3,4-tetrahydro-isoquinolin-1-yl]-phenoxy}-acetic acid | 667 |
| 445 | (±)-(4-Chloro-2-{2-[3-(1-oxo-1,3-dihydro-isoindol-2-yl)-propionyl]-1,2,3,4-tetrahydro-isoquinolin-1-yl}-phenoxy)-acetic acid | 130 |
| 446 | (±)-(4-Chloro-2-{2-[3-(2-methyl-indol-1-yl)-propionyl]-1,2,3,4-tetrahydro-isoquinolin-1-yl}-phenoxy)-acetic acid | 175 |
| 447 | (±)-(4-Chloro-2-{2-[3-(3-methyl-indol-1-yl)-propionyl]-1,2,3,4-tetrahydro-isoquinolin-1-yl}-phenoxy)-acetic acid | 13.9 |
| 448 | (±)-{4-Chloro-2-[2-(3-indazol-1-yl-propionyl)-1,2,3,4-tetrahydro-isoquinolin-1-yl]-phenoxy}-acetic acid | 35.4 |
| 449 | (±)-{4-Chloro-2-[2-(3-3,4-dihydro-2H-quinolin-1-yl-propionyl)-1,2,3,4-tetrahydro-isoquinolin-1-yl]-phenoxy}-acetic acid | 26.1 |
| 450 | (±)-{4-Chloro-2-[2-(3-isobutoxy-propionyl)-1,2,3,4-tetrahydro-isoquinolin-1-yl]-phenoxy}-acetic acid | 403 |
| 451 | (±)-{2-[2-(3-Benzoimidazol-1-yl-propionyl)-1,2,3,4-tetrahydro-isoquinolin-1-yl]-4-chloro-phenoxy}-acetic acid | 64.1 |
| 452 | (±)-(4-Chloro-2-{2-[3-(4-methyl-2-oxo-thiazol-3-yl)-propionyl]-1,2,3,4-tetrahydro-isoquinolin-1-yl}-phenoxy)-acetic acid | 500 |
| 453 | (±)-(4-Chloro-2-{2-[3-(2-oxo-thiazolidin-3-yl)-propionyl]-1,2,3,4-tetrahydro-isoquinolin-1-yl}-phenoxy)-acetic acid | 312 |
| 454 | (±)-(4-Chloro-2-{2-[3-(2,4-dimethyl-phenyl)-propionyl]-1,2,3,4-tetrahydro-isoquinolin-1-yl}-phenoxy)-acetic acid | 69.6 |
| 455 | (±)-(4-Chloro-2-{2-[3-(2,6-dimethyl-pyridin-3-yl)-propionyl]-1,2,3,4-tetrahydro-isoquinolin-1-yl}-phenoxy)-acetic acid | 200 |
| 456 | (±)-(4-Chloro-2-{2-[2-(2,4-dimethyl-phenoxy)-acetyl]-1,2,3,4-tetrahydro-isoquinolin-1-yl}-phenoxy)-acetic acid | 43.6 |
| 457 | (±)-(4-Chloro-2-{2-[3-(1,2-dimethyl-1H-indol-3-yl)-propionyl]-1,2,3,4-tetrahydro-isoquinolin-1-yl}-phenoxy)-acetic acid | 60.8 |
| 458 | (±)-(4-Chloro-2-{2-[3-(5-methoxy-1-methyl-1H-indol-3-yl)-propionyl]-1,2,3,4-tetrahydro-isoquinolin-1-yl}-phenoxy)-acetic acid | 47.5 |
| 459 | (±)-(4-Chloro-2-{2-[3-(5-methoxy-indol-1-yl)-propionyl]-1,2,3,4-tetrahydro-isoquinolin-1-yl}-phenoxy)-acetic acid | 160 |
| 460 | {4-Chloro-2-[(S)-2-(trans-2-ethyl-cyclopropanecarbonyl)-1,2,3,4-tetrahydro-isoquinolin-1-yl]-phenoxy}-acetic acid | 67.8 |
| 461 | {4-Chloro-2-[(S)-2-(trans-2-ethoxy-cyclopropanecarbonyl)-1,2,3,4-tetrahydro-isoquinolin-1-yl]-phenoxy}-acetic acid | 185 |

-continued

| Example | Name | IC$_{50}$ [nM] |
|---|---|---|
| 462 | {4-Chloro-2-[(S)-2-(trans-2-methyl-cyclopropanecarbonyl)-1,2,3,4-tetrahydro-isoquinolin-1-yl]-phenoxy}-acetic acid | 80.9 |
| 463 | (±)-{4-Chloro-2-[2-(3-1H-indol-3-yl-propionyl)-1,2,3,4-tetrahydro-isoquinolin-1-yl]-phenoxy}-acetic acid | 12.1 |
| 464 | {4-Chloro-2-[(S)-2-(trans-2-isopropyl-cyclopropanecarbonyl)-1,2,3,4-tetrahydro-isoquinolin-1-yl]-phenoxy}-acetic acid (diastereoisomer 1) | 789 |
| 465 | {4-Chloro-2-[(S)-2-(trans-2-isopropyl-cyclopropanecarbonyl)-1,2,3,4-tetrahydro-isoquinolin-1-yl]-phenoxy}-acetic acid (diastereoisomer 2) | 53.5 |
| 466 | (±)-{4-Chloro-2-[2-(2,2-dimethyl-cyclopropanecarbonyl)-1,2,3,4-tetrahydro-isoquinolin-1-yl]-phenoxy}-acetic acid | 24.2 |
| 467 | (±)-(4-Chloro-2-{2-[2-(2,4-dimethyl-thiazol-5-yl)-cyclopropanecarbonyl]-1,2,3,4-tetrahydro-isoquinolin-1-yl}-phenoxy)-acetic acid | 396 |
| 468 | (±)-(4-Chloro-2-{2-[2-(6-methyl-pyridin-3-yloxy)-acetyl]-1,2,3,4-tetrahydro-isoquinolin-1-yl}-phenoxy)-acetic acid | 759 |
| 469 | (±)-(4-Chloro-2-{2-[2-(2-methyl-pyridin-3-yloxy)-acetyl]-1,2,3,4-tetrahydro-isoquinolin-1-yl}-phenoxy)-acetic acid | 132 |
| 470 | (±)-(4-Chloro-2-{2-[2-(5-chloro-pyridin-3-yloxy)-acetyl]-1,2,3,4-tetrahydro-isoquinolin-1-yl}-phenoxy)-acetic acid | 152 |
| 471 | (±)-(4-Chloro-2-{2-[2-(2-chloro-pyridin-3-yloxy)-acetyl]-1,2,3,4-tetrahydro-isoquinolin-1-yl}-phenoxy)-acetic acid | 87.6 |
| 472 | (±)-(4-Chloro-2-{2-[2-(6-chloro-pyridin-3-yloxy)-acetyl]-1,2,3,4-tetrahydro-isoquinolin-1-yl}-phenoxy)-acetic acid | 109 |
| 473 | (±)-(4-Chloro-2-{2-[2-(2,6-dichloro-pyridin-4-yloxy)-acetyl]-1,2,3,4-tetrahydro-isoquinolin-1-yl}-phenoxy)-acetic acid | 650 |
| 474 | (±)-(4-Chloro-2-{2-[2-(5-methyl-pyridin-3-yloxy)-acetyl]-1,2,3,4-tetrahydro-isoquinolin-1-yl}-phenoxy)-acetic acid | 198 |
| 475 | (±)-[4-Chloro-2-(2-{2-[2-(2-hydroxy-ethoxy)-pyridin-3-yloxy]-acetyl}-1,2,3,4-tetrahydro-isoquinolin-1-yl)-phenoxy]-acetic acid | 337 |
| 476 | (±)-(4-Chloro-2-{2-[2-(2,6-dimethoxy-pyridin-3-yloxy)-acetyl]-1,2,3,4-tetrahydro-isoquinolin-1-yl}-phenoxy)-acetic acid | 164 |
| 477 | (±)-(4-Chloro-2-{2-[2-(5-methoxy-pyridin-3-yloxy)-acetyl]-1,2,3,4-tetrahydro-isoquinolin-1-yl}-phenoxy)-acetic acid | 288 |
| 478 | (±)-(4-Chloro-2-{2-[2-(5-fluoro-pyridin-3-yloxy)-acetyl]-1,2,3,4-tetrahydro-isoquinolin-1-yl}-phenoxy)-acetic acid | 232 |
| 479 | (±)-(2-{2-[2-(2-Carbamoyl-pyridin-3-yloxy)-acetyl]-1,2,3,4-tetrahydro-isoquinolin-1-yl}-4-chloro-phenoxy)-acetic acid | 199 |
| 480 | (±)-(4-Chloro-2-{2-[2-(2-cyano-pyridin-3-yloxy)-acetyl]-1,2,3,4-tetrahydro-isoquinolin-1-yl}-phenoxy)-acetic acid | 104 |
| 481 | (±)-(4-Chloro-2-{2-[2-(6-trifluoromethyl-pyridin-3-yloxy)-acetyl]-1,2,3,4-tetrahydro-isoquinolin-1-yl}-phenoxy)-acetic acid | 143 |
| 482 | (±)-(4-Chloro-2-{2-[2-(2-fluoro-pyridin-3-yloxy)-acetyl]-1,2,3,4-tetrahydro-isoquinolin-1-yl}-phenoxy)-acetic acid | 199 |
| 483 | (±)-(4-Chloro-2-{2-[2-(3-methyl-3H-imidazo[4,5-b]pyridin-6-yloxy)-acetyl]-1,2,3,4-tetrahydro-isoquinolin-1-yl}-phenoxy)-acetic acid | 470 |
| 484 | (±)-(4-Chloro-2-{2-[2-(2-methoxy-5-methyl-pyridin-3-yloxy)-acetyl]-1,2,3,4-tetrahydro-isoquinolin-1-yl}-phenoxy)-acetic acid | 161 |
| 485 | (±)-(4-Chloro-2-{2-[2-(5,6-dimethoxy-pyridin-3-yloxy)-acetyl]-1,2,3,4-tetrahydro-isoquinolin-1-yl}-phenoxy)-acetic acid | 316 |
| 486 | (±)-(4-Chloro-2-{2-[2-(6-methoxy-pyridin-3-yloxy)-acetyl]-1,2,3,4-tetrahydro-isoquinolin-1-yl}-phenoxy)-acetic acid | 371 |
| 487 | (±)-(4-Chloro-2-{2-[2-(4-chloro-pyridin-3-yloxy)-acetyl]-1,2,3,4-tetrahydro-isoquinolin-1-yl}-phenoxy)-acetic acid | 400 |
| 488 | (±)-(4-Chloro-2-{2-[2-(3-methyl-indol-1-yl)-acetyl]-1,2,3,4-tetrahydro-isoquinolin-1-yl}-phenoxy)-acetic acid | 108 |
| 489 | (±)-(4-Chloro-2-{2-[2-(5-methoxy-indol-1-yl)-acetyl]-1,2,3,4-tetrahydro-isoquinolin-1-yl}-phenoxy)-acetic acid | 319 |
| 490 | (±)-{4-Chloro-2-[2-(2-chloro-benzylcarbamoyl)-1,2,3,4-tetrahydro-isoquinolin-1-yl]-phenoxy}-acetic acid | 15.1 |
| 491 | (±)-{4-Chloro-2-[2-(3-fluoro-benzylcarbamoyl)-1,2,3,4-tetrahydro-isoquinolin-1-yl]-phenoxy}-acetic acid | 19.8 |
| 492 | (±)-[2-(2-Benzylcarbamoyl-1,2,3,4-tetrahydro-isoquinolin-1-yl)-4-chloro-phenoxy]-acetic acid | 16.6 |
| 493 | (±)-{4-Chloro-2-(2-phenethylcarbamoyl-1,2,3,4-tetrahydro-isoquinolin-1-yl)-phenoxy)-acetic acid | 22.5 |
| 494 | (±)-{4-Chloro-2-[2-(4-fluoro-benzylcarbamoyl)-1,2,3,4-tetrahydro-isoquinolin-1-yl]-phenoxy}-acetic acid | 17 |
| 495 | (±)-{4-Chloro-2-[2-(2-fluoro-benzylcarbamoyl)-1,2,3,4-tetrahydro-isoquinolin-1-yl]-phenoxy}-acetic acid | 24.1 |
| 496 | (±)-[2-(2-Butylcarbamoyl-1,2,3,4-tetrahydro-isoquinolin-1-yl)-4-chloro-phenoxy]-acetic acid | 62.7 |
| 497 | (±)-1-(2-Carboxymethoxy-5-fluoro-phenyl)-7-(4-fluoro-phenyl)3,4-dihydro-1H-isoquinoline-2-carboxylic acid benzyl ester | 793 |
| 498 | (±)-1-(2-Carboxymethoxy-5-fluoro-phenyl)-7-pyrimidin-5-yl-3,4-dihydro-1H-isoquinoline-2-carboxylic acid benzyl ester | 381 |
| 499 | (±)-1-(2-Carboxymethoxy-5-fluoro-phenyl)-1,3-dihydro-isoindole-2-carboxylic acid benzyl ester | 25.4 |
| 500 | (±)-1-(2-Carboxymethoxy-5-chloro-phenyl)-5-fluoro-1,3-dihydro-isoindole-2-carboxylic acid benzyl ester | 12.9 |
| 501 | (±)-1-(2-Carboxymethoxy-5-chloro-phenyl)-4-fluoro-1,3-dihydro-isoindole-2-carboxylic acid benzyl ester | 8.12 |
| 502 | (±)-(4-Chloro-2-{2-[2-(2-methoxy-phenoxy)-acetyl]-2,3-dihydro-1H-isoindol-1-yl}-phenoxy)-acetic acid | 56.2 |
| 503 | {4-Chloro-2-[2-trans-(2-phenyl-cyclopropanecarbonyl)-2,3-dihydro-1H-isoindol-1-yl]-phenoxy}-acetic acid | 11.2 |
| 504 | (±)-(4-Chloro-2-{2-[2-(4-fluoro-phenoxy)-acetyl]-2,3-dihydro-1H-isoindol-1-yl}-phenoxy)-acetic acid | 33 |
| 505 | (±)-(4-Chloro-2-{2-[2-(3-pyridin-3-yl-propionyl)-2,3-dihydro-1H-isoindol-1-yl]-phenoxy)-acetic acid | 189 |
| 506 | (±)-{4-Chloro-2-[2-(3-o-tolyl-propionyl)-2,3-dihydro-1H-isoindol-1-yl]-phenoxy}-acetic acid | 78.8 |
| 507 | (±)-{4-Chloro-2-[2-(2-indol-1-yl-acetyl)-2,3-dihydro-1H-isoindol-1-yl]-phenoxy}-acetic acid | 129 |
| 508 | (±)-(4-Chloro-2-{2-[3-(1-ethyl-2-methyl-1H-indol-3-yl)-propionyl]-2,3-dihydro-1H-isoindol-1-yl}-phenoxy)-acetic acid | 127 |
| 509 | (±)-(4-Chloro-2-{2-[2-(quinolin-8-yloxy)-acetyl]-2,3-dihydro-1H-isoindol-1-yl}-phenoxy)-acetic acid | 37.8 |
| 510 | (±)-(4-Chloro-2-{2-[3-(2-methyl-1H-indol-3-yl)-propionyl]-2,3-dihydro-1H-isoindol-1-yl}-phenoxy)-acetic acid | 180 |
| 511 | (±)-(4-Chloro-2-{2-[3-(5-methoxy-1H-indol-3-yl)-propionyl]-2,3-dihydro-1H-isoindol-1-yl}-phenoxy)-acetic acid | 14.8 |
| 512 | (±)-(4-Chloro-2-{2-[2-(2,6-dimethyl-pyridin-3-yloxy)-acetyl]-2,3-dihydro-1H-isoindol-1-yl}-phenoxy)-acetic acid | 42.5 |
| 513 | (±)-(4-Chloro-2-{2-[3-(1-methyl-1H-indol-3-yl)-propionyl]-2,3-dihydro-1H-isoindol-1-yl}-phenoxy)-acetic acid | 25.9 |
| 514 | (±)-{4-Chloro-2-[2-(3-2,3-dihydro-indol-1-yl-propionyl)-2,3-dihydro-1H-isoindol-1-yl]-phenoxy}-acetic acid | 38.8 |
| 515 | (±)-{4-Chloro-2-[2-(3-3,4-dihydro-2H-quinolin-1-yl-propionyl)-2,3-dihydro-1H-isoindol-1-yl]-phenoxy}-acetic acid | 60.1 |
| 516 | (±)-{4-Chloro-2-[2-(3-indazol-1-yl-propionyl)-2,3-dihydro-1H-isoindol-1-yl]-phenoxy}-acetic acid | 12.5 |

| Example | Name | IC$_{50}$ [nM] |
|---|---|---|
| 517 | (±)-(4-Chloro-2-{2-[3-(3-fluoro-phenoxy)-propionyl]-2,3-dihydro-1H-isoindol-1-yl}-phenoxy)-acetic acid | 123 |
| 518 | (±)-(4-Chloro-2-{2-[2-(5-methoxy-benzo[d]isoxazol-3-yl)-acetyl]-2,3-dihydro-1H-isoindol-1-yl}-phenoxy)-acetic acid | 20.1 |
| 519 | (±)-(4-Chloro-2-{2-[3-(3-methyl-indol-1-yl)-propionyl]-2,3-dihydro-1H-isoindol-1-yl}-phenoxy)-acetic acid | 37.4 |
| 520 | (±)-(4-Chloro-2-{2-[3-(4-fluoro-phenoxy)-propionyl]-2,3-dihydro-1H-isoindol-1-yl}-phenoxy)-acetic acid | 130 |
| 521 | (±)-(4-Chloro-2-{2-[2-(2-chloro-benzyloxy)-acetyl]-2,3-dihydro-1H-isoindol-1-yl}-phenoxy)-acetic acid | 9.11 |
| 522 | (±)-(4-Chloro-2-{2-[3-(2-fluoro-phenoxy)-propionyl]-2,3-dihydro-1H-isoindol-1-yl}-phenoxy)-acetic acid | 11.7 |
| 523 | (4-Chloro-2-{2-trans-[2-(3-fluoro-phenyl)-cyclopropanecarbonyl]-2,3-dihydro-1H-isoindol-1-yl}-phenoxy)-acetic acid | 40.5 |
| 524 | (4-Chloro-2-{2-trans-[2-(3-chloro-phenyl)-cyclopropanecarbonyl]-2,3-dihydro-1H-isoindol-1-yl}-phenoxy)-acetic acid | 81.3 |
| 525 | (4-Chloro-2-{2-trans-[2-(2-fluoro-phenyl)-cyclopropanecarbonyl]-2,3-dihydro-1H-isoindol-1-yl}-phenoxy)-acetic acid | 13.5 |
| 526 | (±)-{4-Chloro-2-[5-fluoro-2-(3-indazol-1-yl-propionyl)-2,3-dihydro-1H-isoindol-1-yl]-phenoxy}-acetic acid | 4.53 |
| 527 | (4-Chloro-2-{2-[3-(5-fluoro-indazol-1-yl)-propionyl]-2,3-dihydro-1H-isoindol-1-yl}-phenoxy)-acetic acid (enantiomer 1) | 8.12 |
| 528 | (4-Chloro-2-{2-[3-(4-fluoro-3-methyl-indazol-1-yl)-propionyl]-2,3-dihydro-1H-isoindol-1-yl}-phenoxy)-acetic acid (enantiomer 1) | 33.2 |
| 529 | (4-Chloro-2-{2-[3-(4-chloro-3-methyl-indazol-1-yl)-propionyl]-2,3-dihydro-1H-isoindol-1-yl}-phenoxy)-acetic acid (enantiomer 1) | 78 |
| 530 | (4-Chloro-2-{2-[3-(7-fluoro-3-methyl-indazol-1-yl)-propionyl]-2,3-dihydro-1H-isoindol-1-yl}-phenoxy)-acetic acid (enantiomer 1) | 101 |
| 531 | (4-Chloro-2-{2-[3-(6-fluoro-3-methyl-indazol-1-yl)-propionyl]-2,3-dihydro-1H-isoindol-1-yl}-phenoxy)-acetic acid (enantiomer 1) | 30.9 |
| 532 | (4-Chloro-2-{2-[3-(6-chloro-3-methyl-indazol-1-yl)-propionyl]-2,3-dihydro-1H-isoindol-1-yl}-phenoxy)-acetic acid (enantiomer 1) | 40.7 |
| 533 | (4-Chloro-2-{2-[3-(3-methyl-indazol-1-yl)-propionyl]-2,3-dihydro-1H-isoindol-1-yl}-phenoxy)-acetic acid (enantiomer 1) | 6.09 |
| 534 | (4-Chloro-2-{2-[3-(6-fluoro-indazol-1-yl)-propionyl]-2,3-dihydro-1H-isoindol-1-yl}-phenoxy)-acetic acid (enantiomer 1) | 12.9 |
| 535 | (4-Chloro-2-{2-[3-(4-fluoro-indazol-1-yl)-propionyl]-2,3-dihydro-1H-isoindol-1-yl}-phenoxy)-acetic acid (enantiomer 1) | 15.1 |
| 536 | (4-Chloro-2-{2-[3-(7-chloro-indazol-1-yl)-propionyl]-2,3-dihydro-1H-isoindol-1-yl}-phenoxy)-acetic acid (enantiomer 1) | 110 |
| 537 | (4-Chloro-2-{2-[3-(7-fluoro-indazol-1-yl)-propionyl]-2,3-dihydro-1H-isoindol-1-yl}-phenoxy)-acetic acid (enantiomer 1) | 25.8 |
| 538 | (4-Chloro-2-{2-[3-(4-fluoro-3-methyl-indazol-1-yl)-propionyl]-2,3-dihydro-1H-isoindol-1-yl}-phenoxy)-acetic acid (enantiomer 2) | 704 |
| 539 | (4-Chloro-2-{2-[3-(4-chloro-3-methyl-indazol-1-yl)-propionyl]-2,3-dihydro-1H-isoindol-1-yl}-phenoxy)-acetic acid (enantiomer 2) | 235 |
| 540 | (4-Chloro-2-{2-[3-(7-fluoro-3-methyl-indazol-1-yl)-propionyl]-2,3-dihydro-1H-isoindol-1-yl}-phenoxy)-acetic acid (enantiomer 2) | 633 |
| 541 | (4-Chloro-2-{2-[3-(6-fluoro-3-methyl-indazol-1-yl)-propionyl]-2,3-dihydro-1H-isoindol-1-yl}-phenoxy)-acetic acid (enantiomer 2) | 865 |
| 542 | (4-Chloro-2-{2-[3-(6-chloro-3-methyl-indazol-1-yl)-propionyl]-2,3-dihydro-1H-isoindol-1-yl}-phenoxy)-acetic acid (enantiomer 2) | 881 |
| 543 | (4-Chloro-2-{2-[3-(5-fluoro-indazol-1-yl)-propionyl]-2,3-dihydro-1H-isoindol-1-yl}-phenoxy)-acetic acid (enantiomer 2) | 353 |
| 544 | (4-Chloro-2-{2-[3-(5-chloro-indazol-1-yl)-propionyl]-2,3-dihydro-1H-isoindol-1-yl}-phenoxy)-acetic acid (enantiomer 2) | 340 |
| 545 | (4-Chloro-2-{2-[3-(3-methyl-indazol-1-yl)-propionyl]-2,3-dihydro-1H-isoindol-1-yl}-phenoxy)-acetic acid (enantiomer 2) | 982 |
| 546 | (4-Chloro-2-{2-[3-(6-fluoro-indazol-1-yl)-propionyl]-2,3-dihydro-1H-isoindol-1-yl}-phenoxy)-acetic acid (enantiomer 2) | 210 |
| 547 | (4-Chloro-2-{2-[3-(4-fluoro-indazol-1-yl)-propionyl]-2,3-dihydro-1H-isoindol-1-yl}-phenoxy)-acetic acid (enantiomer 2) | 272 |
| 548 | (4-Chloro-2-{2-[3-(7-chloro-indazol-1-yl)-propionyl]-2,3-dihydro-1H-isoindol-1-yl}-phenoxy)-acetic acid (enantiomer 2) | 715 |
| 549 | (4-Chloro-2-{2-[3-(6-chloro-indazol-1-yl)-propionyl]-2,3-dihydro-1H-isoindol-1-yl}-phenoxy)-acetic acid (enantiomer 2) | 180 |
| 550 | (4-Chloro-2-{2-[3-(4-chloro-indazol-1-yl)-propionyl]-2,3-dihydro-1H-isoindol-1-yl}-phenoxy)-acetic acid (enantiomer 2) | 240 |
| 551 | (4-Chloro-2-{2-[3-(7-fluoro-indazol-1-yl)-propionyl]-2,3-dihydro-1H-isoindol-1-yl}-phenoxy)-acetic acid (enantiomer 2) | 292 |
| 552 | (±)-{4-Chloro-2-[2-(2-fluoro-benzylcarbamoyl)-2,3-dihydro-1H-isoindol-1-yl]-phenoxy}-acetic acid | 19.6 |
| 553 | (±)-{4-Chloro-2-[2-(3-fluoro-benzylcarbamoyl)-2,3-dihydro-1H-isoindol-1-yl]-phenoxy}-acetic acid | 17.4 |
| 554 | (±)-{4-Chloro-2-[2-(4-fluoro-benzylcarbamoyl)-2,3-dihydro-1H-isoindol-1-yl]-phenoxy}-acetic acid | 25.7 |
| 555 | (±)-[2-(2-Benzylcarbamoyl-2,3-dihydro-1H-isoindol-1-yl)-4-chloro-phenoxy]-acetic acid | 14.5 |
| 556 | (±)-[4-Chloro-2-(2-phenethylcarbamoyl-2,3-dihydro-1H-isoindol-1-yl)-phenoxy]-acetic acid | 11.7 |
| 557 | (±)-{4-Chloro-2-[2-(2-chloro-benzylcarbamoyl)-2,3-dihydro-1H-isoindol-1-yl]-phenoxy}-acetic acid | 13.7 |
| 558 | (±)-1-(2-Carboxymethoxy-5-chloro-phenyl)-4,5-dichloro-1,3-dihydro-isoindole-2-carboxylic acid benzyl ester | 16.9 |
| 559 | (±)-1-(2-Carboxymethoxy-5-chloro-phenyl)-4,5-difluoro-1,3-dihydro-isoindole-2-carboxylic acid benzyl ester | 11.2 |
| 560 | {4-Chloro-2-[(S)-2-((1R,2R)-2-o-tolyl-cyclopropanecarbonyl)-1,2,3,4-tetrahydro-isoquinolin-1-yl]-phenoxy}-acetic acid | 3.27 |
| 561 | {4-Chloro-2-[(S)-2-((1S,2S)-2-o-tolyl-cyclopropanecarbonyl)-1,2,3,4-tetrahydro-isoquinolin-1-yl]-phenoxy}-acetic acid | 274 |
| 562 | (4-Chloro-2-{(S)-2-[(1R,2R)-2-(2-trifluoromethyl-phenyl)-cyclopropanecarbonyl]-1,2,3,4-tetrahydro-isoquinolin-1-yl}-phenoxy)-acetic acid | 3.75 |
| 563 | (4-Chloro-2-{(S)-2-[(1S,2S)-2-(2-trifluoromethyl-phenyl)-cyclopropanecarbonyl]-1,2,3,4-tetrahydro-isoquinolin-1-yl}-phenoxy)-acetic acid | 264 |
| 564 | (4-Chloro-2-{(S)-2-[(1R,2R)-2-(3-chloro-phenyl)-cyclopropanecarbonyl]-1,2,3,4-tetrahydro-isoquinolin-1-yl}-phenoxy)-acetic acid | 4.29 |
| 565 | (4-Chloro-2-{(S)-2-[(1R,2R)-2-(3-fluoro-phenyl)-cyclopropanecarbonyl]-1,2,3,4-tetrahydro-isoquinolin-1-yl}-phenoxy)-acetic acid | 2.64 |
| 566 | (4-Chloro-2-{(S)-2-[(1R,2R)-2-(4-fluoro-phenyl)-cyclopropanecarbonyl]-1,2,3,4-tetrahydro-isoquinolin-1-yl}-phenoxy)-acetic acid | 2.17 |
| 567 | (S)-benzyl 1-(5-chloro-2-(2-cyanamido-2-oxoethoxy)phenyl)-3,4-dihydroisoquinoline-2(1H)-carboxylate | 370 |
| 568 | (S)-1-[5-Chloro-2-(2-oxo-2-trifluoromethanesulfonyl-amino-ethoxy)-phenyl]-3,4-dihydro-1H-isoquinoline-2-carboxylic acid benzyl ester | 9.18 |
| 569 | (S)-1-(5-Chloro-2-hydroxycarbamoylmethoxy-phenyl)-3,4-dihydro-1H-isoquinoline-2-carboxylic acid benzyl ester | 120 |
| 570 | (±)-1-[5-Chloro-2-(1H-tetrazol-5-ylmethoxy)-phenyl]-3,4-dihydro-1H-isoquinoline-2-carboxylic acid benzyl ester | 355 |
| 571 | (S)-1-[5-Chloro-2-(5-oxo-4,5-dihydro-[1,3,4]oxadiazol-2-ylmethoxy)-phenyl]-3,4-dihydro-1H-isoquinoline-2-carboxylic acid benzyl ester | 55 |

-continued

| Example | Name | IC$_{50}$ [nM] |
|---|---|---|
| 572 | (±)-1-[5-Chloro-2-(5-oxo-4,5-dihydro-[1,2,4]oxadiazol-3-ylmethoxy)-phenyl]-3,4-dihydro-1H-isoquinoline-2-carboxylic acid benzyl ester | 325 |
| 573 | (±)-1-[5-Chloro-2-(3-hydroxy-isoxazol-5-ylmethoxy)-phenyl]-3,4-dihydro-1H-isoquinoline-2-carboxylic acid benzyl ester | 15.3 |

Radioligand Displacement Assay-Human Serum Albumin (HSA):

Radioligand displacement assay in presence of human serum albumin (HSA) was performed as described above, with following modifications. Binding-Buffer-HSA: Binding-buffer+0.5% Sigma Albumin from Human serum A1887 (instead of 0.1% BSA). A volume of 25 µl test compound, previously diluted in Binding-Buffer—HSA was placed into each well. After addition of 75 µl Binding-Buffer-HSA, 50 µl of $^3$H-PGD$_2$ (at 2.5 nM (220.000 dpm/well) from ANAWA ART0662) was added to each well. Remaining protocol was identical as described above.

References:

Shimizu T, Yamashita A, Hayaishi O, Specific binding of prostaglandin D2 to rat brain synaptic membranes. J. Biol. Chem. 1982. Vol. 257:13570-13575.

Fortini A, Modesti P A, Abbate R, Gensini G F, Neri Semen G G. Heparin does not interfere with prostacyclin and prostaglandin D2 binding to platelets. Thromb. Res. 1985. Vol. 40:319-328.

Sawyer N, Cauchon E, Chateauneuf A, Cruz R P, Nicholson D W, Metters K M, O'Neill G P, Gervais F G. Molecular pharmacology of the human PGD2 receptor CRTH2. Br. J. of Pharmacol. 2002. Vol. 137:1163-1172

Eosinophil Shape Change Assay with Human Plasma

After obtaining informed consent, blood samples were drawn by venipuncture according to the protocol approved by the ethics committee of Basel, Switzerland. Polymorphonuclear leukocytes (containing eosinophils, basophils and neutrophils) were isolated using the Polymorphprep™ method (Axis-Shield). In brief, anticoagulated whole blood was layered onto a Polymorphprep gradient (density 1.113 g/ml) and centrifuged at 500 g for 30 min. The polymorphonuclear cell fraction was harvested and depleted for erythrocytes by hypotonic saline lysis.

The polymorphonuclear cells were resuspended in assay buffer (1×PBS with Ca$^{2+}$/Mg$^{2+}$supplemented with 0.1% BSA, 10 mM HEPES, and 10 mM Glucose, pH 7.4) at 5×10$^6$ cells/ml and stained with anti-CD49d-APC ((APC=Allophycocyanin) for 1 hour at RT. Test compounds, at various concentrations, were preincubated 10 min in human plasma (anticoagulated with a thrombin inhibitor). Then, human plasma was added to the polymorphonuclear cells to 50% of final assay volume with polymorphonuclear cells at 4×10$^6$ cells/ml. After incubation for 10 minutes at 37° C., the polymorphonuclear cells were activated for 5 min at 37° C. by addition of PGD$_2$ at 100 nM final concentration. Activation was stopped by addition of 0.5 ml paraformaldehyde (1%).

Immediately after fixation with paraformaldehyde, the samples were analyzed by FACSCanto flow cytometer (BD Biosciences) and target cells were identified by their forward-scatter (FSC) and side-scatter (SSC) characteristics. Eosinophils were identified by the anti-CD49d-APC signal and their characteristic side-scatter (SSC) profile. Shape change responses, indicative of eosinophil activation, were quantified as the percent of cells with an increased forward-scatter.

Intracellular Calcium Mobilization Assay (FLIPR):

Cells (HEK-293), stably expressing the hCRTH2 receptor under the control of the cytomegalovirus promoter from a single insertion of the expression vector pcDNA5 (Invitrogen), are grown to confluency in DMEM (low glucose, Gibco) medium supplemented with 10% fetal calf serum (Bioconcept, Switzerland) under standard mammalian cell culture conditions (37° C. in a humidified atmosphere of 5% CO$_2$). Cells are detached from culture dishes using a dissociation buffer (0.02% EDTA in PBS, Gibco) for 1 min, and collected by centrifugation at 200 g at rt for 5 min in assay buffer (equal parts of Hank's BSS (HBSS, Bioconcept) and DMEM (low glucose, without phenol red, Gibco)). After incubation for 45 min (37° C. and 5% CO$_2$) in the presence of 1 µM Fluo-4 and 0.04% Pluronic F-127 (both Molecular Probes), and 20 mM HEPES (Gibco) in assay buffer, the cells are washed with and resuspended in assay buffer, then seeded onto 384-well FLIPR assay plates (Greiner) at 50,000 cells in 66 µl per well, and sedimented by centrifugation.

Stock solutions of test compounds are made up at a concentration of 10 mM in DMSO, and serially diluted in assay buffer to concentrations required for inhibition dose response curves. Prostaglandin D$_2$ (Biomol, Plymouth Meeting, PA) is used as an agonist.

A FLIPR Tetra instrument (Molecular Devices) is operated according to the manufacturer's standard instructions, adding 4 µl of test compound dissolved at 10 mM in DMSO and diluted prior to the experiment in assay buffer to obtain the desired final concentration. 10 µl of 80 nM prostaglandin D$_2$ (Biomol, Plymouth Meeting, PA) in assay buffer, supplemented with 0.8% bovine serum albumin (fatty acid content <0.02%, Sigma), is then added to obtain a final concentration of 10 nM and 0.1%, respectively. Changes in fluorescence are monitored before and after the addition of test compounds at $\lambda_{ex}$=488 nm and $\lambda_{em}$=540 nm. Emission peak values above base level after prostaglandin D$_2$ addition are exported after base line subtraction. Values are normalized to high-level control (no test compound added) after subtraction of base line value (no prostaglandin D$_2$ added). The program XLIfit 3.0 (IDBS) is used to fit the data to a single site dose response curve of the equation (A+((B−A)/(1+((C/x)^D)))) and to calculate the IC$_{50}$ values.

The invention claimed is:
1. A compound of formula (I):

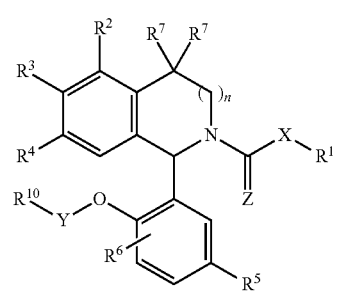

wherein
X represents —NH—, —O— or a bond;
Y represents (C$_1$-C$_4$)alkandiyl;
Z represents O or S;
n represents 0 or 1;

$R^1$ represents
- $(C_4$-$C_6)$alkyl;
- $(C_1$-$C_4)$alkyl which is mono-substituted with $(C_3$-$C_6)$ cycloalkyl, $(C_1$-$C_4)$alkoxy, optionally substituted aryl, optionally substituted heteroaryl, optionally substituted heterocyclyl, optionally substituted aryloxy, optionally substituted heteroaryloxy, optionally substituted aryl-$(C_1$-$C_2)$alkoxy, optionally substituted heteroaryl-$(C_1$-$C_2)$alkoxy, optionally substituted heteroarylsulfanyl or —$NR^8R^9$;
- $(C_2$-$C_4)$alkenyl which is mono-substituted with optionally substituted aryl;
- $(C_2$-$C_4)$alkynyl which is mono-substituted with optionally substituted aryl;
- $(C_3$-$C_6)$cycloalkyl which is mono- or di-substituted with $(C_1$-$C_4)$alkyl, mono-substituted with $(C_1$-$C_4)$alkoxy, mono-substituted with optionally substituted aryl or mono-substituted with optionally substituted heteroaryl;
- optionally substituted aryl; or
- a 10-membered partially unsaturated ring system;

$R^2$ represents hydrogen, $(C_1$-$C_4)$alkyl, $(C_1$-$C_4)$alkoxy, $(C_1$-$C_4)$fluoroalkyl, halogen, $(C_1$-$C_4)$alkylsulfonyl, phenylsulfonyl or $(C_1$-$C_4)$alkylsulfonylamino;

$R^3$ represents hydrogen, $(C_1$-$C_4)$alkoxy or halogen;

$R^4$ represents hydrogen, $(C_1$-$C_4)$alkoxy, halogen, $(C_1$-$C_4)$alkylsulfonyl, optionally substituted aryl or optionally substituted heteroaryl;

$R^5$ represents hydrogen, $(C_1$-$C_4)$alkyl, $(C_1$-$C_4)$alkoxy, $(C_1$-$C_4)$fluoroalkyl, halogen, cyano, —$CONH_2$, optionally substituted aryl, optionally substituted heteroaryl, $(C_1$-$C_4)$alkylsulfonyl, phenylsulfonyl or dimethylaminosulfonyl; and $R^6$ represents hydrogen or halogen; or $R^5$ and $R^6$ together form a methylendioxy-group;

$R^7$ represents hydrogen or methyl;

$R^8$ represents hydrogen or methyl;

$R^9$ represents optionally substituted aryl, optionally substituted arylsulfonyl or optionally substituted heteroarylsulfonyl; and $R^{10}$ represents —$C(O)OH$, —$C(O)NH$—$CN$, —$C(O)NH$—$OH$, —$C(O)NH$—$S(O)_2CF_3$ or optionally substituted heteroaryl;

with the proviso that $R^1$ is different from optionally substituted aryl if X represents —$NH$— or a bond;

or a salt thereof.

2. The compound according to claim 1, wherein
X represents —O— or a bond;
Y represents methandiyl;
Z represents O;
n represents 0 or 1;
$R^1$ represents
- $(C_1$-$C_2)$alkyl which is mono-substituted with optionally substituted aryl, optionally substituted heteroaryl or optionally substituted aryl-$(C_1$-$C_2)$alkoxy; or
- cyclopropyl which is mono-substituted with optionally substituted aryl;

$R^2$ represents hydrogen, trifluoromethyl or fluoro;
$R^3$ represents hydrogen or fluoro;
$R^4$ represents hydrogen;
$R^5$ represents halogen or cyano;
$R^6$ represents hydrogen;
$R^7$ represents hydrogen; and
$R^{10}$ represents —$C(O)OH$;
or a salt thereof.

3. The compound according to claim 1, wherein
X represents —O—;
or a salt thereof.

4. The compound according to claim 1, wherein
X represents a bond;
or a salt thereof.

5. The compound according to claim 1, wherein
Z represents O;
or a salt thereof.

6. The compound according to claim 1, wherein
$R^1$ represents
- $(C_1$-$C_4)$alkyl which is mono-substituted with $(C_3$-$C_6)$ cycloalkyl, optionally substituted aryl, optionally substituted heteroaryl, optionally substituted heterocyclyl, optionally substituted aryloxy, optionally substituted heteroaryloxy, optionally substituted aryl-$(C_1$-$C_2)$alkoxy or optionally substituted heteroaryl-$(C_1$-$C_2)$alkoxy; or
- cyclopropyl which is mono- or di-substituted with $(C_1$-$C_4)$alkyl, mono-substituted with optionally substituted aryl or mono-substituted with optionally substituted heteroaryl;
or a salt thereof.

7. The compound according to claim 1, wherein
$R^2$ represents hydrogen, $(C_1$-$C_4)$alkyl, $(C_1$-$C_4)$alkoxy, $(C_1$-$C_4)$fluoroalkyl or halogen;
or a salt thereof.

8. The compound according to claim 1, wherein
$R^4$ represents hydrogen or halogen;
or a salt thereof.

9. The compound according to claim 1, wherein
$R^5$ represents halogen or cyano;
or a salt thereof.

10. The compound according to claim 1, wherein
$R^7$ represents hydrogen;
or a salt thereof.

11. The compound according to claim 1, wherein
$R^{10}$ represents —$C(O)OH$;
or a salt thereof.

12. The compound according to claim 1, wherein the compound is:
- 1-(2-Carboxymethoxy-5-fluoro-phenyl)-3,4-dihydro-1H-isoquinoline-2-carboxylic acid benzyl ester;
- 1-[2-((S)-1-Carboxy-ethoxy)-5-fluoro-phenyl]-3,4-dihydro-1H-isoquinoline-2-carboxylic acid benzyl ester;
- 1-(2-Carboxymethoxy-5-methyl-phenyl)-3,4-dihydro-1H-isoquinoline-2-carboxylic acid benzyl ester;
- 1-(5-Bromo-2-carboxymethoxy-phenyl)-3,4-dihydro-1H-isoquinoline-2-carboxylic acid benzyl ester;
- 7-Bromo-1-(2-carboxymethoxy-5-fluoro-phenyl)-3,4-dihydro-1H-isoquinoline-2-carboxylic acid benzyl ester;
- 1-(2-Carboxymethoxy-4,5-difluoro-phenyl)-3,4-dihydro-1H-isoquinoline-2-carboxylic acid benzyl ester;
- 5-Bromo-1-(2-carboxymethoxy-5-fluoro-phenyl)-3,4-dihydro-1H-isoquinoline-2-carboxylic acid benzyl ester;
- 1-[2-((R)-1-Carboxy-ethoxy)-5-fluoro-phenyl]-3,4-dihydro-1H-isoquinoline-2-carboxylic acid benzyl ester;
- 1-(2-Carboxymethoxy-5-fluoro-phenyl)-6,7-difluoro-3,4-dihydro-1H-isoquinoline-2-carboxylic acid benzyl ester;
- 1-(5-Bromo-2-carboxymethoxy-phenyl)-6,7-difluoro-3,4-dihydro-1H-isoquinoline-2-carboxylic acid benzyl ester;
- 1-(2-Carboxymethoxy-5-cyano-phenyl)-6,7-difluoro-3,4-dihydro-1H-isoquinoline-2-carboxylic acid benzyl ester;
- 1-(2-Carboxymethoxy-5-fluoro-phenyl)-5-trifluoromethyl-3,4-dihydro-1H-isoquinoline-2-carboxylic acid benzyl ester;

1-[2-((R)-1-Carboxy-ethoxy)-5-cyano-phenyl]-3,4-dihydro-1H-isoquinoline-2-carboxylic acid benzyl ester;
1-(2-Carboxymethoxy-5-fluoro-phenyl)-5,6-difluoro-3,4-dihydro-1H-isoquinoline-2-carboxylic acid benzyl ester;
1-(2-Carboxymethoxy-5-chloro-phenyl)-5,6-difluoro-3,4-dihydro-1H-isoquinoline-2-carboxylic acid benzyl ester;
1-(2-Carboxymethoxy-5-cyano-phenyl)-5,6-difluoro-3,4-dihydro-1H-isoquinoline-2-carboxylic acid benzyl ester;
1-(2-Carboxymethoxy-5-dimethylsulfamoyl-phenyl)-3,4-dihydro-1H-isoquinoline-2-carboxylic acid benzyl ester;
1-(2-Carboxymethoxy-5-chloro-phenyl)-5-fluoro-3,4-dihydro-1H-isoquinoline-2-carboxylic acid benzyl ester;
1-(2-Carboxymethoxy-5-cyano-phenyl)-5-fluoro-3,4-dihydro-1H-isoquinoline-2-carboxylic acid benzyl ester;
1-(2-Carboxymethoxy-5-trifluoromethyl-phenyl)-3,4-dihydro-1H-isoquinoline-2-carboxylic acid benzyl ester;
1-(2-Carboxymethoxy-5-chloro-phenyl)-3,4-dihydro-1H-isoquinoline-2-carboxylic acid benzyl ester;
1-(2-Carboxymethoxy-5-isopropyl-phenyl)-3,4-dihydro-1H-isoquinoline-2-carboxylic acid benzyl ester;
1-(6-Carboxymethoxy-benzo[1,3]dioxol-5-yl)-3,4-dihydro-1H-isoquinoline-2-carboxylic acid benzyl ester;
1-(2-Carboxymethoxy-5-methoxy-phenyl)-3,4-dihydro-1H-isoquinoline-2-carboxylic acid benzyl ester;
(S)-1-(2-Carboxymethoxy-5-cyano-phenyl)-3,4-dihydro-1H-isoquinoline-2-carboxylic acid benzyl ester;
(S)-1-(2-Carboxymethoxy-5-chloro-phenyl)-3,4-dihydro-1H-isoquinoline-2-carboxylic acid benzyl ester;
(S)-1-[2((R)-1-Carboxy-ethoxy)-5-fluoro-phenyl]-3,4-dihydro-1H-isoquinoline-2-carboxylic acid benzyl ester;
(S)-1-[2-((S)-1-Carboxy-ethoxy)-5-fluoro-phenyl]-3,4-dihydro-1H-isoquinoline-2-carboxylic acid benzyl ester;
{4-Fluoro-2-[(S)-2-((trans)-2-phenyl-cyclopropanecarbonyl)-1,2,3,4-tetrahydro-isoquinolin-1-yl]-phenoxy}-acetic acid;
(S)-1-(2-Carboxymethoxy-5-chloro-phenyl)-5-fluoro-3,4-dihydro-1H-isoquinoline-2-carboxylic acid benzyl ester;
(S)-1-(2-Carboxymethoxy-5-cyano-phenyl)-5-fluoro-3,4-dihydro-1H-isoquinoline-2-carboxylic acid benzyl ester;
1-(2-Carboxymethoxy-3,5-difluoro-phenyl)-3,4-dihydro-1H-isoquinoline-2-carboxylic acid benzyl ester;
1-(2-Carboxymethoxy-5-fluoro-phenyl)-5-fluoro-3,4-dihydro-1H-isoquinoline-2-carboxylic acid benzyl ester;
1-(2-Carboxymethoxy-5-fluoro-phenyl)-5-methoxy-3,4-dihydro-1H-isoquinoline-2-carboxylic acid benzyl ester;
1-(2-Carboxymethoxy-5-fluoro-phenyl)-6,7-dimethoxy-3,4-dihydro-1H-isoquinoline-2-carboxylic acid benzyl ester;
1-(2-Carboxymethoxy-5-fluoro-phenyl)-7-methoxy-3,4-dihydro-1H-isoquinoline-2-carboxylic acid benzyl ester;
1-(2-Carboxymethoxy-5-fluoro-phenyl)-5-chloro-3,4-dihydro-1H-isoquinoline-2-carboxylic acid benzyl ester;
1-(2-Carboxymethoxy-5-fluoro-phenyl)-5-methyl-3,4-dihydro-1H-isoquinoline-2-carboxylic acid benzyl ester;
5-Bromo-1-(2-carboxymethoxy-5-fluoro-phenyl)-6-fluoro-3,4-dihydro-1H-isoquinoline-2-carboxylic acid benzyl ester;
1-(2-Carboxymethoxy-5-fluoro-phenyl)-7-fluoro-3,4-dihydro-1H-isoquinoline-2-carboxylic acid benzyl ester;
1-(2-Carboxymethoxy-5-fluoro-phenyl)-5,7-difluoro-3,4-dihydro-1H-isoquinoline-2-carboxylic acid benzyl ester;
1-(2-Carboxymethoxy-5-chloro-phenyl)-5,7-difluoro-3,4-dihydro-1H-isoquinoline-2-carboxylic acid benzyl ester;
1-(2-Carboxymethoxy-5-cyano-phenyl)-5,7-difluoro-3,4-dihydro-1H-isoquinoline-2-carboxylic acid benzyl ester;
{2-[2-(2-Benzo[d]isoxazol-3-yl-acetyl)-1,2,3,4-tetrahydro-isoquinolin-1-yl]-4-fluoro-phenoxy}-acetic acid;
{4-Fluoro-2-[2-(3-methyl-3-phenyl-butyryl)-1,2,3,4-tetrahydro-isoquinolin-1-yl]-phenoxy}-acetic acid;
{4-Fluoro-2-[2-(2-naphthalen-1-yl-acetyl)-1,2,3,4-tetrahydro-isoquinolin-1-yl]-phenoxy}-acetic acid;
{4-Fluoro-2-[2-(2-quinolin-7-yl-acetyl)-1,2,3,4-tetrahydro-isoquinolin-1-yl]-phenoxy}-acetic acid;
{4-Fluoro-2-[2-(2-quinolin-6-yl-acetyl)-1,2,3,4-tetrahydro-isoquinolin-1-yl]-phenoxy}-acetic acid;
{2-[2-(2-2,3-Dihydro-benzo[1,4]dioxin-6-yl-acetyl)-1,2,3,4-tetrahydro-isoquinolin-1-yl]-4-fluoro-phenoxy}-acetic acid;
{4-Fluoro-2-[2-(3-1H-indol-3-yl-propionyl)-1,2,3,4-tetrahydro-isoquinolin-1-yl]-phenoxy}-acetic acid;
(2-{2-[3-(1-Ethyl-2-methyl-1H-indol-3-yl)-propionyl]-1,2,3,4-tetrahydro-isoquinolin-1-yl}-4-fluoro-phenoxy)-acetic acid;
(2-{2-[3-(2,6-Dichloro-phenyl)-propionyl]-1,2,3,4-tetrahydro-isoquinolin-1-yl}-4-fluoro-phenoxy)-acetic acid;
(4-Fluoro-2-{2-[3-(2-fluoro-phenoxy)-propionyl]-1,2,3,4-tetrahydro-isoquinolin-1-yl}-phenoxy)-acetic acid;
[4-Fluoro-2-(2-{2-[4-(5-methyl-tetrazol-1-yl)-phenyl]-acetyl}-1,2,3,4-tetrahydro-isoquinolin-1-yl)-phenoxy]-acetic acid;
(2-{2-[3-(6-Chloro-3-oxo-2,3-dihydro-benzo[1,4]oxazin-4-yl)-propionyl]-1,2,3,4-tetrahydro-isoquinolin-1-yl}-4-fluoro-phenoxy)-acetic acid;
(4-Fluoro-2-{2-[2-(2-methyl-thiazol-4-yl)-acetyl]-1,2,3,4-tetrahydro-isoquinolin-1-yl}-phenoxy)-acetic acid;
{2-[2-(2-Benzo[b]thiophen-3-yl-acetyl)-1,2,3,4-tetrahydro-isoquinolin-1-yl]-4-fluoro-phenoxy}-acetic acid;
{2-[2-(3-Benzothiazol-2-yl-propionyl)-1,2,3,4-tetrahydro-isoquinolin-1-yl]-4-fluoro-phenoxy}-acetic acid;
{2-[2-(2-Biphenyl-4-yl-acetyl)-1,2,3,4-tetrahydro-isoquinolin-1-yl]-4-fluoro-phenoxy}-acetic acid;
{4-Fluoro-2-[2-(2-indol-1-yl-acetyl)-1,2,3,4-tetrahydro-isoquinolin-1-yl]-phenoxy}-acetic acid;
{2-[2-(2-1H-Benzoimidazol-2-yl-acetyl)-1,2,3,4-tetrahydro-isoquinolin-1-yl]-4-fluoro-phenoxy}-acetic acid;
{2-[2-(2-1,3-Dihydro-isoindol-2-yl-acetyl)-1,2,3,4-tetrahydro-isoquinolin-1-yl]-4-fluoro-phenoxy}-acetic acid;
(4-Fluoro-2-{2-[3-(5-methoxy-1H-indol-3-yl)-propionyl]-1,2,3,4-tetrahydro-isoquinolin-1-yl}-phenoxy)-acetic acid;
(4-Fluoro-2-{2-[3-(2-methyl-1H-indol-3-yl)-propionyl]-1,2,3,4-tetrahydro-isoquinolin-1-yl}-phenoxy)-acetic acid;
(4-Fluoro-2-{2-[3-(1-methyl-1H-indol-3-yl)-propionyl]-1,2,3,4-tetrahydro-isoquinolin-1-yl}-phenoxy)-acetic acid;
{4-Fluoro-2-[2-(trans-2-phenyl-cyclopropanecarbonyl)-1,2,3,4-tetrahydro-isoquinolin-1-yl]-phenoxy}-acetic acid;

{4-Chloro-2-[2-(2-cyclopropyl-acetyl)-1,2,3,4-tetrahydro-isoquinolin-1-yl]-phenoxy}-acetic acid;
{4-Chloro-2-[2-(2H-chromene-3-carbonyl)-1,2,3,4-tetrahydro-isoquinolin-1-yl]-phenoxy}-acetic acid;
{4-Chloro-2-[2-(3-methoxy-propionyl)-1,2,3,4-tetrahydro-isoquinolin-1-yl]-phenoxy}-acetic acid;
(4-Chloro-2-{2-[2-(2-chloro-phenyl)-acetyl]-1,2,3,4-tetrahydro-isoquinolin-1-yl}-phenoxy)-acetic acid;
{4-Chloro-2-[2-(2-indol-1-yl-acetyl)-1,2,3,4-tetrahydro-isoquinolin-1-yl]-phenoxy}-acetic acid;
(4-Chloro-2-{2-[3-(2-methyl-1H-indol-3-ye-propionyl]-1,2,3,4-tetrahydro-isoquinolin-1-yl}-phenoxy)-acetic acid;
(4-Chloro-2-{2-[3-(5-methoxy-1H-indol-3-yl)-propionyl]-1,2,3,4-tetrahydro-isoquinolin-1-yl}-phenoxy)-acetic acid;
(4-Chloro-2-{2-[2-(2,6-dimethyl-pyridin-3-yloxy)-acetyl]-1,2,3,4-tetrahydro-isoquinolin-1-yl}-phenoxy)-acetic acid;
(4-Chloro-2-{2-[3-(1-methyl-1H-indol-3-yl)-propionyl]-1,2,3,4-tetrahydro-isoquinolin-1-yl}-phenoxy)-acetic acid;
{4-Chloro-2-[2-(1,2,3,4-tetrahydro-naphthalene-2-carbonyl)-1,2,3,4-tetrahydro-isoquinolin-1-yl]-phenoxy}-acetic acid;
{2-[2-(2-Benzoimidazol-1-yl-acetyl)-1,2,3,4-tetrahydro-isoquinolin-1-yl]-4-chloro-phenoxy}-acetic acid;
{4-Chloro-2-[2-(2-3,4-dihydro-2H-quinolin-1-yl-acetyl)-1,2,3,4-tetrahydro-isoquinolin-1-yl]-phenoxy}-acetic acid;
{4-Chloro-2-[2-(2-indazol-2-yl-acetyl)-1,2,3,4-tetrahydro-isoquinolin-1-yl]-phenoxy}-acetic acid;
(4-Chloro-2-{2-[3-(3-trifluoromethyl-phenyl)-propionyl]-1,2,3,4-tetrahydro-isoquinolin-1-yl}-phenoxy)-acetic acid;
(4-Chloro-2-{2-trans-[2-(2-chloro-phenyl)-cyclopropanecarbonyl]-1,2,3,4-tetrahydro-isoquinolin-1-yl}-phenoxy)-acetic acid;
(4-Chloro-2-{2-[3-(1-phenyl-1H-imidazol-2-yl)-propionyl]-1,2,3,4-tetrahydro-isoquinolin-1-yl}-phenoxy)-acetic acid;
(4-Chloro-2-{2-[3-(4-oxo-2-phenyl-thiazolidin-3-yl)-propionyl]-1,2,3,4-tetrahydro-isoquinolin-1-yl}-phenoxy)-acetic acid;
[4-Chloro-2-(2-{3-[3-(2,3-dimethyl-phenyl)-3H-imidazol-4-yl]-propionyl}-1,2,3,4-tetrahydro-isoquinolin-1-yl)-phenoxy]-acetic acid;
(2-{2-[2-(Biphenyl-2-yloxy)-acetyl]-1,2,3,4-tetrahydro-isoquinolin-1-yl}-4-chloro-phenoxy)-acetic acid;
(4-Chloro-2-{2-[3-(3-fluoro-phenoxy)-propionyl]-1,2,3,4-tetrahydro-isoquinolin-1-yl}-phenoxy)-acetic acid;
{4-Chloro-2-[2-(3-p-tolyloxy-propionyl)-1,2,3,4-tetrahydro-isoquinolin-1-yl]-phenoxy}-acetic acid;
(4-Chloro-2-{2-[3-(4-chloro-phenoxy)-propionyl]-1,2,3,4-tetrahydro-isoquinolin-1-yl}-phenoxy)-acetic acid;
(4-Chloro-2-{2-[3-(2-trifluoromethyl-phenyl)-propionyl]-1,2,3,4-tetrahydro-isoquinolin-1-yl}-phenoxy)-acetic acid;
(4-Chloro-2-{2-[2-(5-fluoro-1H-indol-3-yl)-acetyl]-1,2,3,4-tetrahydro-isoquinolin-1-yl}-phenoxy)-acetic acid;
(4-Chloro-2-{2-[2-(6-methoxy-benzofuran-3-yl)-acetyl]-1,2,3,4-tetrahydro-isoquinolin-1-yl}-phenoxy)-acetic acid;
(4-Chloro-2-{2-[4-(4-chloro-phenyl)-butyryl]-1,2,3,4-tetrahydro-isoquinolin-1-yl}-phenoxy)-acetic acid;
{4-Chloro-2-[2-(3-m-tolyloxy-propionyl)-1,2,3,4-tetrahydro-isoquinolin-1-yl]-phenoxy}-acetic acid;
(4-Chloro-2-{2-[3-(3-chloro-phenoxy)-propionyl]-1,2,3,4-tetrahydro-isoquinolin-1-yl}-phenoxy)-acetic acid;
(4-Chloro-2-{2-[2-(5-chloro-1H-indol-3-yl)-acetyl]-1,2,3,4-tetrahydro-isoquinolin-1-yl}-phenoxy)-acetic acid;
{4-Chloro-2-[2-(4-p-tolyl-butyryl)-1,2,3,4-tetrahydro-isoquinolin-1-yl]-phenoxy}-acetic acid;
(4-Chloro-2-{2-[2-(5-chloro-benzo[b]thiophen-3-yl)-acetyl]-1,2,3,4-tetrahydro-isoquinolin-1-yl}-phenoxy)-acetic acid;
(4-Chloro-2-{2-[2-(5-methoxy-1H-indol-2-yl)-acetyl]-1,2,3,4-tetrahydro-isoquinolin-1-yl}-phenoxy)-acetic acid;
(4-Chloro-2-{2-[2-(5-methyl-benzo[d]isoxazol-3-yl)-acetyl]-1,2,3,4-tetrahydro-isoquinolin-1-yl}-phenoxy)-acetic acid;
(4-Chloro-2-{2-[2-(5-methoxy-benzo[d]isoxazol-3-yl)-acetyl]-1,2,3,4-tetrahydro-isoquinolin-1-yl}-phenoxy)-acetic acid;
(4-Chloro-2-{2-[3-(4-fluoro-phenoxy)-propionyl]-1,2,3,4-tetrahydro-isoquinolin-1-yl}-phenoxy)-acetic acid;
(4-Chloro-2-{2-[4-(4-fluoro-phenyl)-butyryl]-1,2,3,4-tetrahydro-isoquinolin-1-yl}-phenoxy)-acetic acid;
{4-Chloro-2-[2-(3-o-tolyl-propionyl)-1,2,3,4-tetrahydro-isoquinolin-1-yl]-phenoxy}-acetic acid;
{2-[2-(2-Benzyloxy-acetyl)-1,2,3,4-tetrahydro-isoquinolin-1-yl]-4-chloro-phenoxy}-acetic acid;
(4-Chloro-2-{2-[2-(2-chloro-benzyloxy)-acetyl]-1,2,3,4-tetrahydro-isoquinolin-1-yl}-phenoxy)-acetic acid;
{4-Chloro-2-[2-(4-phenyl-butyryl)-1,2,3,4-tetrahydro-isoquinolin-1-yl]-phenoxy}-acetic acid;
(4-Chloro-2-{2-[4-(3-fluoro-phenyl)-butyryl]-1,2,3,4-tetrahydro-isoquinolin-1-yl}-phenoxy)-acetic acid;
(4-Chloro-2-{2-[4-(2,3-dichloro-phenyl)-butyryl]-1,2,3,4-tetrahydro-isoquinolin-1-yl}-phenoxy)-acetic acid;
{4-Chloro-2-[2-(4-m-tolyl-butyryl)-1,2,3,4-tetrahydro-isoquinolin-1-yl]-phenoxy}-acetic acid;
{4-Chloro-2-[2-(4-o-tolyl-butyryl)-1,2,3,4-tetrahydro-isoquinolin-1-yl]-phenoxy}-acetic acid;
(4-Chloro-2-{2-[4-(3-chloro-phenyl)-butyryl]-1,2,3,4-tetrahydro-isoquinolin-1-yl}-phenoxy)-acetic acid;
(4-Chloro-2-{2-[4-(2-chloro-phenyl)-butyryl]-1,2,3,4-tetrahydro-isoquinolin-1-yl}-phenoxy)-acetic acid;
(4-Chloro-2-{2-[4-(3-methoxy-phenyl)-butyryl]-1,2,3,4-tetrahydro-isoquinolin-1-yl}-phenoxy)-acetic acid;
(4-Chloro-2-{2-[4-(2-fluoro-phenyl)-butyryl]-1,2,3,4-tetrahydro-isoquinolin-1-yl}-phenoxy)-acetic acid;
{4-Chloro-2-[2-(trans-2-phenyl-cyclopropanecarbonyl)-1,2,3,4-tetrahydro-isoquinolin-1-yl]-phenoxy}-acetic acid;
{4-Chloro-2-[5-fluoro-2-(trans-2-phenyl-cyclopropanecarbonyl)-1,2,3,4-tetrahydro-isoquinolin-1-yl]-phenoxy}-acetic acid;
{4-Chloro-2-[5-fluoro-2-(3-o-tolyl-propionyl)-1,2,3,4-tetrahydro-isoquinolin-1-yl]-phenoxy}-acetic acid;
{2-[2-(2-Benzyloxy-acetyl)-5-fluoro-1,2,3,4-tetrahydro-isoquinolin-1-yl]-4-chloro-phenoxy}-acetic acid;
(4-Chloro-2-{2-[2-(2-chloro-benzyloxy)-acetyl]-5-fluoro-1,2,3,4-tetrahydro-isoquinolin-1-yl}-phenoxy)-acetic acid;
{4-Chloro-2-[5-fluoro-2-(4-phenyl-butyryl)-1,2,3,4-tetrahydro-isoquinolin-1-yl]-phenoxy}-acetic acid;
{4-Chloro-2-[5-fluoro-2-(3-phenyl-propynoyl)-1,2,3,4-tetrahydro-isoquinolin-1-yl]-phenoxy}-acetic acid;
{4-Fluoro-2-[2-(3-phenyl-propionyl)-1,2,3,4-tetrahydro-isoquinolin-1-yl]-phenoxy}-acetic acid;
[4-Fluoro-2-(2-phenylacetyl-1,2,3,4-tetrahydro-isoquinolin-1-yl)-phenoxy]-acetic acid;

{4-Fluoro-2-[2-(2-phenoxy-acetyl)-1,2,3,4-tetrahydro-isoquinolin-1-yl]-phenoxy}-acetic acid;
{2-[2-(2-Benzyloxy-acetyl)-1,2,3,4-tetrahydro-isoquinolin-1-yl]-4-fluoro-phenoxy}-acetic acid;
{4-Fluoro-2-[2-(4-phenyl-butyryl)-1,2,3,4-tetrahydro-isoquinolin-1-yl]-phenoxy}-acetic acid;
(4-Fluoro-2-{2-[3-(2-methoxy-phenyl)-propionyl]-1,2,3,4-tetrahydro-isoquinolin-1-yl}-phenoxy)-acetic acid;
(4-Fluoro-2-{2-[3-(3-methoxy-phenyl)-propionyl]-1,2,3,4-tetrahydro-isoquinolin-1-yl}-phenoxy)-acetic acid;
(4-Fluoro-2-{2-[3-(4-methoxy-phenyl)-propionyl]-1,2,3,4-tetrahydro-isoquinolin-1-yl}-phenoxy)-acetic acid;
(2-{2-[3-(2-Chloro-phenyl)-propionyl]-1,2,3,4-tetrahydro-isoquinolin-1-yl}-4-fluoro-phenoxy)-acetic acid;
(2-{2-[3-(3-Chloro-phenyl)-propionyl]-1,2,3,4-tetrahydro-isoquinolin-1-yl}-4-fluoro-phenoxy)-acetic acid;
(2-{2-[3-(4-Chloro-phenyl)-propionyl]-1,2,3,4-tetrahydro-isoquinolin-1-yl}-4-fluoro-phenoxy)-acetic acid;
{4-Fluoro-2-[2-(3-o-tolyl-propionyl)-1,2,3,4-tetrahydro-isoquinolin-1-yl]-phenoxy}-acetic acid;
{4-Fluoro-2-[2-(2-naphthalen-2-yl-acetyl)-1,2,3,4-tetrahydro-isoquinolin-1-yl]-phenoxy}-acetic acid;
{4-Fluoro-2-[2-(2-o-tolyloxy-acetyl)-1,2,3,4-tetrahydro-isoquinolin-1-yl]-phenoxy}-acetic acid;
(4-Fluoro-2-{2-[2-(1-methyl-1H-indol-3-yl)-acetyl]-1,2,3,4-tetrahydro-isoquinolin-1-yl}-phenoxy)-acetic acid;
(2-{2-[2-(2-Chloro-phenoxy)-acetyl]-1,2,3,4-tetrahydro-isoquinolin-1-yl}-4-fluoro-phenoxy)-acetic acid;
(4-Fluoro-2-{2-[3-(2-fluoro-phenyl)-propionyl]-1,2,3,4-tetrahydro-isoquinolin-1-yl}-phenoxy)-acetic acid;
{4-Fluoro-2-[2-(2-indan-2-yl-acetyl)-1,2,3,4-tetrahydro-isoquinolin-1-yl]-phenoxy}-acetic acid;
(4-Fluoro-2-{2-[(E)-3-(2-fluoro-phenyl)-acryloyl]-1,2,3,4-tetrahydro-isoquinolin-1-yl}-phenoxy)-acetic acid;
{4-Fluoro-2-[2-((E)-3-o-tolyl-acryloyl)-1,2,3,4-tetrahydro-isoquinolin-1-yl]-phenoxy}-acetic acid;
{4-Fluoro-2-[2-(5-phenyl-pentanoyl)-1,2,3,4-tetrahydro-isoquinolin-1-yl]-phenoxy}-acetic acid;
{4-Fluoro-2-[2-(3-phenoxy-propionyl)-1,2,3,4-tetrahydro-isoquinolin-1-yl]-phenoxy}-acetic acid;
(4-Fluoro-2-{2-[3-(4-methanesulfonyl-phenyl)-propionyl]-1,2,3,4-tetrahydro-isoquinolin-1-yl}-phenoxy)-acetic acid;
{2-[2-(3-2,3-Dihydro-indol-1-yl-propionyl)-1,2,3,4-tetrahydro-isoquinolin-1-yl]-4-fluoro-phenoxy}-acetic acid;
{4-Fluoro-2-[2-(3-o-tolyloxy-propionyl)-1,2,3,4-tetrahydro-isoquinolin-1-yl]-phenoxy}-acetic acid;
(4-Fluoro-2-{2-[2-(2-fluoro-phenoxy)-acetyl]-1,2,3,4-tetrahydro-isoquinolin-1-yl}-phenoxy)-acetic acid;
(4-Fluoro-2-{2-[4-(2-methoxy-phenyl)-butyryl]-1,2,3,4-tetrahydro-isoquinolin-1-yl}-phenoxy)-acetic acid;
(2-{2-[2-(2-Chloro-benzyloxy)-acetyl]-1,2,3,4-tetrahydro-isoquinolin-1-yl}-4-fluoro-phenoxy)-acetic acid;
(4-Chloro-2-{2-[(trans)-2-(3-chloro-phenyl)-cyclopropanecarbonyl]-1,2,3,4-tetrahydro-isoquinolin-1-yl}-phenoxy)-acetic acid;
{4-Chloro-2-[2-((trans)-2-o-tolyl-cyclopropanecarbonyl)-1,2,3,4-tetrahydro-isoquinolin-1-yl]-phenoxy}-acetic acid;
(4-Chloro-2-{2-[(trans)-2-(2-trifluoromethyl-phenyl)-cyclopropanecarbonyl]-1,2,3,4-tetrahydro-isoquinolin-1-yl}-phenoxy)-acetic acid;
(4-Chloro-2-{2-[trans-2-(4-chloro-phenyl)-cyclopropanecarbonyl]-1,2,3,4-tetrahydro-isoquinolin-1-yl}-phenoxy)-acetic acid;
(4-Chloro-2-{2-[trans-2-(2,4-dichloro-phenyl)-cyclopropanecarbonyl]-1,2,3,4-tetrahydro-isoquinolin-1-yl}-phenoxy)-acetic acid;
(4-Chloro-2-{2-[trans-2-(2-methoxy-phenyl)-cyclopropanecarbonyl]-1,2,3,4-tetrahydro-isoquinolin-1-yl}-phenoxy)-acetic acid;
(4-Chloro-2-{2-[trans-2-(2-fluoro-phenyl)-cyclopropanecarbonyl]-1,2,3,4-tetrahydro-isoquinolin-1-yl}-phenoxy)-acetic acid;
(4-Chloro-2-{2-[3-(3-phenyl-3H-[1,2,3]triazol-4-yl)-propionyl]-1,2,3,4-tetrahydro-isoquinolin-1-yl}-phenoxy)-acetic acid;
(4-Chloro-2-{2-[2-(3-phenyl-3H-[1,2,3]triazol-4-ylsulfanyl)-acetyl]-1,2,3,4-tetrahydro-isoquinolin-1-yl}-phenoxy)-acetic acid;
1-(2-Carboxymethoxy-5-fluoro-phenyl)-6-fluoro-3,4-dihydro-1H-isoquinoline-2-carboxylic acid benzyl ester;
1-(2-Carboxymethoxy-5-chloro-phenyl)-3,4-dihydro-1H-isoquinoline-2-carboxylic acid 2-chloro-benzyl ester;
1-(2-Carboxymethoxy-5-fluoro-phenyl)-3,4-dihydro-1H-isoquinoline-2-carboxylic acid 2-chloro-benzyl ester;
1-(2-Carboxymethoxy-5-fluoro-phenyl)-3,4-dihydro-1H-isoquinoline-2-carboxylic acid 2,2-dimethyl-propyl ester;
1-(2-Carboxymethoxy-5-fluoro-phenyl)-3,4-dihydro-1H-isoquinoline-2-carboxylic acid butyl ester;
1-(2-Carboxymethoxy-5-fluoro-phenyl)-3,4-dihydro-1H-isoquinoline-2-carboxylic acid 2-methoxy-phenyl ester;
1-(2-Carboxymethoxy-5-fluoro-phenyl)-3,4-dihydro-1H-isoquinoline-2-carboxylic acid phenyl ester;
1-(2-Carboxymethoxy-5-fluoro-phenyl)-3,4-dihydro-1H-isoquinoline-2-carboxylic acid 2-chloro-phenyl ester;
1-(2-Carboxymethoxy-5-fluoro-phenyl)-3,4-dihydro-1H-isoquinoline-2-carboxylic acid isobutyl ester;
1-(2-Carboxymethoxy-5-fluoro-phenyl)-3,4-dihydro-1H-isoquinoline-2-carboxylic acid 2-methoxy-ethyl ester;
1-(2-Carboxymethoxy-5-fluoro-phenyl)-3,4-dihydro-1H-isoquinoline-2-carboxylic acid 4-methoxy-phenyl ester;
(S)-1-(2-Carboxymethoxy-5-chloro-phenyl)-3,4-dihydro-1H-isoquinoline-2-carboxylic acid 2-chloro-benzyl ester;
1-(2-Carboxymethoxy-5-chloro-phenyl)-5-fluoro-3,4-dihydro-1H-isoquinoline-2-carboxylic acid 2-chloro-benzyl ester;
1-(2-Carboxymethoxy-5-chloro-phenyl)-3,4-dihydro-1H-isoquinoline-2-carboxylic acid 2-(2-chloro-phenyl)-ethyl ester;
1-(2-Carboxymethoxy-5-fluoro-phenyl)-3,4-dihydro-1H-isoquinoline-2-carboxylic acid 2-(2-chloro-phenyl)-ethyl ester;
1-(2-Carboxymethoxy-5-fluoro-phenyl)-3,4-dihydro-1H-isoquinoline-2-carboxylic acid 3-chloro-phenyl ester;
1-(2-Carboxymethoxy-5-chloro-phenyl)-5-fluoro-3,4-dihydro-1H-isoquinoline-2-carboxylic acid 2-(2-chloro-phenyl)-ethyl ester;
1-(2-Carboxymethoxy-5-chloro-phenyl)-4,4-dimethyl-3,4-dihydro-1H-isoquinoline-2-carboxylic acid benzyl ester;
1-(2-Carboxymethoxy-5-fluoro-phenyl)-7-ethanesulfonyl-3,4-dihydro-1H-isoquinoline-2-carboxylic acid benzyl ester;
1-(2-Carboxymethoxy-5-methanesulfonyl-phenyl)-3,4-dihydro-1H-isoquinoline-2-carboxylic acid benzyl ester;
1-(5-Benzenesulfonyl-2-carboxymethoxy-phenyl)-3,4-dihydro-1H-isoquinoline-2-carboxylic acid benzyl ester;

1-(2-Carboxymethoxy-5-ethanesulfonyl-phenyl)-3,4-dihydro-1H-isoquinoline-2-carboxylic acid benzyl ester;
1-(2-Carboxymethoxy-5-fluoro-phenyl)-5-methanesulfonyl-3,4-dihydro-1H-isoquinoline-2-carboxylic acid benzyl ester;
1-(2-Carboxymethoxy-5-fluoro-phenyl)-5-ethanesulfonyl-3,4-dihydro-1H-isoquinoline-2-carboxylic acid benzyl ester;
1-(5-Benzenesulfonyl-1-(2-carboxymethoxy-5-fluoro-phenyl)-3,4-dihydro-1H-isoquinoline-2-carboxylic acid benzyl ester;
1-(2-Carboxymethoxy-5-pyrimidin-5-yl-phenyl)-3,4-dihydro-1H-isoquinoline-2-carboxylic acid benzyl ester;
1-(4-Carboxymethoxy-4'-fluoro-biphenyl-3-yl)-3,4-dihydro-1H-isoquinoline-2-carboxylic acid benzyl ester;
(2-{2-[2-(3-Chloro-benzyloxy)-acetyl]-1,2,3,4-tetrahydro-isoquinolin-1-yl}-4-fluoro-phenoxy)-acetic acid;
(2-{2-[2-(4-Chloro-benzyloxy)-acetyl]-1,2,3,4-tetrahydro-isoquinolin-1-yl}-4-fluoro-phenoxy)-acetic acid;
(4-Fluoro-2-{2-[2-(2-methyl-benzyloxy)-acetyl]-1,2,3,4-tetrahydro-isoquinolin-1-yl}-phenoxy)-acetic acid;
(4-Fluoro-2-{2-[2-(3-methyl-benzyloxy)-acetyl]-1,2,3,4-tetrahydro-isoquinolin-1-yl}-phenoxy)-acetic acid;
(4-Fluoro-2-{2-[2-(4-methyl-benzyloxy)-acetyl]-1,2,3,4-tetrahydro-isoquinolin-1-yl}-phenoxy)-acetic acid;
(4-Fluoro-2-{2-[2-(3-methoxy-benzyloxy)-acetyl]-1,2,3,4-tetrahydro-isoquinolin-1-yl}-phenoxy)-acetic acid;
(4-Fluoro-2-{2-[2-(4-methoxy-benzyloxy)-acetyl]-1,2,3,4-tetrahydro-isoquinolin-1-yl}-phenoxy)-acetic acid;
(4-Fluoro-2-{2-[2-(1-methyl-1H-pyrazol-3-ylmethoxy)-acetyl]-1,2,3,4-tetrahydro-isoquinolin-1-yl}-phenoxy)-acetic acid;
(4-Fluoro-2-{2-[2-(2-methoxy-benzyloxy)-acetyl]-1,2,3,4-tetrahydro-isoquinolin-1-yl}-phenoxy)-acetic acid;
[2-(2-Benzylcarbamoyl-1,2,3,4-tetrahydro-isoquinolin-1-yl)-4-fluoro-phenoxy]-acetic acid;
[4-Fluoro-2-(2-phenethylcarbamoyl-1,2,3,4-tetrahydro-isoquinolin-1-yl)-phenoxy]-acetic acid;
{4-Fluoro-2-[2-(2-methoxy-benzylcarbamoyl)-1,2,3,4-tetrahydro-isoquinolin-1-yl]-phenoxy}-acetic acid;
{4-Chloro-2-[2-(2-methoxy-benzylcarbamoyl)-1,2,3,4-tetrahydro-isoquinolin-1-yl]-phenoxy}-acetic acid;
{2-[2-(2-Chloro-benzylcarbamoyl)-1,2,3,4-tetrahydro-isoquinolin-1-yl]-4-fluoro-phenoxy}-acetic acid;
(2-{2-[2-(2-Chloro-phenyl)-ethylcarbamoyl]-1,2,3,4-tetrahydro-isoquinolin-1-yl}-4-fluoro-phenoxy)-acetic acid;
{2-[2-(2-Benzenesulfonylamino-acetyl)-1,2,3,4-tetrahydro-isoquinolin-1-yl]-4-fluoro-phenoxy}-acetic acid;
(2-{2-[2-(3,5-Dimethyl-isoxazole-4-sulfonylamino)-acetyl]-1,2,3,4-tetrahydro-isoquinolin-1-yl}-4-fluoro-phenoxy)-acetic acid;
(4-Fluoro-2-{2-[2-(3-fluoro-benzenesulfonylamino)-acetyl]-1,2,3,4-tetrahydro-isoquinolin-1-yl}-phenoxy)-acetic acid;
(4-Fluoro-2-{2-[2-(2-fluoro-benzenesulfonylamino)-acetyl]-1,2,3,4-tetrahydro-isoquinolin-1-yl}-phenoxy)-acetic acid;
(2-{2-[2-(3,4-Difluoro-benzenesulfonylamino)-acetyl]-1,2,3,4-tetrahydro-isoquinolin-1-yl}-4-fluoro-phenoxy)-acetic acid;
(2-{2-[2-(N-Benzenesulfonyl-N-methyl-amino)-acetyl]-1,2,3,4-tetrahydro-isoquinolin-1-yl}-4-fluoro-phenoxy)-acetic acid;
[4-Fluoro-2-(2-{2-[N-(3-fluoro-benzenesulfonyl)-N-methyl-amino]-acetyl}-1,2,3,4-tetrahydro-isoquinolin-1-yl)-phenoxy]-acetic acid;
[2-(2-{2-[N-(3,4-Difluoro-benzenesulfonyl)-N-methyl-amino]-acetyl}-1,2,3,4-tetrahydro-isoquinolin-1-yl)-4-fluoro-phenoxy]-acetic acid;
1-(5-Carbamoyl-2-carboxymethoxy-phenyl)-3,4-dihydro-1H-isoquinoline-2-carboxylic acid benzyl ester;
1-[2-Carboxymethoxy-5-(5-thioxo-4,5-dihydro-[1,2,4]oxadiazol-3-yl)-phenyl]-3,4-dihydro-1H-isoquinoline-2-carboxylic acid benzyl ester;
1-(2-Carboxymethoxy-4-fluoro-phenyl)-3,4-dihydro-1H-isoquinoline-2-carboxylic acid benzyl ester;
1-(2-Carboxymethoxy-6-fluoro-phenyl)-3,4-dihydro-1H-isoquinoline-2-carboxylic acid benzyl ester;
1-[2-(3-Carboxy-propoxy)-5-fluoro-phenyl]-3,4-dihydro-1H-isoquinoline-2-carboxylic acid benzyl ester;
{4-Cyano-2-[2-(trans-2-phenyl-cyclopropanecarbonyl)-1,2,3,4-tetrahydro-isoquinolin-1-yl]-phenoxy}-acetic acid;
1-(2-Carboxymethoxy-5-cyano-phenyl)-3,4-dihydro-1H-isoquinoline-2-carboxylic acid benzyl ester;
(R)-1-[2-(1-Carboxy-ethoxy)-5-chloro-phenyl]-3,4-dihydro-1H-isoquinoline-2-carboxylic acid benzyl ester;
(S)-1-(2-Carboxymethoxy-5-fluoro-phenyl)-3,4-dihydro-1H-isoquinoline-2-carboxylic acid benzyl ester;
1-(2-Carboxymethoxy-5-fluoro-phenyl)-5-methanesulfonylamino-3,4-dihydro-1H-isoquinoline-2-carboxylic acid benzyl ester;
1-(2-Carboxymethoxy-5-[1,2,3]triazol-1-yl-phenyl)-3,4-dihydro-1H-isoquinoline-2-carboxylic acid benzyl ester;
1-(2-Carboxymethoxy-5-[1,2,3]triazol-2-yl-phenyl)-3,4-dihydro-1H-isoquinoline-2-carboxylic acid benzyl ester; or
{4-Chloro-2-[2-(2-methoxy-benzylthiocarbamoyl)-1,2,3,4-tetrahydro-isoquinolin-1-yl]-phenoxy}-acetic acid;
or a salt thereof.

13. The compound according to claim 1, wherein the compound is:
1-(2-Carboxymethoxy-5-chloro-phenyl)-6-fluoro-3,4-dihydro-1H-isoquinoline-2-carboxylic acid benzyl ester;
1-(2-Carboxymethoxy-5-chloro-phenyl)-3,4-dihydro-1H-isoquinoline-2-carboxylic acid 2-bromo-benzyl ester;
(S)-1-(2-Carboxymethoxy-5-chloro-phenyl)-5,6-difluoro-3,4-dihydro-1H-isoquinoline-2-carboxylic acid benzyl ester;
1-(2-Carboxymethoxy-5-chloro-phenyl)-1,3-dihydro-isoindole-2-carboxylic acid benzyl ester;
{4-Chloro-2-[(S)-2-((1R,2R)-2-phenyl-cyclopropanecarbonyl)-1,2,3,4-tetrahydro-isoquinolin-1-yl]-phenoxy}-acetic acid;
1-(2-Carboxymethoxy-5-chloro-phenyl)-3,4-dihydro-1H-isoquinoline-2-carboxylic acid 2-methoxy-benzyl ester;
1-(2-Carboxymethoxy-5-chloro-phenyl)-3,4-dihydro-1H-isoquinoline-2-carboxylic acid 2-fluoro-benzyl ester;
1-(2-Carboxymethoxy-5-chloro-phenyl)-3,4-dihydro-1H-isoquinoline-2-carboxylic acid 2-methyl-benzyl ester;
1-(2-Carboxymethoxy-5-chloro-phenyl)-3,4-dihydro-1H-isoquinoline-2-carboxylic acid 2-trifluoromethyl-benzyl ester;
1-(2-Carboxymethoxy-5-chloro-phenyl)-3,4-dihydro-1H-isoquinoline-2-carboxylic acid 3-methoxy-benzyl ester;
1-(2-Carboxymethoxy-5-chloro-phenyl)-3,4-dihydro-1H-isoquinoline-2-carboxylic acid 3-fluoro-benzyl ester;
1-(2-Carboxymethoxy-5-chloro-phenyl)-3,4-dihydro-1H-isoquinoline-2-carboxylic acid 3-methyl-benzyl ester;
1-(2-Carboxymethoxy-5-chloro-phenyl)-3,4-dihydro-1H-isoquinoline-2-carboxylic acid 3-trifluoromethyl-benzyl ester;

1-(2-Carboxymethoxy-5-chloro-phenyl)-3,4-dihydro-1H-isoquinoline-2-carboxylic acid 2,4-dichloro-benzyl ester;
1-(2-Carboxymethoxy-5-chloro-phenyl)-3,4-dihydro-1H-isoquinoline-2-carboxylic acid 2,3-dichloro-benzyl ester;
1-(2-Carboxymethoxy-5-chloro-phenyl)-3,4-dihydro-1H-isoquinoline-2-carboxylic acid 2,6-dichloro-benzyl ester;
1-(2-Carboxymethoxy-5-chloro-phenyl)-3,4-dihydro-1H-isoquinoline-2-carboxylic acid 2,6-dimethoxy-benzyl ester;
1-(2-Carboxymethoxy-5-chloro-phenyl)-3,4-dihydro-1H-isoquinoline-2-carboxylic acid 2,4-dimethyl-benzyl ester;
1-(2-Carboxymethoxy-5-chloro-phenyl)-3,4-dihydro-1H-isoquinoline-2-carboxylic acid 2,3-dimethyl-benzyl ester;
1-(2-Carboxymethoxy-5-chloro-phenyl)-3,4-dihydro-1H-isoquinoline-2-carboxylic acid 2,6-dimethyl-benzyl ester;
1-(2-Carboxymethoxy-5-chloro-phenyl)-3,4-dihydro-1H-isoquinoline-2-carboxylic acid 2,4-difluoro-benzyl ester;
1-(2-Carboxymethoxy-5-chloro-phenyl)-3,4-dihydro-1H-isoquinoline-2-carboxylic acid 2,3-difluoro-benzyl ester;
1-(2-Carboxymethoxy-5-chloro-phenyl)-3,4-dihydro-1H-isoquinoline-2-carboxylic acid 2,6-difluoro-benzyl ester;
1-(2-Carboxymethoxy-5-chloro-phenyl)-3,4-dihydro-1H-isoquinoline-2-carboxylic acid 2,4,6-trimethyl-benzyl ester;
1-(2-Carboxymethoxy-5-chloro-phenyl)-3,4-dihydro-1H-isoquinoline-2-carboxylic acid 2-chloro-6-fluoro-benzyl ester;
1-(2-Carboxymethoxy-5-chloro-phenyl)-3,4-dihydro-1H-isoquinoline-2-carboxylic acid 2,5-dichloro-benzyl ester;
1-(2-Carboxymethoxy-5-chloro-phenyl)-3,4-dihydro-1H-isoquinoline-2-carboxylic acid 2,4-dimethoxy-benzyl ester;
1-(2-Carboxymethoxy-5-chloro-phenyl)-3,4-dihydro-1H-isoquinoline-2-carboxylic acid 2,3-dimethoxy-benzyl ester;
1-(2-Carboxymethoxy-5-chloro-phenyl)-3,4-dihydro-1H-isoquinoline-2-carboxylic acid 2,6-dimethyl-pyridin-3-ylmethyl ester;
1-(2-Carboxymethoxy-5-chloro-phenyl)-3,4-dihydro-1H-isoquinoline-2-carboxylic acid 3-cyano-benzyl ester;
1-(2-Carboxymethoxy-5-chloro-phenyl)-3,4-dihydro-1H-isoquinoline-2-carboxylic acid 2,5-difluoro-benzyl ester;
1-(2-Carboxymethoxy-5-chloro-phenyl)-3,4-dihydro-1H-isoquinoline-2-carboxylic acid 5-chloro-2-fluoro-benzyl ester;
1-(2-Carboxymethoxy-5-chloro-phenyl)-3,4-dihydro-1H-isoquinoline-2-carboxylic acid 2-chloro-5-fluoro-benzyl ester;
1-(2-Carboxymethoxy-5-chloro-phenyl)-3,4-dihydro-1H-isoquinoline-2-carboxylic acid cyclohexylmethyl ester;
1-(2-Carboxymethoxy-5-chloro-phenyl)-3,4-dihydro-1H-isoquinoline-2-carboxylic acid 1-methyl-1H-pyrazol-3-ylmethyl ester;
1-(2-Carboxymethoxy-5-chloro-phenyl)-3,4-dihydro-1H-isoquinoline-2-carboxylic acid cyclopentylmethyl ester;
1-(2-Carboxymethoxy-5-chloro-phenyl)-3,4-dihydro-1H-isoquinoline-2-carboxylic acid isobutyl ester;
1-(2-Carboxymethoxy-5-chloro-phenyl)-3,4-dihydro-1H-isoquinoline-2-carboxylic acid butyl ester;
1-(2-Carboxymethoxy-5-chloro-phenyl)-3,4-dihydro-1H-isoquinoline-2-carboxylic acid 2-methoxy-ethyl ester;
1-(2-Carboxymethoxy-5-chloro-phenyl)-3,4-dihydro-1H-isoquinoline-2-carboxylic acid cyclopropylmethyl ester;
1-(2-Carboxymethoxy-5-chloro-phenyl)-3,4-dihydro-1H-isoquinoline-2-carboxylic acid 3,5-dimethyl-pyrazol-1-ylmethyl ester;
1-(2-Carboxymethoxy-5-chloro-phenyl)-3,4-dihydro-1H-isoquinoline-2-carboxylic acid 5-methyl-isoxazol-3-ylmethyl ester;
1-(2-Carboxymethoxy-5-chloro-phenyl)-3,4-dihydro-1H-isoquinoline-2-carboxylic acid 1,5-dimethyl-1H-pyrazol-3-ylmethyl ester;
1-(2-Carboxymethoxy-5-chloro-phenyl)-3,4-dihydro-1H-isoquinoline-2-carboxylic acid 4-chloro-benzyl ester;
(S)-1-(2-Carboxymethoxy-5-chloro-phenyl)-3,4-dihydro-1H-isoquinoline-2-carboxylic acid thiazol-2-ylmethyl ester;
(S)-1-(2-Carboxymethoxy-5-chloro-phenyl)-3,4-dihydro-1H-isoquinoline-2-carboxylic acid 2-(4-methyl-thiazol-5-yl)-ethyl ester;
(S)-1-(2-Carboxymethoxy-5-chloro-phenyl)-3,4-dihydro-1H-isoquinoline-2-carboxylic acid 5-methyl-thiazol-2-ylmethyl ester;
(S)-1-(2-Carboxymethoxy-5-chloro-phenyl)-3,4-dihydro-1H-isoquinoline-2-carboxylic acid 4-methyl-thiazol-2-ylmethyl ester;
(S)-1-(2-Carboxymethoxy-5-chloro-phenyl)-3,4-dihydro-1H-isoquinoline-2-carboxylic acid 2-methyl-thiazol-5-ylmethyl ester;
(S)-1-(2-Carboxymethoxy-5-chloro-phenyl)-3,4-dihydro-1H-isoquinoline-2-carboxylic acid 2-methyl-thiazol-4-ylmethyl ester;
(S)-1-(2-Carboxymethoxy-5-chloro-phenyl)-3,4-dihydro-1H-isoquinoline-2-carboxylic acid 3-methyl-isoxazol-5-ylmethyl ester;
(S)-1-(2-Carboxymethoxy-5-chloro-phenyl)-3,4-dihydro-1H-isoquinoline-2-carboxylic acid 4-methyl-isoxazol-3-ylmethyl ester;
(S)-1-(2-Carboxymethoxy-5-chloro-phenyl)-3,4-dihydro-1H-isoquinoline-2-carboxylic acid 3,5-dimethyl-isoxazol-4-ylmethyl ester;
(S)-1-(2-Carboxymethoxy-5-chloro-phenyl)-3,4-dihydro-1H-isoquinoline-2-carboxylic acid pyrazin-2-ylmethyl ester;
(S)-1-(2-Carboxymethoxy-5-chloro-phenyl)-3,4-dihydro-1H-isoquinoline-2-carboxylic acid pyrimidin-4-ylmethyl ester;
(S)-1-(2-Carboxymethoxy-5-chloro-phenyl)-3,4-dihydro-1H-isoquinoline-2-carboxylic acid pyrimidin-5-ylmethyl ester;
(S)-1-(2-Carboxymethoxy-5-chloro-phenyl)-3,4-dihydro-1H-isoquinoline-2-carboxylic acid phenethyl ester;
(S)-1-(2-Carboxymethoxy-5-chloro-phenyl)-3,4-dihydro-1H-isoquinoline-2-carboxylic acid 2-(3-fluoro-phenyl)-ethyl ester;
(S)-1-(2-Carboxymethoxy-5-chloro-phenyl)-3,4-dihydro-1H-isoquinoline-2-carboxylic acid 2-methyl-2H-pyrazol-3-ylmethyl ester;
(S)-1-(2-Carboxymethoxy-5-chloro-phenyl)-3,4-dihydro-1H-isoquinoline-2-carboxylic acid 2,5-dimethyl-2H-pyrazol-3-ylmethyl ester;

(S)-1-(2-Carboxymethoxy-5-chloro-phenyl)-3,4-dihydro-1H-isoquinoline-2-carboxylic acid 2-(2-ethyl-5-methyl-2H-pyrazol-3-yl)-ethyl ester;

(S)-1-(2-Carboxymethoxy-5-chloro-phenyl)-3,4-dihydro-1H-isoquinoline-2-carboxylic acid 3-methyl-3H-imidazol-4-ylmethyl ester;

(S)-1-(2-Carboxymethoxy-5-chloro-phenyl)-3,4-dihydro-1H-isoquinoline-2-carboxylic acid 2-(3,5-dimethyl-pyrazol-1-yl)-ethyl ester;

(S)-1-(2-Carboxymethoxy-5-chloro-phenyl)-3,4-dihydro-1H-isoquinoline-2-carboxylic acid 4-methyl-pyrazol-1-ylmethyl ester;

(S)-1-(2-Carboxymethoxy-5-chloro-phenyl)-3,4-dihydro-1H-isoquinoline-2-carboxylic acid benzothiazol-2-ylmethyl ester;

(S)-1-(2-Carboxymethoxy-5-chloro-phenyl)-3,4-dihydro-1H-isoquinoline-2-carboxylic acid benzooxazol-2-ylmethyl ester;

(S)-1-(2-Carboxymethoxy-5-chloro-phenyl)-3,4-dihydro-1H-isoquinoline-2-carboxylic acid 1-methyl-1H-indazol-3-ylmethyl ester;

(S)-1-(2-Carboxymethoxy-5-chloro-phenyl)-3,4-dihydro-1H-isoquinoline-2-carboxylic acid indazol-1-ylmethyl ester;

(S)-1-(2-Carboxymethoxy-5-chloro-phenyl)-3,4-dihydro-1H-isoquinoline-2-carboxylic acid benzo[d]isoxazol-3-ylmethyl ester;

(S)-1-(2-Carboxymethoxy-5-chloro-phenyl)-5,6-difluoro-3,4-dihydro-1H-isoquinoline-2-carboxylic acid thiazol-2-ylmethyl ester;

(S)-1-(2-Carboxymethoxy-5-chloro-phenyl)-5,6-difluoro-3,4-dihydro-1H-isoquinoline-2-carboxylic acid 2-(4-methyl-thiazol-5-yl)-ethyl ester;

(S)-1-(2-Carboxymethoxy-5-chloro-phenyl)-5,6-difluoro-3,4-dihydro-1H-isoquinoline-2-carboxylic acid 5-methyl-thiazol-2-ylmethyl ester;

(S)-1-(2-Carboxymethoxy-5-chloro-phenyl)-5,6-difluoro-3,4-dihydro-1H-isoquinoline-2-carboxylic acid 4-methyl-thiazol-2-ylmethyl ester;

(S)-1-(2-Carboxymethoxy-5-chloro-phenyl)-5,6-difluoro-3,4-dihydro-1H-isoquinoline-2-carboxylic acid 2-methyl-thiazol-5-ylmethyl ester;

(S)-1-(2-Carboxymethoxy-5-chloro-phenyl)-5,6-difluoro-3,4-dihydro-1H-isoquinoline-2-carboxylic acid 2-methyl-thiazol-4-ylmethyl ester;

(S)-1-(2-Carboxymethoxy-5-chloro-phenyl)-5,6-difluoro-3,4-dihydro-1H-isoquinoline-2-carboxylic acid 3-methyl-isoxazol-5-ylmethyl ester;

(S)-1-(2-Carboxymethoxy-5-chloro-phenyl)-5,6-difluoro-3,4-dihydro-1H-isoquinoline-2-carboxylic acid 4-methyl-isoxazol-3-ylmethyl ester;

(S)-1-(2-Carboxymethoxy-5-chloro-phenyl)-5,6-difluoro-3,4-dihydro-1H-isoquinoline-2-carboxylic acid 3,5-dimethyl-isoxazol-4-ylmethyl ester;

(S)-1-(2-Carboxymethoxy-5-chloro-phenyl)-5,6-difluoro-3,4-dihydro-1H-isoquinoline-2-carboxylic acid pyrazin-2-ylmethyl ester;

(S)-1-(2-Carboxymethoxy-5-chloro-phenyl)-5,6-difluoro-3,4-dihydro-1H-isoquinoline-2-carboxylic acid pyrimidin-4-ylmethyl ester;

(S)-1-(2-Carboxymethoxy-5-chloro-phenyl)-5,6-difluoro-3,4-dihydro-1H-isoquinoline-2-carboxylic acid phenethyl ester;

(S)-1-(2-Carboxymethoxy-5-chloro-phenyl)-5,6-difluoro-3,4-dihydro-1H-isoquinoline-2-carboxylic acid 2-(3-fluoro-phenyl)-ethyl ester;

(S)-1-(2-Carboxymethoxy-5-chloro-phenyl)-5,6-difluoro-3,4-dihydro-1H-isoquinoline-2-carboxylic acid 2-methyl-2H-pyrazol-3-ylmethyl ester;

(S)-1-(2-Carboxymethoxy-5-chloro-phenyl)-5,6-difluoro-3,4-dihydro-1H-isoquinoline-2-carboxylic acid 2,5-dimethyl-2H-pyrazol-3-ylmethyl ester;

(S)-1-(2-Carboxymethoxy-5-chloro-phenyl)-5,6-difluoro-3,4-dihydro-1H-isoquinoline-2-carboxylic acid 2-(2-ethyl-5-methyl-2H-pyrazol-3-yl)-ethyl ester;

(S)-1-(2-Carboxymethoxy-5-chloro-phenyl)-5,6-difluoro-3,4-dihydro-1H-isoquinoline-2-carboxylic acid 3-methyl-3H-imidazol-4-ylmethyl ester;

(S)-1-(2-Carboxymethoxy-5-chloro-phenyl)-5,6-difluoro-3,4-dihydro-1H-isoquinoline-2-carboxylic acid 2-(3,5-dimethyl-pyrazol-1-yl)-ethyl ester;

(S)-1-(2-Carboxymethoxy-5-chloro-phenyl)-5,6-difluoro-3,4-dihydro-1H-isoquinoline-2-carboxylic acid 4-methyl-pyrazol-1-ylmethyl ester;

(S)-1-(2-Carboxymethoxy-5-chloro-phenyl)-5,6-difluoro-3,4-dihydro-1H-isoquinoline-2-carboxylic acid benzothiazol-2-ylmethyl ester;

(S)-1-(2-Carboxymethoxy-5-chloro-phenyl)-5,6-difluoro-3,4-dihydro-1H-isoquinoline-2-carboxylic acid benzooxazol-2-ylmethyl ester;

(S)-1-(2-Carboxymethoxy-5-chloro-phenyl)-5,6-difluoro-3,4-dihydro-1H-isoquinoline-2-carboxylic acid 1-methyl-1H-indazol-3-ylmethyl ester;

(S)-1-(2-Carboxymethoxy-5-chloro-phenyl)-5,6-difluoro-3,4-dihydro-1H-isoquinoline-2-carboxylic acid indazol-1-ylmethyl ester;

(S)-1-(2-Carboxymethoxy-5-chloro-phenyl)-5,6-difluoro-3,4-dihydro-1H-isoquinoline-2-carboxylic acid benzo[d]isoxazol-3-ylmethyl ester;

(S)-1-(2-Carboxymethoxy-5-chloro-phenyl)-6-fluoro-3,4-dihydro-1H-isoquinoline-2-carboxylic acid thiazol-2-ylmethyl ester;

(S)-1-(2-Carboxymethoxy-5-chloro-phenyl)-6-fluoro-3,4-dihydro-1H-isoquinoline-2-carboxylic acid 2-(4-methyl-thiazol-5-yl)-ethyl ester;

(S)-1-(2-Carboxymethoxy-5-chloro-phenyl)-6-fluoro-3,4-dihydro-1H-isoquinoline-2-carboxylic acid 5-methyl-thiazol-2-ylmethyl ester;

(S)-1-(2-Carboxymethoxy-5-chloro-phenyl)-6-fluoro-3,4-dihydro-1H-isoquinoline-2-carboxylic acid 4-methyl-thiazol-2-ylmethyl ester;

(S)-1-(2-Carboxymethoxy-5-chloro-phenyl)-6-fluoro-3,4-dihydro-1H-isoquinoline-2-carboxylic acid 2-methyl-thiazol-5-ylmethyl ester;

(S)-1-(2-Carboxymethoxy-5-chloro-phenyl)-6-fluoro-3,4-dihydro-1H-isoquinoline-2-carboxylic acid 2-methyl-thiazol-4-ylmethyl ester;

(S)-1-(2-Carboxymethoxy-5-chloro-phenyl)-6-fluoro-3,4-dihydro-1H-isoquinoline-2-carboxylic acid 3-methyl-isoxazol-5-ylmethyl ester;

(S)-1-(2-Carboxymethoxy-5-chloro-phenyl)-6-fluoro-3,4-dihydro-1H-isoquinoline-2-carboxylic acid 4-methyl-isoxazol-3-ylmethyl ester;

(S)-1-(2-Carboxymethoxy-5-chloro-phenyl)-6-fluoro-3,4-dihydro-1H-isoquinoline-2-carboxylic acid pyrazin-2-ylmethyl ester;

(S)-1-(2-Carboxymethoxy-5-chloro-phenyl)-6-fluoro-3,4-dihydro-1H-isoquinoline-2-carboxylic acid pyrimidin-4-ylmethyl ester;

(S)-1-(2-Carboxymethoxy-5-chloro-phenyl)-6-fluoro-3,4-dihydro-1H-isoquinoline-2-carboxylic acid pyrimidin-5-ylmethyl ester;

(S)-1-(2-Carboxymethoxy-5-chloro-phenyl)-6-fluoro-3,4-dihydro-1H-isoquinoline-2-carboxylic acid phenethyl ester;
(S)-1-(2-Carboxymethoxy-5-chloro-phenyl)-6-fluoro-3,4-dihydro-1H-isoquinoline-2-carboxylic acid 2-(3-fluoro-phenyl)-ethyl ester;
(S)-1-(2-Carboxymethoxy-5-chloro-phenyl)-6-fluoro-3,4-dihydro-1H-isoquinoline-2-carboxylic acid 2-methyl-2H-pyrazol-3-ylmethyl ester;
(S)-1-(2-Carboxymethoxy-5-chloro-phenyl)-6-fluoro-3,4-dihydro-1H-isoquinoline-2-carboxylic acid 2,5-dimethyl-2H-pyrazol-3-ylmethyl ester;
(S)-1-(2-Carboxymethoxy-5-chloro-phenyl)-6-fluoro-3,4-dihydro-1H-isoquinoline-2-carboxylic acid 2-(2-ethyl-5-methyl-2H-pyrazol-3-yl)-ethyl ester;
(S)-1-(2-Carboxymethoxy-5-chloro-phenyl)-6-fluoro-3,4-dihydro-1H-isoquinoline-2-carboxylic acid 3-methyl-3H-imidazol-4-ylmethyl ester;
(S)-1-(2-Carboxymethoxy-5-chloro-phenyl)-6-fluoro-3,4-dihydro-1H-isoquinoline-2-carboxylic acid 2-(3,5-dimethyl-pyrazol-1-yl)-ethyl ester;
(S)-1-(2-Carboxymethoxy-5-chloro-phenyl)-6-fluoro-3,4-dihydro-1H-isoquinoline-2-carboxylic acid 4-methyl-pyrazol-1-ylmethyl ester;
(S)-1-(2-Carboxymethoxy-5-chloro-phenyl)-6-fluoro-3,4-dihydro-1H-isoquinoline-2-carboxylic acid benzothiazol-2-ylmethyl ester;
(S)-1-(2-Carboxymethoxy-5-chloro-phenyl)-6-fluoro-3,4-dihydro-1H-isoquinoline-2-carboxylic acid benzooxazol-2-ylmethyl ester;
(S)-1-(2-Carboxymethoxy-5-chloro-phenyl)-6-fluoro-3,4-dihydro-1H-isoquinoline-2-carboxylic acid 1-methyl-1H-indazol-3-ylmethyl ester;
(S)-1-(2-Carboxymethoxy-5-chloro-phenyl)-6-fluoro-3,4-dihydro-1H-isoquinoline-2-carboxylic acid indazol-1-ylmethyl ester;
(S)-1-(2-Carboxymethoxy-5-chloro-phenyl)-6-fluoro-3,4-dihydro-1H-isoquinoline-2-carboxylic acid benzo[d]isoxazol-3-ylmethyl ester;
(S)-1-(2-Carboxymethoxy-5-chloro-phenyl)-5,6-difluoro-3,4-dihydro-1H-isoquinoline-2-carboxylic acid 2-fluoro-benzyl ester;
(S)-1-(2-Carboxymethoxy-5-chloro-phenyl)-5,6-difluoro-3,4-dihydro-1H-isoquinoline-2-carboxylic acid 3-fluoro-benzyl ester;
(S)-1-(2-Carboxymethoxy-5-chloro-phenyl)-5,6-difluoro-3,4-dihydro-1H-isoquinoline-2-carboxylic acid 2,3-difluoro-benzyl ester;
(S)-1-(2-Carboxymethoxy-5-chloro-phenyl)-6-fluoro-3,4-dihydro-1H-isoquinoline-2-carboxylic acid 2-fluoro-benzyl ester;
(S)-1-(2-Carboxymethoxy-5-chloro-phenyl)-6-fluoro-3,4-dihydro-1H-isoquinoline-2-carboxylic acid 3-fluoro-benzyl ester;
(S)-1-(2-Carboxymethoxy-5-chloro-phenyl)-6-fluoro-3,4-dihydro-1H-isoquinoline-2-carboxylic acid 2,3-difluoro-benzyl ester;
(S)-1-(2-Carboxymethoxy-5-chloro-phenyl)-3,4-dihydro-1H-isoquinoline-2-carboxylic acid 3-fluoro-benzyl ester;
(S)-1-(2-Carboxymethoxy-5-chloro-phenyl)-3,4-dihydro-1H-isoquinoline-2-carboxylic acid 2-methoxy-benzyl ester;
(S)-1-(2-Carboxymethoxy-5-chloro-phenyl)-3,4-dihydro-1H-isoquinoline-2-carboxylic acid 2-fluoro-benzyl ester;
(S)-1-(2-Carboxymethoxy-5-chloro-phenyl)-5-fluoro-3,4-dihydro-1H-isoquinoline-2-carboxylic acid 3-fluoro-benzyl ester;
(S)-1-(2-Carboxymethoxy-5-chloro-phenyl)-5-fluoro-3,4-dihydro-1H-isoquinoline-2-carboxylic acid 2-fluoro-benzyl ester;
1-(2-Carboxymethoxy-5-chloro-phenyl)-3,4-dihydro-1H-isoquinoline-2-carboxylic acid 4-methyl-benzyl ester;
1-(2-Carboxymethoxy-5-chloro-phenyl)-3,4-dihydro-1H-isoquinoline-2-carboxylic acid 4-methoxy-benzyl ester;
1-(2-Carboxymethoxy-5-chloro-phenyl)-3,4-dihydro-1H-isoquinoline-2-carboxylic acid 4-fluoro-benzyl ester;
1-(2-Carboxymethoxy-5-chloro-phenyl)-3,4-dihydro-1H-isoquinoline-2-carboxylic acid 4-trifluoromethyl-benzyl ester;
1-(2-Carboxymethoxy-5-chloro-phenyl)-3,4-dihydro-1H-isoquinoline-2-carboxylic acid 3-chloro-benzyl ester;
1-(2-Carboxymethoxy-5-chloro-phenyl)-7-fluoro-3,4-dihydro-1H-isoquinoline-2-carboxylic acid benzyl ester;
1-(2-Carboxymethoxy-phenyl)-3,4-dihydro-1H-isoquinoline-2-carboxylic acid benzyl ester;
1-(2-Carboxymethoxy-5-chloro-phenyl)-6-fluoro-3,4-dihydro-1H-isoquinoline-2-carboxylic acid benzyl ester;
(4-Chloro-2-{2-[3-(5-fluoro-3-methyl-indol-1-yl)-propionyl]-1,2,3,4-tetrahydro-isoquinolin-1-yl}-phenoxy)-acetic acid;
(4-Chloro-2-{2-[3-(6-methoxy-pyrrolo[2,3-b]pyridin-1-yl)-propionyl]-1,2,3,4-tetrahydro-isoquinolin-1-yl}-phenoxy)-acetic acid;
(4-Chloro-2-{2-[3-(4,6-dimethoxy-pyrrolo[2,3-b]pyridin-1-yl)-propionyl]-1,2,3,4-tetrahydro-isoquinolin-1-yl}-phenoxy)-acetic acid;
(4-Chloro-2-{2-[3-(4,6-dimethoxy-indol-1-yl)-propionyl]-1,2,3,4-tetrahydro-isoquinolin-1-yl}-phenoxy)-acetic acid;
{4-Chloro-2-[2-(3-indol-1-yl-propionyl)-1,2,3,4-tetrahydro-isoquinolin-1-yl]-phenoxy}-acetic acid;
(4-Chloro-2-{2-[3-(5-fluoro-indol-1-yl)-propionyl]-1,2,3,4-tetrahydro-isoquinolin-1-yl}-phenoxy)-acetic acid;
(4-Chloro-2-{2-[3-(7-chloro-indol-1-yl)-propionyl]-1,2,3,4-tetrahydro-isoquinolin-1-yl}-phenoxy)-acetic acid;
{4-Chloro-2-[2-(3-pyrrolo[3,2-b]pyridin-1-yl-propionyl)-1,2,3,4-tetrahydro-isoquinolin-1-yl]-phenoxy}-acetic acid;
(4-Chloro-2-{2-[3-(4-methoxy-indol-1-yl)-propionyl]-1,2,3,4-tetrahydro-isoquinolin-1-yl}-phenoxy)-acetic acid;
(4-Chloro-2-{2-[3-(3-chloro-indazol-1-ye-propionyl]-1,2,3,4-tetrahydro-isoquinolin-1-yl}-phenoxy)-acetic acid;
(4-Chloro-2-{2-[3-(6-methyl-indol-1-yl)-propionyl]-1,2,3,4-tetrahydro-isoquinolin-1-yl}-phenoxy)-acetic acid;
(4-Chloro-2-{2-[3-(6-chloro-indol-1-yl)-propionyl]-1,2,3,4-tetrahydro-isoquinolin-1-yl}-phenoxy)-acetic acid;
(4-Chloro-2-{2-[3-(4-fluoro-indol-1-yl)-propionyl]-1,2,3,4-tetrahydro-isoquinolin-1-yl}-phenoxy)-acetic acid;
(4-Chloro-2-{2-[3-(6-fluoro-indol-1-yl)-propionyl]-1,2,3,4-tetrahydro-isoquinolin-1-yl}-phenoxy)-acetic acid;
(4-Chloro-2-{2-[3-(6-methoxy-indol-1-yl)-propionyl]-1,2,3,4-tetrahydro-isoquinolin-1-yl}-phenoxy)-acetic acid;
(4-Chloro-2-{(S)-6-fluoro-2-[3-(5-fluoro-indazol-1-yl)-propionyl]-1,2,3,4-tetrahydro-isoquinolin-1-yl}-phenoxy)-acetic acid;
(4-Chloro-2-{(S)-6-fluoro-2-[3-(3-methyl-indazol-1-yl)-propionyl]-1,2,3,4-tetrahydro-isoquinolin-1-yl}-phenoxy)-acetic acid;

(4-Chloro-2-{(S)-2-[3-(6-chloro-indazol-1-yl)-propionyl]-6-fluoro-1,2,3,4-tetrahydro-isoquinolin-1-yl}-phenoxy)-acetic acid;
(4-Chloro-2-{2-[3-(3-chloro-pyrrolo[2,3-b]pyrazin-5-yl)-propionyl]-1,2,3,4-tetrahydro-isoquinolin-1-yl}-phenoxy)-acetic acid;
(4-Chloro-2-{2-[2-(2-methoxy-phenoxy)-acetyl]-1,2,3,4-tetrahydro-isoquinolin-1-yl}-phenoxy)-acetic acid;
(4-Chloro-2-{2-[2-(4-fluoro-phenoxy)-acetyl]-1,2,3,4-tetrahydro-isoquinolin-1-yl}-phenoxy)-acetic acid;
(4-Chloro-2-{2-[2-(quinolin-8-yloxy)-acetyl]-1,2,3,4-tetrahydro-isoquinolin-1-yl}-phenoxy)-acetic acid;
(4-Chloro-2-{2-[2-(4-chloro-phenoxy)-acetyl]-1,2,3,4-tetrahydro-isoquinolin-1-yl}-phenoxy)-acetic acid;
(4-Chloro-2-{2-[trans-2-(4-fluoro-phenyl)-cyclopropanecarbonyl]-1,2,3,4-tetrahydro-isoquinolin-1-yl}-phenoxy)-acetic acid;
(4-Chloro-2-{2-[trans-2-(3-chloro-phenyl)-cyclopropanecarbonyl]-1,2,3,4-tetrahydro-isoquinolin-1-yl}-phenoxy)-acetic acid;
{4-Chloro-2-[2-(trans-2-o-tolyl-cyclopropanecarbonyl)-1,2,3,4-tetrahydro-isoquinolin-1-yl]-phenoxy}-acetic acid;
(4-Chloro-2-{2-[trans-2-(2-trifluoromethyl-phenyl)-cyclopropanecarbonyl]-1,2,3,4-tetrahydro-isoquinolin-1-yl}-phenoxy)-acetic acid;
(4-Chloro-2-{2-[trans-2-(3-fluoro-phenyl)-cyclopropanecarbonyl]-1,2,3,4-tetrahydro-isoquinolin-1-yl}-phenoxy)-acetic acid;
(4-Chloro-2-{2-[trans-2-(3-methoxy-phenyl)-cyclopropanecarbonyl]-1,2,3,4-tetrahydro-isoquinolin-1-yl}-phenoxy)-acetic acid;
{4-Chloro-2-[2-(trans-2-m-tolyl-cyclopropanecarbonyl)-1,2,3,4-tetrahydro-isoquinolin-1-yl]-phenoxy}-acetic acid;
{4-Chloro-2-[6-fluoro-2-(trans-2-phenyl-cyclopropanecarbonyl)-1,2,3,4-tetrahydro-isoquinolin-1-yl]-phenoxy}-acetic acid;
(4-Chloro-2-{6-fluoro-2-[trans-2-(2-trifluoromethyl-phenyl)-cyclopropanecarbonyl]-1,2,3,4-tetrahydro-isoquinolin-1-yl}-phenoxy)-acetic acid;
(4-Chloro-2-{2-[2-(trans-2-chloro-phenyl)-cyclopropanecarbonyl]-6-fluoro-1,2,3,4-tetrahydro-isoquinolin-1-yl}-phenoxy)-acetic acid;
{4-Chloro-2-[6-fluoro-2-(trans-2-o-tolyl-cyclopropanecarbonyl)-1,2,3,4-tetrahydro-isoquinolin-1-yl]-phenoxy}-acetic acid;
(4-Chloro-2-{2-[2-(2,6-dimethyl-pyridin-3-yloxy)-acetyl]-6-fluoro-1,2,3,4-tetrahydro-isoquinolin-1-yl}-phenoxy)-acetic acid;
(4-Chloro-2-{6-fluoro-2-[3-(1-methyl-1H-indol-3-yl)-propionyl]-1,2,3,4-tetrahydro-isoquinolin-1-yl}-phenoxy)-acetic acid;
{4-Chloro-2-[6-fluoro-2-(3-o-tolyl-propionyl)-1,2,3,4-tetrahydro-isoquinolin-1-yl]-phenoxy}-acetic acid;
(4-Chloro-2-{6-fluoro-2-[4-(2-fluoro-phenyl)-butyryl]-1,2,3,4-tetrahydro-isoquinolin-1-yl}-phenoxy)-acetic acid;
(4-Chloro-2-{2-[2-(2-chloro-benzyloxy)-acetyl]-6-fluoro-1,2,3,4-tetrahydro-isoquinolin-1-yl}-phenoxy)-acetic acid;
{4-Chloro-2-[2-(3-2,3-dihydro-indol-1-yl-propionyl)-1,2,3,4-tetrahydro-isoquinolin-1-yl]-phenoxy}-acetic acid;
(4-Chloro-2-{2-[3-(3-methyl-indol-1-yl)-propionyl]-1,2,3,4-tetrahydro-isoquinolin-1-yl}-phenoxy)-acetic acid;
{4-Chloro-2-[2-(3-indazol-1-yl-propionyl)-1,2,3,4-tetrahydro-isoquinolin-1-yl]-phenoxy}-acetic acid;
{4-Chloro-2-[2-(3-3,4-dihydro-2H-quinolin-1-yl-propionyl)-1,2,3,4-tetrahydro-isoquinolin-1-yl]-phenoxy}-acetic acid;
(4-Chloro-2-{2-[2-(2,4-dimethyl-phenoxy)-acetyl]-1,2,3,4-tetrahydro-isoquinolin-1-yl}-phenoxy)-acetic acid;
(4-Chloro-2-{2-[3-(5-methoxy-1-methyl-1H-indol-3-yl)-propionyl]-1,2,3,4-tetrahydro-isoquinolin-1-yl}-phenoxy)-acetic acid;
{4-Chloro-2-[2-(3-1H-indol-3-yl-propionyl)-1,2,3,4-tetrahydro-isoquinolin-1-yl]-phenoxy}-acetic acid;
{4-Chloro-2-[2-(2,2-dimethyl-cyclopropanecarbonyl)-1,2,3,4-tetrahydro-isoquinolin-1-yl]-phenoxy}-acetic acid;
{4-Chloro-2-[2-(2-chloro-benzylcarbamoyl)-1,2,3,4-tetrahydro-isoquinolin-1-yl]-phenoxy}-acetic acid;
{4-Chloro-2-[2-(3-fluoro-benzylcarbamoyl)-1,2,3,4-tetrahydro-isoquinolin-1-yl]-phenoxy}-acetic acid;
[2-(2-Benzylcarbamoyl-1,2,3,4-tetrahydro-isoquinolin-1-yl)-4-chloro-phenoxy]-acetic acid;
[4-Chloro-2-(2-phenethylcarbamoyl-1,2,3,4-tetrahydro-isoquinolin-1-yl)-phenoxy]-acetic acid;
{4-Chloro-2-[2-(4-fluoro-benzylcarbamoyl)-1,2,3,4-tetrahydro-isoquinolin-1-yl]-phenoxy}-acetic acid;
{4-Chloro-2-[2-(2-fluoro-benzylcarbamoyl)-1,2,3,4-tetrahydro-isoquinolin-1-yl]-phenoxy}-acetic acid;
1-(2-Carboxymethoxy-5-fluoro-phenyl)-1,3-dihydro-isoindole-2-carboxylic acid benzyl ester;
1-(2-Carboxymethoxy-5-chloro-phenyl)-5-fluoro-1,3-dihydro-isoindole-2-carboxylic acid benzyl ester;
1-(2-Carboxymethoxy-5-chloro-phenyl)-4-fluoro-1,3-dihydro-isoindole-2-carboxylic acid benzyl ester;
{4-Chloro-2-[2-trans-(2-phenyl-cyclopropanecarbonyl)-2,3-dihydro-1H-isoindol-1-yl]-phenoxy}-acetic acid;
(4-Chloro-2-{2-[2-(4-fluoro-phenoxy)-acetyl]-2,3-dihydro-1H-isoindol-1-yl}-phenoxy)-acetic acid;
(4-Chloro-2-{2-[2-(quinolin-8-yloxy)-acetyl]-2,3-dihydro-1H-isoindol-1-yl}-phenoxy)-acetic acid;
(4-Chloro-2-{2-[3-(5-methoxy-1H-indol-3-yl)-propionyl]-2,3-dihydro-1H-isoindol-1-yl}-phenoxy)-acetic acid;
(4-Chloro-2-{2-[2-(2,6-dimethyl-pyridin-3-yloxy)-acetyl]-2,3-dihydro-1H-isoindol-1-yl}-phenoxy)-acetic acid;
(4-Chloro-2-{2-[3-(1-methyl-1H-indol-3-yl)-propionyl]-2,3-dihydro-1H-isoindol-1-yl}-phenoxy)-acetic acid;
{4-Chloro-2-[2-(3-2,3-dihydro-indol-1-yl-propionyl)-2,3-dihydro-1H-isoindol-1-yl]-phenoxy}-acetic acid;
{4-Chloro-2-[2-(3-indazol-1-yl-propionyl)-2,3-dihydro-1H-isoindol-1-yl]-phenoxy}-acetic acid;
(4-Chloro-2-{2-[2-(5-methoxy-benzo[d]isoxazol-3-yl)-acetyl]-2,3-dihydro-1H-isoindol-1-yl}-phenoxy)-acetic acid;
(4-Chloro-2-{2-[3-(3-methyl-indol-1-yl)-propionyl]-2,3-dihydro-1H-isoindol-1-yl}-phenoxy)-acetic acid;
(4-Chloro-2-{2-[2-(2-chloro-benzyloxy)-acetyl]-2,3-dihydro-1H-isoindol-1-yl}-phenoxy)-acetic acid;
(4-Chloro-2-{2-[3-(2-fluoro-phenoxy)-propionyl]-2,3-dihydro-1H-isoindol-1-yl}-phenoxy)-acetic acid;
(4-Chloro-2-{2-trans-[2-(3-fluoro-phenyl)-cyclopropanecarbonyl]-2,3-dihydro-1H-isoindol-1-yl}-phenoxy)-acetic acid;
(4-Chloro-2-{2-trans-[2-(2-fluoro-phenyl)-cyclopropanecarbonyl]-2,3-dihydro-1H-isoindol-1-yl}-phenoxy)-acetic acid;
{4-Chloro-2-[5-fluoro-2-(3-indazol-1-yl-propionyl)-2,3-dihydro-1H-isoindol-1-yl]-phenoxy}-acetic acid;

(4-Chloro-2-{2-[3-(5-fluoro-indazol-1-yl)-propionyl]-2,3-dihydro-1H-isoindol-1-yl}-phenoxy)-acetic acid;
(4-Chloro-2-{2-[3-(4-fluoro-3-methyl-indazol-1-yl)-propionyl]-2,3-dihydro-1H-isoindol-1-yl}-phenoxy)-acetic acid;
(4-Chloro-2-{2-[3-(6-fluoro-3-methyl-indazol-1-yl)-propionyl]-2,3-dihydro-1H-isoindol-1-yl}-phenoxy)-acetic acid;
(4-Chloro-2-{2-[3-(6-chloro-3-methyl-indazol-1-yl)-propionyl]-2,3-dihydro-1H-isoindol-1-yl}phenoxy)-acetic acid;
(4-Chloro-2-{2-[3-(3-methyl-indazol-1-yl)-propionyl]-2,3-dihydro-1H-isoindol-1-yl}-phenoxy)-acetic acid;
(4-Chloro-2-{2-[3-(6-fluoro-indazol-1-yl)-propionyl]-2,3-dihydro-1H-isoindol-1-yl}-phenoxy)-acetic acid;
(4-Chloro-2-{2-[3-(4-fluoro-indazol-1-yl)-propionyl]-2,3-dihydro-1H-isoindol-1-yl}-phenoxy)-acetic acid;
(4-Chloro-2-{2-[3-(7-fluoro-indazol-1-yl)-propionyl]-2,3-dihydro-1H-isoindol-1-yl}-phenoxy)-acetic acid;
{4-Chloro-2-[2-(2-fluoro-benzylcarbamoyl)-2,3-dihydro-1H-isoindol-1-yl]-phenoxy}-acetic acid;
{4-Chloro-2-[2-(3-fluoro-benzylcarbamoyl)-2,3-dihydro-1H-isoindol-1-yl]-phenoxy}-acetic acid;
{4-Chloro-2-[2-(4-fluoro-benzylcarbamoyl)-2,3-dihydro-1H-isoindol-1-yl]-phenoxy}-acetic acid;
[2-(2-Benzylcarbamoyl-2,3-dihydro-1H-isoindol-1-yl)-4-chloro-phenoxy]-acetic acid;
[4-Chloro-2-(2-phenethylcarbamoyl-2,3-dihydro-1H-isoindol-1-yl)-phenoxy]-acetic acid;
{4-Chloro-2-[2-(2-chloro-benzylcarbamoyl)-2,3-dihydro-1H-isoindol-1-yl]-phenoxy}-acetic acid;
1-(2-Carboxymethoxy-5-chloro-phenyl)-4,5-dichloro-1,3-dihydro-isoindole-2-carboxylic acid benzyl ester;
1-(2-Carboxymethoxy-5-chloro-phenyl)-4,5-difluoro-1,3-dihydro-isoindole-2-carboxylic acid benzyl ester;
{4-Chloro-2-[(S)-2-((1R,2R)-2-o-tolyl-cyclopropanecarbonyl)-1,2,3,4-tetrahydro-isoquinolin-1-yl]-phenoxy}-acetic acid;
(4-Chloro-2-{(S)-2-[(1R,2R)-2-(2-trifluoromethyl-phenyl)-cyclopropanecarbonyl]-1,2,3,4-tetrahydro-isoquinolin-1-yl}-phenoxy)-acetic acid;
(4-Chloro-2-{(S)-2-[(1R,2R)-2-(3-chloro-phenyl)-cyclopropanecarbonyl]-1,2,3,4-tetrahydro-isoquinolin-1-yl}-phenoxy)-acetic acid;
(4-Chloro-2-{(S)-2-[(1R,2R)-2-(3-fluoro-phenyl)-cyclopropanecarbonyl]-1,2,3,4-tetrahydro-isoquinolin-1-yl}-phenoxy)-acetic acid;
(4-Chloro-2-{(S)-2-[(1R,2R)-2-(4-fluoro-phenyl)-cyclopropanecarbonyl]-1,2,3,4-tetrahydro-isoquinolin-1-yl}-phenoxy)-acetic acid;
(S)-1-[5-Chloro-2-(2-oxo-2-trifluoromethanesulfonylamino-ethoxy)-phenyl]-3,4-dihydro-1H-isoquinoline-2-carboxylic acid benzyl ester;
(S)-1-[5-Chloro-2-(5-oxo-4,5-dihydro-[1,3,4]oxadiazol-2-ylmethoxy)-phenyl]-3,4-dihydro-1H-isoquinoline-2-carboxylic acid benzyl ester; or
1-[5-Chloro-2-(3-hydroxy-isoxazol-5-ylmethoxy)-phenyl]-3,4-dihydro-1H-isoquinoline-2-carboxylic acid benzyl ester;
or a salt thereof.

14. The compound according to claim 1, wherein the salt thereof is a pharmaceutically acceptable salt.

15. A pharmaceutical composition comprising a compound according claim 1, or a pharmaceutically acceptable salt thereof, and a pharmaceutically acceptable carrier.

16. A method of treating a disease or disorder, comprising administering an effective amount of the compound of claim 1, or a pharmaceutically acceptable salt thereof, to a subject in need thereof, wherein the disease or disorder is associated with a prostaglandin D2 receptor, and wherein the disease or disorder is asthma, allergic rhinitis, allergic nephritis conjunctivitis, atopic dermatitis, food allergy, anaphylactic shock, urticaria, eczema, Churg-Strauss Syndrome or allergic sinusitis.

* * * * *